(12) United States Patent
Janetka et al.

(10) Patent No.: US 8,937,167 B2
(45) Date of Patent: Jan. 20, 2015

(54) COMPOUNDS AND METHODS FOR TREATING BACTERIAL INFECTIONS

(75) Inventors: James W. Janetka, St. Louis, MO (US); Zhenfu Han, St. Louis, MO (US); Scott Hultgren, St. Louis, MO (US); Jerome S. Pinkner, St. Louis, MO (US); Corinne Cusumano, St. Louis, MO (US)

(73) Assignee: Washington University, St. Louis, MO (US)

(*) Notice: Subject to any disclaimer, the term of this patent is extended or adjusted under 35 U.S.C. 154(b) by 50 days.

(21) Appl. No.: 13/453,991

(22) Filed: Apr. 23, 2012

(65) Prior Publication Data
US 2012/0309701 A1    Dec. 6, 2012

Related U.S. Application Data

(63) Continuation-in-part of application No. PCT/US2010/053848, filed on Oct. 22, 2010, and a continuation-in-part of application No. PCT/US2012/024169, filed on Feb. 7, 2012, application No. 13/453,991, filed on Apr. 23, 2012, which is a continuation-in-part of application No. PCT/US2012/024169, filed on Feb. 7, 2012.

(60) Provisional application No. 61/254,135, filed on Oct. 22, 2009, provisional application No. 61/254,135, filed on Oct. 22, 2009, provisional application No. 61/384,535, filed on Sep. 20, 2010, provisional application No. 61/440,260, filed on Feb. 7, 2011, provisional application No. 61/451,455, filed on Mar. 10, 2011.

(51) Int. Cl.
| | |
|---|---|
| A61K 31/7034 | (2006.01) |
| A61K 31/7042 | (2006.01) |
| A61K 31/706 | (2006.01) |
| C07H 15/207 | (2006.01) |
| C07H 19/056 | (2006.01) |
| C07H 15/22 | (2006.01) |

(52) U.S. Cl.
CPC ............ C07H 15/207 (2013.01); C07H 19/056 (2013.01); C07H 15/22 (2013.01)
USPC .................................. 536/4.1; 514/27; 514/35

(58) Field of Classification Search
None
See application file for complete search history.

(56) References Cited

U.S. PATENT DOCUMENTS

| | | |
|---|---|---|
| 6,962,791 B2 | 11/2005 | Hultgren |
| 7,790,183 B2 | 9/2010 | Darouiche |

| | | |
|---|---|---|
| 2007/0167378 A1 | 7/2007 | Saraiva et al. |
| 2008/0171706 A1 | 7/2008 | Berglund |
| 2008/0268006 A1 | 10/2008 | Molin |

FOREIGN PATENT DOCUMENTS

| | | |
|---|---|---|
| EP | 0383092 A2 | 8/1990 |
| EP | 0383092 A3 | 3/1992 |
| WO | 9514028 A2 | 5/1995 |
| WO | 0110386 A2 | 2/2001 |
| WO | 2005089733 A2 | 9/2005 |
| WO | 2011050323 A1 | 4/2011 |
| WO | 2011073112 A2 | 6/2011 |

OTHER PUBLICATIONS

Han et al. J. Med. Chem. 2010, 53, 4779-4792.*
Irani et al. Indian J. Chem., Sect. B: Org. Chem. Incl. Med. Chem. 30 (1991) 5, 519-521, abstract only.*
Klein et al. J. Med. Chem. 2010, 53, 8627-8641, published Nov. 24, 2010.*
Han et al. J. Med. Chem. 2012, 55, 3945-3959, published Mar. 26, 2012.*
Cusumano et al. Sci Transl Med vol. 3, Issue 109, 109ra115, Nov. 16, 2011.*
International Search Report and Written Opinion dated May 29, 2012 from parent International application No. PCT/US12/24169, 8 pgs.
International Search Report and Written Opinion dated Dec. 23, 2010 from parent International application No. PCT/US10/53848, 9 pgs.
Touaibia, Mannosylated G(0) Dendrimers with Nanomolar Affinities to Escherichia coli FimH, ChemMedChem, 2007, pp. 1190-1201, vol. 2.
Abdel-Megeid, F. et al., "Preparation and Some Reactions of D-Glucosyl Derivatives of 2-Thioxo-1,3,4-Oxadiazoles and 2-Thioxo-1,3,4-Thiadiazoles and Their 2-Oxo Analogues," Carbohydrate Res., 1977, pp. 95-102, vol. 59.
Abgottspon, D. et al., "In vivo Evaluation of FimH Antagonists—A Novel Class of Antimicrobials for the Treatment of Urinary Tract Infection," Chimia, 2012, pp. 166-169, vol. 66, No. 4.
Abgottspon, D. et al., "Development of an aggregation assay to screen FimH antagonists," J. Microb. Methods, 2010, pp. 249-255, vol. 82.
Bouckaert, J. et al., "Receptor binding studies disclose a novel class of high-affinity inhibitors of the Escherichia coli FimH adhesion," Mol. Microb., 2005, pp. 441-455, vol. 55, No. 2.
Cusumano, C. et al., "Treatment and Prevention of Urinary Tract Infection with Orally Active FimH Inhibitors," www.ScienceTranslationalMedicine.org, Nov. 16, 2011, pp. 1-10, vol. 3, Issue 109.
Durka, M. et al., "The functional valency of dodecamannosylated fullerenes with Escherichia coli FimH-towards novel bacterial antiadhesives," Chem. Commun., 2011, pp. 1321-1323, vol. 47.
Extended European Search Report from related European Patent Application No. 10825785.8 dated Jan. 7, 2014, 10 pages.
Firon, N. et al., "Interaction of Mannose-Containing Oligosaccharides With the Fimbrial Lectin of Escherichia coli," Biochem. and Biophys. Res. Commun., Apr. 29, 1982, pp. 1426-1432, vol. 105, No. 4.
Firon, N. et al., "Aromatic Alpha-Glycosides of Mannose Are Powerful Inhibitors of the Adherence of Type 1 Fimbriated Escherichia coli to Yeast and Intestinal Epitherlial Cells," Infection and Immunity, Feb. 1987, pp. 472-476, vol. 55, No. 2.

(Continued)

Primary Examiner — Layla Bland
(74) Attorney, Agent, or Firm — Polsinelli PC

(57) ABSTRACT

The present invention encompasses compounds and methods for treating urinary tract infections.

11 Claims, 87 Drawing Sheets
(50 of 87 Drawing Sheet(s) Filed in Color)

(56) References Cited

OTHER PUBLICATIONS

Furneaux, R. et al., "New mannotriosides and trimannosides as potential ligands for mannose-specific binding proteins," Can. J. Chem., 2002, pp. 964-972, vol. 80.

Gouin, S. et al., "Synthetic Multimeric Heptyl Mannosides as Potent Antiadhesives of Uropathogenic *Escherichia coli*," ChemMedChem., 2009, pp. 749-755, vol. 4.

Grabosch, C. et al., "Squaric Acid Monoamide Mannosides as Ligands for the Bacterial Lectin FimH: Covalent Inhibition or Not?," Chem. Bio. Chem., 2011, pp. 1066-1074, vol. 12.

Guiton, P. et al., "Combinatorial Small-Molecule Therapy Prevents Uropathogenic *Escherichia coli* Catheter-Associated Urinary Tract Infections in Mice," Antimicrob. Agents Chemother., Sep. 2012, pp. 4738-4745, vol. 56, No. 9.

Han, Z. et al., "Structure-Based Drug Design and Optimization of Mannoside Bacterial FimH Antagonists," J. Med. Chem., 2010, pp. 4779-4792, vol. 53.

Han, Z. et al., "Lead Optimization Studies on FimH Antagonists: Discovery of Potent and Orally Bioavailable Ortho-Substituted Biphenyl Mannosides," J. Med. Chem., 2012, pp. 3945-3959, vol. 55.

Hartmann, M. et al., "The Bacterial Lectin FimH, a Target for Drug Discovery—Carbohydrate Inhibitors of Type 1 Fimbriae-Mediated Bacterial Adhesion," Eur. J. Org. Chem., 2011, pp. 1-28, vol. 2011.

Haskins, W. et al., "Relations between Rotary Power and Structure in the Sugar Group. XXXV. Some 2'-Naphthyl 1-Thioglycoprranosides and their Acetates," J. Am. Chem. Soc., Jul. 19, 1947, pp. 1668-1672, vol. 69, No. 7.

Hung, C-S. et al., "Structural basis of tropism of *Escherichia coli* to the bladder during urinary tract infection," Mol. Microb., 2002, pp. 903-915, vol. 44, No. 4.

Irani, R. et al., "Stannic Chloride Promoted Synthesis of Mannosides," Indian J. Chem., Sect. B: Org. Chem. Incl. Med. Chem. 30, 1991, 5, 519-521; Natl. Chem. Lab., Pune 411 008, India; EN, 1 page (Abstract Only).

Jiang, X. et al., "Antiadhesion Therapy for Urinary Tract Infections-A Balanced PK/PD Profile Proved to Be Key for Success," J. Med. Chem., 2012, pp. 4700-4713, vol. 55.

Klein T. et al., "FimH Antagonists for the Oral Treatment of Urinary Tract Infections: From Design and Synthesis to in Vitro and in Vivo Evaluation," J. Med. Chem., 2010, pp. 8627-8641, vol. 53.

Kostakioti, M. et al., "Distinguishing the Contribution of Type 1 Pili from That of Other QseB-Misregulated Factors when QseC Is Absent during Urinary Tract Infection," Infect. Immun., Aug. 2012, pp. 2826-2834, vol. 80, No. 8.

Lindhorst, T. et al., "Inhibition of the type 1 fimbriae-mediated adhesion of *Escherichia coil* to erythrocytes by multiantennary alpha-mannosyl clusters: The effect of multivalency," Glycoconjugate J., 1998, pp. 605-613, vol. 15.

Nagahori, N. et al., "Inhibition of Adhesion of Type 1 Fimbriated *Escherichia coli* to Highly Mannosylated Ligands," ChemBioChem, 2002, pp. 836-844, vol. 3.

Pang, L. et al., "FimH Antagonists: Structure-Activity and Structure-Property Relationships for Biphenyl alpha-D-Mannopyranosides," ChemMedChem., 2012, pp. 1404-1422, vol. 7.

Qian, X. et al., "Arrays of Self-Assembled Monolayers for Studying Inhibition of Bacterial Adhesion," Anal. Chem., 2002, pp. 1805-1810, vol. 74.

Rabbani, S. et al., "Expression of the carbohydrate recognition domain of FimH and development of a competitive binding assay," Anal. Biochem., 2010, pp. 188-195, vol. 407.

Scharenberg, M. et al., "Target Selectivity of FimH Antagonists," J. Med. Chem., 2012, pp. 9810-9816, vol. 55.

Scharenberg, M. et al., "A Flow Cytometry-Based Assay for Screening FimH Antagonists," Assay and Drug Development Technologies, Oct. 2011, pp. 455-464, vol. 9, No. 5.

Schwardt, O. et al., "Design, synthesis and biological evaluation of mannosyl triazoles as FimH antagonists," Bioorg. Med. Chem., 2011, pp. 6454-6473, vol. 19.

Shuman, D. et al., "Synthesis and Biological Activity of Certain 8-Mercaptopurine and 6-Mercaptopyrimidine S-Nucleosides," J. Med. Chem., Jul. 1969, pp. 653-657, vol. 12, No. 4.

Sperling, O. et al., "Evaluation of the carbohydrate recognition domain of the bacterial adhesion FimH: design, synthesis and binding properties of mannoside ligands," Org. Biomol. Chem., 2006, pp. 3913-3922, vol. 4.

Taile, V. et al., Journal of Heterocyclic Chemistry, Jul. 17, 2010, pp. 903-907, vol. 47, No. 4.

Touaibia, M. et al., "Glycodendrimers as Anti-Adhesion Drugs Against Type 1 Fimbriated *E. coli* Uropathogenic Infections," Mini-Rev. in Med. Chem., 2007, pp. 1270-1283, vol. 7.

Touaibia, M. et al., "Tri- and hexavalent mannoside clusters as potential inhibitors of type 1 fimbriated bacteria using pentaerythritol and triazole linkages," Chem. Commun., 2007, pp. 380-382.

Touaibia, M. et al., "Mannosylated G(0) Dendrimers with Nanomolar Affinities to *Escherichia coli* FimH," ChemMedChem., 2007, pp. 1190-1201, vol. 2.

Walter, M. et al., "A Modular System for the Preparation of Diazirine-Labeled Mannose Derivatives Using Thiourea Bridging," Synthesis, 2006, pp. 952-958, No. 6.

Wellens, A. et al., "Intervening with Urinary Tract Infections Using Anti-Adhesives Based on the Crystal Structure of the FimH-Oligomannose-3 Complex," PLoS ONE, Apr. 2008, pp. 1-13, vol. 3, Issue 4, e2040.

Bognar, R. et al., "N-Glycosyl Derivatives: Part III. The subsequent installation of the aglycone. Synthesis of Nglycosyl derivatives of 2-amino-thiazole, 2-amino-1 ,3,4-thiadiazole and 5-amino-1 ,2,3,4-thiatriazols," Carbohyd. Res., 1967, pp. 320-328, vol. 5, with English Abstract.

Stoll, von A. et al., "The furocoumarin and the beta-D-glucosido-furocumarinsaure from the seeds of *Coronilla* species," Helvetica Chimica Acta, 1950, pp. 1637-1647, vol. XXXIII, Fasciculus VI, No. 211-212, with English Abstract.

\* cited by examiner

| Strain | Position | | | | | | | | | | | | | IBCs present (hrs PI) |
|---|---|---|---|---|---|---|---|---|---|---|---|---|---|---|
| | 30 | 48 | 83 | 87 | 91 | 99 | 127 | 138 | 184 | 187 | 216 | 227 | 290 | |
| ASB1 | T | A | S | G | S | N | A | G | V | R | Y | N | Q | 6,24 |
| ASB2 | T | A | S | G | N | N | A | G | V | R | Y | N | Q | 6,24 |
| ASB3 | T | A | S | G | N | S | A | G | V | H | Y | N | Q | 6,24 |
| ASB4 | T | A | S | G | N | S | A | G | V | R | Y | N | Q | 6 |
| ASB5 | T | V | S | G | S | N | T | G | V | R | Y | N | Q | 24 (rare) |
| acute1 | T | V | S | G | N | S | A | G | V | R | Y | N | Q | 12 (rare) |
| acute2 | T | A | S | G | N | S | A | G | V | R | F | N | Q | 6 (rare) |
| acute3 | T | V | S | G | N | S | A | G | V | R | Y | N | Q | 3 (rare) |
| acute4 | T | A | S | S | S | N | A | G | V | R | Y | N | Q | - |
| rUTI1 | A | A | S | G | N | S | A | R | V | R | Y | S | K | - |
| rUTI2 | T | A | S | G | N | S | A | G | V | R | F | N | Q | 6 |
| rUTI3 | T | V | S | G | N | S | A | G | V | R | Y | N | Q | 6 (few) |
| rUTI4 | T | A | S | G | S | N | A | G | A | R | Y | N | Q | 24 |
| rUTI5 | T | A | S | G | N | S | A | G | V | R | Y | N | Q | 3 |
| pyelo1 | T | A | S | G | N | S | A | G | V | R | Y | N | K | 6 |
| pyelo2 | T | A | S | G | N | S | A | G | V | R | Y | N | Q | 6 |
| pyelo3 | T | V | S | G | S | N | A | G | V | R | Y | N | Q | - |
| pyelo4 | T | A | S | G | S | N | A | G | V | R | Y | N | Q | 6 |
| UTI89 | T | A | A | G | S | N | A | G | V | R | Y | N | Q | 3,6,24 |

FIG. 7

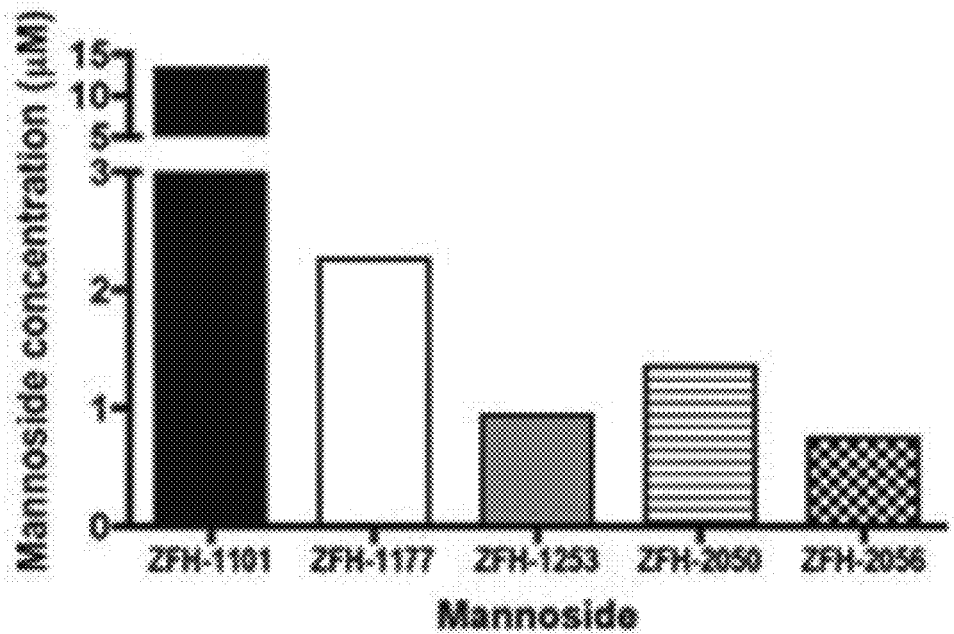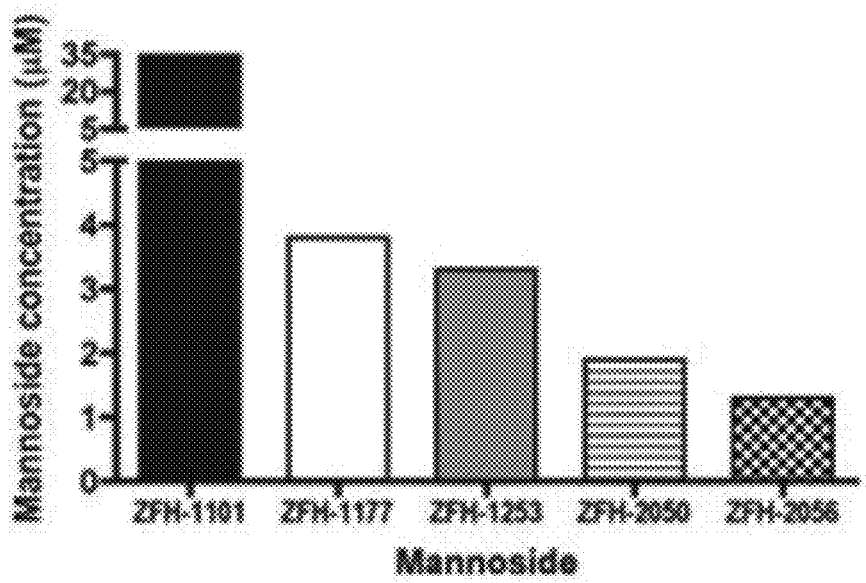
*FIG. 19*

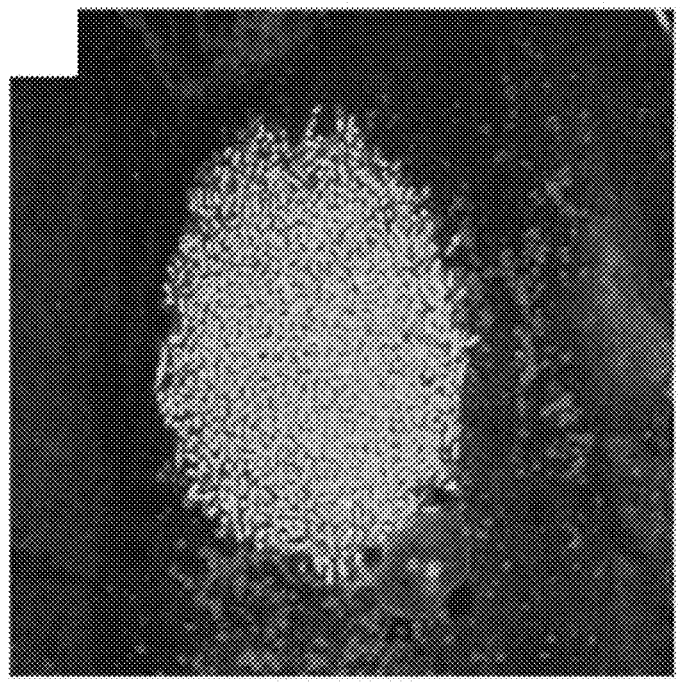
Untreated
IP ZFH-2056
FIG. 20

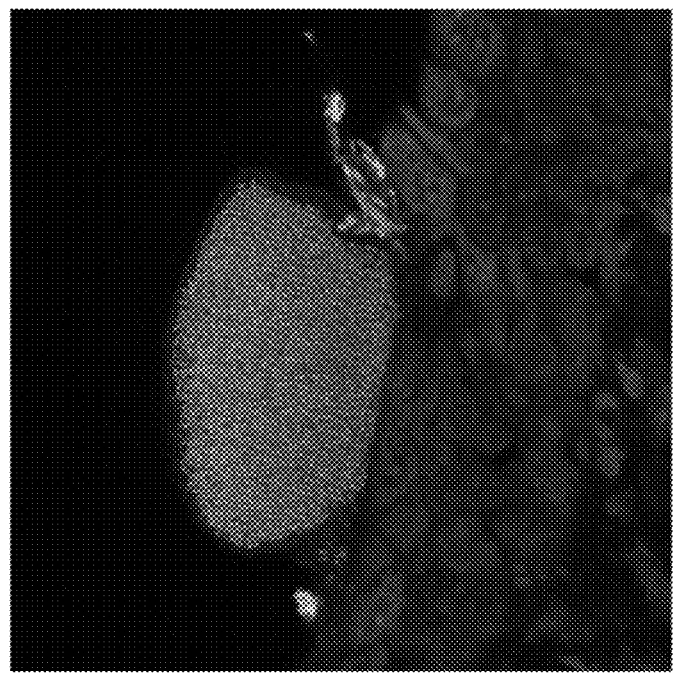
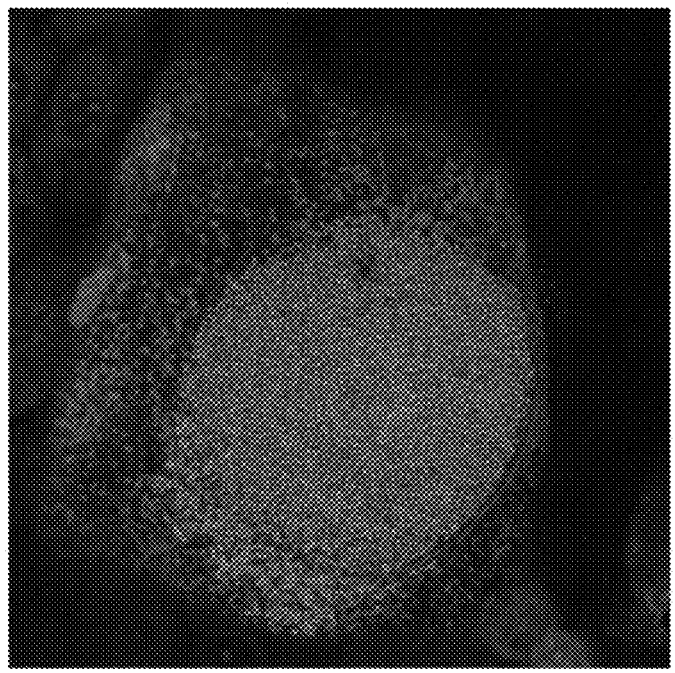
FIG. 28

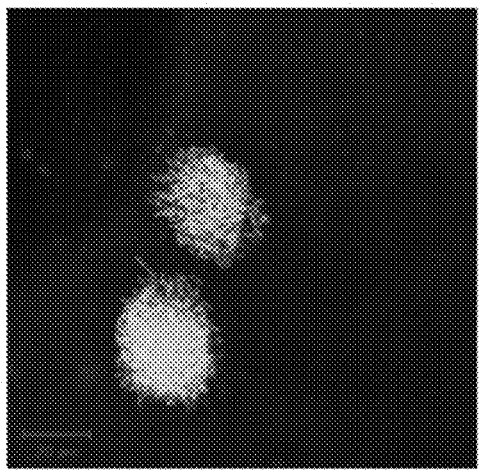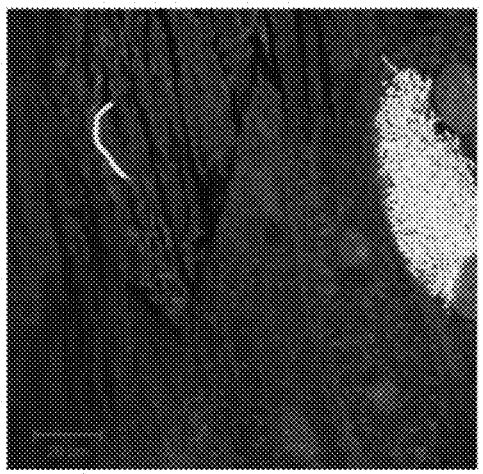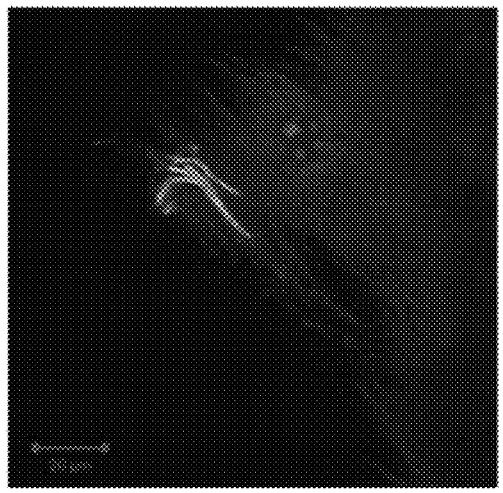
FIG. 35

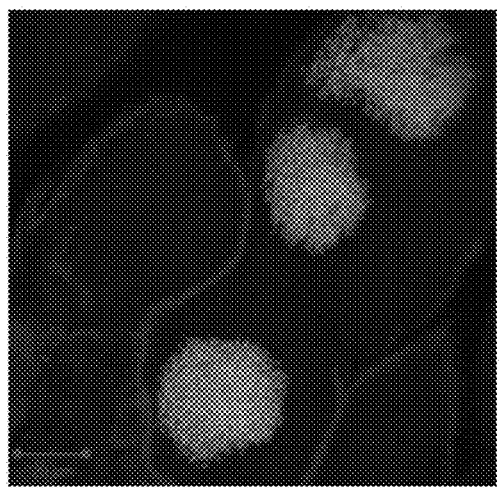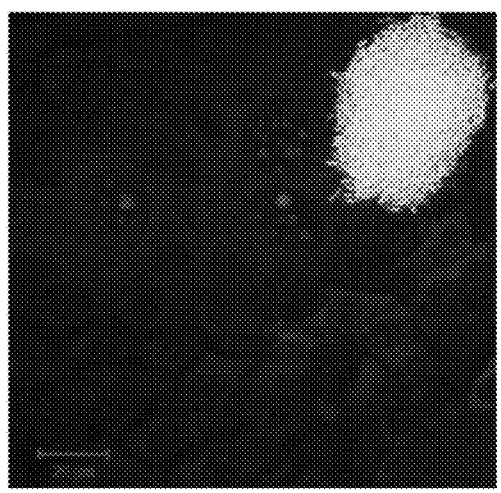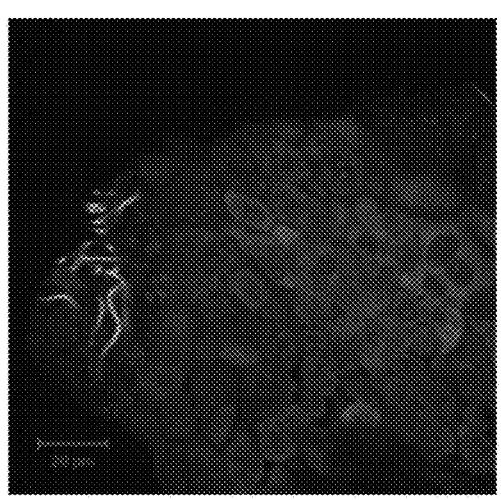
FIG. 35

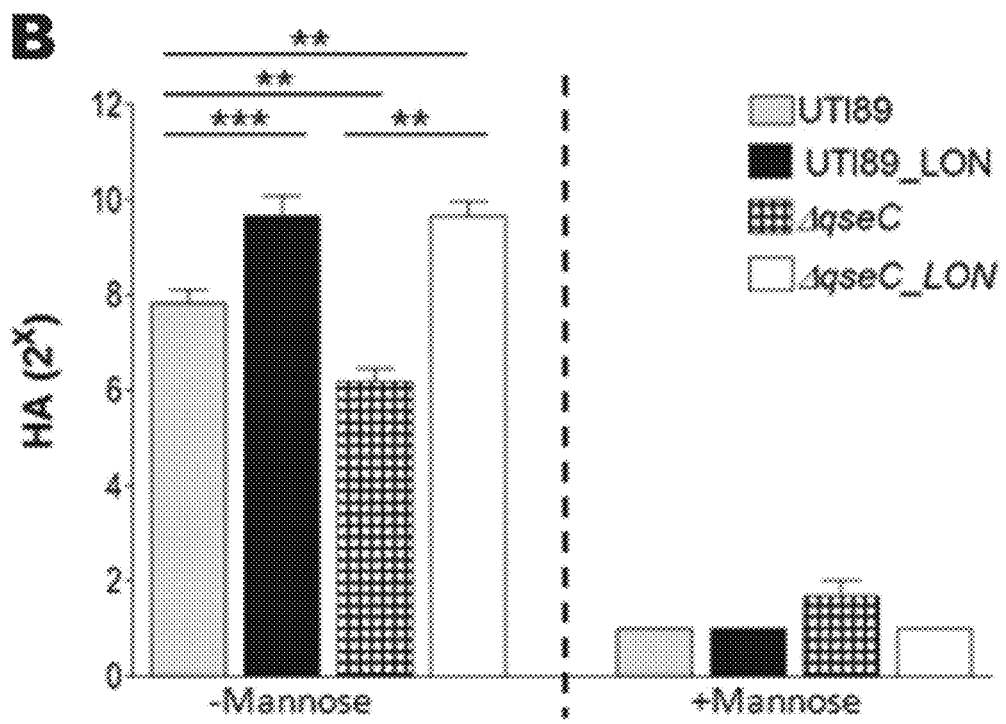
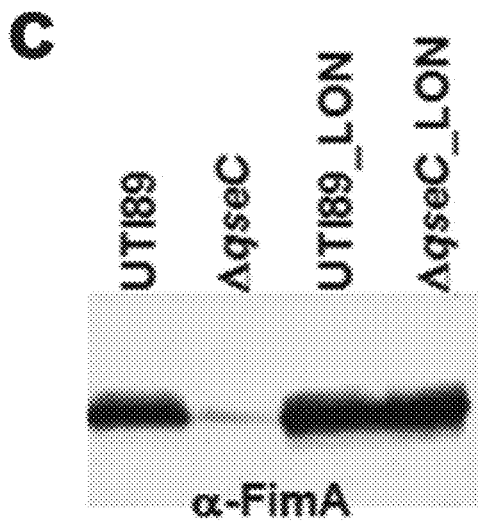
FIG. 53

COMPOUNDS AND METHODS FOR TREATING BACTERIAL INFECTIONS

CROSS REFERENCE TO RELATED APPLICATIONS

This application is a Continuation in Part of PCT/US2010/053848, filed Oct. 22, 2010, which claims the priority of U.S. provisional application No. 61/254,135, filed Oct. 22, 2009, U.S. provisional application No. 61/384,535, filed Sep. 20, 2010, and U.S. provisional application No. 61/321,738, filed Apr. 7, 2010, and this application is a Continuation in Part of PCT/US2012/024169, which claims the priority of U.S. provisional application No. 61/440,260, filed Feb. 7, 2011, and U.S. provisional application No. 61/451,455, filed Mar. 10, 2011, which is hereby incorporated by reference in its entirety.

GOVERNMENTAL RIGHTS

This invention was made with government support under grants numbered 1RC1DK086378, RO1AI029549, P50DK064540 and RO1BK051406-12 each of which were awarded by the National Institutes of Health. The government has certain rights in the invention.

FIELD OF THE INVENTION

The present invention encompasses compounds and methods for treating urinary tract infections.

BACKGROUND OF THE INVENTION

Urinary tract infection (UTI) caused by uropathogenic *Escherichia coli* (UPEC) is one of the most common infectious diseases in women. The morbidity and economic impact are enormous, with over $2.5 billion spent annually on treatment. Further, recurrent infections are a significant problem despite appropriate antibiotic therapy of the index case. The high rates of recurrence, and the large numbers of women that end up in urology clinics due to their chronic recurrent UTIs highlights the need for a better understanding of the pathogenic mechanisms involved in this disease and the development of new and better therapies.

Gram-negative bacteria are the causative agents of a wide variety of acute and chronic infectious diseases. Many of these infections are initiated by a critical interaction between host ligands (frequently polysaccharide moieties) and bacterial adhesins (frequently expressed at the distal tip of polymeric pilus fibers assembled by the chaperone/usher pathway). The mannose binding FimH adhesin of type 1 pili is critical for the colonization and invasion into the bladder epithelium. After invasion, UPEC are able to rapidly multiply inside superficial umbrella cells of the bladder forming biofilm-like intracellular bacterial communities (IBCs). Upon maturation, bacteria disperse from the IBC, spread to neighboring cells, and form next generation IBCs. This is the mechanism by which UPEC rapidly amplify in numbers in the urinary tract and cause disease.

The X-ray crystal structure of FimH bound to mannose showed that mannose is bound in a negatively charged pocket on FimH. The mannose binding site is highly conserved as it is invariant in 300 fimH genes sequenced from clinical UPEC strains. Thus, FimH is the critical node of the entire UPEC pathogenic cascade.

Recurrence is a serious problem for many women. Women who present with an initial episode of acute UTI have a 25-44% chance of developing a second and a 3% chance of experiencing three episodes within six months of the initial UTI. Recurrence occurs despite appropriate antibiotic treatment and clearance of the initial infection from the urine. A large percentage of recurrent UTI are caused by the same strain of bacteria as the initial infection. One study followed 58 women and found that 68% of recurrences were caused by the same initial index strain of UPEC as determined by restriction fragment length polymorphism (RFLP) analysis. In a separate study, 50% of recurrent strains isolated from female college students appeared genotypically identical to the bacterial strain corresponding to the initial UTI. Another long-term prospective study demonstrated that the same strain of UPEC can cause a recurrent UTI up to 3 years later. The high frequency of same-strain recurrences supports the notion that a UPEC reservoir can exist in the affected individual. The inventors have shown that a quiescent intracellular reservoir (QIR) can form in the bladder tissue itself after acute infection and persist even after antibiotic therapy and urine cultures become sterile. Thus, reactivation of bacteria in QIRs may also be a contributing factor in recurrent UTIs.

Therefore, there is a need for effective treatments that can cure urinary tract infections and prevent the formation of quiescent intracellular reservoir that are the source of so many recurrent infections.

SUMMARY OF THE INVENTION

One aspect of the present invention encompasses a compound comprising formula (I):

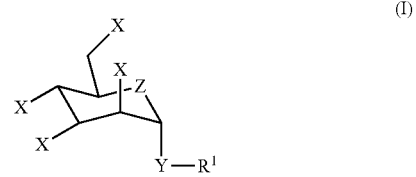

wherein:

X is selected from the group consisting of hydrogen, $OR^2$, $SR^2$, and $NR^z$;

Z is selected from the group consisting of O, S, $CR^3$ and $NR^4$;

Y is selected from the group consisting of oxygen, sulfur, $CR^3$, $NR^4$, $-N(R^5)CO-$, $-CH_2N(R^5)-$, $-CH_2N(R^5)CO-$, $CO_2$, $SO_2$, $-CH_2O-$, $-CH_2S-$, $CO$, $-CON(R^5)-$, $-SO_2N(R^5)-$, $-O(CH_2)_n-$, $-S(CH_2)_n-$, $-N(CH_2)_n-$, $-(CH_2)_n-$, $NR^5$, and an optionally substituted alkyl, alkene, alkyne, or heterocycle;

$R^2$ is independently selected from the group consisting of hydrogen, $COR^x$, $CONR^x$, hydrocarbyl, and substituted hydrocarbyl;

$R^3$, $R^4$, $R^5$ are independently selected from the group consisting of hydrogen, hydrocarbyl, and substituted hydrocarbyl;

$R^z$ is independently selected from the group consisting of hydrogen hydrocarbyl, substituted hydrocarbyl, $-COR^x$, $-CONR^xR^xSO_2R^x$, and $-CO_2R^x$;

$R^x$ is independently selected from the group consisting of hydrogen, $NR^4R^5$, and an optionally substituted alkyl, cycloalkyl, heterocycle, or aryl;

n is an integer from 1 to 10; and $R^1$ is selected from the group comprising Formulas (IIIA), (IIIB), (IV), (V), (VI), (VII) and (VIII):

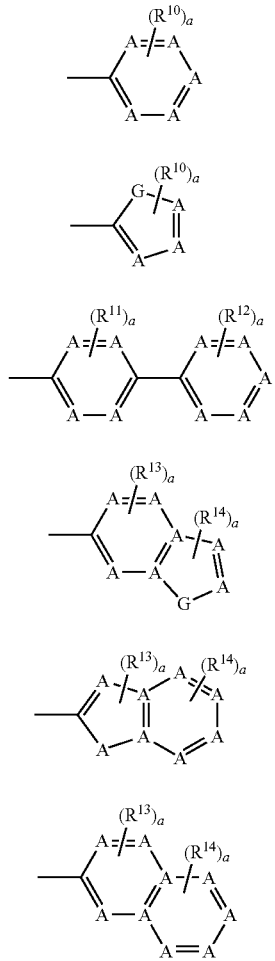

wherein:

A is independently selected from the group consisting of $CR^6$ and N;

G is selected from the group consisting of S, O, $CR^8$, and $NR^9$;

$R^6$, $R^8$ and $R^9$ are independently selected from the group consisting of hydrogen, hydrocarbyl, and substituted hydrocarbyl;

$R^{10}$, $R^{11}$, $R^{12}$, $R^{13}$ and $R^{14}$ are independently selected from the group consisting of hydrogen, —$OR^{15}$, —$NR^{15}R^{16}$, —$NR^{15}COR^{16}$, —$NR^{15}CO_2R^{16}$, —$NR^{15}CONR^{16}$, —$NR^{15}SO_2R^{16}$, —$COR^{15}$, —$SO_2R^{15}$, nitro, cyano, halogen, aryl, heterocycle, —$COOR^{15}$, —$CONR^{16}R^{17}$, —$SO_2NR^{18}R^{19}$, alkenyl, alkynyl, hydrocarbyl, and substituted hydrocarbyl;

$R^{15}$, $R^{16}$, $R^{17}$, $R^{18}$, $R^{19}$ are independently selected from the group consisting of hydrogen, hydrocarbyl, substituted hydrocarbyl, aryl, and heterocycle, and $R^{16}$ and $R^{17}$ together can optionally form a ring, and $R^{18}$ and $R^{19}$ together can optionally form a ring; and a is either the integer 1 or the integer 2.

Another aspect of the invention encompasses a compound (II):

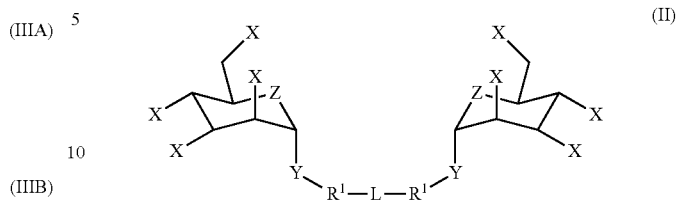

wherein

X is selected from the group consisting of hydrogen, $OR^2$, $SR^2$, and $NR^z$;

Z is selected from the group consisting of O, S, $CR^3$ and $NR^4$;

Y is selected from the group consisting of oxygen, sulfur, $CR^3$, $NR^4$, —$N(R^5)CO$—, —$CH_2N(R^5)$—, —$CH_2N(R^5)CO$—, $CO_2$, $SO_2$, —$CH_2O$—, —$CH_2S$—, CO, —CON$(R^5)$—, —$SO_2N(R^5)$—, —$O(CH_2)_n$—, —$S(CH_2)_n$—, —$N(CH_2)_n$—, —$(CH_2)_n$—, $NR^5$, and an optionally substituted alkyl, alkene, alkyne, or heterocycle;

L is selected from —$O(CH_2)_nO$—, —$S(CH_2)_nS$—, —$N(CH_2)_nN$—, —$(CH_2)_n$—, —$O[(CH_2)_mO(CH_2)_n]_xO$—, —$N(CH_2)_m$—O—$(CH_2)_nN$—, heterocycle, alkene, alkyne, —$CON[(CH_2)_mO(CH_2)_n]_xNCO$—, —$SO_2N[(CH_2)m$—O—$(CH_2)n]xNO_2S$—, and NCO$[(CH_2)_mO(CH_2)_n]_xCON$—, where L is bound to a ring of $R^1$ at a meta or para position;

$R^2$ is independently selected from the group consisting of hydrogen, $COR^x$, $CONR^x$, hydrocarbyl, and substituted hydrocarbyl;

$R^3$, $R^4$, $R^5$ are independently selected from the group consisting of hydrogen, hydrocarbyl, and substituted hydrocarbyl, $R^z$ is independently selected from the group consisting of hydrogen hydrocarbyl, substituted hydrocarbyl, —$COR^x$, —$CONR^xR^xSO_2R^x$, and —$CO_2R^x$;

$R^x$ is independently selected from the group consisting of hydrogen, $NR^4R^5$, and an optionally substituted alkyl, cycloalkyl, heterocycle, or aryl;

m, n, and x are integers from 1 to 10; and $R^1$ is selected from the group comprising Formulas (IIIA), (IIIB), (IV), (V), (VI), (VII) and (VIII):

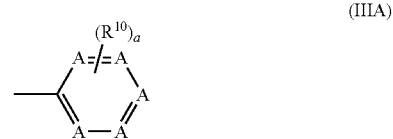

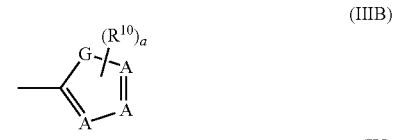

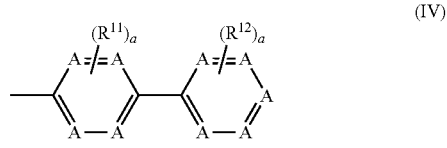

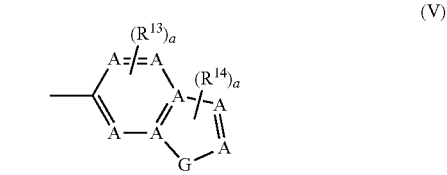

-continued

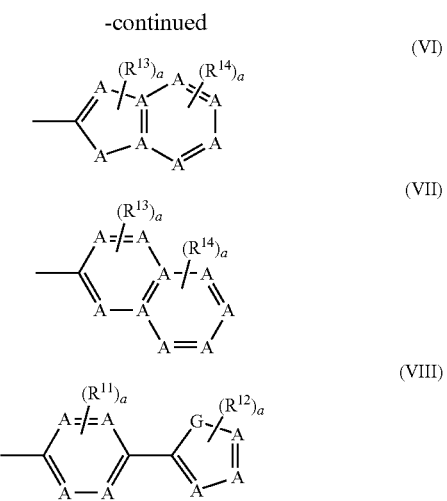

wherein
A is independently selected from the group consisting of CR$^6$ and N;
G is selected from the group consisting of S, O, CR$^8$, and NR$^9$;
R$^6$, R$^8$ and R$^9$ are independently selected from the group consisting of hydrogen, hydrocarbyl, and substituted hydrocarbyl;
R$^{10}$, R$^{11}$, R$^{12}$, R$^{13}$ and R$^{14}$ are independently selected from the group consisting of hydrogen, —OR$^{15}$, —NR$^{15}$R$^{16}$, —NR$^{15}$COR$^{16}$, —NR$^{15}$CONR$^{16}$, —NR$^{15}$SO$_2$R$^{16}$, —COR$^{15}$, —SO$_2$R$^{15}$, nitro, cyano, halogen, aryl, heterocycle, —COOR$^{15}$, —CONR$^{16}$R$^{17}$, —SO$_2$NR$^{18}$R$^{19}$, alkenyl, alkynyl, hydrocarbyl, and substituted hydrocarbyl;
R$^{15}$, R$^{16}$, R$^{17}$, R$^{18}$, R$^{19}$ are independently selected from the group consisting of hydrogen, hydrocarbyl, substituted hydrocarbyl, aryl, and heterocycle, and R$^{16}$ and R$^{17}$ together can optionally form a ring, and R$^{18}$ and R$^{19}$ together can optionally form a ring; and
a is either the integer 1 or the integer 2.

Yet another aspect of the present invention encompasses a method of treating a urinary tract infection. The method comprises administering a compound of the invention to a subject in need thereof.

Still another aspect of the invention encompasses a method of reducing the resistance of a bacterium to a bactericidal compound. The method comprises administering a compound of the invention to a subject in need thereof.

Other aspects and iterations of the invention are described below.

REFERENCE TO COLOR FIGURES

The application file contains at least one photograph executed in color. Copies of this patent application publication with color photographs will be provided by the Office upon request and payment of the necessary fee.

BRIEF DESCRIPTION OF THE FIGURES

FIG. 7 depicts the alignment of FimH sequence from a panel of clinical isolates previously examined. 18 clinical isolates examined for IBC formation were used to assess the different FimH sequences. The bold columns represent the residues identified as under positive selection. The residues highlighted in aqua represent residues that differ from UTI89.

can cross freely through bacterial outer membranes and bind to periplasmic chaperones (7). Pilicides block the interaction of chaperone-subunit complexes with the outer membrane usher (8) and prevent pilus assembly (9 & 10).

Figure 13A:
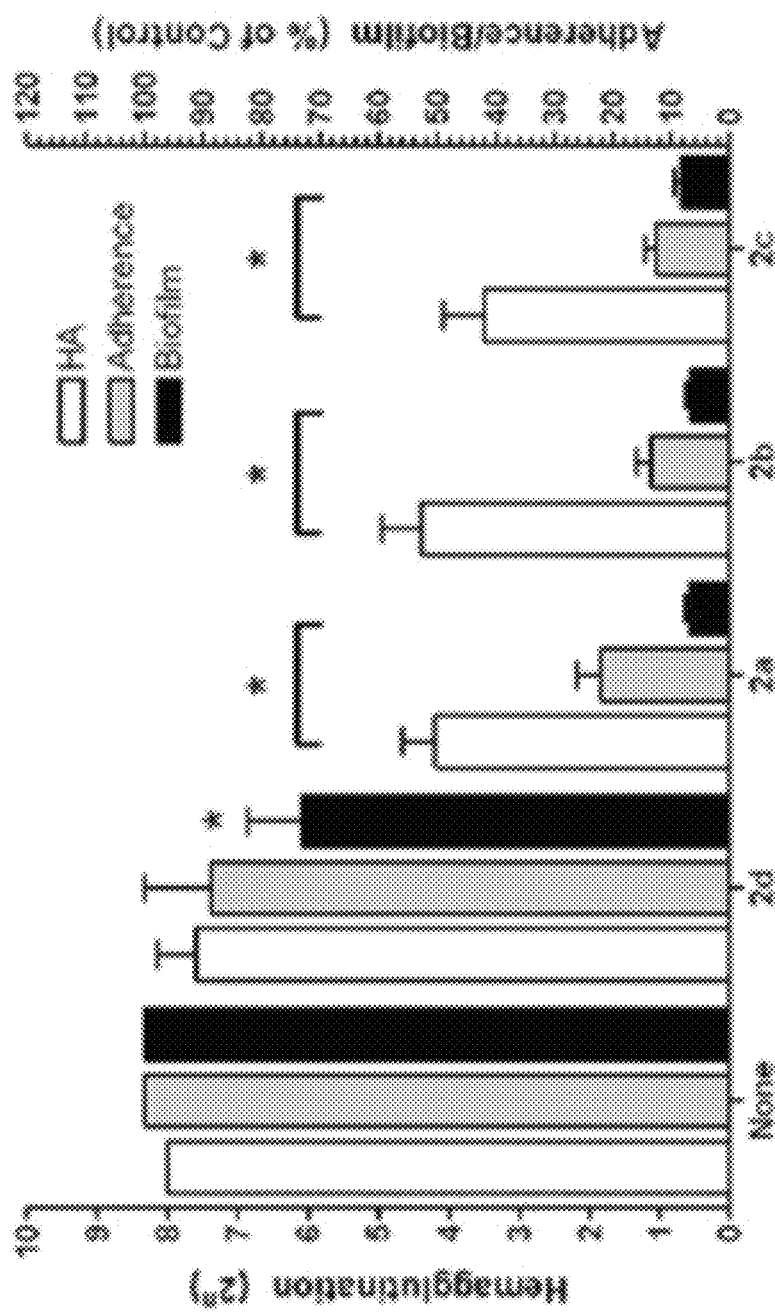
Figure 13B:
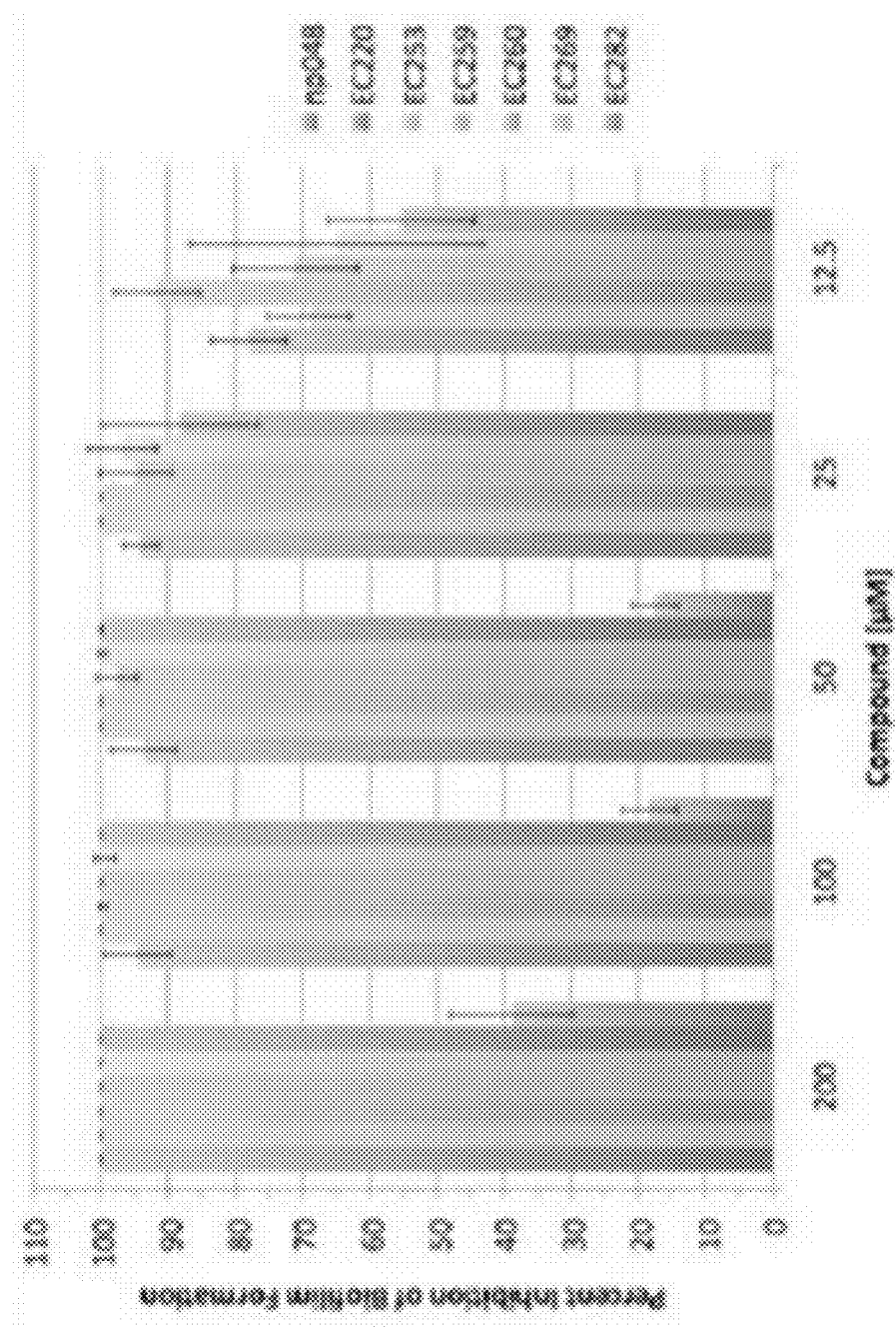
Figure 13C:
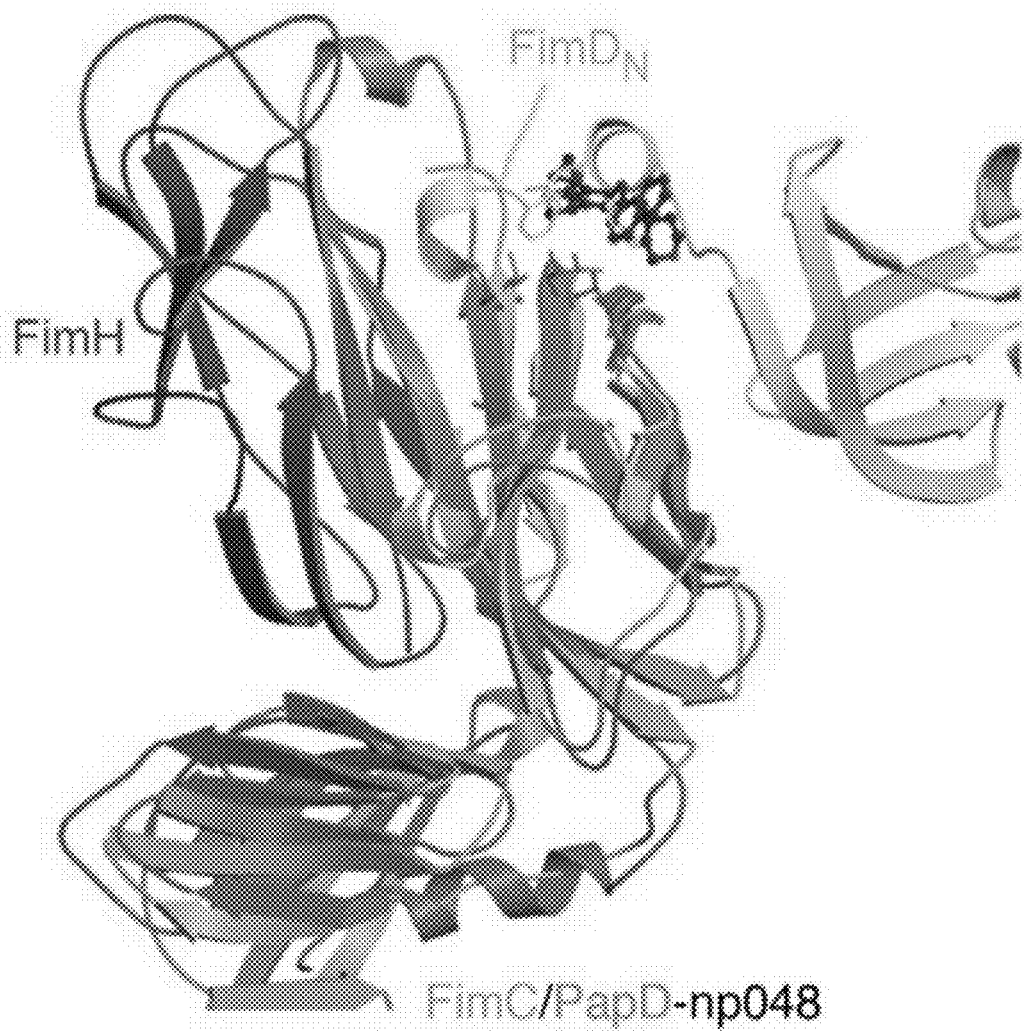

FIG. 13 Effect of pilicides on pilus function and pilicide interaction with the PapD chaperone. (A) E. coli NU14 was grown in the presence of pilicides 2d, 2a, 2b and 2c (np048) (3.5 mM each). HA titers, adherence to 5637 bladder cells, and the ability to form biofilms was determined. (B) New pilicides EC220-EC282 exhibit significant improvement in biofilm inhibitory activity compared to the original pilicide, np048. (C) PapD-np048 complex in overlay with the FimD1-125 N-terminal usher domain in complex with the FimC-FimH158-279 chaperone/adhesin complex. PapD and np048 are shown in light blue ribbon and ball-and-stick representation, respectively. FimC, FimH158-279 and FimD1-125 N-terminal domain are shown in magenta, green and yellow, respecitvely.

Figure 14:
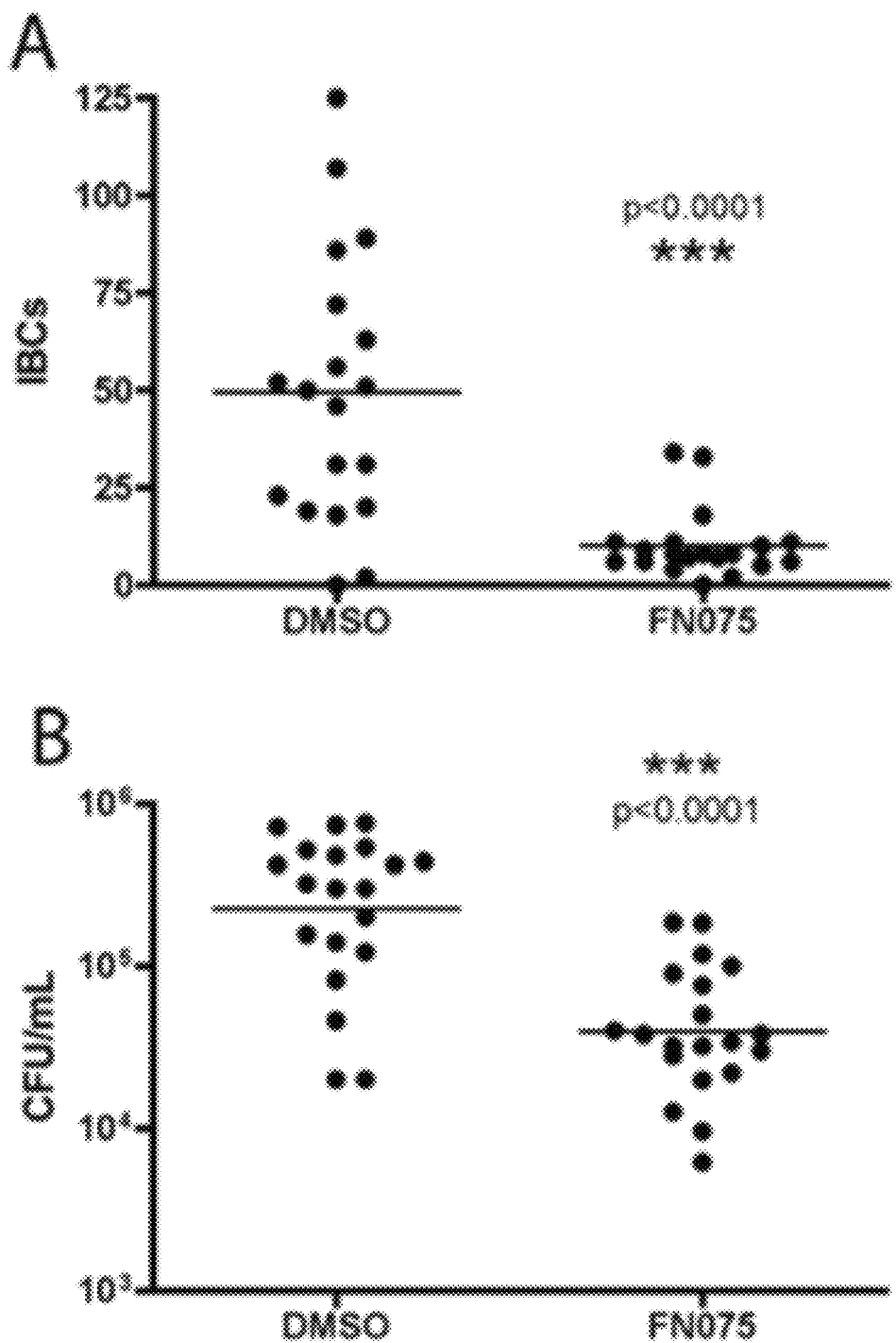

FIG. 14 depicts a graph showing that UTI89 bacteria, when inoculated in the presence of FN075, makes significantly less IBCs in the bladder (A) and has a significantly reduced bacterial load within the bladder at 6 hours post-infection (B). p<0.0001.

Figure 15:
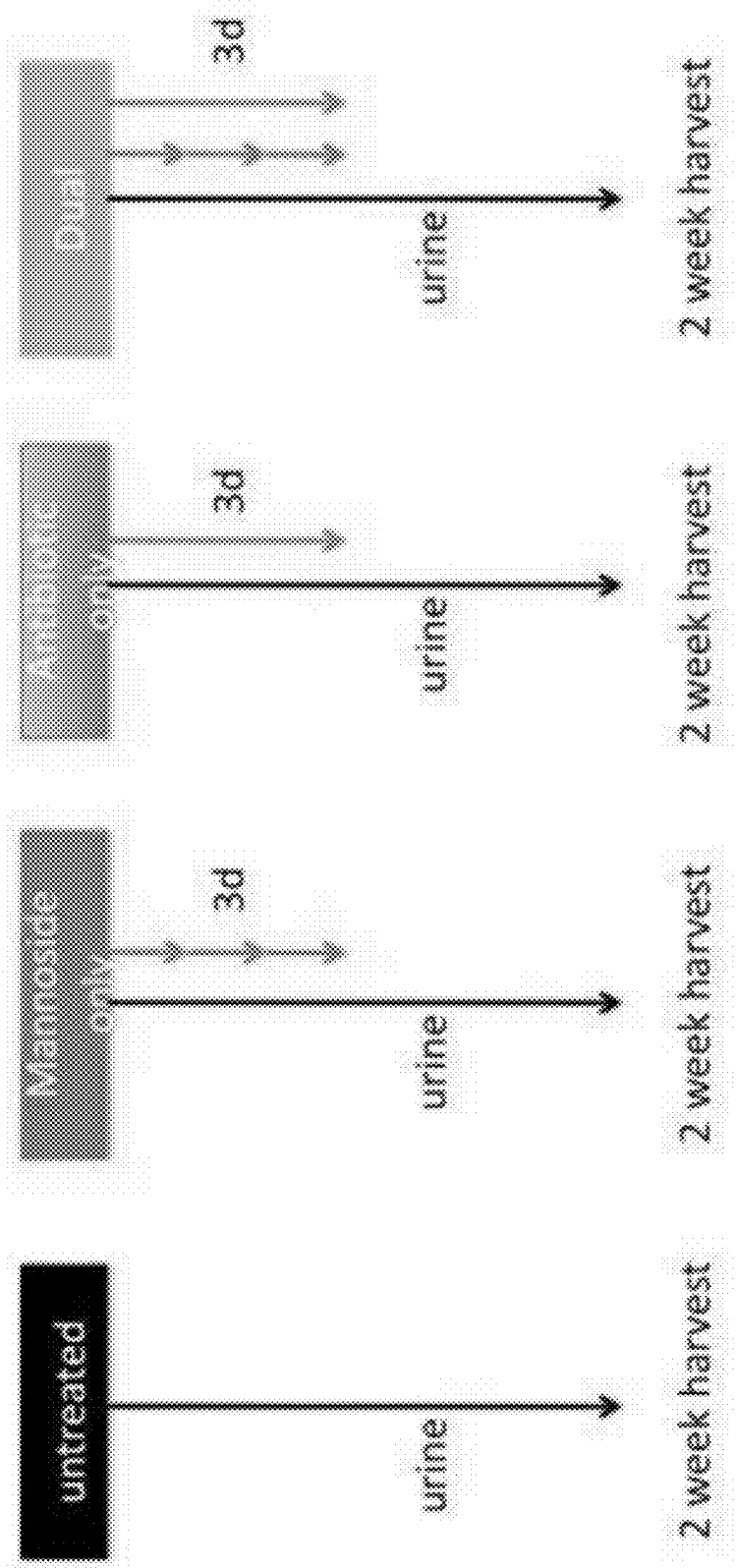

FIG. 15 depicts a representation of an efficacy study in mice using mannoside alone, antibiotic treatment alone, or dual mannoside/antibiotic treatment.

Figure 16:
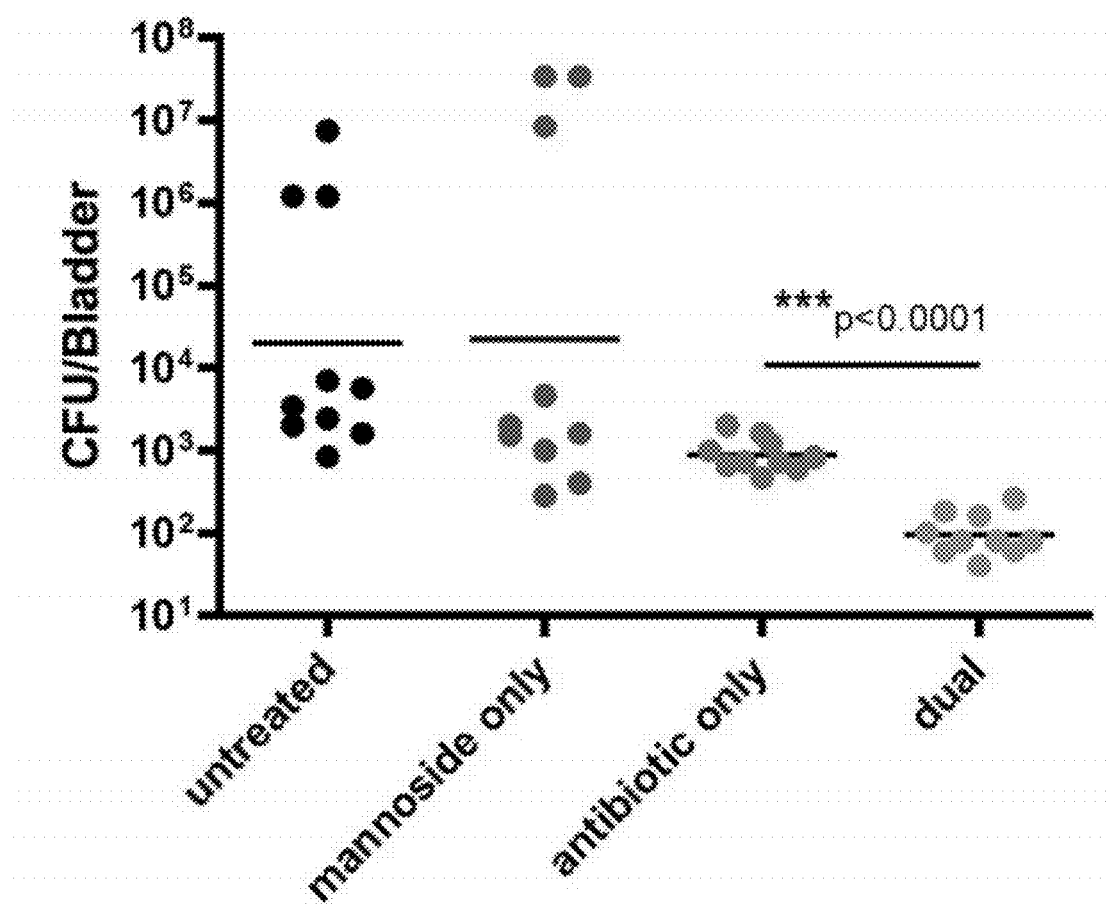

FIG. 16 depicts a graph showing that dual treatment of mice inoculated with bacteria showed significantly lower levels of bacteria in the bladder than antibiotics alone.

Figure 17:
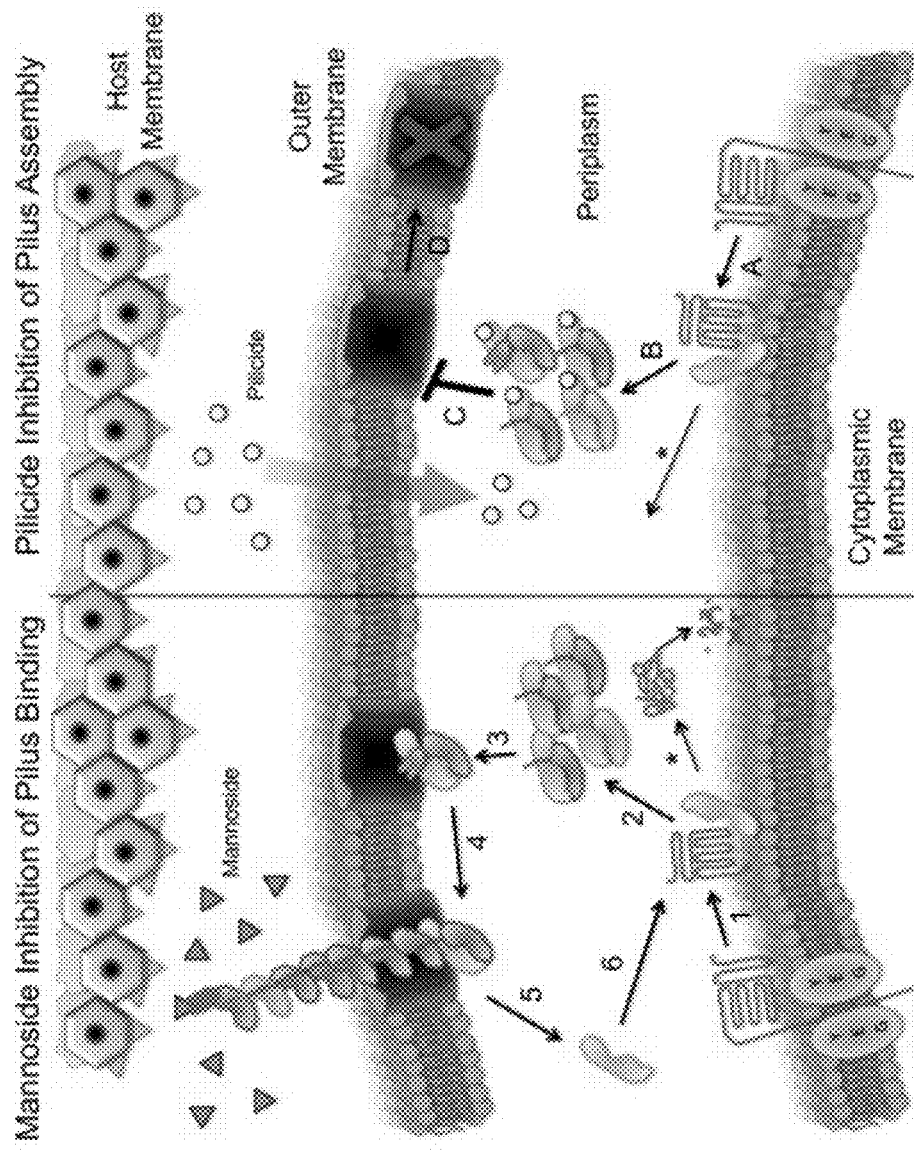

FIG. 17 depicts a diagram illustrating two strategies to inhibit bacterial binding to host cells. The schematic diagram shows the model of chaperone-assisted pilus assembly and the mode of mannoside (left panel) and pilicide (right panel) action. During normal pilus biogenesis, newly synthesized pilus subunits cross into the periplasm via the Sec secretion pathway. These pilus subunits bind to their periplasmic chaperone proteins (orange molecules) and fold into correct confirmations (1). In the absence of the chaperones, pilus subunits are degraded (*). Chaperone-subunit complexes (2) are transported to the outer membrane usher proteins (blue cylinders) for assembly (3). Pilus assembly follows an ordered process with the chaperone-adhesin complexes as the initiators (4). As subunits are assembled into the growing pilus, accompanying chaperones disassociate from the membrane complexes (5), which could potentially be recycled to bind newly synthesized subunits. Mannosides (teal triangles) interact with the pilus adhesin and prevent binding to mannosylated residues (light brown triangles) on the surface of epithelial cells. Pilicides (yellow circles) can cross freely through bacterial outer membranes and bind to periplasmic chaperones (B). Pilicides block the interaction of chaperone-subunit complexes with the outer membrane usher (C) and prevent pilus assembly (D).

FIG. 18 depicts diagrams illustrating chaperone-subunit donor strand exchange (DSE) and donor strand complementation (DSC). (A) Each subunit consists of six of the seven strands of a standard immunoglobulin (Ig)-fold and an N-terminal extension (Nte). (B) In order to form a stable structure prior to incorporation into the growing fiber, the chaperone donates the missing seventh strand of the subunit in a process called donor strand complementation (DSC). (C) During pilus assembly, the free Nte of one subunit displaces the chaperone bound to another subunit and serves as the seventh strand of the Ig-like fold in a process called donor strand exchange (DSE).

Figure 19A:
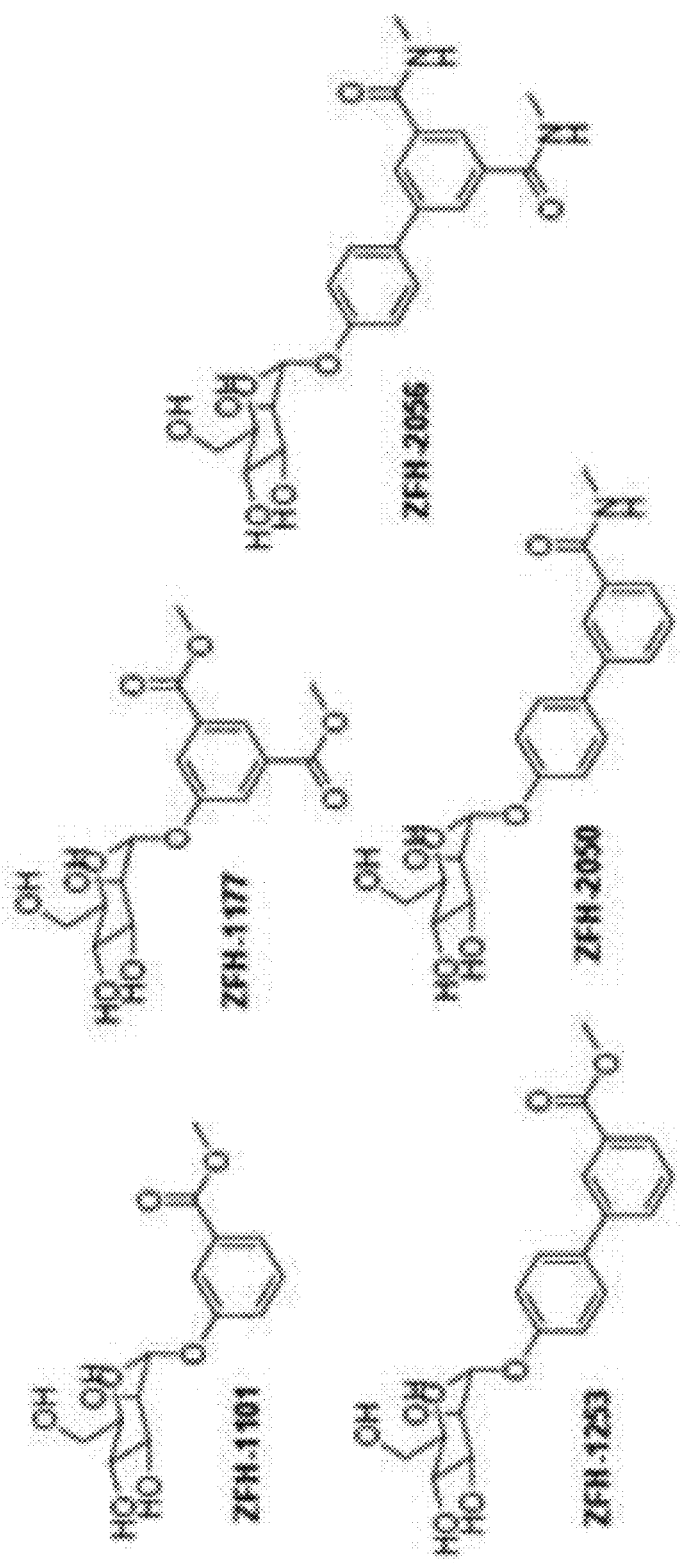
Figure 19D:
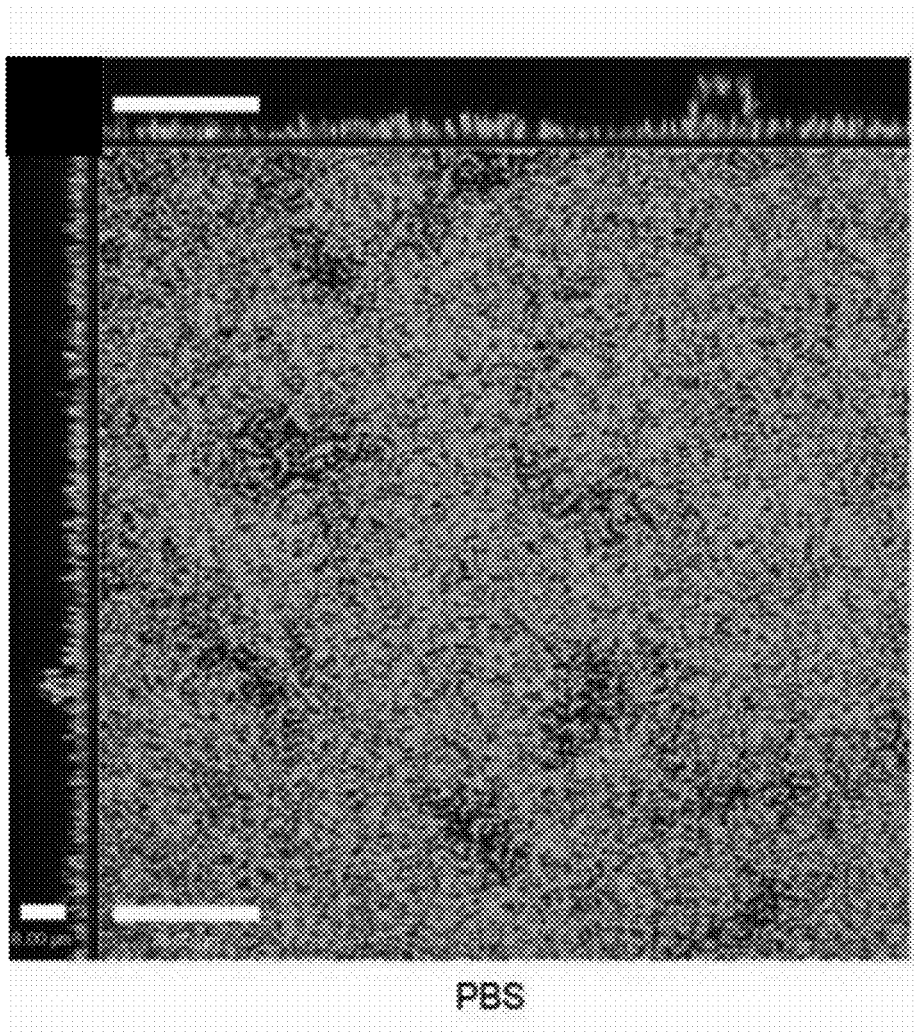
Figure 19E:
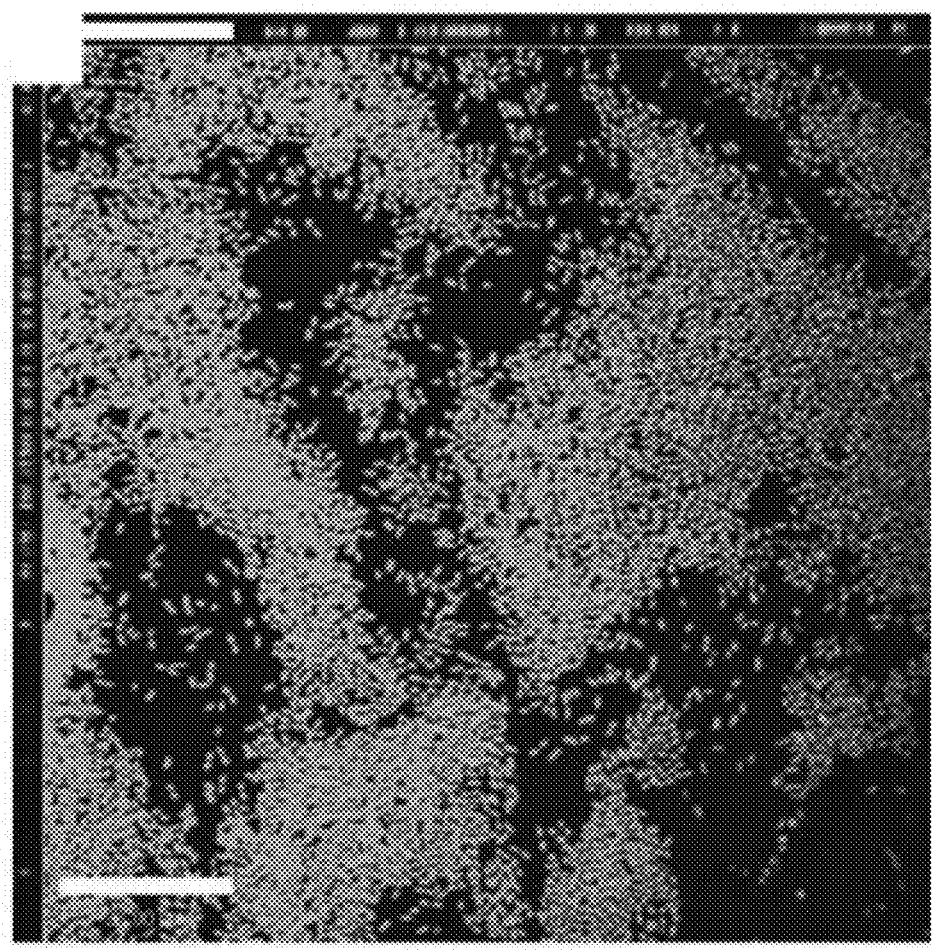

FIG. 19 depicts the inhibition and disruption of UTI89 biofilm by mannoside and phase switching of UTI89 in the presence of mannoside. (a) Structure of mannosides. (b) The median inhibitory concentration (1050) of mannoside on UTI89 biofilm formation. (c) The 1050 of mannoside on UTI89 biofilm disruption. After treatment with mannoside, the amount of UTI89 biofilm was measured. Bars show the mean value of the experiments (n=3). (d and e) ZFH-2056 (Compound 50) dispersed biofilm as measured by confocal microscopy of UTI89 biofilms grown for 24 h, then incubated for an additional 16 h in the absence (d) or presence (e) of 0.3 µM ZFH-2056.

Figure 20:
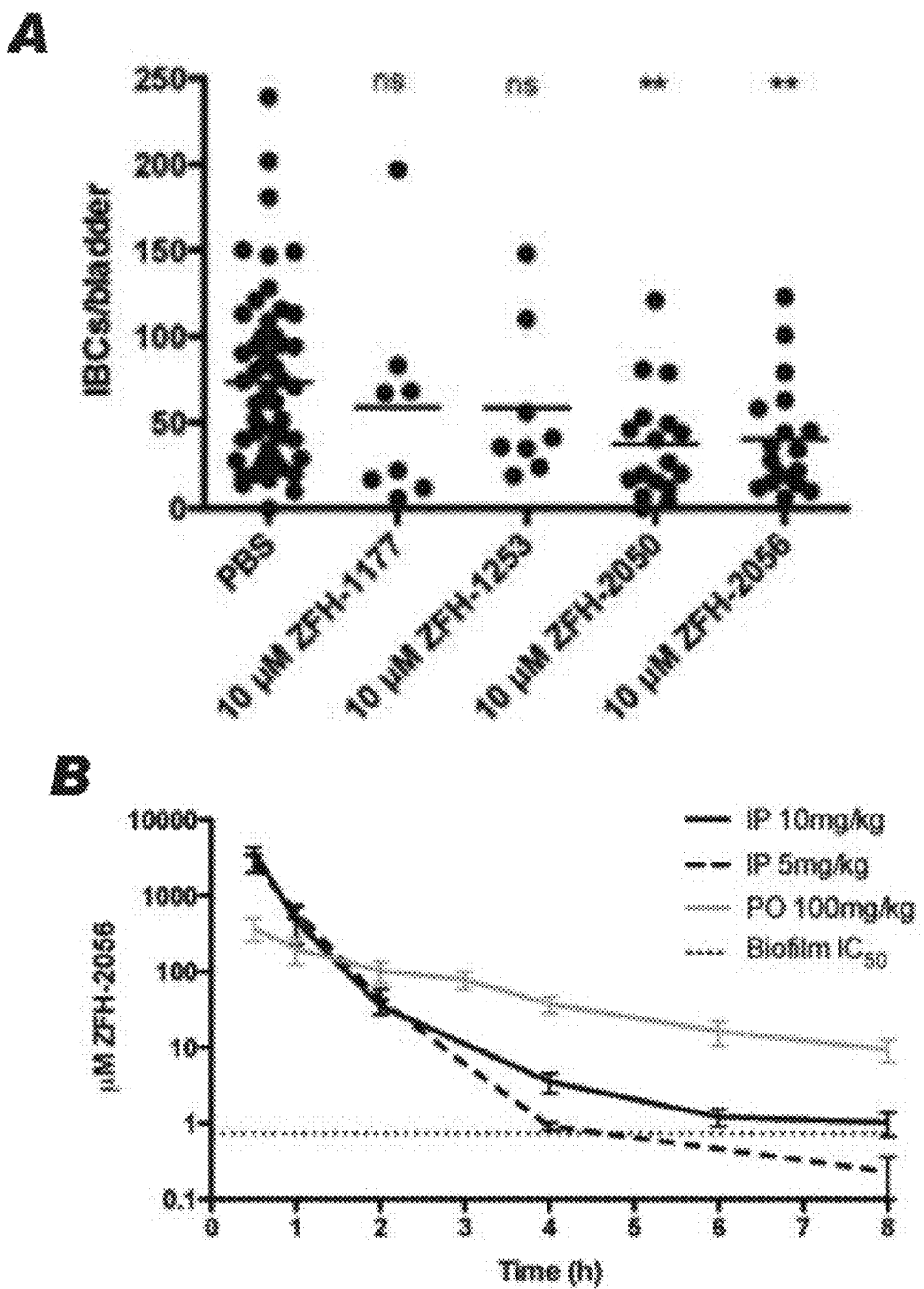
Figure 20:
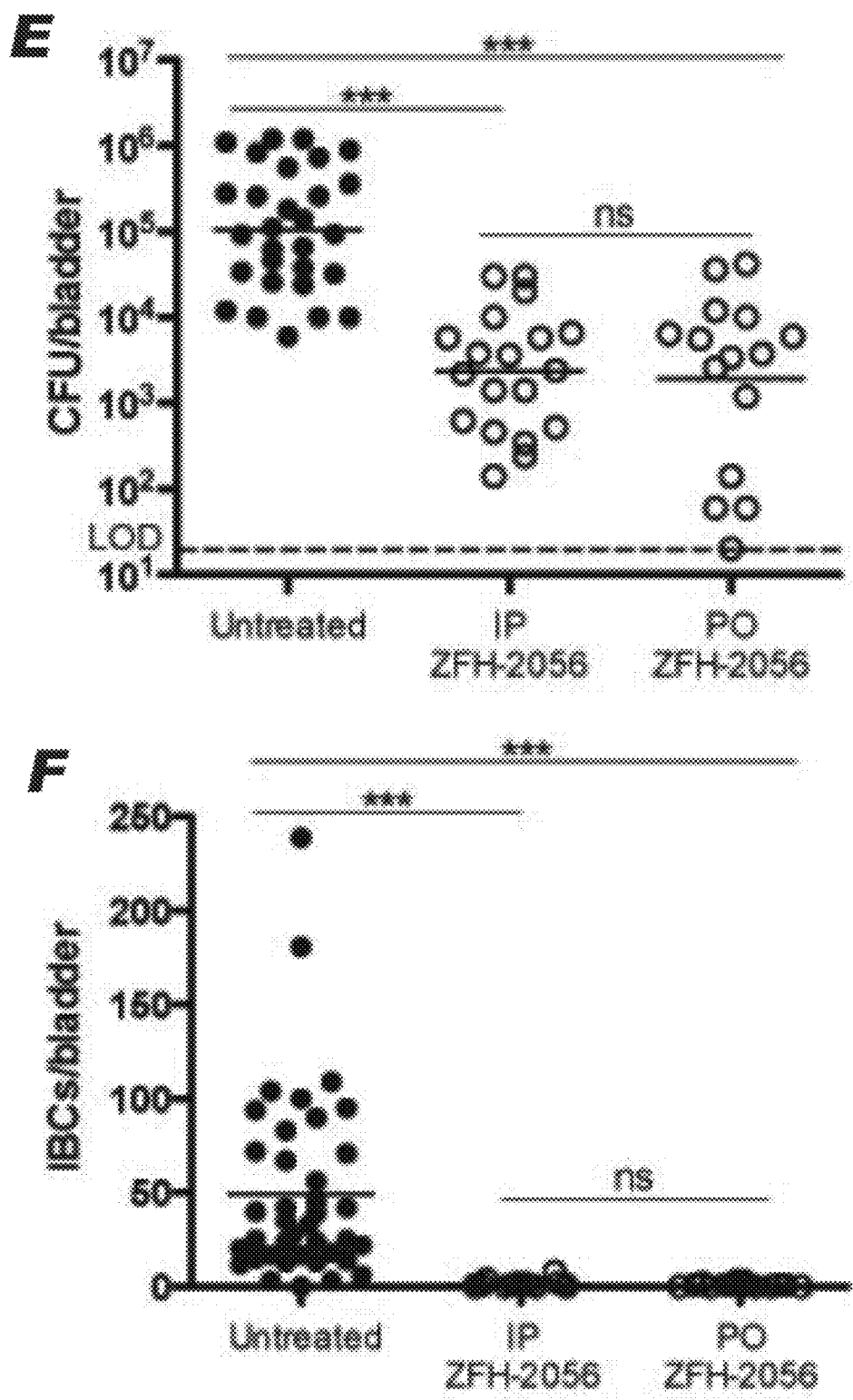

FIG. 20 depicts the mannoside effect on UTI89 colonization. (a) Pretreatment of UTI89 with mannosides ZFH-2050 (Compound 49) and ZFH-2056 (Compound 50) resulted in reduced IBC formation at 6 hpi. (b) Urine PK analysis of ZFH-2056 (Compound 50) (n>3 mice) showing amounts in urine over time for each dosing regimen indicated. Horizontal dashed line is at IC50 (0.74 µM) as determined by the biofilm inhibition assay. (c and d) Confocal microscopy of bladders from untreated (c) and ZFH-2056-treated (d) mice. Bacteria were stained with SYTO9 (green) and the bladder luminal surface was stained with WGA (red). The image in c shows a normal, robust IBC whereas the arrows in d indicate luminal bacteria. (e) Total bacterial CFUs at 6 hpi from untreated mice or mice treated with ZFH-2056 either by IP (5 mg/kg) or oral (100 mg/kg) dosing 30 min prior to inoculation of UTI89. (f) IBC quantification at 6 hpi from untreated mice or mice treated with ZFH-2056 either by IP (5 mg/kg) or oral (100 mg/kg) dosing 30 min prior to inoculation of UTI89. (g) 6 hpi ex vivo gentamicin protection assay revealed both luminal and intracellular bacteria are significantly reduced upon IP (5 mg/kg) pretreatment of mice with ZFH-2056. Bars indicate geometric mean. Statistical significance according to Mann-Whitney is at P<0.01, *P<0.0001. ns, not significant; LOD, limit of detection.

FIG. 21 depicts mannoside synergy with TMP-SMZ at reducing UTI89 colonization. (a) Total bacterial CFUs were quantitated 6 hpi. UTI89 colonization was reduced in mice treated with ZFH-2056 (Compound 50), TMP-SMZ and TMP-SMZ+ZFH-2056. There was further decreased colonization in TMP-SMZ+ZFH-2056-treated mice over ZFH-2056 or TMP-SMZ alone. PBC-1 colonization was reduced in mice treated with ZFH-2056 and TMP-SMZ+ZFH-2056, but not TMP-SMZ alone. Enhanced efficacy as measured by bacterial CFUs was observed upon treatment with TMP-SMZ+ZFH-2056 over ZFH-2056 or TMP-SMZ treatment alone. Bars indicate geometric mean. Statistical significance according to Mann-Whitney is at *P<0.05, P<0.01, *P<0.0001. ns, not significant; LOD, limit of detection. (b) Growth curve of PBC-1 with TMP-SMZ in the absence (solid line) or presence (dashed line) of 100 µM ZFH-2056. SMZ concentration is 5×TMP concentration listed.

Figure 22:
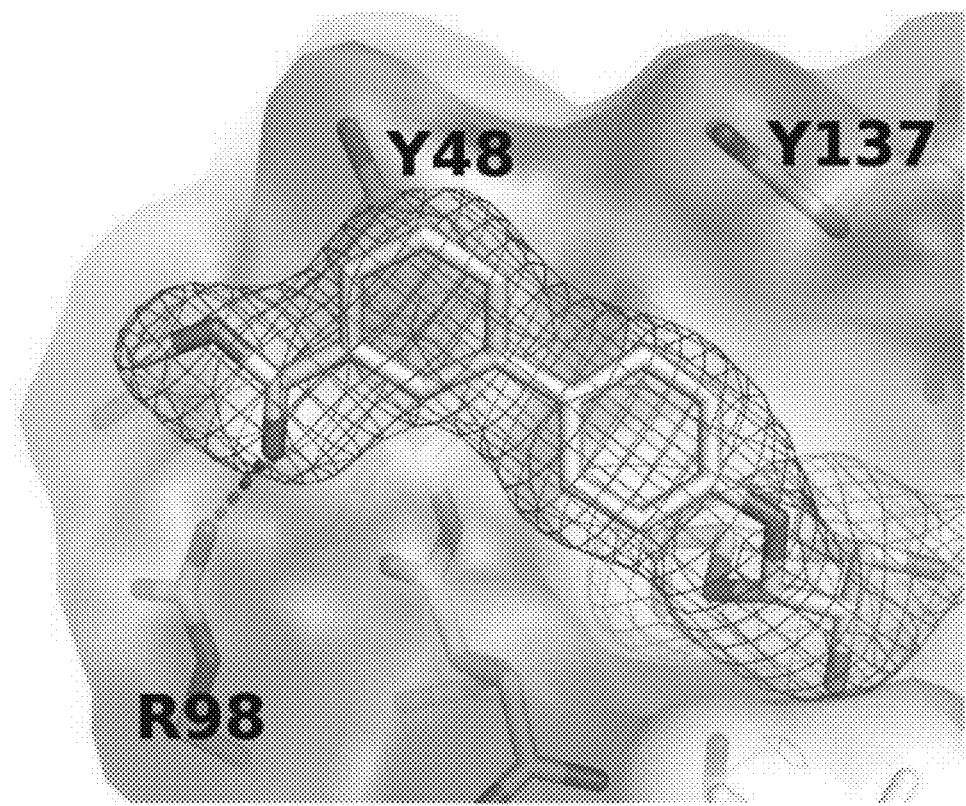

FIG. 22 depicts X-ray structure of biphenyl mannoside meta-methyl ester (Compound 29) with electron density (mesh) calculated with 2Fo-Fc coefficients, contoured at 1 sigma. Interaction with the Arg-98-Glu-50 salt bridge (dashes), pi-pi stacking with Tyr-48 and hydrophobic interaction with Tyr-137 are shown. Surface electrostatic potential of FimH, calculated with APBS, is displayed such that pure blue and red would be +4kT/e and −4kT/e respectively.

Figure 23:
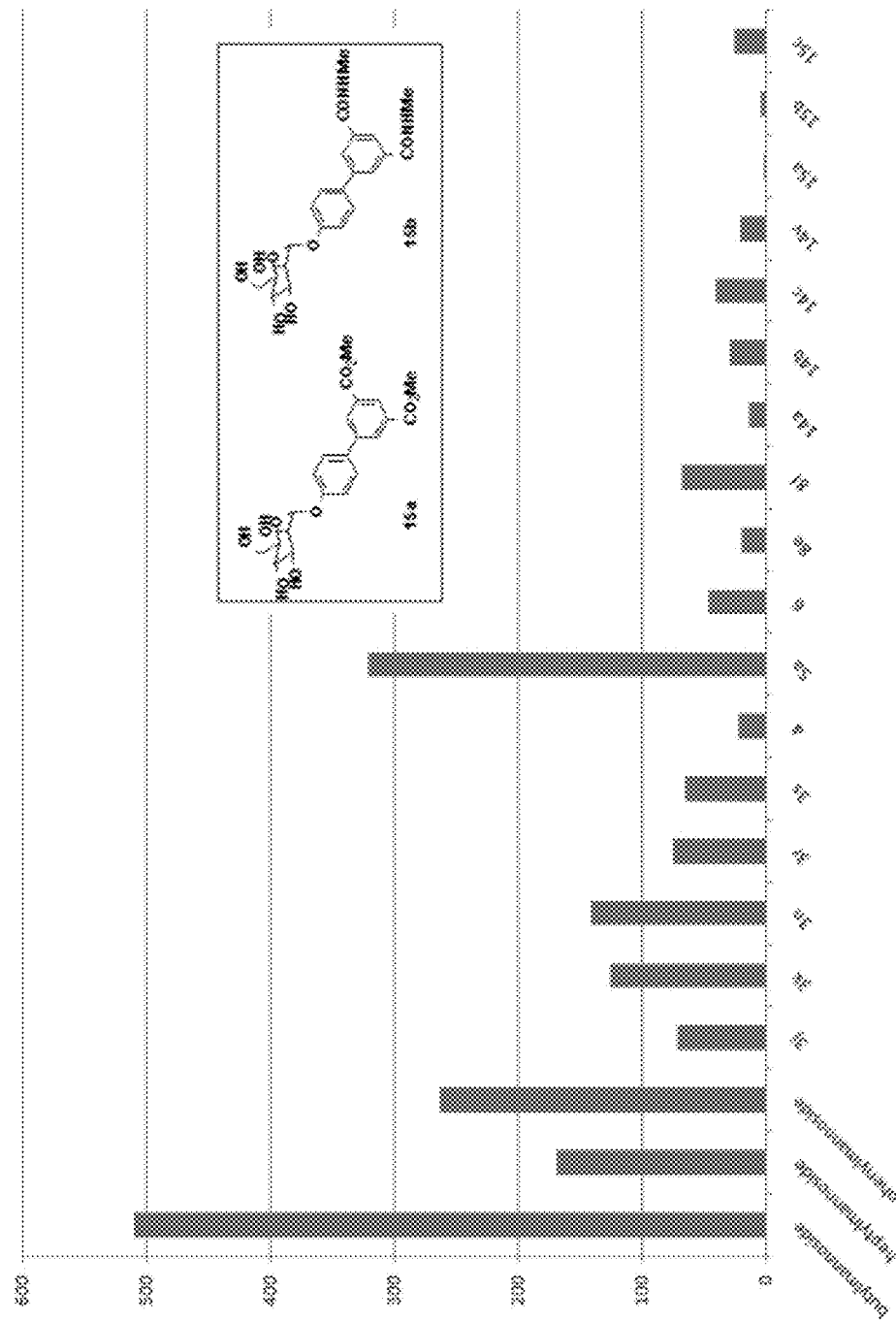

FIG. 23 depicts the correlation of HA Titer and Binding Data.

Figure 24:
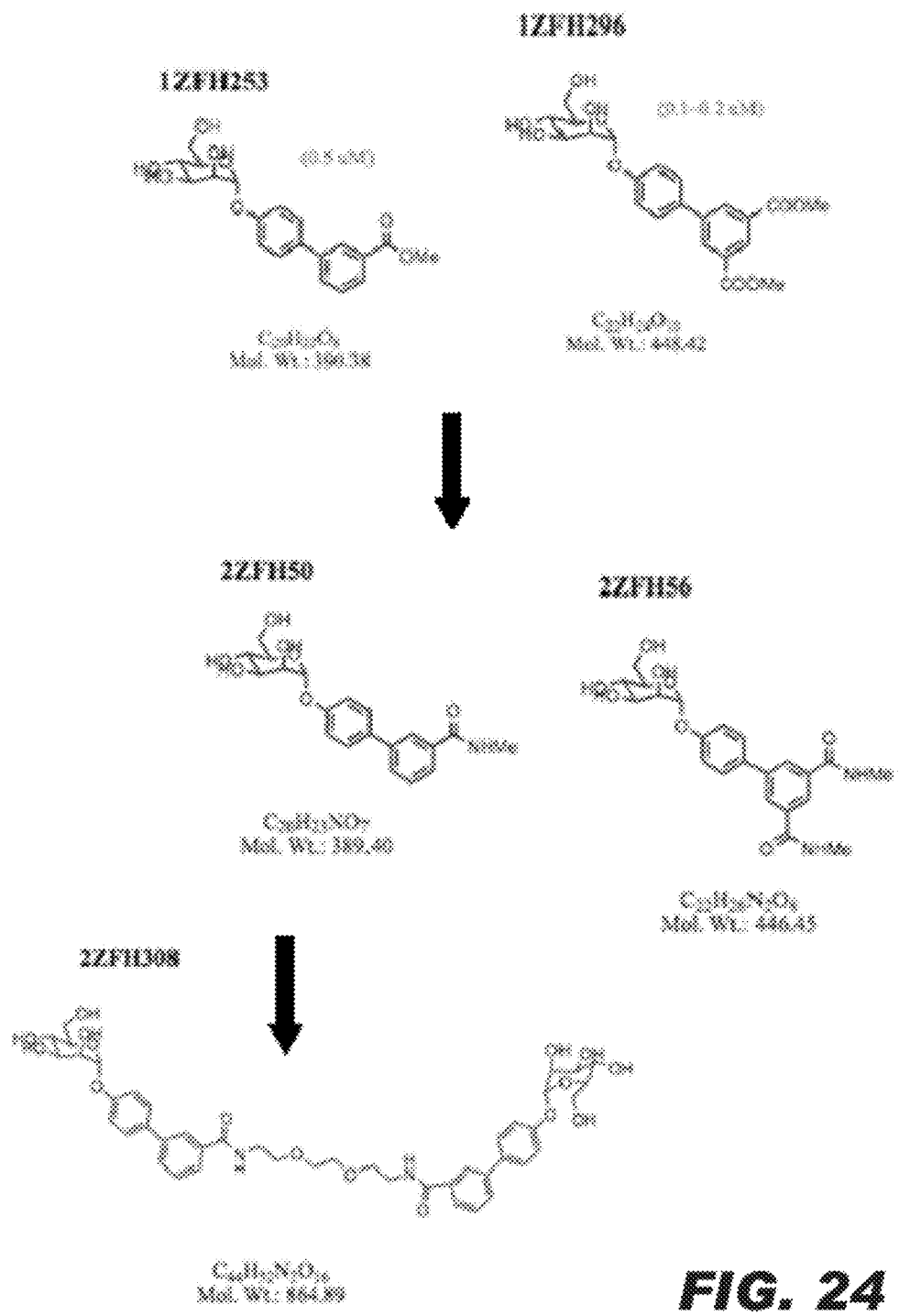

FIG. 24 depicts mannoside esters and their amidated counterparts with enhanced solubility.

Figure 25A:
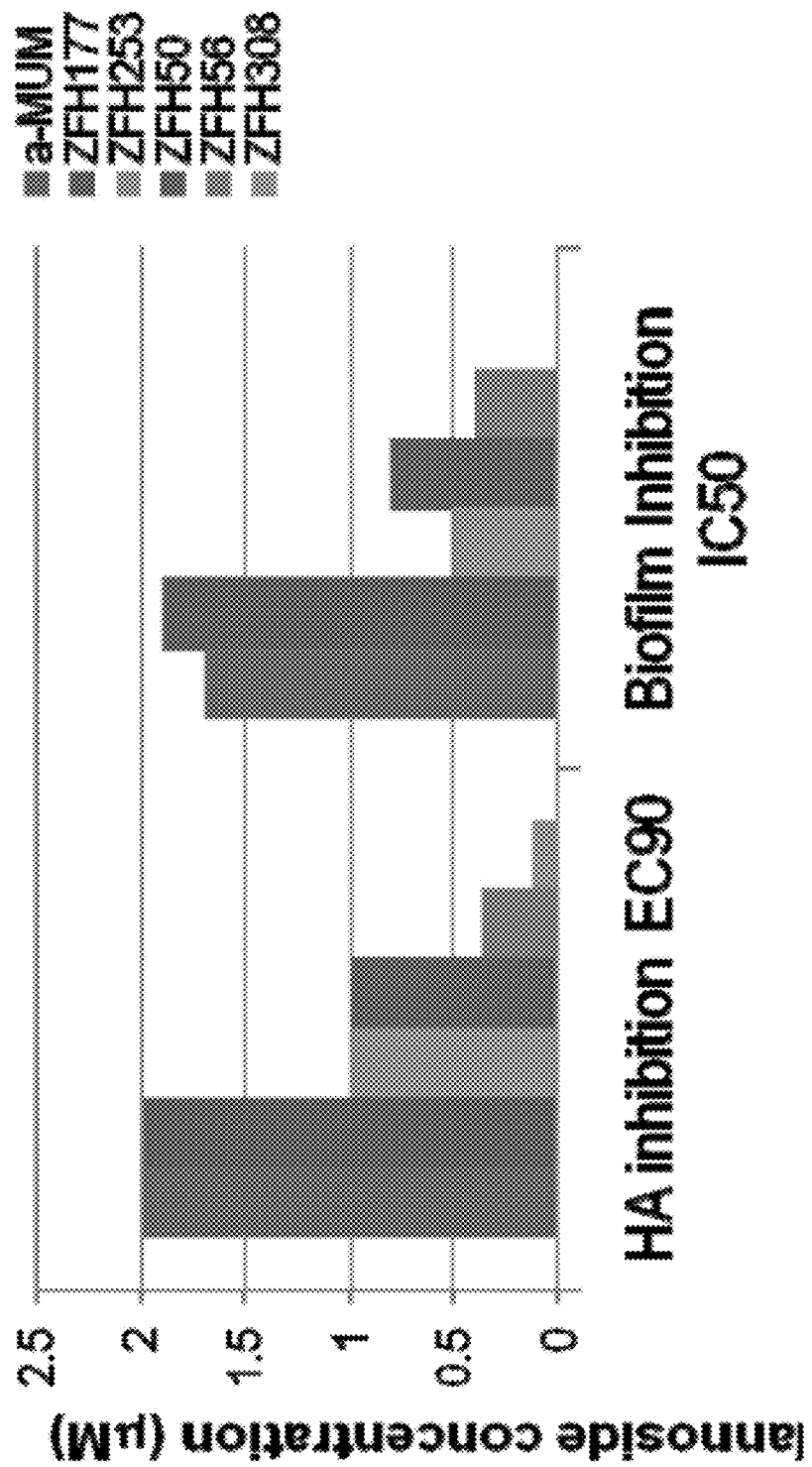
Figure 25B:
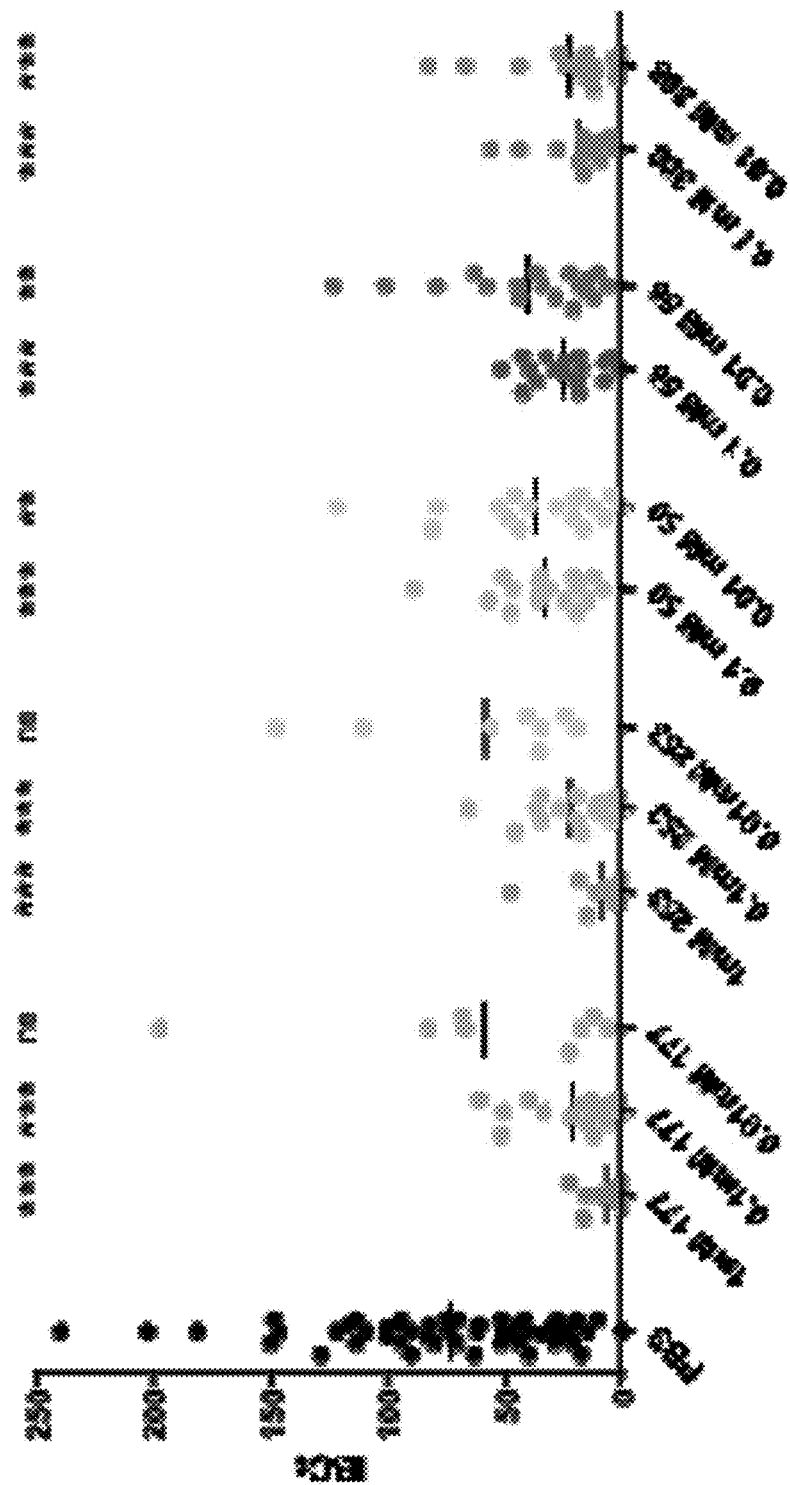

FIG. 25 depicts results of hemagglutination (A) and LacZ quantification of IBCs (B).

Figure 26:
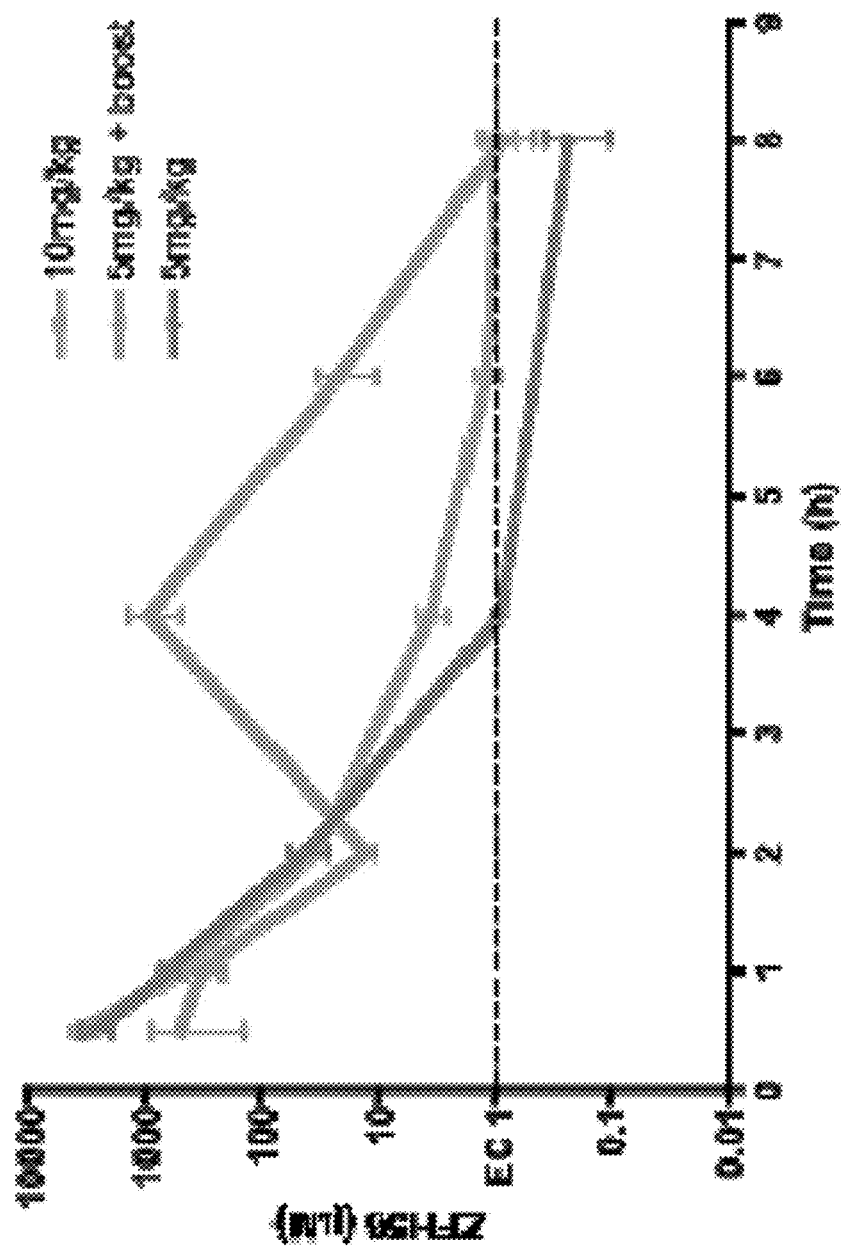

FIG. 26 depicts the pharmacokinetic results of ZFH56 (Compound 50) injected IP and PO into mice.

Figure 27:
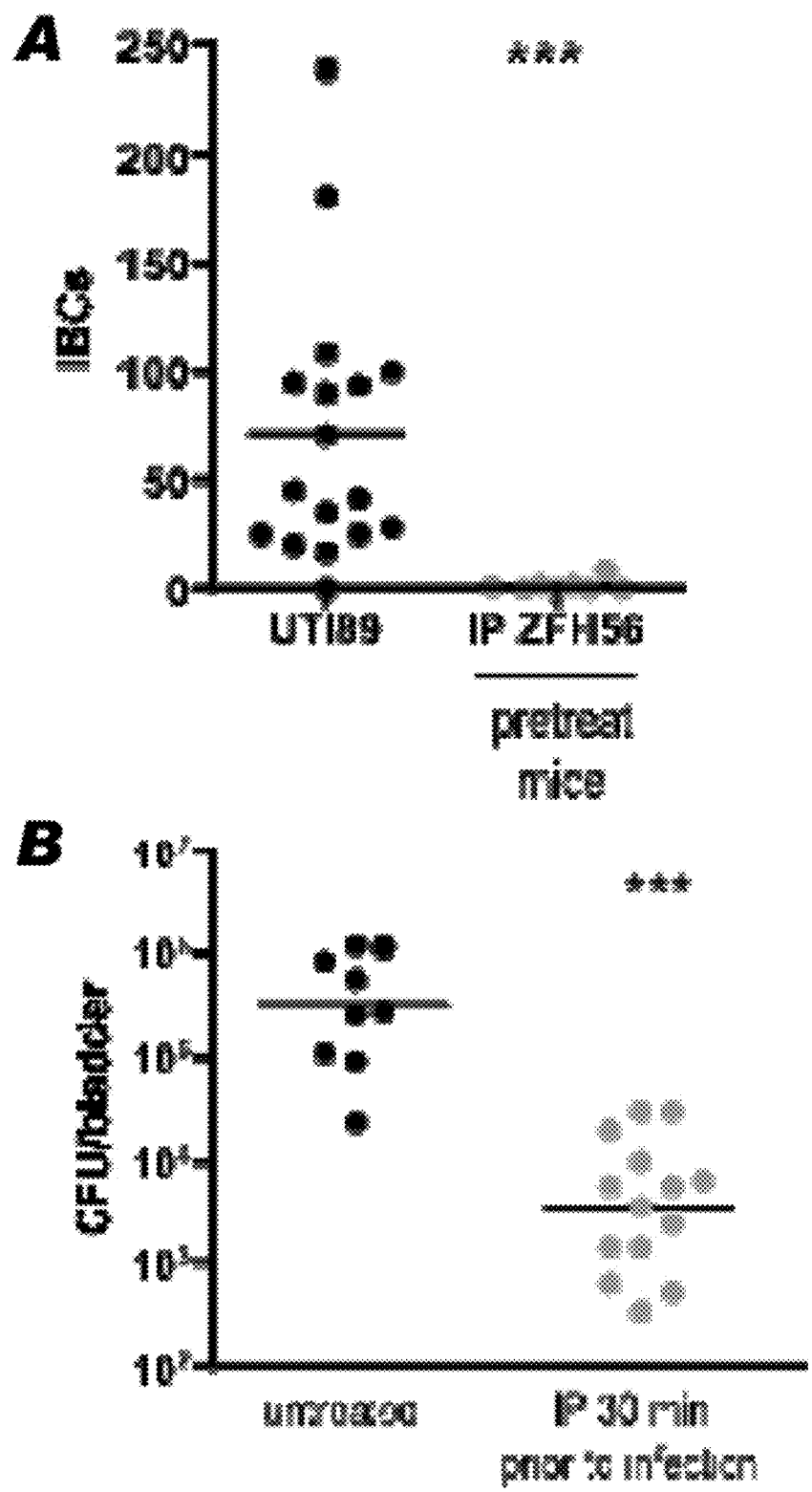
Figure 27C:
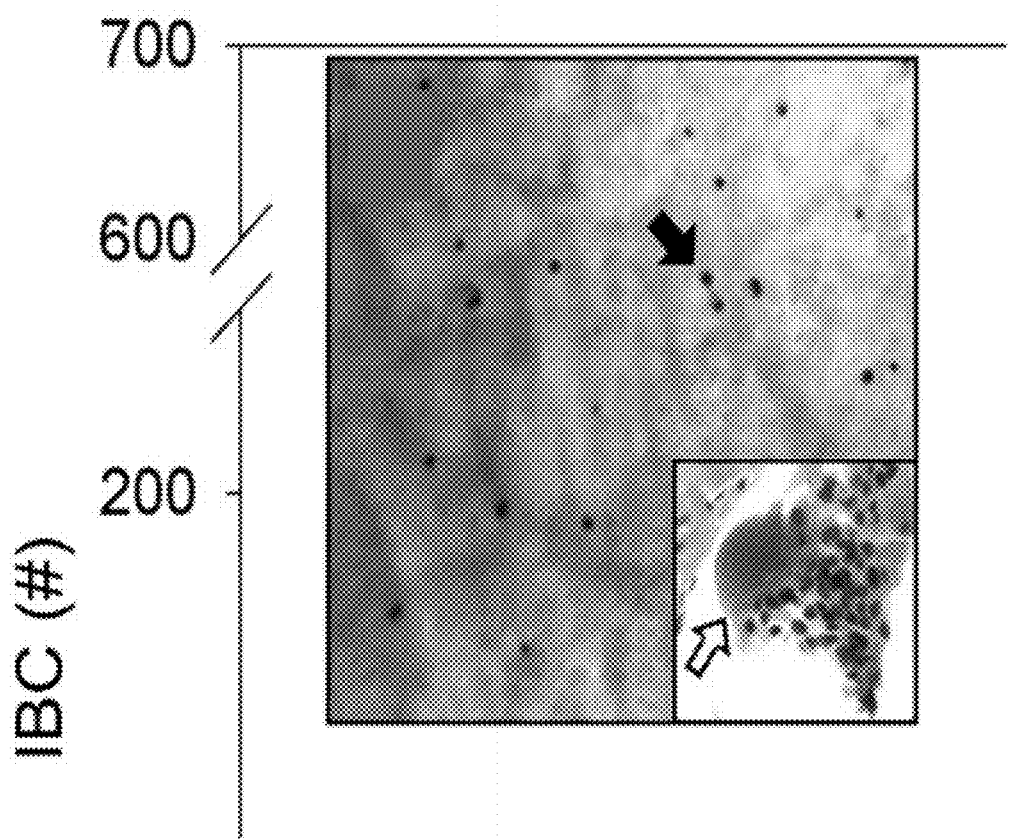

FIGS. 27 (A-C) depicts IBC numbers and lacZ staining in mice treated with ZFH56 (Compound 50).

Figure 28C:
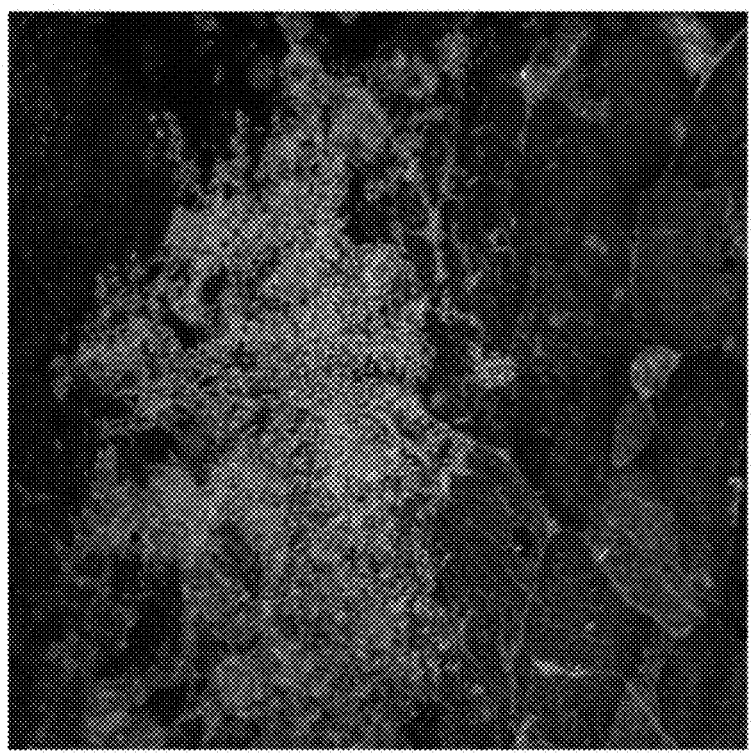

FIGS. 28 (A-C) depicts fluorescent microscopy imaging of infected bladders treated with ZFH56 (Compound 50).

Figure 29:
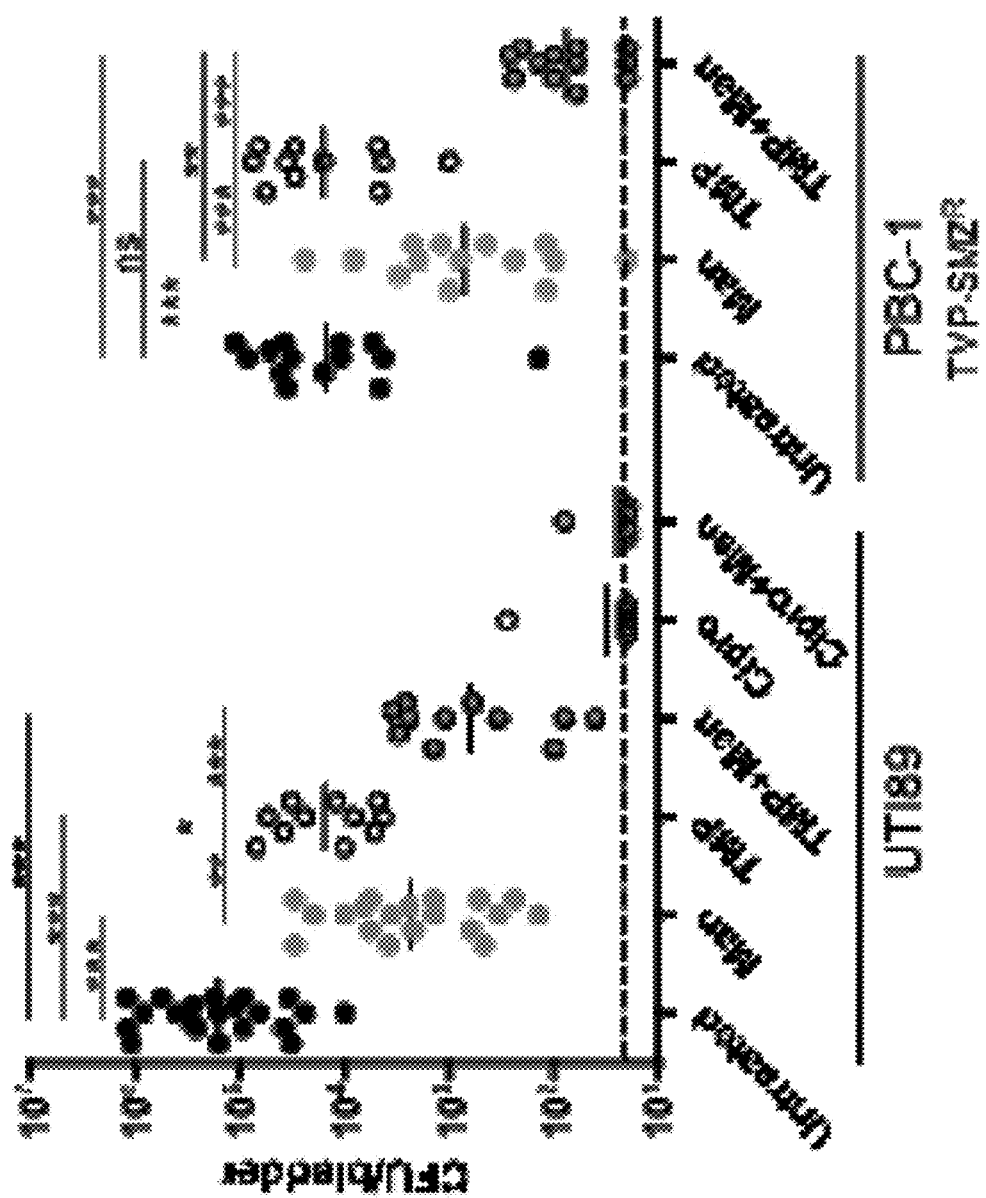

FIG. 29 depicts efficacy studies of mannosides against TMP-SMZ resistant strains.

Figure 30:
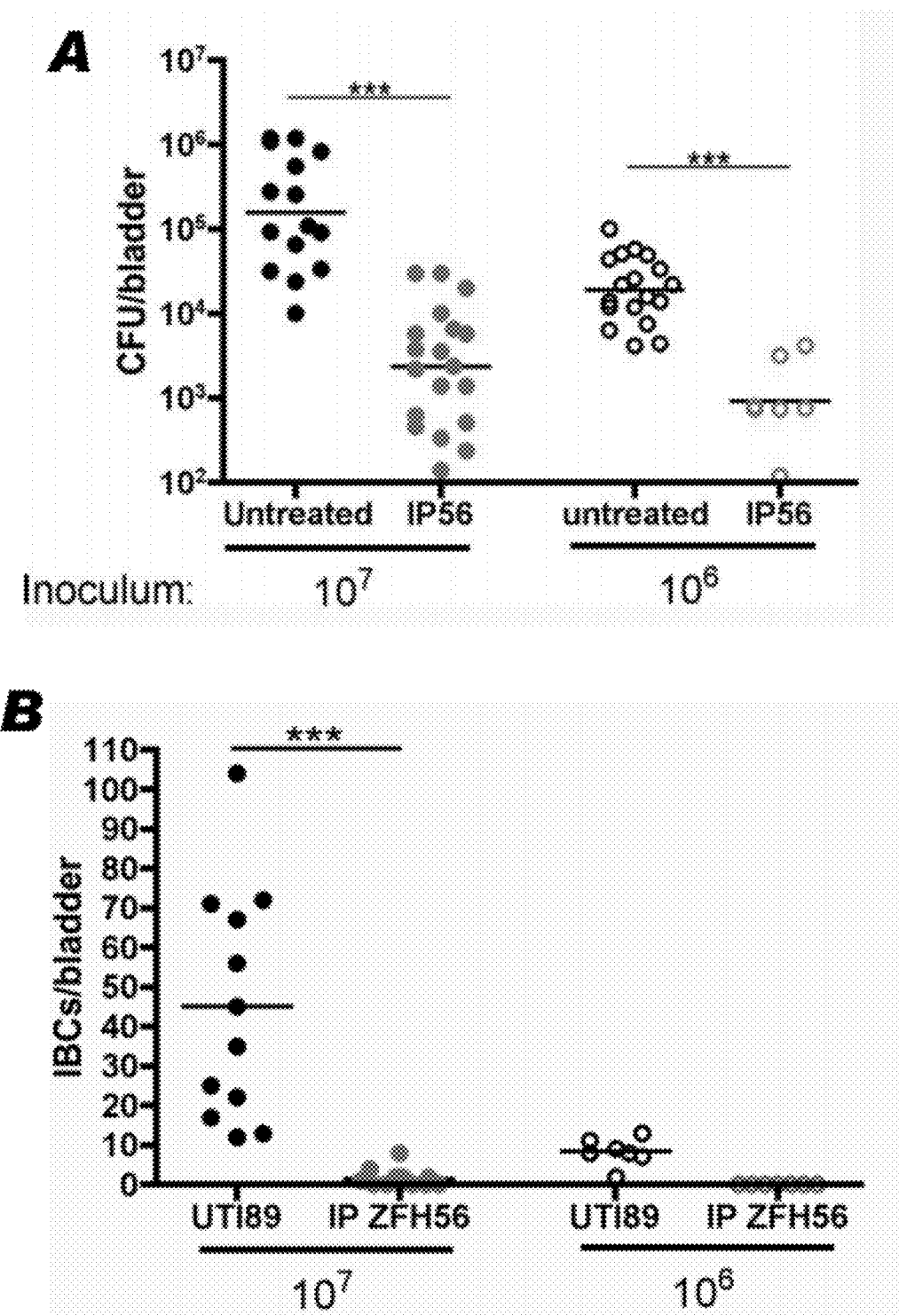
Figure 30C:
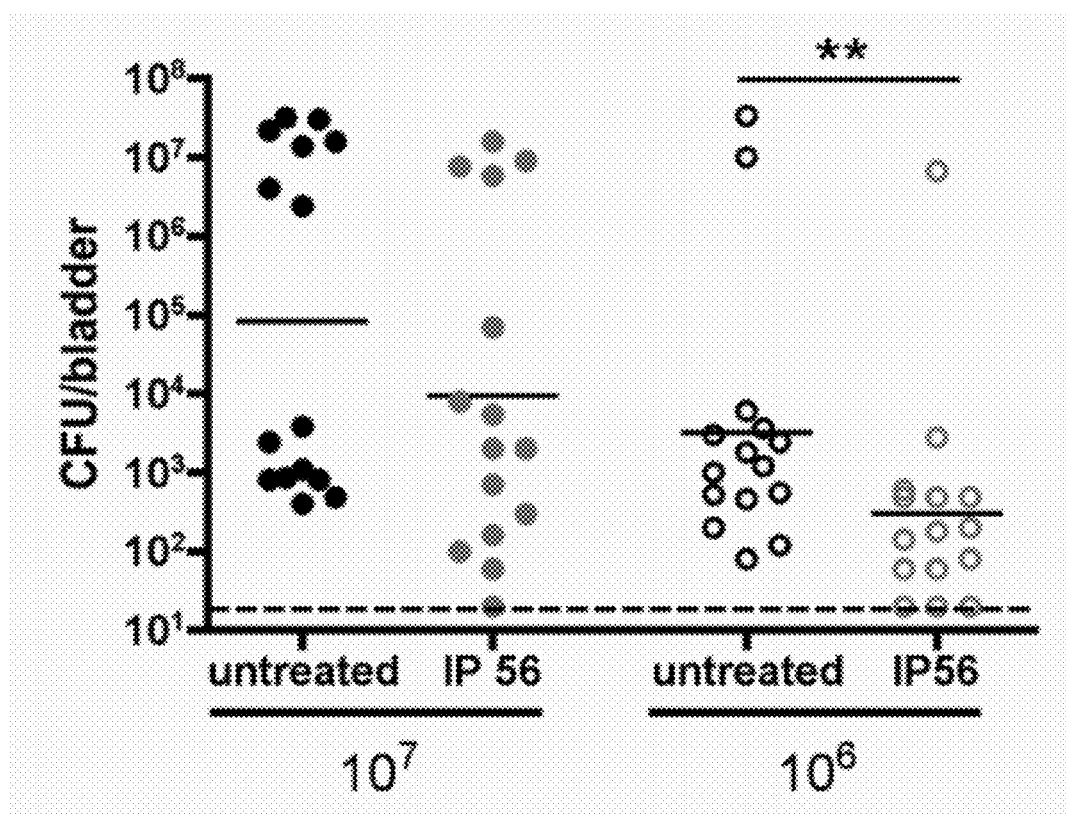

FIGS. 30 (A-C) depicts efficacy of ZFH56 (Compound 50) under various doses of inoculum.

Figure 31:
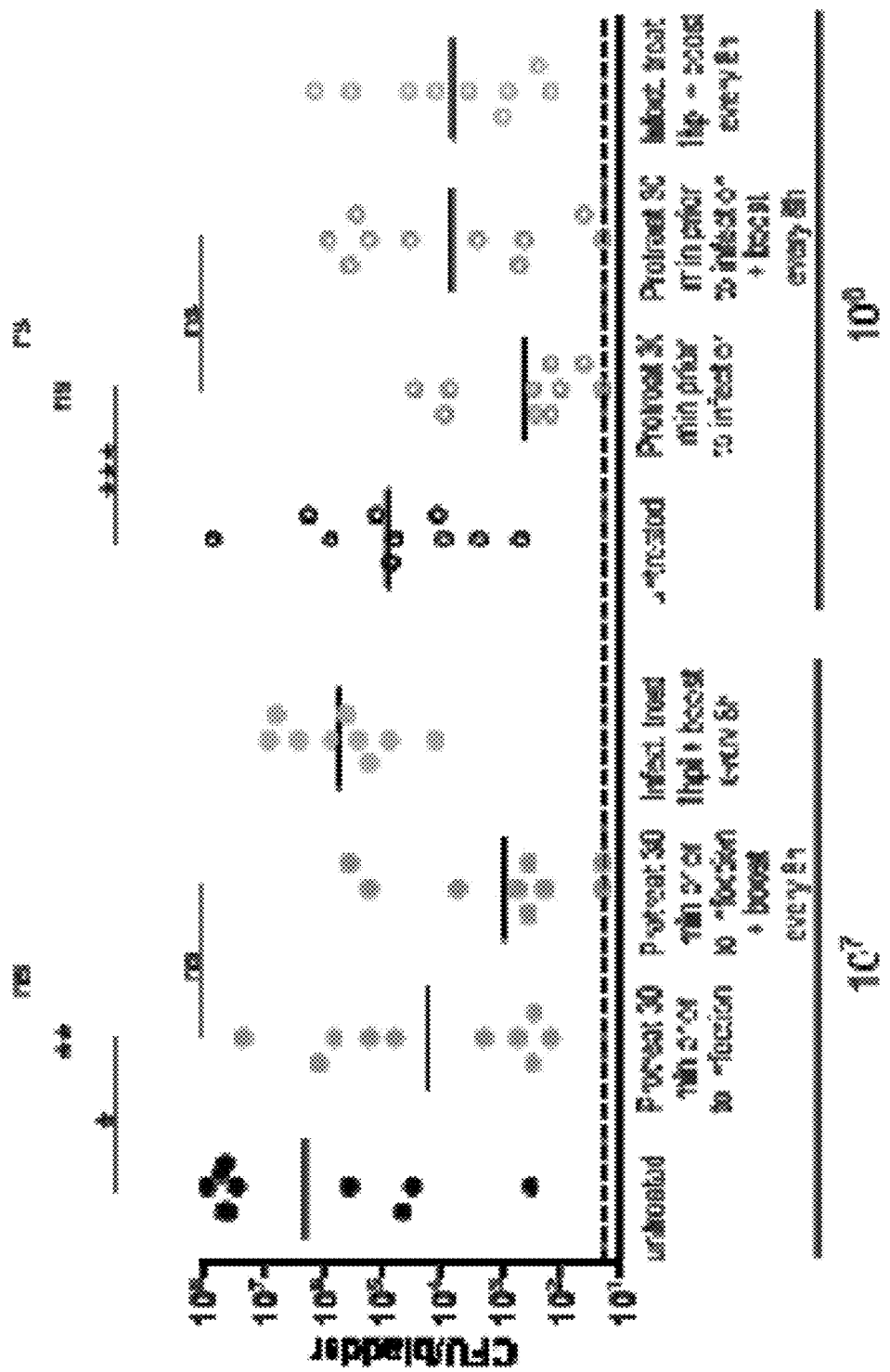

FIG. 31 depicts efficacy studies of ZFH56 (Compound 50) with compound dose boosting.

Figure 32A:
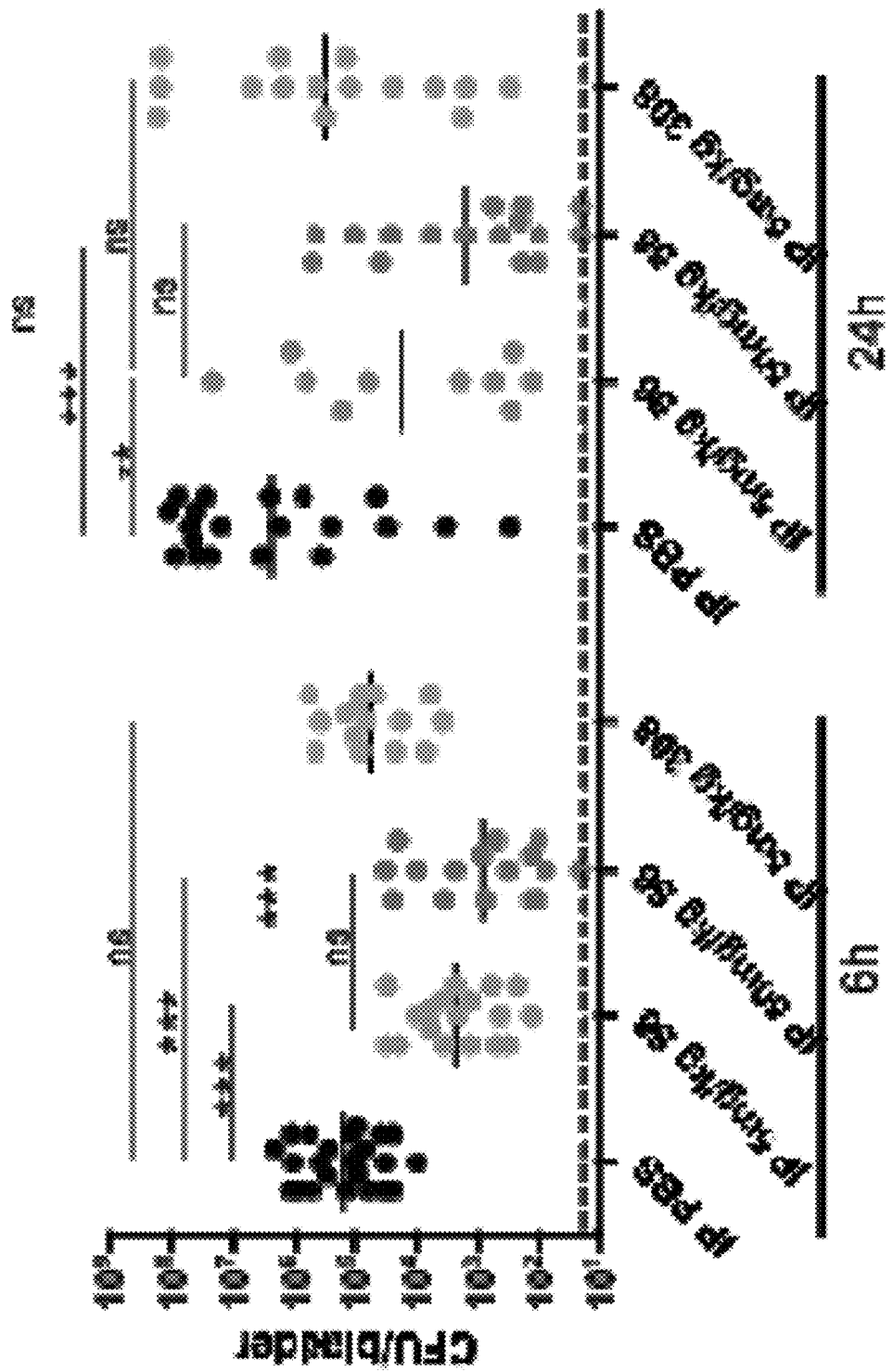

FIG. 32A depicts time course of infection and treatment with mannosides.

Figure 32B:
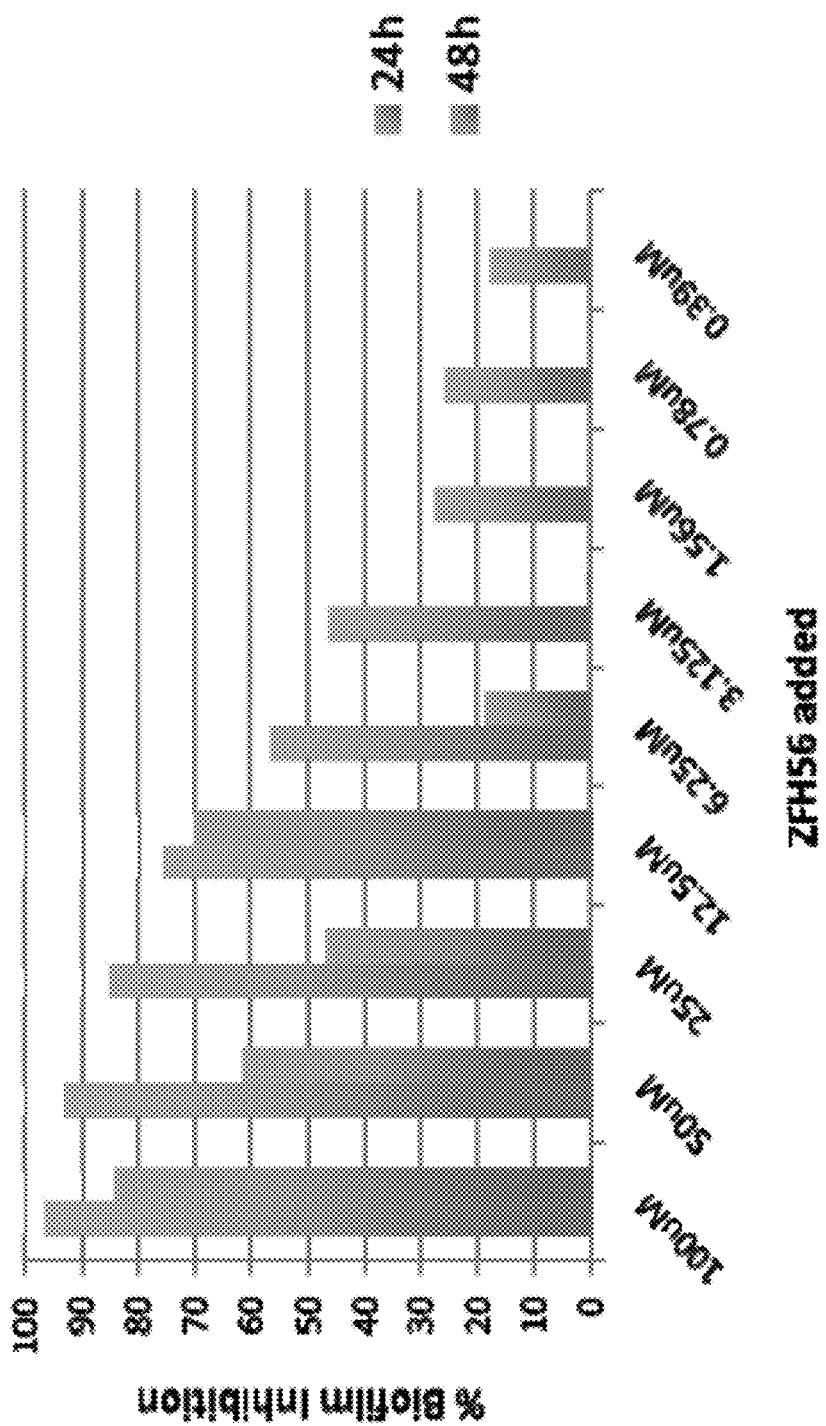

FIG. 32B depicts inhibition of preformed biofilm by ZFH56 (Compound 50).

Figure 33:
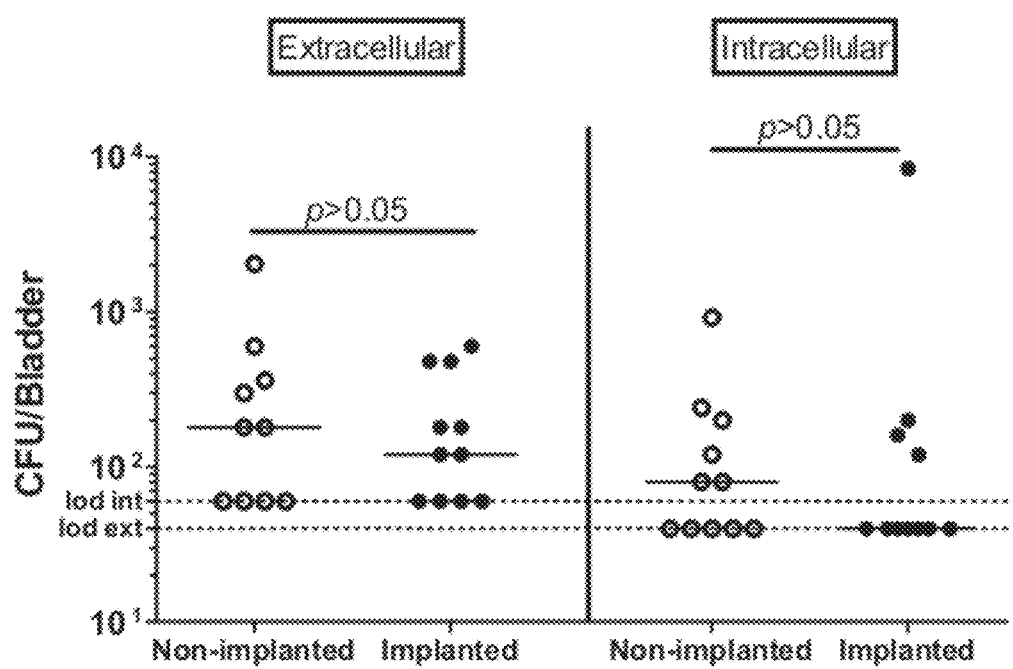

FIG. 33. depicts a graph showing that there is no defect in UTI89 invasion following implantation. Graph represents bacterial titers from homogenized bladders from non-implanted (○) or implanted (●) animals infected with UTI89 3hpi following gentamicin protection assay. Horizontal dashed lines represent the limit of detection (lod) for viable bacteria (Int=intracellular, Ext=Extracellular). Each symbol represents a mouse from two independent experiments with n=5/condition. The horizontal bars represent the median of each dataset; p value by the Mann Whitney U test.

Figure 34:
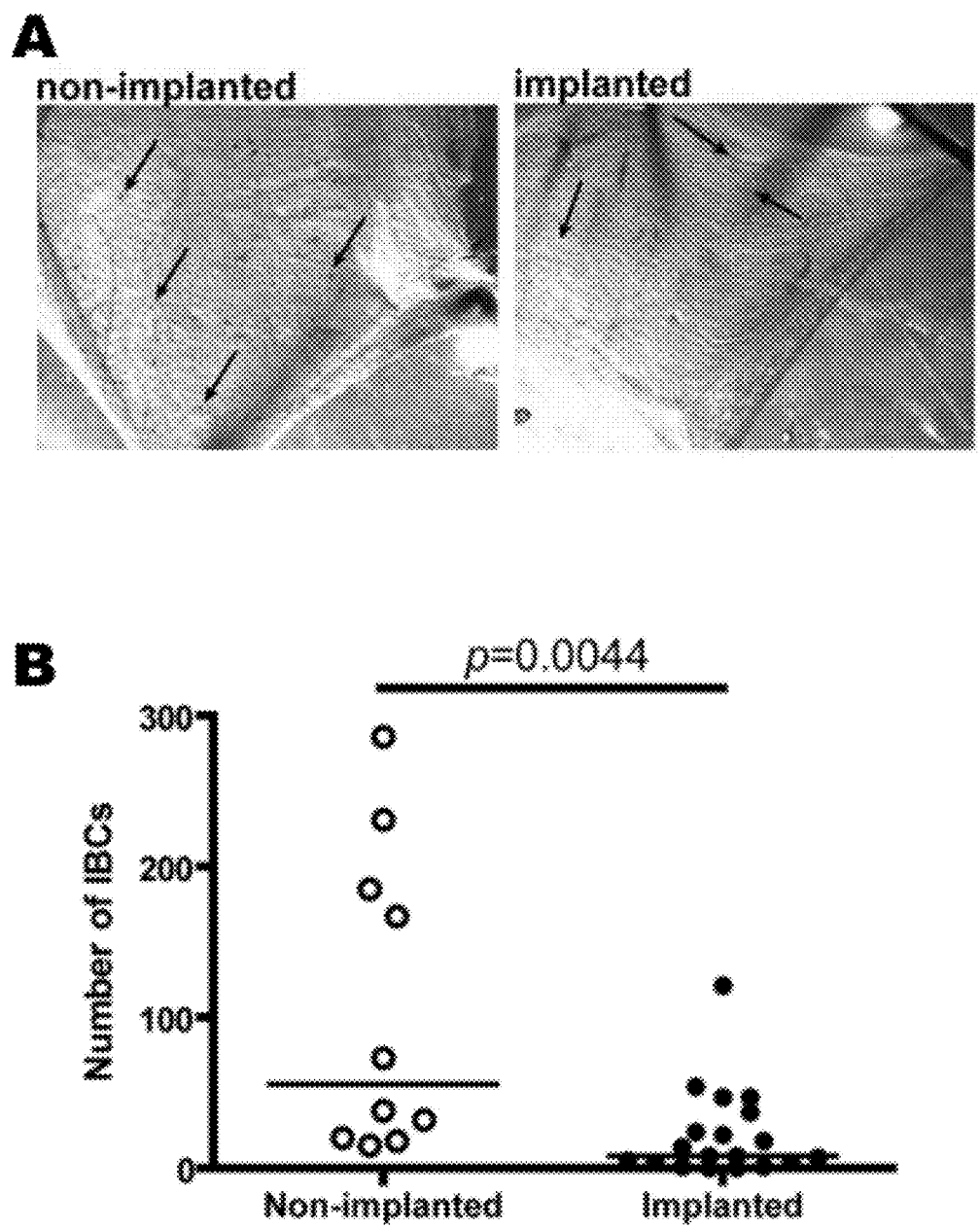

FIG. 34 depicts microscope images and a graph showing that uropathogenic E. coli produce IBCs in the superficial umbrella cells of implanted bladders. (A) Representative images of splayed bladders of female C57Bl/6Ncr mice infected with UTI89 6hpi in the absence (non-implanted) or presence (Implanted) of implants following LacZ staining. Each black arrow indicates a purple speck, indicative of an IBC. (B) Quantification of IBC formation following LacZ staining at 6hpi. Each symbol represents IBC number from a single mouse from two independent experiments with n=5/group. p value obtained from the Mann Whitney U test. (C) Representative CLSM images of whole bladders from non-implanted and implanted animals infected with UTI89 ectopically expressing GFP (Green), stained with DNA dye SYTO83 (Red) and Alexa-fluor 633-conjugate of WGA (Blue) reveal the presence of IBC within umbrella cells. Scale bar=20 μm.

Figure 36:
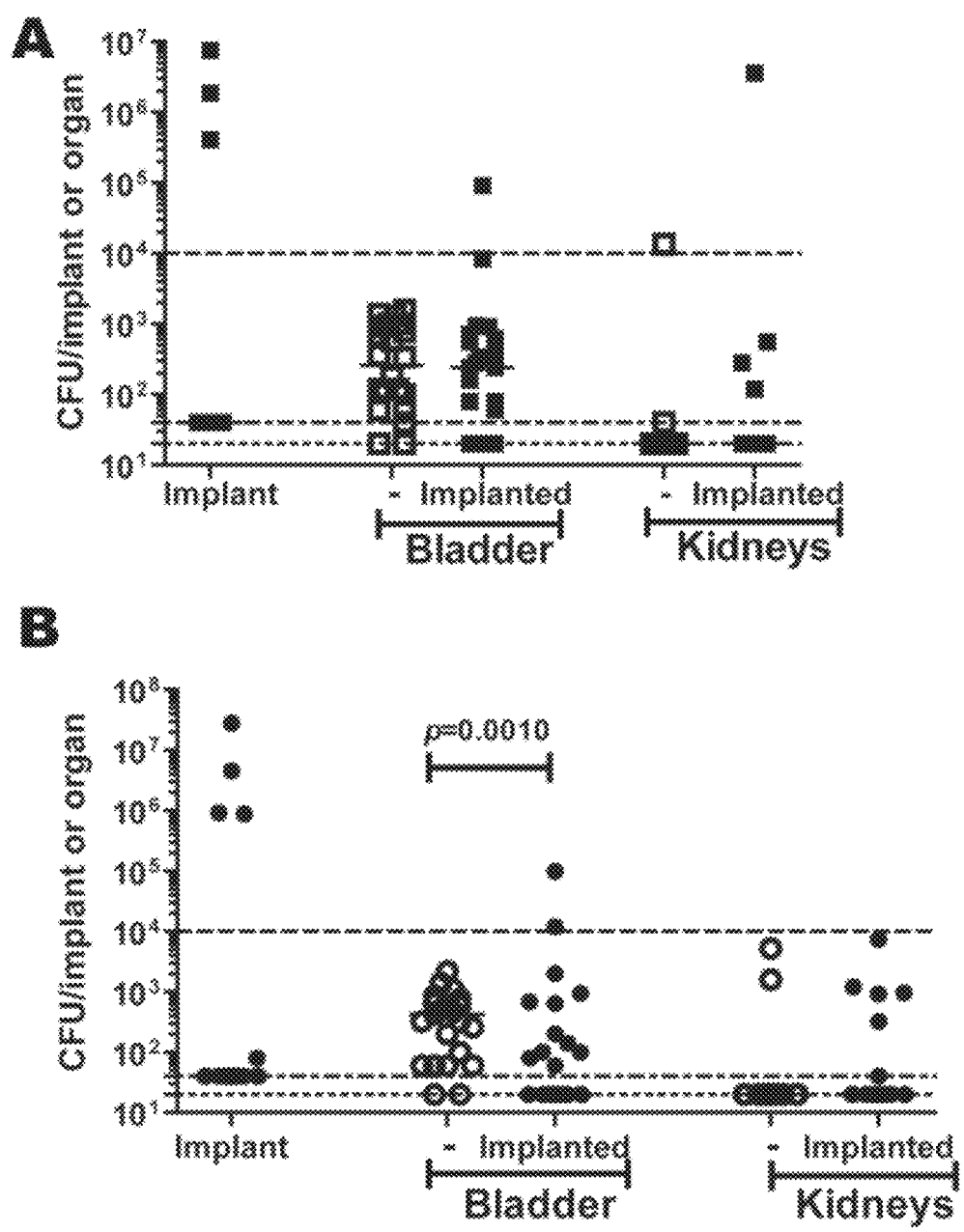

FIG. 35 depicts micrographs showing that IBC and filamentation occur following urinary catheterization. Representative CLSM images of whole bladders from non-implanted and implanted animals infected with UTI89 ectopically expressing GFP (Green), stained with DNA dye SYTO83 (Red) and Alexa-fluor 633-conjugate of WGA (Blue) reveal the presence of multiple IBCs within single umbrella cells (A-B), that unlike non-implanted bladders (C), the underlying epithelium is exposed following urinary catheterization (D-F), depict the absence of bacterial colonization of the exposed underlying epithelium in implanted animals (D-F), and the presence of filamenting bacteria in umbrella cells (E-F). Scale bar=20 μm FIG. 36 depicts two graphs showing that UPEC reservoir reactivation can lead to urinary implant and bladder colonization. Graphs represent bacterial titers in log scale recovered from implants, homogenized bladders and kidneys of non-bacteriuric animals 14 days post infection with UTI89HK:: GFP that were non-implanted or implanted for 3 day (A) or 5 days (B). Horizontal dashed lines represent the limit of detection for viable bacteria. Each symbol represents a mouse from at least two independent experiments with n=10-20/group/ experiment. The horizontal bars represent the median of each dataset; p value by the Mann Whitney U test.

Figure 37:
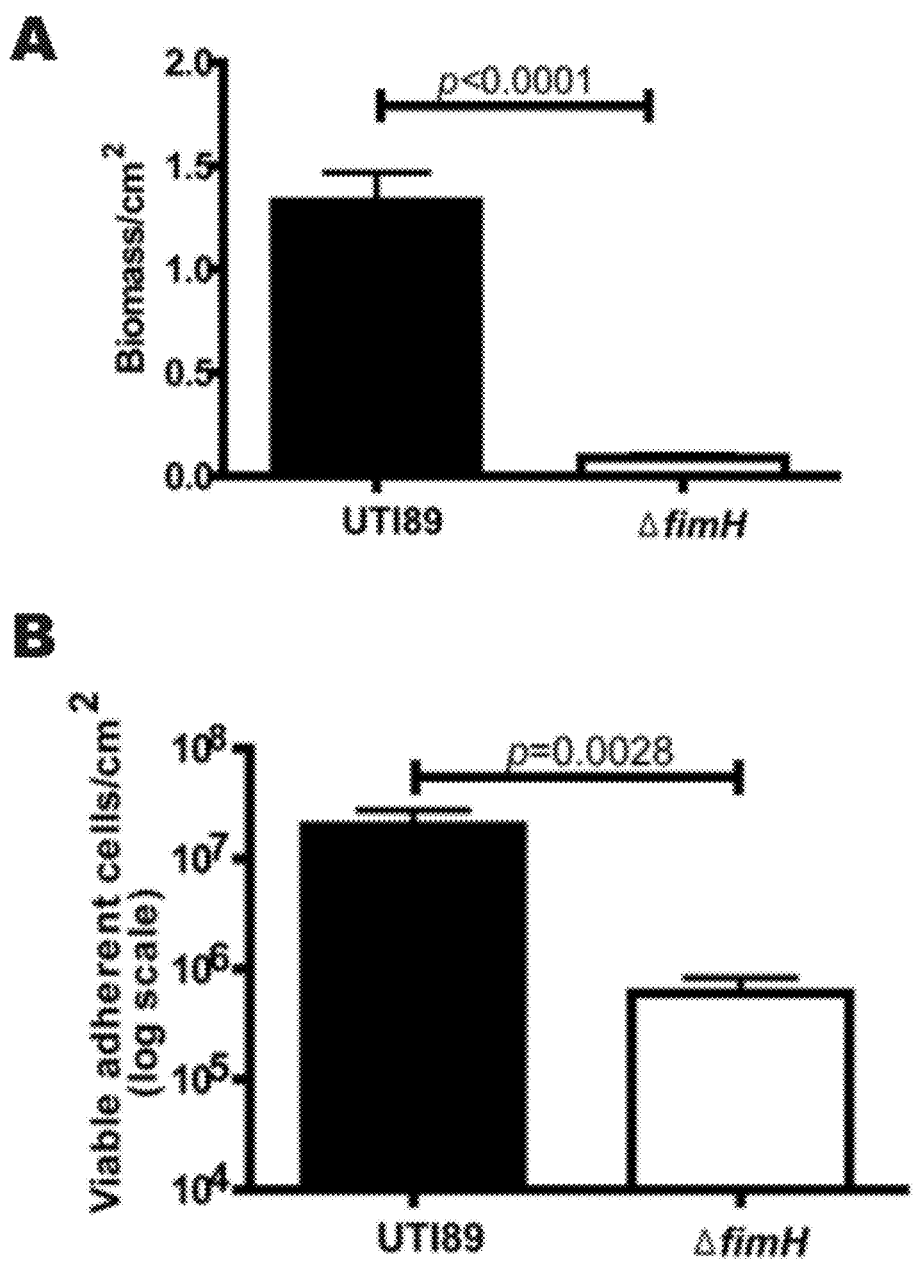

FIG. 37 depicts two graphs showing that deletion of fimH reduces biofilm formation and attenuates UPEC virulence. Graphs represent crystal violet based quantification (A) and CFU enumeration in logarithmic scale (log scale) (B) of 24 h old UTI89 and UTI89ΔfimH (ΔfimH) biofilms under human urine flow on silicone tubings at 37° C. indicating that ΔfimH is defective in biofilm formation under these conditions. Bars represent mean of three independent experiments, error bars indicate standard error of the mean (SEM). p values from Mann Whitney U test. (C) Graph represents bacterial titers in log scale recovered from implants, homogenized bladders and kidneys of non-implanted (open symbols) and implanted (closed symbols) infected with either UTI89 (square) or ΔfimH (circle) for 24 h. Horizontal dashed lines represent the limit of detection for viable bacteria. Each symbol represents a mouse from at least two independent experiments with n=5/group. The horizontal bars represent the median of each dataset; *p<0.05 and ***p<0.0005 by the Mann Whitney U test.

FIG. 38 depicts two graphs showing that S pili and curli are not critical for UPEC virulence following urinary catheterization. Graphs represent bacterial titers in log scale recovered at 24 hpi from implants, homogenized bladders and kidneys of (A) implanted animals infected with either UTI89 (●) or UTI89 mutant strains deficient in type 1 pili, ΔfimH (■), S pili ΔsfaA-H(▲), both type 1 and S pili ΔsfaA-HΔ-fimB-H(♦) and (B) non-implanted (open symbols) or implanted (closed symbols) animals infected with UTI89 (○,●), ΔfimH (□, ■) or UTI89 mutant strains deficient in curli components ΔcsgA (Δ, ▲) and ΔcsgBΔcsgG (♦, ◊). Horizontal dashed lines represent the limit of detection for viable bacteria. Each symbol represents a mouse from at least two independent experiments with n=5/group. The horizontal bars represent the median of each dataset; *p<0.05, *p<0.005p<0.0005, ns corresponds to p>0.05 by the Mann Whitney U test.

Figure 39:
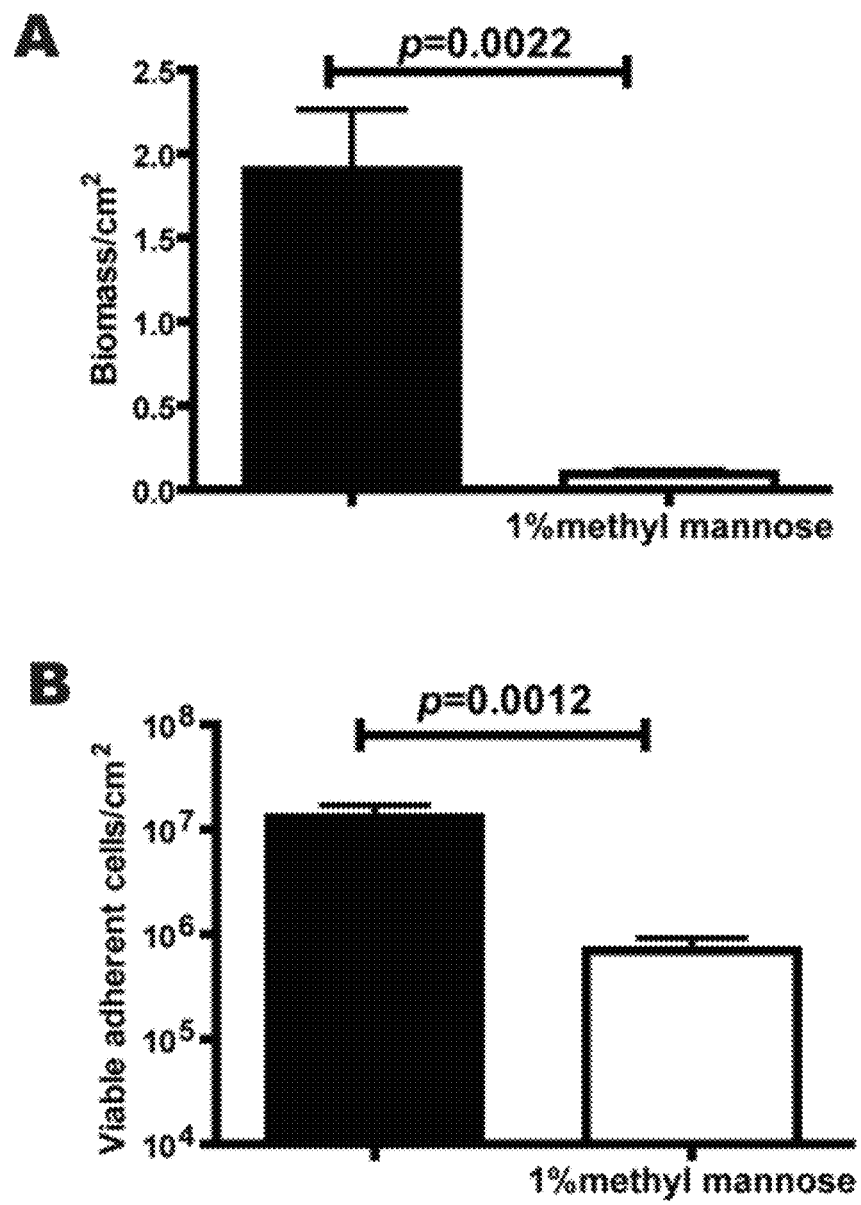

FIG. 39 depicts two graphs showing that methyl mannose inhibits UPEC biofilm in human urine. Graphs represent crystal violet based quantification (A) and CFU enumeration in logarithmic scale (log scale) (B) of 24 h old UTI89 biofilms in human urine with or without 1% methyl mannose under flow on silicone tubings at 37° C. indicating that methyl mannose prevents UPEC biofilm formation. Bars represent mean of three independent experiments, error bars indicate standard error of the mean (SEM). p values from Mann Whitney U test.

FIG. 40 depicts two graphs showing that mannoside treatment prevents IBC formation and UPEC virulence when used in combination with TMP-SMZ. (A) Graph represents IBC enumeration from LacZ staining of splayed bladders of female C57Bl/6Ncr mice treated i.p. with mannoside or saline prior to transurethral implantation and inoculation with UTI89 6 hpi. Each symbol represents IBC number from a single mouse from two independent experiments with n=5/ group. p value obtained from the Mann Whitney U test. (B) Graph represents bacterial titers in log scale recovered at 6 hpi from implants, homogenized bladders and kidneys of animals treated with saline (○), mannoside (□), TMP-SMZ (●) and TMP-SMZ+Mannoside (■) prior to urinary implantation and inoculation with UTI89. Horizontal dashed lines represent the limit of detection for viable bacteria. Each symbol represents a mouse from at least two independent experiments with n=5/group. The horizontal bars represent the median of each dataset; *p<0.05, p<0.0005, *p<0.0005, ns corresponds to p>0.05 by the Mann Whitney U test.

Figure 41:
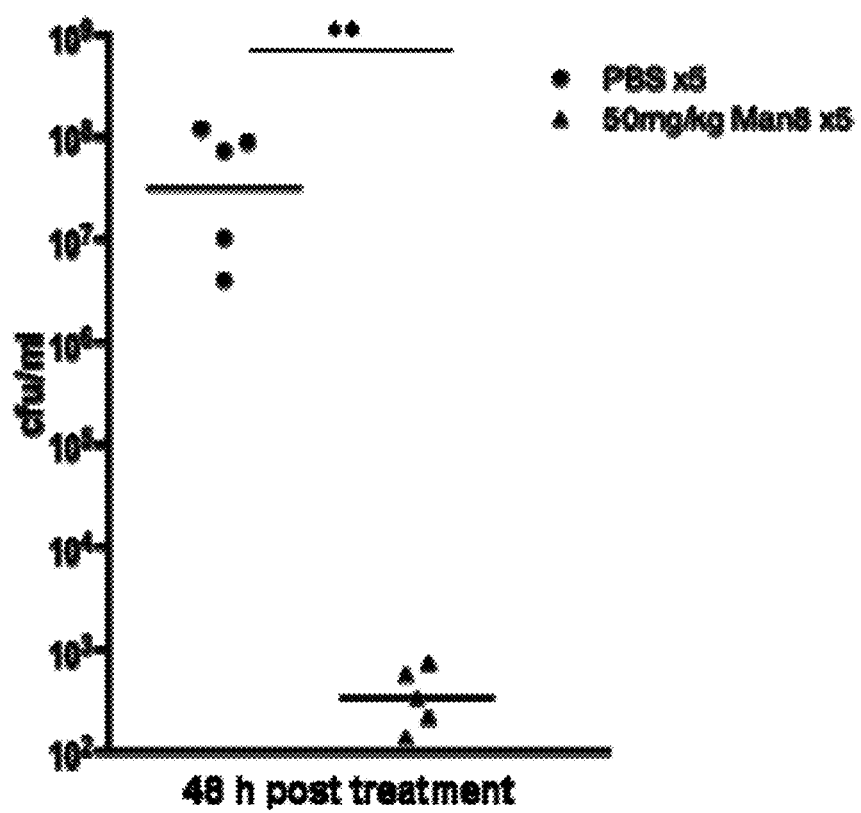

FIG. 41 depicts a graph showing that treatment of chronic mice with 5 doses of Mannoside 8 eliminates UPEC from the bladder. Mannoside 8 treatment (▲), PBS treatment (●).

Figure 42:
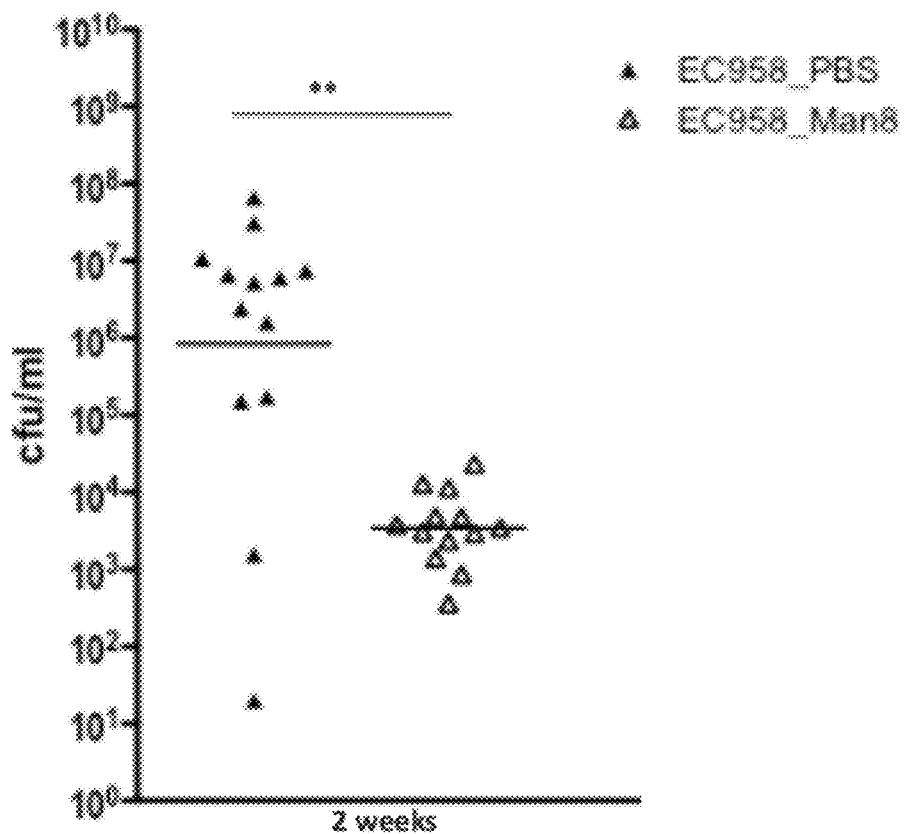

FIG. 42 depcist a graph showing that Mannoside 8 is effective against the multidrug resistant UPEC isolate EC958. Mannoside 8 treatment (Δ), PBS treatment (▲).

Figure 43A:
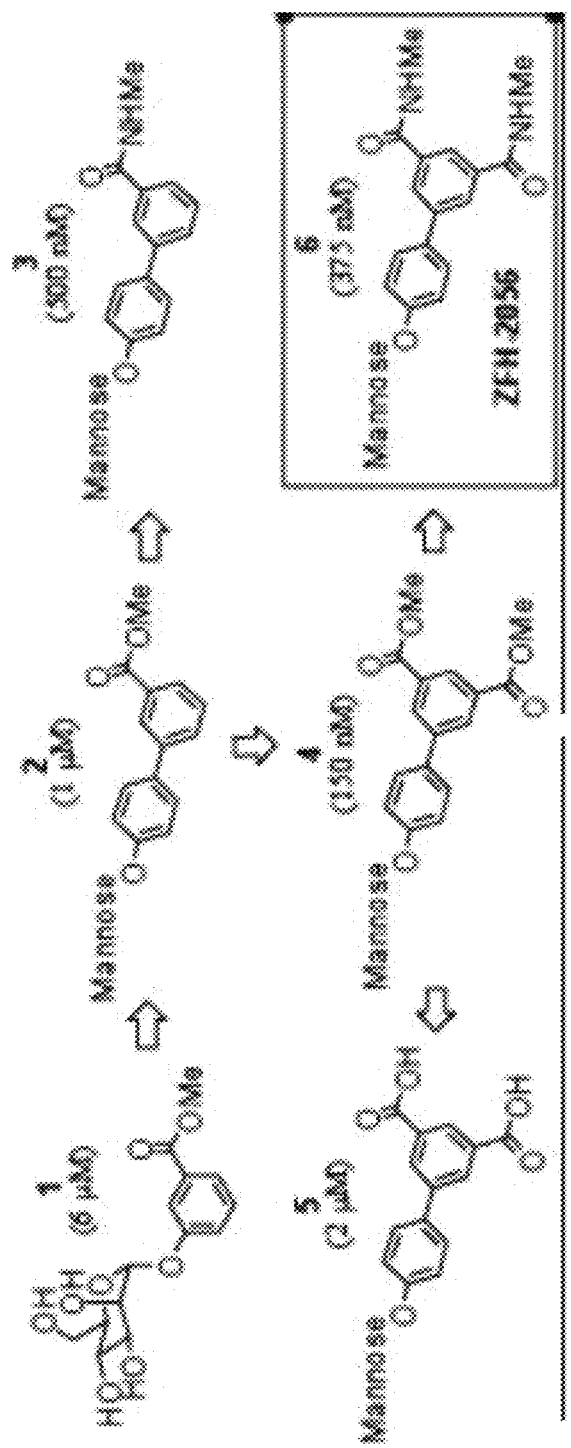
Figure 43:
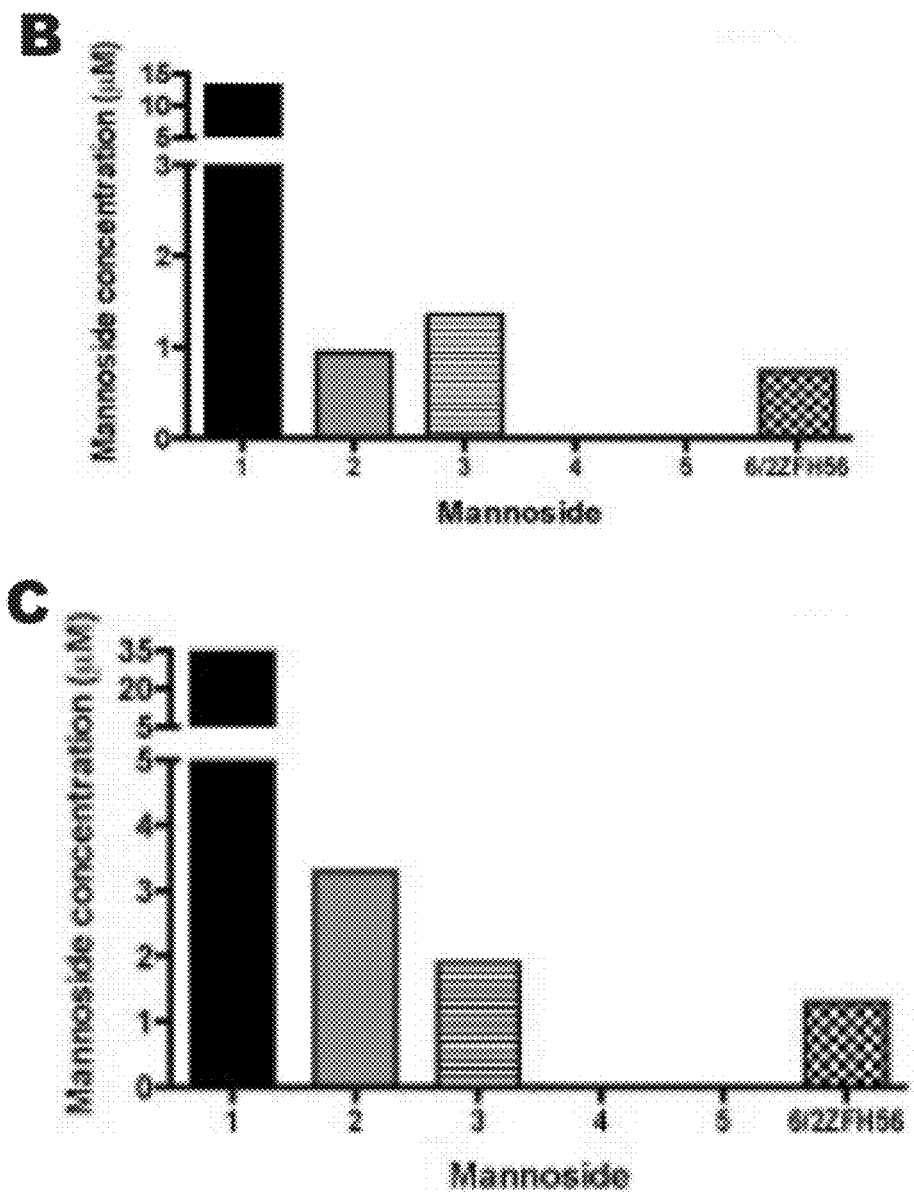

FIG. 43 depicts inhibition, prevention and disruption of UTI89 biofilm by mannoside. (A), Discovery of biphenyl mannoside lead FimH inhibitors. Cellular HAI titers (EC$_{>90}$) are shown in parentheses. (B) The median inhibitory concentration (IC$_{50}$) of mannosides 1-3 and 6 on UTI89 biofilm formation. Mannoside was added at the initiation of biofilm formation. (C) The IC50 of 1-3 and 6 on UTI89 biofilm prevention. Mannoside was added 24 h after biofilm growth was initiated and % biofilm was calculated 16 h after addition of mannoside. Bars show the mean value of the experiments (n=3). (D, E) 6 dispersed biofilm as measured by confocal microscopy of UTI89 biofilms grown for 24 h (D), then incubated for an additional 16 h in the presence of 0.3 μM 6 (E).

Figure 44:
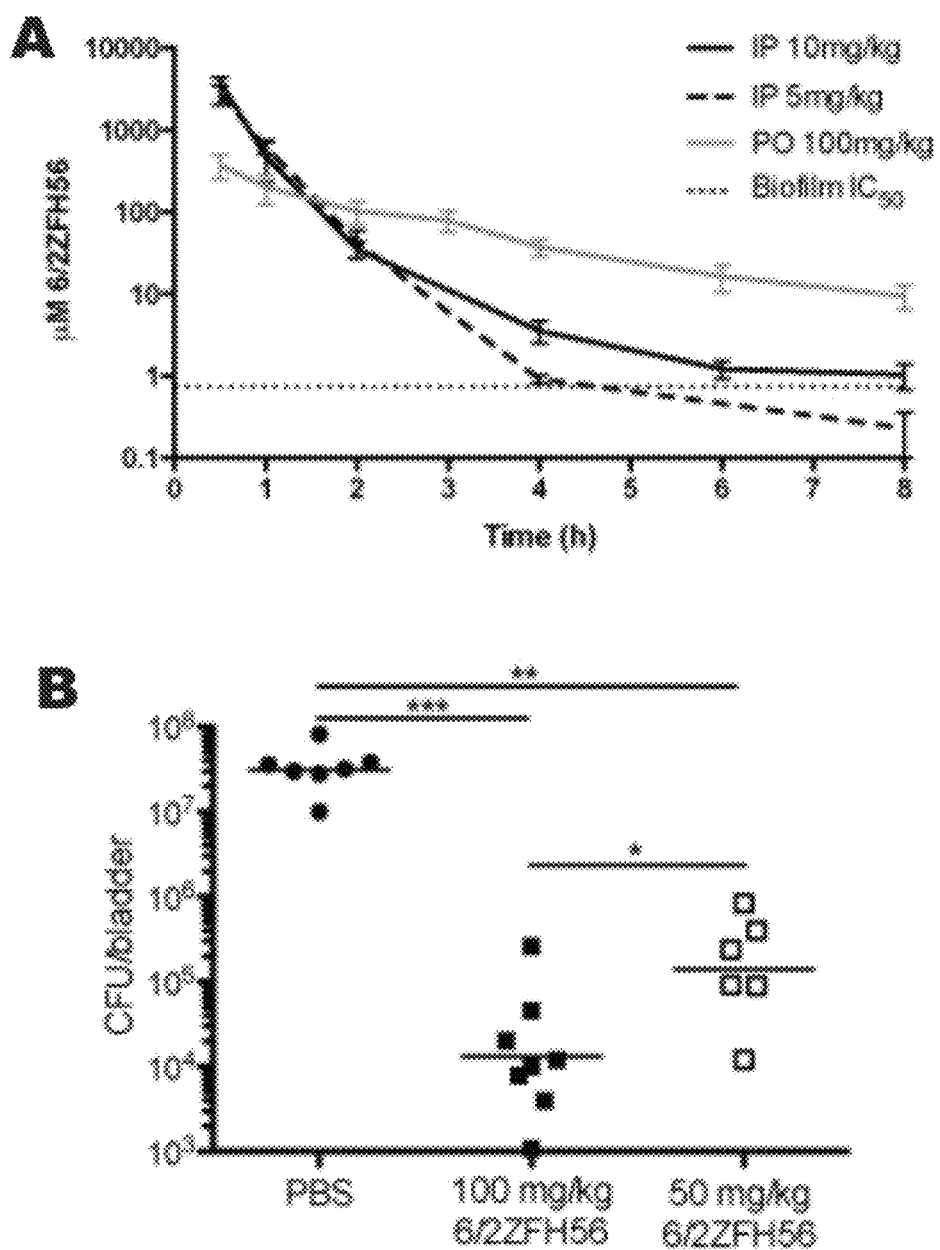

FIG. 44 depicts mannoside effect on UTI89 colonization. (A) Urine PK analysis of 6 (n 3 mice) showing amounts in urine over time for each dosing regimen indicated. Horizontal dashed line is at IC$_{50}$ (0.74 μM) as determined by the biofilm inhibition assay. (B) Mannoside effectively treats UTI. Chronically infected mice were treated with PBS or 6 (PO, 100 and 50 mg/kg). 6 hours post-treatment bacterial counts in the bladder were enumerated. In the mannoside-treated groups, there was a significant 3-log drop in bacterial load relative to PBS-treated mice. (C, D) Confocal microscopy of bladders from PBS-treated (C) and 6-treated (D) mice. Bacteria were stained with SYTO9 (green) and the bladder luminal surface was stained with WGA (red). The image in C shows a normal, robust IBC whereas the arrows in D indicate luminal bacteria. (E) Total bacterial CFUs at 6 hpi from mice treated with PBS or 6 either by IP (5 mg/kg) or oral (100 mg/kg) dosing 30 min prior to inoculation of UTI89. (F) IBC quantification at 6 hpi from mice treated with PBS or 6 either by IP (5 mg/kg) or oral (100 mg/kg) dosing 30 min prior to inoculation of UTI89. (G) 6 hpi ex vivo gentamicin protection assay revealed both luminal and intracellular bacteria are significantly reduced upon IP (5 mg/kg) pretreatment of mice with 6. Bars indicate geometric mean. Statistical significance according to Mann-Whitney is at *P<0.05, P<0.01, *P<0.0001. ns, not significant; LOD, limit of detection.

Figure 45:
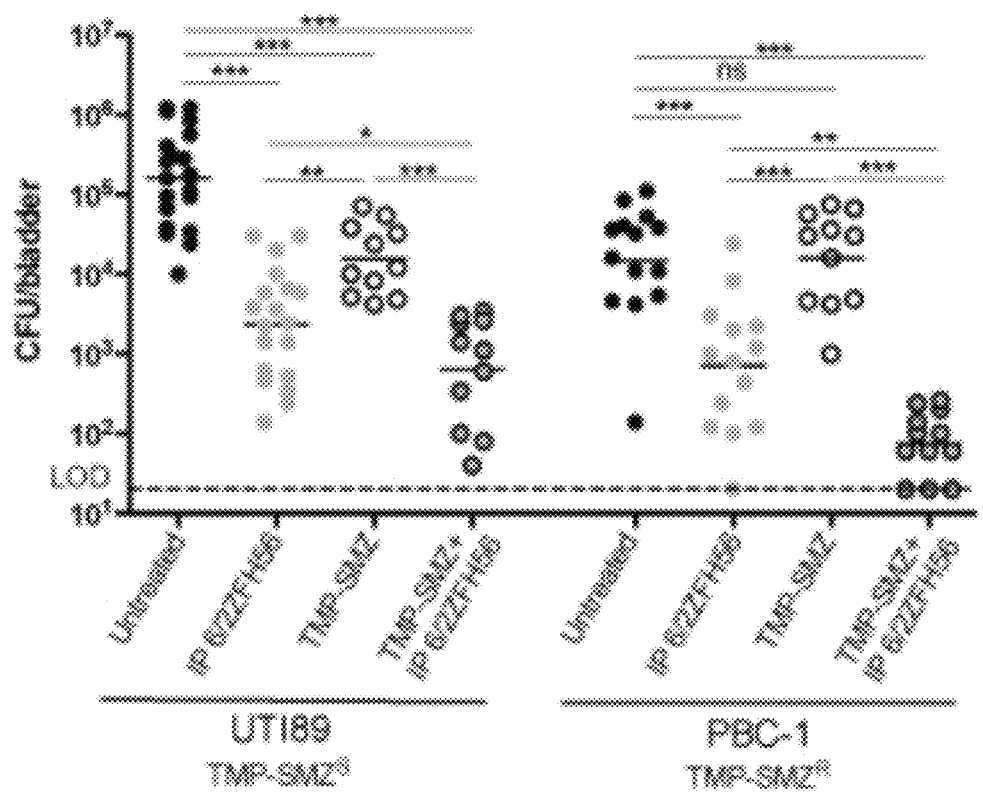

FIG. 45 depicts mannoside potentiates TMP-SMZ treatment. Total bacterial CFUs were quantified 6 hpi. UTI89 colonization was reduced in mice treated with 6, TMP-SMZ and TMP-SMZ+6. There was further decreased colonization in TMP-SMZ+6-treated mice over 6 or TMP-SMZ alone. PBC-1 colonization was reduced in mice treated with 6 and TMP-SMZ+6, but not TMP-SMZ alone. Enhanced efficacy as measured by bacterial CFUs was observed upon treatment with TMP-SMZ+6 over 6 or TMP-SMZ treatment alone. Bars indicate geometric mean. Statistical significance according to Mann-Whitney is at *P<0.05, P<0.01, *P<0.0001. ns, not significant; LOD, limit of detection.

Figure 46:
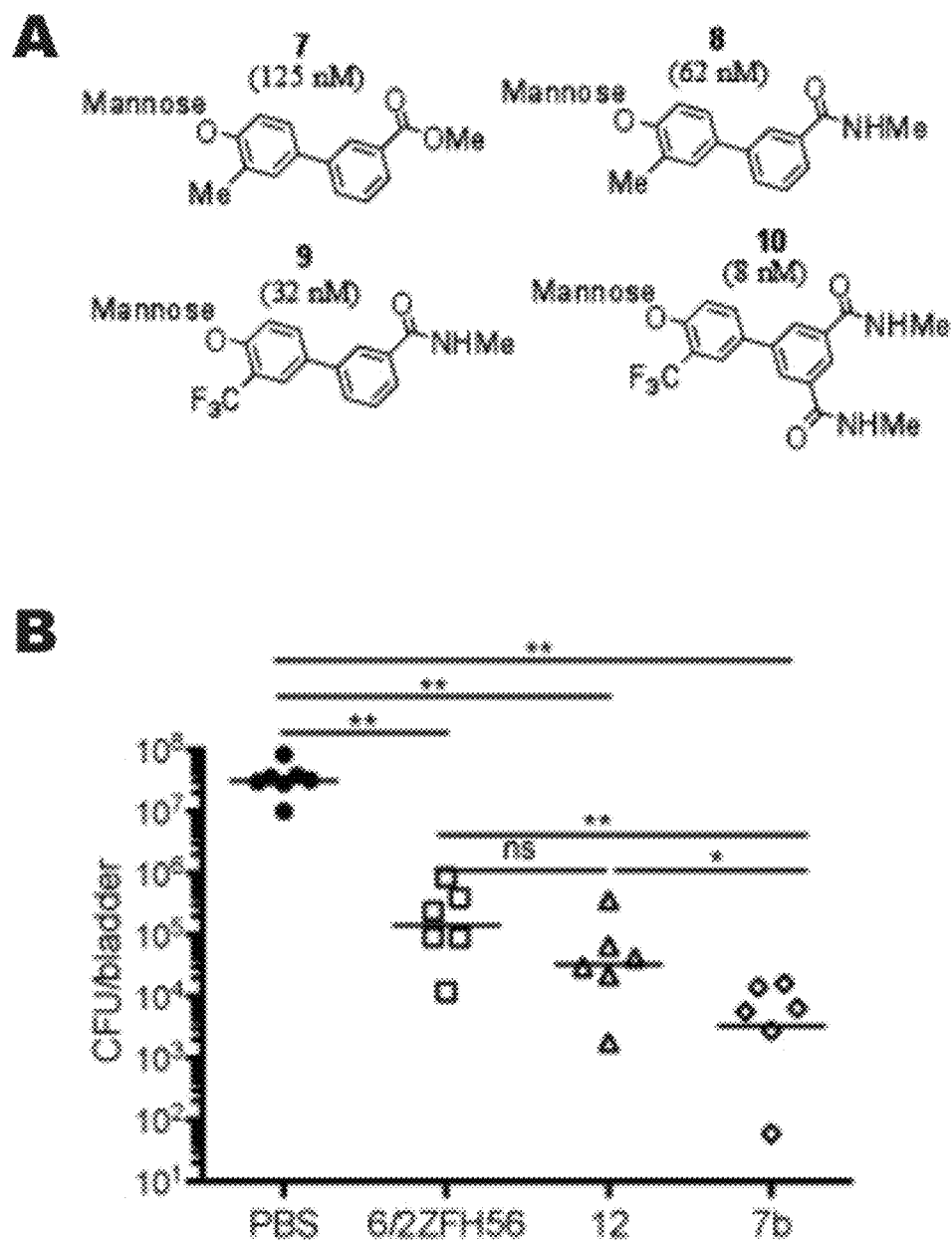
Figure 46C:
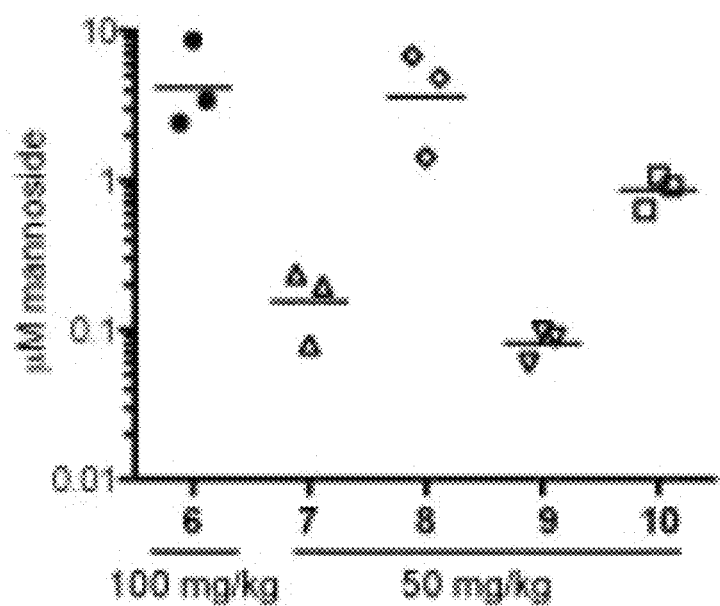

FIG. 46 depicts newly designed mannosides show enhanced PK and potency at treating infection. (A) Optimized ortho-methyl and trifluoromethyl substituted biphenyl mannosides. Cellular HAI titers (EC$_{>90}$) are shown in parentheses. (B) Mannosides show improved PK. Mannosides 8 and 10 dosed at 50 mg/kg had equivalent levels of compound in the urine 6 h post-treatment relative to mannoside 6 dosed at 100 mg/kg. (C) Chronically infected mice were treated with PBS or mannoside 6, 10 or 8 (PO, 50 mg/kg). 6 hours posttreatment bacterial counts in the bladder were enumerated. In the mannoside-treated groups, there was a significant 3-log drop in bacterial load relative to PBS-treated mice. The optimized mannoside 8 showed increased efficacy over 6.

Figure 47:
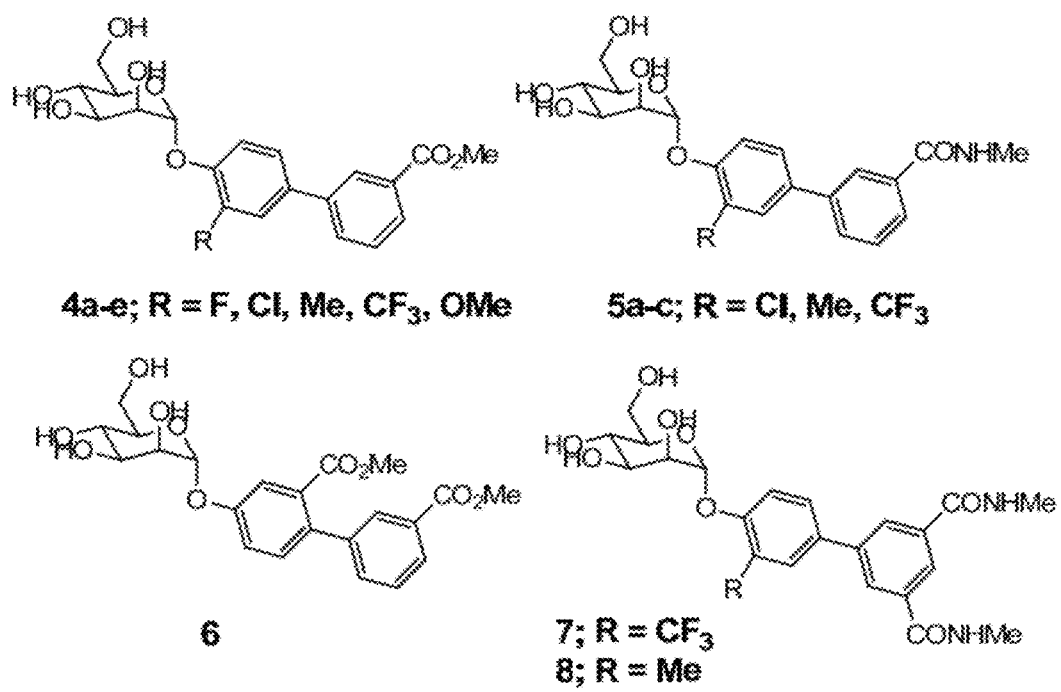

FIG. 47 depicts structures of substituted biphenyl mannosides.

Figure 48:
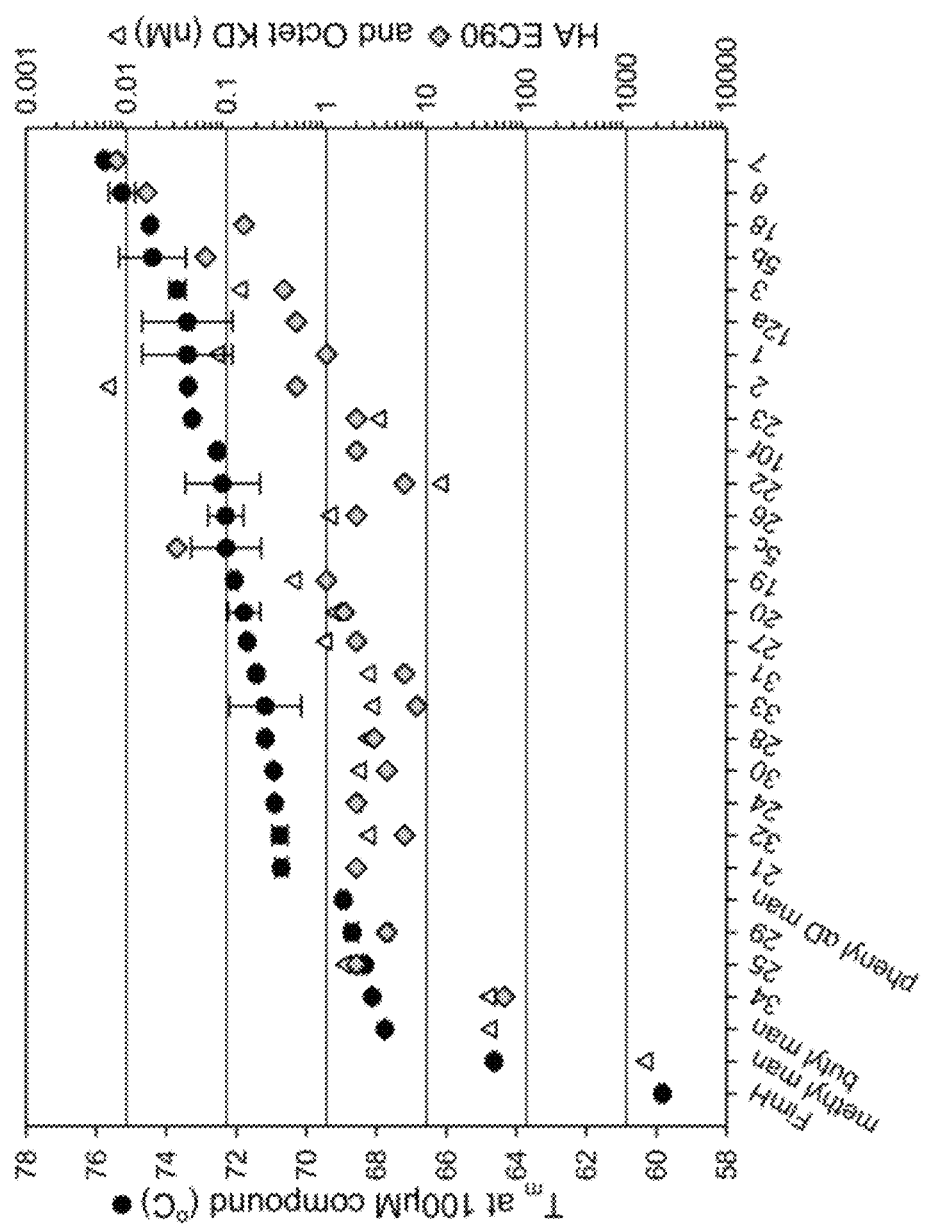

FIG. 48 depicts a graph showing curves of HAI, Octet and DSF assay results.

Figure 49:
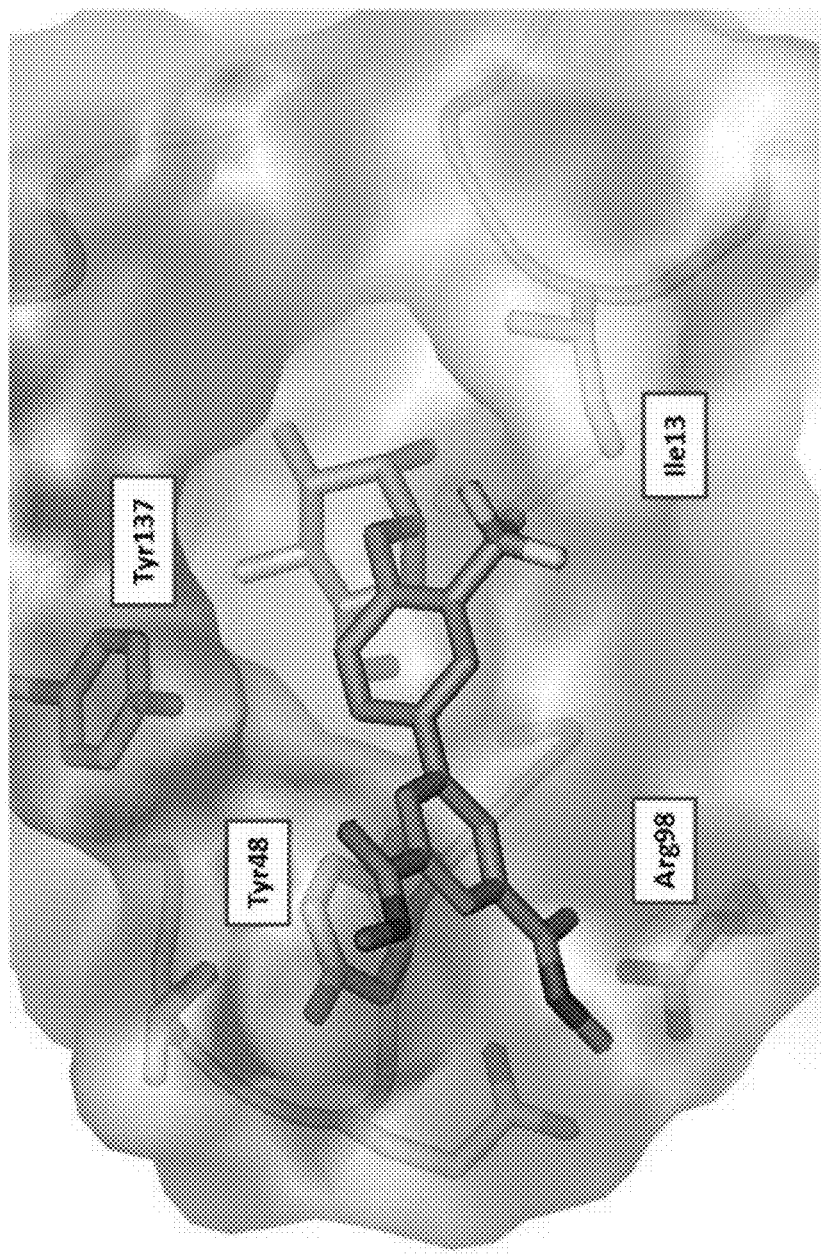

FIG. 49 depicts a proposed model of mannoside 7 bound to FimH calculated with APBS (Adaptive Poisson-Boltzmann Solver) software using PDB code: 3MCY.

Figure 50:
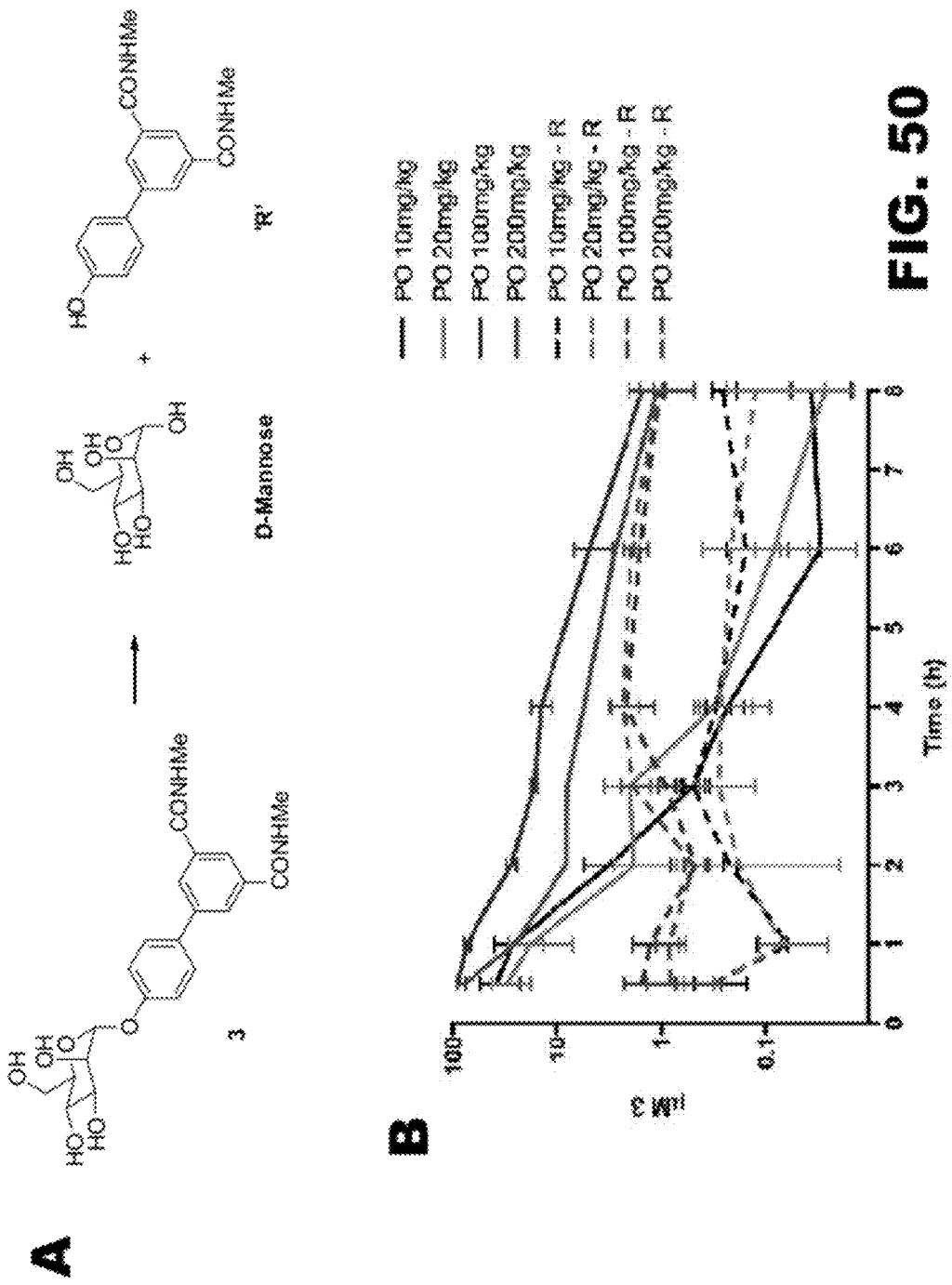

FIG. 50 depicts (A) Metabolic lability of the mannoside 3 glycosidic bond from hydrolysis to mannose and biphenol; (B) Elimination kinetics and clearance of mannoside 3 and biphenol (R) hydrolysis product in mouse urine.

Figure 51A:
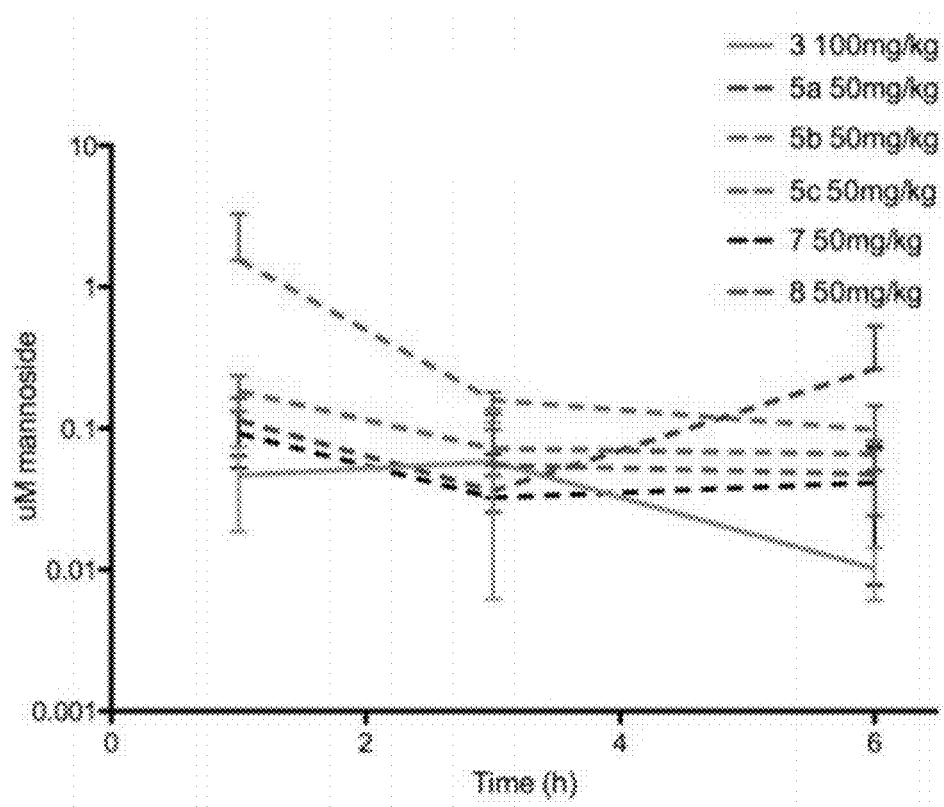
Figure 51B:
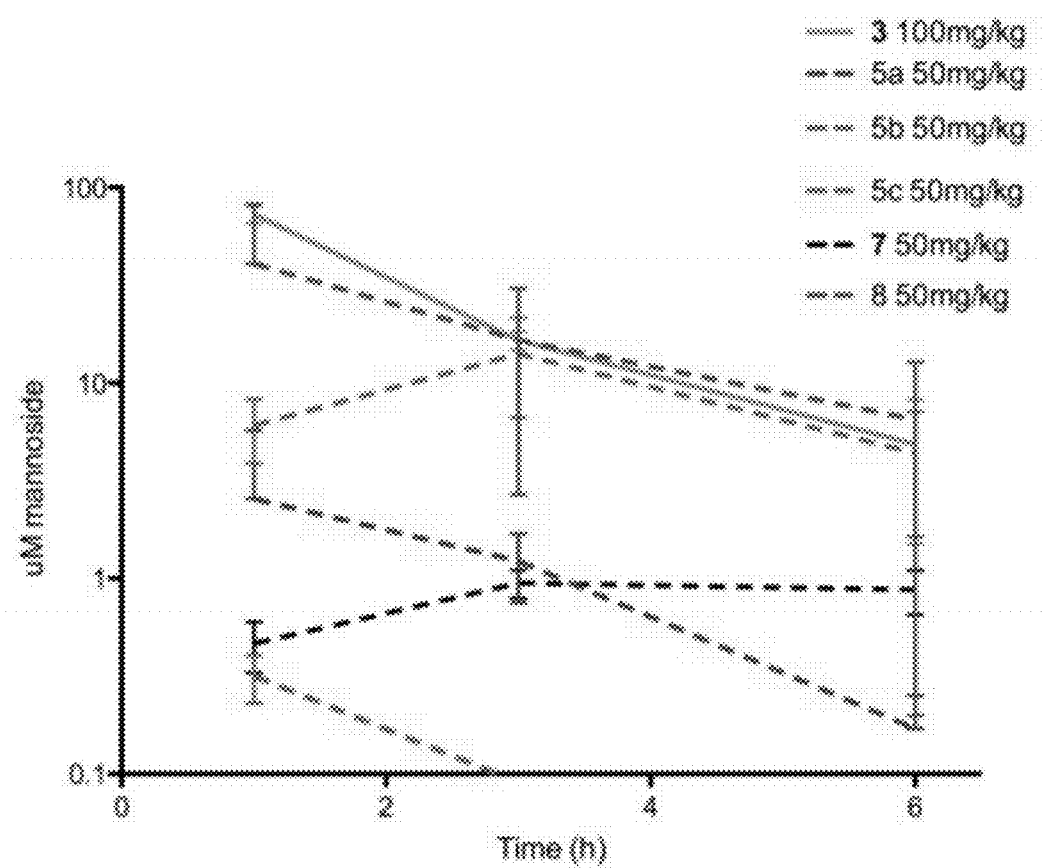

FIG. 51 depicts (A). Plasma pharmacokinetics of optimized ortho-substituted mannosides 5a-c, 7, 8 and mannoside 3. (B) Elimination clearance kinetics of optimized ortho-substituted mannosides 5a-c, 7, 8 and mannoside 3 in urine.

Figure 52:
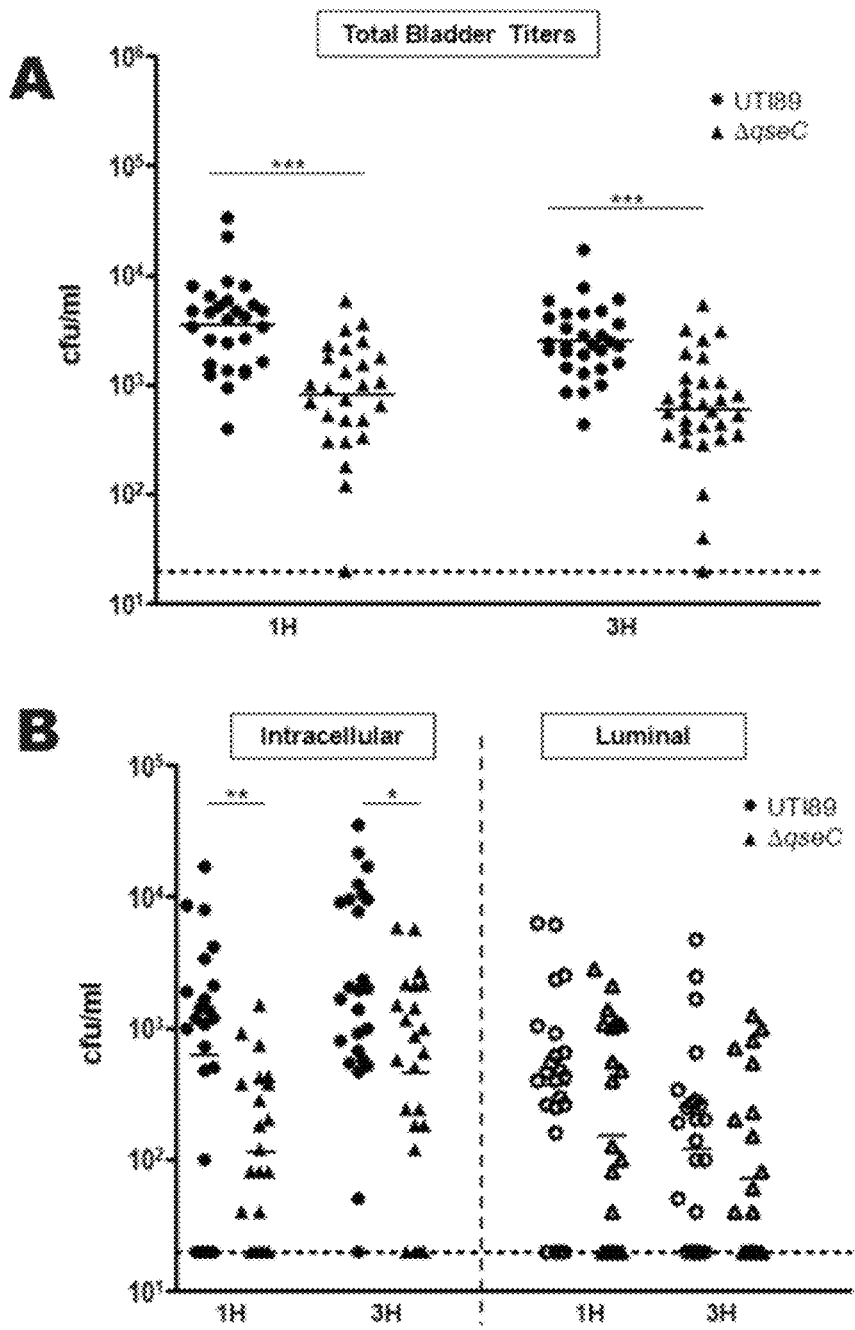

FIG. 52 depicts two graphs showing that UTI89ΔqseC has a defect in bladder invasion. (A) Bladder titers at 1 and 3 h.p.i showing decreased overall bacterial numbers recovered from bladders infected with UTI89ΔqseC compared to those infected with wt UTI89. (B) Bacterial titers recovered from gentamicin-treated bladders (intracellular population) after washing 3 times with PBS to remove the extracellular, adherent bacteria (luminal population). Fewer UTI89ΔqseC bacteria are internalized, indicating that the qseC mutant is less efficient in invading the host bladder compared to wt UTI89. The average of 3 independent experiments is shown (*, P<0.02; **, P<0.003, by two-tailed Mann-Whitney).

Figure 53A:
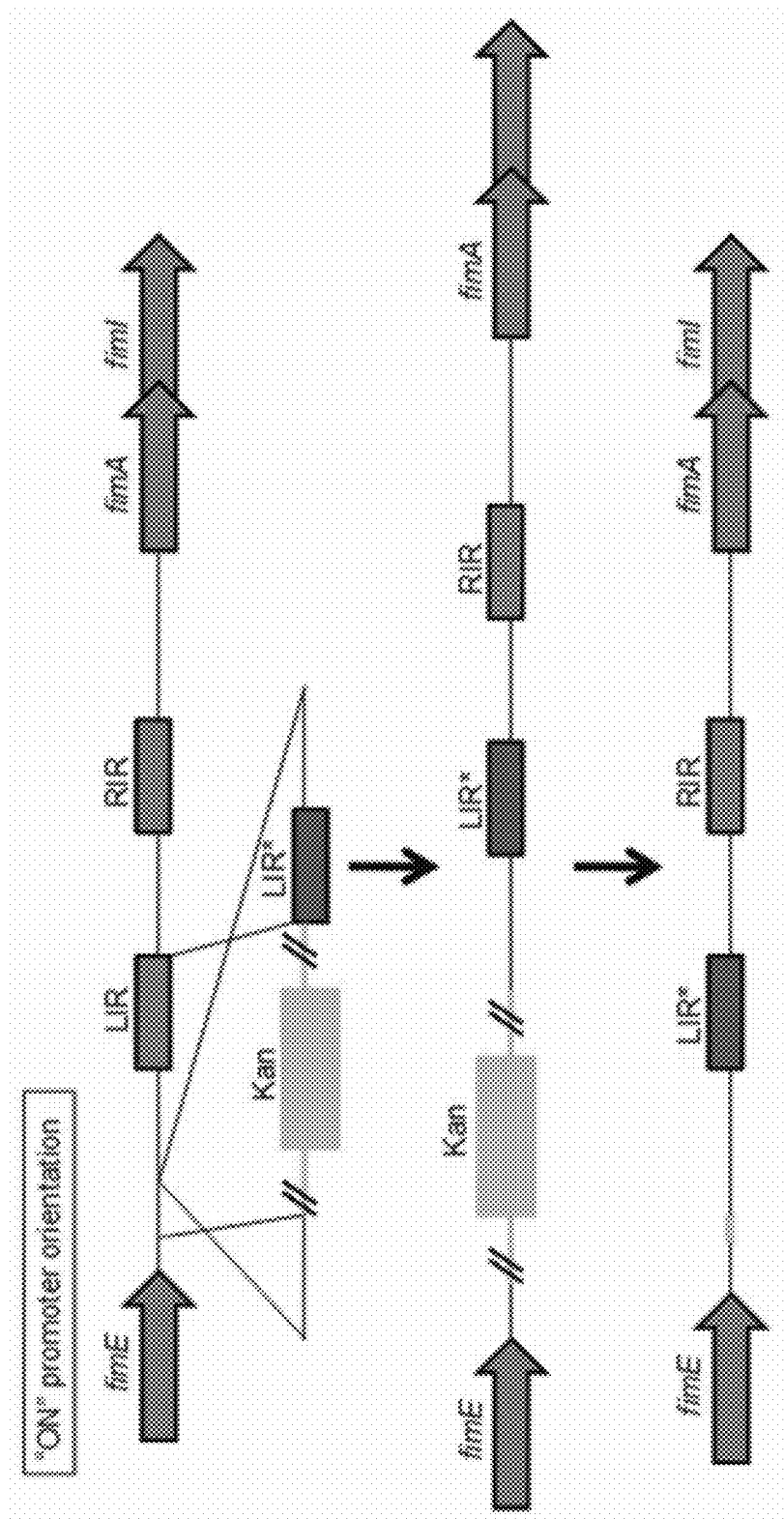
Figure 53D:
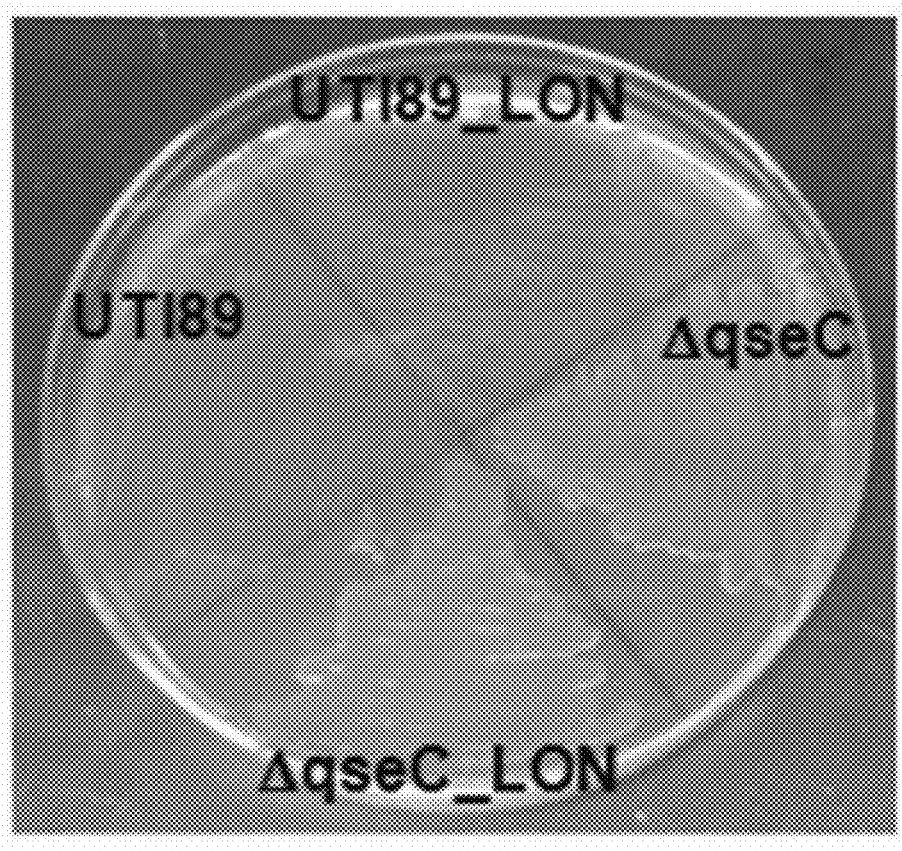

FIG. 53 depicts a diagram detailing and data showing that restoring production of type 1 pili in UTI89ΔqseC does not influence other ΔqseC-mediated defects. (A) Schematic showing the strategy used to lock the phase-variable fim promoter in the ON orientation. (B) Hemagglutination assays and (C) western blot analyses depicting restoration of type 1 pili expression in UTI89ΔqseC locked ON strain (Δqse-C_LON). (D) Assessment of curli production on YESCA-CR agar verifies that, similarly to UTI89ΔqseC, UTI89ΔqseC_LON remains defective for curli expression, exhibiting a white and smooth morphotype. In contrast, wt UTI89 and UTI89_LON appear red, dry and rough a phenotype indicative of curli expression.

Figure 54:
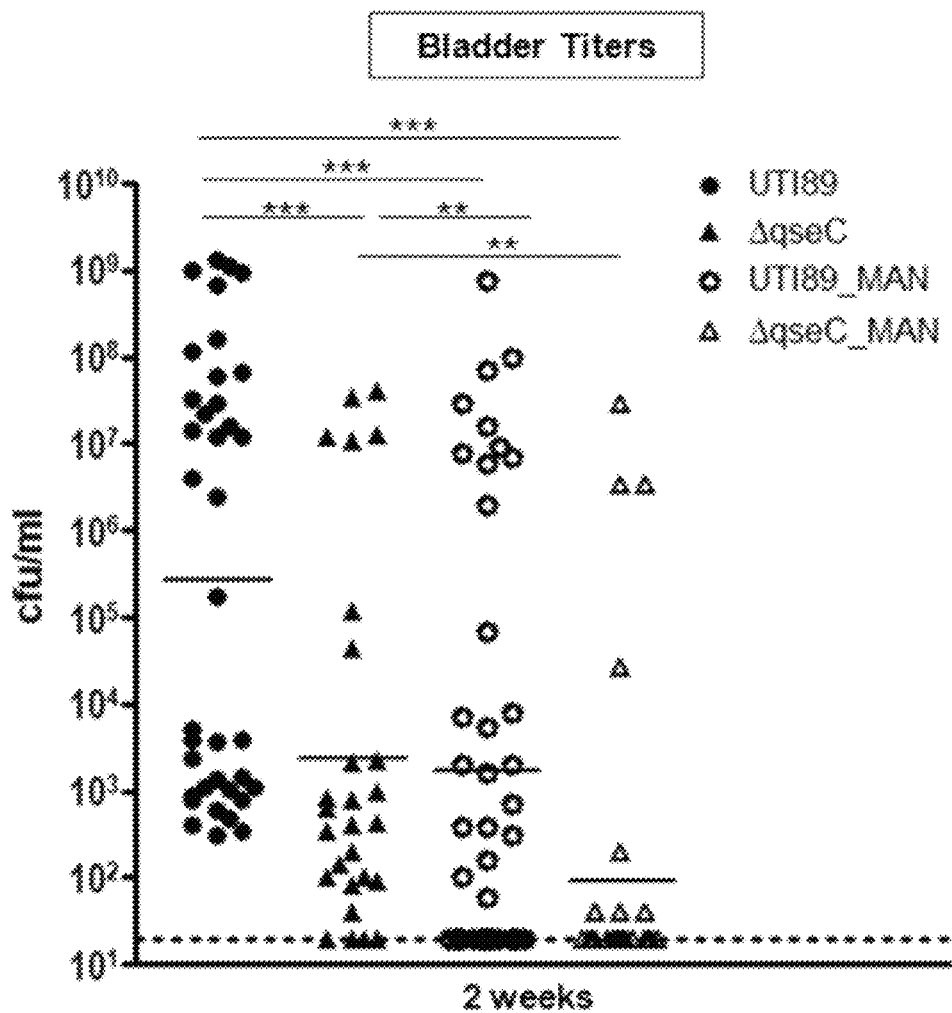

FIG. 54 depicts a graph showing co-inhibition of type 1 pili and QseC as a prophylactic measure for UTIs. Chart depicting the bladder cfu obtained at 2 wks post infection from mice pre-treated with mannoside and subsequently infected with either wt UTI89, or UTI89ΔqseC (used as a proxy for a QseC inhibitor). Significantly fewer cfu (1.5-log reduction) were obtained from pre-treated mice infected with UTI89ΔqseC. The average of 3 independent experiments is shown (, P<0.01; *, P<0.001, by two-tailed Mann-Whitney). UTI89_MAN, mice pre-treated with mannoside and challenged with wt UTI89; ΔqseC_MAN, mice pre-treated with mannoside and challenged with UTI89ΔqseC; UTI89, mice pre-treated with PBS and challenged with wt UTI89; ΔqseC, mice pre-treated with PBS and challenged with UTI89ΔqseC.

DETAILED DESCRIPTION

Compounds that inhibit the function of type I pili of bacteria have been developed. The compounds may be useful for the treatment of urinary tract infections. Significantly, the compounds may prevent bacterial colonization and invasion of the bladder tissue to prevent infection and the establishment of reservoirs that can serve as a source of recurrent infections. The invention also encompasses methods of use of a compound of the invention.

I. Compounds

One aspect of the invention is a compound of Formula (I):

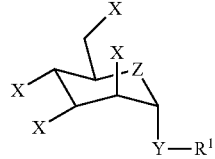
(I)

wherein:
- X is selected from the group consisting of hydrogen, $OR^2$, $SR^2$, and $NR^z$;
- Z is selected from the group consisting of O, S, $CR^3$ and $NR^4$;
- Y is selected from the group consisting of oxygen, sulfur, $CR^3$, $NR^4$, —N($R^5$)CO—, —$CH_2$N($R^5$)—, —$CH_2$N($R^5$)CO—, $CO_2$, $SO_2$, —$CH_2$O—, —$CH_2$S—, CO, —CON($R^5$)—, —$SO_2$N($R^5$)—, —O$(CH_2)_n$—, —S$(CH_2)_n$—, —N$(CH_2)_n$—, —$(CH_2)_n$—, $NR^5$, and an optionally substituted alkyl, alkene, alkyne, or heterocycle;
- $R^2$ is independently selected from the group consisting of hydrogen, $COR^x$, $CONR^x$, hydrocarbyl, and substituted hydrocarbyl;
- $R^3$, $R^4$, $R^5$ are independently selected from the group consisting of hydrogen, hydrocarbyl, and substituted hydrocarbyl;
- $R^z$ is independently selected from the group consisting of hydrogen, hydrocarbyl, substituted hydrocarbyl, —$COR^x$, —$CONR^xR^xSO_2R^x$, and —$CO_2R^x$;
- $R^x$ is independently selected from the group consisting of hydrogen, $NR^4R^5$, and an optionally substituted alkyl, cycloalkyl, heterocycle, or aryl;
- n is an integer from 1 to 10; and
- $R^1$ is selected from the group comprising Formulas (IIIA), (IIIB), (IV), (V), (VI), (VII) and (VIII):

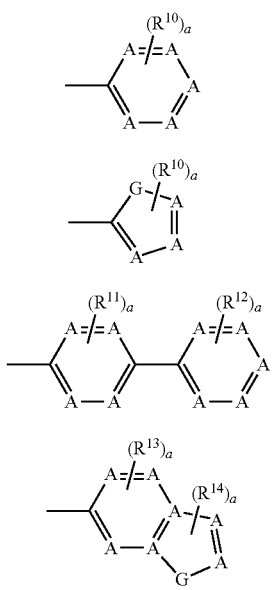

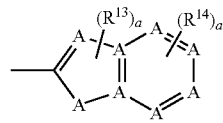

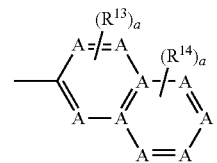

wherein:
- A is independently selected from the group consisting of $CR^6$ and N;
- G is selected from the group consisting of S, O, $CR^8$, and $NR^9$;
- $R^6$, $R^8$ and $R^9$ are independently selected from the group consisting of hydrogen, hydrocarbyl, and substituted hydrocarbyl;
- $R^{10}$, $R^{11}$, $R^{12}$, $R^{13}$ and $R^{14}$ are independently selected from the group consisting of hydrogen, —$OR^{15}$, —$NR^{15}R^{16}$, —$NR^{15}COR^{16}$, —$NR^{15}CO_2R^{16}$, —$NR^{15}CONR^{16}$, —$NR^{15}SO_2R^{16}$, —$COR^{15}$, —$SO_2R^{15}$, nitro, cyano, halogen, aryl, heterocycle, —$COOR^{15}$, —$CONR^{16}R^{17}$, —$SO_2NR^{18}R^{19}$, alkenyl, alkynyl, hydrocarbyl, and substituted hydrocarbyl;
- $R^{15}$, $R^{16}$, $R^{17}$, $R^{18}$, $R^{19}$ are independently selected from the group consisting of hydrogen, hydrocarbyl, substituted hydrocarbyl, aryl, and heterocycle, and $R^{16}$ and $R^{17}$ together can optionally form a ring, and $R^{18}$ and $R^{19}$ together can optionally form a ring; and
- a is either the integer 1 or the integer 2.

One embodiment of formula (I), where $R^1$ is formula (IIIA), comprises formula (IX):

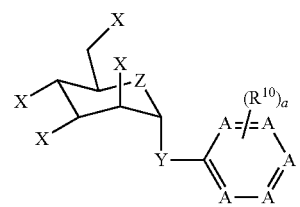
(IX)

wherein:
- X is selected from the group consisting of hydrogen, $OR^2$, $SR^2$, $NR^z$;
- Z is selected from the group consisting of O, S, $CR^3$ and $NR^4$;
- Y is selected from the group consisting of oxygen, sulfur, $CR^3$, $NR^4$, —N($R^5$)CO—, —$CH_2$N($R^5$)—, —$CH_2$N($R^5$)CO—, $CO_2$, $SO_2$, —$CH_2$O—, —$CH_2$S—, CO, —CON($R^5$)—, —$SO_2$N($R^5$)—, —O$(CH_2)_n$—, —S$(CH_2)_n$—, —N$(CH_2)_n$—, —$(CH_2)_n$—, $NR^5$, and an optionally substituted alkyl, alkene, alkyne, or heterocycle;
- $R^2$, $R^3$, $R^4$, $R^5$ are independently selected from the group consisting of hydrogen, hydrocarbyl, and substituted hydrocarbyl;
- n is an integer from 1 to 10;

A is independently selected from the group consisting of $CR^6$ and N;

$R^6$, $R^8$ and $R^9$ are independently selected from the group consisting of hydrogen, hydrocarbyl, and substituted hydrocarbyl;

$R^{10}$ is independently selected from the group consisting of hydrogen, —$OR^{15}$, —$NR^{15}R^{16}$, —$NR^{15}COR^{16}$, —$NR^{15}CO_2R^{16}$, —$NR^{15}CONR^{16}$, —$NR^{15}SO_2R^{16}$, —$COR^{15}$, —$SO_2R^{15}$, nitro, cyano, halogen, aryl, heterocycle, —$COOR^{15}$, —$CONR^{16}R^{17}$, —$SO_2NR^{18}R^{19}$, alkenyl, alkynyl, hydrocarbyl, and substituted hydrocarbyl;

$R^{15}$, $R^{16}$, $R^{17}$, $R^{18}$, $R^{19}$ are independently selected from the group consisting of hydrogen, hydrocarbyl, substituted hydrocarbyl, aryl, and heterocycle, and $R^{16}$ and $R^{17}$ together can optionally form a ring, and $R^{18}$ and $R^{19}$ together can optionally form a ring;

$R^z$ is independently selected from the group consisting of hydrogen hydrocarbyl, substituted hydrocarbyl, —$COR^x$, —$CONR^xR^xSO_2R^x$, and —$CO_2R^x$;

$R^x$ is independently selected from the group consisting of hydrogen, —$NR^4R^5$, and an optionally substituted alkyl, cycloalkyl, heterocycle, or aryl; and a is either the integer 1 or the integer 2.

In an exemplary embodiment of a compound of formula (IX), $R^{10}$ is aryl or heterocycle.

Another embodiment of formula (I), where $R^1$ is formula (IIIB), comprises formula (X):

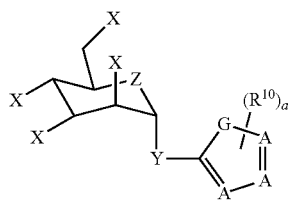

(X)

wherein

X is selected from the group consisting of hydrogen, $OR^2$, $SR^2$, and $NR^z$;

Z is selected from the group consisting of O, S, $CR^3$ and $NR^4$;

Y is selected from the group consisting of oxygen, sulfur, $CR^3$, $NR^4$, —$N(R^5)CO$—, —$CH_2N(R^5)$—, —$CH_2N(R^5)CO$—, $CO_2$, $SO_2$, —$CH_2O$—, —$CH_2S$—, CO, —$CON(R^5)$—, —$SO_2N(R^5)$—, —$O(CH_2)_n$—, —$S(CH_2)_n$—, —$N(CH_2)_n$—, —$(CH_2)_n$—, $NR^5$, and an optionally substituted alkyl, alkene, alkyne, or heterocycle;

$R^2$ is independently selected from the group consisting of hydrogen, —$COR^x$, and —$CONR^x$;

$R^3$, $R^4$, $R^5$ are independently selected from the group consisting of hydrogen, hydrocarbyl, and substituted hydrocarbyl;

$R^z$ is independently selected from the group consisting of hydrogen hydrocarbyl, substituted hydrocarbyl, —$COR^x$, —$CONR^xR^xSO_2R^x$, and —$CO_2R^x$;

$R^x$ is independently selected from the group consisting of hydrogen, —$NR^4R^5$, and an optionally substituted alkyl, cycloalkyl, heterocycle, or aryl;

n is an integer from 1 to 10;

A is independently selected from the group consisting of $CR^6$ and N;

G is selected from the group consisting of S, O, $CR^8$, and $NR^9$;

$R^6$, $R^8$ and $R^9$ are independently selected from the group consisting of hydrogen, hydrocarbyl, and substituted hydrocarbyl;

$R^{10}$ is independently selected from the group consisting of hydrogen, $OR^{15}$, $NR^{15}R^{16}$, $NR^{15}COR^{16}$, $NR^{15}CO_2R^{16}$, $NR^{15}CONR^{16}$, $NR^{15}SO_2R^{16}$, $COR^{15}$, $SO_2R^{15}$, nitro, cyano, halogen, aryl, heterocycle, $COOR^{15}$, $CONR^{16}R^{17}$, $SO_2NR^{18}R^{19}$, alkenyl, alkynyl, hydrocarbyl, and substituted hydrocarbyl; and $R^{15}$, $R^{16}$, $R^{17}$, $R^{18}$, $R^{19}$ are independently selected from the group consisting of hydrogen, hydrocarbyl, substituted hydrocarbyl, aryl, and heterocycle, and $R^{16}$ and $R^{17}$ together can optionally form a ring, and $R^{18}$ and $R^{19}$ together can optionally form a ring; and a is either the integer 1 or the integer 2.

Yet another embodiment of formula (I), where $R^1$ is formula (IV), comprises formula (XI):

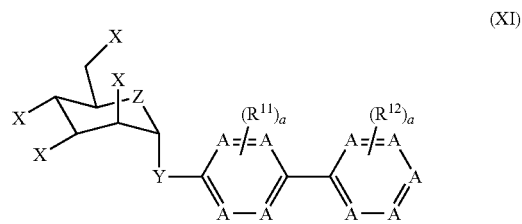

(XI)

wherein

X is selected from the group consisting of hydrogen, $OR^2$, $SR^2$, $NR^z$;

Z is selected from the group consisting of O, S, $CR^3$ and $NR^4$;

Y is selected from the group consisting of oxygen, sulfur, $CR^3$, $NR^4$, —$N(R^5)CO$—, —$CH_2N(R^5)$—, —$CH_2N(R^5)CO$—, $CO_2$, $SO_2$, —$CH_2O$—, —$CH_2S$—, CO, —$CON(R^5)$—, —$SO_2N(R^5)$—, —$O(CH_2)_n$—, —$S(CH_2)_n$—, —$N(CH_2)_n$—, —$(CH_2)_n$—, $NR^5$, and an optionally substituted alkyl, alkene, alkyne, or heterocycle;

$R^2$, $R^3$, $R^4$, $R^5$ are independently selected from the group consisting of hydrogen, hydrocarbyl, and substituted hydrocarbyl;

n is an integer from 1 to 10;

A is independently selected from the group consisting of $CR^6$ and N;

$R^6$, $R^8$ and $R^9$ are independently selected from the group consisting of hydrogen, hydrocarbyl, and substituted hydrocarbyl;

$R^{11}$ and $R^{12}$ are independently selected from the group consisting of hydrogen, —$OR^{15}$, —$NR^{15}R^{16}$, —$NR^{15}COR^{16}$, —$NR^{15}CO_2R^{16}$, —$NR^{15}CONR^{16}$, —$NR^{15}SO_2R^{16}$, —$COR^{15}$, —$SO_2R^{15}$, nitro, cyano, halogen, aryl, heterocycle, $COOR^{15}$, $CONR^{16}R^{17}$, $SO_2NR^{18}R^{19}$, alkenyl, alkynyl, hydrocarbyl, and substituted hydrocarbyl;

$R^{15}$, $R^{16}$, $R^{17}$, $R^{18}$, $R^{19}$ are independently selected from the group consisting of hydrogen, hydrocarbyl, substituted hydrocarbyl, aryl, and heterocycle, and $R^{16}$ and $R^{17}$ together can optionally form a ring, and $R^{18}$ and $R^{19}$ together can optionally form a ring;

$R^z$ is independently selected from the group consisting of hydrogen hydrocarbyl, substituted hydrocarbyl, —$COR^x$, —$CONR^xR^xSO_2R^x$, and —$CO_2R^x$;

$R^x$ is independently selected from the group consisting of hydrogen, $-NR^4R^5$, and an optionally substituted alkyl, cycloalkyl, heterocycle, or aryl; and a is either the integer 1 or the integer 2.

Still another embodiment of formula (I), where $R^1$ is formula (V), comprises formula (XII):

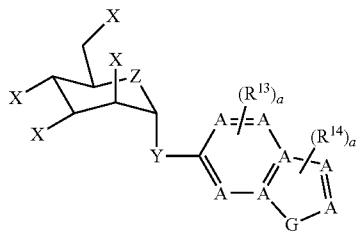

(XII)

wherein
X is selected from the group consisting of hydrogen, $OR^2$, $SR^2$, $NR^z$;
Z is selected from the group consisting of O, S, $CR^3$ and $NR^4$;
Y is selected from the group consisting of oxygen, sulfur, $CR^3$, $NR^4$, $-N(R^5)CO-$, $-CH_2N(R^5)-$, $-CH_2N(R^5)CO-$, $CO_2$, $SO_2$, $-CH_2O-$, $-CH_2S-$, $CO$, $-CON(R^5)-$, $-SO_2N(R^5)-$, $-O(CH_2)_n-$, $-S(CH_2)_n-$, $-N(CH_2)_n-$, $-(CH_2)_n-$, $NR^5$, and an optionally substituted alkyl, alkene, alkyne, or heterocycle;
$R^2$, $R^3$, $R^4$, $R^5$ are independently selected from the group consisting of hydrogen, hydrocarbyl, and substituted hydrocarbyl;
n is an integer from 1 to 10
A is independently selected from the group consisting of $CR^6$ and N;
G is selected from the group consisting of S, O, $CR^8$, and $NR^9$;
$R^6$, $R^8$ and $R^9$ are independently selected from the group consisting of hydrogen, hydrocarbyl, and substituted hydrocarbyl;
$R^{13}$ and $R^{14}$ are independently selected from the group consisting of hydrogen, $-OR^{15}$, $-NR^{15}R^{16}$, $-NR^{15}COR^{16}$, $-NR^{15}CO_2R^{16}$, $-NR^{15}CONR^{16}$, $-NR^{15}SO_2R^{16}$, $-COR^{15}$, $-SO_2R^{15}$, nitro, cyano, halogen, aryl, heterocycle, $COOR^{15}$, $CONR^{16}R^{17}$, $SO_2NR^{18}R^{19}$, alkenyl, alkynyl, hydrocarbyl, and substituted hydrocarbyl;
$R^{15}$, $R^{16}$, $R^{17}$, $R^{18}$, $R^{19}$ are independently selected from the group consisting of hydrogen, hydrocarbyl, substituted hydrocarbyl, aryl, and heterocycle, and $R^{16}$ and $R^{17}$ together can optionally form a ring, and $R^{18}$ and $R^{19}$ together can optionally form a ring;
$R^z$ is independently selected from the group consisting of hydrogen hydrocarbyl, substituted hydrocarbyl, $-COR^x$, $-CONR^xR^xSO_2R^x$, and $-CO_2R^x$;
$R^x$ is independently selected from the group consisting of hydrogen, $-NR^4R^5$, and an optionally substituted alkyl, cycloalkyl, heterocycle, or aryl; and
a is either the integer 1 or the integer 2.

Yet still another embodiment of formula (I), where $R^1$ is formula (VI), comprises formula (XIII):

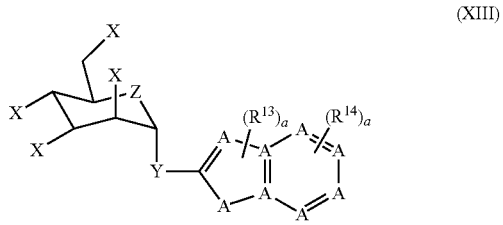

(XIII)

wherein
X is selected from the group consisting of hydrogen, $OR^2$, $SR^2$, $NR^z$;
Z is selected from the group consisting of O, S, $CR^3$ and $NR^4$;
Y is selected from the group consisting of oxygen, sulfur, $CR^3$, $NR^4$, $-N(R^5)CO-$, $-CH_2N(R^5)-$, $-CH_2N(R^5)CO-$, $CO_2$, $SO_2$, $-CH_2O-$, $-CH_2S-$, $CO$, $-CON(R^5)-$, $-SO_2N(R^5)-$, $-O(CH_2)_n-$, $-S(CH_2)_n-$, $-N(CH_2)_n-$, $-(CH_2)_n-$, $NR^5$, and an optionally substituted alkyl, alkene, alkyne, or heterocycle;
$R^2$, $R^3$, $R^4$, $R^5$ are independently selected from the group consisting of hydrogen, hydrocarbyl, and substituted hydrocarbyl;
n is an integer from 1 to 10;
A is independently selected from the group consisting of $CR^6$ and N;
$R^6$ is independently selected from the group consisting of hydrogen, hydrocarbyl, and substituted hydrocarbyl;
$R^{13}$ and $R^{14}$ are independently selected from the group consisting of hydrogen, $-OR^{15}$, $-NR^{15}R^{16}$, $-NR^{15}COR^{16}$, $-NR^{15}CO_2R^{16}$, $-NR^{15}CONR^{16}$, $-NR^{15}SO_2R^{16}$, $-COR^{15}$, $-SO_2R^{15}$, nitro, cyano, halogen, aryl, heterocycle, $COOR^{15}$, $CONR^{16}R^{17}$, $SO_2NR^{18}R^{19}$, alkenyl, alkynyl, hydrocarbyl, and substituted hydrocarbyl;
$R^{15}$, $R^{16}$, $R^{17}$, $R^{18}$, $R^{19}$ are independently selected from the group consisting of hydrogen, hydrocarbyl, substituted hydrocarbyl, aryl, and heterocycle, and $R^{16}$ and $R^{17}$ together can optionally form a ring, and $R^{18}$ and $R^{19}$ together can optionally form a ring;
$R^z$ is independently selected from the group consisting of hydrogen hydrocarbyl, substituted hydrocarbyl, $-COR^x$, $-CONR^xR^xSO_2R^x$, and $-CO_2R^x$;
$R^x$ is independently selected from the group consisting of hydrogen, $-NR^4R^5$, and an optionally substituted alkyl, cycloalkyl, heterocycle, or aryl; and
a is either the integer 1 or the integer 2.

Still another embodiment of formula (I), where $R^1$ is formula (VII), comprises formula (XIV):

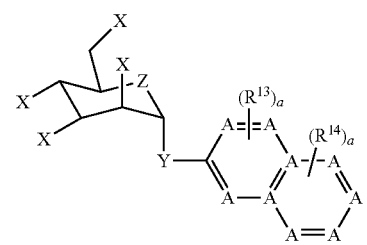

(XIV)

wherein
X is selected from the group consisting of hydrogen, $OR^2$, $SR^2$, $NR^z$;
Z is selected from the group consisting of O, S, $CR^3$ and $NR^4$;
Y is selected from the group consisting of oxygen, sulfur, $CR^3$, $NR^4$, —$N(R^5)CO$—, —$CH_2N(R^5)$—, —$CH_2N(R^5)CO$—, $CO_2$, $SO_2$, —$CH_2O$—, —$CH_2S$—, $CO$, —$CON(R^5)$—, —$SO_2N(R^5)$—, —$O(CH_2)_n$—, —$S(CH_2)_n$—, —$N(CH_2)_n$—, —$(CH_2)_n$—, $NR^5$, and an optionally substituted alkyl, alkene, alkyne, or heterocycle;
$R^2$, $R^3$, $R^4$, $R^5$ are independently selected from the group consisting of hydrogen, hydrocarbyl, and substituted hydrocarbyl;
n is an integer from 1 to 10;
A is independently selected from the group consisting of $CR^6$ and N;
$R^6$ is independently selected from the group consisting of hydrogen, hydrocarbyl, and substituted hydrocarbyl;
$R^{13}$ and $R^{14}$ are independently selected from the group consisting of hydrogen, —$OR^{15}$, —$NR^{15}R^{16}$, —$NR^{15}COR^{16}$, —$NR^{15}CO_2R^{16}$, —$NR^{15}CONR^{16}$, —$NR^{15}SO_2R^{16}$, —$COR^{15}$, —$SO_2R^{15}$, nitro, cyano, halogen, aryl, heterocycle, $COOR^{15}$, $CONR^{16}R^{17}$, $SO_2NR^{15}R^{19}$, alkenyl, alkynyl, hydrocarbyl, and substituted hydrocarbyl;
$R^{15}$, $R^{16}$, $R^{17}$, $R^{18}$, $R^{19}$ are independently selected from the group consisting of hydrogen, hydrocarbyl, substituted hydrocarbyl, aryl, and heterocycle, and $R^{16}$ and $R^{17}$ together can optionally form a ring, and $R^{18}$ and $R^{19}$ together can optionally form a ring;
$R^z$ is independently selected from the group consisting of hydrogen hydrocarbyl, substituted hydrocarbyl, —$COR^x$, —$CONR^xR^xSO_2R^x$, and —$CO_2R^x$;
$R^x$ is independently selected from the group consisting of hydrogen, —$NR^4R^5$, and an optionally substituted alkyl, cycloalkyl, heterocycle, or aryl; and
a is either the integer 1 or the integer 2.

A further embodiment of formula (I), where $R^1$ is formula (VIII), comprises formula (XV):

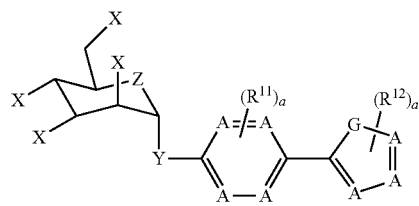

(XV)

wherein
X is selected from the group consisting of hydrogen, $OR^2$, $SR^2$, and $NR^z$;
Z is selected from the group consisting of O, S, $CR^3$ and $NR^4$;
Y is selected from the group consisting of oxygen, sulfur, $CR^3$, $NR^4$, —$N(R^5)CO$—, —$CH_2N(R^5)$—, —$CH_2N(R^5)CO$—, $CO_2$, $SO_2$, —$CH_2O$—, —$CH_2S$—, $CO$, —$CON(R^5)$—, —$SO_2N(R^5)$—, —$O(CH_2)_n$—, —$S(CH_2)_n$—, —$N(CH_2)_n$—, —$(CH_2)_n$—, $NR^5$, and an optionally substituted alkyl, alkene, alkyne, or heterocycle;

$R^2$, $R^3$, $R^4$, $R^5$ are independently selected from the group consisting of hydrogen, hydrocarbyl, and substituted hydrocarbyl;
n is an integer from 1 to 10;
A is independently selected from the group consisting of $CR^6$ and N;
G is selected from the group consisting of S, O, $CR^8$, and $NR^9$;
$R^6$, $R^8$ and $R^9$ are independently selected from the group consisting of hydrogen, hydrocarbyl, and substituted hydrocarbyl;
$R^{11}$ and $R^{12}$ are independently selected from the group consisting of hydrogen, —$OR^{15}$, —$NR^{15}R^{16}$, —$NR^{15}COR^{16}$, —$NR^{15}CO_2R^{16}$, —$NR^{15}CONR^{16}$, —$NR^{15}SO_2R^{16}$, —$COR^{15}$, —$SO_2R^{15}$, nitro, cyano, halogen, aryl, heterocycle, $COOR^{15}$, $CONR^{16}R^{17}$, $SO_2NR^{18}R^{19}$, alkenyl, alkynyl, hydrocarbyl, and substituted hydrocarbyl;
$R^{15}$, $R^{16}$, $R^{17}$, $R^{18}$, $R^{19}$ are independently selected from the group consisting of hydrogen, hydrocarbyl, substituted hydrocarbyl, aryl, and heterocycle, and $R^{16}$ and $R^{17}$ together can optionally form a ring, and $R^{18}$ and $R^{19}$ together can optionally form a ring;
$R^z$ is independently selected from the group consisting of hydrogen hydrocarbyl, substituted hydrocarbyl, —$COR^x$, —$CONR^xR^xSO_2R^x$, and —$CO_2R^x$;
$R^x$ is independently selected from the group consisting of hydrogen, —$NR^4R^5$, and an optionally substituted alkyl, cycloalkyl, heterocycle, or aryl; and
a is either the integer 1 or the integer 2.

A still further another embodiment of formula (I), where $R^1$ is formula (IV), comprises formula (XVI):

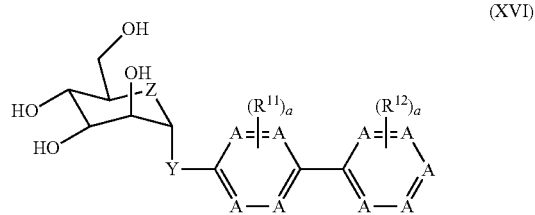

(XVI)

wherein
Z is selected from the group consisting of O, S, $CR^3$ and $NR^4$;
Y is selected from the group consisting of O, S, $CR^3$, and $NR^4$;
A is independently selected from the group consisting of $CR^6$ and N;
$R^3$, $R^4$, and $R^6$ are independently selected from the group consisting of hydrogen, hydrocarbyl, and substituted hydrocarbyl;
$R^{11}$ is independently selected from the group consisting of hydrogen, —$NR^5$, —$OR^5$, nitro, cyano, chloro, bromo, iodo, fluoro, —$COOR^{15}$, —$CONR^{16}R^{17}$, —$SO_2R^{15}$, —$SO_2NR^{18}R^{19}$, methyl, hydrocarbyl, and substituted hydrocarbyl;
$R^{12}$ is independently selected from the group consisting of hydrogen, —$OR^{15}$, —$NR^{15}R^{16}$, —$NR^{15}COR^{16}$, —$NR^{15}CO_2R^{16}$, —$NR^{15}CONR^{16}$, —$NR^{15}SO_2R^{16}$, —$COR^{15}$, —$SO_2R^{15}$, nitro, cyano, halogen, aryl, heterocycle, —$COOR^{15}$, —$CONR^{16}R^{17}$, $SO_2NR^{18}R^{19}$, hydrocarbyl, and substituted hydrocarbyl; and
$R^{15}$, $R^{16}$, $R^{17}$, $R^{18}$, $R^{19}$ are independently selected from the group consisting of hydrogen, hydrocarbyl, substituted hydrocarbyl, aryl, and heterocycle, and $R^{16}$ and $R^{17}$ together can optionally form a ring, and $R^{18}$ and $R^{19}$ together can optionally form a ring; and
a is either the integer 1 or the integer 2.

A still further another embodiment of formula (I), where $R^1$ is formula (IV), comprises formula (XVII):

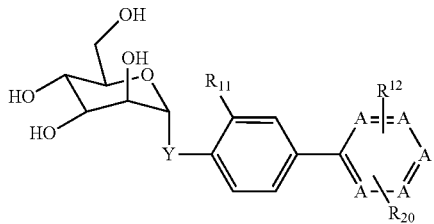

(XVII)

wherein
Y is selected from the group consisting of O, S, $CR^3$, and $NR^4$;
A is independently selected from the group consisting of $CR^6$ and N;
$R^3$, $R^4$, and $R^6$ are independently selected from the group consisting of hydrogen, hydrocarbyl, and substituted hydrocarbyl;
$R^{11}$ is selected from the group consisting of hydrogen, —$NR^5$, —$OR^5$, nitro, cyano, chloro, bromo, iodo, fluoro, —$COOR^{15}$, —$CONR^{16}R^{17}$, —$SO_2R^{15}$, —$SO_2NR^{18}R^{19}$, methyl, hydrocarbyl, and substituted hydrocarbyl;
$R^{12}$ is selected from the group consisting of hydrogen, —$OR^{15}$, —$NR^{15}R^{16}$, —$NR^{15}COR^{16}$, —$NR^{15}CO_2R^{16}$, —$NR^{15}CONR^{16}$, —$NR^{15}SO_2R^{16}$, —$COR^{15}$, —$SO_2R^{15}$, nitro, cyano, halogen, aryl, heterocycle, —$COOR^{15}$, —$CONR^{16}R^{17}$, —$SO_2NR^{18}R^{19}$, hydrocarbyl, and substituted hydrocarbyl;
$R^{20}$ is selected from the group consisting of —$NR^{15}SO_2R^{16}$, —$COOR^{15}$, —$NR^{15}CONR^{16}$, —$CONR^{16}R^{17}$, —$SO_2NR^{18}R^{19}$; and
$R^{15}$, $R^{16}$, $R^{17}$, $R^{18}$, $R^{19}$ are independently selected from the group consisting of hydrogen, hydrocarbyl, substituted hydrocarbyl, aryl, and heterocycle, and $R^{16}$ and $R^{17}$ together can optionally form a ring, and $R^{18}$ and $R^{19}$ together can optionally form a ring.

In a preferred embodiment of formula (XVII), $R^{11}$ is selected from the group consisting of chloro, bromo, iodo, and fluoro, $R^{12}$ is selected from the group consisting of nitro, cyano, —$COOR^{15}$, —$CONR^{16}R^{17}$, and —$SO_2NR^{18}R^{19}$, and $R^{20}$ is selected from the group consisting of —$COOR^{15}$, —$NR^{15}CONR^{16}$, —$CONR^{16}R^{17}$, and —$SO_2NR^{18}R^{19}$.

In another preferred embodiment of formula (XVII), $R^{11}$ is chloro, $R^{12}$ is selected from the group consisting of nitro, cyano, —$COOR^{15}$, —$CONR^{16}R^{17}$, and —$SO_2NR^{18}R^{19}$, and $R^{20}$ is selected from the group consisting of —$COOR^{15}$, —$NR^{15}CONR^{16}$, —$CONR^{16}R^{17}$, and —$SO_2NR^{18}R^{19}$.

A yet further embodiment of formula (I), where $R^1$ is formula (VIII), comprises formula (XVIII):

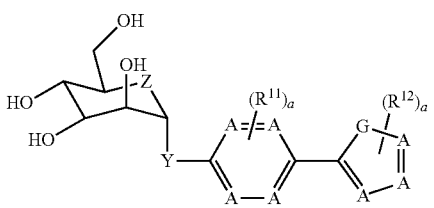

(XVIII)

wherein
Z is selected from the group consisting of O, S, $CR^3$ and $NR^4$;
Y is selected from the group consisting of O, S, $CR^3$, and $NR^4$;
A is independently selected from the group consisting of $CR^6$ and N;
G is selected from the group consisting of S, O, $CR^8$, and $NR^9$;
$R^3$, $R^4$, $R^6$, $R^8$, and $R^9$ are independently selected from the group consisting of hydrogen, hydrocarbyl, and substituted hydrocarbyl;
$R^{11}$ is independently selected from the group consisting of hydrogen, —$NR^5$, —$OR^5$, nitro, cyano, chloro, bromo, iodo, fluoro, —$COOR^{15}$, —$CONR^{16}R^{17}$, —$SO_2R^{15}$, —$SO_2NR^{18}R^{19}$, methyl, hydrocarbyl, and substituted hydrocarbyl;
$R^{12}$ is independently selected from the group consisting of hydrogen, —$OR^{15}$, —$NR^{15}R^{16}$, —$NR^{15}COR^{16}$, —$NR^{15}CO_2R^{16}$, —$NR^{15}CONR^{16}$, —$NR^{15}SO_2R^{16}$, —$COR^{15}$, —$SO_2R^{15}$, nitro, cyano, halogen, aryl, heterocycle, —$COOR^{15}$, —$CONR^{16}R^{17}$, $SO_2NR^{18}R^{19}$, hydrocarbyl, and substituted hydrocarbyl; and
$R^{15}$, $R^{16}$, $R^{17}$, $R^{18}$, $R^{19}$ are independently selected from the group consisting of hydrogen, hydrocarbyl, substituted hydrocarbyl, aryl, and heterocycle, and $R^{16}$ and $R^{17}$ together can optionally form a ring, and $R^{18}$ and $R^{19}$ together can optionally form a ring; and
a is either the integer 1 or the integer 2.

In some embodiments of formula (I), where $R^1$ is formula (VIII), comprises formula (XIX):

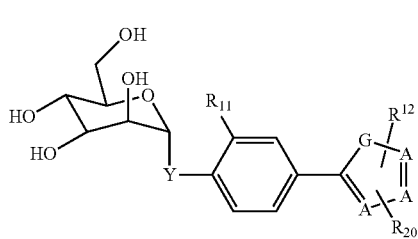

(XIX)

wherein
Y is selected from the group consisting of O, S, $CR^3$, and $NR^4$;
A is independently selected from the group consisting of $CR^6$ and N;
G is selected from the group consisting of S, O, $CR^8$, and $NR^9$;
$R^3$, $R^4$, $R^6$, $R^8$, and $R^9$ are independently selected from the group consisting of hydrogen, hydrocarbyl, and substituted hydrocarbyl;
$R^{11}$ is independently selected from the group consisting of hydrogen, —$NR^5$, —$OR^5$, nitro, cyano, chloro, bromo, iodo, fluoro, —$COOR^{16}$, —$CONR^{16}R^{17}$, —$SO_2R^{16}$, —$SO_2NR^{18}R^{19}$, methyl, hydrocarbyl, and substituted hydrocarbyl;
$R^{12}$ is independently selected from the group consisting of hydrogen, —$OR^{15}$, —$NR^{15}R^{16}$, —$NR^{15}COR^{16}$, —$NR^{15}CO_2R^{16}$, —$NR^{15}CONR^{16}$, —$NR^{15}SO_2R^{16}$, —$COR^{15}$, —$SO_2R^{15}$, nitro, cyano, halogen, aryl, heterocycle, —$COOR^{15}$, —$CONR^{16}R^{17}$, $SO_2NR^{18}R^{19}$, hydrocarbyl, and substituted hydrocarbyl; and
$R^{15}$, $R^{16}$, $R^{17}$, $R^{18}$, $R^{19}$ are independently selected from the group consisting of hydrogen, hydrocarbyl, substituted hydrocarbyl, aryl, and heterocycle, and $R^{16}$ and $R^{17}$ together can optionally form a ring, and $R^{18}$ and $R^{19}$ together can optionally form a ring.

In a preferred embodiment of formula (XIX), $R^{11}$ is selected from the group consisting of chloro, bromo, iodo, and fluoro, $R^{12}$ is selected from the group consisting of —COOR$^{15}$, and —CONR$^{16}R^{17}$, and $R^{20}$ is selected from the group consisting of —COOR$^{15}$, —NR$^{15}$CONR$^{16}$, —CONR$^{16}R^{17}$, and —SO$_2$NR$^{18}R^{19}$.

In another preferred embodiment of formula (XVII), $R^{11}$ is chloro, $R^{12}$ is selected from the group consisting of —COOR$^{15}$, and —CONR$^{16}R^{17}$, and $R^{20}$ is selected from the group consisting of —COOR$^{15}$, —NR$^{15}$CONR$^{16}$, —CONR$^{16}R^{17}$, and —SO$_2$NR$^{18}R^{19}$.

Another aspect of the present invention is a compound of formula (II):

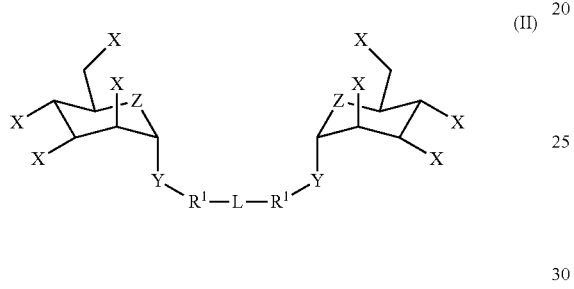

(II)

wherein

X is selected from the group consisting of hydrogen, OR$^2$, SR$^2$, and NR$^z$;

Z is selected from the group consisting of O, S, CR$^3$ and NR$^4$;

Y is selected from the group consisting of oxygen, sulfur, CR$^3$, NR$^4$, —N(R$^5$)CO—, —CH$_2$N(R$^5$)—, —CH$_2$N (R$^5$)CO—, CO$_2$, SO$_2$, —CH$_2$O—, —CH$_2$S—, CO, —CON(R$^5$)—, —SO$_2$N(R$^5$)—, —O(CH$_2$)$_n$—, —S(CH$_2$)$_n$—, —N(CH$_2$)$_n$—, —(CH$_2$)$_n$—, NR$^5$, and an optionally substituted alkyl, alkene, alkyne, or heterocycle;

L is selected from —O(CH$_2$)$_n$O—, —S(CH$_2$)$_n$S—, —N(CH$_2$)$_n$N—, —(CH$_2$)$_n$—, —O[(CH$_2$)$_m$O (CH$_2$)$_n$]$_x$O—, —N(CH$_2$)$_m$—O—(CH$_2$)$_n$N—, heterocycle, alkene, alkyne, —CON[(CH$_2$)$_m$O (CH$_2$)$_n$]$_x$NCO—, —SO$_2$N[(CH$_2$)m—O—(CH$_2$)n] xNO$_2$S—, and NCO[(CH$_2$)$_m$O(CH$_2$)$_n$]$_x$CON—, where L is bound to a ring of R$^1$ at a meta or para position;

R$^2$ is independently selected from the group consisting of hydrogen, COR$^x$, CONR$^x$, hydrocarbyl, and substituted hydrocarbyl;

R$^3$, R$^4$, R$^5$ are independently selected from the group consisting of hydrogen, hydrocarbyl, and substituted hydrocarbyl, R$^z$ is independently selected from the group consisting of hydrogen hydrocarbyl, substituted hydrocarbyl, —COR$^x$, —CONR$^x$R$^x$SO$_2$R$^x$, and —CO$_2$R$^x$;

R$^x$ is independently selected from the group consisting of hydrogen, NR$^4$R$^5$, and an optionally substituted alkyl, cycloalkyl, heterocycle, or aryl;

m, n, and x are integers from 1 to 10; and

R$^1$ is selected from the group comprising Formulas (IIIA), (IIIB), (IV), (V), (VI), (VII) and (VIII):

(IIIA)

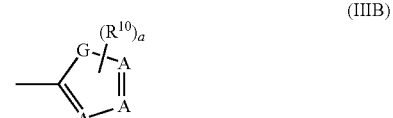

(IIIB)

(IV)

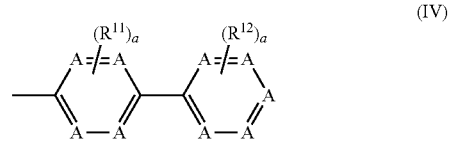

(V)

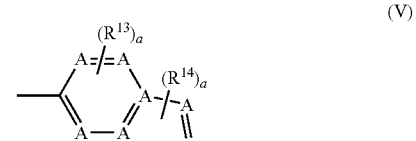

(VI)

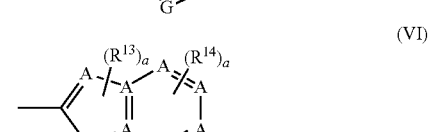

(VII)

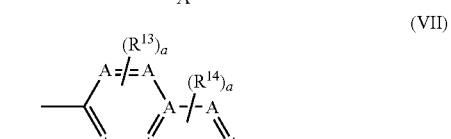

(VIII)

wherein

A is independently selected from the group consisting of CR$^6$ and N;

G is selected from the group consisting of S, O, CR$^8$, and NR$^9$;

R$^6$, R$^8$ and R$^9$ are independently selected from the group consisting of hydrogen, hydrocarbyl, and substituted hydrocarbyl;

R$^{10}$, R$^{11}$, R$^{12}$, R$^{13}$ and R$^{14}$ are independently selected from the group consisting of hydrogen, —OR$^{15}$, —NR$^{15}R^{16}$, —NR$^{15}$COR$^{16}$, —NR$^{15}$CO$_2R^{16}$, —NR$^{15}$CONR$^{16}$, —NR$^{15}$SO$_2R^{16}$, —COR$^{15}$, —SO$_2R^{15}$, nitro, cyano, halogen, aryl, heterocycle, —COOR$^{15}$, —CONR$^{16}R^{17}$, —SO$_2$NR$^{18}R^{19}$, alkenyl, alkynyl, hydrocarbyl, and substituted hydrocarbyl;

R$^{15}$, R$^{16}$, R$^{17}$, R$^{18}$, R$^{19}$ are independently selected from the group consisting of hydrogen, hydrocarbyl, substituted hydrocarbyl, aryl, and heterocycle, and R$^{16}$ and R$^{17}$ together can optionally form a ring, and R$^{18}$ and R$^{19}$ together can optionally form a ring; and a is either the integer 1 or the integer 2.

In an exemplary alternative of each of the foregoing embodiments, a compound comprising formula (I) is a compound comprising any of the Formulas in Table 15.

In a further exemplary alternative of each of the foregoing embodiments, a compound comprising formula (I) is compound number 50, 75, 76, or 77.

Another aspect of the invention is a compound of Formula (XXI):

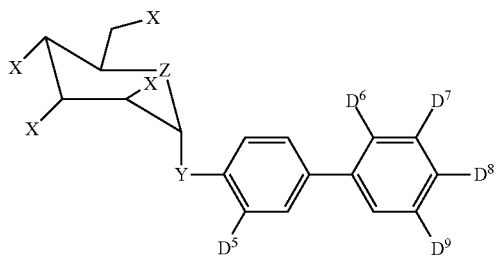

wherein
X is selected from the group consisting of hydrogen, $OD^2$, $SD^2$, $ND^z$;
Z is selected from the group consisting of O, S, $CD^3$ and $ND^4$;
Y is oxygen;
$D^2$, $D^3$, and $D^4$ are independently selected from the group consisting of hydrogen, hydrocarbyl, and substituted hydrocarbyl;
$D^5$ is selected from the group consisting of $CF_3$, halogen, $CH_3$, OMe, hydrocarbyl, and substituted hydrocarbyl;
$D^6$, $D^7$, $D^8$, and $D^9$ are independently selected from the group consisting of hydrogen, —$COD^{10}D^{11}$, —$COND^{10}D^{11}$, —$COOD^{12}$, and —$ND^{12}COND^{10}$, or $D^6$ and $D^7$ may optionally form a cycloalkyl or heterocyclo ring, $D^7$ and $D^8$ may optionally form a cycloalkyl or heterocyclo ring, and $D^8$ and $D^9$ may optionally form a cycloalkyl or heterocyclo ring; and
$D^{10}$, $D^{11}$, and $D^{12}$ are independently selected from the group consisting of hydrogen, hydrocarbyl, substituted hydrocarbyl, aryl, and heterocycle;
$D^{18}$ and $D^{19}$ are independently selected from the group consisting of hydrogen, hydrocarbyl, and substituted hydrocarbyl;
$D^z$ is independently selected from the group consisting of hydrogen, hydrocarbyl, substituted hydrocarbyl, —$COD^x$, —$COND^xD^xSO_2D^x$, and —$CO_2D^x$; and
$D^x$ is independently selected from the group consisting of hydrogen, —$ND^{18}D^{19}$, and an optionally substituted alkyl, cycloalkyl, heterocycle, or aryl.

In one embodiment, a compound of the invention comprises Formula (XXI), wherein
X is selected from the group consisting of $OD^2$;
Z is selected from the group consisting of O, S, $CD^3$ and $ND^4$;
Y is oxygen;
$D^2$, $D^3$, and $D^4$ are independently selected from the group consisting of hydrogen, hydrocarbyl, and substituted hydrocarbyl;
$D^5$ is selected from the group consisting of $CF_3$, halogen, $CH_3$, and OMe;
$D^6$, $D^7$, $D^8$, and $D^9$ are independently selected from the group consisting of hydrogen, —$COD^{10}D^{11}$, —$COND^{10}D^{11}$, —$COOD^{12}$, and —$ND^{12}COND^{10}$, or $D^6$ and $D^7$ may optionally form a cycloalkyl or heterocyclo ring, $D^7$ and $D^8$ may optionally form a cycloalkyl or heterocyclo ring, and $D^8$ and $D^9$ may optionally form a cycloalkyl or heterocyclo ring; and
$D^{10}$, $D^{11}$, and $D^{12}$ are independently selected from the group consisting of hydrogen, hydrocarbyl, substituted hydrocarbyl, aryl, and heterocycle.

In another embodiment, a compound of the invention comprises Formula (XXI), wherein
X is selected from the group consisting of $OD^2$;
Z is selected from the group consisting of O, S, $CD^3$ and $ND^4$;
Y is oxygen;
$D^2$, $D^3$, and $D^4$ are independently selected from the group consisting of hydrogen, hydrocarbyl, and substituted hydrocarbyl;
$D^5$ is selected from the group consisting of $CF_3$, halogen, $CH_3$, and OMe;
$D^6$ and $D^8$ are hydrogen;
$D^7$ and $D^9$ are independently selected from the group consisting of hydrogen, —$COD^{10}D^{11}$, —$COND^{10}D^{11}$, —$COOD^{12}$, and —$ND^{12}COND^{10}$; and
$D^{10}$, $D^{11}$, and $D^{12}$ are independently selected from the group consisting of hydrogen, hydrocarbyl, substituted hydrocarbyl, aryl, and heterocycle.

In yet another embodiment, a compound of the invention comprises Formula (XXI), wherein
X is OH;
Z is O;
Y is oxygen;
$D^2$, $D^3$, and $D^4$ are independently selected from the group consisting of hydrogen, hydrocarbyl, and substituted hydrocarbyl;
$D^5$ is selected from the group consisting of $CF_3$, halogen, $CH_3$, and OMe;
$D^6$ and $D^8$ are hydrogen;
$D^7$ and $D^9$ are independently selected from the group consisting of hydrogen, —$CONHCH_3$, —$COOCH_3$, and —$NHCONH_2$.

Another aspect of the invention is a compound of Formula (XXII):

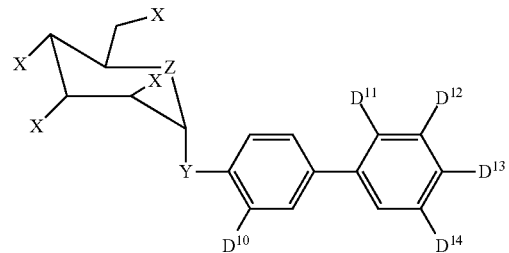

wherein
X is selected from the group consisting of hydrogen, $OD^2$, $SD^2$, $ND^z$;
Z is selected from the group consisting of O, S, $CD^3$ and $ND^4$;
Y is selected from the group consisting of sulfur, $CD^3$, $ND^4$, —$N(D^{18})CO$—, —$CH_2N(D^{18})$—, —$CH_2N(D^{18})CO$—, $CO_2$, $SO_2$, —$CH_2O$—, —$CH_2S$—, $CO$, —$CON(D^{18})$—, —$SO_2N(D^{18})$—, —$O(CH_2)_n$—, —$S(CH_2)_n$—, —$N(CH_2)_n$—, —$(CH_2)_n$—, $ND^{18}$, and an optionally substituted alkyl, alkene, alkyne, or heterocycle;
n is an integer from 1 to 10;
$D^2$, $D^3$, and $D^4$ are independently selected from the group consisting of hydrogen, hydrocarbyl, and substituted hydrocarbyl;

$D^{10}$ is selected from the group consisting of hydrogen, $CF_3$, halogen, $CH_3$, OMe, hydrocarbyl, and substituted hydrocarbyl;

$D^{11}$, $D^{12}$, $D^{13}$, and $D^{14}$ are independently selected from the group consisting of hydrogen, $—COD^{15}D^{16}$, $—COND^{15}D^{16}$, $—COOD^{17}$, and $—ND^{17}COND^{15}$, or $D^{11}$ and $D^{12}$ may optionally form a cycloalkyl or heterocyclo ring, $D^{12}$ and $D^{13}$ may optionally form a cycloalkyl or heterocyclo ring, and $D^{13}$ and $D^{14}$ may optionally form a cycloalkyl or heterocyclo ring;

$D^{15}$, $D^{16}$, and $D^{17}$ are independently selected from the group consisting of hydrogen, hydrocarbyl, substituted hydrocarbyl, aryl, and heterocycle;

$D^{18}$ and $D^{19}$ are independently selected from the group consisting of hydrogen, hydrocarbyl, and substituted hydrocarbyl; and $D^z$ is independently selected from the group consisting of hydrogen hydrocarbyl, substituted hydrocarbyl, $—COD^x$, $—COND^xD^xSO_2D^x$, and $—CO_2D^x$; and $D^x$ is independently selected from the group consisting of hydrogen, $—ND^{18}D^{19}$, and an optionally substituted alkyl, cycloalkyl, heterocycle, or aryl.

In one embodiment, a compound of the invention comprises Formula (XXII), wherein X is $OD^2$;

Z is selected from the group consisting of O, S, $CD^3$ and $ND^4$;

Y is selected from the group consisting of sulfur, $CD^3$, $ND^4$, $—N(D^{18})CO—$, $—CH_2N(D^{18})—$, $—CH_2N(D^{18})CO—$, $CO_2$, $SO_2$, $—CH_2O—$, $—CH_2S—$, $CO$, $—CON(D^{18})—$, $—SO_2N(D^{18})—$, $—O(CH_2)_n—$, $—S(CH_2)_n—$, $—N(CH_2)_n—$, $—(CH_2)_n—$, $ND^{18}$, and an optionally substituted alkyl, alkene, alkyne, or heterocycle;

n is an integer from 1 to 10;

$D^2$, $D^3$, $D^4$ and $D^{18}$ are independently selected from the group consisting of hydrogen, hydrocarbyl, and substituted hydrocarbyl;

$D^{10}$ is selected from the group consisting of hydrogen, $CF_3$, halogen, $CH_3$, and OMe;

$D^{11}$, $D^{12}$, $D^{13}$, and $D^{14}$ are independently selected from the group consisting of hydrogen, $—COD^{15}D^{16}$, $—COND^{15}D^{16}$, $—COOD^{17}$, and $—ND^{17}COND^{15}$, or $D^{11}$ and $D^{12}$ may optionally form a cycloalkyl or heterocyclo ring, $D^{12}$ and $D^{13}$ may optionally form a cycloalkyl or heterocyclo ring, and $D^{13}$ and $D^{14}$ may optionally form a cycloalkyl or heterocyclo ring; and $D^{15}$, $D^{16}$, and $D^{17}$ are independently selected from the group consisting of hydrogen, hydrocarbyl, substituted hydrocarbyl, aryl, and heterocycle.

In another embodiment, a compound of the invention comprises Formula (XXII), wherein X is $OD^2$;

Z is selected from the group consisting of O, S, $CD^3$ and $ND^4$;

Y is selected from the group consisting of sulfur, $CD^3$, $ND^4$, $—N(D^{18})CO—$, $—CH_2N(D^{18})—$, $—CH_2N(D^{18})CO—$, $CO_2$, $SO_2$, $—CH_2O—$, $—CH_2S—$, $CO$, $—CON(D^{18})—$, $—SO_2N(D^{18})—$, $—O(CH_2)_n—$, $—S(CH_2)_n—$, $—N(CH_2)_n—$, $—(CH_2)_n—$, and $ND^{18}$;

n is an integer from 1 to 10;

$D^2$, $D^3$, $D^4$ and $D^{18}$ are independently selected from the group consisting of hydrogen, hydrocarbyl, and substituted hydrocarbyl;

$D^{10}$ is selected from the group consisting of hydrogen, $CF_3$, halogen, $CH_3$, and OMe;

$D^{11}$, $D^{12}$, $D^{13}$, and $D^{14}$ are independently selected from the group consisting of hydrogen, $—COD^{15}D^{16}$, $—COND^{15}D^{16}$, $—COOD^{17}$, $—ND^{17}COND^{15}$; and $D^{15}$, $D^{16}$, and $D^{17}$ are independently selected from the group consisting of hydrogen, hydrocarbyl, substituted hydrocarbyl, aryl, and heterocycle.

In yet another embodiment, a compound of the invention comprises Formula (XXII), wherein X is OH;

Z is selected from the group consisting of O, S, $CD^3$ and $ND^4$;

Y is selected from the group consisting of sulfur, $CD^3$, $ND^4$, $—N(D^{18})CO—$, and $—CH_2N(D^{18})$;

$D^3$, $D^4$ and $D^{18}$ are independently selected from the group consisting of hydrogen, hydrocarbyl, and substituted hydrocarbyl;

$D^{10}$ is selected from the group consisting of hydrogen, $CF_3$, halogen, $CH_3$, and OMe;

$D^{11}$ and $D^{13}$ are hydrogen; and $D^{12}$ and $D^{14}$ are independently selected from the group consisting of hydrogen, $—CONHCH_3$, $—COOCH_3$, and $—NHCONH_2$.

In still yet another embodiment, a compound of the invention comprises Formula (XXII), wherein X is OH;

Z is selected from the group consisting of O, S, $CD^3$ and $ND^4$;

Y is selected from the group consisting of $CD^3$ and $—CH_2N(D^{18})$;

$D^3$, $D^4$ and $D^{18}$ are independently selected from the group consisting of hydrogen, hydrocarbyl, and substituted hydrocarbyl;

$D^{10}$ is selected from the group consisting of hydrogen, $CF_3$, halogen, $CH_3$, and OMe;

$D^{11}$ and $D^{13}$ are hydrogen; and $D^{12}$ and $D^{14}$ are independently selected from the group consisting of hydrogen, $—CONHCH_3$, $—COOCH_3$, and $—NHCONH_2$.

Yet another aspect of the invention is a compound of the Formula (XXIII):

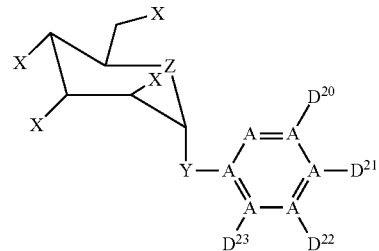

wherein

X is selected from the group consisting of hydrogen, $OD^2$, $SD^2$, $ND^z$;

Z is selected from the group consisting of O, S, $CD^3$ and $ND^4$;

Y is selected from the group consisting of oxygen, sulfur, $CD^3$, $ND^4$, $—N(D^5)CO—$, $—CH_2N(D^5)—$, $—CH_2N(D^5)CO—$, $CO_2$, $SO_2$, $—CH_2O—$, $—CH_2S—$, $CO$, $—CON(D^5)—$, $—SO_2N(D^5)—$, $—O(CH_2)_n—$, $—S(CH_2)_n—$, $—N(CH_2)_n—$, $—(CH_2)_n—$, $ND^5$, and an optionally substituted alkyl, alkene, alkyne, or heterocycle;

$D^2$, $D^3$, $D^4$, $D^5$ are independently selected from the group consisting of hydrogen, hydrocarbyl, and substituted hydrocarbyl;

n is an integer from 1 to 10;

A is independently selected from the group consisting of $CD^6$ and N;

$D^6$ is selected from the group consisting of hydrogen, hydrocarbyl, and substituted hydrocarbyl;

$D^{20}$ and $D^{22}$ are selected from the group consisting of hydrogen and —$COOD^{15}$;

$D^{21}$ is selected from the group consisting of hydrogen, a five membered cycloalkyl or heterocyclo ring, and a halogen;

$D^{23}$ is selected from the group consisting of hydrogen, halogen, hydrocarbyl, and substituted hydrocarbyl;

$D^{15}$ is selected from the group consisting of hydrogen, hydrocarbyl, substituted hydrocarbyl, aryl, and heterocycle;

$D^z$ is independently selected from the group consisting of hydrogen hydrocarbyl, substituted hydrocarbyl, —$COD^x$, —$COND^xD^xSO_2D^x$, and —$CO_2D^x$; and $D^x$ is independently selected from the group consisting of hydrogen, —$ND^4D^5$, and an optionally substituted alkyl, cycloalkyl, heterocycle, or aryl.

In one embodiment, a compound of the invention comprises Formula (XXIII), wherein X is $OD^2$;

Z is selected from the group consisting of O, S, $CD^3$ and $ND^4$;

Y is selected from the group consisting of oxygen, $CD^3$, —$CH_2N(D^5)CO$—;

$D^2$, $D^3$, $D^4$, $D^5$ are independently selected from the group consisting of hydrogen, hydrocarbyl, and substituted hydrocarbyl;

A is $CD^6$;

$D^6$ is selected from the group consisting of hydrogen, hydrocarbyl, and substituted hydrocarbyl;

$D^{20}$ and $D^{22}$ are selected from the group consisting of hydrogen and —$COOD^{15}$;

$D^{21}$ is selected from the group consisting of hydrogen, halogen, and a five membered cycloalkyl or heterocyclo ring;

$D^{23}$ is selected from the group consisting of hydrogen, halogen, hydrocarbyl, and substituted hydrocarbyl; and $D^{15}$ is selected from the group consisting of hydrogen, hydrocarbyl, substituted hydrocarbyl, aryl, and heterocycle.

In another embodiment, a compound of the invention comprises Formula (XXIII), wherein X is OH;

Z is selected from the group consisting of O, S, $CD^3$ and $ND^4$;

Y is selected from the group consisting of oxygen, $CD^3$, —$CH_2N(D^5)CO$—;

$D^3$, $D^4$, and $D^5$ are independently selected from the group consisting of hydrogen, hydrocarbyl, and substituted hydrocarbyl;

A is $CD^6$;

$D^6$ is selected from the group consisting of hydrogen, hydrocarbyl, and substituted hydrocarbyl;

$D^{20}$ and $D^{22}$ are selected from the group consisting of hydrogen and —$COOD^{15}$;

$D^{21}$ is selected from the group consisting of hydrogen, halogen, a five membered cycloalkyl or heterocyclo ring;

$D^{23}$ is selected from the group consisting of hydrogen, halogen, hydrocarbyl, and substituted hydrocarbyl; and $D^{15}$ is selected from the group consisting of hydrogen, hydrocarbyl, substituted hydrocarbyl, aryl, and heterocycle.

In yet another embodiment, a compound of the invention comprises Formula (XXIII), wherein X is OH;

Z is selected from the group consisting of O, S, $CD^3$ and $ND^4$;

Y is selected from the group consisting of oxygen, $CD^3$, —$CH_2N(D^5)CO$—;

$D^3$, $D^4$, and $D^5$ are independently selected from the group consisting of hydrogen, hydrocarbyl, and substituted hydrocarbyl;

A is $CD^6$;

$D^6$ is selected from the group consisting of hydrogen, hydrocarbyl, and substituted hydrocarbyl;

$D^{20}$ and $D^{22}$ are —$COOD^{15}$;

$D^{21}$ and $D^{23}$ and hydrogen; and $D^{15}$ is selected from the group consisting of hydrogen, hydrocarbyl, substituted hydrocarbyl, aryl, and heterocycle.

In still yet another embodiment, a compound of the invention comprises Formula (XXIII), wherein X is OH;

Z is selected from the group consisting of O, S, $CD^3$ and $ND^4$;

Y is selected from the group consisting of oxygen, $CD^3$, —$CH_2N(D^5)CO$—;

$D^3$, $D^4$, $D^5$, $D^8$, and $D^9$ are independently selected from the group consisting of hydrogen, hydrocarbyl, and substituted hydrocarbyl;

A is $CD^6$;

$D^6$ is selected from the group consisting of hydrogen, hydrocarbyl, and substituted hydrocarbyl;

$D^{20}$ and $D^{22}$ are hydrogen;

$D^{21}$ is selected from the group consisting of hydrogen, halogen,

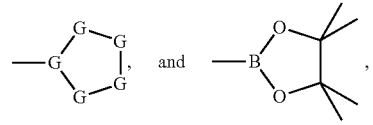

wherein G is selected from the group consisting of S, O, $CD^8$, and $ND^9$; and $D^{23}$ is selected from the group consisting of hydrogen, halogen, hydrocarbyl, and substituted hydrocarbyl.

Still yet another aspect of the invention encompasses a compound of Formula (XXIV):

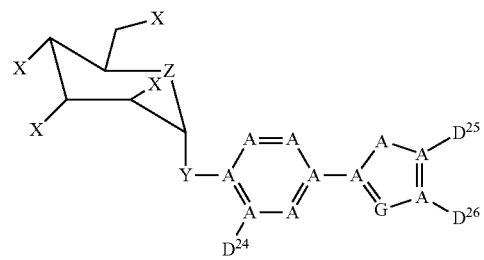

wherein

X is selected from the group consisting of hydrogen, $OD^2$, $SD^2$, and $ND^z$;

Z is selected from the group consisting of O, S, $CD^3$ and $ND^4$;

Y is selected from the group consisting of oxygen, sulfur, $CD^3$, $ND^4$, —$N(D^5)CO$—, —$CH_2N(D^5)$—, —$CH_2N(D^5)CO$—, $CO_2$, $SO_2$, —$CH_2O$—, —$CH_2S$—, $CO$, —$CON(D^5)$—, —$SO_2N(D^5)$—, —$O(CH_2)_n$—, —$S(CH_2)_n$—, —$N(CH_2)_n$—, —$(CH_2)_n$—, $ND^5$, and an optionally substituted alkyl, alkene, alkyne, or heterocycle;

$D^2$, $D^3$, $D^4$, $D^5$ are independently selected from the group consisting of hydrogen, hydrocarbyl, and substituted hydrocarbyl;

n is an integer from 1 to 10;

A is independently selected from the group consisting of $CD^6$ and N;

G is selected from the group consisting of S, O, $CD^8$, and $ND^9$;

$D^6$, $D^8$ and $D^9$ are independently selected from the group consisting of hydrogen, hydrocarbyl, and substituted hydrocarbyl;

$D^{24}$ is selected from the group consisting of hydrogen, halogen, hydrocarbyl, and substituted hydrocarbyl;

$D^{25}$ and $D^{26}$ is selected from the group consisting of hydrogen, —$NHCONH_2$, —$COOMe$, and —$CONHMe$, and $D^{25}$ and $D^{26}$ can optionally form a cycloalkyl or heterocyclo ring;

$D^z$ is independently selected from the group consisting of hydrogen hydrocarbyl, substituted hydrocarbyl, —$COD^x$, —$COND^xD^xSO_2D^x$, and —$CO_2D^x$; and $D^x$ is independently selected from the group consisting of hydrogen, —$ND^4D^5$, or an optionally substituted alkyl, cycloalkyl, heterocycle, or aryl.

In one embodiment, a compound of the invention encompasses Formula (XXIV) wherein:

X is selected from the group consisting of hydrogen, $OD^2$, and $SD^2$;

Z is selected from the group consisting of O, S, $CD^3$ and $ND^4$;

Y is selected from the group consisting of oxygen, sulfur, $CD^3$, $ND^4$, —$N(D^5)CO$—, —$CH_2N(D^5)$—, —$CH_2N(D^5)CO$—, $CO_2$, $SO_2$, —$CH_2O$—, —$CH_2S$—, $CO$, —$CON(D^5)$—, —$SO_2N(D^5)$—, —$O(CH_2)_n$—, —$S(CH_2)_n$—, —$N(CH_2)_n$—, —$(CH_2)_n$—, $ND^5$, and an optionally substituted alkyl, alkene, alkyne, or heterocycle;

$D^2$, $D^3$, $D^4$, $D^5$ are independently selected from the group consisting of hydrogen, hydrocarbyl, and substituted hydrocarbyl;

n is an integer from 1 to 10;

A is independently selected from the group consisting of $CD^6$ and N;

G is selected from the group consisting of S, O, $CD^8$, and $ND^9$;

$D^6$, $D^8$ and $D^9$ are independently selected from the group consisting of hydrogen, hydrocarbyl, and substituted hydrocarbyl;

$D^{24}$ is selected from the group consisting of hydrogen, halogen, hydrocarbyl, and substituted hydrocarbyl;

$D^{25}$ and $D^{26}$ is selected from the group consisting of hydrogen, —$NHCONH_2$, —$COOMe$, and —$CONHMe$, or $D^{25}$ and $D^{26}$ can optionally form a cycloalkyl or heterocyclo ring.

In another embodiment, a compound of the invention encompasses Formula (XXIV) wherein:

X is $OD^2$;

Z is selected from the group consisting of O, S, $CD^3$ and $ND^4$;

Y is selected from the group consisting of oxygen, sulfur, $CD^3$, $ND^4$, —$N(D^5)CO$—, —$CH_2N(D^5)$—, —$CH_2N(D^5)CO$—, $CO_2$, $SO_2$, —$CH_2O$—, —$CH_2S$—, $CO$, —$CON(D^5)$—, —$SO_2N(D^5)$—, —$O(CH_2)_n$—, —$S(CH_2)_n$—, —$N(CH_2)_n$—, —$(CH_2)_n$—, and $ND^5$;

$D^2$, $D^3$, $D^4$, $D^5$ are independently selected from the group consisting of hydrogen, hydrocarbyl, and substituted hydrocarbyl;

n is an integer from 1 to 10;

A is independently selected from the group consisting of $CD^6$ and N;

G is selected from the group consisting of S, O, $CD^8$, and $ND^9$;

$D^6$, $D^8$ and $D^9$ are independently selected from the group consisting of hydrogen, hydrocarbyl, and substituted hydrocarbyl;

$D^{24}$ is selected from the group consisting of hydrogen, halogen, hydrocarbyl, and substituted hydrocarbyl;

$D^{25}$ and $D^{26}$ are selected from the group consisting of hydrogen, —$NHCONH_2$, —$COOMe$, and —$CONHMe$, or $D^{25}$ and $D^{26}$ can optionally form the structure:

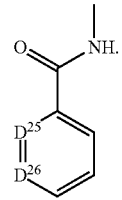

In yet another embodiment, a compound of the invention encompasses a compound of Formula (XXIV) wherein:

X is $OD^2$;

Z is selected from the group consisting of O, S, $CD^3$ and $ND^4$;

Y is selected from the group consisting of oxygen, $CD^3$, $ND^4$, and —$CH_2N(D^5)$—;

$D^2$, $D^3$, $D^4$, $D^5$ are independently selected from the group consisting of hydrogen, hydrocarbyl, and substituted hydrocarbyl;

A is independently selected from the group consisting of $CD^6$ and N;

G is selected from the group consisting of S, O, $CD^8$, and $ND^9$;

$D^6$, $D^8$ and $D^9$ are independently selected from the group consisting of hydrogen, hydrocarbyl, and substituted hydrocarbyl;

$D^{24}$ is selected from the group consisting of hydrogen, halogen, $CH_3$, $CF_3$, and OMe;

$D^{25}$ and $D^{26}$ are selected from the group consisting of hydrogen, —$NHCONH_2$, —$COOMe$, and —$CONHMe$, or $D^{25}$ and $D^{26}$ can optionally form the structure

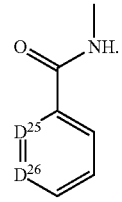

In an exemplary alternative of each of the foregoing embodiments, a compound comprising Formula (XXI) is a compound comprising any of the Formulas in Table 21 or 22.

In a further exemplary alternative of each of the foregoing embodiments, a compound of the invention is 4ZFH284 or 4ZFH269 from Table 22.

In certain embodiments, the sugar residue of the above compounds may encompass any stereoisomer of mannose. In other embodiments, the sugar residue of the above compounds may encompass any stereoisomer of mannose other than glucose. In an exemplary embodiment, the sugar residue of the above compounds is alpha D mannose.

Exemplary methods of synthesizing a compound of the invention are detailed in the Examples.

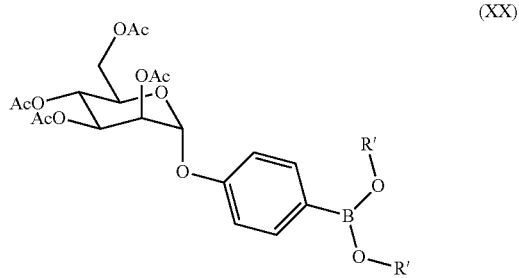

A compound of the invention may also be an intermediate in the synthesis of a compound of formula (I)-(XIX). For instance, in one embodiment, a compound of the invention may be an ester intermediate in the synthesis of a compound of formula (I)-(XIX). In another embodiment, a compound of the invention may be a boronate ester of a mannoside or a boronic acid ester of a mannoside. In yet another embodiment, a compound of the invention may have the formula (XX), wherein R' is selected from H, alkyl, or both R' groups may together form a ring (for instance, see the synthesis of compound 77 detailed in the Examples below). In still another embodiment, a compound of the invention may be a compound illustrated in Schemes 1, 2, 3, $1^a$, $2^a$, $3^a$, $4^a$, or $5^a$ in the Examples below.

A compound of the invention may also comprise an imaging agent, such as a fluorescent moiety. For example, see compounds 98 and 99 of Table 15. In an exemplary embodiment, the imaging agent is bound to the sugar portion of a compound of the invention, either directly, or via a linker.

Compounds of the invention may block the function of FimH of the type I pili of pathogenic bacteria and prevent bacterial adherence and invasion and thus prevent bacterial amplification in the IBC and subsequent spreading and repeated rounds of amplification via new generation IBCs.

FimH functional assays used to measure activity of the compounds are known to individuals skilled in the art. Non-limiting examples of functional assays include hemmagglutination titer using guinea pig red blood cells, affinity of binding to FimH, and the ability of the compounds to prevent biofilm formation.

In some embodiments, activity of the compound is measured using hemmagglutination titer of guinea pig red blood cells. Hemagglutination of guinea pig red blood cells by type1 piliated UPEC is dependent upon FimH mannose binding ability and serial dilutions allow a quantitative analysis. Hemagglutination titer may generally be defined as the amount of compound required for decreasing hemagglutination by 75%. In some embodiments, the hemmagglutination titer of the compound of the invention may be less than about 14, 13, 12, 11, 10, 9, 8, 7, 6, 5, 4, 3, 2, or 1 µM. In a preferred alternative of the embodiments, the hemmagglutination titer of the compound of the invention may be less than about 9 µM. In another preferred alternative of the embodiments, the hemmagglutiantion titer of the compound of the invention may be less than about 7 µM. In yet another preferred alternative of the embodiments, the hemmagglutination titer of the compound of the invention may less than about 1 µM.

In yet other embodiments, activity of the compound may be measured using the ability of the compound to prevent or disrupt biofilm formation. In general, titration curves measuring the ability of a compound inhibit biofilm formation may be performed to determine the $IC_{50}$. In some embodiments, the $IC_{50}$ of the compound may be less than about 700, 600, 500, 400, 300, 200 or 100 µM. In other embodiments, the $IC_{50}$ of the compound may be less than about 500, 400, 300, 200, 100, 50, 40, 30, 20 10, 9, 8, 7, 6, or 5 µM. In preferred embodiments, the $IC_{50}$ of the compound may be less than about 20 µM. In other preferred embodiments, the $IC_{50}$ of the compound may be less than about 9 µM.

II. Combinations

Another aspect of the present invention encompasses a combination of a compound of the invention (described in Section I above) with one or more bactericidal compounds. In some embodiments, a compound of the invention may comprise a combination with 1, 2, 3, 4, or 5 bactericidal compounds. In one embodiment, the bactericidal compound is an antibiotic. Suitable antibiotics are known in the art, and may include Amikacin, Gentamicin, Kanamycin, Neomycin, Netilmicin, Tobramycin, Paromomycin, Geldanamycin, Herbimycin, Carbacephem, Loracarbef, Ertapenem, Doripenem, Imipenem/Cilastatin, Meropenem, Cefadroxil, Cefazolin, Cefalotin, Cefalexin, Cephalosporins, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime, Ceftobiprole, Teicoplanin, Vancomycin, Telavancin, Clindamycin, Lincomycin, Azithromycin, Clarithromycin, Dirithromycin, Erythromycin, Roxithromycin, Troleandomycin, Telithromycin, Spectinomycin, Aztreonam, Furazolidone, Nitrofurantoin, Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Temocillin, Ticarcillin, Bacitracin, Colistin, Polymyxin B, Ciprofloxacin, Enoxacin, Gatifloxacin, Levofloxacin, Lomefloxacin, Moxifloxacin, Nalidixic acid, Norfloxacin, Ofloxacin, Trovafloxacin, Grepafloxacin, Sparfloxacin, Temafloxacin, Mafenide, Sulfonamidochrysoidine, Sulfacetamide, Sulfadiazine, Silver sulfadiazine, Sulfamethizole, Sulfamethoxazole (SMZ), Sulfanilimide, Sulfasalazine, Sulfisoxazole, Trimethoprim (TMP), TrimethoprimSulfamethoxazole (such as Bactrim, Septra), Demeclocycline, Doxycycline, Minocycline, Oxytetracycline, Tetracycline, Clofazimine, Dapsone, Capreomycin, Cycloserine, Ethambutol, Ethionamide, Isoniazid, Pyrazinamide, Rifampicin, Rifabutin, Rifapentine, Streptomycin, Arsphenamine, Chloramphenicol, Fosfomycin, Fusidic acid, Linezolid, Metronidazole, Mupirocin, Platensimycin, Quinupristin/Dalfopristin, Rifaximin, Thiamphenicol, or Timidazole. In an exemplary embodiment, the antibiotic is TMP, SMZ, or a combination thereof.

III. Pharmaceutical Compositions

Yet another aspect of the invention encompasses a pharmaceutical composition. A compound of the invention described in section I above may exist in tautomeric, geometric or stereoisomeric forms. The present invention contemplates all such compounds, including cis- and trans-geometric isomers, E- and Z-geometric isomers, R- and S-enantiomers, diastereomers, d-isomers, l-isomers, the racemic mixtures thereof and other mixtures thereof. Pharmaceutically acceptable salts of such tautomeric, geometric or stereoisomeric forms are also included within the invention. The terms "cis" and "trans", as used herein, denote a form of geometric isomerism in which two carbon atoms connected by a double bond will each have a hydrogen atom on the same side of the double bond ("cis") or on opposite sides of the double bond ("trans"). Some of the compounds described contain alkenyl groups, and are meant to include both cis and trans or "E" and "Z" geometric forms. Furthermore, some of the compounds described contain one or more stereocenters and are meant to include R, S, and mixtures of R and S forms for each stereocenter present.

In a further embodiment, the inhibitors of the present invention may be in the form of free bases or pharmaceutically acceptable acid addition salts thereof. The term "pharmaceutically-acceptable salts" are salts commonly used to form alkali metal salts and to form addition salts of free acids or free bases. The nature of the salt may vary, provided that it is pharmaceutically acceptable. Suitable pharmaceutically acceptable acid addition salts of compounds for use in the present methods may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, stearic, algenic, algenic, hydroxybutyric, salicylic, galactaric and galacturonic acid. Suitable pharmaceutically-acceptable base addition salts of compounds of use in the present methods include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine-(N-methylglucamine) and procaine. All of these salts may be prepared by conventional means from the corresponding compound by reacting, for example, the appropriate acid or base with any of the compounds of the invention.

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can be used. Mixtures of solvents and wetting agents such as those discussed above are also useful.

Solid dosage forms for oral administration may include capsules, tablets, pills, powders, and granules. In such solid dosage forms, the compound is ordinarily combined with one or more adjuvants appropriate to the indicated route of administration. If administered per os, the compound can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, or magnesium or calcium carbonate or bicarbonate. Tablets and pills can additionally be prepared with enteric coatings.

For therapeutic purposes, formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art. For instance, a compound of the invention may be administered with a carrier. Non-limiting examples of such a carrier include protein carriers and lipid carriers.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The amount of the compound of the invention that may be combined with the carrier materials to produce a single dosage of the composition will vary depending upon the subject and the particular mode of administration. Those skilled in the art will appreciate that dosages may also be determined with guidance from Goodman & Goldman's The Pharmacological Basis of Therapeutics, Ninth Edition (1996), Appendix II, pp. 1707-1711 and from Goodman & Goldman's The Pharmacological Basis of Therapeutics, Tenth Edition (2001), Appendix II, pp. 475-493.

A compound of the invention may also be formulated as a prodrug. Such a prodrug formulation may increase the bioavailability of a compound of the invention. In one embodiment, the sugar portion of a compound of the invention may encompass a prodrug. In another embodiment $R^1$ may comprise a prodrug. Non-limiting examples of a compound of the invention formulated as a prodrug include the compounds below:

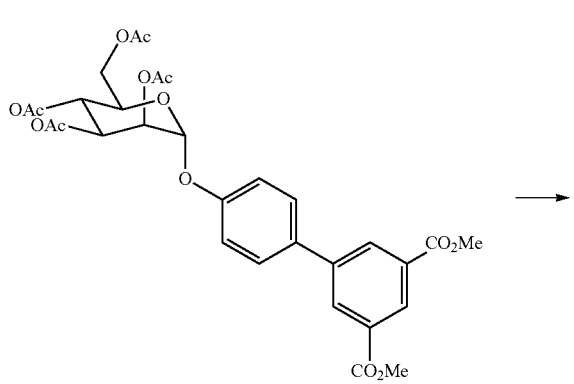

PRODRUG
Compound 35-tetraacetate

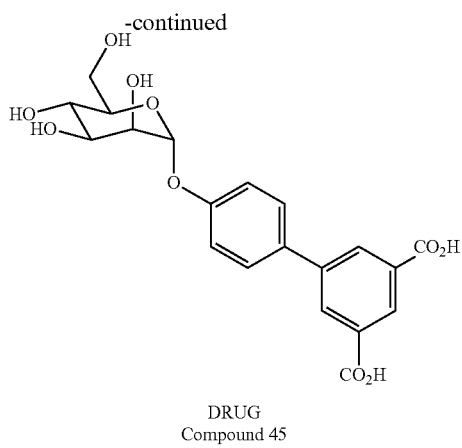

DRUG
Compound 45

IV. Methods of the Invention

Compounds of the invention may be used in methods of treating a bacterial infection and methods of reducing resistance to a bactericidal compound in a bacterium.

(a) Methods of Treating a Bacterial Infection

One embodiment of the invention encompasses a method for treating bacterial infections. As used herein, "treating" refers to preventing infection in a subject not currently infected, and reducing or eliminating infection in a subject that is currently infected. Generally, such a method comprises administering a pharmaceutical composition comprising a compound of the invention to a subject. As used herein, "subject" includes any mammal prone to urinary tract infections by $E.$ $coli$. In one embodiment, a subject is prone to recurring UTIs. In some embodiments, a subject may not have clinical symptoms of a UTI. In such embodiments, the subject may have a latent infection. In other embodiments, a subject may have clinical symptoms of a UTI.

In some embodiments, a compound of the invention may be administered to a subject in combination with a bactericidal compound as described in Section II above. When administered in a combination, a compound of the invention may be administered before, simultaneously, or after administration of a bactericidal compound. When administered before or after a bactericidal compound, the time between administration of a compound of the invention and a bactericidal compound may be about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 min. In another embodiment, the time between administration of a compound of the invention and a bactericidal compound may be about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, or 72 hours.

A compound or pharmaceutical composition of the invention may be administered by several different means that will deliver a therapeutically effective dose. Such compositions may be administered orally, parenterally, by inhalation spray, rectally, intradermally, intracisternally, intraperitoneally, transdermally, bucally, as an oral or nasal spray, topically (i.e. powders, ointments or drops), or via a urinary cathetar in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. In an exemplary embodiment, the pharmaceutical composition will be administered in an oral dosage form. Formulation of drugs is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

The amount of a compound of the invention that constitutes an "effective amount" can and will vary. The amount will depend upon a variety of factors, including whether the administration is in single or multiple doses, and individual subject parameters including age, physical condition, size, and weight. Those skilled in the art will appreciate that dosages may also be determined with guidance from Goodman & Goldman's The Pharmacological Basis of Therapeutics, Ninth Edition (1996), Appendix II, pp. 1707-1711 and from Goodman & Goldman's The Pharmacological Basis of Therapeutics, Tenth Edition (2001), Appendix II, pp. 475-493.

In order to selectively control the release of an inhibitor to a particular region of the gastrointestinal tract for release, the pharmaceutical compositions of the invention may be manufactured into one or several dosage forms for the controlled, sustained or timed release of one or more of the ingredients. In this context, typically one or more of the ingredients forming the pharmaceutical composition is microencapsulated or dry coated prior to being formulated into one of the above forms. By varying the amount and type of coating and its thickness, the timing and location of release of a given ingredient or several ingredients (in either the same dosage form, such as a multi-layered capsule, or different dosage forms) may be varied.

In an exemplary embodiment, the coating may be an enteric coating. The enteric coating generally will provide for controlled release of the ingredient, such that drug release can be accomplished at some generally predictable location in the lower intestinal tract below the point at which drug release would occur without the enteric coating. In certain embodiments, multiple enteric coatings may be utilized. Multiple enteric coatings, in certain embodiments, may be selected to release the ingredient or combination of ingredients at various regions in the lower gastrointestinal tract and at various times.

As will be appreciated by a skilled artisan, the encapsulation or coating method can and will vary depending upon the ingredients used to form the pharmaceutical composition and coating, and the desired physical characteristics of the microcapsules themselves. Additionally, more than one encapsulation method may be employed so as to create a multi-layered microcapsule, or the same encapsulation method may be employed sequentially so as to create a multi-layered microcapsule. Suitable methods of microencapsulation may include spray drying, spinning disk encapsulation (also known as rotational suspension separation encapsulation), supercritical fluid encapsulation, air suspension microencapsulation, fluidized bed encapsulation, spray cooling/chilling (including matrix encapsulation), extrusion encapsulation, centrifugal extrusion, coacervation, alginate beads, liposome encapsulation, inclusion encapsulation, colloidosome encapsulation, sol-gel microencapsulation, and other methods of microencapsulation known in the art. Detailed information concerning materials, equipment and processes for preparing coated dosage forms may be found in Pharmaceutical Dosage Forms: Tablets, eds. Lieberman et al. (New York: Marcel Dekker, Inc., 1989), and in Ansel et al., Pharmaceutical Dosage Forms and Drug Delivery Systems, 6th Ed. (Media, Pa.: Williams & Wilkins, 1995).

A bacterium may be contacted with a compound of the invention in vivo, in vitro, in situ, or ex vivo. In some embodiments, a bacterium may be directly contacted with the compound of the invention. In other embodiments, an intracellular bacterium may be contacted with a compound of the invention. Suitable cells comprising one or more bacteria may be grown, sub-cultured, stored and manipulated using standard techniques known to individuals skilled in the art. Cell culture and microbiological techniques for growing, culturing, storing, and manipulating cells comprising one or more bacteria are commonly known in the art.

(b) Methods of Reducing Bactericidal Resistance

Another method of the invention comprises reducing the resistance of a bacterium to a bactericidal compound. Such a method comprises contacting a bacterium resistant to a bactericidal compound with a compound of the invention. For instance, a subject infected with a bacterium resistant to a bactericidal compound may be administered a compound of the invention, as described in section IV(a) above. In an exemplary embodiment, a method comprises contacting a bacterium resistant to an antibiotic with a compound of the invention. In a further exemplary embodiment, a method comprises contacting a bacterium resistant to TMP or SMZ with a compound of the invention.

Methods of measuring resistance of a bacterium to an antibiotic are known in the art. For more details, see the examples.

(c) Methods of Treating Catheter-Associated Urinary Tract Infections

In a further embodiment, a method of the invention encompasses a method for treating catheter-associated urinary tract infections. As used herein, "treating" refers to preventing infection in a subject not currently infected, and reducing or eliminating infection in a subject that is currently infected. Generally, such a method comprises administering a pharmaceutical composition comprising a compound of the invention to a subject. For this embodiment, "subject" refers to any mammal with an indwelling urinary catheter. In one embodiment, a subject with a urinary catheter is prone to recurring UTIs. In some embodiments, a subject with a urinary catheter may not have clinical symptoms of a UTI. In such embodiments, the subject may have a latent infection. In other embodiments, a subject with a urinary catheter may have clinical symptoms of a UTI.

In some embodiments, a compound of the invention may be administered to a subject in combination with a bactericidal compound as described in Section II and IV(a) above.

V. Coatings

An additional aspect of the present invention encompasses coatings comprising a compound of the invention. Such a coating may be used on a medical device to prevent bacterial adherence or infection of the host. Suitable means of coating medical devices are known in the art. In one embodiment, a catheter may be coated with a compound of the invention. In another embodiment, a urinary catheter may be coated with a compound of the invention.

VI. Nutritional Supplement

An alternative aspect of the present invention encompasses a nutritional supplement that comprises a compound of the invention. Such a supplement may be used to treat a bacterial infection as described in section IV above.

DEFINITIONS

The term "acyl," as used herein alone or as part of another group, denotes the moiety formed by removal of the hydroxyl group from the group—COON of an organic carboxylic acid, e.g., RC(O)—, wherein R is R', $R_1O$—, $R'R_2N$—, or $R_1S$—, $R_1$ is hydrocarbyl, heterosubstituted hydrocarbyl, or heterocyclo and $R_2$ is hydrogen, hydrocarbyl or substituted hydrocarbyl.

The term "acyloxy," as used herein alone or as part of another group, denotes an acyl group as described above bonded through an oxygen linkage (—O—), e.g., RC(O)O— wherein R is as defined in connection with the term "acyl."

Unless otherwise indicated, the alkyl groups described herein are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

As used herein, the term "functional group" includes a group of atoms within a molecule that is responsible for certain properties of the molecule and/or reactions in which it takes part. Non-limiting examples of functional groups include, alkyl, carboxyl, hydroxyl, amino, sulfonate, phosphate, phosphonate, thiol, alkyne, azide, halogen, and the like.

The terms "halogen" or "halo" as used herein alone or as part of another group refer to chlorine, bromine, fluorine, and iodine.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "heteroaromatic" as used herein alone or as part of another group denote optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, carbocycle, aryl, heterocyclo, alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

The following examples illustrate various iterations of the invention.

Example 1

Uropathogenic *E. coli* (UPEC) Pathogenesis in the Urinary Tract

Figure 1:
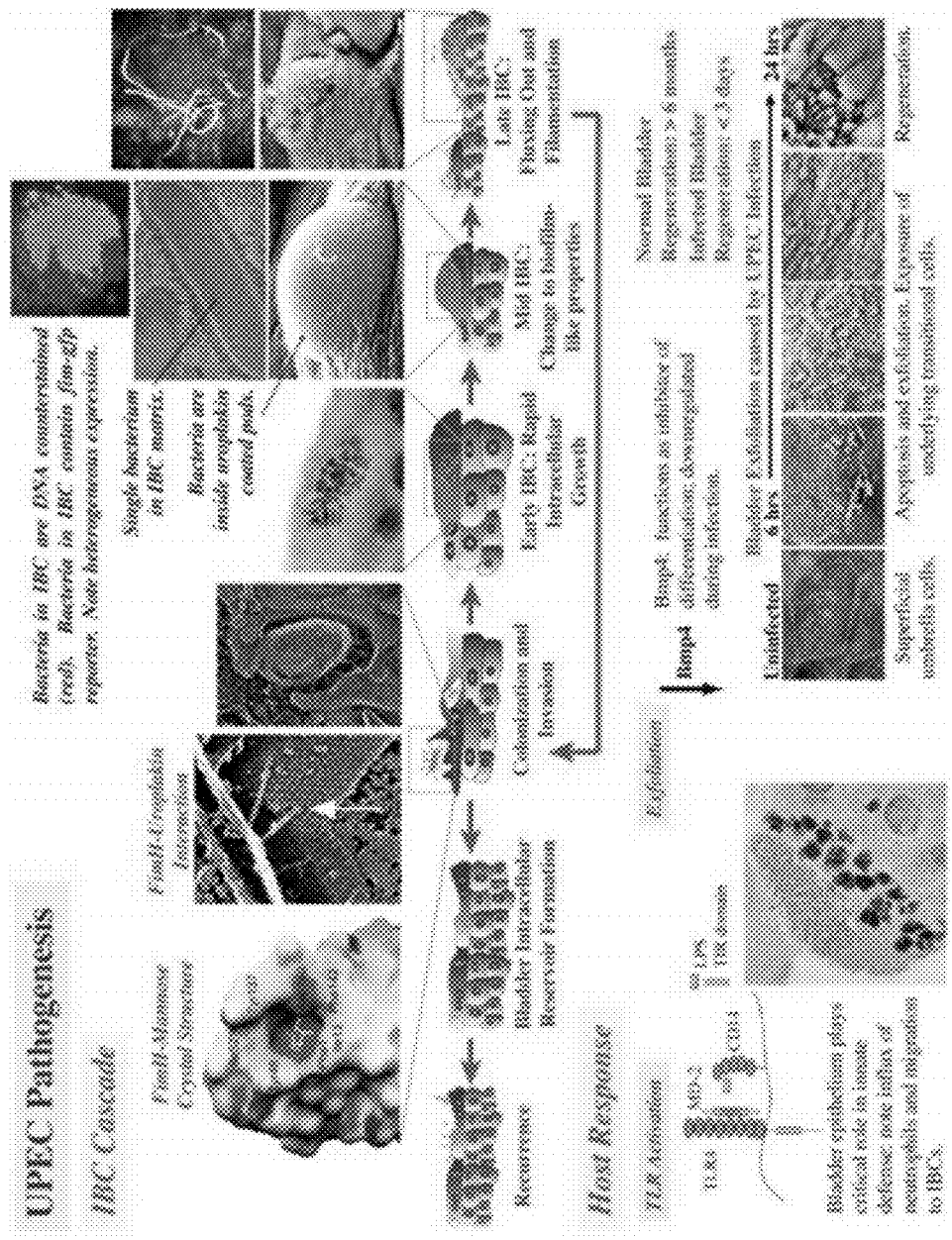
FIG. 1 depicts images and diagrams detailing uropathogenic *E. coli* pathogenesis.

Clinically, it has been presumed that UPEC infection consists of a relatively simple extracellular colonization of the luminal surface after inoculation of fecal flora into the bladder via the urethra. In contrast, using a murine model of UPEC infection of the UT, the inventors have detailed an unexpectedly complex UPEC pathogenesis cycle that involves both intracellular and extracellular niches (FIG. 1). Using genetic, biochemical and cell biological approaches together with a variety of imaging techniques including transmission, quick freeze-deep etch and scanning electron microscopy, as well as confocal and time lapse video microscopy, the inventors discovered that UPEC invade bladder facet cells via a FimH-dependent mechanism (see below). After invasion, cytoplasmic intracellular bacterial communities (IBCs) are formed. Rapid replication of the initial invading bacteria results in the formation of an early IBC of loosely-packed rod-shaped bacteria. The bacteria continue to replicate and progress to form a large densely packed mid-stage IBC of morphologically coccoid bacteria, with biofilm-like characteristics including positive periodic acid-Schiff (PAS) staining and differential gene expression throughout the community. After the IBC matures, bacteria detach from the biomass, often become filamentous, and spread to neighboring cells forming new generation IBCs. Thus, the IBC pathway facilitates massive expansion of the invading bacteria in a niche protected from host defenses. Translational studies have shown that the majority of UPEC isolates form IBCs when introduced into the murine bladder and that IBCs and filamentous bacteria occur in the urine of human UTI patients. Population dynamic studies conducted by the inventors using ex vivo gentamicin protection assays demonstrated that ~$10^4$ UPEC of an initial $10^7$ inoculum invaded the bladder tissue within 15 minutes after infection and that one percent of the invaded bacteria went on to form IBCs, resulting in an average of 100 IBCs per infected mouse bladder. If this is extrapolated to the human situation, innate defenses in the bladder most likely prevent the majority of bacterial inoculation events into the bladder from leading to disease. However, the ramifications of the IBC cascade are striking. Invasion of a single infecting bacterium can lead to rapid expansion of the infection via IBC formation, replicating within hours to $10^4$ bacteria and even higher numbers followed by dispersal of the bacteria from the biomass and spreading to neighboring cells to reinitiate the IBC cascade. This process allows the bacteria to gain a critical foothold. Bacterial descendents of the acute IBC cascade have been shown using a murine model, to be able to form a quiescent intracellular reservoir (QIR) that can persist, protected from antibiotics and seemingly undetected by the host immune system even after the acute infection is resolved and bacteria are no longer detectable in the urine. Bacteria in the QIR can later seed a recurrent infection, manifested by IBC formation, bacteruria and inflammation.

Example 2

FimH as a Therapeutic Target

There are several key implications from understanding UPEC pathogenesis. Mannosides and pilicides that block FimH function will prevent bacterial adherence and invasion and thus prevent bacterial amplification in the IBC and subsequent spreading and repeated rounds of amplification via new generation IBCs. These compounds will have potent therapeutic activity by preventing bacterial expansion which may also have the consequence of eliminating or significantly reducing the QIR thus reducing predisposition to recurrent infection.

Type 1 pili/FimH are Critical for UPEC Pathogenesis in the UT.

Type 1 pili are essential cystitis virulence determinants. Using scanning and high-resolution EM and the mouse cystitis model developed by the inventors, it was shown that adhesive type 1 piliated bacteria are able to bind and invade host superficial umbrella cells, while UPEC lacking type 1 pili are not. Colonization and invasion of the bladder epithelium is dependent on the FimH adhesion located at the distal end of the pilus that binds mannose residues on bladder epithelial cells. High-resolution freeze-dry/deep-etch EM revealed that FimH interacts directly with receptors on the luminal surface of the bladder (FIG. 1). Standard gentamicin protection assays of infected tissue culture cells and ex vivo gentamicin treatment of infected bladders demonstrated that fimH$^+$ type 1 piliated clinical cystitis isolates, but not fimH$^-$ mutants, could invade bladder epithelial cells. Using immunohistochemistry and Pfim-gfp transcriptional fusions it was demonstrated that type 1 pili are expressed within IBCs. Using high-resolution EM, pilus-like fibers radiating from bacteria and interacting with matrix material within the intracellular IBC were also visualized (FIG. 1). These results combined with work showing that type 1 pili are required for biofilm formation in in vitro systems led to the hypothesis that type 1 pili promote IBC formation and/or maintenance. Therefore, an anhydrotetracycline (AHT) inducible fim strain was constructed which can be "pre-piliate" UTI89 in vitro by growth in AHT before infecting mouse bladders, allowing the initial invasion event to normally. However, once inoculated into the mouse, AHT is no longer present, fim transcription ceases and piliation is diluted upon each bacterial division. Using this system, the earliest events of colonization and invasion were identical between the wild type and conditional strain. However, the inability of the conditional strain to produce type 1 pili intracellularly abolished its ability to form IBCs, as shown by confocal microscopy, and thus dramatically attenuated virulence as determined by CFUs at later time points. These results strongly suggest that type 1 pili are required for the survival and proliferation of UPEC within superficial facet cells. Additionally, this conditional mutant is significantly impaired in its ability to form QIRs, arguing that the bacteria in QIRs are descendents and thus dependent on the acute IBC cascade.

Structural Studies of FimH and its Ligand.

Figure 2:
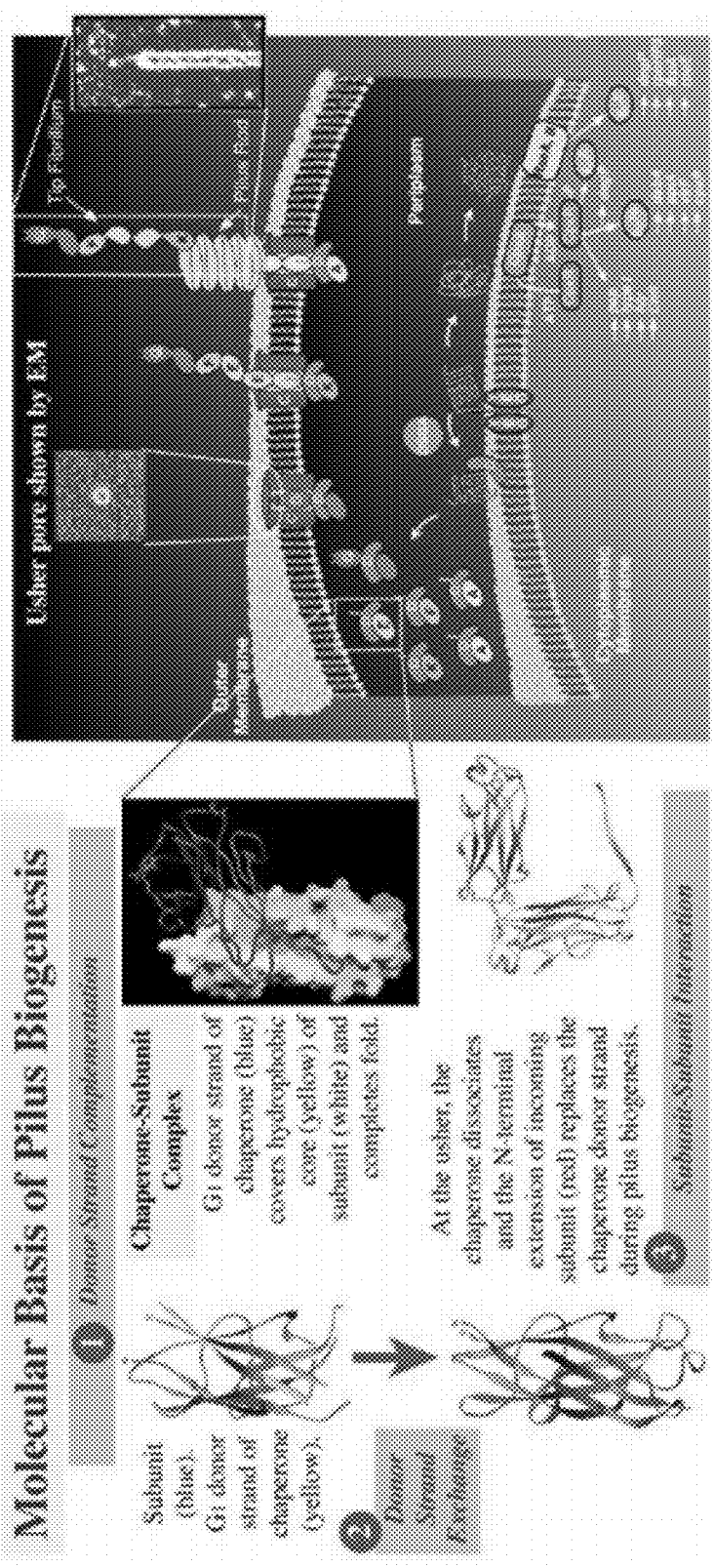
FIG. 2 depicts chaperone/usher mediated pilus biogenesis as shown for the pilus system.
Figure 3:
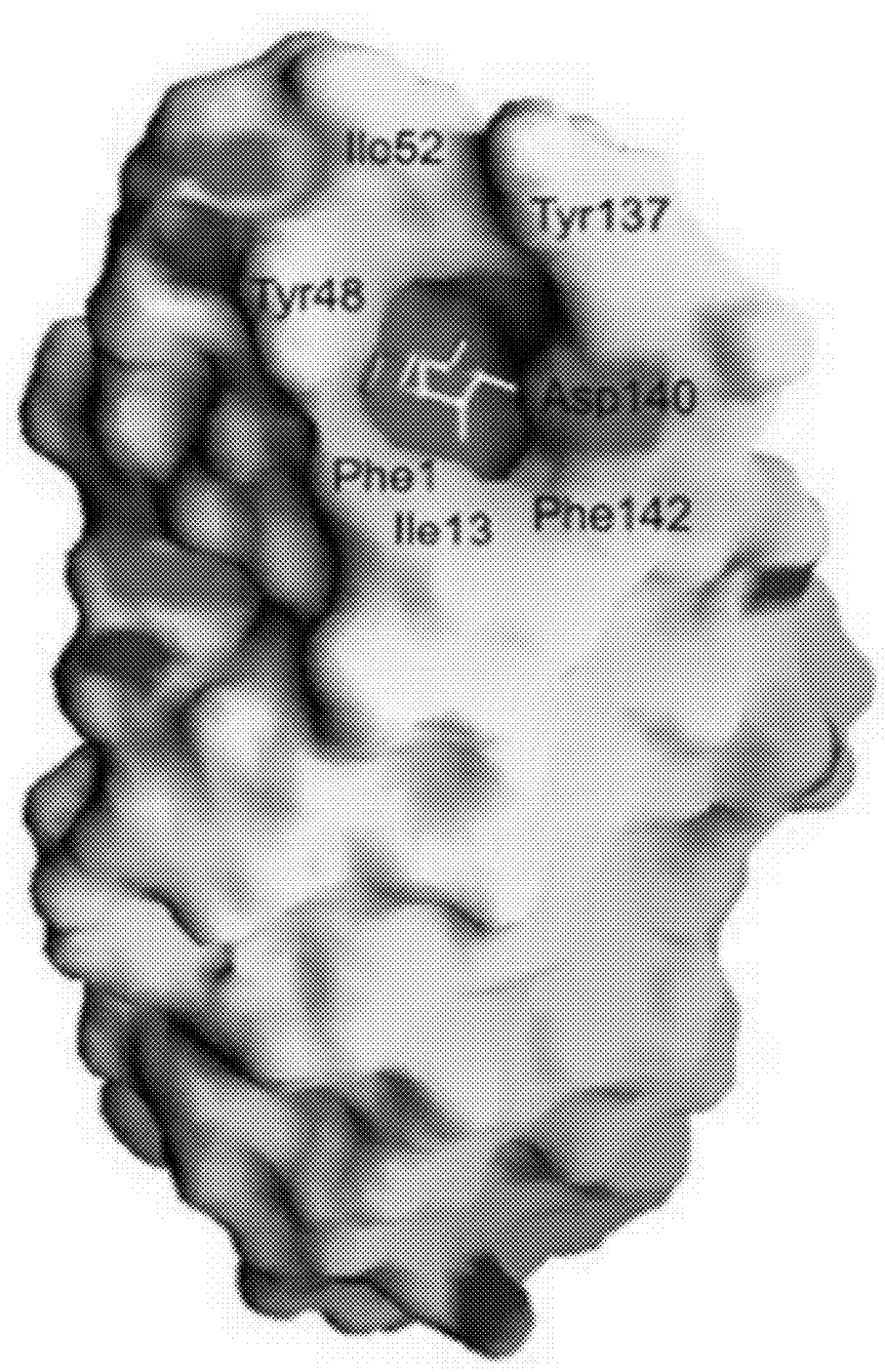
FIG. 3 depicts a GRASP view of the FimH adhesion domain bound to a D-mannose residue (shown in stick). Red=acidic residues. Blue=basic residues.

Adhesive type 1 pili are prototypic structures of a family of adhesive fibers produced by diverse Gram-negative bacteria via the chaperone/usher assembly pathway. Using biochemistry, mutational studies, nuclear magnetic resonance, and x-ray crystallography, the molecular basis of pili assembled by the chaperone/usher pathway in gram-negative bacteria, including type 1 pili of UPEC, were delineated (FIG. 2) The three dimensional structure of FimH bound to its mannose receptor was solved in order to gain a molecular snapshot of a critical initial event in UTI pathogenesis (FIG. 3).

Figure 4:
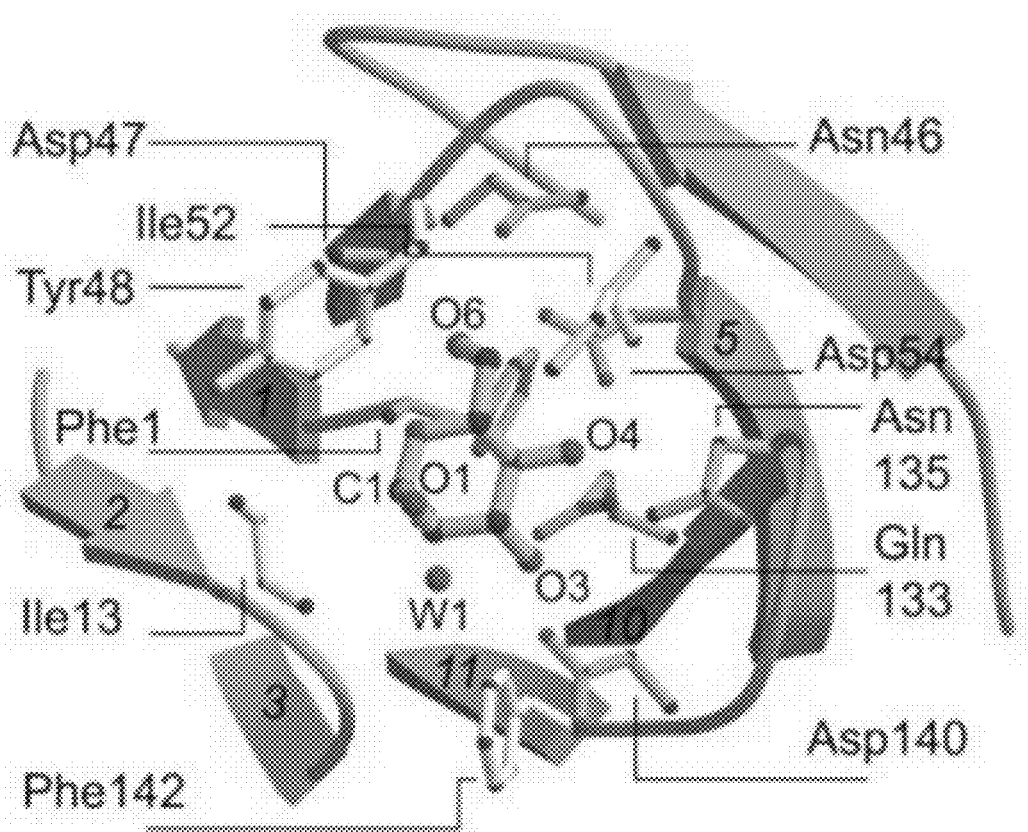
FIG. 4 depicts a ribbon representation of the receptor binding pocket in complex with the mannose. The D-mannose (pink), the mannose interacting residues (green) and the residues of the hydrophobic ridge around the pocket (white) are shown as ball-and-stick model.

FimH is a two domain protein, with a receptor binding domain linked to a typical pilin domain that joins the adhesin to the pilus fiber. The structure of the complex of the FimC chaperone bound to FimH (which was bound to D-mannopyranoside) was determined to 2.8 Å resolution. The mannose binding site of FimH is a deep negatively charged pocket at the tip of its receptor-binding domain. The FimH pocket engages in extensive hydrogen bonding to mannose (FIG. 4), which are abundant in the oligosaccharide moieties of uroplakins that coat the lumenal surface of the bladder epithelium. A hydrophobic ridge surrounds the mannose binding pocket in a manner that may facilitate polar interactions within the FimH pocket. Mutational studies revealed that each residue is critical in mannose binding and pathogenesis, emphasizing why the pocket is invariant among UPEC isolates.

Development of Anti-Adhesives.

Figure 5:
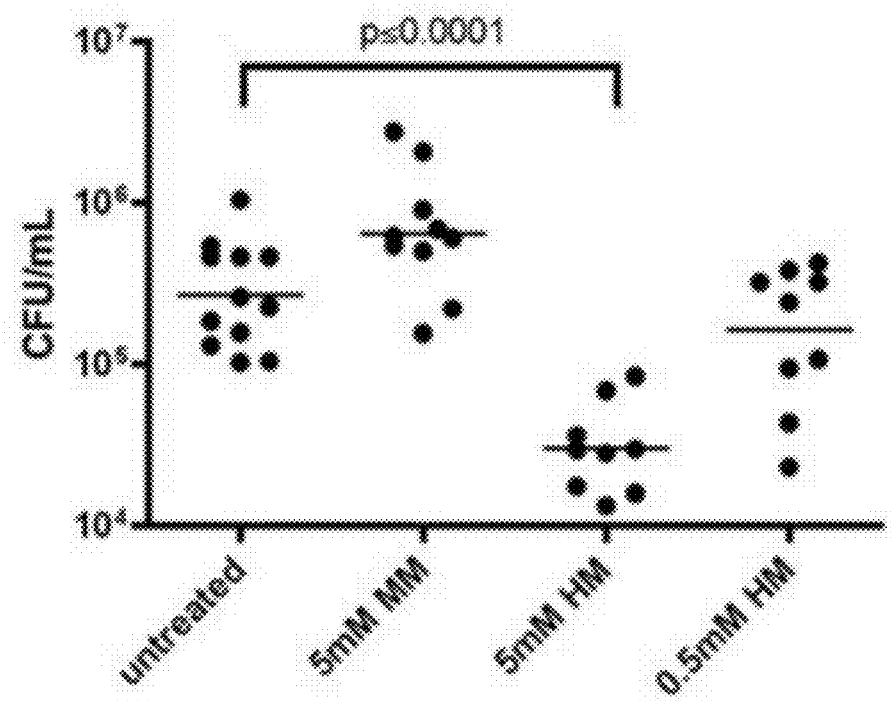
FIG. 5 depicts a graph showing the reduction of bacterial load in the bladder upon incubation with heptyl mannose at 6 hours post-infection. HM=heptyl mannose, MM=methyl mannose, p value obtained by Mann-Whitney test.

The FimH-mannose interaction was further investigated in an effort to develop potential ligand-based antagonists of UTIs. The chitobiose unit on oligomannose was found to bridge various mannose derivatives to the asparagine in the Asn-X-Ser/Thr motif of FimH resulting in higher affinity binding. Crystallization of FimH in complex with oligomannose-3 revealed the mechanism of this higher affinity binding. The non-reducing Man4 anchors into the mannose-binding pocket while the GlcNAc folds over Thr51 allowing specific interactions with a hydrophobic tyrosine gate. Heptyl mannoside mimics the GlcNAc tail of oligomannose-3 and extends it further to increase interactions outside the binding pocket resulting in high affinity binding (Kd=5 nM). Based on the high affinity of heptyl mannose for FimH, the ability of heptyl mannose to reduce bacterial infection in our mouse model of UTI was tested. First, biofilm formation as a surrogate for IBCs formed in the bladder was evaluated. Heptyl mannose at 1 mM inhibited UPEC biofilm formation in vitro, suggesting that the mannose binding properties of the FimH adhesin is required for biofilm formation. Thus, UPEC strain UTI89 was incubated with heptyl mannose prior to inoculation into the bladders of mice. This resulted in a significant attenuation of virulence at 6 hours post-infection at 5 mM heptyl mannose (FIG. 5). The ability of these compounds to significantly attenuate virulence establishes mannosides as a potential treatment for UTI. Therefore, more potent mannosides that mimic the natural receptor for FimH but with increased affinity and avidity in order to ultimately block bacterial colonization, invasion, IBC formation and disease were developed as described below.

Example 3

Genetic Analysis of UPEC Baterial Isolates

Figure 6:
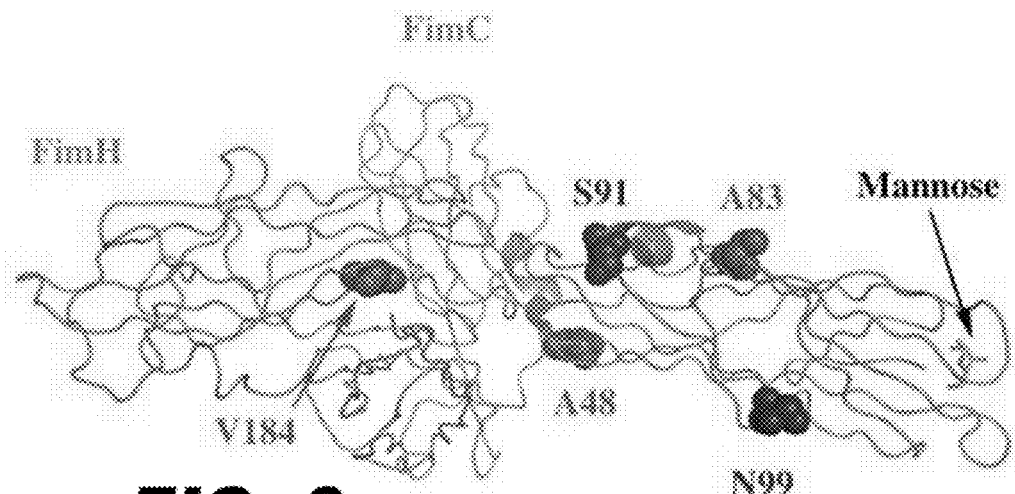
FIG. 6 depicts FimH residues under positive selection. Green represents the adhesin FimH and gray represents the chaperone FimC. Residues in red are under positive selection. Residues in blue are not under positive selection. All residues are located outside the mannose binding pocket.

Due to the necessity of FimH, it was tested to see if this gene was under positive selection. Through sequencing of more than 200 isolates, the majority of which were UTI isolates, it was discovered that residues on FimH are evolving under positive selection, none of which were in the mannose binding pocket. These residues are A48, A83 and V184 in UT189 (FIG. 6). Mutants were constructed containing the other naturally occurring amino acids commonly found at the positively selected positions. A mutation of A83 to a serine resulted in a defect in binding in vitro, however only a log drop in bacterial titers were observed in vivo. The double mutant containing a valine at position 48 and an alanine at position 184 resulted in a severe defect in vivo based on bacterial titers and no defect in the ability to bind mannose in vitro. Mutations in the non-positively selected amino acids had no detectable effect. This study shows that residues outside the binding pocket are also important to FimH's function in vivo suggesting there is more to FimH than just its ability to bond to the surface of the bladder through its mannose binding pocket.

Since FimH has been the only essential virulence factor determined to date, it was investigated if the FimH from UT189 would result in establishing a more robust infection if it was put into a clinical isolate containing an altered FimH. A panel of clinical isolates was examined for their ability to form IBCs (FIG. 7). Isolates with a valine at position 48 seemed to perform worse in vivo in regards to IBC formation.

Example 4

Role of FimH in Infection

To assess FimH's role in infection, the native FimH of the clinical strain acute 4 (FIG. 7) was replaced with the FimH sequence from UT189 under the control of the native promoter. This was done through lambda red recombinase. The acute4 FimH was first deleted and replaced with a chloramphenicol (Cm) cassette. The Cm cassette was then replaced with UT189 FimH. The isolate was then sequenced to confirm proper sequence.

Figure 8A:
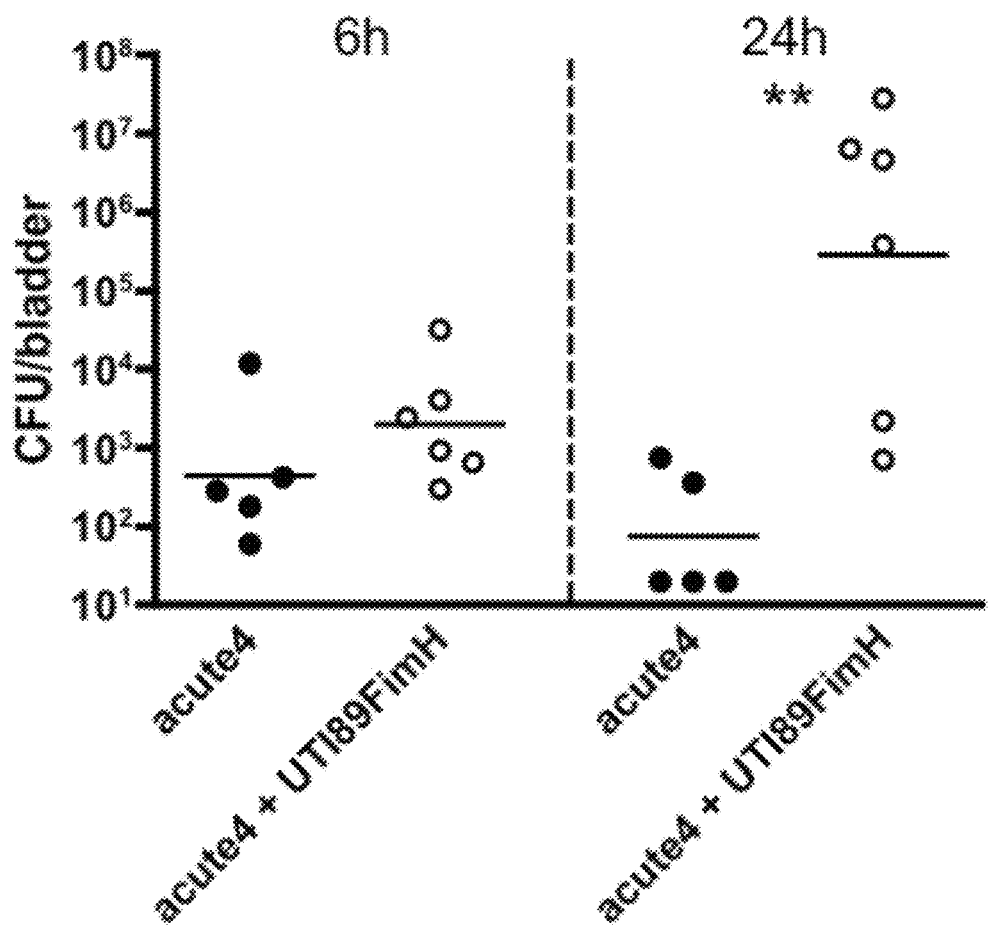
FIG. 8 depicts bacterial load and IBC formation of isolate acute4 with its native FimH and UTI89's FimH. The FimH sequence from acute4 was replaced with the fimH sequence of UTI89 on the chromosome. (A) Depicts results obtained using bacterial titers, and (B) depicts results obtained using IBC formation.
Figure 8B:
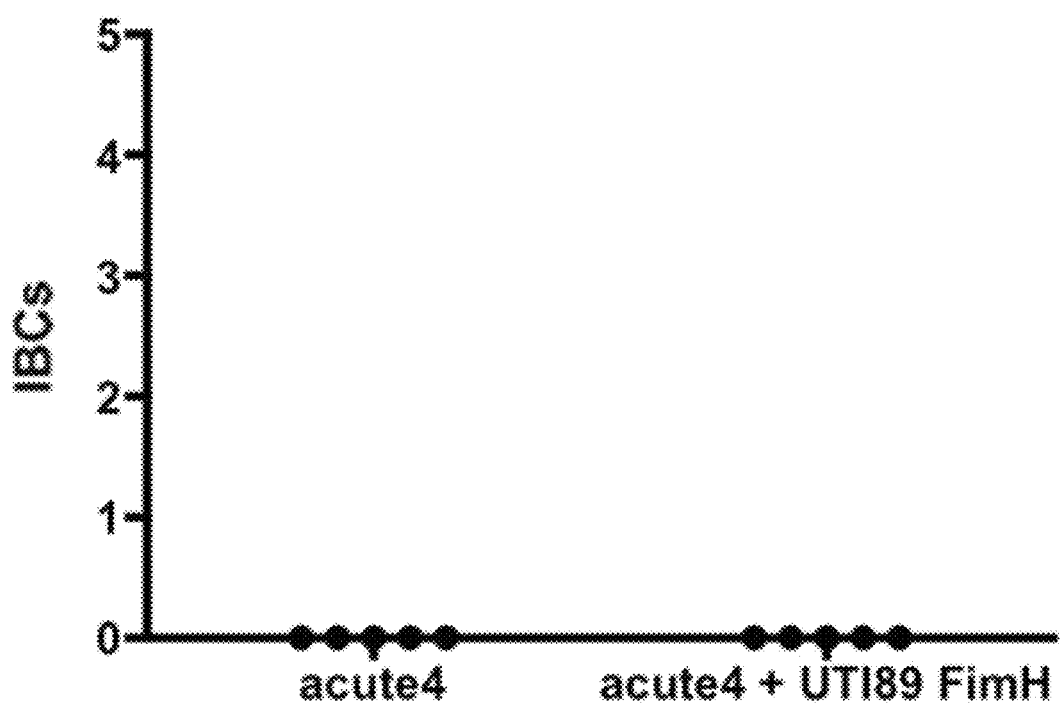

Acute4 and acute4+UT189FimH were grown 2×24 hours to obtain type 1 expression. C3H/HeN mice were then inoculated with $10^7$ of either strain. For bacterial titers (FIG. 8A), bladders were harvested at 6 and 24 hours post-infection. At 6 hours post-infection there was no significant difference in bacterial load between the two stains and both strains were much lower that a typical UT189 6 hour titer (~$10^6$). However, at 24 hours post-infection, acute4+UT189FimH significantly colonized the murine bladder more than actue 4 (p<0.001 by Mann-Whitney). 24 hour titers in the acute4+UT189FimH isolate were equivalent to what is typically observed with UT189. For IBC formation (FIG. 8B), LacZ staining was performed at 6 hours post-infection. No IBCs were observed in either isolate.

Example 5

Synthesis of Compounds

The compounds of the present invention may be prepared in a number of ways well known to one skilled in the art of organic synthesis. More specifically, the novel compounds of this invention may be prepared using the reactions and techniques described herein. In the description of the synthetic methods described below, it is to be understood that all proposed reaction conditions, including choice of solvent, reaction atmosphere, reaction temperature duration of the experiment and workup procedures, are chosen to be the conditions standard for that reaction. It is understood by one skilled in the art of organic synthesis that the functionality present on various portions of the molecule must be compatible with the reagents and reactions proposed. Such restrictions to the substituents, which are not compatible with the reaction conditions, will be apparent to one skilled in the art and alternate methods must then be used. Unless otherwise stated, the starting materials for the examples contained herein are either commercially available or are readily prepared by standard methods from known materials. The compounds of Formula (I) and (II) may be synthesized through standard organic chemistry methodology and purification known to those trained in the skill and art by using commercially available starting materials and reagents. General procedures for synthesizing the compounds of the invention are as follows:

The chemical synthesis of compounds with the general Formula (I) and (II) is achieved using the routes described in Scheme 1 starting from commercially available α-D-mannose, α-D-mannose pentaacetate (Route A), or α-methyl-D mannose (Route B). Shown in Scheme 1A, Lewis-acid mediated glycosidation of α-D-mannose pentaacetate followed by acetate ester hydrolysis with sodium methoxide yields glycosides of Formula (I). Further chemical transformation of the substituent R¹ may be accomplished using standard synthetic organic procedures such as, but not limited to, metal-mediated aryl Suzuki coupling reactions through aryl bromide or aryl boronate ester glycosides, shown in Scheme 2A and 2B, respectively, to produce exemplified compounds of Formula (I) described in Tables 1-9. All compounds are also listed in Table 15.

Scheme 1. Generic synthesis of oxygen (Y = O) and sulfur (Y = S) glycosides encompassed by general Formulas (I) and (II).

Route A:

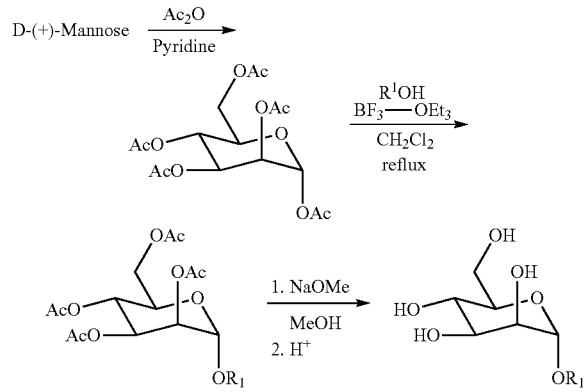

Route B:

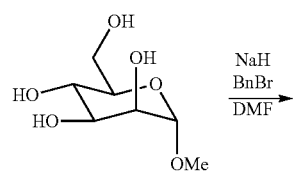

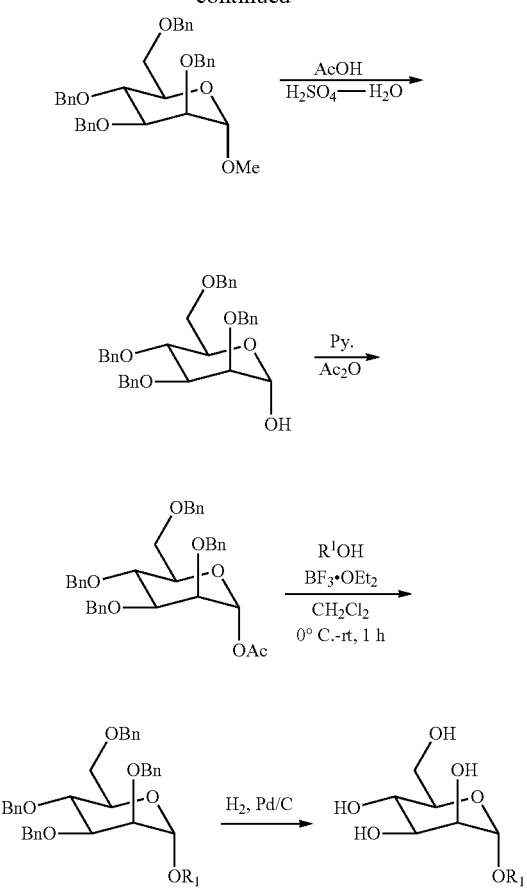

Scheme 2. Examples of synthetic modification of arylglycosides by metal-catalyzed Suzuki-type coupling to generate compounds of general Formulas (III), (IV), and (VIII).

A.

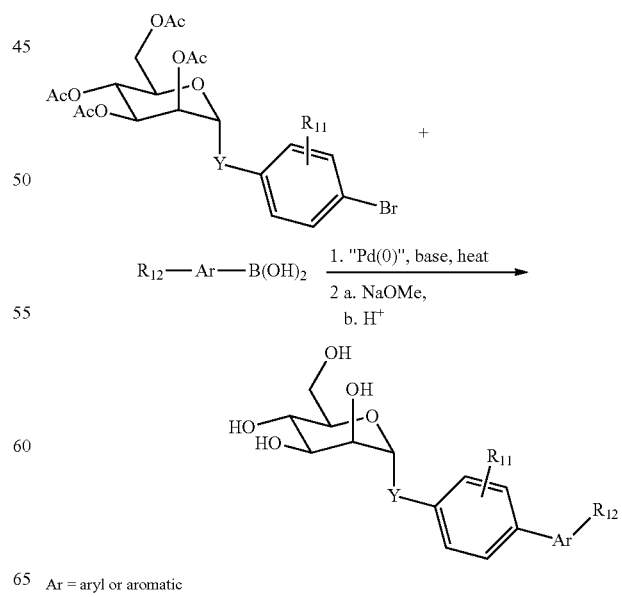

Ar = aryl or aromatic

B.

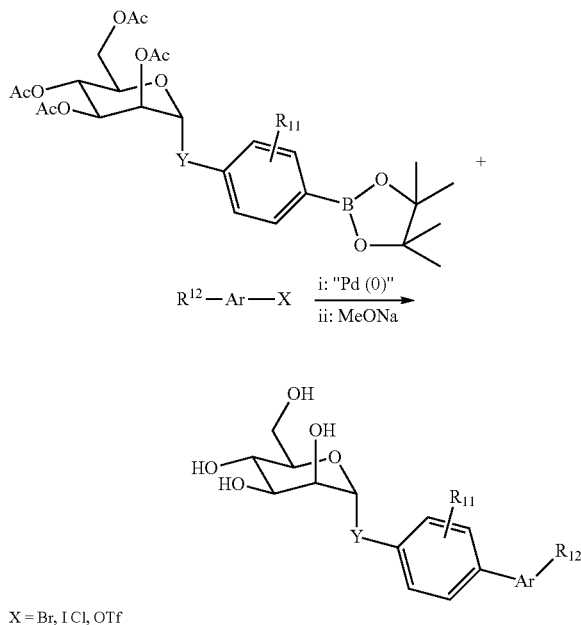

X = Br, I Cl, OTf

The compounds of Formula (I) may be transformed into compounds of Formula (II) as described in Scheme 3 by employing various functional groups (R¹) and linkers(L), such as, but not limited to, alkyl ethers, esters, amines and amides.

The invention is further described with reference to the following illustrative examples in which, unless stated otherwise:

(i) temperatures are given in degrees Celsius (° C.); operations are carried out at roomtemperature or ambient temperature, that is, in a range of 18-25° C., unless otherwise stated;

(ii) solutions are dried over anhydrous sodium sulphate or magnesium sulphate; evaporation of organic solvent is carried out using a rotary evaporator under reduced pressure (4.5-30 mmHg) with a bath temperature of up to 60° C.;

(iii) chromatography means flash chromatography on silica gel; thin layer chromatography (TLC) is carried out on silica gel plates;

(iv) in general, the course of reactions are followed by TLC or liquid chromatography/mass spectroscopy (LC/MS) and reaction times are given for illustration only;

(v) final products have satisfactory proton nuclear magnetic resonance (NMR) spectra and/or mass spectra data;

(vi) yields are given for illustration only and are not necessarily those which can be obtained by diligent process development; preparations are repeated if more material is required;

(vii) when given, nuclear magnetic resonance (NMR) data is in the form of delta (a) values for major diagnostic protons, given in part per million (ppm) relative to tetra methylsilane (TMS) as an internal standard, determined at 300 MHz ind₃-MeOD unless otherwise stated;

(viii) chemical symbols have their usual meanings;

(ix) solvent ratio is given in volume:volume (v/v) terms;

Scheme 3. Example of synthesis of divalent compounds of the general Formula (II).

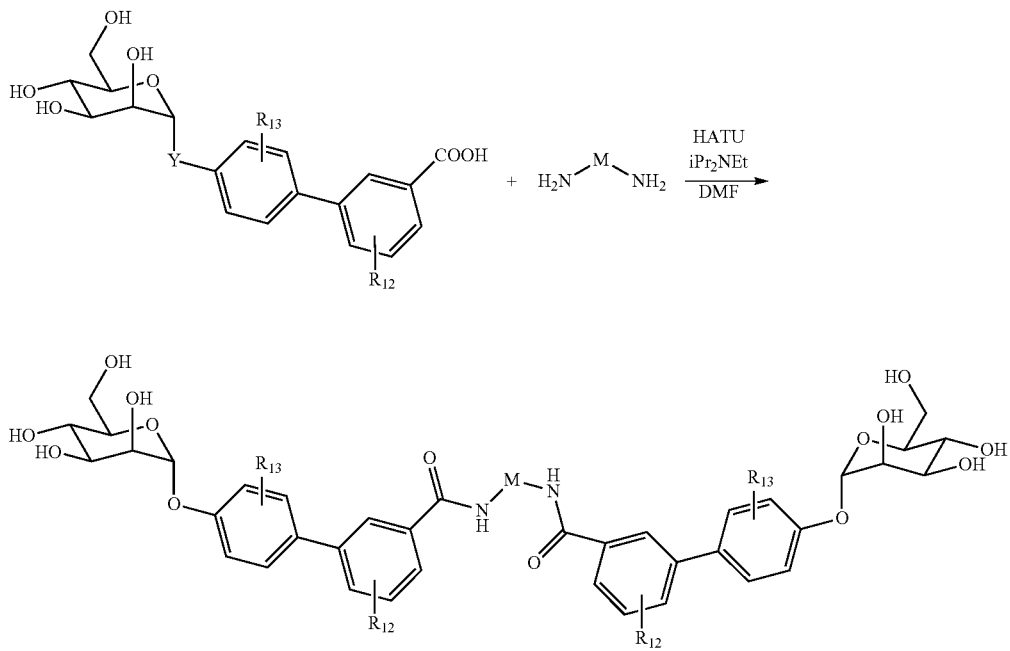

M = [(CH₂)ₙO(CH₂)ₒ]ₙ
L = N[(CH₂)ₙO(CH₂)ₒ]ₙN, (x) Purification of the compounds is carried out using one or more of the following methods:
a) flash chromatography on regular silica gel;
b) flash chromatography on silica gel using an MPLC separation system (Teledyne ISCO):prepackednormal phase flash column cartridge, flow rate, 10-80 ml/min;
c) Preparatory HPLC system using a reverse-phase C18 column, 100×20 mm, 5 µM (or larger) and eluting with combinations of water (0.1% TFA) and MeCN (0.1% TFA) as the mobile phase;

(xi) the following abbreviations have been used:
Ac acetyl;
CIV concentrated in vacuo;
RTandrt room temperature;
BOC tert-butoxycarbonyl;
HATU 2-(7-Aza-1H-benzotriazole-1-yl)-1,1,3,3-tetramethyluronium hexafluorophosphate;
DIPEA N,N-diisopropylethylamine;
CBZ benzyloxycarbonyl;
Bn benzyl;
DCM dichloromethane;
DMF N,N-dimethylformamide;
DMSO dimethylsulfoxide;
NMP N-methyl-2-pyrrolidinone;
EtOAc ethyl acetate;
ether diethyl ether;
EtOH ethanol;
THF tetrahydrofuran;
MeOH methanol;
MeCN acetonitrile;
TFA trifluoracetic acid; and
TEA triethylamine.

1. General Procedures for the Preparation of Mannosides when α-D-Mannose Pentaacetate is Used as the Starting Material: Methyl 3-[4-[(2R,3S,4S,5S,6R)-3,4,5-trihydroxy-6-(hydroxymethyl)tetrahydropyran-2-yl]oxyphenyl]benzoate (29)

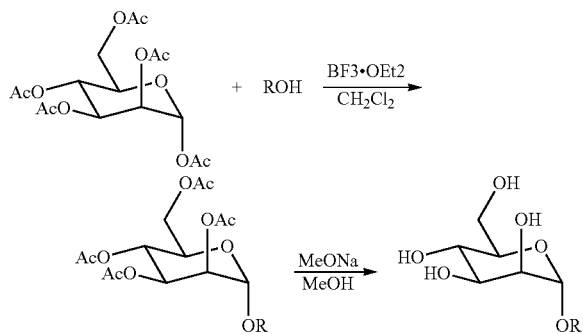

1.1

1.1 Methyl 3-[4-[(2R,3S,4S,5R,6R)-3,4,5-triacetoxy-6-(acetoxymethyl)tetrahydropyran-2-yl]oxyphenyl]benzoate: Under nitrogen atmosphere, at 0° C. boron trifluoride diethyl etherate (0.128 g, 0.90 mmol) was added dropwise into the solution of α-D-mannose pentaacetate (0.120 g, 0.3 mmol) and methyl 3-(4-hydroxyphenyl)benzoate (0.140 g, 0.6 mmol) in 6 ml of $CH_2Cl_2$. After a few mins the mixture was heated to reflux and kept stirring for more than 36 hrs. The reaction was then quenched with water and extracted with $CH_2Cl_2$. The $CH_2Cl_2$ layer was collected, dried with $Na_2SO_4$, concentrated. The resulting residue was purified by silica gel chromatography with hexane/ethyl acetate combinations as eluent, giving rise to methyl 3-[4-[(2R,3S,4S,5R,6R)-3,4,5-triacetoxy-6-(acetoxymethyl)tetrahydropyran-2-yl]oxyphenyl]benzoate (0.136 g) in 81% yield. $^1$H NMR (300 MHz, $CDCl_3$) σ ppm 8.23 (m, 1H), 7.99 (m, 1H), 7.74 (m, 1H), 7.57 (m, 2H), 7.50 (t, J=7.8 Hz, 1H), 7.18 (m, 2H), 5.59 (dd, J=3.6, 9.9 Hz, 1H), 5.58 (d, J=1.5 Hz, 1H), 5.48 (dd, J=2.1, 3.3 Hz, 1H), 5.39 (t, J=10.2 Hz, 1H), 4.30 (dd, J=5.4, 12.3 Hz, 1H), 4.06~4.15 (m, 2H), 3.95 (s, 3H), 2.15 (s, 3H), 2.06 (s, 3H), 2.05 (s, 3H), 2.04 (s, 3H); MS (ESI): found: [M+H]$^+$, 559.1.

1.2 Methyl 3-[4-[(2R,3S,4S,5S,6R)-3,4,5-trihydroxy-6-(hydroxymethyl)tetrahydropyran-2-yl]oxyphenyl]benzoate (29): Methyl 3-[4-[(2R,3S,4S,5R,6R)-3,4,5-triacetoxy-6-(acetoxymethyl)tetrahydropyran-2-yl]oxyphenyl]benzoate (0.120 g) was stirred in 6 mL of methanol with catalytic amount of sodium methoxide (0.02 M) at room temperature overnight. H$^+$ exchange resin (DOWEX 50WX4-100) was added to neutralize the mixture. The resin was filtered off and the filtrate was concentrated, then dried in vacuo giving rise to pure product 29 (0.084 g) in quantitative yield. $^1$H NMR (300 MHz, $CD_3OD$) a ppm 8.21 (m, 1H), 7.95 (m, 1H), 7.83 (m, 1H), 7.59 (m, 2H), 7.53 (m, 1H), 7.23 (m, 2H), 5.55 (d, J=1.8 Hz, 1H), 4.03 (dd, J=1.8, 3.3 Hz, 1H), 3.91~3.96 (m, 4H), 3.70~3.82 (m, 3H), 3.59~3.65 (m, 1H); MS (ESI): found: [M+H]$^+$, 391.1. (see Table 1).

2. Procedures for the preparation of mannosides when 2,3,4,6-tetra-β-benzyl-1-acetyl-α-D-man nopyranoseis used as the starting material: [3-[(2R,3S,4S,5S,6R)-3,4,5-trihydroxy-6-(hydroxymethyl)tetrahydropyran-2-yl]oxyphenyl] acetate (42):

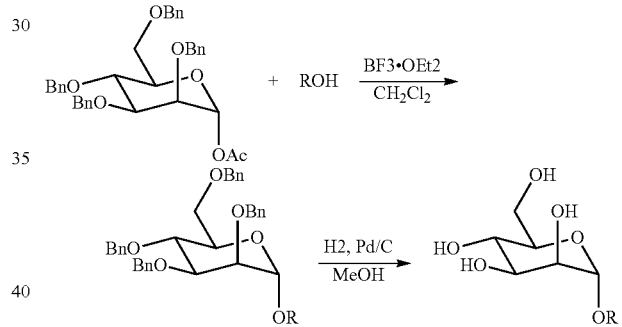

2.1 [3-[(2R,3S,4S,5R,6R)-3,4,5-Tribenzyloxy-6-(benzyloxymethyl)tetrahydropyran-2-yl]oxyphenyl]acetate: Under nitrogen atmosphere, at 0° C. boron trifluoride diethyl etherate (0.051 g, 0.36 mmol) was added dropwise into the solution of 2,3,4,6-tetra-O-benzyl-1-acetyl-α-D-mannopyranose (0.106 g, 0.18 mmol) and resorcinol monoacetate (0.055 g, 0.36 mmol) in 7 ml of $CH_2Cl_2$. The mixture was stirred at 0° C. and monitored by TLC. The reaction was then quenched with water and extracted with $CH_2Cl_2$. The $CH_2Cl_2$ layer was collected, dried with $Na_2SO_4$, concentrated. The resulting residue was purified by silica gel chromatography with hexane/ethyl acetate combinations as eluent to give [3-[(2R,3S,4S,5R,6R)-3,4,5-tribenzyloxy-6-(benzyloxymethyl)tetrahydropyran-2-yl]oxyphenyl]acetate (0.093 g) in 75% yield. $^1$H NMR (300 MHz, $CDCl_3$) δ ppm 7.15~7.40 (m, 21H), 6.88~6.91 (m, 1H), 6.81 (t, J=2.4 Hz, 1H), 6.73~6.76 (m, 1H), 5.58 (d, J=1.8 Hz, 1H), 4.90 (d, J=10.8 Hz, 1H), 4.78 (s, 2H), 4.64~4.69 (m, 3H), 4.52 (d, J=10.8 Hz, 1H), 4.45 (d, J=12.3 Hz, 1H), 4.05~4.18 (m, 2H), 3.94 (t, J=2.4 Hz, 1H), 3.77~3.85 (m, 2H), 3.64~3.70 (m, 1H), 2.27 (s, 3H). MS (ESI): found: [M+Na], 697.2.

2.2 [3-[(2R,3S,4S,5S,6R)-3,4,5-trihydroxy-6-(hydroxymethyl)tetrahydropyran-2-yl]oxyphenyl]acetate (42): Under hydrogen atmosphere [3-[(2R,3S,4S,5R,6R)-3,4,5-tribenzyloxy-6-(benzyloxymethyl) tetrahydropyran-2-yl]oxyphenyl] acetate (0.085 g, 0.13 mmol) was stirred with Pd/C(10 wt. %)

(0.132 g, 0.063 mmol) in ethanol (6 mL) and ethyl acetate (6 mL). The reaction was monitored by TLC until it went into completion. The mixture was filtered through a celite plug. The filtrate was concentrated then dried in vacuo furnishing pure 42 (0.040 g) in quantitative yield. $^1$H NMR (300 MHz, CD$_3$OD) δ ppm 7.30 (t, J=8.1 Hz, 1H), 7.00 (m, 1H), 6.90 (t, J=2.1 Hz, 1H), 6.76 (m, 1H), 5.47 (d, J=1.8 Hz, 1H), 4.00 (dd, J=1.8, 3.3 Hz, 1H), 3.88 (dd, J=3.3, 9.3 Hz, 1H), 3.68~3.79 (m, 3H), 3.54~3.61 (m, 1H). MS (ESI): found: [M+H]$^+$, 314.9. (see Table 2).

3. Procedure for the preparation of 5-[4-[(2R,3S,4S,5S,6R)-3,4,5-Trihydroxy-6-(hydroxymethyl)tetrahydropyran-2-yl]oxyphenyl]benzene-1,3-dicarboxylic acid (45):

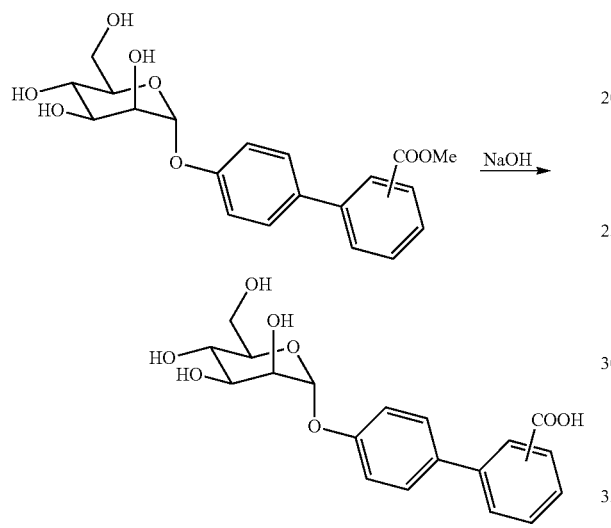

35 (0.025 g, 0.056 mmol) was added into 7 mL methanol. Then 0.20 M NaOH aqueous (3 mL) was added. The mixture was stirred at rt overnight. H$^+$ exchange resin (DOWEX 50WX4-100) was added to neutralize the mixture. The resin was filtered off and the filtrate was concentrated, then dried in vacuo giving rise to pure product 45 (0.023 g) in quantitative yield. $^1$H NMR (300 MHz, METHANOL-d$_4$) δ ppm 3.59-3.67 (m, 1H) 3.70-3.84 (m, 3H) 3.94 (dd, J=3.30, 9.30 Hz, 1H) 4.05 (dd, J=3.30, 1.80 Hz, 1H) 5.56 (d, J=1.80 Hz, 1H) 7.26 (m, 2H) 7.63 (m, 2H) 8.41 (d, J=1.50 Hz, 2H) 8.57 (t, J=1.50 Hz, 1H). MS (ESI): found: [M+Na]$^+$, 443.0. (see Table 3).

4. Procedure for the preparation of N1,N3-dimethyl-5-[4-[(2R,3S,4S,5S,6R)-3,4,5-trihydroxy-6-(hydroxymethyl)tetrahydropyran-2-yl]oxyphenyl]benzene-1,3-dicarboxamide (50):

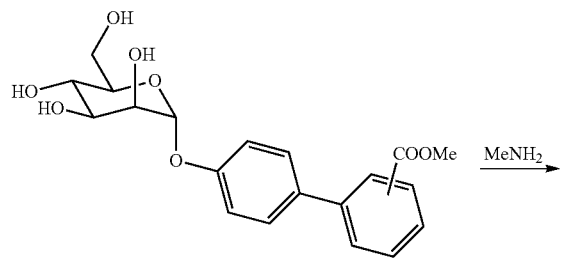

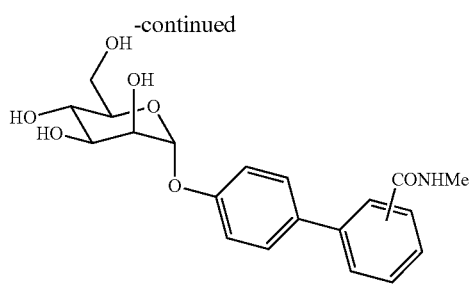

35 (0.050 g, 0.11 mmol) was stirred with 15 mL of MeNH$_2$/EtOH (33 wt. %) at rt for 40 hrs. The solvent was removed and the residue was dried in vacuo to afford pure 50 (0.050 g) in quantitative yield. $^1$H NMR (300 MHz, METHANOL-d$_4$) δ ppm 2.96 (s, 6H) 3.61-3.66 (m, 1H) 3.67-3.84 (m, 3H) 3.86-3.97 (m, 1H) 4.04 (dd, J*3.30, 1.92 Hz, 1H) 5.56 (d, J⁻1.92 Hz, 1H) 7.21-7.34 (m, 2H) 7.63-7.74 (m, 2H) 8.13-8.26 (m, 3H). MS (ESI): found: [M+H]$^+$, 447.4. (see Table 4).

5. Procedures for the preparation of biphenyl mannoside derivatives through Suzuki coupling reaction: 3-[4-[(2R,3S,4S,5S,6R)-3,4,5-trihydroxy-6-(hydroxymethyl)tetrahydropyran-2-yl]oxyphenyl]benzonitrile (62)

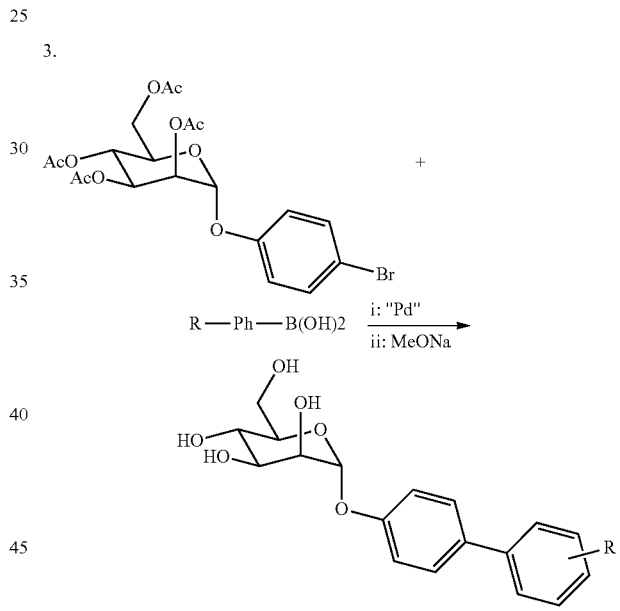

5.1 [(2R,3S,4S,5R,6R)-3,4,5-Triacetoxy-6-[4-(3-cyanophenyl)phenoxy]tetrahydropyran-2-yl]methyl acetate: Under nitrogen atmosphere, the mixture of acetyl-protected 4-bromophenyl α-D-mannoside (0.101 g, 0.2 mmol), m-cyanophenylboronic acid (0.044 g, 0.3 mmol), cesium carbonate (0.196 g, 0.6 mmol) and tetrakis(triphenylphosphine)palladium (0.023 g, 0.02 mmol) in dioxane/water (5 mL/1 mL) was heated at 80° C. with stirring for 1 h. The solvent was removed and the resulting residue was purified by silica gel chromatography with hexane/ethyl acetate combinations as eluent to give [(2R,3S,4S,5R,6R)-3,4,5-triacetoxy-6-[4-(3-cyanophenyl)phenoxy]tetrahydropyran-2-yl]methyl acetate (0.080 g) in 76% yield. $^1$H NMR (300 MHz, CDCl$_3$) δ ppm 7.82 (t, J=1.5 Hz, 1H), 7.76 (dt, J=7.69, 1.65 Hz, 1H), 7.58~7.65 (m, 1H), 7.47~7.57 (m, 3H), 7.16~7.24 (m, 2H), 5.55~5.65 (m, 2H), 5.47 (dd, J=3.57, 1.92 Hz, 1H), 5.39 (t, J=9.9 Hz, 1H), 4.25~4.34 (m, 1H), 4.04~4.17 (m, 2H), 2.22 (s, 3H), 2.06 (s, 3H), 2.05 (s, 3H), 2.04 (s, 3H). MS (ESI): found: [M+Na]$^+$, 548.7.

5.2 3-[4-[(2R,3S,4S,5S,6R)-3,4,5-Trihydroxy-6-(hydroxymethyl)tetrahydropyran-2-yl]oxyphenyl]benzonitrile (62):

[(2R,3S,4S,5R,6R)-3,4,5-Triacetoxy-6-[4-(3-cyanophenyl)phenoxy]tetrahydropyran-2-yl]methyl acetate (0.075 g) was stirred in 6 mL of methanol with catalytic amount of sodium methoxide (0.02 M) at room temperature overnight. H+ exchange resin (DOWEX 50WX4-100) was added to neutralize the mixture. The resin was filtered off and the filtrate was concentrated, then dried in vacuo giving rise to pure product 62 (0.045 g) in 88% yield. $^1$H NMR (300 MHz, CD$_3$OD) δ ppm 3.55~3.65 (m, 1H), 3.67~3.83 (m, 3H), 3.84~3.99 (m, 1H), 4.03 (dd, J=3.43, 1.79 Hz, 1H), 5.55 (J=1.65 Hz, 1H), 7.16~7.33 (m, 2H), 7.54~7.75 (m, 4H), 7.83~8.01 (m, 2H). MS (ESI): found: [M+H]+, 358.3. (see Table 5)

6. Procedures for the preparation of biphenyl mannoside derivatives through Suzuki coupling reaction: Methyl 5-[4-[(2R,3S,4S,5S,6R)-3,4,5-trihydroxy-6-(hydroxymethyl)tetrahydropyran-2-yl]oxyphenyl]pyridine-3-carboxylate (77)

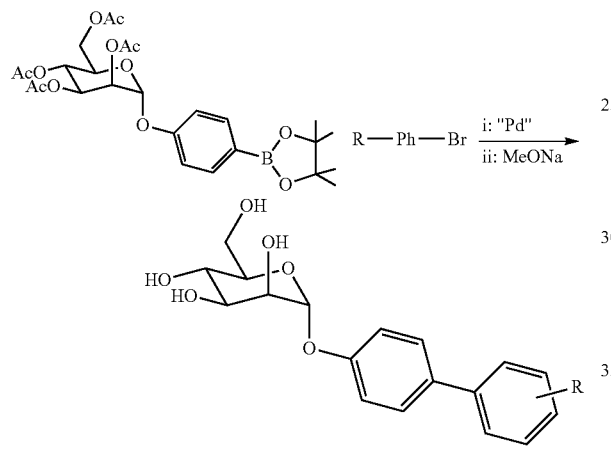

6.1 [(2R,3S,4S,5R,6R)-4,5-diacetoxy-6-(acetoxymethyl)-2-[4-(4,4,5,5-tetramethyl-1,3,2-dioxaborolan-2-yl)phenoxy]tetrahydropyran-3-yl]acetate:

Under nitrogen atmosphere, the mixture of acetyl-protected 4-bromophenyl δ-D-mannoside (2.791 g, 5.55 mmol), bis(pinacolato)diboron (1.690 g, 6.66 mmol), potassium acetate (2.177 g, 22.18 mmol) and (1.1'-bis(diphenylphosohino)ferrocene)dichloropalladium (II) (0.244 g, 0.33 mmol) in DMSO (50 ml) was heated at 80° C. with stirring for 2.5 h. The solvent was removed and the resulting residue was purified by silica gel chromatography with hexane/ethyl acetate combinations as eluent to give [(2R,3S,4S,5R,6R)-4,5-diacetoxy-6-(acetoxymethyl)-2-[4-(4,4,5,5-tetramethyl-1,3,2-dioxaborolan-2-yl)phenoxy]tetrahydropyran-3-yl]acetate (2.48 g) in 81% yield. $^1$H NMR (300 MHz, CHLOROFORM-d) δ ppm 1.33 (s, 12H) 1.98-2.12 (m, 9H) 2.20 (s, 3H) 3.93-4.19 (m, 2H) 4.21-4.36 (m, 1H) 5.32-5.42 (m, 1H) 5.45 (dd, J=3.57, 1.92 Hz, 1H) 5.51-5.62 (m, 2H) 7.00-7.15 (m, 2H) 7.67-7.84 (m, 2H). MS (ESI): found: [M+Na]+, 573.2.

6.2 Methyl 5-[4-[(2R,3S,4S,5S,6R)-3,4,5-trihydroxy-6-(hydroxymethyl)tetrahydropyran-2-yl]oxyphenyl]pyridine-3-carboxylate (77):

Under nitrogen atmosphere, the mixture of R2R,3S,4S,5R,6R)-4,5-diacetoxy-6-(acetoxymethyl)-2-[4-(4,4,5,5-tetramethyl-1,3,2-dioxaborolan-2-yl)phenoxy]tetrahydropyran-3-yl]acetate (0.132 g, 0.24 mmol), methyl 5-bromonicotinate (0.043 g, 0.2 mmol), cesium carbonate (0.196 g, 0.6 mmol) and tetrakis(triphenylphosphine)palladium (0.023 g, 0.02 mmol) in dioxane/water (5 mL/1 mL) was heated at 80° C. with stirring for 1 h. After cooling down, the mixture was filtered through silica gel column to remove the metal catalyst and salts with hexane/ethyl acetate (2/1) containing 2% triethylamine as eluent. The filtrate was concentrated, and then dried in vacuo. Into the residue, 6 mL of methanol with catalytic amount of sodium methoxide (0.02 M) was added and the mixture was stirred at room temperature overnight. H+ exchange resin (DOWEX 50WX4-100) was added to neutralize the mixture. The resin was filtered off and the filtrate was concentrated. The resulting residue was purified by silica gel chromatography with CH$_2$Cl$_2$/MeOH combinations containing 2% NH/H$_2$O as eluent, giving rise to 77 (0.031 g) in 40% yield. $^1$H NMR (300 MHz, CD$_3$OD) δ ppm 3.53-3.65 (m, 1H) 3.67-3.83 (m, 3H) 3.89-3.96 (m, 1H) 3.99 (s, 3H) 4.04 (dd, J=3.43, 1.79 Hz, 1H) 5.57 (d, J=1.92 Hz, 1H) 7.22-7.37 (m, 2H) 7.58-7.73 (m, 2H) 8.54 (t, J=2.06 Hz, 1H) 8.97 (d, J=2.20 Hz, 1H) 9.04 (d, J=1.92 Hz, 1H). MS (ESI): found: [M+H]+, 392.1. (see Table 6).

7. Procedure for the Preparation of Mannosides Via Amide Coupling Reaction:

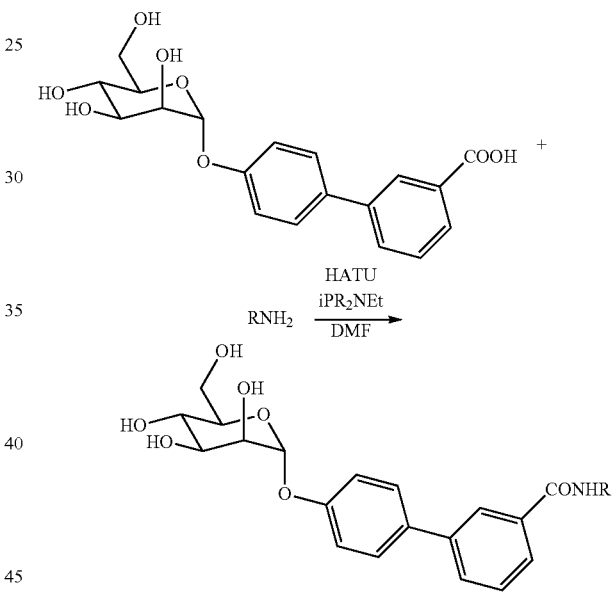

3-[4-[(2R,3S,4S,5S,6R)-3,4,5-trihydroxy-6-(hydroxymethyl)tetrahydropyran-2-yl]oxyphenyl]-N-[2-[2-[2-[[3-[4-[(2R,3S,4S,5S,6R)-3,4,5-trihydroxy-6-(hydroxymethyl)tetrahydropyran-2-yl]oxyphenyl]benzoyl]amino]ethoxy]ethoxy]ethyl]benzamide (82): Under nitrogen atmosphere, at 0° C. anhydrous DMF (5 mL) was added into the RB flask containing 44 (0.062 g, 0.165 mmol) and HATU (0.069 g, 0.182 mmol). After stirring for 10 min, 1,2-bis(2-aminoethoxy)ethane (0.0123 g, 0.083 mmol), then N,N-diisopropylethylamine (0.024 g, 0.182 mmol) were added. The mixture was stirred overnight while being warmed to rt naturally. The solvent was removed and the residue was purified by HPLC (C18, 15*150 mm column; eluent: acetonitrile/water (0.1% TFA)) to give 82(0.044 g) in 82% yield. $^1$H NMR (300 MHz, METHANOL-d$_4$) δ ppm 3.51-3.65 (m, 6H), 3.65-3.82 (m, 14H), 3.88-3.96 (m, 2H), 4.03 (dd, J=3.57, 1.92 Hz, 2H), 5.52 (d, J=1.65 Hz, 2H), 7.14-7.24 (m, 4H), 7.40-7.50 (m, 2H), 7.53-7.63 (m, 4H), 7.66-7.77 (m, 4H), 8.00 (t, J=1.65 Hz, 2H). MS (ESI): found: [M+H]+, 865.9. (see Table 7).

8. Procedures for the Preparation of Fluorescent Mannoside(99 and 100):

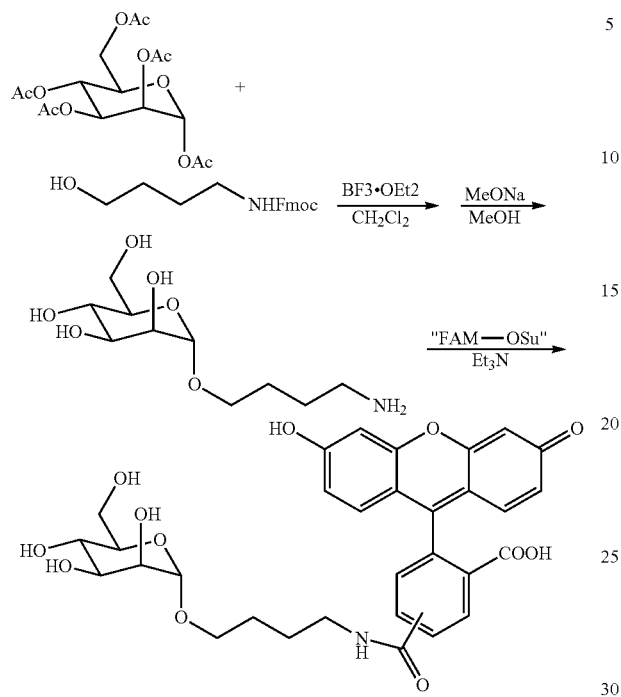

8.1 [(2S,3S,4S,5R,6R)-4,5-diacetoxy-6-(acetoxymethyl)-2-[4-(9Hfluoren-9-ylmethoxycarbonylamino)butoxy]tetrahydropyran-3-yl]acetate: Under nitrogen atmosphere, at 0° C. boron trifluoride diethyl etherate (0.115 g, 0.81 mmol) was added dropwise into the solution of α-D-mannose pentaacetate (0.107 g, 0.27 mmol) and 4-(Fmoc-amino)-1-butanol (0.168 g, 0.54 mmol) in 5 ml of $CH_2Cl_2$. After a few mins the mixture was heated to reflux and kept stirring for more than 36 hrs. The reaction was then quenched with water and extracted with $CH_2Cl_2$. The $CH_2Cl_2$ layer was collected, then dried with $Na_2SO_4$, filtered, and concentrated. The resulting residue was purified by silica gel chromatography with hexane/ethyl acetate combinations as eluent to give [(2S,3S,4S,5R,6R)-4,5-diacetoxy-6-(acetoxymethyl)-2-[4-(9H-fluoren-9-ylmethoxycarbonylamino)butoxy]tetrahydropyran-3-yl] acetate (0.106 g) in 60% yield. $^1$H NMR (300 MHz, $CDCl_3$) δ ppm 1.48~1.79 (m, 4H), 2.01 (s, 3H), 2.05 (s, 3H), 2.11 (s, 3H), 2.17 (s, 3H), 3.25 (m, 2H), 3.50 (m, 1H), 3.73 (m, 1H), 3.91~4.04 (m, 1H), 4.05~4.18 (m, 1H), 4.18~4.37 (m, 2H), 4.41 (d, J=6.87 Hz, 2H), 4.74~4.94 (m, 2H), 5.17~5.41 (m, 3H), 7.29~7.37 (m, 2H), 7.37~7.47 (m, 2H), 7.61 (d, J=7.42 Hz, 2H), 7.78 (d, J=7.42 Hz, 2H). MS (ESI): found: [M+H]$^+$, 642.2.

8.2 (2S,3S,4S,5S,6R)-2-(4-aminobutoxy)-6-(hydroxymethyl)tetrahydropyran-3,4,5-triol (98): R2S,3S,4S,5R,6R)-4,5-diacetoxy-6-(acetoxymethyl)-2-[4-(9H-fluoren-9-ylmethoxycarbonylamino)butoxy]tetrahydropyran-3-yl] acetate (0.106 g, 0.165 mmol) was stirred in 6 mL of methanol with catalytic amount of sodium methoxide (0.02M) at rt overnight. The solvent was removed and the residue was purified by silica gel chromatography with combination of ammonia aqueous/methanol as eluent to afford 98 (0.036 g) in 88% yield. $^1$H NMR (300 MHz, $CD_3OD$) δ ppm 1.46~1.78 (m, 4H), 2.61~2.88 (m, 2H), 3.41~3.55 (m, 2H), 3.59 (t, J=9.3 Hz, 1H), 3.65~3.87 (m, 5H), 4.75 (d, J=1.65 Hz, 1H). MS (ESI): found: [M+H]$^+$, 252.1.

8.3-Fluorescent mannosides(99 and 100): The mixture of 98 (0.018 g, 0.070 mmol), 5-(and -6)-carboxyfluoresceinsuccinimidyl ester (0.022 g, 0.046 mmol) and triethylamine (0.058 g, 0.57 mmol) in DMF (2 mL) was stirred overnight. After removing the solvent, the residue was purified by silica gel chromatography with dichloromethane/methanol combination as eluent, giving rise to 99 and 100 (0.023 g) in 82% yield. MS (ESI): found: [M+H]$^+$, 610.6. (see Table 8).

9. Procedures for the preparation of (2R,3S,4S,5S,6S)-2-(hydroxymethyl)-6-(4-phenyltriazol-1-yl)tetrahydropyran-3,4,5-triol (101):

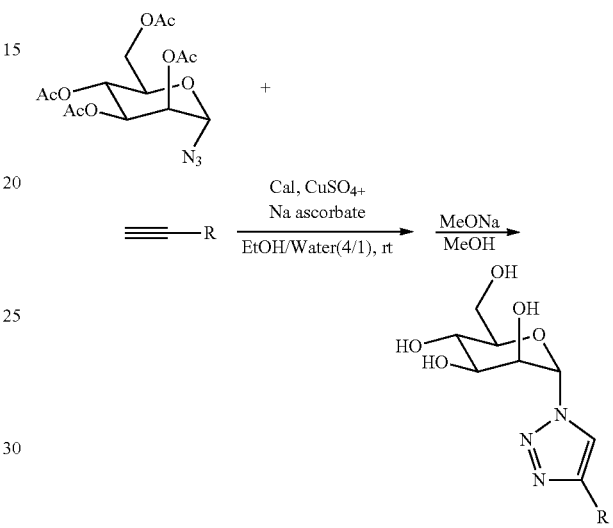

9.1 [(2S,3S,4S,5R,6R)-4,5-diacetoxy-6-(acetoxymethyl)-2-(4-phenyltriazol-1-yl)tetrahydropyran-3-yl]acetate: Under nitrogen atmosphere, EtOH/$H_2O$ (4 mL/1 mL) was added into the RB flask containing α-azido-D-mannose tetraacetate (0.075 g, 0.2 mmol), phenyl acetylene (0.026 g, 0.24 mmol), copper (II) sulfate pentahydrate (0.01 g, 0.04 mmol) and sodium ascorbate (0.016 g, 0.08 mmol). The mixture was stirred at room temperature overnight. The solvent was removed and the residue was purified by silica gel chromatography with hexane/ethyl acetate combination as eluent, giving rise to [(2S,3S,4S,5R,6R)-4,5-diacetoxy-6-(acetoxymethyl)-2-(4-phenyltriazol-1-yl)tetrahydropyran-3-yl] acetate (0.030 g) in 31% yield. $^1$H NMR (300 MHz, CHLOROFORM-d) δ ppm 2.05-2.12 (m, 9H) 2.20 (s, 3H) 3.89-3.99 (m, 1H) 4.08 (dd, J=12.50, 2.61 Hz, 1H) 4.40 (dd, J=12.50, 5.36 Hz, 1H) 5.40 (t, J=8.79 Hz, 1H) 5.95-6.04 (m, 2H) 6.07 (d, J=2.75 Hz, 1H) 7.34-7.53 (m, 3H) 7.79-7.92 (m, 2H) 7.96 (s, 1H). MS (ESI): found: [M+Na], 498.1.

9.2 (2R,3S,4S,5S,6S)-2-(hydroxymethyl)-6-(4-phenyltriazol-1-yl)tetrahydropyran-3,4,5-triol (101): [(2S,3S,4S,5R,6R)-4,5-diacetoxy-6-(acetoxymethyl)-2-(4-phenyltriazol-1-yl)tetrahydropyran-3-yl]acetate (0.028 g, 0.059 mmol) was stirred in 6 mL of methanol with catalytic amount of sodium methoxide (0.02 M) at room temperature overnight. H$^+$ exchange resin (DOWEX 50WX4-100) was added to neutralize the mixture. The resin was filtered off and the filtrate was concentrated, then dried in vacuo giving rise to pure product 101 (0.015 g) in quantitative yield. $^1$H NMR (300 MHz, $CD_3OD$) δ ppm 3.34-3.44 (m, 1H) 3.70-3.92 (m, 3H) 4.12 (dd, J=8.52, 3.57 Hz, 1H) 4.71-4.80 (m, 1H) 6.08 (d, J=2.75 Hz, 1H) 7.30-7.41 (m, 1H) 7.41-7.51 (m, 2H) 7.77-7.90 (m, 2H) 8.51 (s, 1H). (ESI): found: [M+Na]$^+$, 330.2. (see Table 9)

10. Procedures for the preparation of Methyl 3-[4-[[(2S,3S,4S,5S,6R)-3,4,5-trihydroxy-6-(hydroxymethyl)tetrahydropyran-2-yl]amino]phenyl]benzoate (102):

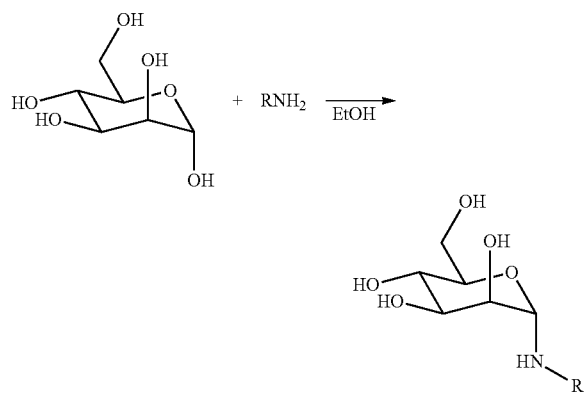

α-D-mannose (0.360 g, 2 mmol) and methyl 4'-aminobiphenyl-3-carboxylate (0.454 g, 2 mmol) in ethanol (5 mL) was heated to 55° C. for 17 h. After cooling down to rt, the white precipitate formed was collected by filtration. The precipitate was washed with ethanol (3 mL) two times, then dried in vacuo to afford pure 102 in 77% yield. $^1$H NMR (300 MHz, ACETONITRILE-d3 and D2O) δ ppm 3.28-3.38 (m, 1H) 3.54-3.59 (m, 2H) 3.64-3.71 (m, 2H) 3.86 (s, 3H) 3.88-3.92 (m, 1H) 4.89 (d, J=1.10 Hz, 1H) 6.80-6.91 (m, 2H) 7.44-7.58 (m, 3H) 7.75-7.90 (m, 2H) 8.11-8.20 (m, 1H). (ESI): found: [M+H]$^+$, 390.1.

11. Procedures for the preparation of methyl 3-[4-[(2R,3S,4S,5S,6R)-3,4,5-trihydroxy-6-(hydroxymethyl)tetrahydropyran-2-yl]sulfanylphenyl]benzoate (103):

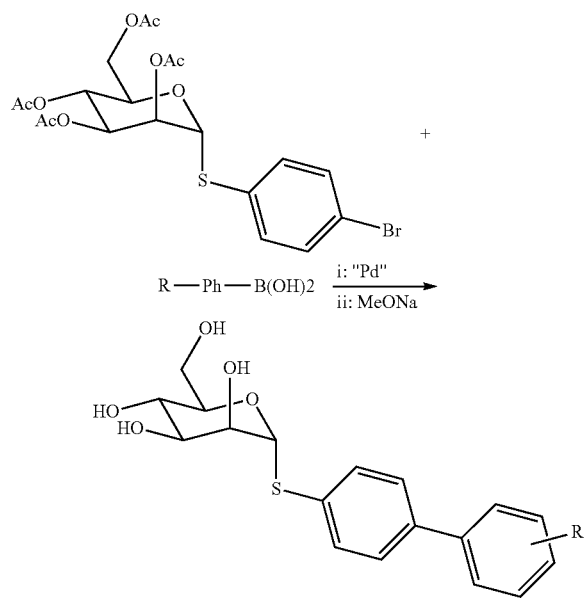

11.1 [(2R,3S,4S,5R,6R)-4,5-Diacetoxy-6-(acetoxymethyl)-2-(4-bromophenyl)sulfanyl-tetrahydropyran-3-yl]acetate: Under nitrogen atmosphere, at 0° C. boron trifluoride diethyl etherate (0.427 g, 3.0 mmol) was added dropwise into the solution of α-D-mannose pentaacetate (0.390 g, 1.0 mmol) and 4-bromobenzenethiol (0.378 g, 2.0 mmol) in 6 ml of CH$_2$Cl$_2$. After a few mins the mixture was warmed to rt and kept stirring for 48 hrs. The reaction was then quenched with water and extracted with CH$_2$Cl$_2$. The CH$_2$Cl$_2$ layer was collected, dried with Na$_2$SO$_4$, filtered, and concentrated. The resulting residue was purified by silica gel chromatography with hexane/ethyl acetate combinations as eluent, giving rise to R2R,3S,4S,5R,6R)-4,5-diacetoxy-6-(acetoxymethyl)-2-(4-bromophenyl)sulfanyl-tetrahydropyran-3-yl]acetate (0.40 g) in 77% yield. $^1$H NMR (300 MHz, CHLOROFORM-d) δ ppm 2.01-2.10 (m, 9H) 2.16 (s, 3H) 4.10 (dd, J=12.09, 2.47 Hz, 1H) 4.30 (dd, J=12.09, 6.04 Hz, 1H) 4.43-4.61 (m, 1H) 5.24-5.40 (m, 2H) 5.43-5.52 (m, 2H) 7.32-7.39 (m, 2H) 7.42-7.49 (m, 2H). MS (ESI): found: [2M+H]$^+$, 1039.1.

11.2 Methyl 3-[4-[(2R,3S,4S,5S,6R)-3,4,5-trihydroxy-6-(hydroxymethyl)tetrahydropyran-2-yl]sulfanylphenyl]benzoate (103):

Under nitrogen atmosphere, the mixture of [(2R,3S,4S,5R,6R)-4,5-diacetoxy-6-(acetoxymethyl)-2-(4-bromophenyl)sulfanyl-tetrahydropyran-3-yl]acetate (0.20 g, 0.39 mmol), 3-methoxycarbonylphenylboronic acid (0.106 g, 0.59 mmol), cesium carbonate (0.381 g, 1.17 mmol) and tetrakis(triphenylphosphine)palladium (0.045 g, 0.04 mmol) in dioxane/water (5 mL/1 mL) was heated at 80° C. with stirring for 1 h. After cooling down, the mixture was filtered through silica gel column to remove the metal catalyst and salts with hexane/ethyl acetate (2/1) as eluent. The filtrate was concentrated, and then dried in vacuo. Into the residue, 6 mL of methanol with catalytic amount of sodium methoxide (0.02 M) was added and the mixture was stirred at room temperature overnight. H$^+$ exchange resin (DOWEX 50WX4-100) was added to neutralize the mixture. The resin was filtered off and the filtrate was concentrated. The resulting residue was purified by HPLC(C18, 15*150 mm column; eluent: acetonitrile/water (0.1% TFA)) to give 103 (0.095 g) in 63% yield. $^1$H NMR (300 MHz, CD$_3$OD) δ ppm 3.66-3.91 (m, 4H) 3.94 (s, 3H) 4.01-4.16 (m, 2H) 5.51 (d, J=1.37 Hz, 1H) 7.51-7.69 (m, 5H) 7.81-7.93 (m, 1H) 8.00 (dt, J=7.83, 1.44 Hz, 1H) 8.24 (t, J=1.65 Hz, 1H). MS (ESI): fou: [M nd+H]$^+$, 407.1.

12. Procedures for the preparation of methyl 3-[4-[[(2S,3S,4S,5S,6R)-3,4,5-trihydroxy-6-(hydroxymethyl)tetrahydropyran-2-carbonyl]amino]phenyl]benzoate (104):

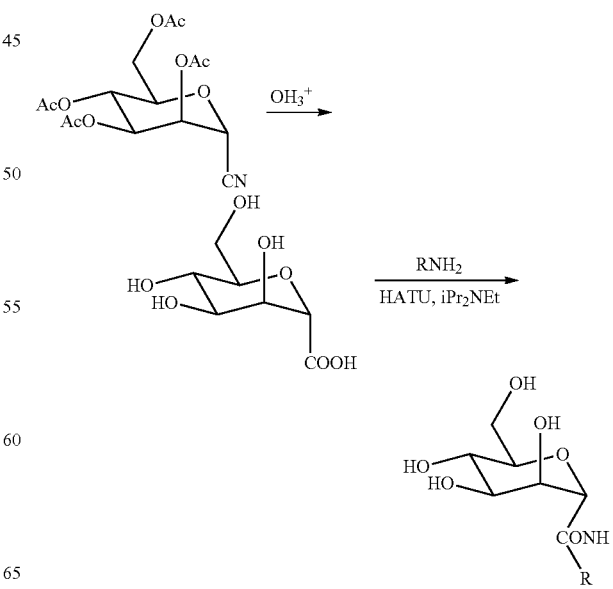

The solution of α-cyano-D-mannose tetraacetate (0.107 g, 0.3 mmol) in 25% hydrochloric acid was heated at 50° C. for 48 h. The solvent was removed. Water (10 ml) and H⁺ exchange resin (DOWEX 50WX4-100) was added and kept stirring for 5 mins. The resin was filtered off and the filtrate was concentrated, and then dried in vacuo. Into the resulting residue, HATU (0.274 g, 0.72 mmol) and anhydrous DMF (6 ml) were added at 0° C. After stirring for 10 min, methyl 4'-aminobiphenyl-3-carboxylate (0.164 g, 0.72 mmol), then N,N-diisopropylethylamine (0.233 g, 1.80 mmol) were added. The mixture was stirred overnight while being warmed to rt naturally. The solvent was removed and the residue was purified by silica gel chromatography with CH$_2$Cl$_2$/MeOH combinations as eluent to give 104 (0.066 g) in 52% yield. $^1$H NMR (300 MHz, CD$_3$OD) δ ppm 3.50 (dt, J=4.67, 2.33 Hz, 1H) 3.58-3.65 (m, 2H) 3.76 (dd, J=11.81, 7.42 Hz, 1H) 3.86-4.03 (m, 4H) 4.52 (t, J=2.61 Hz, 1H) 4.57 (d, J=2.75 Hz, 1H) 7.55 (t, J=7.69 Hz, 1H) 7.60-7.68 (m, 2H) 7.68-7.76 (m, 2H) 7.82-7.91 (m, 1H) 7.97 (dt, J=7.69, 1.37 Hz, 1H) 8.21-8.28 (m, 1H). MS (ESI): found: [M+H]⁺, 418.1.

Example 6

Structure-Based Drug Design and Optimization of Mannoside Bacterial FimH Antagonists As shown in Scheme 1, α-D-mannoside derivatives were prepared using traditional Lewis acid mediated glycosidation. [3]Reaction of acylated α-D-(+)-mannose 1a with a variety of phenols and BF$_3$-OEt$_2$ resulted in exclusive formation of the α-isomer mannosides 2. Subsequent deacylation with NaOMe in methanol gave the desired aryl mannosides 3-8 in good yield. Biological activity against FimH was evaluated using a guinea pig red blood cell-based hemagglutination (HA) assay (ref) in which the concentration of the mannoside on reducing agglutination by 50% was used as the primary endpoint (50% HA titer). This assay was preferred to a simple FimH binding assay for screening and developing SAR since it assesses the compound's ability to prevent bacterially-mediated adhesion directly in a cellular assay.

Scheme 1$^a$

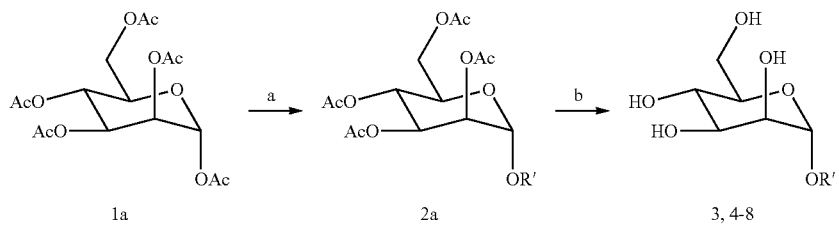
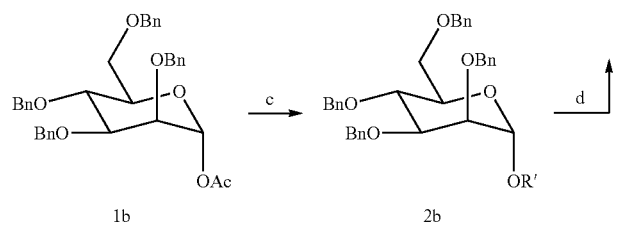

$^a$Reagents and conditions: (a) R'OH, BF$_3$—OEt$_2$, CH$_2$Cl$_2$, reflux; (b) (i) NaOMe, MeOH; (ii) H⁺ exchange resin; (c) R'OH, BF$_3$—OEt$_2$, CH$_2$Cl$_2$, 0° C. to 25° C.; (d) H$_2$, 10% Pd/C, MeOH.

As shown in Table 10, it was found that the general trend that 2- and 3-substitution was optimal for potency relative to 4-substitution in most examples with the exception of the acyl anilines 3q-s in which this trend was dramatically reversed. Ortho-substituted chlorophenyl 3g, cyanophenyl 3m, and meta-substituted methyl ester 3j all showed an impressive greater than 5-fold improvement in potency relative to parent phenyl mannoside 3a. Interestingly, carboxylic acid 3j lost 10-fold potency relative to matched pair methyl ester 3j showing a 50% HA titer of only 60 µM. Incorporation of an additional methyl ester in the 5-position of 3j, as with compound 4, resulted in a relatively large 3-fold enhancement in potency. Benzylic analogs 5a and 5b (pictured below) which have different conformational space and flexibility relative to direct phenyl substitution of the anomeric oxygen, as with to matched pairs 3a and 3b, show a 2-fold decrease (50% HA titer=60 µM) in potency.

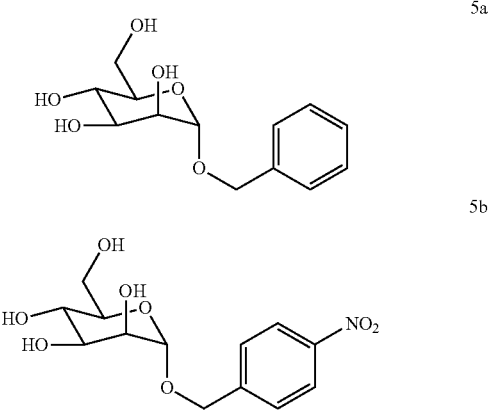

TABLE 10

SAR of simple aryl substitution mannoside library.

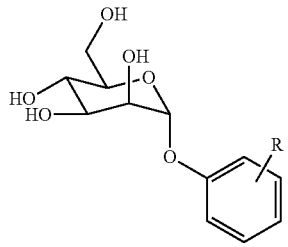

| Compound | R | HA 50% Titer (μM) |
|---|---|---|
| 3a | H | 30 |
| 3b | 4-NO$_2$ | 31 |
| 3c | 3-NO$_2$ | 16 |
| 3d | 4-NH$_2$ | 32 |
| 3e | 3-Me | 4 |
| 3f | 4-Me | 8 |
| 3g | 2-Cl | 4 |
| 3h | 3-Cl | 8 |
| 3i | 4-Cl | 32 |
| 3j | 3-CO$_2$Me | 8 |
| 3l | 3-CO$_2$H | 60 |
| 3m | 2-CN | 6 |
| 3n | 3-CN | 23 |
| 3o | 4-CN | 30 |
| 3p | 4-OMe | 8 |
| 3q | 2-NHAc | 125 |
| 3r | 3-NHAc | 12 |
| 3s | 4-NHAc | 8 |
| 3t | 3-CONH$_2$ | 16 |
| 3u | 4-CONH$_2$ | 15 |
| 3w | 4-CH$_2$CO$_2$Me | 30 |
| 4 | 3,5-CO$_2$Me | 2 |

Upon examination of the X-ray structures of α-D-butylmannoside and oligomannose-3 coupled with docking studies of the monophenyl inhibitors bound to FimH, it was encouraging to observe that additional improvements in binding affinity could be achieved by addition of a second aryl or aliphatic ring system in anticipation of introducing both additional hydrophobic and π-π stacking interactions with Tyr-48 and Tyr-137 as seen from the directionality of the butyl side chain in butylmannoside and position of the second mannose residue in oligomannose-3.

To this end, analogs with an additional ring system either directly attached or fused ring to the parent aryl mannosides of Table 10 were explored. It was discovered that a variety of ring systems were tolerated (Table 11) relative to the previously described coumarin analog 4-methylumbellferyl-α-D-mannoside 6. The most attractive inhibitor in this series of compounds was the 4'-biphenyl derivative 8e bearing a methyl ester off the meta position of the second aryl ring and showing a 2-fold improvement relative to 6 displaying an HA titer 1 μM. In order to determine the source of this potency enhancement and aid in further improvements, a high-resolution X-ray crystal structure of 8e bound to FimH was obtained. Shown in FIG. 22, inhibitor 8e binds in a very complementary "lock and key" fashion to the FimH binding pocket. The mannose ring is making conserved interactions with the mannose-binding pocket similar to those described previously while the two aromatic rings of the biphenyl moiety exist in a non-planar conformation allowing for a π-stacking and hydrophobic interactions with Tyr-48 and other residues encompassing the exterior hydrophobic cleft of FimH. The π-stacking interaction with Tyr 48 occurs on the opposite side of the phenyl ring than that engaged by oligomannose-3, which inserts itself into the open "tyrosine gate" formed by Tyr-48 and Tyr-137. Thus, 8e engages the "tyrosine gate" in a way that results in alteration of the extended FimH binding pocket through closure of the tyrosine gate upon rotation of Tyr-48. This binding mode places the ester of 8e within H-bonding distance to a salt bridge formed between Arg-98 and Glu-50 (FIG. 22). It is noteworthy that the HA 50% titer for Methylaman is >1 mM making compound 8e greater than 1000-fold more potent from the addition of the biphenyl ester.

TABLE 11

SAR of multi-ring system analogs.

| Compound | R | HA 50% titer EC$_{90}$ (μM) |
|---|---|---|
| 6 | | 2 |
| 7a | | 8 |
| 7b | | 6 |
| 7c | | 4 |
| 7d | | 2 |
| 7e | | 2 |
| 8a | | 62 |
| 8b | | 6 |

TABLE 11-continued

SAR of multi-ring system analogs.

| Compound | R | HA 50% titer EC$_{90}$ (μM) |
|---|---|---|
| 8c | 4-phenylphenyl (biphenyl) | 8 |
| 8d | 3-benzoylphenyl | 8 |
| 8e | 4'-(methyl)-biphenyl-3-CO$_2$Me | 1 |
| 8f | 4'-(methyl)-biphenyl-4-CO$_2$Me | 4 |
| 8g | 4-(pyridin-3-yl)phenyl | 2 |
| 8h | 4-(pyridin-4-yl)phenyl | 2 |

This observation lead to investigating replacing the mannose with alternate sugars or mimics since the biphenyl portion alone provides a significant contribution to biological activity presumably from tighter binding to FimH. It was decided to start by replacing the mannose portion of 8e with glucose since all chiral centers are identical except for the 3-hydroxyl group adjacent to the anomeric center, being of R stereochemistry in mannose and S in glucose (Scheme 2). Standard Lewis acid mediated glycosidation gave isomeric mixtures at the anomeric center favoring the undesired α-isomer, conversely to the clean formation of the α-isomer seen for the mannosides. Correspondingly, reaction of benzoyl protected α-D-glucose 9 with phenol 10 using BF$_3$-OEt$_2$ followed debenzoylation yielded both the α-D glucoside 11a and α-D-glucoside 11b in a 3:7 ratio. Unfortunately, neither glucoside isomer showed activity in the hemagglutination assay even up to a concentration of 2.5 mM. Therefore, modification of a single chiral hydroxyl group stereocenter on the mannoside is sufficient to significantly decrease biological activity, presumably resulting from the inability to tightly bind FimH. Upon analysis of the specific interactions realized from α-D-mannose bound to FimH,[4] this hydroxyl group is making an H-bonding interaction with the N-terminal residue of FimH and a water molecule contained inside the binding pocket. In any event, this finding demonstrates the exquisite specificity of FimH for mannose epitopes which has enabled UPEC bacteria to exclusively recognize mannose-presenting cells.

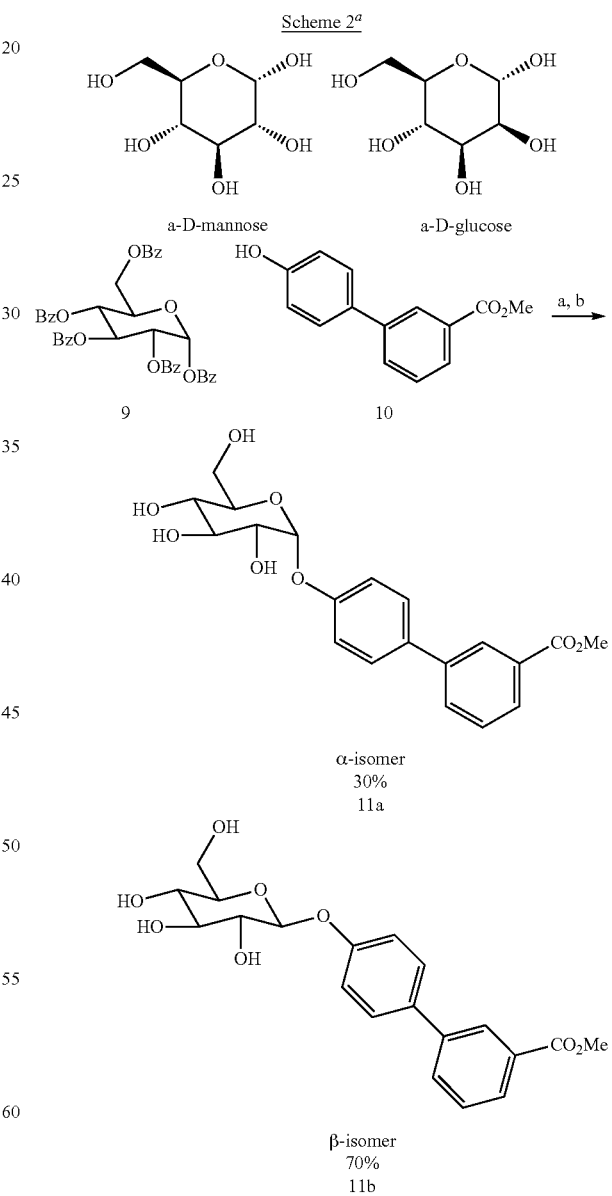

Scheme 2[a]

[a]Reagents and conditions: (a) R'OH, BF$_3$—OEt$_2$, CH$_2$Cl$_2$, 0° C. to 25° C.; (d) NaOMe, MeOH.

Next, the biaryl portion of the mannoside was optimized by undertaking an extensive SAR evaluation of the second ring through a modified Toplisstype evaluation of substituents. This focused set of compounds was designed with some bias toward improving interactions with Arg-98 and Glu-50 but also with interest in elucidating the importance of ring electronic properties as a means to improve the stacking interaction with Tyr-48. A few initial analogs were prepared using the synthetic route outlined previously in Scheme 1 but a more convergent synthesis was developed based on Suzuki coupling of arylbromide intermediate 12 as shown in Scheme 3.

before to generate the final target compounds 14 or 15a displayed in Table 12. Di-ester 15a was further functionalized to di-methyl amide 15b by reaction with dimethylamine or converted to di-acid 15c by basic hydrolysis in methanol. Upon evaluation of HA titers, the matched pair meta-substituted methyl amide 14a was equipotent to ester 8e while reverse amide 14b and free acid 14c displayed moderately lower potencies of 2 μM and 4 μM respectively. The latter result was surprising since these modifications were designed to introduce an electrostatic interaction with Arg-98 and disrupt the Arg-98/Glu-50 salt bridge. On the other hand, sulfonamide 14r has equivalent potency to carboxamide 14a providing

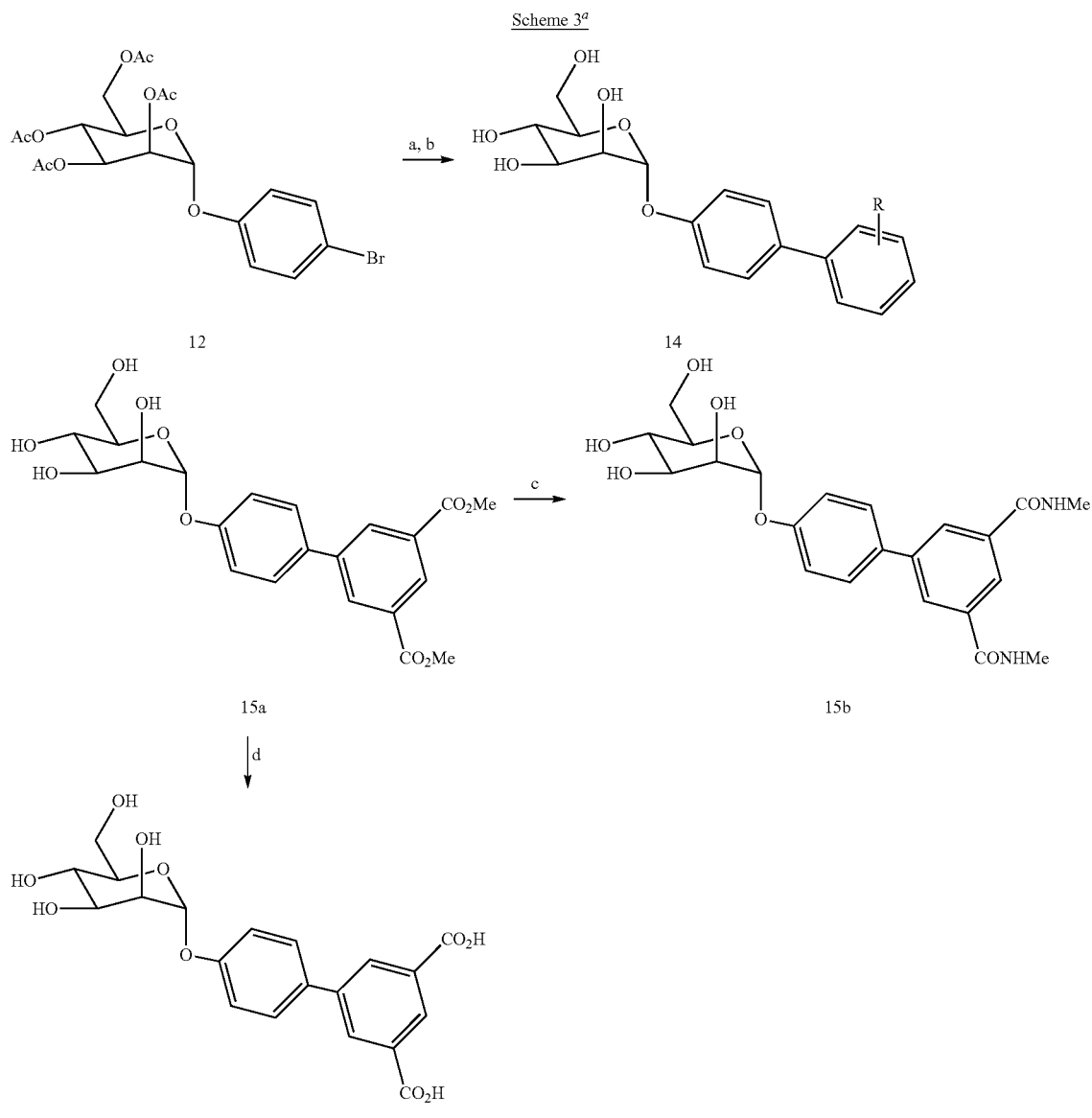

$^a$Reagents and conditions: (a) RPh—B(OR)$_2$, Pd(Ph$_3$P)$_4$, dioxane/water (4:1), Cs$_2$CO$_3$, 80° C. (b)

Employing standard Suzuki conditions by reaction of aryl boronic acids or esters with Pd(Ph$_3$P)$_4$ and Cs$_2$CO$_2$, 12 was converted to protected biphenyl mannosides 13 in good yield. The acylated biaryl mannosides 13 were then deprotected as further evidence that a hydrogen bond acceptor is required for optimal potency presumably from interaction with Arg-98. From analysis of ortho, meta, and para matched pairs, it was obvious that para-substitution was least preferred for activity while meta substitution was preferred to ortho substitution. This preference for meta substitution was most pronounced with the methyl alcohols 14g and 14h where the ortho analog 14g was over 5-fold less potent with an HA titer of only 16 μM. It was surmised that this large substituent results in an increased rotation of the two rings out of the plane causing a non-productive alignment for interactions with Tyr-48. Although a majority of the analogs tested contained electron withdrawing groups, in general electron donating groups such as the methyl alcohols 14g-i and phenols 14j-l were less active in the HA titer assay. The most potent of the mono-substituted mannosides is meta nitro derivative 14m with a 50% HA titer of 0.5 μM. It is possible that the partial negative charge on the nitro oxygen atoms allow for an optimized H-bond acceptor-donor interaction with Arg-98 coupled with the increased electron withdrawing ability of the nitro group possibly enhancing stacking interactions with Tyr-48.

TABLE 12

SAR of substituted biphenyl mannosides.

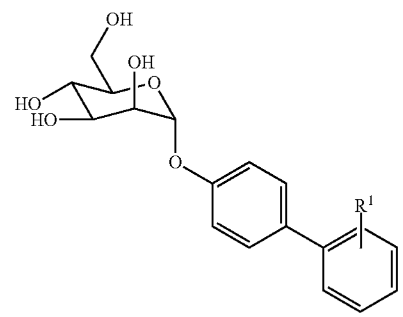

| Compound | $R_1$ | HA 50% titer $EC_{90}$ (μM) |
|---|---|---|
| 14a | 3-CONHMe | 1 |
| 14b | 3-NHAc | 2 |
| 14c | $3\text{-}CO_2H$ | 4 |
| 14d | 2-CN | 2 |
| 14e | 3-CN | 1 |
| 14f | 4-CN | 8 |
| 14g | $2\text{-}CH_2OH$ | 16 |
| 14h | $3\text{-}CH_2OH$ | 3 |
| 14i | $4\text{-}CH_2OH$ | 6 |
| 14j | 2-OH | 8 |
| 14k | 3-OH | 4 |
| 14l | 4-OH | 6 |
| 14m | 2-OMe | 1 |
| 14n | 3-OMe | 1.5 |
| 14o | $2\text{-}NHSO_2Me$ | 12 |
| 14p | $3\text{-}NHSO_2Me$ | 2 |
| 14q | $2\text{-}SO_2NHMe$ | 4 |
| 14r | $3\text{-}SO_2NHme$ | 1 |
| 14s | $3\text{-}NO_2$ | 0.5 |
| 14t | $4\text{-}NO_2$ | 2 |
| 14u | $2\text{-}CONH_2$ | 6 |
| 14v | $3\text{-}CONH_2$ | 2 |
| 14w | $2\text{-}CF_3$ | 8 |
| 14x | $3\text{-}CF_3$ | 2 |
| 14y | 3-F | 6 |
| 15a | $3,5\text{-}CO_2Me$ | 0.15 |
| 15b | 3,5-CONHMe | 0.37 |
| 15c | $3,5\text{-}CO_2H$ | 2 |

Perhaps the most unexpected finding from this study was that addition of another ester or amide substituted in the other meta position such as di-ester 15a and di-methyl amide 15b resulted in the two most potent mannoside inhibitors of FimH with activities of 150 nM and 370 nM, respectively. With respect to di-ester 15a this constitutes a 7-fold improvement in activity relative to mono ester 8e. The di-amide 15b, while slightly less potent, has much improved solubility relative to di-ester 15a. It was hypothesized that the addition of the second ester or amide serves a two-fold purpose for improving activity: First, the electron withdrawing group results in less electron density of the aryl ring thus improving π-π stacking interactions with Tyr48. Second, the mono-ester (or amide) analog can presumably access conformations in which the aryl ring is not in close proximity to Arg-98 whereas the meta di-ester (or di-amide) analog likely exists only in conformations where the ester or amide resides in close proximity to Arg-98 resulting in less entropic loss upon binding and a lower energy bound conformation resulting in increased binding affinity and potency.

In order to more accurately determine the relative contributions of both binding affinity to FimH versus other compound properties to the potency seen in the cellular HA titer assay, a high-throughput fluorescence polarization (FP) (or anisotropy) competitive binding assay was developed using a fluorescent-labeled mannoside ligand shown in Scheme 4. Synthesis was achieved as before using Lewis acid mediated glycosylation with protected aminoalcohol 17 followed by dual Fmoc and acyl deprotection of intermediate 18 to give free amine 19. Subsequent reaction of 5(6)FAM-OSu with 19 using triethylamine in DMF gave the desired fluorescently tagged FAM-mannoside 20.

Scheme 4[a]

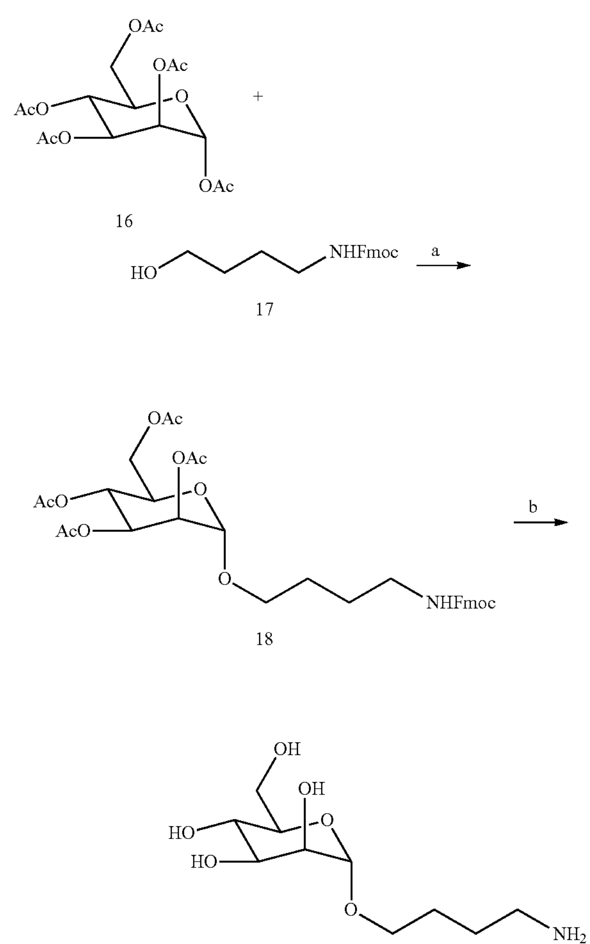

16

17

18

19

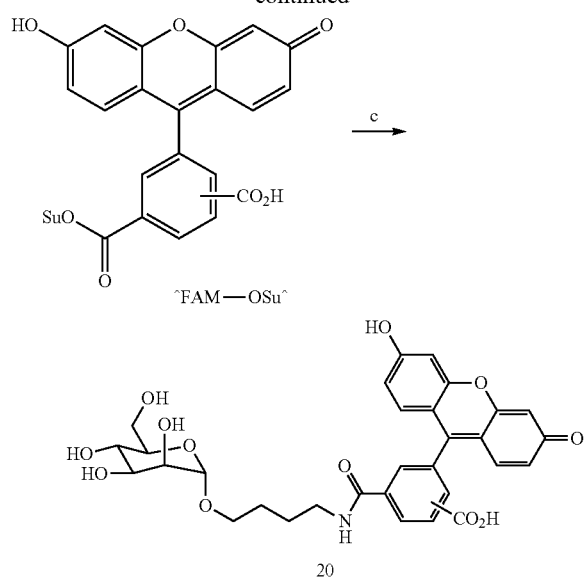

[a]Reagents and conditions: (a) BF$_3$—OEt$_2$, CH$_2$Cl$_2$, reflux; (b) (i) NaOMe, MeOH; (c) 19, Et$_3$N, DMF.

The $K_D$ for FAM mannoside 20 was measured to be 0.17 μM while the 50% HA titer was only 125 μM. Twenty mannoside ligands with structural diversity and activities were evaluated in the HA titer cell assay ranging from 150 nM to 125 μM for their ability to competitively inhibit binding of FAM 20. Interestingly, it was found that all potently competed for FimH binding having $EC_{50}$'s less than 0.25 μM but having no clear correlation of $EC_{50}$ with the activity found in the HA cell assay (Table 13). Although there was over a 60-fold range in cellular potency, there was only about a 5-fold range in binding affinity (FIG. 23). In addition, there was also no linear correlation of data with the two assays. Simple alkyl mannosides have the highest drop in cell activity as demonstrated with butylmannoside having the most dramatic difference with a 510-fold drop in cell activity relative to binding.

TABLE 13

Binding affinity of selected mannosides in fluorescence polarization assay.

| Compound | FP Binding $EC_{50}$ (μM) | HA 50% titer (μM) |
| --- | --- | --- |
| 6 (MeUmbman) | 0.044 | 2 |
| 8e | 0.052 | 1 |
| 8f | 0.059 | 4 |
| 3k | 0.064 | 8 |
| 14b | 0.07 | 2 |
| 14a | 0.075 | 1 |
| 15a | 0.077 | 0.15 |
| 14v | 0.078 | 2 |
| 3j | 0.084 | 6 |
| 15b | 0.087 | 0.37 |
| Heptylman | 0.089 | 15 |
| 4 | 0.091 | 2 |
| 14p | 0.097 | 2 |
| 14c | 0.099 | 4 |
| 3a | 0.114 | 30 |
| 3s | 0.122 | 8 |
| 3r | 0.160 | 12 |

TABLE 13-continued

Binding affinity of selected mannosides in fluorescence polarization assay.

| Compound | FP Binding $EC_{50}$ (μM) | HA 50% titer (μM) |
| --- | --- | --- |
| 3n | 0.162 | 23 |
| 5a | 0.187 | 60 |
| Butylman | 0.245 | 125 |

Interestingly, the most potent biphenyl mannoside series shows a modest correlation of binding affinity having a much smaller drop in cell activity relative to binding. The di-ester 15a and di-amide 15b show the best correlation with only a 2-fold and 4-fold difference in cell potency vs. binding. It is important to note that even though these two analogs are the most potent in the HA titer cell assay, they have about 2-fold less binding affinity in the FP assay than the tightest binding mannosides. While it is unclear why there is no correlation of binding to activity in the cell, there is a moderate correlation when compounds with binned affinities are compared. However, the latter observation cannot explain the non-linear increase in cell activity of 15a and 15b relative to the mono-substituted biphenyl mannosides. Perhaps differential binding kinetics including varied on rates and off rates of mannoside analogs to FimH can provide a plausible explanation for the latter. It is worth mentioning that the previously reported $K_D$ values obtained through surface plasmon resonance (SPR) for 6 (MeUmbaman), butylmannoside, and Heptylaman are 20 nM, 151 nM, and 5 nM respectively. While the result for butylmannoside is similar, the FP assay suggests MeUmbaman is the most potent (44 nM) being 2-fold more potent than Heptylaman (89 nM). Considering both the lack of correlation between binding affinity and biological activity in the cell plus the variability seen comparing two separate binding assays, the HA titer assay coupled with the use of structural information is a preferred route for medicinal chemistry optimization of mannoside FimH ligands. Nonetheless, based on the HA titer cellular data, mannoside 15a is the most potent FimH antagonist reported to date and represents an excellent lead candidate for further optimization of the monovalent mannosides toward a novel preclinical candidate with tremendous therapeutic potential for treating urinary tract infections.

The development of multivalent and dendrimeric mannosides has been the major focus of previous work on FimH antagonists since simple mannosides, while having respectable binding affinity to FimH, show poor cellular activity in the HA assay. It has been demonstrated that multivalent mannosides are effective at increasing avidity through a phenomenon termed "cluster effect" resulting in an overall increased binding affinity when calculated per mannoside monomer. Therefore, it was of interest to determine if the improved monovalent mannosides 15a and 15b would produce a similar increase in avidity or cluster effect previously reported for dendrimeric mannosides. For synthetic simplicity, a model system based on monoamide 14a was chosen. A symmetrical divalent mannoside was designed by connecting two monomers via an amide based linker to the two biphenyl rings (Scheme 5). Accordingly, dimeric inhibitors based on 14a were synthesized by coupling carboxylic acid 13c to either diamine 2-(2-aminoethoxy)ethanamine or 2-[2-(2-aminoethoxy)ethoxy]ethanamine yielding diamides 21 and 22 respectively using standard HATU coupling conditions with Hunig's base in DMF. The shorter chain analog 21 showed a 50% HA titer of 0.75 μM thus showing no noticeable improvement relative to 14a, while the longer ethylene glycol linked diamide 22 displayed an almost 8-fold increase in activity with an impressive HA titer of 130 nM. This constitutes a 4-fold increase in avidity relative to the expected potency of 500 nM based on two monomeric units of 14a. In addition to increased potency, 22 has much improved solubility relative to 21 making it an ideal starting point for further optimization. Although these analogs have less potential to be effective as oral agents relative to the monovalent mannosides, the divalent mannosides are very useful chemical research tools and can potentially be developed into topical or intravenously dosed antibacterial agents.

of HA titer and biofilm formation than anything commercially available and previously tested, some by as much as 2 logs.

i. Hemagglutination of guinea pig red blood cells by type1 piliated UPEC is dependent upon FimH mannose binding ability. Serial dilutions allow a quantitative analysis using this assay.

ii. Compounds that decrease hemagglutination by 75% were then tested in a type 1 dependent biofilm assay. First, the ability of mannoside derivatives to prevent UPEC type 1

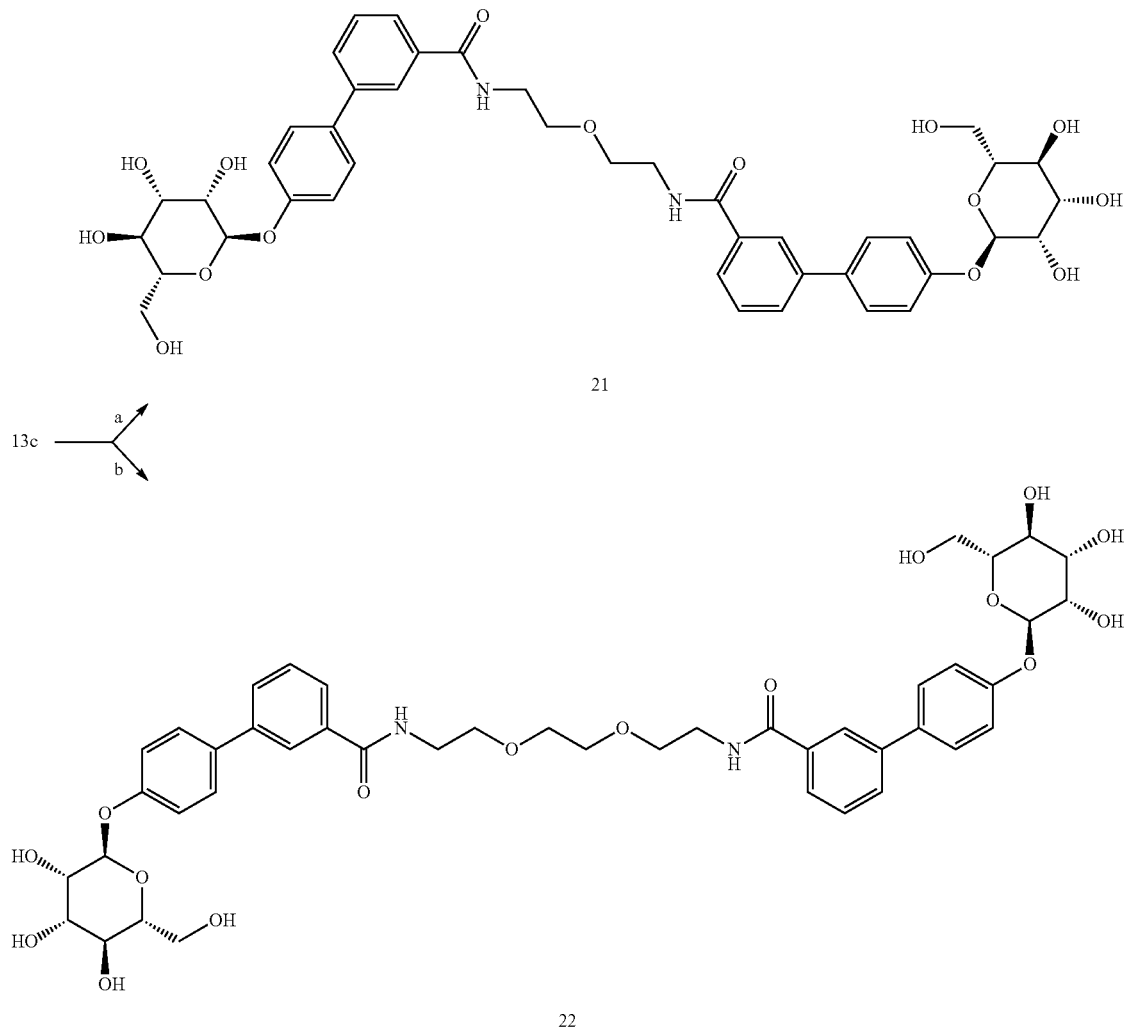

$^a$Reagents and conditions: (a) HATU, [H$_2$N(CH$_2$)$_2$]$_2$O, DIPEA, DMF; (b) HATU, [H$_2$N(CH$_2$)$_2$OCH$_2$]$_2$, DIPEA, DMF.

Example 7

In Vitro Analysis of Mannoside Inhibitors

Three FimH function assays were used to screen mannosides for inhibitory function, and are described below. Selected results for the SAR and testing of these compounds are presented in Examples 5 and 6, and show that some synthesized and tested compounds are more potent inhibitors dependent biofilm formation in the published Kolter assay was measured as optimized for the prototypic UTI89 strain used in these assays. Mannoside derivatives that allow growth but inhibit biofilm formation at 50% or greater were verified by repeating the biofilm assay and performing titration curves to determine the IC$_{50}$. A more rigorous assay tested the ability of the strongest inhibitory mannoside derivatives to reverse hemagglutination of guinea pig red blood cells and to disrupt preformed type 1 dependent biofilms.

iii. A fluorescent polarization assay was developed and miniaturized to monitor the direct binding of a synthesized fluorescently labeled butyl mannose derivative to the FimH receptor as well as competitive displacement by other synthetic mannosides. This fluorescent polarization assay provides a rapid method for monitoring improvements to receptor affinity during the synthetic process, as well as providing Kd binding affinity measurements.

Example 8

Crystallography

Figure 9:
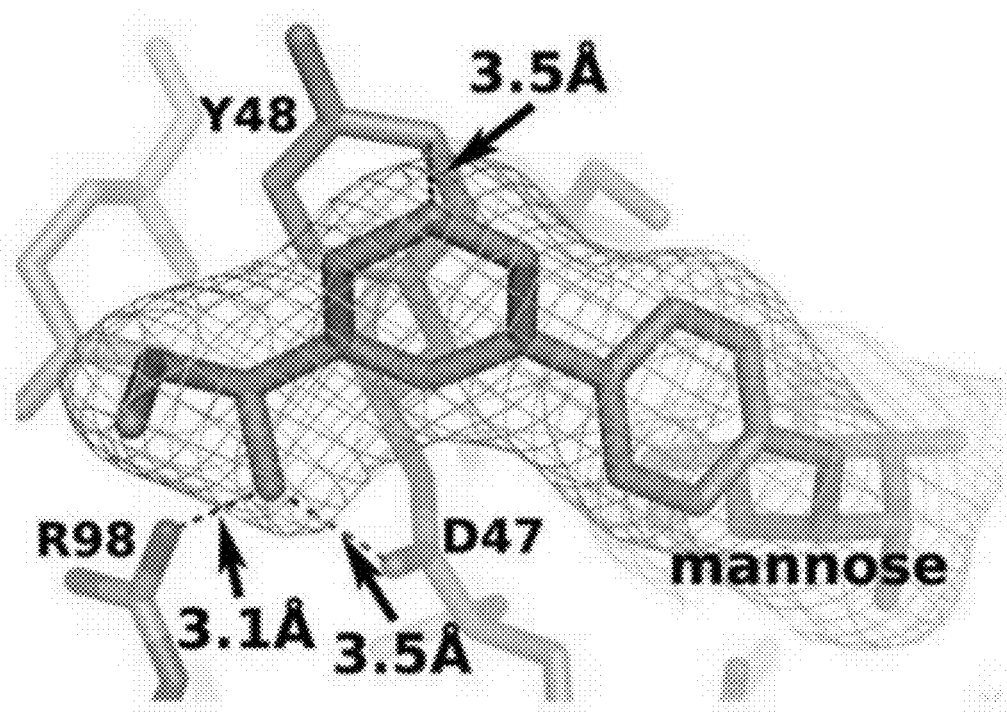
FIG. 9 depicts the structure of FimH with the compound number 15 in Table 1, illustrating interactions formed by compound number 15 with FimHA that are not shared with monomannose. Compound number 15 is shown in the final refined electron density calculated to 2.55 Å with 2Fo-Fc coefficients and contoured at 1σ.

In order to further rationally design better mannoside derivatives to inhibit FimH binding the most efficient inhibitors, such as ZFH253, with the FimH adhesin domain (FimH$_A$) were crystallized to detail their interactions with FimH (FIG. 9).

The adhesin domain of FimH (residues 1-175 with a C-terminal 6-histidine tag, hereafter FimHA) was cloned into a pTRC99 plasmid and expressed in *E. coli*. FimH$_A$ was purified from bacterial periplasm by passage over cobalt affinity (Talon; Clontech) and Q Sepharose (GE Healthcare) columns. Protein was subsequently dialyzed against 10 mM MES at pH 6.5 and concentrated to 15 mg/ml for crystallization trials. FimH$_A$ crystallized in 20% ethanol, 100 mM imidazole pH 8.0, and 200 mM MgCl2. Tetragonal bipyramidal crystals measuring 150×150 pm formed in two days and did not diffract unless slowly dehydrated over the course of at least 12 hours. The FimH$_A$-ZFH253 complex was therefore formed by soaking individual crystals in a stabilizing solution initially containing 15% ethanol, 100 mM imidazole pH 8.0, 200 mM MgCl2, 10% PEG200, 5% glycerol and 1 mM ZFH253. Individual crystals were placed in 150 μl stabilizing solution and allowed to dehydrate to one-third their original volume over the course of 24 hours. Crystals were then harvested without further cryopretection and plunged into liquid nitrogen. Crystals diffracted to 2.55 Å at beamline 4.2.2 at the Advanced Light Source. The structure of FimFI$_A$-ZFH253 was solved by molecular replacement with the program PHASER using a previously-solved model of FimH$_A$ with its methylmannose ligand removed as the search model (PDB ID 1 UWF).

An initial map calculated with Fo-Fc coefficients showed unambiguous difference density for ZFH253 occupying the mannose binding pocket of all four copies of FimHA present in the asymmetric unit. These studies showed that the mannose portion of ZFH253 engages in conserved interactions with FimH$_A$. ZFH253 buries 293 Å$^2$ (calculated with PISA). This places ZFH253 between monomannose, which buries approximately 185 Å$^2$, and oligomannose-3, which buries 388 Å$^2$. Relative to monomannose, most of the additional surface area is buried by the two phenyl groups of ZFH253, which do not engage the "tyrosine gate" of Tyr48 and Tyr137 but orient toward Tyr48 such that the phenyl group most distal to the mannose moiety forms a close pi-stacking interaction with Tyr48 (FIG. 9). This interaction mimics the aromatic-to-saccharide stacking between Tyr48 and Man3 of oligomannose-3 that contributes to the high affinity of high-mannose epitopes to FimH in vivo. Additionally, the terminal carboxyl group of ZFH253 forms two hydrogen bonds with FimH (FIG. 9), offering a structural basis for its 16-fold increase in potency in the HA titer assay over ZFH296, which contains only two unsubstituted phenyl groups. Further, the FimH$_A$/ZFH253 crystal structure suggested several avenues for rational improvement of mannoside derivatives. First, there is an ordered water at 2.7 Å from the carboxyl group of the first carbon of the mannose ring that forms close hydrogen bonds with the N-terminus, the main-chain carbonyl of Phe1, and the epsilon oxygen of Gln133. Extension of this carboxyl group by two bond lengths would allow the mannoside to engage these interactions. There is a second ordered water 4.7 Å from an ortho carbon of the first phenyl group of the mannoside that could be coordinated by a hydrogen bond donor. Importantly, the FimH$_A$/ZFH253 crystal structure serves as proof of concept that computational docking may serve as a useful tool in rational design of related mannosides. The conformation of ZFH253 seen in the crystal structure is essentially identical to that of a lowest-energy conformer generated by OMEGA2 and docked into a previous crystal structure of FimH by FRED (OpenEye, Inc.). This approach will speed the design of further compounds, with additional crystallography for the exploration of scaffolds other than the biphenyl group of ZFH253.

Example 9

Inhibition of In Vivo Functions of FimH

Figure 10:
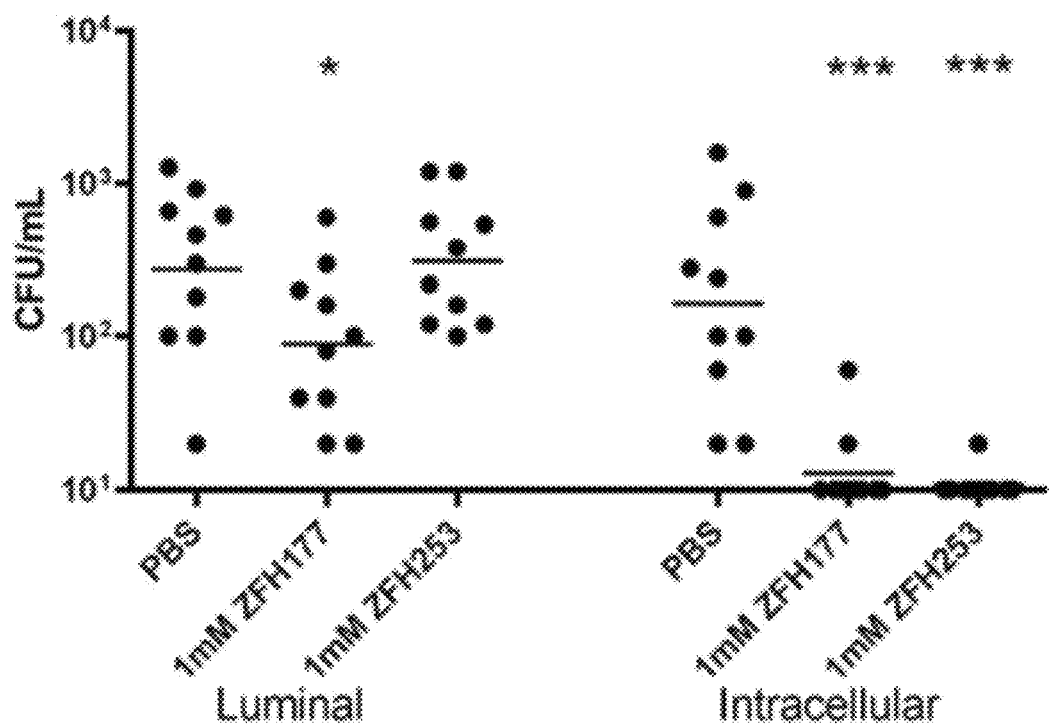
FIG. 10 depicts a graph showing that mannosides number 7 and number 15 (Table 1) reduced intracellular bacteria at 1 hour post-infection. A 1 hour gentamicin protection assay was used to evaluate the amount of bacteria present in the luminal versus intracellular fraction in the presence of mannosides number 7 and number 15. A small decrease was seen in the luminal fraction in the presence of mannoside number 7 (p<0.05) whereas a significant decrease was seen in the intracellular fraction in the presence of either mannoside (p<0.0001).

Based on the extensive elucidation of the UPEC pathogenic cascade, critical nodes in pathogenesis that mannosides would target and thereby have powerful and potent therapeutic ramifications were identified. The first step in the UPEC pathway involves FimH-mediated colonization of the bladder epithelium via the recognition of mannose receptors. Bacterial invasion into superficial bladder umbrella cells can then ensue. By preventing bacterial attachment, mannosides will also inhibit the subsequent invasion of bacteria into the bladder epithelial cells. To test this, a well-established gentamicin protection assay that allows the determination of the luminally bound fraction versus the intracellular fraction was utilized (FIG. 10). In the presence of mannosides ZFH177 and ZFH253 there was a significant reduction in intracellular bacteria at 1 hour post-infection arguing that the mannosides are disrupting specific type 1-mediated binding required for subsequent invasion. It is not clear why a reduction was not observed in the luminal UPEC population. This may be due to contamination from bacteria in the urine or bacteria that are non-specifically associated with the epithelium. In any case, blocking invasion blocks the ability of the bacteria to rapidly expand in numbers. This is due to the ability of the mannosides to block the IBC mechanism.

Figure 11A:
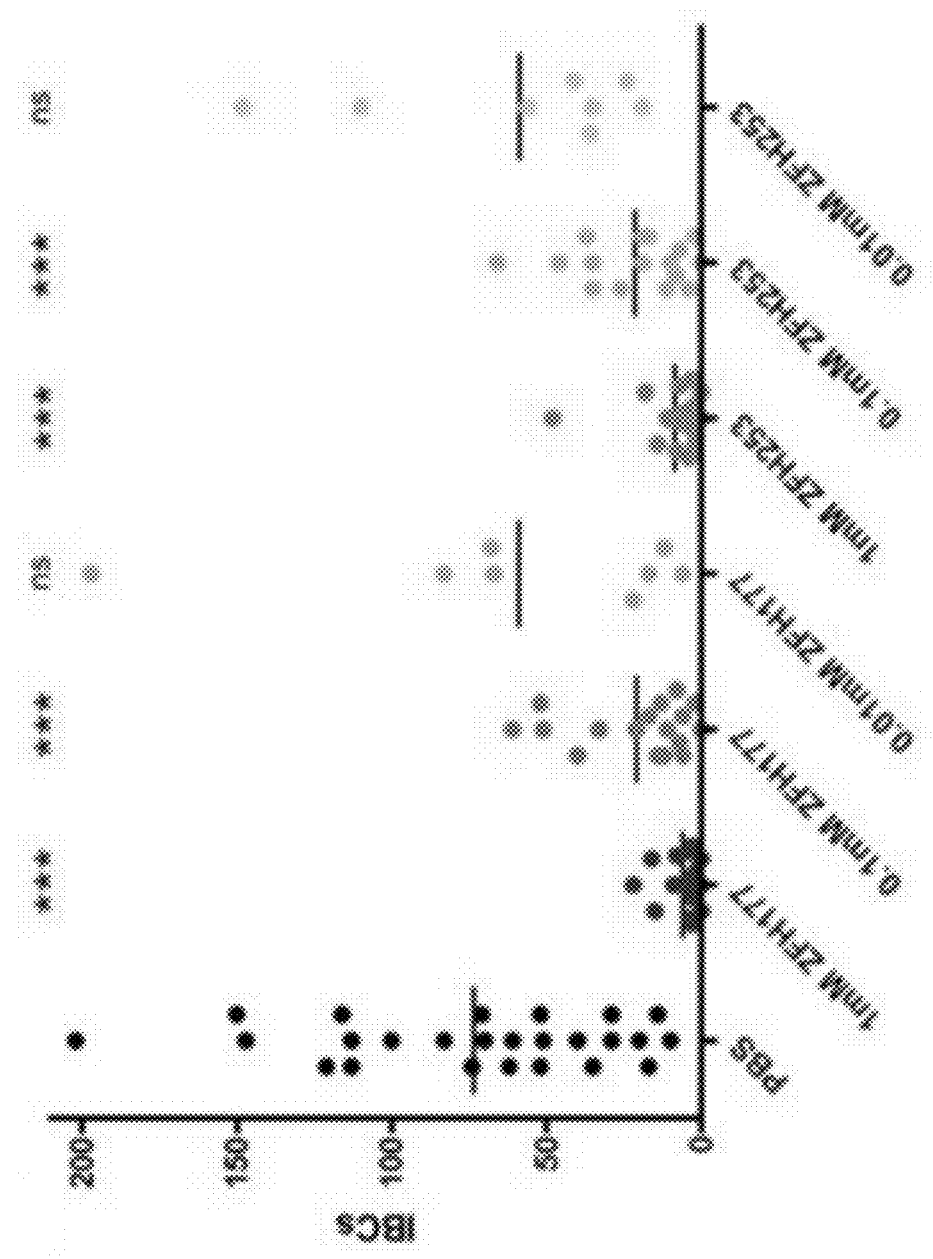
FIG. 11 depicts graphs showing that mannosides number 7 and number 15 reduce infection capacity in vivo. (A) 6 hour LacZ reveals significantly reduced IBCs at 1 mM and 0.1 mM mannoside for both mannosides number 7 and number 15 (p<0.0001). (B) 6 hour bacterial load quantification reveals significantly reduced colonization with 1 mM mannoside number 7 and 1 mM mannoside number 15 treated bacteria, p<0.001 and p<0.01, respectively.
Figure 11B:
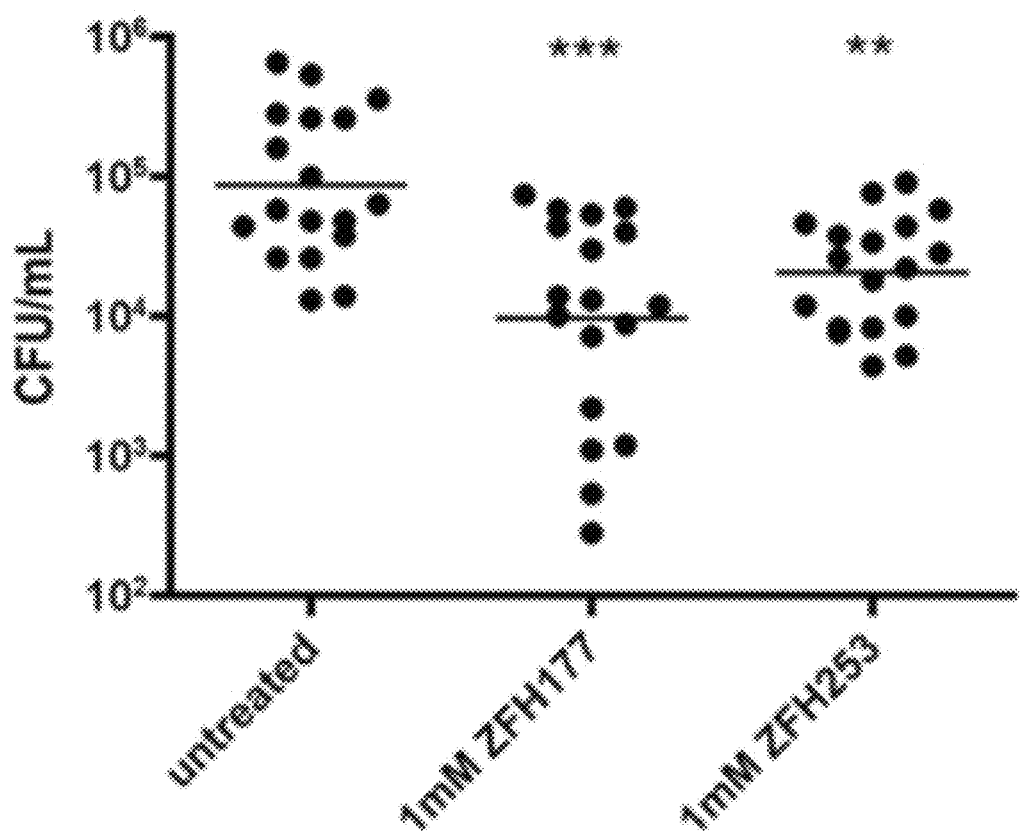

After invasion, UPEC are able to rapidly replicate to form IBCs, thus dramatically expanding in numbers. After maturation of the IBC, bacteria are able to disperse from the biomass and spread to neighboring cells to expand the buildup in bacterial numbers via next generation IBC. The ability of mannosides to block IBC formation was evaluated based on LacZ staining of whole mount bladders, a protocol developed to enumerate IBCs. Whole bladder titers were also determined by quantifying colony forming units (CFUs) at 6 hours post-infection and later time points as test compounds were further developed. In the presence of mannosides ZFH177 and ZFH253 there was a significant decrease in IBCs observed 6 hours post-infection at concentrations as low as 0.1 mM and almost no IBCs observed at 1 mM Mannoside (FIG. 11A). A significant decrease was also seen in CFUs at 6 hours post-infection with 1 mM ZFH177 and ZFH253 (FIG. 11B). These results strongly argue that the mannosides are able to inhibit first round IBC formation by preventing FimH-mediated binding and invasion into the bladder epithelial cells. The success of these experiments suggested that these compounds would have dramatic potential as potent therapeutics for treating UTI, the most common bacterial infection in highly industrialized countries.

Example 10

Pharmokinetics/Bioavailability/Toxicity

Pharmokinetic, bioavailability and evaluation of toxicity studies will be performed to elucidate the effectiveness of synthesized mannosides in treating UTI. Using these studies we will identify: i. the kinetics by which the mannoside is excreted in the urine, ii. the dosage administered to the mouse versus the amount that reaches the urine to obtain 1 mM and 0.1 mM concentrations (determined effective through above results), iii. the length of time the mannoside remains in the urine after one dose and iv. the presence of mannoside within the tissue, namely the bladder. The most effective way of delivering the mannoside (oral, IP or tail vein) with no toxicity to the animal will be determined. Toxicity will be evaluated based on animal survival and weight loss/gain of treated animals relative to non-treated animals. Urine was evaluated for mannoside presence and concentration using LC-MS. The delivery method, dose and timing, which gave the highest levels in the urine were then used in treatment trials.

Example 11

Mannosides as Inhibitors of UTI

Once the proper delivery method, dose and timing will be determined, female mice will be pre-treated with mannoside (two doses) prior to infection (using our well-developed mouse model of UTI) and treated with mannoside throughout the course of infection to maintain efficacious levels within the urine. The potency of the mannoside in preventing UTI based on CFUs in the bladder will be assessed at 6 hours, 48 hours and 2 weeks post-infection and IBC formation at 6 hours post-infection compared to untreated mice.

The ability of mannosides to treat established infections will be also tested. Mice will be treated with mannoside at 24 hours post-infection and the effect on bacterial clearance will be assessed by determining CFUs in the bladder 24 and 48 hours and two weeks post-mannoside treatment. The last set of experiments mimic a potential situation within the clinic.

These experiments will show that inhibition of binding of the FimH adhesin to the bladder epithelium can eliminate infection. The above experiments also establish that the mannosides block the formation of QIRs, which proves their efficacy in reducing the predisposition of the host to suffer a recurrent infection. Due to increasing antibiotic resistance and high rates of recurrence, these compounds introduce an entirely new means of treating microbial infections, using an anti-virulence agent instead of an antimicrobial.

Example 12

Figure 12:
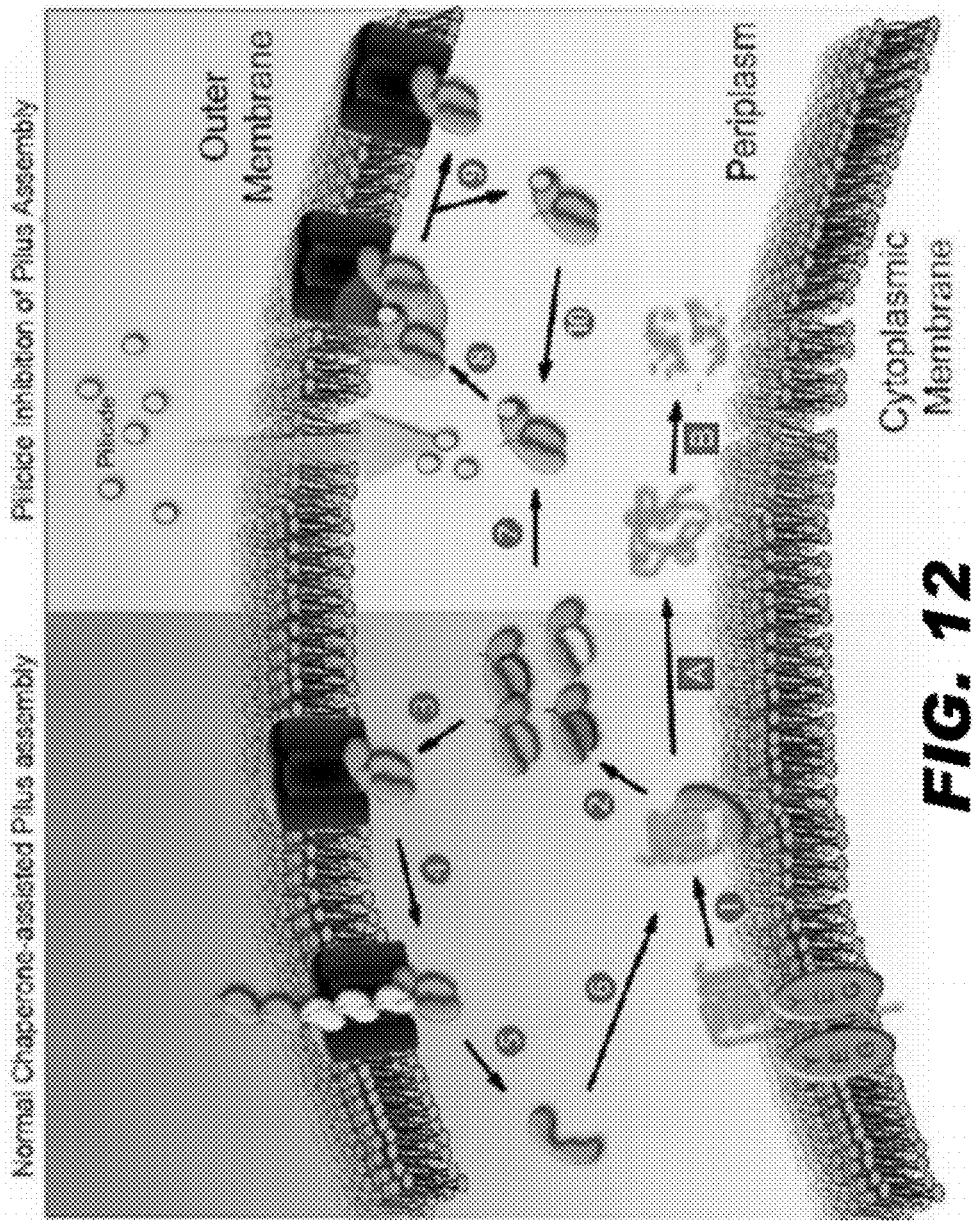
FIG. 12 depicts a diagram showing a pilicide inhibit bacterial pilus biogenesis. The schematic diagram shows the model of chaperone-assisted pilus assembly and the mode of pilicide action. During normal pilus biogenesis, newly synthesized pilus subunits cross into the periplasm via the Sec secretion pathway. These pilus subunits bind to their periplasmic chaperone proteins (orange molecules) and fold into correct confirmations (1). In the absence of the chaperones [A], pilus subunits are degraded [B]. Chaperone-subunit complexes (2) are transported to the outer membrane usher proteins (blue cylinders) for assembly (3). Pilus assembly follows an ordered process with the chaperone-adhesin complexes as the initiatiors (4). As subunits are assembled into the growing pilus, accompanying chaperones disassociate from the membrane complexes (5), which could potentially be recycled to bind newly synthesized subunits. Pilicides (yellow circles)

Investigation of Dual Therapy with Adhesion and Pilus Assembly Inhibitors and/or Antibiotics Due to the critical nature of type 1 pili in UPEC pathogenesis, in addition to the work to develop high affinity inhibitors of FimH binding described above, the extensive structural and functional knowledge of the mechanism of pili assembly by the chaperone/usher pathway (see biosketch) was used to develop efficient inhibitors of pilus biogenesis ("pilicides") (FIG. 12). The most efficient pilicides show greater than 90% inhibition of hemagglutination and type 1 dependent biofilm at concentrations in the low micromolar range (FIG. 13). Further, the structural basis by which pilicide block pilus assembly were identified. These compounds were rationally designed based on a 2-pyridone scaffold that has affinity for beta-sheet structures. One of the best pilicides to date, FN075, was able to achieve significant attenuation of virulence as measured by CFUs and IBC formation (FIG. 14).

Using pilicides and mannosides in combination would potentially give a "double hit" to this critical type 1 pilus system, potentially resulting in synergy by inhibiting pre-existing type 1 pilus function while eliminating the ability to produce new pili. Combination therapy using the most effective mannoside inhibitors and pilicides with antibiotics were tested. In one experiment, groups of mice were treated with ZFH56 mannoside treatment only, with antibiotic treatment only, or with a dual treatment (mannoside+antibiotic). One group of untreated mice was used as a control (FIG. 15).

For mannoside treatment, bacteria were incubated with 1 mM ZFH56 prior to inoculation. Every 24 h for 3 days, mice were transurethrally inoculated with 1 mM ZFH56. For antibiotic treatment, mice were inoculated with UTI89 and immediately given antibiotics in the drinking water for 3 days. Antibiotics used were trimethoprim-sulfamethoxazole (SXT) at 54 and 270 mg/ml, respectively. For dual treatment, bacteria were incubated with 1 mM ZFH56 prior to inoculation. Every 24 h for 3 days, mice were transurethrally inoculated with 1 mM ZFH56. Additionally, mice were immediately given antibiotics in the drinking water for 3 days as in the antibiotic only treatment. Urine was collected every day for 13 days. At 2 weeks, mice were sacrificed and bladders were titered.

Dual treatment showed significantly lower levels of bacteria in the bladder than antibiotics alone (FIG. 16).

Example 13

Bacterial Adhesion—A Source of Alternate Antibiotic Targets

Introduction

More than a century ago, the discovery of Penicillin marked a significant, albeit not immediately recognized, advance in the field of medicine. By the middle of the 20$^{th}$ century this naturally occurring fungal antibiotic had single-handedly vanquished the biggest wartime killer—infected wounds. Just four years after the mass production of penicillin began in 1943, resistant microbes started to appear beginning with *Staphylococcus aureus*, followed shortly thereafter by *Streptococcus pneumoniae* and *Neiserria gonorrheae*. Today this list includes antibiotic resistant *Enterococcus, Salmonella, Mycobacterium tuberculosis* and *Escherichia coli*, to name just a few. The bacterial infections which contribute most to human disease are also those in which emerging and microbial resistance is most evident: diarrheal diseases, respiratory tract infections, urinary tract infections, meningitis, sexually transmitted infections, and hospital acquired infections. Thus, there is dire need for new therapeutics to save the lives and ease the suffering of millions of people.

Rising Antibiotic Resistance

The antibiotics that are available today are primarily variations on a single theme—bacterial eradication based on inhibition of essential molecular processes required for bacterial growth (bacteriostatic) or cellular maintenance (bactericidal). Some target cell-wall biosynthesis, whereas others inhibit protein synthesis or DNA replication. These life or death treatments put selective pressure on the bacteria to adapt or die, selecting for antibiotic resistance. Second generation drugs were developed to combat the resistances that arose, however, they employed the same general mechanism of action. In addition, while some last resort drugs have minimal resistance thus far, they are much more expensive, often are more toxic and typically unavailable to many countries around the world. Consequences of treatment failure due to antibiotic resistance are high with greater morbidity, mortality and transmission of the resistant organism. Even if pharmaceutical companies increased efforts to develop next generation replacement drugs, bacterial evolution is outpacing drug development for these classes of antibiotics. We are nearing an end to the seemingly endless flow of antimicrobial drugs. We are now faced with a long list of microbes that have found ways to circumvent different structural classes of drugs and are no longer susceptible to most, if not all, therapeutic regimens. New tactics and weapons are needed to combat bacteria that are, owing to evolution and selection, moving targets.

Alternative Antibiotic Targets

Targeting bacterial virulence is an alternative approach to the development of new classes of antimicrobials that can be used to specifically target and disarm pathogens in the host, while leaving commensal bacteria unperturbed. Prevention of the activity of virulence factors will render the bacteria less able to colonize and give beneficial symbionts and the host immune system time to eradicate the disease causing pathogen prior to colonization or facilitate clearing of an established infection. Furthermore, stripping microorganisms of their virulence properties without threatening their existence may offer a reduced selective pressure for drug-resistant mutations and provide increased potency. Upon exposure to the host, bacteria respond by the production of an arsenal of virulence factors to combat host immune responses and facilitate persistence in their desired niche. There are many examples of virulence factors that represent potential therapeutic targets. Polysaccharide capsules prevent phagocytosis. Siderophores facilitate iron acquisition. Flagella promote motility and chemotaxis. Some bacterial species secrete toxins that alter and disrupt the eukaryotic host cell resulting in disease. Yet another strategy employed by bacteria is the production of a molecular syringe, known as a type three secretion system, that injects effectors into the host cell causing disease. Another fundamental virulence property of nearly all microbes is their ability to adhere to host cells. This step is typically crucial in pathogenesis and without it bacteria are more likely to be eradicated by the host. Bacterial adhesins typically mediate attachment to a specific receptor with stereochemical specificity, a process that is thought to determine the host and tissue tropisms of a pathogen. While many virulence factors may represent attractive therapeutic targets, this review will focus on two strategies to develop anti-virulence therapeutics based on targeting adhesive pili using uropathogenic *E. coli* (UPEC) as the model system. The first strategy depends on competitively inhibiting bacterial binding to host cells through addition of exogenous carbohydrates that mimic host ligands. The second strategy targets the mechanism by which adhesive pili are assembled thus inhibiting bacterial adhesion to host cells. Thus, both strategies could be used in synergy: the first compound prevents bacterial attachment and colonization by occupying the binding pocket of the bacterial adhesin while the second compound enters the cell and prevents future pilus production. Such a two-pronged approach could eliminate adherence to host cells and promote clearance of the bacteria.

Pili in Bacteria

Pathogens are capable of presenting multiple adhesins that can be expressed differentially to permit binding in specific sites and at particular times over the course of a complex infectious cycle. To achieve this, many bacterial species possess long filamentous structures known as pili or fimbriae extending from their surfaces. Pili are extracellular polymers that also have been shown to play a role in invasion, biofilm formation, cell motility, and protein and DNA transport across membranes. Pilus formation is common to many pathogenic bacteria, both Gram-negative and Gram-positive pathogens. Despite the diversity in pilus structure and biogenesis, assembly mechanisms among Gram-negative and Gram-positive bacteria are conserved within each group. Gram-positive pili are formed by covalent polymerization of pilin subunits in a process that requires a dedicated sortase enzyme. In contrast, Gram-negative pili are typically formed by non-covalent homopolymerization of major pilus subunit proteins. This review will focus on a major family of adhesive pili in Gram-negative bacteria that are classified by their mechanism of assembly; the so-called chaperone/usher (CU) pili (Table 14).

In Gram-negative bacteria, one of the best-characterized pilus assembly systems is the CU pathway. Hundreds of operons encoding CU systems have been reported in a plethora of pathogenic organisms with as many as twelve encoded by a single organism. Examples of CU-assembled adhesive virulence fibers include: Type 1 and P pili predominately on UPEC that cause urinary tract infection (UTI), S pili of *E. coli* strains that cause sepsis, meningitis and UTI and Hif pili of *Haemophilus influenza* which causes otitis media. The causative agents of whooping cough (*Bordetella pertussis*), gastroenteritis (*Salmonella typhimurium*), and pneumonia (*Klebsiella pneumoniae*) also assemble fibers through the CU pathway. Additionally there are 'non-pilus adhesins' assembled by the CU pathway that are generally homopolymers composed of a single protein subunit, like the Afa/Dr family of adhesins of *E. coli* and the polymeric F1 capsular antigen of *Yersinia pestis*. The ubiquitous nature of this pathway paves the way for a potentially broad-spectrum anti-virulence therapeutic that disrupts the assembly of the pilus fibers thus eliminating bacterial colonization.

Pili in UTI

Of the CU pathway assembled pili, P and type 1 pili are the most extensively characterized. Type 1 pili are expressed throughout the Enterobacteriaceae family but have been shown to be essential for UPEC in colonization of the urinary epithelium. UPEC is the leading causative agent for greater than 80% of UTIs which is one of the most common bacterial infections in industrialized countries. UTIs are a significant burden, resulting in more than 8 million outpatient visits per year in the United States and expended costs of US $3.5 billion annually for evaluation and treatment. Women are the most frequent sufferers—a female has a 60% chance of suffering from at least one UTI in her lifetime. Additionally, up to 44% of women who present with an initial episode of UTI will experience recurrence. While the increased likelihood of recurrence it not entirely understood, data suggests that bacteria can persist within bladder tissue despite antibiotic treatments, and may serve as bacterial reservoirs for recurrent infections.

Type 1 pili are expressed by virtually all UPEC isolates. The FimH adhesin at the tip of type 1 pili achieves specific binding to host cells within the urinary tract. FimH specifically binds mannose groups that abundantly decorate uroplakins on the luminal surface of the bladder. A deep, negatively charged pocket in the N-terminal receptor-binding domain of FimH accommodates the mannose with stereochemical specificity. Once bound, a pathogenic cascade is initiated that involves several distinct phases as examined in the murine cystitis model and human UTIs. Numerous innate defenses are activated early in an attempt to stem off the infection. These defenses include, cytokine induction followed by inflammation, iron sequestering, exfoliation of the colonized epithelial cells and sheer forces elicited by urine flow. Even if UPEC successfully invade into a bladder epithelial cell, the bladder cell has been shown to be able to expel UPEC, potentially serving as an additional innate defense. However, if UPEC are able to escape into the cytoplasm of superficial umbrella cells, they are able to rapidly replicate to form tightly packed intracellular bacterial communties (IBCs) with biofilm-like qualities. Within the urothelial cells, the bacteria are protected from the flow of urine and host defenses. Eventually UPEC detach from the IBC, disperse and initiate new rounds of IBC formation. This represents a mechanism by which a single invasion event dependent on type 1 pili adhesion can lead to rapid bacterial expansion and colonization of the urinary tract. IBC formation occurs in the acute states of infection. One long-term outcome of infection is that UPEC are also able to form a quiescent intracellular reservoir (QIR) within the bladder. Bacteria in the QIR do not rapidly replicate, but remain dormant, hidden from the immune system and antibiotics. They are then able to reestablish an infection at later timepoints post-treatment resulting in a recurrence. Due to this alternative pathway of continuous colonization, UT's are more frequently being identified as chronic infections. Detailed analysis of the UPEC pathogenic cascade has identified several potential targets to inhibit virulence, such as siderophores, capsule and flagella. However, type 1 pili represent a particularly attractive drug target because they are ubiquitous among UPEC, and are required to initiate a pathogenic cascade that evades the host immune system and can lead to acute, chronic, persistent or asymptomatic infection. Disruption of type 1 pili function could break the cycle of chronic infection.

New Drug Development Strategies to Inhibit Pilus Mediated Function

Carbohydrates of various forms are abundantly expressed on the animal cell surface. Microbes have taken advantage of this property and evolved with the ability to adhere to sugar receptors in an organ-specific manner for colonization and infection. Sugars are commonly involved in cell recognition and communication playing important roles in microbial adherence and uptake, colonization and biofilm formation, and in virulence. Since bacterial adhesion to host cells is extremely specific, exogenous sugars can block binding to carbohydrate receptors and competitively displace or inhibit bacteria from attachment to cells. The ability to impair bacterial adhesion represents an ideal strategy to combat bacterial pathogenesis because it targets an important early step in the infectious process, and would also be suitable for use as a prophylactic to prevent infection. In the case of UPEC, knowledge of the structural basis of how FimH recognizes the mannose receptor, has lead to the development of a ligand-based antagonist, termed mannoside, that mimics the natural receptor for FimH but with increased affinity and avidity. Mannosides effectively block the adhesive properties of type 1 pili by inhibiting bacterial colonization, invasion, IBC formation and disease. Furthermore, the sequence of approximately 300 fimH genes of clinical UPEC isolates showed that the mannose-binding pocket is invariant. Thus mannosides are a powerful new class of therapeutics that could have a potent therapeutic effect by preventing UPEC pathogenesis and disease. This approach can be readily extended to other adherent organisms by tailoring the anti-adhesive compounds to antagonize their specific receptor-ligand interactions (FIG. 17). Indeed, sugars designed to target adhesive structures of organisms such a *Pseudomonas aeruginosa, Stapyhlococcus* and *Streptococcus* have already proved efficacious at inhibiting adherence in vitro.

The goal of the second strategy is to interrupt pilus assembly, which, like the first strategy, blocks pilus-mediated adhesion and subsequent disease. To disrupt pilus assembly, one must first understand the mechanisms employed by bacteria to form fibers. Chaperone-usher mediated assembly prevents premature subunit aggregation and facilitates the ordered secretion, folding and assembly of hundreds of thousands of subunits into fibers on the surface of a bacterium.

Figure 18A:
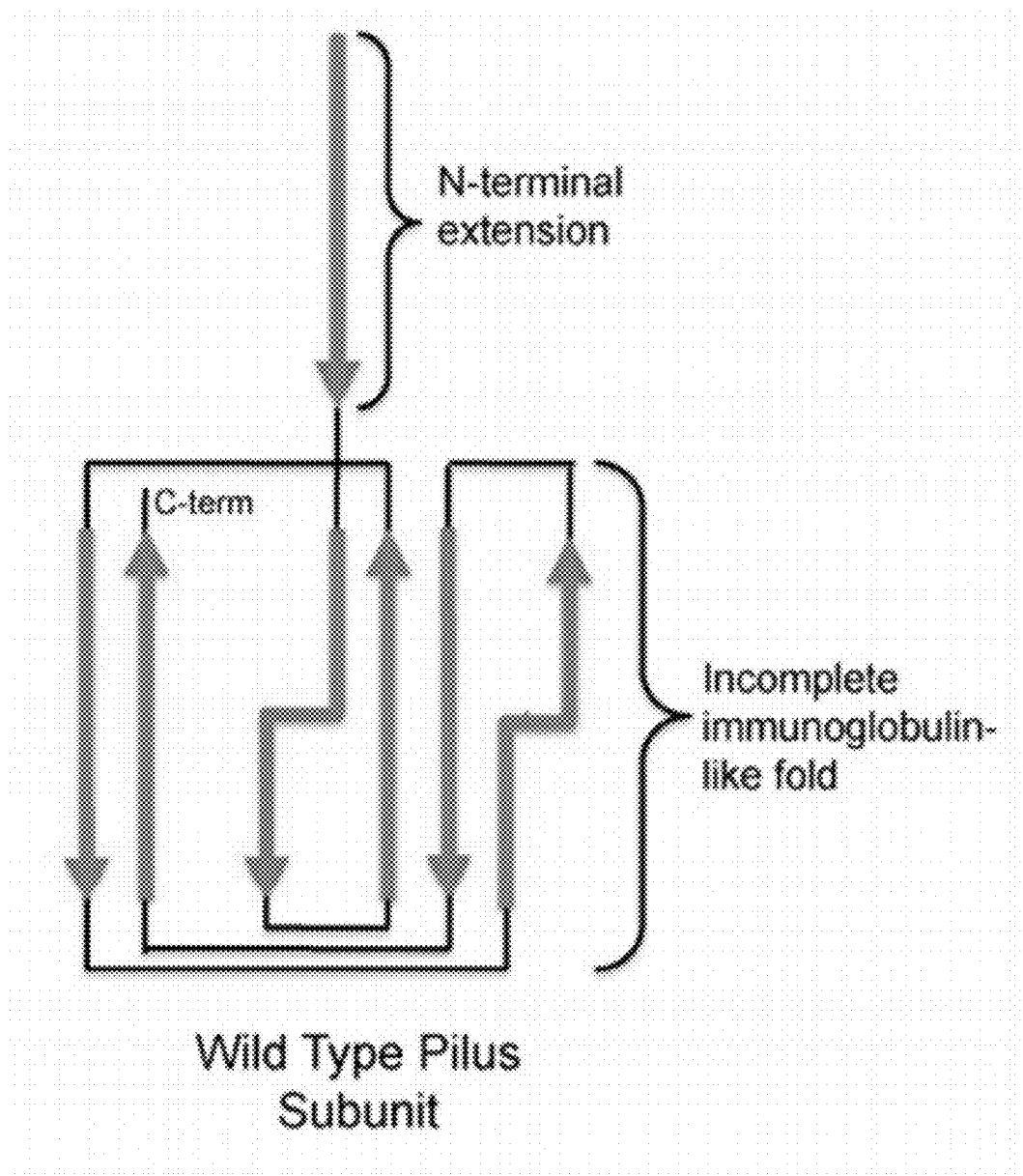
Figure 18B:
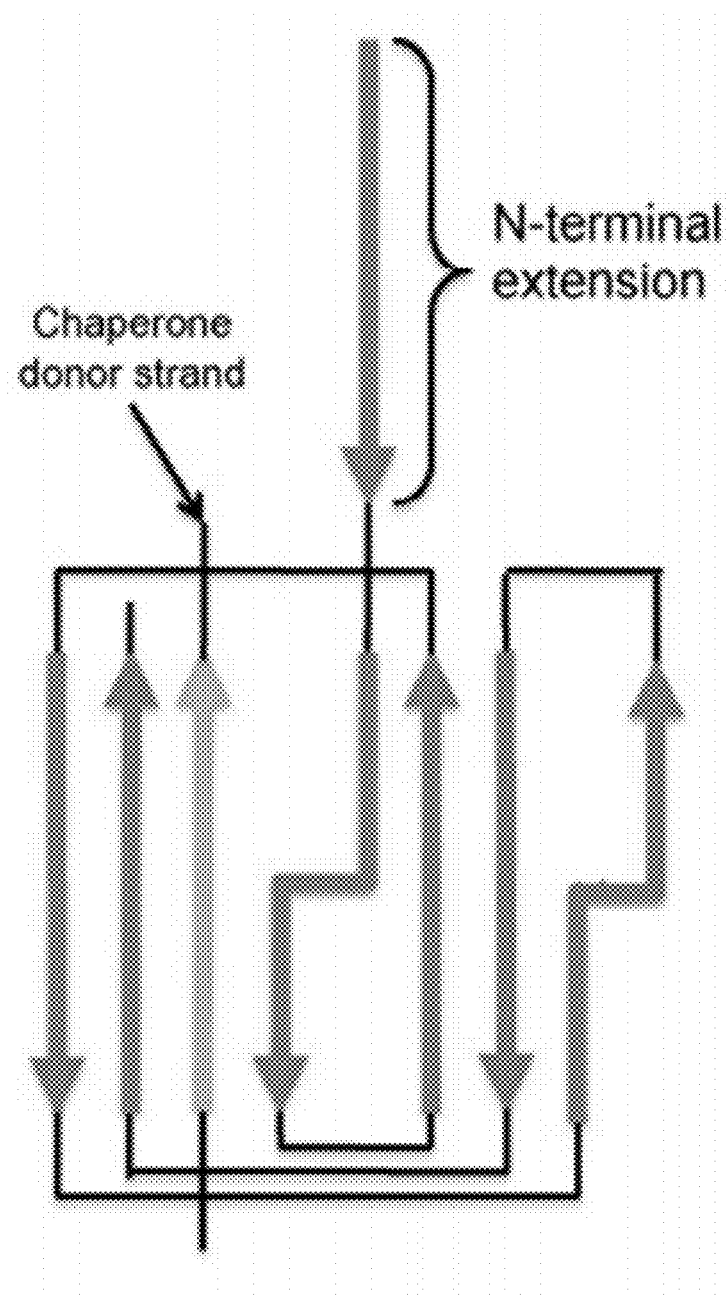
Figure 18C:
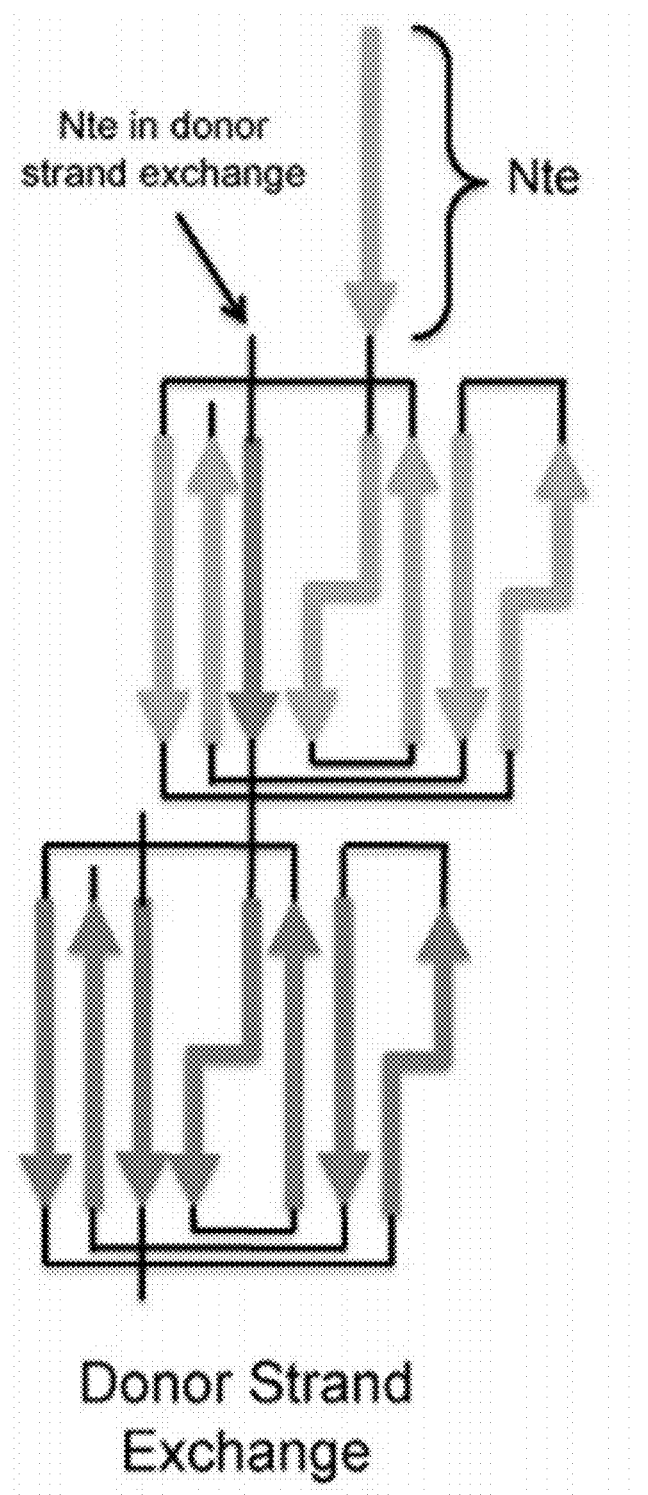

Components of the pilus are secreted through the general secretory pathway into the periplasm. Once in the periplasmic space, a specific chaperone binds each pilus subunit to facilitate proper folding and prevent premature assembly of subunits. Each subunit consists of six of the seven strands of a standard immunoglobulin (Ig)-fold and an N-terminal extension (Nte) (FIG. 18A). In order to form a stable structure prior to incorporation into the growing fiber, the chaperone donates structural information to each subunit, its G1 β strand, to compensate for the missing seventh strand of the subunit in a process called donor strand complementation (DSC) (FIG. 18B). DSC prevents aggregation of the subunits prior to fiber formation. The pilin/chaperone complex is then delivered to the usher, which is a pore in the outer membrane and serves as a platform for pilus assembly. During pilus assembly, the free Nte of one subunit displaces the chaperone bound to another subunit and serves as the seventh strand of the Ig-like fold in a process called donor strand exchange (DSE) (FIG. 18C). DSE leads to the polymerization of the fiber extending from the bacterium. Since chaperone-usher systems are necessary for the assembly of extracellular adhesive organelles in a wide range of pathogens, inhibitors may serve as broad-range anti-virulence therapeutics, an attractive feature that would enhance the marketability of an effective drug.

Pilicides are a class of pilus inhibitors that target chaperone function and inhibit pilus biogenesis. A recent study (Pinkner J S et al: PNAS (2006) 103(47):17897-17902) identified a new class of pilicides based on a bi-cyclic 2-pyridone chemical scaffold that inhibit pilus assembly by binding to the chaperone and disrupting the chaperone-usher interaction. As a result, pilicides inhibit pilus dependent activities such as colonization, invasion and biofilm formation. Biofilms are structured communities of microorganisms encapsulated within a self-developed polymeric matrix that defends them against antibiotics and the host immune system. They are of great medical importance, accounting for over 80% of microbial infections in the body. Pilicides target regions on the chaperone that are highly conserved among chaperone-usher pathways and are thus able to inhibit assembly of multiple pilus systems (type 1 and P pili of *E. coli*) (FIG. 17). Pyridinones also avoid the severe drawbacks observed for peptide-based drugs; poor absorption after oral administration, rapid enzymatic degradation, and quick excretion.

Another distinct mechanism of adhesive fiber assembly among Gram-negative bacteria is fibers assembled by the extracellular nucleation/precipitation pathway (curli). Curli are proteinaceous fibers found on enteric bacteria such as *E. coli* and *Salmonella* spp. Despite curli's unclear role in pathogenesis, their biochemical and structural properties resemble eurkaryotic amyloid fibers found in neurodegenerative diseases, such as Alzheimer's, Parkinson's, and prion diseases making them an ideal model system to study amyloid biogenesis. Curli are heteropolymers that consist of a major subunit, CsgA, and minor subunit, CsgB. CsgA and CsgB are secreted into the extracellular milieu via the outer membrane pore, CsgG. With the help of two chaperone-like proteins, CsgE and CsgF, CsgA is nucleated into a fiber by CsgB. Curli fibers have been implicated in biofilm formation, environmental survival and resistance to sanitizing agents. A recent study (Cegelski L et al: submitted) showed that derivatives of the 2-pyridone compounds mentioned above were able to inhibit curli assembly giving them the name curlicides. The lack of curli fibers prevented curlidependent biofilm formation and reduced infection load in vivo as measured by the murine model of UTI. Pilicides and curlicides selectively disrupt a protein-protein interaction required for the biogenesis of a bacterial virulence factor instead of targeting a process essential for survival.

Employing both anti-virulence strategies, inhibition of receptor binding and disruption of pilus assembly, could result in very potent anti-adhesive therapeutics. For example, synergistic effects could be obtained by inhibiting preexisting type 1 pilus function through mannosides while also eliminating the ability to produce new pili through pilicides. Furthermore, if infection is not entirely controlled by the two-pronged approach, antibiotics can be added, however, at much lower concentration to reduce the opportunity to develop resistance. Type 1 pili are an essential virulence factor for colonization of the urinary tract and are the most extensively studied chaperone-usher fimbrial system. Thus, they have been described in this review as an excellent target resulting in the development of new prototypic therapeutics to treat UTIs. This new drug class could translate into a multitude of other therapies for Gram-negative infections.

Conclusion

While this review focuses on the development of therapeutics to inhibit adhesion, there are many other virulence factors employed by bacteria to colonize and persist within the host. The general strategy of inhibiting virulence factors rather than essential growth factors changes the paradigm of drug development and reduces the evolutionary pressure for bacteria to develop resistance. Bacteria can survive in the presence anti-virulence drugs, but will be eliminated by the host immune system prior to establishing a foothold. Furthermore, since a complex virulence mechanism is targeted, if mutants arise, they will most likely be avirulent. If the host immune system cannot resolve any residual infection, it is possible to couple anti-virulence therapeutics with traditional antibiotics although at lower doses thus reducing resistance potential. A commitment to developing therapeutics that target virulence requires a serious change in our perspective for treating infectious diseases and increased efforts should be focused on bringing these new therapeutics from bench to bedside.

Example 14

Orally Active Mannosides Subvert Antibiotic Resistance of *E. coli* in Bladder Infection In this example, therapeutic utility of mannosides that are competitive, high-affinity inhibitors of FimH mannose binding activity is analyzed, as measured by biofilm formation, type 1 pilus expression and bladder colonization, invasion and IBC formation. The mannose binding site of FimH consists of a deep acidic pocket surrounded by a ridge of hydrophobic residues. The acidic amino acid residues of the binding pocket are invariant in all UPEC and mutational studies showed that altering any of these residues abolishes binding to mannose and attenuates virulence. From the rational design and optimization of mannosides, several potent inhibitors of FimH-dependent hemagglutination were identified, including ZFH-1101, ZFH-1177, ZFH-1253, ZFH-2050 and ZFH-2056 (FIG. 19a). These mannosides were evaluated first for their ability to inhibit biofilm formation or disrupt preformed biofilms. Biofilm inhibition was evaluated on FimH-dependent UTI89 biofilms grown on PVC in LB at room temperature. The median inhibitory concentration ($IC_{50}$) values for each of the compounds were found to be in the low micromolar range. Compounds ZFH-1253 and ZFH-2056 were the most potent biofilm inhibitors with $IC_{50}$ values of 0.94 and 0.74 µM, respectively (FIG. 19b). Biofilm disruption was evaluated by the addition of mannosides to preformed 24 h biofilms followed by growth for an additional 16 h. All five mannosides were shown to facilitate dispersal of the preformed biofilm. The $IC_{50}$ values for dispersal were higher than those concentrations needed to prevent biofilm formation, however the efficacy trend remained the same (FIG. 19c). Visualization of mannoside-treated PVC biofilms by confocal microscopy showed that ZFH-2056 treated biofilm lacked continuity as demonstrated by holes in the biofilm, and it lacked the tall mushroom-like structures observed in untreated biofilm (FIGS. 19 d,e). Biofilm causes many antibiotic treatment failures since antibiotics are unable to penetrate its dense matrix. These results demonstrate that mannoside can prevent biofilm formation and dissolve preformed biofilms arguing that mannosides may augment antibiotic efficacy by altering bacterial community behavior.

To test the efficacy of the mannosides in vivo, UTI89 expressing type 1 pili were pre-incubated with mannosides, inoculated into mice and IBCs were quantitated at 6 hours post-infection (hpi). The efficacy of compounds ZFH-1177, ZFH-1253, ZFH-2050 and ZFH-2056 in inhibiting IBC formation correlated with their potency observed in the in vitro assays. The most significant reduction in IBCs occurred with as little as 10 µM ZFH-2050 or ZFH-2056 (FIG. 20a). These studies identified ZFH-2056 as the most potent compound tested in preventing colonization.

Pharmacokinetic (PK) studies with ZFH-2056 evaluated in vivo dosing conditions after intraperitoneal (IP) injection or oral (PO) gavage. ZFH-2056 was dosed IP and compound levels in the urine were evaluated at several timepoints by HPLC using mass spectrometry (MS) detection. Doses of 5 mg/kg and 10 mg/kg resulted in concentrations of nearly 5 mM in the urine 30 min after treatment (FIG. 20b). Eight hours after dosing, ZFH-2056 remained at levels equal to or slightly below the IC50 (0.74 µM) as determined by biofilm inhibition. Since oral dosing is the desired route of delivery, we next evaluated the concentration of drug after 100 mg/kg PO of ZFH-2056. The latter resulted in a 10 fold lower initial concentration of ZFH-2056 versus IP but, significantly, urine levels were 10-fold higher at 8 hours post-dosing. It is noteworthy that >95% of drug cleared to the urine is intact with the remaining<5% being the hydrolysis products, D-mannose and phenol.

Figure 20G:
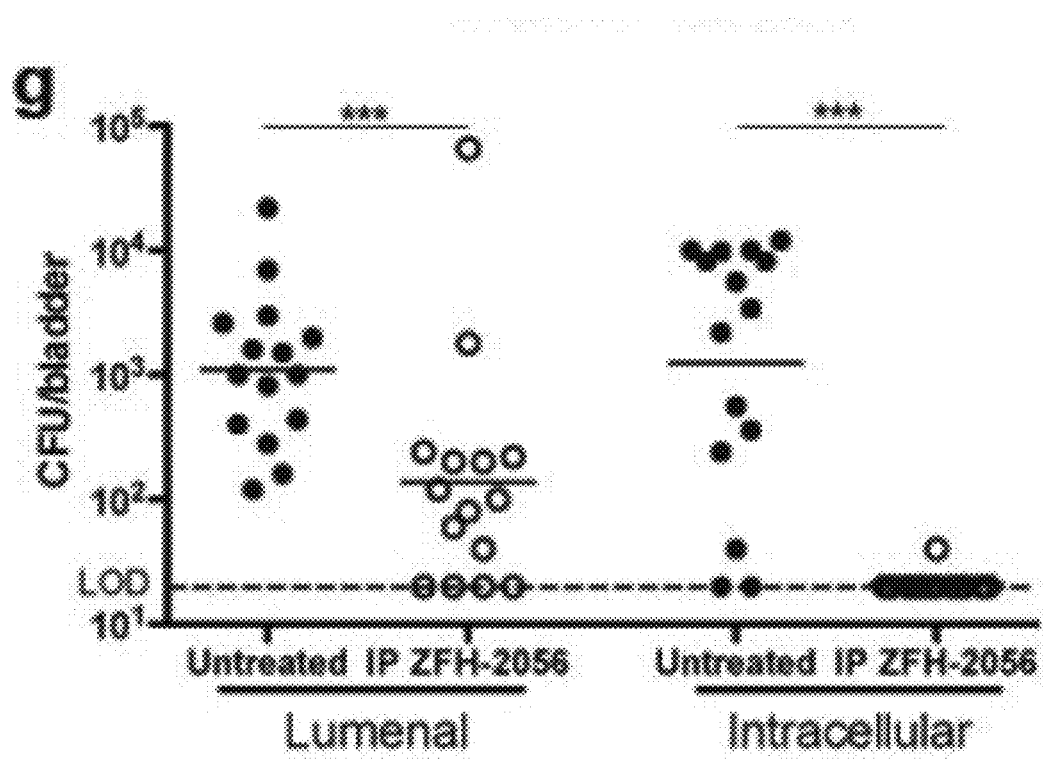

The efficacy of in vivo mannoside treatment was evaluated after dosing animals with mannoside either IP or PO 30 min prior to infecting with UTI89. At 6 hpi the bladders were removed and total bacterial CFUs were quantitated. In both the IP and PO treated cohort, there was a significant drop in bacterial counts demonstrating the efficacy of mannoside in reducing overall colonization of the bladder (FIG. 20e). Furthermore, IBC quantification showed a significant reduction in IBCs in the mice that were pretreated with mannoside by either the IP or oral route (FIG. 20f). To test whether mannoside reduced IBC formation by blocking UPEC invasion into the bladder tissue, gentamicin treatment assays were performed. Gentamicin efficiently kills extracellular UPEC but is unable to penetrate tissue and thus intracellular bacteria survive gentamicin treatment 18. In the ZFH-2056-treated mice, gentamicin treatment of the bladders eliminated all CFUs (FIG. 20g). In bladders from untreated mice, $10^3$-$10^4$ CFUs remained after gentamicin treatment. These results argued that mannoside effectively prevented UPEC penetration into the bladder tissue. Confocal microscopy confirmed these results. Bladders of the untreated cohort showed normal, robust IBC formation (FIG. 20c) whereas IBCs were rarely seen in the mannoside treated mouse bladders but bacteria were observed on the bladder epithelial surface (FIG. 20d). These results demonstrate that mannosides prevent bacterial invasion into the bladder tissue and significantly reduce infection in the bladder.

Figure 21A:
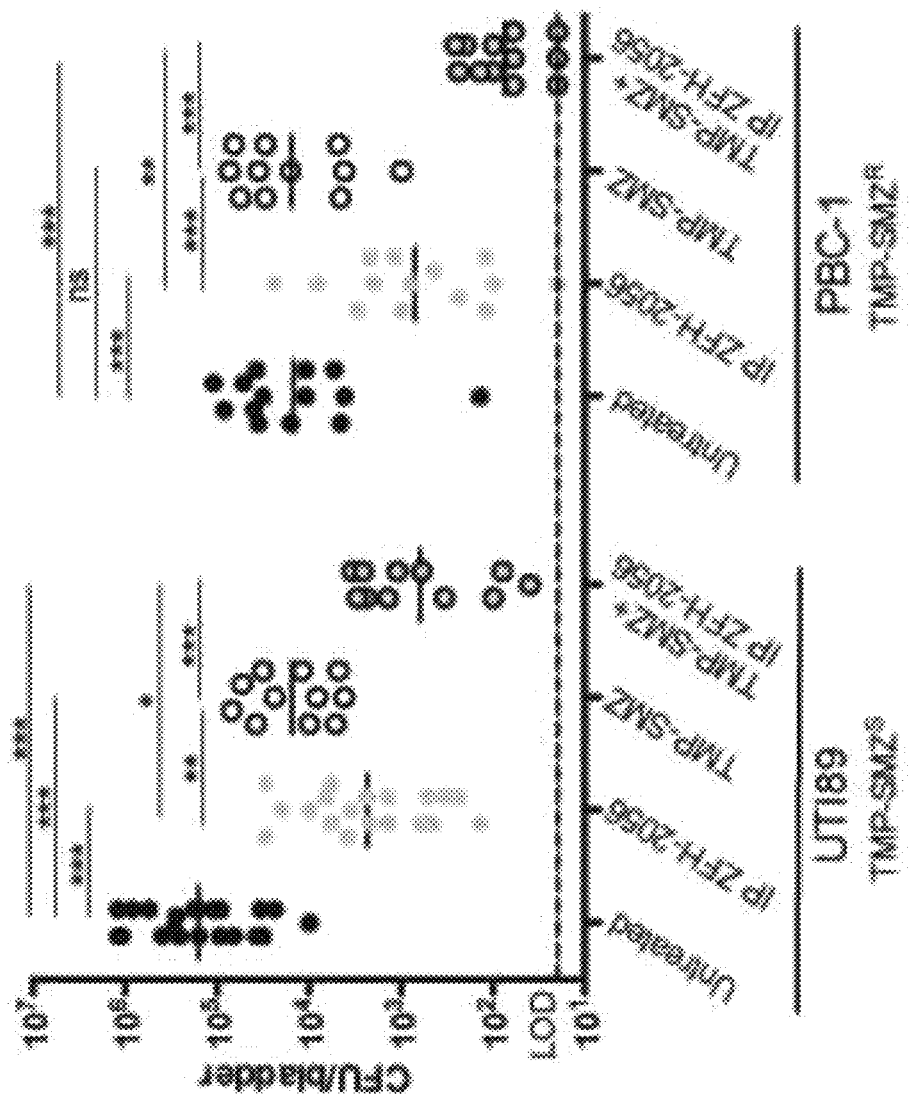
Figure 21B:
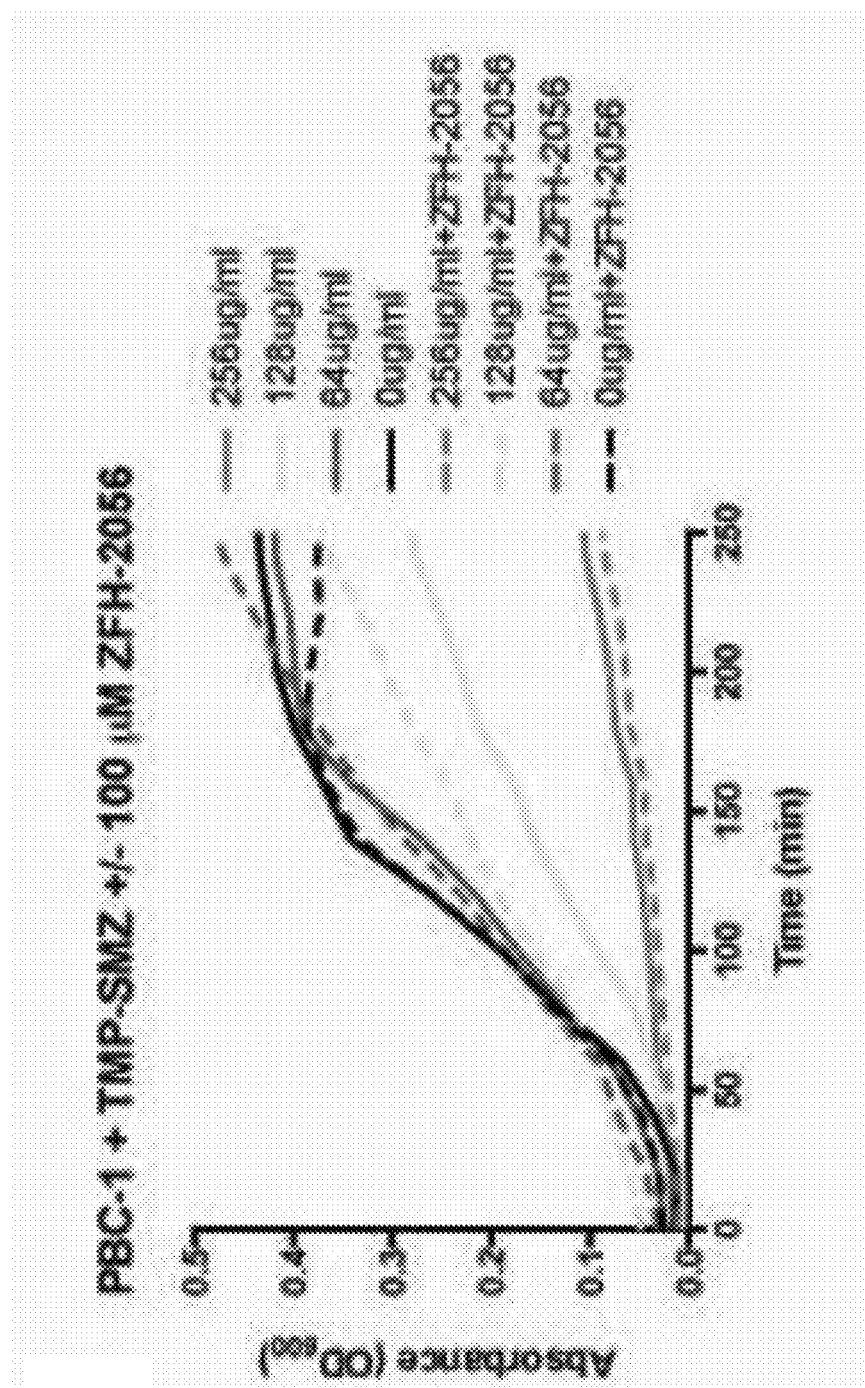

The first-line treatment of choice for UTI has long been a 3-day course of TMP-SMZ. However, resistance to TMP-SMZ is on the rise. Furthermore, humans have a 38% carriage rate of TMP-SMZ resistant (TMP-SMZR) strains, and these numbers are even higher in low resource countries with a 94% carriage rate. TMP-SMZ is known to concentrate in the urine. Therefore, it was reasoned that by preventing bacterial invasion into the bladder tissue, mannoside may have an anti-virulence synergism with TMP-SMZ and may circumvent the TMP-SMZ resistance problem. This was tested in mice given TMP-SMZ for 3 days prior to inoculation with either UTI89 or TMP-SMZR strain, PBC-1. Mice were either untreated or IP treated with mannoside ZFH-2056 30 min prior to inoculation with bacteria. After inoculation with UTI89 or PBC-1, bacterial CFUs were quantitated 6 hpi. Upon treatment with only ZFH-2056 there was a significant drop in bacterial load of both strains in the bladder. As expected, treatment with TMP-SMZ alone resulted in a significant drop in bacterial load in the UTI89-infected mice but had no effect on PBC-1, since it is resistant to TMP-SMZ. In the dual treatment group there was a significant drop in bacterial CFUs compared to mannoside alone or TMP-SMZ alone for both strains which was most pronounced for PBC-1 (FIG. 21a). The observation that TMP-SMZR strain PBC-1 was able to succumb to antibiotic treatment in the presence of mannoside suggested that either mannoside increases the efficacy of TMP-SMZ killing or that it exposes the bacteria to concentrations at or above the MIC necessary for killing. Mannoside was not found to increase the efficacy of TMP-SMZ killing when bacteria were grown in varying concentrations of TMP-SMZ with and without 100 µM of ZFH-2056 (FIG. 21b). This analysis revealed that the TMP-SMZ resistant strain had a MIC of 256 and 1280 pg/ml, respectively. Furthermore the HA titer of PBC-1 after growth in varying concentrations of TMP-SMZ showed that type 1 pili function was not affected by antibiotic (data not shown). It has long been known that TMP concentrates in the urine, and this serendipitous feature is one reason TMP-SMZ has been the antibiotic of choice for UTI over the last several decades. Using MS, the concentration of TMP-SMZ was measured in the urine of mice after 3 days of treatment with 54 µg/ml and 270 µg/ml TMP and SMZ, respectively. TMP concentrations were determined to be 9.95+/−4.36 mg/ml. SMZ was present at 67.17+/−32.51 µg/ml. These results show that by preventing bacterial invasion, mannoside keeps UPEC extracellular thus exposing them to TMP concentrations in the urine that are well above the MIC of the UPEC strain. This enables the killing of bacteria that clinically are resistant to TMP-SMZ. Thus, the invasion of the TMP-SMZR UPEC strain PBC-1 into bladder tissue protected it from the exposure of TMP-SMZ concentrations of antibiotic necessary for killing. However, mannoside prevented access of the bacteria to the intracellular compartment and thus kept the bacteria extracellular where TMP-SMZ concentrates to high levels in the urine, resulting in their succumbing to killing by the antibiotic. These results highlight the importance of the intracellular pathway in bacterial persistence. Not only do the bacteria escape the immune system in their intracellular niche, they are also able to escape exposure to effective antibiotics.

Methods for Example 13

UTI89 biofilm was grown in LB+/− mannoside for 24 h at 22° C. in PVC plates and quantitated using crystal violet. UTI89 biofilm for confocal microscopy was grown in LB for 24 h at 22° C. on PVC coverslips. Mannoside was then added and biofilm was grown for an additional 16 h. Coverslips were then washed in PBS, fixed in 2% paraformaldehyde and stained with SYTO9 prior to confocal microscopy. For all animal experiments UTI89 or PBC-1 was grown 2×24 h statically in LB at 37° C. and inoculated at a dose of $1 \times 10^7$ bacteria in 50 µl. All mice used were female C3H/HeN (Jackson). For the pretreatment studies, bacteria were incubated with mannoside for 20 min prior to inoculation into the mouse. For IP dosing, 50 µl of 2 mg/ml (5 mg/kg) or 4 mg/ml (10 mg/kg) ZFH-2056 in PBS was injected into the mouse 30 min prior to inoculation of bacteria. For oral dosing, 100 µl of 20 mg/ml (100 mg/kg) ZFH-2056 in 8% DMSO was inoculated with a gavage needle 30 min prior to inoculation of bacteria. Mass spectrometry was used to quantify urinary mannoside or TMP-SMZ concentrations. For CFU counts, bladders were harvested at 6 hpi and placed in 1 mL PBS. Bladders were then homogenized, diluted and plated on LB. After growth at 37° C. overnight, bacterial counts were determined. LacZ staining and gentamicin protection assays were performed at 6 hpi. For antibiotic experiments, mice were given TMP-SMZ in the drinking water at a concentration of 54 µg/ml and 270 µg/ml, respectively. Water was changed daily with fresh antibiotics. Standard growth curve assays and hemagglutination assays were performed with TMP-SMZ. All statistical analysis performed was a two-tailed Mann-Whitney U test.

Bacterial strains. UTI89 is a prototypical cystitis isolate of serotype O18:K1:H7. PBC-1 is a TMP-SMZR strain of serotype OX13:K1:H10 isolated from a 59 year old asymptomatic female with a history of recurrent UTI and diagnosis of primary biliary cirrhosis.

Synthesis of mannosides. Following the procedure outlined in Han et. al. 2010 (J Med Chem 53 (12), 4779-4792), ZFH-2056 was synthesized on a multi-gram scale with >98% purity by HPLC and NMR.

Biofilm assay. UTI89 was grown in LB broth in wells of PVC microtiter plates at 23° C. in the presence of individual mannosides at varying concentrations. After 48 h of growth, wells were rinsed with water and stained with crystal violet for quantification as described. For biofilm disruption activity in PVC plates, UTI89 was grown in LB broth in wells of PVC microtiter plates at 23° C. After 24 h of growth, mannoside was added and biofilms were grown for an additional 16 h. Wells were then rinsed, stained with crystal violet and quantified. For biofilm disruption activity on PVC coverslips, UTI89 was grown in LB broth in 50 mL conicals containing PBC coverslips at 23° C. After 24 h of growth, 0.3 µM ZFH-2056 was added and biofilm was grown for an additional 16 h. Coverslips were then rinsed, fixed with 2% paraformaldehyde (v/v), stained with SYTO9 (1:1000 in PBS; Molecular Probes) and observed with a Zeiss LSM410 confocal laser scanning microscope under a 63× objective.

Animal infections. Bacteria were grown under type 1 pili-inducing conditions (2×24 h at 37° C. statically in LB). The bacteria were harvested and resuspended to an $OD_{600}$ of 0.5 in PBS. Eight-week-old C3H/HeN (Harlan) female mice were anesthetized by inhalation of isoflurane and infected via transurethral catheterization with 50 µl of the bacterial suspension, resulting in 1-2×10$^7$ inoculum. At 6 hpi, mice were sacrificed by cervical dislocation under anesthesia and the bladders were immediately harvested and processed as described below. All animal studies using mice were approved by the Animal Studies Committee of Washington University (Animal Protocol Number 20100002).

Enumeration of bladder IBCs. For bacterial pretreatment experiments, mannoside was added to the bacterial suspension and incubated for 20 min. For animal pretreatment experiments, mannoside ZFH-2056 was administered either IP (5 mg/kg) or orally (100 mg/kg) 30 min prior to inoculation with UTI89. To accurately count the number of IBCs, mice were sacrificed 6 hpi and bladders were aseptically removed, bisected, splayed on silicone plates and fixed in 2% paraformaldehyde (v/v). IBCs, readily discernable as punctate violet spots, were quantified by LacZ staining of whole bladders.

Pharamacokinetic analysis. For intraperitoneal dosing, 50 µl of a 2 mg/ml (5 mg/kg) or 4 mg/ml (10 mg/kg) solution of ZFH-2056 in PBS was injected into the peritoneal cavity of the mouse. For oral dosing, 100 µl of a 20 mg/ml (100 mg/kg) solution of ZFH-2056 in 8% DMSO was inoculated with a gavage needle into the mouse stomach. Urine was collected at 30 min, 1, 2, 3, 4, 6, and 8 h post-treatment. An equal volume of 10 µM internal standard (ZFH-2050) was added to the urine. Mannosides were extracted from the urine by loading on C18 columns (100 mg, Waters), washing with 30% methanol, and eluting with 60% methanol. Vacuum-concentrated eluates were analyzed using liquid chromatography-mass spectrometry system 30 with a lower heated capillary temperature of 190° C. and a gradient as follows: Solvent B (80% acetonitrile in 0.1% formic acid) was held constant at 5% for 5 minutes, increased to 44% B by 45 minutes, and then to a 95% B by 65 minutes. SRM mode quantification was performed with collision gas energy of 30% for the following MS/MS transitions (precursor m/z/product m/z): compound ZFH-2056, 447/285; compound ZFH-2050, 390/228. Absolute quantification was achieved by comparison to a calibration curve.

Bladder tissue bacterial titer determination. Mannoside ZFH-2056 was administered either IP (5 mg/kg) or orally (100 mg/kg) 30 min prior to inoculation with UTI89. To enumerate the bacteria present, mice were sacrificed at 6 hpi and bladders were aseptically removed and homogenized in 1 ml PBS, serially diluted and plated onto LB agar plates. CFU was enumerated after 16 h of growth at 37° C.

Confocal microscopy. Mannoside ZFH-2056 was administered IP (5 mg/kg) 30 min prior to inoculation with UTI89. To visualize bacterial behavior within the bladder, mice were sacrificed at 6 hpi and bladders were aseptically removed, bisected, splayed on silicone plates revealing the luminal surface and fixed in 2% paraformaldehyde (v/v). The splayed bladders were then incubated for 20 min at room temperature with (i) SYTO9 (1:1000 in PBS; Molecular Probes) to stain bacteria and (ii) Alexa Fluor 594-conjugated wheat germ agglutinin (WGA; 1:1000 in PBS; Molecular Probes) to stain the bladder luminal surface. Bladders were rinsed with PBS, mounted using Prolong Gold antifade reagent (Invitrogen) and examined with a Zeiss LSM510 confocal laser scanning microscope under a 63× objective. SYTO9 and WGA were excited at 488 and 594 nm, respectively.

Gentamicin protection assay. To enumerate bacteria present in the intracellular versus extracellular compartments, bladders were aseptically harvested at 6 hpi. The bladders were then bisected twice and washed three times in 500 µl of PBS each. The wash fractions were pooled, lightly spun at 500 rpm for 5 min to pellet exfoliated bladder cells, serially diluted, and plated onto LB agar to obtain the luminal fraction. The bladders were treated with 100 µg of gentamicin/ml for 90 min at 37° C. After treatment, the bladders were washed twice with PBS to eliminate residual gentamicin, homogenized in 1 ml of PBS, serially diluted, and plated onto LB agar to enumerate the CFUs in the intracellular fraction.

Antibiotic treatment. Mice were given TMP-SMZ in the drinking water at a concentration of 54 µg/ml and 270 µg/ml, respectively. Water was changed daily for 3 days prior to inoculation with UTI89. Mice remained on TMP-SMZ during the infection. To determine TMP-SMZ concentration in the urine, urine was collected after 3 days of TMP-SMZ treatment and quantified by LC-MS following addition of sulfisoxazole as an internal standard.

Growth curve. An overnight culture of PBC-1 was diluted 1:1000 in LB in the absence or presence of TMP-SMZ and/or mannoside ZFH-2056. The highest concentration of TMP-SMZ used was 512 µg/ml and 2560 µg/ml, respectively. Two-fold dilutions of TMP-SMZ were performed. Mannoside ZFH-2056 was added at 100 µM. Growth curves were performed in a 96-well plate at 37° C. with A600 readings taken every 30 min for 8 h.

Hemagglutination assay. PBC-1 was grown statically in LB in the absence or presence of TMP-SMZ for 2×24 h at 37° C. The highest concentration of TMP-SMZ used was 256 µg/ml and 1280 µg/ml, respectively. Two-fold dilutions of TMP-SMZ were performed. Hemagglutination assays for mannose-sensitive agglutination of guinea pig red blood cells were performed as previously described.

Statistical analysis. Observed differences in bacterial titers and IBC numbers were analyzed for significance using the nonparametric Mann-Whitney U test (Prizm; GraphPad Software).

Example 15

Improving Solubility and Potency of Mannosides

Amide groups were added to the insoluble 1ZFH253 and 1ZFH296 mannosides to produce mannoside compounds with increased solubility as shown in the FIG. 24. A divalent compound was also produced using 2ZFH50. The efficacy of these compounds along with 1ZFH177 was tested in an in vitro inhibition of hemagglutination and biofilm assays (FIG. 25). These results demonstrate improved in vitro potency of mannosides comprising enhanced solubility.

ZFH56 was injected IP into mice at various doses and levels of the compound were measured in the animal (FIG. 26). 10 mg/kg, 5 mg/kg or 5 mg/kg followed by a 4 hour boost were injected into animals.

IBC numbers were also determined in animals pretreated with ZFH56 (FIG. 27). ZFH56 also altered the pathogenic pathway as measured by confocal microscopy (FIG. 28). ZFH56 also showed increased efficacy against TMP-SMZ resistant strains (FIG. 29).

Example 16

Testing Against Various Inoculum Levels

An inoculum of 10$^7$ is likely well above the physiological dose typically found in a human. It is likely that only a few bacteria are inoculated into the urinary tract for a successful infection. Thus, a lower dose of bacteria was introduced to the mouse and determined whether this increased the efficacy of mannoside ZFH56 (FIG. 30). In order to obtain a consistent infection in the mouse model of UTI the dose could only be lowered by 10 fold. With an inoculum of UTI89 of $10^6$, there was a significant decrease (p<0.0001) in bacterial titers in the ZFH56 treated mice compared to the untreated mice. However, the level of infection in the mannoside treated mice at both the $10^7$ and $10^6$ inoculum was approximately equivalent suggesting that the lower dose did not further enhance efficacy of the mannoside. Using IBC counts in the bladder at the lower dose there were no IBCs observed in the ZFH56 treated mice at the $10^6$ inoculum. However the overall number of IBCs in the untreated mice were also much lower. Since there were no IBCs at 6 h in the $10^6$ inoculum, it was hypothesized that the level of infection at 2 weeks post-infection would be significantly lower. Evaluation of 2 week titers revealed a significant decrease in bacterial load in the mannoside treated bladders with the $10^6$ inoculum. This data suggests that upon lowering the inoculum, mannoside is able to significantly reduce colonization at 2 wpi with a single dose of 5 mg/kg ZFH56 30 min prior to inoculation of UTI89.

PK studies with IP dosing revealed that after injection, mannoside ZFH56 is rapidly eliminated in the urine and is mostly gone by 6-8 h post injection. Thus the mice were boosted with 5 mg/kg mannoside ZFH56 every 8 h to maintain a constant presence of mannoside in the mouse. This experiment comprised 4 groups: (1) untreated, (2) pretreat by IP injection of 5 mg/kg ZFH56 30 min prior to inoculation with UTI89, (3) pretreat by IP injection of 5 mg/kg ZFH56 30 min prior to inoculation plus 2 additional treatments every 8 h, and (4) inoculation with UTI89 followed by IP treatment with 5 mg/kg ZFH56 1 h post-infection and 2 additional treatments every 8 h. Mice were harvested at 24 hpi. This was done with the $10^7$ and $10^6$ inoculum of UTI89. There was a significant drop in bacterial titers with the single pretreatment of ZFH56 with both inoculum doses. In the mice inoculated with $10^7$ UTI89 there was further efficacy of ZFH56 upon boosting. However, this same effect was not observed with the 106 inoculum. With both inoculums there was no efficacy observed upon post-infection treatment with ZFH56. These data suggest that mannoside is currently most efficacious when used prophylactically (FIG. 31).

Next, it was determined if a 10 fold increase in ZFH56 would increase efficacy and if the divalent ZFH308 was as efficacious as ZFH56 at 5 mg/kg (FIG. 32). Mice were treated with 5 mg/kg ZFH56, 50 mg/kg ZFH56 or 5 mg/kg ZFH308 30 min prior to infection with $10^7$ UTI89. At 6 and 24 hpi bladders were harvested and titered. At 6 hpi, 5 mg/kg ZFH56 and 50 mg/kg ZFH56 both significantly inhibited bacterial infection. However, 50 mg/kg ZFH56 did not significantly enhance efficacy over the 5 mg/kg ZFH56 dose. 5 mg/kg ZFH308 did not significantly reduce bacterial infection at 6 hpi. At 24 hpi, both 5 mg/kg and 50 mg/kg ZFH56 significantly reduced bacterial titers. 50 mg/kg ZFH56 showed slight enhancement over 5 mg/kg ZFH56 relative to untreated mice. Again ZFH308 did not show efficacy in reducing infection. Thus, 5 mg/kg ZFH56 seems to be the optimal dose for inhibiting bacterial infection and the divalent ZFH308 does not show enhanced efficacy over the monovalent compound.

Example 17

ZFH56 Disrupts Preformed Biofilm

UTI89 was grown in LB in PVC plates and allowed to form biofilm at RT for 24 or 48 h. At 24 or 48 h, varying concentrations of mannoside ZFH56 was added. Biofilm was then allowed to grow for another 24 h at RT. Biofilm formation was then quantitated using the standard crystal violet assay. Results showed that ZFH56 was able to disrupt preformed biofilm (FIG. 32). At 24 h the 1050 for biofilm disruption was ~6 µM and at 48 h the 1050 was ~25 µM. This shows that not only can mannoside inhibit biofilm formation it can dissolve biofilm that has already formed.

Introduction for Examples 18-22

Catheter-associated urinary tract infections (CAUTIs) often arise from multidrug resistant Gram-positive and Gram-negative bacterial colonization and biofilm aggregation on the surface of indwelling urologic devices such as urinary catheters, rendering treatment very difficult. Uropathogenic *Escherichia coli* (UPEC), the primary cause of community-acquired UTI, account for 50% of nosocomial UTIs, including CAUTIs. Yet, very little is known about its pathogenesis following urinary catheterization, which results in the disruption of the normal mechanical and antimicrobial defenses of the bladder. Previous reports using human biopsies and rodent models of infections have shown that the catheterized bladder is edematous and highly inflamed with immune cell infiltration and pro-inflammatory cytokine production, an environment quite different from that which UPEC encounters in a non-catheterized bladder. We hypothesized that these profound catheter-related changes may affect UPEC pathogenesis.

The UPEC pathogenic cascade has been extensively characterized in a non-catheterized murine model of cystitis. UPEC elaborate on their surface adhesive type 1 pili which mediate binding to and invasion of superficial umbrella cells lining the bladder epithelium. Once intracellular UPEC can escape into the cytoplasm, replicate rapidly and undergo morphological differentiation within bladder epithelial cells to produce mature intracellular bacterial communities (IBCs) of ~$10^4$-$10^5$ bacteria with biofilm-like properties. UPEC then flux out from infected cells and can reinvade neighboring cells and start the process de novo. This acute phase of UPEC infection can lead to the development of chronic cystitis, pyelonephritis, and the formation of quiescent intracellular reservoirs (QIRs) with absence of bacteriuria. Detailed understanding of the critical steps of this pathogenic cascade has led to the development of small molecule inhibitors called mannosides. Mannosides specifically target the bacterial type 1 pili tip adhesin, FimH, which binds to mannosylated residues present on the surface of the bladder epithelium. Rationally designed to interfere and prevent FimH interaction with these residues, mannosides inhibit UPEC binding and invasion of the superficial umbrella cells during urinary tract infections (UTIs). Mannosides, in combination with existing antibiotic-based UTI therapy, have recently been shown to be effective in preventing and treating UPEC infections in non-catheterized infection models. The present study investigates whether this therapeutic approach could be beneficial in the prevention and treatment of CAUTIs.

In Examples 18-22, the optimized murine model of foreign body-associated UTI that closely mimics CAUTI was used to investigate the consequences of urinary catheterization on the pathophysiology of UPEC infection. For these studies, several UPEC virulence parameters, including the contribution of type 1 pili, IBC formation, and QIR reactivation, were assessed. The results obtained indicate that urinary catheterization provides UPEC with the opportunity to exploit the extracellular milieu of the bladder via type 1 pili-mediated biofilm formation on the surface of the foreign body, which results in a shift in the niche population. Administration of mannosides in combination with trimethoprim/sulfamethoxazole prior to urinary catheterization prevents UPEC colonization of the urinary tract. These Examples provide important insights into the mechanisms underlying UPEC-mediated CAUTI, and informs efforts to design better therapeutic approaches to prevent and potentially treat these infections.

Materials and Methods for Examples 18-22

Bacterial Strains and Growth Conditions

All strains used in this study and their characteristics are listed in Table 16. Unless otherwise specified, a single colony of E. coli grown on Luria Bertani (LB, Becton Dickinson) agar plate supplemented with appropriate antibiotics was inoculated into LB broth and grown statically at 37° C. for 18 h.

TABLE 16

Strains used in this study

| Species and Strains | Relevant Antibiotic resistance | Characteristics |
|---|---|---|
| UTI89 | | Parental UPEC UTI89 strain, cystitis isolate |
| UTI89ΔfimH | | UTI89 with an in-frame deletion of fimH, type 1 pili defective |
| UTI89ΔsfaA-H | | UTI89 with an in-frame deletion of sfa operon, S pili defective |
| UTI89ΔsfaA-HΔfimB-H | $Kan^R Cm^R$ | UTI89 with in-frame deletion of the sfa operon and the fim operon from fimB to fimH, S and type1 pili defective |
| UTI89ΔcsgA | | UTI89 with an in-frame deletion of csgA, curli deficient |
| UTI89ΔcsgBΔcsgG | | UTI89 with in-frame deletions of csgB and csgG, curli deficient |
| UTI89HK::GFP | $Kan^R$ | UTI89 with an insertion of kanamycin cassette and GFP at the HK site |
| UTI89pCOMGFP | $Kan^R$ | UTI89 ectopically expressing GFP from pCOM plasmid |

In Vitro Cultivation and Quantification of Biofilms.

Biofilms were grown as described by Ferrieres et al. (2007; FEMS Immun. Med. Micro 51:212) on All Silicone Foley catheters (Bard Medical, GA) or silicone tubing (Thermo Fisher Scientific Inc., PA) and modified as follows. All tubing and connectors in the system were autoclaved and ethanol sterilized prior to use. The system was assembled similar to the previously described flow-chamber system. Priming of the catheter or the silicone tubing occurred at 37° C. for 20 min by flowing pre-warmed pooled human urine. Urine was collected from healthy volunteers as approved by the Institutional Review Board of Washington University in St. Louis. Pooled samples were spun at 10000×g for 15 min, filtered through 33 μM filters, and, if necessary, stored at 4° C. for no more than 3 days. Three milliliters of stationary-phase E. coli from overnight cultures were diluted to $1-2\times10^6$ CFU/ml in human urine and injected into the catheter or silicone tubing using a 30 cc gauge needle. The bacteria were allowed to attach to the substratum for 1 h before urine flow via Watson-Marlow peristaltic pump 205S was resumed at 0.5 ml min$^{-1}$. When indicated, urine was supplemented with 1% methyl mannose (Sigma, Mo.) prior to the experiment. After 24 hours, the remaining medium was exchanged for sterile ddH$_2$O that was allowed to flow at 0.5 ml min$^{-1}$ to remove residual urine and non-adherent bacteria in the system. The liquid from catheter or silicone tubing was then removed by capillary action onto absorbent paper. The tubing was cut into pieces for CFU enumeration or crystal violet staining, respectively. For CFU enumeration, at least three pieces (1 cm in length) of incubated tubing were separately further cut into smaller pieces and placed into 1 ml PBS. Adherent cells were detached by sonication (10 min) and vigorous vortexing (3 min). Viable bacterial counts were assessed by serial dilution on LB plate with appropriate antibiotics. Crystal violet staining was used to determine biofilm biomass. At least 3 pieces of incubated tubing (3 cm in length) were filled with 0.5% crystal violet at room temperature for 10 min. Excess dye was removed by washing three times with ddH$_2$O and dried by capillary action on absorbent paper. The bound crystal violet was then dissolved in 200 μl of 33% acetic acid and absorbance measured at 595 nm. The amount of biofilm was expressed as CFU/ml per cm$^2$ and A595/cm$^2$. The experiment was repeated at least three times with different urine samples.

Animal Implantation and Infections.

Six to seven week-old female wild-type C57BL/6Ncr mice purchased from the National Cancer Institute (NCI) were used in this study. Experiments were performed following one week adaptation in the animal facility after arrival from NCI. Animals were implanted and infected with the indicated bacterial strain as previously described. Briefly, seven to eight week-old female mice were anesthetized by inhalation of isoflurane and implanted with platinum-cured silicone tubing (4-5 mm in length) (Implanted). Immediately following implantation, 50 μl of ~$1-2\times10^7$ CFU bacteria in 1×PBS were introduced in the bladder lumen by transurethral inoculation. Non-implanted animals were inoculated in the same manner. Animals were sacrificed at indicated time points by cervical dislocation under anesthesia inhalation. Bladders and kidneys were aseptically harvested. Subsequently, the silicone implant was retrieved from the bladder when present, placed in PBS, sonicated for 10 min and then vortexed at maximum speed for 3 min. Bladder and kidneys from each mouse were homogenized in PBS. Samples were serially diluted and plated on LB agar plates supplemented with appropriate antibiotics. CFU were enumerated after 24 h incubation at 37° C. In all cases, experiments were performed at least twice with n=5 mice/strain/condition. All studies and procedures were approved by the Animal Studies Committee at Washington University School of Medicine.

Mannoside and Antibiotic Treatment.

SdfFor pretreatment experiments, 50 μl mannoside (mannoside 6; 5 mg/kg mouse body weight) or PBS was administered intraperitoneally 30 min prior to implantation as previously described. As indicated for pre-infection treatment, trimethoprim/sulfamethoxazole (TMP-SMZ) was added to the drinking water for three days prior to infection at 54 and 270 μg/ml, respectively. The drinking water was changed every 24 h. To assess the effects of mannoside and/or TMP-SMZ on established infections, animals were implanted and infected for 24 h. At 24 hpi, TMP-SMZ was added to the drinking at the concentrations indicated above and mannoside 6 or PBS was administered i.p. 6 h prior to sacrifice. Animals were sacrificed 48 hpi.

UPEC Reservoir Reactivation.

Non-implanted animals were infected with UTI89HK::GFP as described above. At fourteen days post infection, urine was collected, serially diluted and plated for CFU and a subset of animals implanted as described above. Animals determined to be bacteriuric (bacterial loads greater than or equal to $10^4$ CFU/ml in urine) as counted on titer plates the next day were eliminated from further study. QIR reactivation post-implantation was assessed by CFU enumeration of bacteria on implants and in the organs 3 or 5 days post-implantation (17 or 19 dpi). UTI89HK::GFP titers greater than $10^4$ CFU/ml on implants or bladders were considered reactivation events. Measures of reactivation events of animals, which were non-bacteruric at 14 dpi but non-implanted served as controls.

IBC enumeration and visualization. Implanted and non-implanted animals were infected with UTI89 for 6 h. When indicated, mannoside 6 (5 mg/kg) or PBS was administered i.p. at 30 min prior to implantation. At 6 hpi, bladders were harvested, bisected, splayed on silicone plates and fixed in 2% paraformaldehyde. LacZ staining of whole bladders was performed as previously described. Punctate violet spots characteristic of IBCs were enumerated by light microscopy.

For IBC visualization, animals were infected with UTI89 constitutively expressing GFP (UTI89 pCom-GFP). At the indicated time point, bladders were removed, bisected, splayed, and fixed as described above. The splayed bladders were then incubated for 20 min at room temperature with Alexa Fluor 633-conjugated wheat germ agglutinin (WGA; 1:1000 in PBS; Molecular Probes) for staining of the bladder surface and, when indicated, SYTO83 (1:1000 in PBS; Molecular Probes) to stain bacteria. Bladders were rinsed with PBS, mounted using Prolong Gold antifade reagent (Invitrogen) and examined with a Zeiss LSM510 confocal laser scanning microscope under a 63× objective. SYTO83 and WGA were excited at 543 and 633 nm, respectively.

Gentamicin Protection Assay.

To quantify intracellular and extracellular bacteria, bladders were aseptically harvested at 3 and 6 hpi. Bladders were cut in 4 parts and washed three times in 500 µl PBS. The wash fractions were pooled, centrifuged at 500 rpm for 5 min to pellet exfoliated bladder cells. The supernatants were then serially diluted and plated on LB agar supplemented with appropriate antibiotics, which were incubated at 37° C. for 24 hrs to obtain extracellular bacterial CFU counts. Rinsed bladders were then treated with 100 µg/ml gentamicin for 90 min at 37° C. Following gentamicin treatment, the bladder tissue was washed twice with PBS to eliminate residual antibiotics, homogenized in 1 ml PBS, and bacterial CFU counts of determined as above to determine the levels of intracellular bacteria (protected from gentamicin killing).

Statistical Methods.

Comparisons between groups were conducted by nonparametric Mann-Whitney U test using GraphPad Prism (GraphPad software, version 5). Values below the limit of detection for in vivo experiments (20 CFU for organs, 40 CFU for implants) were assigned the appropriate LOD value for statistical analyses. All tests were two tailed, and a p-value less than 0.05 was considered significant. Colonization and infection was defined as organs/implants with bacterial titers above the limit of detection.

Example 18

Figure 34C:
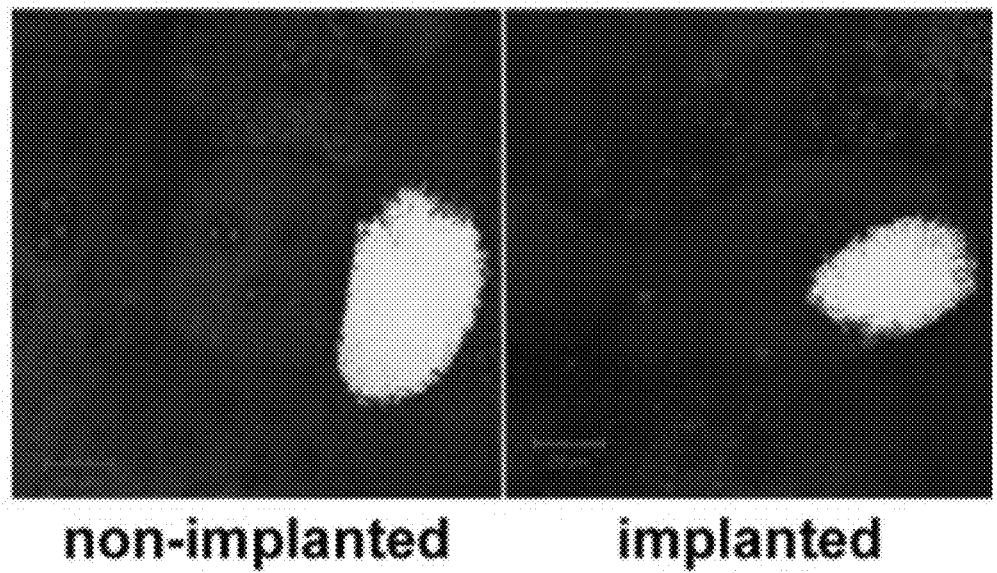

UPEC Adherence, Invasion, and IBC Morphology are Unaltered in Catheterized Bladders IBC formation occurs in the pathogenesis of UPEC in non-catheterized patients and has been shown in mouse models to be critical for infection. To assess the effects of urinary catheterization on IBC formation, 4-5 mm platinum-cured silicone tubing sections were implanted in the bladders of C57Bl/6Ncr female mice, which were then immediately infected with $1-2 \times 10^7$ CFU of the well-studied virulent UPEC strain UTI89 by transurethral catheterization. Gentamicin protection assays performed at 3 hpi revealed no statistical difference in either the extracellular or intracellular UPEC populations in the presence or absence of implants (FIG. 33), indicating no gross defect in bacterial invasion in implanted animals. IBC formation within both implanted and non-implanted bladders was assessed by LacZ staining and confocal scanning laser microscopy (CSLM) at 6 hpi (FIG. 34A). Inoculation of UPEC into implanted animals resulted in significantly fewer IBCs with a median of 8 IBCs/bladder (p=0.0044; FIG. 34B) compared to non-implanted animals in which IBC numbers ranged up to >250 IBCs/bladder with a median of 55 IBCs/bladder. However, bacterial CFU in implanted bladders were similar to those in non-implanted animals (data not shown). To account for this observation, we postulated that IBC morphology might be different in implanted animals. However, IBCs formed in implanted animals were observed to be overall similar in size and shape as those produced in non-implanted bladders (FIG. 34C). UPEC were also seen to produce multiple IBCs within one umbrella cell and filamentous bacterial clumps in both catheter implanted and non-implanted bladders at 6 hpi (FIG. 35). UPEC colonization at 6 hpi was selectively localized in the remaining umbrella cells and not observed in the exposed underlying epithelium in implanted bladders (FIG. 35). Together, these findings indicate that urinary catheterization negatively impacts IBC formation by UPEC, possibly due to a correlated increase in exfoliation.

Example 19

Bacteria Originating from Existing UPEC Reservoirs can Seed Urinary Implant Colonization One troubling possible outcome of the UPEC pathogenic cascade is the establishment of quiescent intracellular reservoirs (QIR) in the underlying epithelial layers, which have been shown can be a source of recurrent UTIs (rUTIs). QIRs were shown to be reactivated following treatment with protamine sulfate, a chemical that leads to exfoliation of the superficial umbrella cells of the uroepithelium. Like protamine sulfate, we have previously shown that urinary catheterization causes severe damage to the protective uroepithelial layer. Thus, we hypothesized that urinary catheterization might also reactivate existing UPEC reservoirs, resulting in bacteruria, catheter colonization and further dissemination. To test this hypothesis, mice were infected with $1-2 \times 10^7$ CFU UTI89HK::GFP and infection allowed to resolve over the course of 2 weeks. On day 14 post-infection, urine was collected from each animal to assess infection state prior to urinary implantation of a subset of these animals. Those animals in which titering of urines 14 dpi indicating bacteriuria ($\geq 10^4$ CFU/ml) were considered to have active (non-resolved and or recurrent) infection and were removed from further analysis. The remaining mice were presumed to either have completely cleared the infection or to have established QIRs with bacteria loads between $10^1$ and $10^4$ CFU/ml. 3 or 5 days post implantation, reservoir reactivation was assessed by bacterial colonization of implants and bladder. On day 3 post implantation, UPEC UTI89HK::GFP was recovered from implants in 3 of 26 implanted mice (~11.5%). One mouse with implant had bladder colonization greater than $10^4$ CFU/ ml compared to none of the 22 similarly infected but non-implanted animals (FIG. 36A). There was no significant difference between groups at 3 dpi. For mice assessed at 5 days post-implantation, UTI89HK::GFP was recovered from implants of 4 out of 32 animals (~13%) with two of them having bladder titers greater than $10^4$ CFU/ml (FIG. 36B) compared to 0 out of 23 in non-implanted animals. Interestingly, there were overall significantly fewer bacteria recovered from the bladders of implanted animals compared to non-implanted animals at 5 dpi (p=0.0010), suggesting that either reactivated reservoirs are cleared by the immune response prior to day 5 following implantation or increased exfoliation prevents establishment of persistent infections. Together, these data indicate that urinary catheter colonization can occur from previous urinary infections even if those infections appear by bacteriuria counts to have been resolved.

Example 20

FimH is Required for Biofilm Formation and UPEC Colonization of the Urinary Tract Following Catheter Implantation Biofilm formation is a critical component of CAUTI pathophysiology. We have previously shown that UPEC is able to produce biofilms on the surface of the foreign body and is recovered for the catheterized murine bladder at very high titers. Type 1 pili are major UPEC virulence factors that have been shown to be critical for biofilm aggregation, IBC formation, and other aspects of UPEC uropathogenesis. Thus, we assessed the contribution of these extracellular pili as well as other UPEC fibers, including curli which contribute to biofilm formation or S pili associated with E. coli clinical isolates producing strong biofilms, to biofilm formation in filtered human urine under flow conditions and UPEC-mediated CAUTI in vivo. Deletion of the gene for the tip adhesin of type 1 pili, FimH, in UTI89 resulted in significantly (p<0.0001) lower biomass (FIG. 37A) and an approximate 2-fold reduction in adherent viable bacteria (FIG. 37B) in biofilms formed in human urine in vitro. These data indicate that type 1 pili are a major contributor to UPEC biofilm formation in urine. The biofilm defect was specifically associated with the fimH mutant under these conditions, and was not observed following deletions of the sfa operon to prevent S pili formation, csgA required for curli fiber formation, or a component of the flagellar system fliC (data not shown).

Figure 37C:
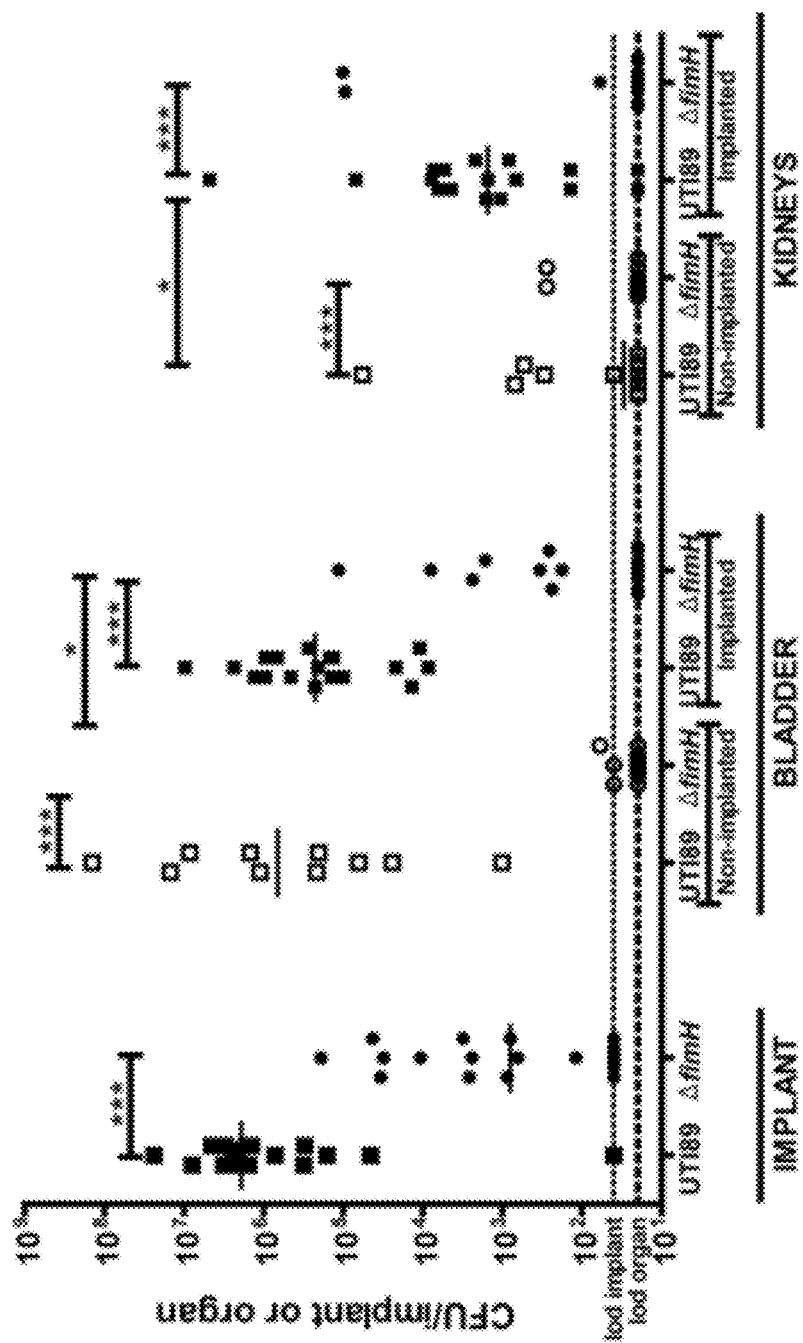
Figure 38A:
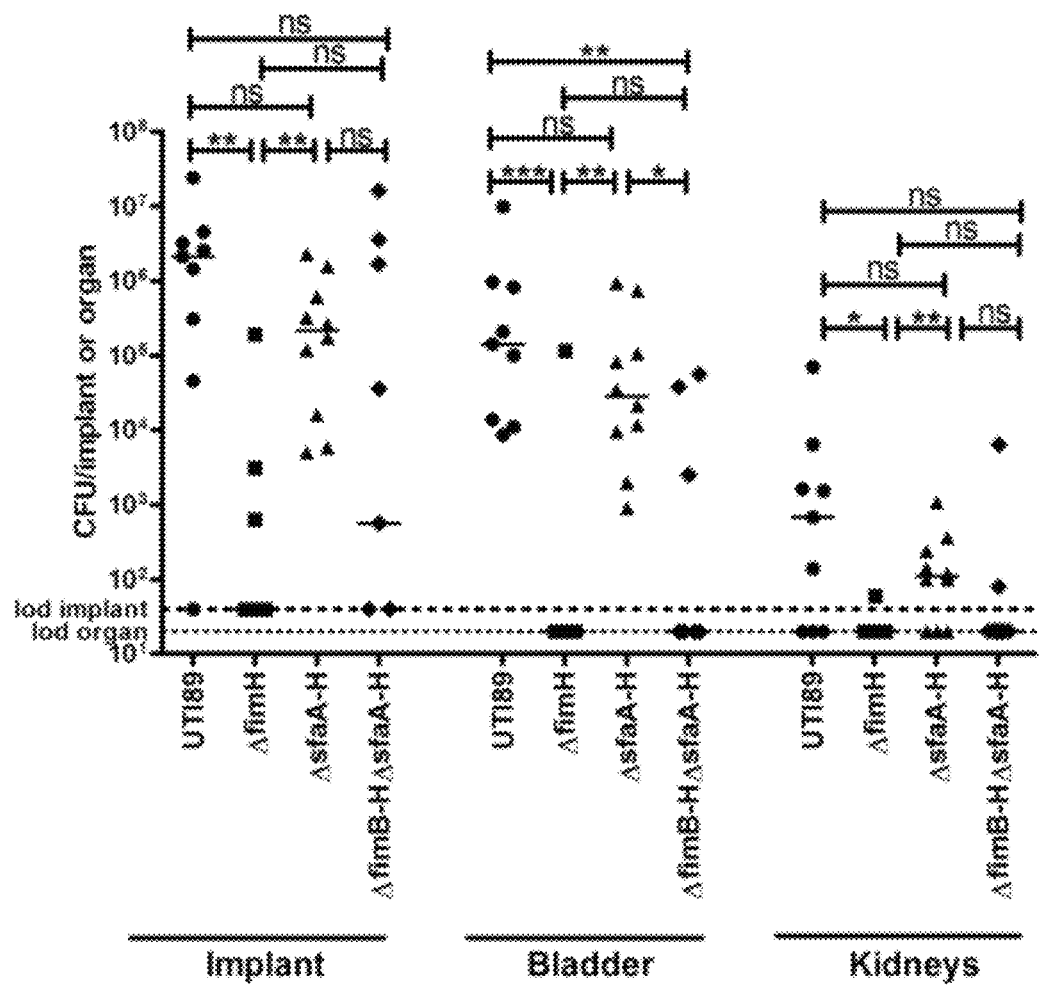
Figure 38B:
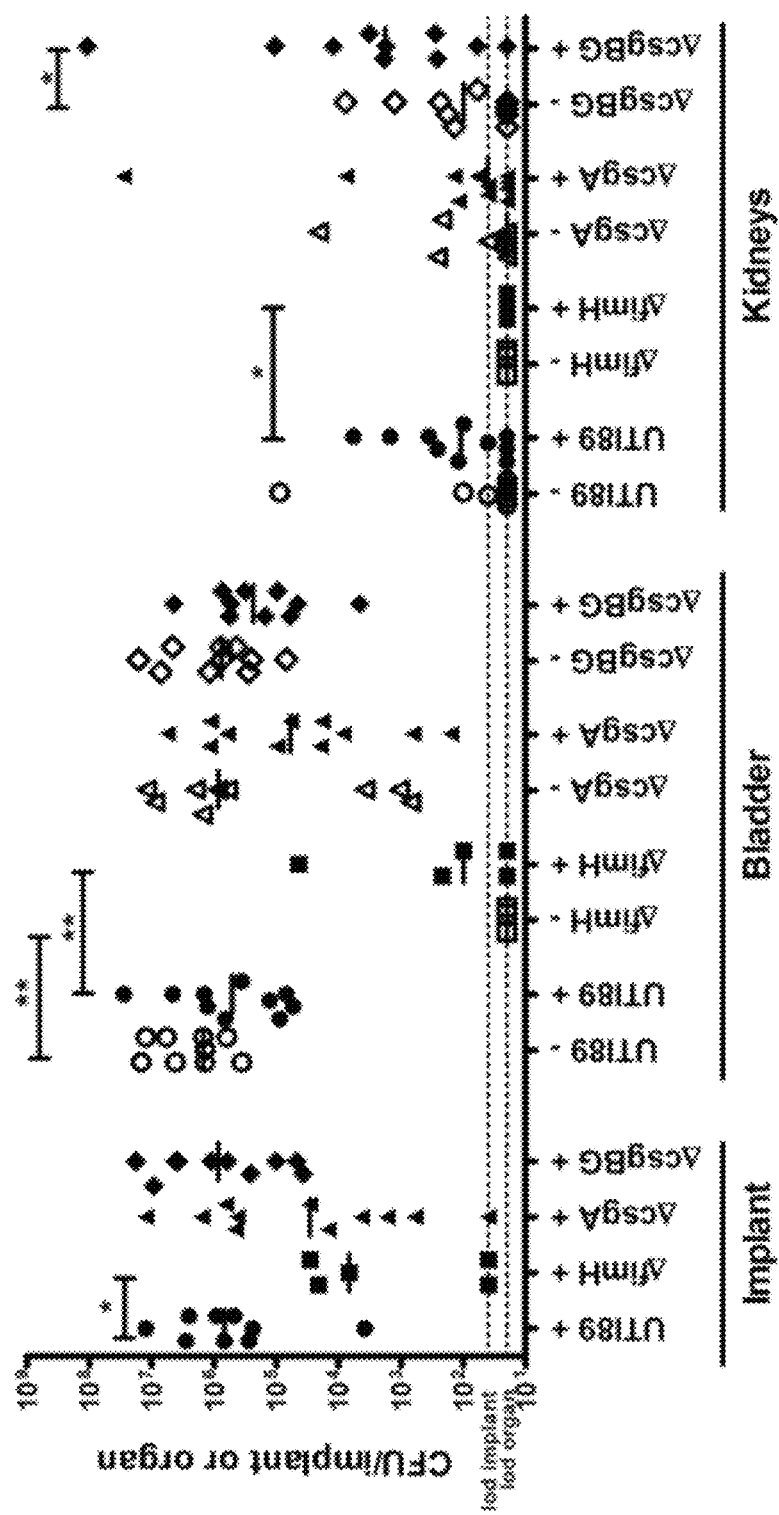

In vivo, similar to findings in a murine model of cystitis, UTI89ΔfimH is severely attenuated in the murine model of foreign body-associated UTI (FIG. 37C). UTI89ΔfimH displayed >3 log fewer CFU in the bladder and was unable to ascend to the kidneys at 24 hpi. Further, deletion of fimH resulted in significant reduction in implant colonization (p<0.0001). Similar to in vitro experiments, S-pili are not required for CAUTI since UTI89ΔsfaA-His as virulent as wildtype UTI89 and a double deletion of both sfaA-H and fimB-H recapitulated the UTI89ΔfimH phenotype (FIG. 38A). Furthermore, components of the curli system important for biofilm formation in vitro under certain conditions, but not in human urine (FIG. 37A-B), were also dispensable during CAUTI (FIG. 38B). The residual binding to implants and bladders in implanted animals could therefore be attributed to other pili or biofilm determinants. Together, these data strongly suggest that the tip adhesin FimH of type I pili is a critical determinant of UPEC virulence in mediating biofilm formation and virulence during CAUTI.

Example 21

Mannoside Treatment Reduces IBC Formation

Having established that FimH is required for UPEC virulence in implanted bladders, we investigated this as a potential therapeutic target for CAUTI using small molecules inhibitors designed to interfere with FimH binding to mannosylated residues. This family of small molecules, called mannosides, has recently been shown to prevent acute and chronic UPEC infections and potentiated the effectiveness of antibiotics in combinatorial treatment.

To investigate the potential therapeutic effects of mannosides on CAUTI, we first assessed the inhibitory effects of methyl-α-D-mannopyranoside (methyl mannose), on UTI89 biofilm formation in urine under flow. Similar to the deletion of fimH (FIG. 37A), UTI89 biofilms grown in presence of 1% methyl mannose had significantly reduced biomass (p=0.0022) and biofilm-adherent cells (p=0.0012), compared to untreated controls (FIG. 39). Since methyl mannose is a FimH antagonist, these data confirm the critical role of type 1 pili to biofilm formation in urine as was previously described for biofilms formed in LB media.

Figure 40A:
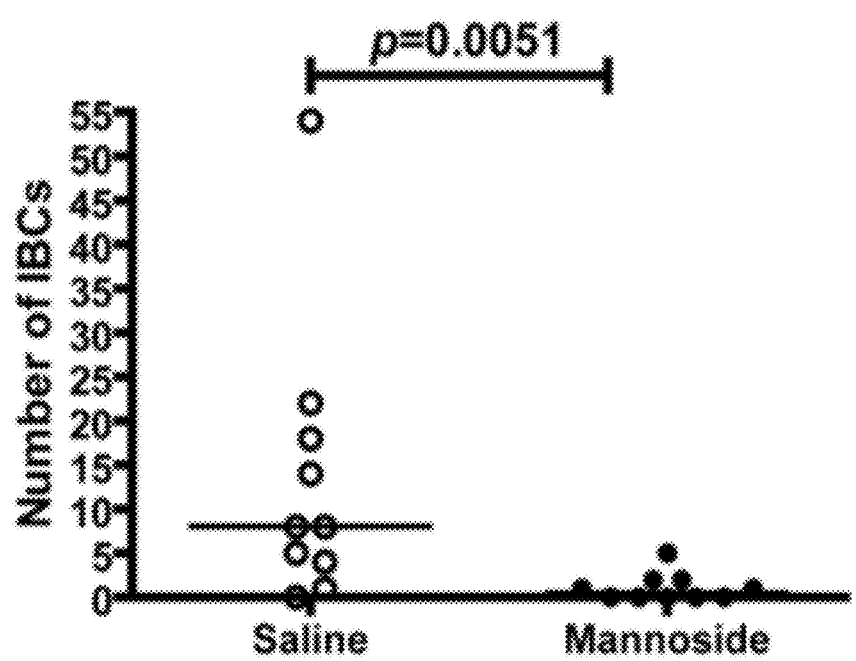
Figure 40B:
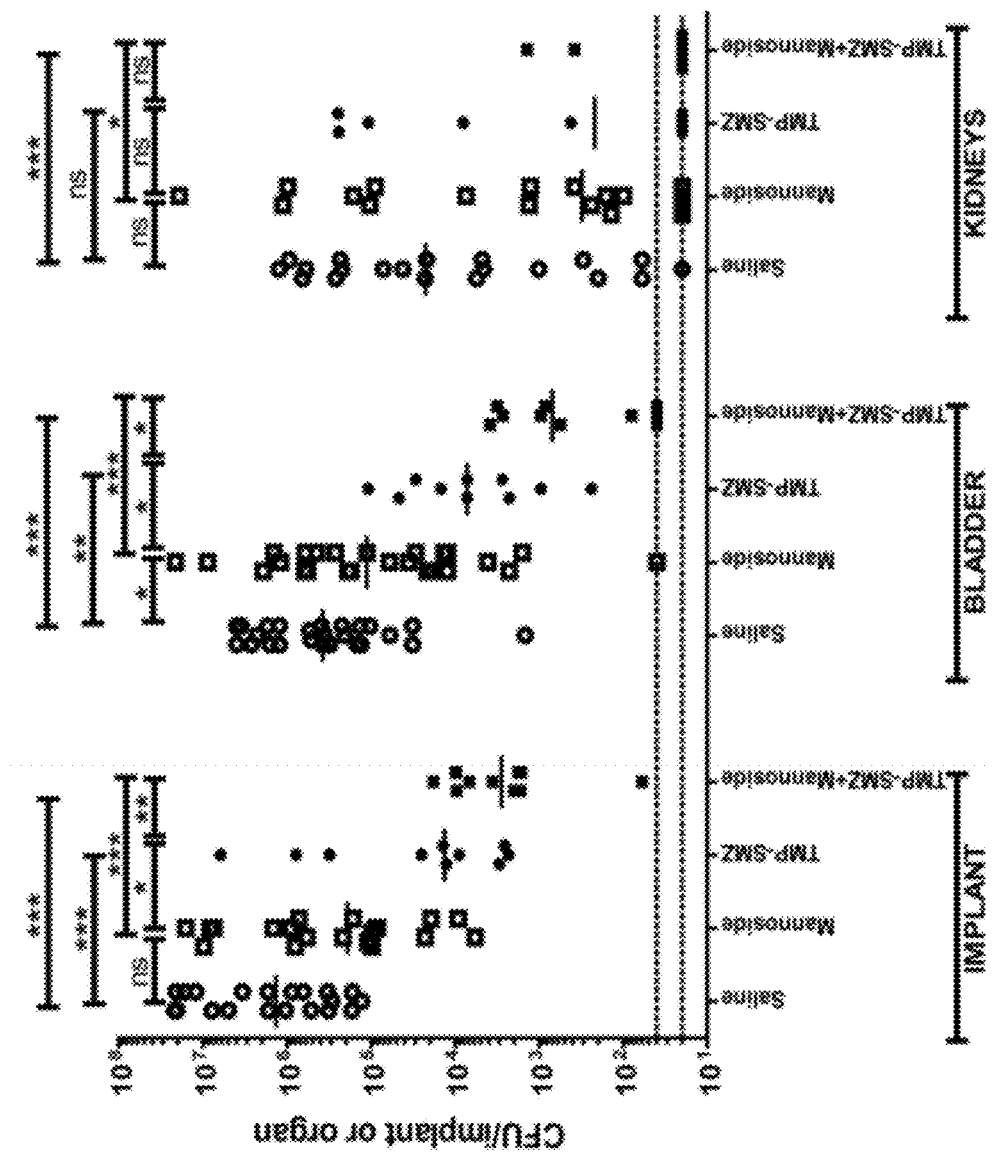

The effects of mannoside treatment were then assessed in vivo by using IBC formation as well as implant and urinary tract colonization as benchmarks of disease progression. Mice were treated intraperitoneally (i.p.) with saline or 5 mg/kg of mannoside 6, which is more potent than methyl mannose in vitro and in vivo, in PBS 30 min prior to urinary implantation. Catheter implantation was immediately followed by transurethral inoculation of UTI89. IBC formation and bacterial colonization were assayed by LacZ staining and CFU enumeration of implants, bladders, and kidneys at 6 hpi and 24 hpi, respectively. As shown in FIGS. 40A and 40B, mannoside treatment further reduced IBC formation (p=0.0051) and bladder colonization (p=0.0114) in implanted animals at 6 hpi, suggesting that this treatment prevents intracellular infection. While eliminated from their intracellular niche, data further indicated that UPEC were able to persist in the extracellular milieu where they can colonize the surface of the implants to relatively similar levels as saline-treated animals (p=0.0547) (FIG. 40B). No statistical difference was observed in kidney colonization in the presence or absence of mannosides (FIG. 40B). By 24 hpi, a time point at which the mannosides have been eliminated from the bladder, similar bacterial loads were recovered from implants, bladders, and kidneys in implanted animals in the presence or absence of mannoside treatment (data not shown).

Example 22

Mannoside Treatment Increases the Efficiency of TMP-SMZ in Preventing UPEC Colonization In order to examine whether mannosides could prevent establishment of CAUTI when used in combination with antibiotics, animals were treated with 54 and 270 µg/ml of TMP-SMZ, respectively, in their drinking water for three days and then treated with saline or mannoside (5 mg/kg) i.p. 30 min prior to implantation and bacterial inoculation. At 6 hpi, UPEC colonized the implants and bladders at significantly lower levels in animals that only received antibiotics compared to those who received water or were only administered mannoside (FIG. 40B). Interestingly, mannoside treatment in addition to TMP-SMZ further decreased UPEC colonization of implants, bladders, and kidneys compared to treatment with antibiotic alone (p<0.0005 in all cases). Furthermore, treatment with mannosides alone did not reduce bacterial titers from a 24 h old UPEC infection and in combination with TMP-SMZ showed no additive effects on established UPEC CAUTI 24 hpi (data not shown). Together, these findings indicate that virulence-targeted therapies in combination with established antibiotic treatment can help prevent or delay the onset of CAUTI and that further research is warranted for enhancing mannosides potential as therapeutics against CAUTIs.

Discussion for Examples 18-22

UPEC is the major etiological agents of CAUTI. Yet, the molecular mechanisms of urinary catheter and bladder colonization following urinary catheterization have not been elucidated. Studies in an optimized murine model of foreign body-associated UTI10 show that urinary catheterization favors UPEC exploitation of the bladder extracellular milieu. This occurs via type 1 pili-dependent biofilm formation on the surface of silicone implants in the murine bladder. The data further indicate that of the biofilm determinants tested, type 1 pili are necessary for implant, bladder, and kidney colonization during CAUTI; providing definitive experimental evidence for previous reports postulating that type 1 pili may be required for UPEC persistence during CAUTIs. Interestingly, fimH-deficient UPEC strains have the ability to adhere to some extent to the surface of the foreign body, probably using other biofilm determinants such as other chaperone-usher pili systems, curli, or surface adhesins.

In addition to colonizing the foreign body in the bladder lumen, UPEC is able to exploit intracellular niches in implanted animals, albeit to a lesser degree than in non-implanted animals, by invading and producing IBCs in the early stages of infection. Reduced IBC formation in implanted animals may be a result of loss of the host superficial facet cells in which IBCs form due to increased exfoliation or damage to the uroepithelium following urinary catheterization. Nonetheless, this finding is of particular interest for treatment strategies against UPEC-mediated CAUTI. In humans, removal of the contaminated urinary catheter is the preferred method for treatment of these infections; however, the presence of bacteria in an intracellular compartment protected from host immune defenses and antibiotic treatment requires more comprehensive approaches as intracellular UPEC can lead to re-infection of a novel catheter or serve as a nidus for future UTI.

Quiescent intracellular reservoirs are an important outcome of UPEC pathogenic cascade because they are proposed to be a mechanism of recurrent UTI following damage to the uroepithelium. Findings from the current study indicate that urinary implantation of animals with a history of UTI can lead to bladder infection and implant colonization with the UPEC causing the first infection. This finding suggests that in addition to introduction of extracellular and periurethral bacteria, urinary catheter colonization can occur from bacteria originating from pre-existing reservoirs or other niches within the urinary tract not appreciated by assessment of bacteriuria. Interestingly, by day 5 following implantation in animals with a history of UTI, there is overall a significant reduction in the number of QIRs compared to that in non-implanted animals as assessed by bladder CFU. This reduction in bacterial load could be a result of enhanced immune-mediated clearance of infected cells or to exfoliation of infected cells in implanted animals. These hypotheses are currently being evaluated.

The identification of FimH as a critical virulence factor during UPEC CAUTI provides an interesting avenue for the development of novel preventative measures against these infections. In fact, there has recently been an upsurge in recommendations and guidelines for management of CAUTIs and rUTIs in catheterized patients, with a particular focus on preventative measures including the limited use of catheters and even the prophylatic use of antibiotics prior and following catheter removal. However, the inappropriate use of antibiotics can worsen the problems of increasing antibiotic resistance. Accordingly, the present study suggests that the use of small molecules inhibitors, such as mannosides, in combination with existing UTI treatment regimes, can lead to prevention or delay of UPEC colonization. Mannosides, were rationally designed to interfere with FimH-mediated binding to mannosylated proteins on the surface of the uroepithelium. Recent studies show that the use of mannosides in combination with antibiotics is highly effective in preventing IBC formation and acute stages of UPEC infection as well as treating chronic cystitis. Similarly, pretreatment with mannosides further prevents IBC formation following UPEC infection of implanted bladders and reduces UPEC binding to the uroepithelium. However, the presence of the abiotic implant surface provided a favorable environment for adherence of extracellular bacteria. The inability of mannoside treatment to eliminate UPEC from the implant, given that the experimental evidence that mannose inhibits UPEC biofilm on catheter material in urine in vitro, may be due to the lack of urine flow in this implanted murine model. It is possible that if it were possible to truly catheterize mice in a manner analogous to clinical catheterization of humans in which urine flows through the catheter that mannoside may have a more efficacious effect on implant clearance. Nonetheless, by preventing invasion and shifting UPEC's niche to the extracellular milieu, mannosides enhanced the bacteriocidal efficacy of antibiotics, such as TMP-SMZ, which does not cross host cell membranes. Mannosides could also be used in combination with bacterial interference strategy being offered as alternatives in the prevention of CAUTI. Previous reports have shown that pre-colonization of urinary catheters with an avirulent *E. coli* strain 83972 delays the onset of CAUTI in catheterized patients. Thus, it is quite possible that if used in combination with mannosides, UPEC will be kept from the intracellular niche as well as from binding to the catheter during bacterial interference with the avirulent strain. An attractive avirulent strain should be able to colonize the catheter in a type 1-independent manner to prevent invasion into urothelial cell, however *E. coli* strain 83972 enhanced binding to silicone catheter requires ectopic expression of fim. However, the therapeutic effects of mannoside 6 could not be recapitulated in our model of CAUTI (data not shown), possibly because the small molecules are ineffective at disrupting established biofilms in vivo or that UPEC may employ additional type 1 pili-independent mechanisms for maintaining biofilms. It is a well-established fact that the extracellular matrix of bacterial biofilms is impermeable to antimicrobial and antibiotics, providing a safe haven for the microbes within. Further research is thus needed for better therapeutics against CAUTIs. Nonetheless, the prophylatic use of mannosides prior to urinary catheterization can help reduce the rate of recurrent UT's from intracellular bacterial reservoirs following the removal of contaminated catheters.

Urinary catheterization is a necessary medical procedure that causes major damage to the urinary tract. Pathogens, such as UPEC, take advantage of this compromised environment to exploit new and existing niches and establish severe infections. This report uncovers important molecular mechanisms underlying UPEC pathogenesis following urinary catheterization. It raises important questions regarding the deleterious consequences of urinary catheterization and the origins of urinary catheter colonization. These novel aspects of CAUTI pathophysiology, especially the presence of intracellular bacterial niches even in presence of urinary catheters, should thus be taken into consideration for better diagnosis and the development of anti-virulence based preventative and therapeutic approaches against these infections.

Example 23

Treatment of Chronic Mice with 5 Doses of Mannoside 8 Eliminates UPEC from the Bladder Mice were infected with the uropathogenic E. coli (UPEC) strain UTI89. Animals that established chronic infection were treated at day 12 post infection with 5 doses of 50 mg/kg of Mannoside 8 administered 8 h apart (mice treated with PBS in the same way were included as controls). Mice were sacrificed 48 h post initial dose and bladder titers were enumerated.

The results clearly show a greatly reduced titer of UPEC in mice treated with Mannoside 8 versus control mice treated with PBS (FIG. 41).

Example 24

Mannoside 8 is Effective Against the Multidrug Resistant UPEC Isolate EC958

Mice were infected with the multidrug resistant (MDR) UPEC strain EC958. Animals that established chronic infection were treated at day 12 post infection with 1 dose of 50 mg/kg of Mannoside 8 (mice treated with PBS in the same way were included as controls). Mice were sacrificed 6 h post initial dose and bladder titers were enumerated.

The results show that titers of MDR UPEC in mice treated with Mannoside 8 had significantly lower titers of the MDR UPEC compared to MDR UPEC titers in control mice treated with PBS (FIG. 42).

Introduction for Examples 25-29

The development of antibiotics to broadly treat infections has led to significant advances in human health. Increasing bacterial resistance to traditional antibiotics and the dearth of programs to develop innovative antibiotics threatens to reverse these advances. This has been described as an impending "public health crisis". For example, over 15 million women suffer from urinary tract infections (UTI) annually in the U.S. with an estimated cost exceeding $2.5 billion. Uropathogenic E. coli (UPEC) account for up to 85% of all UTIs, which are exacerbated by increasing antimicrobial resistance. Resistance of UPEC to the antibiotic cocktail, trimethoprim-sulfamethoxazole (TMP-SMZ) has increased significantly in the past decade and thus therapy has increasingly required the use of last-line antibiotics such as fluoroquinolones, leading to increased treatment costs and an associated rise in multidrug resistance. These developments make UTI one of the most visible manifestations of increasing gram-negative antibiotic resistance. Recurrent UTI in healthy women is a major problem despite the fact that standard antibiotic treatment typically results in clearance of bacteriuria.

The two relevant niches during acute UTI are tissue and urine. The ability of bacteria to associate within the tissue niche is critical for establishing infection. Extracellular adhesive fibers known as pili are promising targets of anti-virulence therapeutics as they are critical factors for colonizing and invading host tissues and forming biofilms. UPEC use the chaperone/usher pathway to assemble type 1 pili tipped with the FimH adhesin. FimH mediates binding to mannosylated receptors present on the luminal surface of mammalian bladder epithelial cells, which facilitates bacterial invasion into these cells. Subversion of innate expulsion mechanisms requires entry into the cytoplasm where a single UPEC can replicate rapidly into $10^4$-$10^5$ bacteria, which aggregate in a type 1 dependent manner into a biofilm-like intracellular bacterial community (IBC) that protects UPEC from host defenses and antibiotics. Bacteria later disperse from the IBC to spread to neighboring cells. FimH-dependent IBCs and the filaments that emerge from them commonly exist in women with recurrent cystitis as revealed in a clinical study of 100 women as IBC formation is thought to represent a mechanism that allows UPEC to rapidly expand in numbers. Virulence factors that increase the fitness of UPEC in the urinary tract are predicted to be under positive selection and the fimH gene is under positive selection in clinical isolates of UPEC, consistent with its role in human disease. FimH is found in virtually all UPEC, the mannose binding pocket is invariant and mutations which disrupt mannose binding are attenuated. Previous studies support the utility of mannosides, to disrupt FimH function, as an effective therapeutic strategy to treat UTI our refs. The rational X-ray structure based design and synthesis of novel biphenyl mannosides FimH inhibitors were recently described, starting from phenyl mannoside 1 (FIG. 43A). In the following examples, it is shown that lead compound 6 (2ZFH56) and newly developed orally bioavailable mannosides are potent and fast acting antibacterial compounds. It is demonstrated that these mannosides are effective at treating and preventing UTI in mice as well as potentiating the antimicrobial effects of TMP-SMZ.

Example 25

Mannosides Disrupt and Inhibit the Formation of Biofilms

Figure 43D:
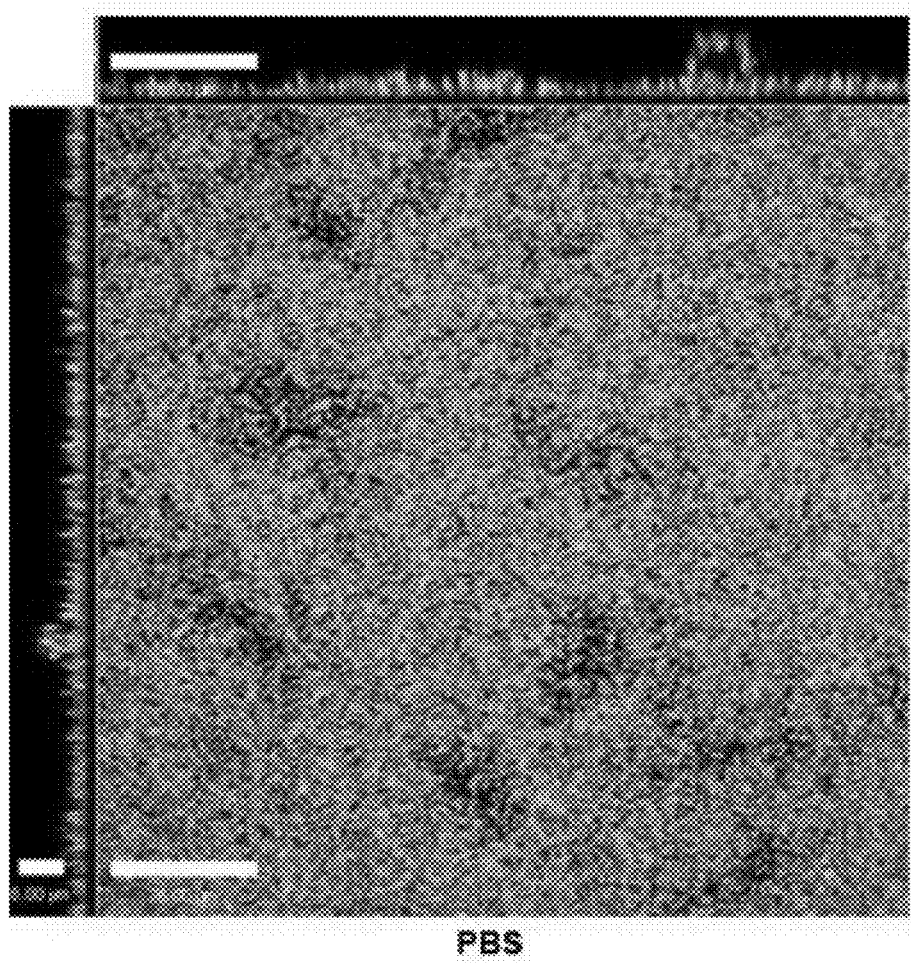
Figure 43E:
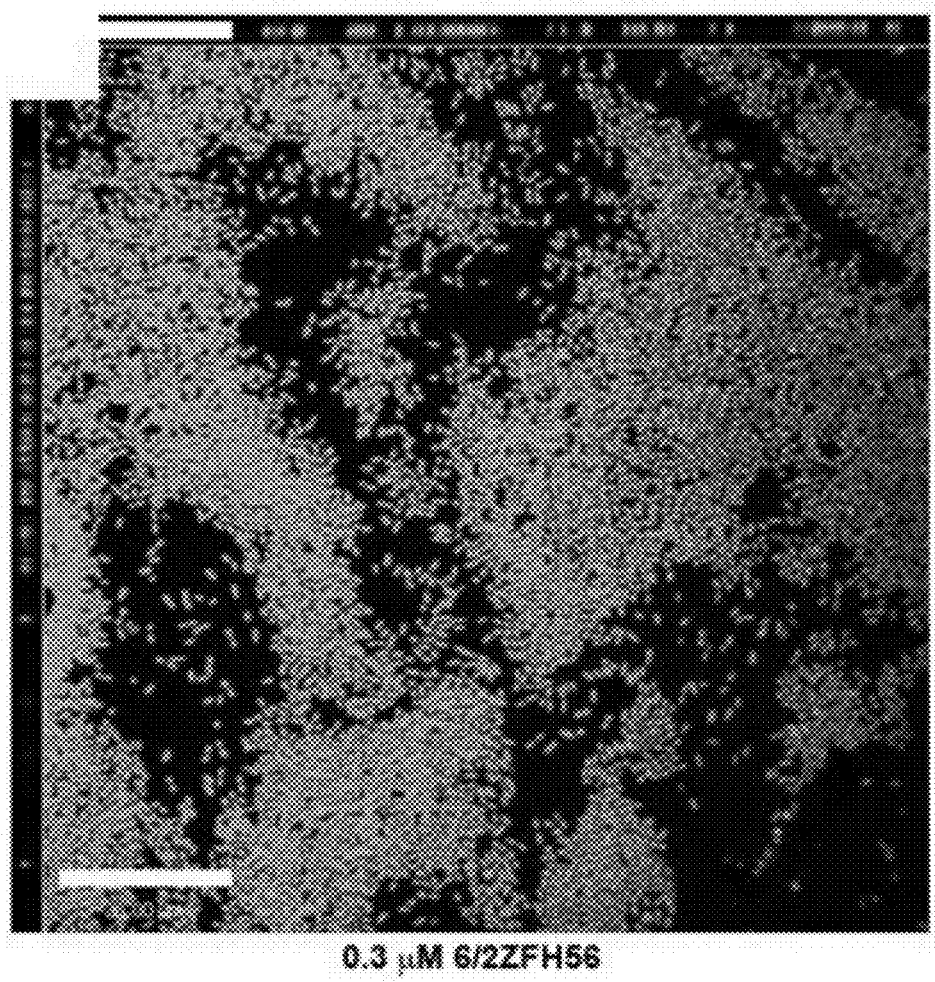

Functional activity of mannoside FimH inhibitors 1-6 (FIG. 43A) was first assessed in vitro using a hemagglutination and UPEC biofilm assays. The relative ability of compounds to block biofilm formation and disrupt preformed biofilms was used to prioritize and select compounds for further in vivo evaluation. Biofilm formation is complex and the multiple determinants that contribute to their development and maintenance may vary depending on growth conditions, medium and substrates. E. coli biofilm formation in LB at room temperature on polyvinyl chloride (PVC) is dependent on type 1 pili and therefore these conditions were used to determine the efficacy of the mannosides. The median inhibitory concentration ($IC_{50}$) values for compounds 1-3 and 6 were all low micromolar but compound 6 showed the best activity with an $IC_{50}$ of 0.74 µM (FIG. 43B). In addition to preventing the formation of biofilms, it was also found that the mannosides inhibited the buildup up of preformed biofilms (FIG. 43C). Confocal microscopy of preformed biofilms treated with mannoside 6 showed effective disruption of a preformed biofilm, likely explaining in part, the activity seen in FIG. 43C. Furthermore, preformed biofilms treated with 6 lacked continuity as seen by gaping holes and lack of the tall mushroom-like structures observed in untreated biofilms (FIG. 43D, E). The propensity of E. coli to form biofilms contributes to antibiotic treatment failures since antibiotics are unable to penetrate the dense biofilm matrix providing compelling evidence that biofilm inhibitors can potentiate the effects of antibiotics.

Example 26

Mannoside is Efficacious at Clearing Severe Infection

From the in vitro studies in Example 25, mannosides 4 and 6 showed similar activity in the hemagglutination inhibition (HAI) assay which is predictive of relative activity in biofilm inhibition. However, the ester group in compound 4 was unstable for oral dosing and it was found that its hydrolysis product 5 was 13-fold less potent. Mannoside 6 which contains an amide in place of the ester, was not only equipotent to 4 but was also more stable plus had increased solubility and thus was selected as our lead compound for initial in vivo evaluation. Pharmacokinetic (PK) studies with lead compound 6 in mice was performed using intraperitoneal (IP) injection and oral (PO) gavage. Following IP dosing, 6 concentrations in the urine were quantified at several time points using HPLC and mass spectrometry (MS). Doses of 5 mg/kg and 10 mg/kg resulted in concentrations of 1 mM in the urine 30 min after treatment (FIG. 44A). Eight hours after administration, 6 levels remained near the $IC_{50}$ (0.74 µM) of biofilm inhibition. The mouse PK of 6 dosed orally was next evaluated at several concentrations up to 200 mg/kg. A 100 mg/kg dose of 6 resulted in 3-fold higher concentrations relative to IP (10 mg/kg) eight hours post-dosing demonstrating some oral bioavailability of 6. It is also noteworthy that >95% of drug was excreted in the urine unchanged and no apparent toxicity was observed up to a 200 mg/kg dose as measured by survival and weight gain/loss.

In order to determine the therapeutic potential of 6 for treating chronic UTIs, a unique preclinical murine model was adopted. In humans, the ultimate outcome of UPEC infection of the urinary tract ranges from asymptomatic bacteriuria to acute self-limiting infection to chronic/recurrent UTI. Similarly, the outcome of UTI in C3H/HeN mice ranges from self-limiting to long-lasting, chronic cystitis characterized by persistent, high titer bacteriuria (>$10^4$ colony forming units (CFU)/ml), high titer bacterial bladder burdens at sacrifice >2 weeks post-infection (wpi), chronic inflammation, and urothelial necrosis. The acute host response, within the first 24 hours, to tissue-associated UPEC has been shown to determine disease outcome including predisposition to chronic/recurrent UTI. Thus, C3H/HeN mice were infected with 1×$10^7$ CFU of UTI89 and mice developing chronic cystitis, as determined by persistent urine titers of >$10^6$ through 2 weeks post infection (wpi), were PO treated at 2 wpi with 6 at a single dose of 100 or 50 mg/kg to evaluate the ability of mannoside to treat UTI. 6 hours post-treatment bacterial counts in the bladder were enumerated. A dramatic 3-log drop in bacterial titers was observed suggesting mannoside is efficacious at clearing severe infection within 6 hours of oral delivery of a chronic long lasting infection (FIG. 44B).

Example 27

Prophylactic Use of Mannoside

Figure 44C:
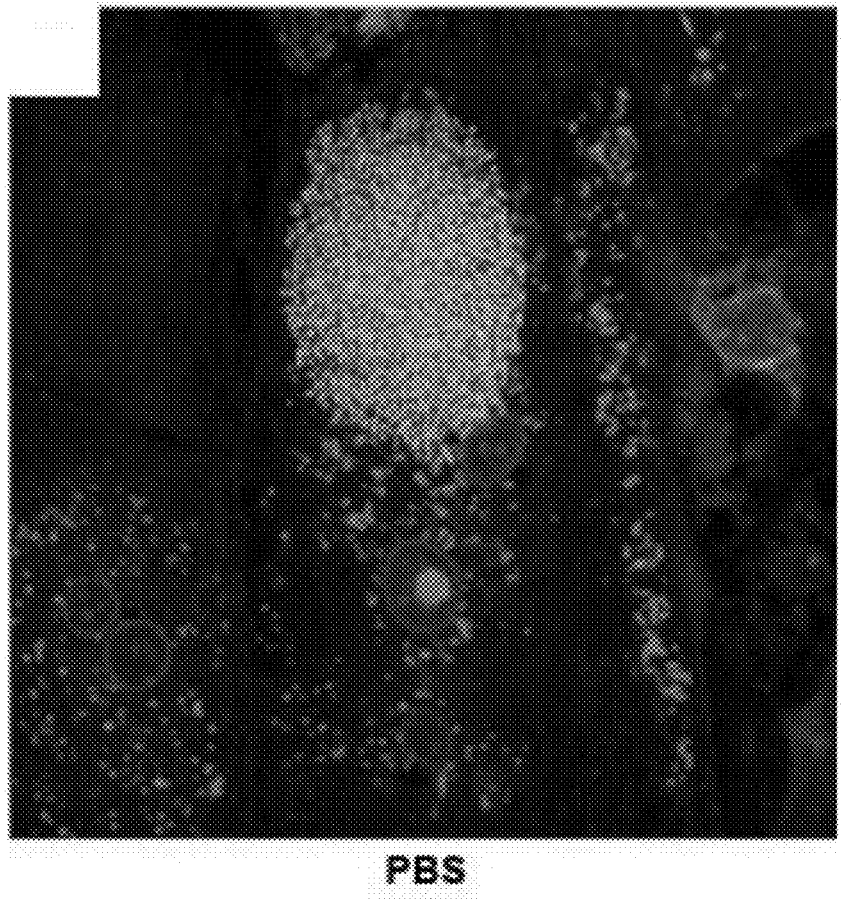
Figure 44D:
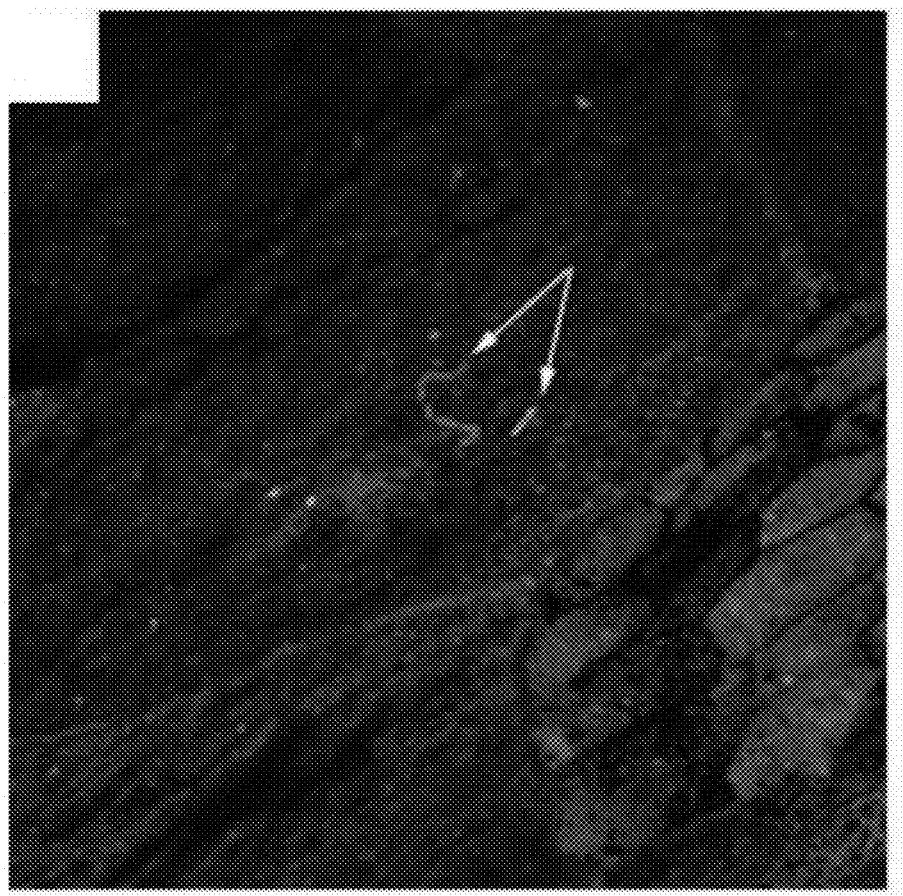
Figure 44:
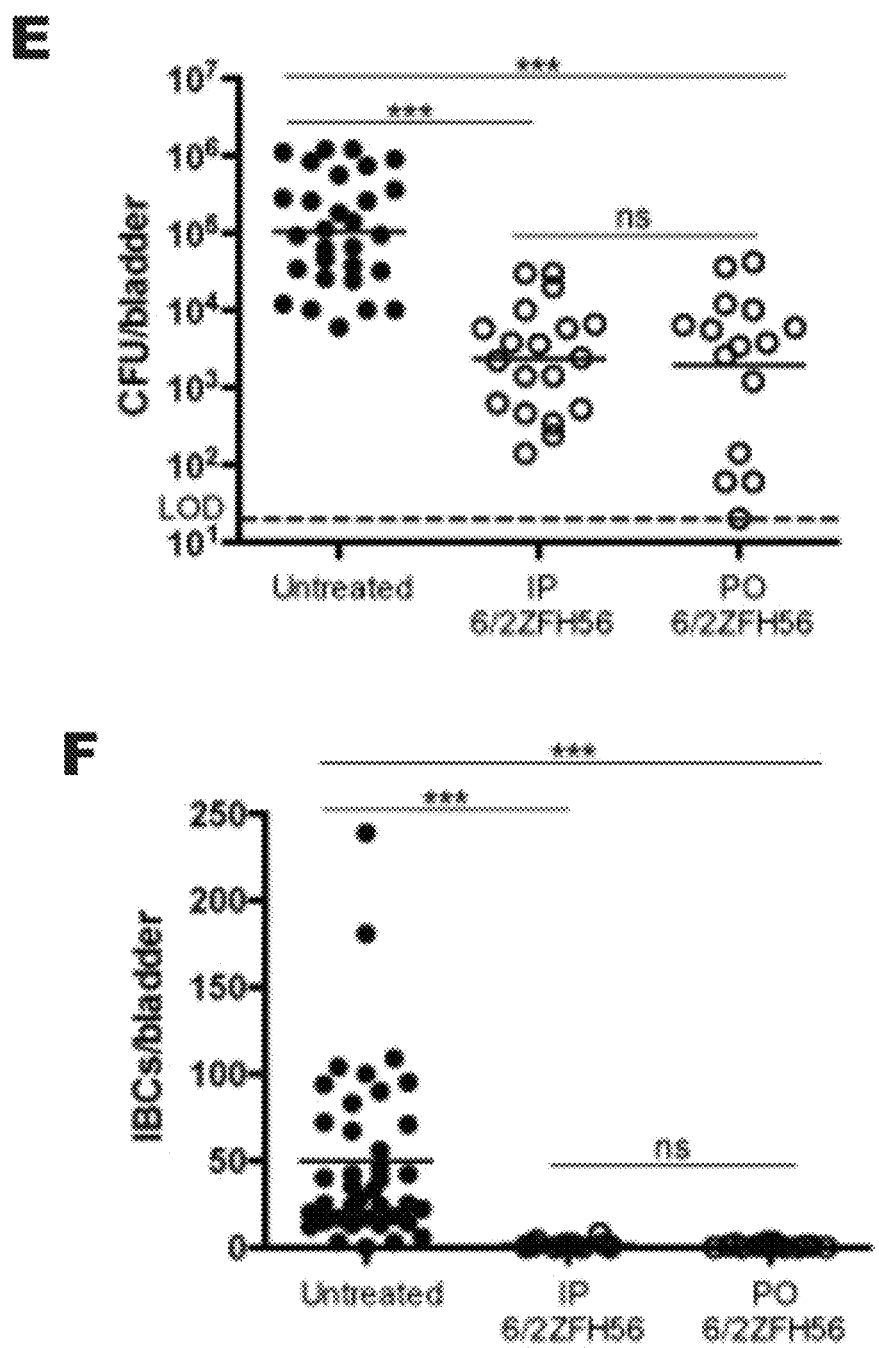
Figure 44G:
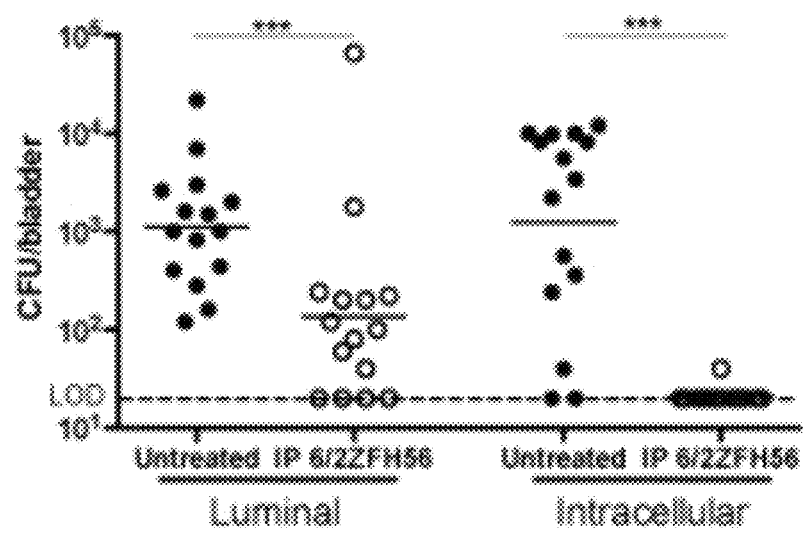

Since 6 successfully treated chronic cystitis, it was of interest to elucidate if mannosides could also prevent a UTI as a prospective prophylactic therapy. To mimic this clinical scenario, the efficacy of 6 in in vivo treatment was evaluated by dosing mice either IP or PO 30 min prior to infecting with UTI89. At 6 hours post infection (hpi), bladders were removed and total bacterial CFUs were quantified. In both the IP and PO treated cohorts a significant drop in bacterial counts was observed, demonstrating the efficacy of 6 in reducing overall UPEC colonization of the bladder (FIG. 44E). Furthermore, there was also a significant reduction of IBCs in the mice that were pretreated with mannoside (FIG. 44F). To demonstrate 6 reduced IBC formation by blocking UPEC invasion into the bladder tissue, gentamicin treatment assays were performed. Gentamicin kills extracellular UPEC but is unable to penetrate tissue and thus intracellular bacteria survive treatment. It was found that in the 6-treated mice, gentamicin treatment of the bladders eliminated all CFUs (FIG. 44G). In bladders from untreated mice, $10^3$-$10^4$ CFUs remained after gentamicin treatment, reflecting the bacteria present that had invaded the bladder epithelium and thus circumvented the treatment. Confocal microscopy of bladders in the untreated cohort showed normal, robust IBC formation (FIG. 44C) whereas IBCs were rarely seen in the mannoside treated mouse bladders however bacteria were observed in the bladder luminal compartment (FIG. 44D). These results demonstrate that a mannoside FimH inhibitor prevents bacterial invasion into the bladder tissue and significantly reduces infection in the bladder. This novel class of orally active biphenyl mannosides has potential utility for the treatment of women suffering from chronic/recurrent UT's as an alternative to prophylactic antibiotic treatment and would significantly benefit women with increased incidence of UTI due to sexual intercourse.

Example 28

Mannosides Inhibit the Invasion of UPEC into the Bladder Tissue and Potentiate the Efficacy of TMP-SMZ The first-line treatment of choice for UTI has traditionally been a 3-day course of TMP-SMZ. Women suffering from chronic/recurrent UTIs are often given TMP-SMZ prophylactically to prevent recurrence. However, resistance to this TMP-SMZ regimen is rapidly expanding. It was hypothesized that by preventing bacterial invasion into the bladder tissue, a FimH inhibitor may result in anti-virulence synergism with TMP-SMZ and may curtail or circumvent the problem of TMP-SMZ resistance. This theory was evaluated in a preclinical animal model where mice given TMP-SMZ for 3 days were infected with either UTI89 or the TMP-SMZR strain, PBC-1. Mice were IP treated with 6 30 min prior to inoculation with bacteria and compared to a control group of untreated animals. After inoculation with UTI89 or PBC-1, bacterial CFUs were quantified at 6 hpi. As expected, treatment with TMP-SMZ alone resulted in a significant drop in bacterial load in the UTI89-infected mice but had no effect on PBC-1, since it is resistant to TMP-SMZ. Upon treatment with 6 alone there was a significant drop in bacterial load of both strains in the bladder. In the dual treatment group there was also a significant drop in bacterial CFUs compared to mannoside alone or TMP-SMZ alone for both strains which was most pronounced for PBC-1 (FIG. 45). It was determined that the presence of mannoside had no effect on growth or killing efficiency of either strain during growth in vitro in the presence or absence of TMPSMZ. Therefore, the observation that in combination with 6, the TMP-SMZR strain PBC-1 succumbed to antibiotic treatment suggested that the mannoside potentiates the efficacy of TMP-SMZ by a unique mechanism. Based on growth curves in TMP-SMZ, PBC-1 was calculated to have a Minimum Inhibition Concentration (MIC) of 256 and 1280 μg/ml for TMP and SMZ, respectively and UTI89 was calculated to have an MIC of 0.05 μg/ml TMP and 0.25 μg/ml SMZ. The presence of mannoside had no effect on growth or killing efficiency of either strain. It is well established that TMP concentrates in the urine and this serendipitous feature is a major reason TMP-SMZ has been the preferred antibiotic for UTI over the last several decades. Using quantitative HPLC-MS, the concentration of TMP-SMZ was measured in the urine of mice after 3 days of treatment with 54 μg/ml and 270 μg/ml TMP and SMZ, respectively. TMP concentrations were determined to be 9.95+/−4.36 mg/ml and SMZ at 67.17+/−32.51 μg/ml. These results indicate that by preventing bacterial invasion, 6 compartmentalizes the microbes to the bladder lumen thus exposing them to TMP-SMZ concentrations above the MIC of PBC-1, resulting in augmentation of bacterial cell killing. Presumably TMP-SMZ concentrations reach tissue concentrations above the MIC needed for UTI89 killing but fail to reach tissue levels needed for killing PBC-1. These results clearly highlight the importance of the intracellular pathway in bacterial persistence. In addition to escaping the immune system in their intracellular niche, bacteria are also able to evade exposure to antibiotics as highlighted by the clinically TMP-SMZ resistant strain. In summary, mannosides could benefit those women on suppressive antibiotic therapy by inhibiting the invasion of UPEC into the bladder tissue and potentiating the efficacy of TMP-SMZ creating a cost-effective treatment, which is predicted to lower the rate of treatment failures.

Example 29

Mannoside Optimization

While 6 shows good efficacy in vivo, it was sought to identify optimized mannosides with further improved pharmacokinetics in particular those encompassing increased cell permeability and thus better oral bioavailability and bladder tissue penetration. The inherent polarity of mannosides and other sugar-derived compounds often limits their cellular permeability and increasing their hydrophobicity (LogP/LogD) is predicted to improve the latter. Computational modeling of mannosides bound to FimH suggested that the ortho-position of the biphenyl ring attached to mannose is aimed at Tyr137 and improved hydrophobic contact could be achieved by substitution. The increased hydrophobicity was not only predicted to improve FimH binding affinity but also the oral bioavailability and bladder tissue penetration relative to starting mannoside 6. Furthermore, these derivatives will likely display increased metabolic stability through protection of the glycosidic bond from hydrolysis both in the gut and by α-mannosidases. Thus, a matched pair analysis was performed of monoamide 3 compared to ortho-substituted analogs bearing methyl, trifluoromethyl, and chloro groups. The compounds were evaluated for their potency in the hemagglutination inhibition (HAI) assay and it was discovered that all biphenyl ring substitutions yielded more potent inhibitors (FIG. 46A). Ortho-chloro mannoside 7 inhibited hemagglutination with a potency of 125 nM which is 10-fold better than matched pair 3 while the ortho-methyl analog 8 was even 2-fold more active (HAI=62 nM). Substitution with trifluoromethyl gave the most potent analog 9 with an HAI=32 nM. This data suggests that our prediction for increased hydrophobic contact with Tyr137 might explain this enhanced potency since the trifluoromethyl analog 9 has the largest hydrophobic surface area and also shows the highest activity. However, it is also possible that the orientation of the phenyl rings are altered slightly and conformationally restricted in a more productive form conducive to improved FimH binding. In any case, the outcome of this preliminary study directed us to develop ortho-trifluoromethyl diamide 10 which is exponentially more potent than any previously reported mannoside FimH inhibitor with an HAI=8 nM. This unprecedented level of potency corresponds to a 15,000-fold improvement over butyl-α-D-mannoside (125 μM) and is 50-fold better than lead 6. Based on their improved in vitro properties, we tested the optimized mannosides for mouse oral PK (FIG. 46B) and found at 50 mg/kg compounds 8 and 10 yielded the highest concentrations in urine at 6 hours post dosing with 8 displaying equivalent concentrations to 100 mg/kg of mannoside 6. Due to their enhanced potency and optimal PK, mannosides 8 and 10 were selected for further testing in our chronic infection mouse model. C3H/HeN mice having chronic cystitis at 2 weeks post infection were treated with 6, 8 or 10. Treatment with 8 and 10 resulted in a significant and dramatic 4 log reduction in bacterial counts in the bladder 6 hours posttreatment (FIG. 4c). Although ortho-trifluoromethyl diamide 10 is 8-fold more potent in vitro than ortho-methyl monoamide 8, it was found that when dosed orally at 50 mg/kg 8 showed better efficacy in vivo. 8 reduced bacterial CFUs in the bladder almost 2 Log units better than 6 at the identical 50 mg/kg dose and was still more efficacious than a 100 mg/kg dose of 6. These results can be explained by increased FimH inhibition combined with improved PK of the ortho-substituted mannosides relative to 6. Mannoside 8 represents a very promising lead preclinical candidate for the oral treatment and prevention of recurrent urinary tract infections.

Discussion for Examples 25-29

The efficacy of anti-virulence compounds in vivo has not been extensively characterized. Herein, the most potent orally active small molecule FimH antagonists described are reported to date. This is also the first demonstration that a mannoside FimH inhibitor shows therapeutic potential for treating an established chronic urinary tract infection in vivo. These innovative compounds also show excellent efficacy in vivo when used prophylactically. Furthermore, the mechanism of action displayed by FimH inhibitors keeps bacteria extracellular and sensitizes a TMP-SMZ resistant strain by prolonging exposure to antibiotic levels above its MIC. This enhanced susceptibility may help overcome the rising problem of TMP-SMZ resistance amongst E. coli. Not only are these anti-virulence FimH antagonists effective as a treatment against UTI, but their oral availability represents a major step toward effective preclinical optimization and drug development. Alternative management strategies are needed for patients suffering from chronic/recurrent UTIs. Prophylactic administration of mannoside alone or in combination with TMP-SMZ could potentially reduce the incidence of treatment failure and shorten the time span of currently administered suppressive therapy. A shift to reduce the use of fluoroquinolones would provide both a more cost-effective treatment option as well as slow the spread of resistance to this class of antibiotics. Given that resistance to antibiotic therapy is rapidly increasing, it is time to reconsider standard UTI therapy in order to preserve the effectiveness of current antibiotics. The use of FimH inhibitors as a targeted therapeutic strategy benefits from the fact that it is not broad spectrum and will specifically target those bacteria expressing type 1 pili, ubiquitous amongst UPEC. Given the unique welldefined clinical population of patients with UTI, of which nearly 85% of the cases are caused by UPEC, the narrow spectrum afforded by mannosides provides an advantage over alternative therapies and other broad spectrum anti-virulence drugs currently in clinical trials. It is predicted that mannosides either dosed alone or in combination with commonly used antibiotics can treat almost all initial and chronic UTIs.

Outside of UTI, cell-cell adherence to host tissues is the first step in most infectious diseases. Thus, due to the commonality of adhesion mechanisms in bacterial and viral pathogenesis, similar but unique anti-virulence compounds can be tailored to treat a multitude of infectious diseases. The results in Examples 25-29 validate the utility of employing a rational approach to study the molecular mechanisms of pathogenesis and resulted in the discovery and development of potential anti-virulence therapeutics, which specifically target mechanisms essential in UPEC pathogenesis. In conclusion, these studies have the potential to revolutionize current approaches to both antimicrobial and anti-viral treatment and provides not only new opportunities for effectively treating a broad range of infectious diseases, but also the potential to curtail the ever expanding medical crisis of pathogen resistance to traditional antibiotics.

Methods for Example 25-29

UTI89 biofilm was grown in LB+/− mannoside for 24 h at 22° C. in PVC plates and quantified using crystal violet. UTI89 biofilm for confocal microscopy was grown in LB for 24 h at 22° C. on PVC coverslips followed by mannoside treatment for 16 h. For all animal experiments UTI89 or PBC-1 was grown 2×24 h statically in LB at 37° C. and inoculated at a dose of 1×10$^7$ bacteria in 50 µl. All mice used were female C3H/HeN (Harlan). For the chronic UTI model, mice were infected for 2 weeks prior to treatment with mannoside. For IP dosing, 50 µl of 2 mg/ml (5 mg/kg) or 4 mg/ml (10 mg/kg) 6 in PBS was injected into the mouse 30 min prior to inoculation of bacteria. For oral dosing, 100 µl of 10 mg/ml (50 mg/kg) or 20 mg/ml (100 mg/kg) mannoside in 8% DMSO was inoculated with a gavage needle 30 min prior to inoculation of bacteria. Mass spectrometry was used to quantify urinary mannoside or TMP-SMZ concentrations. For CFU counts, bladders were harvested at 6 hpi and placed in 1 mL PBS. Bladders were then homogenized, diluted and plated on LB. After growth at 37° C. overnight, bacterial counts were determined. LacZ staining and gentamicin protection assays were performed at 6 hpi. For antibiotic experiments, mice were given TMP-SMZ in the drinking water at a concentration of 54 µg/ml and 270 µg/ml, respectively. Water was changed daily with fresh antibiotics. Standard growth curve and hemagglutination assays were performed. All statistical analysis performed was a two-tailed Mann-Whitney U test. Compounds I-6 were prepared as outlined in Han et. al. (2010; J. Med. Chem. 53:4779). Compounds 7-10 were prepared using slightly modified procedures. All compounds are >95% pure as determined by HPLC/MS and $^1$H NMR.

Bacterial Strains.

UTI89 is a prototypical cystitis isolate of serotype O18:K1:H7. PBC-1 is a TMP-SMZ® strain of serotype OX13:K1:H10 isolated from a 59 year old asymptomatic female with a history of recurrent UTI and diagnosis of primary biliary cirrhosis.

Synthesis of Mannosides

1. General synthesis, purification, and analytical chemistry procedures. Starting materials, reagents, and solvents were purchased from commercial vendors unless otherwise noted. $^1$H NMR spectra were measured on a Varian 300 MHz NMR instrument. The chemical shifts were reported as δ ppm relative to TMS using residual solvent peak as the reference unless otherwise noted. The following abbreviations were used to express the multiplicities: s=singlet; d=doublet; t=triplet; q=quartet; m=multiplet; br=broad. High-performed liquid chromatography (HPLC) was carried out on GILSON GX-281 using Waters C18 5 µM, 4.6*50 mm and Waters Prep C18 5 µM, 19*150 mm reverse phase columns, eluted with a gradient system of 5:95 to 95:5 acetonitrile:water with a buffer consisting of 0.05% TFA. Mass spectra (MS) were performed on HPLC/MSD using electrospray ionization (ESI) for detection. All reactions were monitored by thin layer chromatography (TLC) carried out on Merck silica gel plates (0.25 mm thick, 60F254), visualized by using UV (254 nm) or dyes such as KMnO$_4$, p-Anisaldehyde and CAM. Silica gel chromatography was carried out on a Teledyne ISCO CombiFlash purification system using pre-packed silica gel columns (12 g~330 g sizes). All compounds used for biological assays are greater than 95% purity based on NMR and HPLC by absorbance at 220 nm and 254 nm wavelengths.

2. Experimental Procedure for the Preparation of Mannoside 8

2.1 [(2R,3S,4S,5R,6R)-4,5-diacetoxy-6-(acetoxymethyl)-2-(4-bromo-2-methyl-phenoxy)tetrahydropyran-3-yl]acetate.

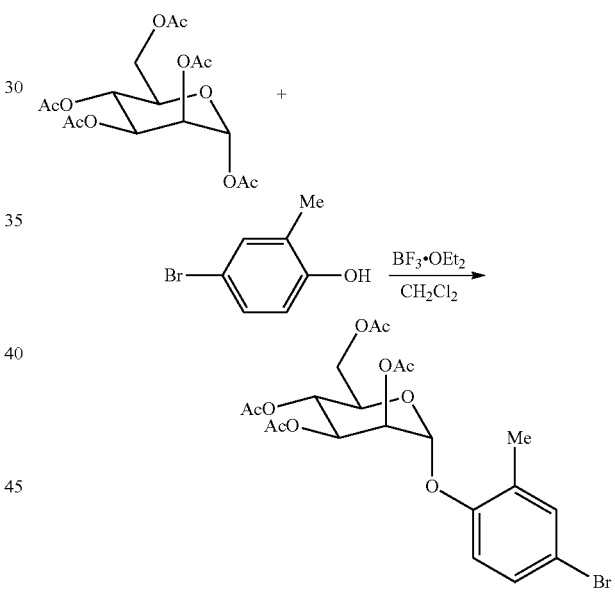

Under nitrogen atmosphere and at room temperature, boron trifluoride diethyl etherate (3.41 g, 24 mmol) was added dropwise into the solution of α-D-mannose pentaacetate (3.12 g, 8 mmol) and 4-bromo-2-methylphenol (2.99 g, 16 mmol) in 100 ml of anhydrous CH$_2$Cl$_2$. After a few mins the mixture was heated to reflux and kept stirring for 45 hrs. The reaction was then quenched with water and extracted with CH$_2$Cl$_2$. The CH$_2$Cl$_2$ layer was collected dried with Na$_2$SO$_4$, concentrated. The resulting residue was purified by silica gel chromatography with hexane/ethyl acetate combinations as eluent, giving the title compound (3.22 g) in 77% yield. $^1$H NMR (300 MHz, CHLOROFORM-d) δ 7.18-7.38 (m, 2H), 6.97 (d, J=8.79 Hz, 1H), 5.50-5.59 (m, 1H), 5.43-5.50 (m, 2H), 5.32-5.42 (m, 1H), 4.28 (dd, J=5.63, 12.50 Hz, 1H), 3.99-4.15 (m, 2H), 2.27 (s, 3H), 2.20 (s, 3H), 2.02-2.11 (three singlets, 9H); MS (ESI): found: [M+Na]+, 539.0.

2.2 N-methyl-3-[3-methyl-4-[(2R,3S,4S,5S,6R)-3,4,5-trihydroxy-6-(hydroxymethyl)tetrahydropyran-2-yl]oxy-phenyl]benzamide (8).

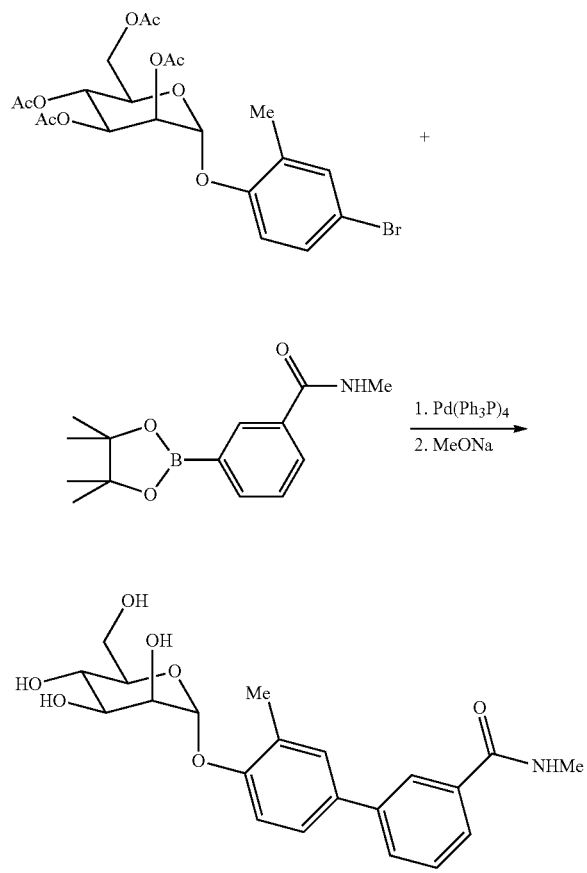

Under nitrogen atmosphere, the mixture of [(2R,3S,4S,5R,6R)-4,5-diacetoxy-6-(acetoxymethyl)-2-(4-bromo-2-methyl-phenoxy)tetrahydropyran-3-yl]acetate (0.517 g, 1 mmol), 3-(N-Methylaminocarbonyl)phenylboronic acid pinacol ester (0.392 g, 1.5 mmol), cesium carbonate (0.977 g, 3 mmol) and tetrakis(triphenylphosphine)palladium (0.116 g, 0.1 mmol) in dioxane/water (15 mL/3 mL) was heated at 80° C. with stirring for 1 h under a nitrogen atmosphere. After cooling to RT, the mixture was filtered through silica gel column to remove the metal catalyst and salts with hexane/ethyl acetate combinations as eluent. The filtrate was concentrated, and then dried in vacuo. The residue was diluted with 15 mL of methanol containing a catalytic amount of sodium methoxide (0.02 M) and the mixture was stirred at RT overnight. H+ exchange resin (DOWEX 50WX4-100) was added to neutralize the mixture. The resin was filtered off and the filtrate was concentrated. The resulting residue was purified by silica gel chromatography with $CH_2Cl_2$/MeOH combinations as eluent, giving the title compound (0.260 g) in 64% yield for two steps. $^1$H NMR (300 MHz, METHANOL-d4) δ 7.94 (t, J=1.65 Hz, 1H), 7.57-7.72 (m, 2H), 7.33-7.50 (m, 3H), 7.23 (d, J=8.52 Hz, 1H), 5.48 (d, J=1.92 Hz, 1H), 4.00 (dd, J=1.79, 3.43 Hz, 1H), 3.83-3.94 (m, 1H), 3.60-3.76 (m, 3H), 3.46-3.58 (m, 1H), 2.87 (s, 3H), 2.24 (s, 3H). MS (ESI): found: [M+H]+, 404.2.

Mannosides 7 and 9 were prepared following a similar procedure to the synthesis of 8.

3. Experimental Procedure for the Preparation of Mannoside 10

3.1 [(2R,3S,4S,5R,6R)-4,5-diacetoxy-6-(acetoxymethyl)-2-(4-bromo-2-trifluoromethylphenoxy) tetrahydropyran-3-yl]acetate.

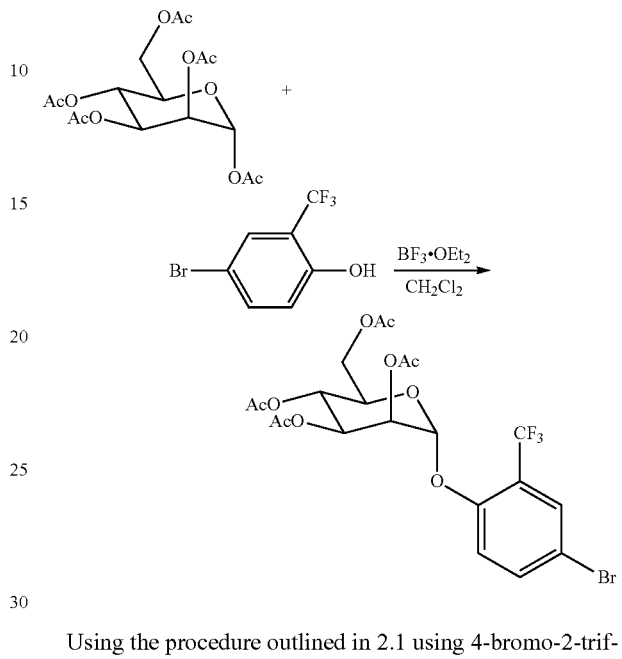

Using the procedure outlined in 2.1 using 4-bromo-2-trifluoromethylphenol, the title compound was obtained (2.5 g) in 54% yield. $^1$H NMR (300 MHz, CHLOROFORM-d) δ 7.75 (d, J=2.20 Hz, 1H), 7.61 (dd, J=2.47, 8.79 Hz, 1H), 7.15 (d, J=8.79 Hz, 1H), 5.61 (d, J=1.65 Hz, 1H), 5.32-5.58 (m, 3H), 4.28 (dd, J=5.22, 12.36 Hz, 1H), 3.95-4.22 (m, 2H), 2.21 (s, 3H), 2.07 (s, 3H), 2.06 (s, 3H), 2.04 (s, 3H); MS (ESI): found: [M+Na]+, 593.0.

3.2 N1,N3-dimethyl-5-(4,4,5,5-tetramethyl-1,3,2-dioxaborolan-2-yl)benzene-1,3-dicarboxamide.

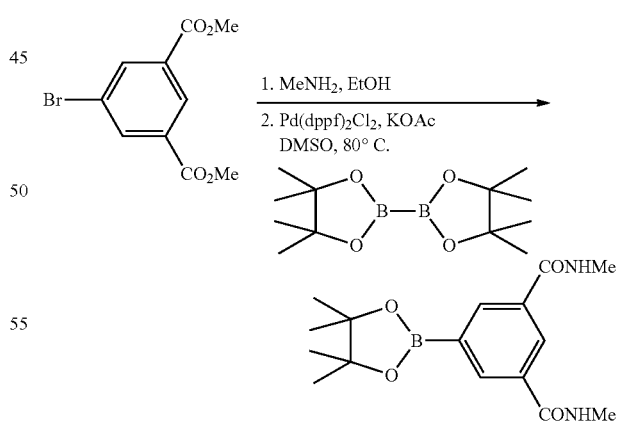

Dimethyl 5-bromobenzene-1,3-dicarboxylate (10.6 g, 36.8 mmol) was dissolved in a 33 wt % solution of methylamine in EtOH (30 mL) and stirred for 6 h at RT. The precipitate that formed during the reaction was filtered to give 5.3 g (53%) of the intermediate 5-bromo-N1,N3-dimethylbenzene-1,3-dicarboxamide as a white solid. Concentration of the remaining filtrate yielded an additional 4.6 g (46%) of product. 5-bromo-N1,N3-dimethyl-benzene-1,3-dicarboxamide (5.3 g, 19.5 mmol), Pd(dppf)$_2$Cl$_2$ (0.87 g, 1.2 mmol), di-pinacolborane (6.1 g, 24 mmol), and potassium acetate (7.8 g, 80 mmol) were dissolved in DMSO (100 mL). The solution was stirred under vacuum and then repressurized with nitrogen. This process was repeated 3 times and then the resultant mixture was stirred at 80° C. for 5 h under a nitrogen atmosphere. After removal of the solvent under high vacuum, the crude material was purified by silica gel chromatography to give the title compound as a light tan solid (2.2 g, 35%). $^1$H NMR (300 MHz, DMSO-d6 δ8.63 (m, 2H), 8.41 (t, J=1.51 Hz, 1H), 8.23 (d, J=1.65 Hz, 2H), 2.80 (s, 3H), 2.78 (s, 3H), 1.33 (s, 12H). MS (ESI): found: [M+H]+, 319.2.

3.3 N1,N3-dimethyl-5-[3-(trifluoromethyl)-4-[(2R,3S,4S,5S,6R)-3,4,5-trihydroxy-6-(hydroxymethyl)tetrahydropyran-2-yl]oxy-phenyl]benzene-1,3-dicarboxamide (10).

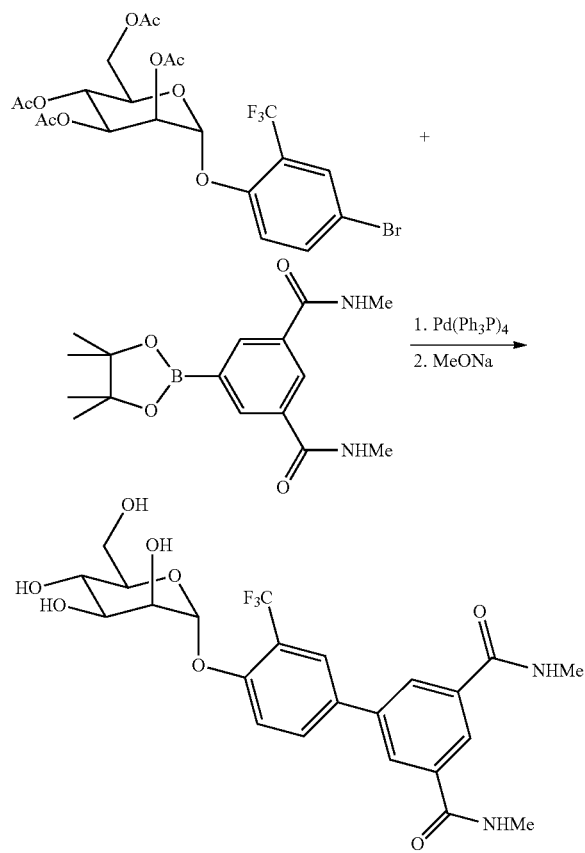

Using the procedure outlined in 2.2 with [(2R,3S,4S,5R,6R)-4,5-diacetoxy-6-(acetoxymethyl)-2-(4-bromo-2-trifluoromethyl-phenoxy)tetrahydropyran-3-yl]acetate (0.57 g) and N1,N3-dimethyl-5-(4,4,5,5-tetramethyl-1,3,2-dioxaborolan-2-yl)benzene-1,3-dicarboxamide (0.48 g), the title compound was obtained (0.340 g) in 69% yield for the two steps. $^1$H NMR (300 MHz, METHANOL-d4) δ 8.17-8.24 (m, 1H), 8.14 (d, J=1.65 Hz, 2H), 7.92 (d, J=1.92 Hz, 1H), 7.87 (dd, J=2.20, 8.79 Hz, 1H), 7.57 (d, J=8.79 Hz, 1H), 5.64 (d, J=1.65 Hz, 1H), 4.04 (dd, J=1.65, 3.30 Hz, 1H), 3.87-3.96 (dd, 1H), 3.64-3.83 (m, 3H), 3.48-3.63 (m, 1H), 2.93 (s, 6H). MS (ESI): found: [M+H]+, 515.1.

Biofilm Assay.

UTI89 was grown in LB broth in wells of PVC microtiter plates at 23° C. in the presence of individual mannosides at varying concentrations. After 48 h of growth, wells were rinsed with water and stained with crystal violet for quantification as described. For biofilm disruption activity in PVC plates, UTI89 was grown in LB broth in wells of PVC microtiter plates at 23° C. After 24 h of growth, mannoside was added and biofilms were grown for an additional 16 h. Wells were then rinsed, stained with crystal violet and quantified. For biofilm disruption activity on PVC coverslips, UTI89 was grown in LB broth in 50 mL conicals containing PBC coverslips at 23° C. After 24 h of growth, 0.3 μM ZFH-2056 was added and biofilm was grown for an additional 16 h. Coverslips were then rinsed, fixed with 2% paraformaldehyde (v/v), stained with SYTO9 (1:1000 in PBS; Molecular Probes) and observed with a Zeiss LSM410 confocal laser scanning microscope under a 63× objective.

Animal Infections.

Bacteria were grown under type 1 pili-inducing conditions (2×24 h at 37° C. statically in LB). The bacteria were harvested and resuspended to an OD$_{600}$ of 0.5 in PBS. Eight-week-old C3H/HeN (Harlan) female mice were anesthetized by inhalation of isoflurane and infected via transurethral catheterization with 50 μl of the bacterial suspension, resulting in 1-2×10$^7$ inoculum. At 6 hpi, mice were sacrificed by cervical dislocation under anesthesia and the bladders were immediately harvested and processed as described below. All animal studies using mice were approved by the Animal Studies Committee of Washington University (Animal Protocol Number 20100002).

Chronic Infection.

Mice were infected with UTI89 and the infection was allowed to continue for 2 weeks. At 12 days post-infection, urine was collected and titered to determine mice chronically infected (urine titers >10$^6$). At 2 wpi, chronically infected mice were treated PO with 50 mg/kg or 100 mg/kg of mannoside. 6 h posttreatment, mice were sacrificed and bladders were aseptically removed and homogenized to determine tissue titers.

Enumeration of Bladder IBCs.

For animal pretreatment experiments, mannoside ZFH-2056 was administered either IP (5 mg/kg) or orally (100 mg/kg) 30 min prior to inoculation with UTI89. To accurately count the number of IBCs, mice were sacrificed 6 hpi and bladders were aseptically removed, bisected, splayed on silicone plates and fixed in 2% paraformaldehyde (v/v). IBCs, readily discernable as punctate violet spots, were quantified by LacZ staining of whole bladders.

Pharamacokinetic Analysis.

For intraperitoneal dosing, 50 μl of a 2 mg/ml (5 mg/kg) or 4 mg/ml (10 mg/kg) solution of 6 in PBS was injected into the peritoneal cavity of the mouse. For oral dosing, 100 μl of a 20 mg/ml (100 mg/kg) solution of ZFH-2056 in 8% DMSO was inoculated with a gavage needle into the mouse stomach. Urine was collected at 30 min, 1, 2, 3, 4, 6, and 8 h post-treatment. An equal volume of 10 μM internal standard (ZFH-2050) was added to the urine. Mannosides were extracted from the urine by loading on C18 columns (100 mg, Waters), washing with 30% methanol, and eluting with 60% methanol. Vacuum-concentrated eluates were analyzed using liquid chromatography-mass spectrometry system with a lower heated capillary temperature of 190° C. and a gradient as follows: Solvent B (80% acetonitrile in 0.1% formic acid) was held constant at 5% for 5 minutes, increased to 44% B by 45 minutes, and then to a 95% B by 65 minutes. SRM mode quantification was performed with collision gas energy of 30% for the following MS/MS transitions (precursor m/z/ product m/z): compound 6, 447/285; compound 3, 390/228. Absolute quantification was achieved by comparison to a calibration curve.

Bladder Tissue Bacterial Titer Determination.

Mannoside ZFH-2056 was administered either IP (5 mg/kg) or orally (100 mg/kg) 30 min prior to inoculation with UTI89. To enumerate the bacteria present, mice were sacrificed at 6 hpi and bladders were aseptically removed and homogenized in 1 ml PBS, serially diluted and plated onto LB agar plates. CFU was enumerated after 16 h of growth at 37° C.

Confocal Microscopy.

Mannoside 6 was administered IP (5 mg/kg) 30 min prior to inoculation with UTI89. To visualize bacterial behavior within the bladder, mice were sacrificed at 6 hpi and bladders were aseptically removed, bisected, splayed on silicone plates revealing the luminal surface and fixed in 2% paraformaldehyde (v/v). The splayed bladders were then incubated for 20 min at room temperature with (i) SYTO9 (1:1000 in PBS; Molecular Probes) to stain bacteria and (ii) Alexa Fluor 594-conjugated wheat germ agglutinin (WGA; 1:1000 in PBS; Molecular Probes) to stain the bladder luminal surface. Bladders were rinsed with PBS, mounted using Prolong Gold antifade reagent (Invitrogen) and examined with a Zeiss LSM510 confocal laser scanning microscope under a 63× objective. SYTO9 and WGA were excited at 488 and 594 nm, respectively.

Gentamicin Protection Assay.

To enumerate bacteria present in the intracellular versus extracellular compartments, bladders were aseptically harvested at 6 hpi. The bladders were then bisected twice and washed three times in 500 µl of PBS each. The wash fractions were pooled, lightly spun at 500 rpm for 5 min to pellet exfoliated bladder cells, serially diluted, and plated onto LB agar to obtain the luminal fraction. The bladders were treated with 100 µg of gentamicin/ml for 90 min at 37° C. After treatment, the bladders were washed twice with PBS to eliminate residual gentamicin, homogenized in 1 ml of PBS, serially diluted, and plated onto LB agar to enumerate the CFUs in the intracellular fraction.

Antibiotic Treatment.

Mice were given TMP-SMZ in the drinking water at a concentration of 54 µg/ml and 270 µg/ml, respectively. Water was changed daily for 3 days prior to inoculation with UTI89. Mice remained on TMP-SMZ during the infection. To determine TMP-SMZ concentration in the urine, urine was collected after 3 days of TMP-SMZ treatment and quantified by LC-MS following addition of sulfisoxazole as an internal standard.

Growth Curve.

An overnight culture of PBC-1 was diluted 1:1000 in LB in the absence or presence of TMP-SMZ and/or mannoside 6. The highest concentration of TMP-SMZ used was 512 µg/ml and 2560 µg/ml, respectively. Two-fold dilutions of TMP-SMZ were performed. Mannoside 6 was added at 100 µM. Growth curves were performed in a 96-well plate at 37° C. with $A_{600}$ readings taken every 30 min for 8 h. Minimum inhibitory concentration (MIC) was calculated as the lowest concentration of antibiotic that prevented growth of the bacterial strain.

Statistical Analysis.

Observed differences in bacterial titers and IBC numbers were analyzed for significance using the nonparametric Mann-Whitney U test (Prizm; GraphPad Software)

Introduction for Examples 30-36

FimH is a mannose-specific bacterial lectin located at the tip of type 1 pili, an adhesive fiber produced by uropathogenic E. coli (UPEC). FimH is known to bind to mannosylated human uroplakins that coat the luminal surface of the bladder and has also been shown to be involved in invasion of human bladder cells and mast cells, triggering apoptosis and exfoliation and inducing elevated levels of cAMP. Furthermore, FimH recognizes N-linked oligosaccharides on beta1 and alpha3 integrins, which are expressed throughout the urothelium. Murine uroplakin is highly homologous to human and FimH has been shown to facilitate bacterial colonization and invasion of the bladder epithelium in murine models. Internalized UPEC are exocytosed in a TLR-4 dependent process; however, bacteria can escape into the host cell cytoplasm, where they are able to subvert expulsion and innate defenses by aggregating into biofilm-like intracellular bacterial communities (IBCs) in a FimH dependent process. Subsequently, UPEC disperse from the IBC, escape into the bladder lumen, and re-initiate the process by binding and invading naive epithelial cells where they are able to establish quiescent intracellular reservoirs that can persist in a dormant state, tolerant to antibiotic therapy and subsequently serve as seeds for recurrent infection. In humans, the severity of UTI was increased and the immunological response was greater in children with infections caused by type 1 piliated UPEC strains and type 1 pilus expression has been shown to be essential for UTI in mouse models. In addition, a recent study concluded that type 1 pili play an important role in human cystitis and it has been reported that type 1 pili fulfill "Molecular Koch's postulates of microbial pathogenesis. In agreement with these findings and in support of a role for FimH in humans, it has been shown that the fimH gene is under positive selection in human clinical isolates of UPEC. Aspects of the UPEC pathogenic cascade extensively characterized in a murine model of infection have been documented in samples from human clinical studies such as filamentation and IBC formation. Targeted inhibitors of FimH adhesion which block both E. coli invasion and biofilm formation thus hold promising therapeutic potential as new antibacterials for the treatment of UTI and the prevention of recurrence. The discovery of simple D-mannose derivatives as inhibitors of bacterial adherence was first reported almost three decades ago but early mannosides showed only weak inhibition of bacterial adhesion. Consequently, the vast majority of research in this area has been focused on multivalent mannosides, which have been pursued in an effort to improve binding avidity to type 1 pili, which can be present in large numbers on a single bacterium (up to hundreds). While substantial progress has been made with this approach, these high molecular weight structures are not suitable for in vivo evaluation or clinical development as oral drugs. The recent X-ray crystal structures of D-mannose, butyl mannoside, and mannotriose bound to FimH have enabled the rational structure-based design of tighter binding alkyl-, phenyl- and biphenyl-mannoside FimH inhibitors. The urgency for developing new orally bioavailable FimH inhibitors as a targeted strategy for the treatment of UTI alternative to broad spectrum antibiotics is reinforced by the rate of recurrence seen in these type of infections as well as increasing clinical resistance of UPEC to first line antibiotic treatments.

Example 30

Tight Binding Ortho-substituted Biphenyl Mannosides

A matched pair analysis was performed of monoester 1 compared to ortho-substituted analogs bearing halogen and small alkyl groups shown in FIG. 47. The compounds were evaluated for their potency in the hemagglutination inhibition (HAI) assay and it was discovered that all biphenyl ring substitutions yielded more potent inhibitors (Table 17). Ortho-Cl mannoside 4b had a HAI Titer $EC_{90}$ of 30 nM which is more than 30-fold better than matched pair 1 while the Me analog 4c was 8-fold more active (HAI Titer $EC_{90}$=120 nM). Substitution with CF3 gave the most potent analog 4d with an HAI Titer $EC_{90}$ of 30 nM whereas the OMe (4e) and F (4a) analogs showed smaller improvements in activity following the trend CF3>Cl=Me>OMe>F. This data suggests that increased hydrophobic contact with the tyrosine gate and Ile52, or with Ile13 at the opposite ridge of the mannose binding pocket could explain this enhanced potency since better activity correlates well with increased hydrophobicity as evidenced by the fact that fluoro analog 4a shows no improvement in activity relative to unsubstituted matched pair 1 and the trifluoromethyl analog 4c which has the largest hydrophobic surface area shows the highest activity. However, it is possible that the orientation of both phenyl rings are altered slightly and are restricted to a conformation more conducive to improved FimH binding with Tyr137, Tyr48, Ile52, Ile13 and/or Arg98 residues.

were also explored with substitution on the meta position, exemplified by ester 6, which retains potency relative to 1 but did not lead to any enhancement. Ortho-CF3 7 and Me 8 diamide matched pairs to original lead compound 3 were next developed which were exponentially more potent than any previously reported mannoside FimH inhibitors with an HAI Titer $EC_{90}$ of 8 nM and 16 nM, respectively. This unprecedented level of cellular activity corresponds to a 200,000-fold improvement over α-D-mannose and a 15,000-fold improvement over an early reported inhibitor butyl-α-D-mannoside (HAI Titer EC90=125 µM) and 50-fold better than previous lead compound 3.

The biofilm inhibition assay was utilized to test these mannosides' ability to prevent bacteria from forming IBCs, a critical pathogenic process in the development of UTIs. As shown in Table 17, the Biofilm Prevention $IC_{50}$s correlate quite well with the potencies determined by the HAI assay. Introduction of an ortho-substituent (e.g. methyl) to the biphenyl mannoside improved the biofilm activity by 8-fold from mannoside 2 ($IC_{50}$=1.35 µM) to mannoside 5b ($IC_{50}$=0.16 µM). This data confirmed the mannoside's func-

TABLE 17

Potency enhancement and PAMPA data from ortho-substitution of biphenyl mannosides.

| Compound | HAI Titer $EC_{>90}$ (µM) | Biofilm Prevention $IC_{50}$ (µM) | MW (g/mol) | PSA | $CLogD_{7.4}$ | PAMPA $LogP_e$ (cm$^2$/sec) |
|---|---|---|---|---|---|---|
| 1 (ester) | 1.00 | 0.94 | 390.4 | 126 | 1.17 | −5.42 |
| 4a (F) | 0.75 | | 408.4 | 126 | 1.00 | |
| 4b (Cl) | 0.03 | 0.26 | 424.8 | 126 | 1.64 | −4.29 |
| 4c (Me) | 0.12 | 0.33 | 404.4 | 126 | 1.82 | |
| 4d (CF$_3$) | 0.03 | 0.17 | 458.4 | 126 | 1.62 | −3.91 |
| 4e (OMe) | 0.19 | 0.89 | 420.4 | 135 | 0.47 | |
| 6 (m-CO$_2$Me) | 1.0 | | 448.4 | 152 | 0.93 | −4.08 |
| 2 (amide) | 0.50 | 1.35 | 389.4 | 128 | 0.28 | |
| 5a (Cl) | 0.12 | 0.52 | 423.8 | 128 | 0.75 | |
| 5b (Me) | 0.06 | 0.16 | 403.4 | 128 | 0.93 | −3.89 |
| 5c (CF$_3$) | 0.03 | 0.13 | 457.4 | 128 | 0.73 | |
| 3 (di-amide) | 0.37 | 0.74 | 446.4 | 158 | 0.71 | −4.51 |
| 7 (CF$_3$) | 0.01 | 0.043 | 514.5 | 158 | 1.15 | −6.27 |
| 8 (Me) | 0.02 | 0.073 | 460.5 | 158 | 1.35 | −8.46 |

Table 17. Potency enhancement and PAMPA data from ortho-substitution of biphenyl mannosides.

| Compound | HAI Titer $EC_{>90}$ (µM) | Biofilm Prevention $IC_{50}$ (µM) | MW (g/mol) | PSA | $CLogD_{7.4}$ | PAMPA $LogP_e$ (cm$^2$/sec) |
|---|---|---|---|---|---|---|
| 1 (ester) | 1.00 | 0.94 | 390.4 | 126 | 1.17 | −5.42 |
| 4a (F) | 0.75 | | 408.4 | 126 | 1.00 | |
| 4b (Cl) | 0.03 | 0.26 | 424.8 | 126 | 1.64 | −4.29 |
| 4c (Me) | 0.12 | 0.33 | 404.4 | 126 | 1.82 | |
| 4d (CF$_3$) | 0.03 | 0.17 | 458.4 | 126 | 1.62 | −3.91 |
| 4e (OMe) | 0.19 | 0.89 | 420.4 | 135 | 0.47 | |
| 6 (m-CO$_2$Me) | 1.0 | | 448.4 | 152 | 0.93 | −4.08 |
| 2 (amide) | 0.50 | 1.35 | 389.4 | 128 | 0.28 | |
| 5a (Cl) | 0.12 | 0.52 | 423.8 | 128 | 0.75 | |
| 5b (Me) | 0.06 | 0.16 | 403.4 | 128 | 0.93 | −3.89 |
| 5c (CF$_3$) | 0.03 | 0.13 | 457.4 | 128 | 0.73 | |
| 3 (di-amide) | 0.37 | 0.74 | 446.4 | 158 | 0.71 | −4.51 |
| 7 (CF$_3$) | 0.01 | 0.043 | 514.5 | 158 | 1.15 | −6.27 |
| 8 (Me) | 0.02 | 0.073 | 460.5 | 158 | 1.35 | −8.46 |

The outcome of this preliminary study directed the investigation of analogs which were more metabolically stable and soluble than esters such as amides 5a-c (FIG. 47 and Table 17). A similar trend was observed (CF3>Me>Cl) with CF3 amide 5c having the best activity but in this case the Me analog 5b showed better activity than Cl analog 5a. Analogs tional effect and activity on UPEC derived from FimH inhibition with a secondary assay. Biofilm $IC_{50}$s were utilized in conjunction with pharmacokinetic parameters as a key measure of the predicted lowest effective mannoside concentration in the urine required for efficacy in vivo to be discussed vide infra.

Mannosides were synthesized by traditional Lewis acid mediated glycosylation of mannose penta-acetate by reaction with 2-substituted 4-bromophenols using BF3 etherate (Scheme 1). Suzuki cross-coupling with commercially available 3-substituted phenyl boronic acid derivatives gave protected ortho-substituted 4'-biphenyl mannosides in excellent yields and subsequent deprotection with NaOMe gave mannosides 4-5. 6 was prepared following the procedure previously described. Synthesis of di-amides 7-8 followed a similar procedure but required the synthesis of 3,5-di-(N-methyl aminocarbonyl)phenyl boronic acid pinacol ester 9. Shown in Scheme 1, amidation of dimethyl 5-bromoisophthalate by reaction of methylamine in ethanol proceeded in quantitative yield to give N,N-dimethyl 5-bromoisophthalamide. Installation of the boronate ester was accomplished by Pd-mediated coupling with bis(pinacolato)diboron to give 9. Suzuki coupling and deprotection as before yielded compounds 7-8.

Scheme 1$^a$. Synthesis of ortho-substituted biphenyl mannosides

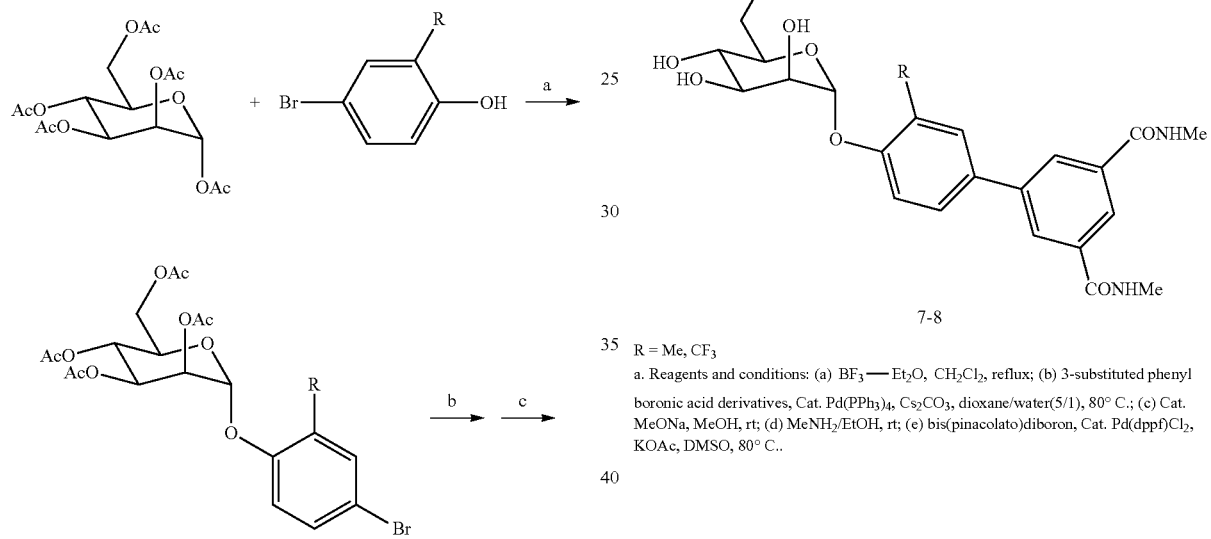

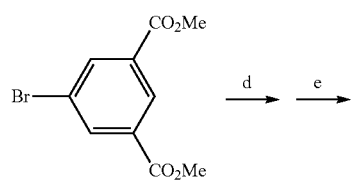

X = O, NH
R = F, Cl, Me, CF$_3$, OMe

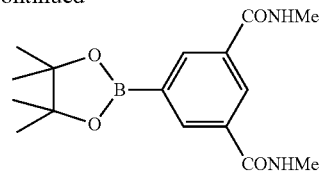

9

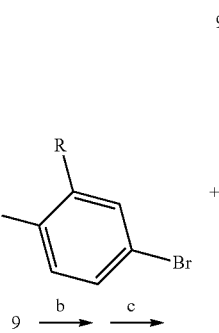

7-8

R = Me, CF$_3$ a. Reagents and conditions: (a) BF$_3$—Et$_2$O, CH$_2$Cl$_2$, reflux; (b) 3-substituted phenyl boronic acid derivatives, Cat. Pd(PPh$_3$)$_4$, Cs$_2$CO$_3$, dioxane/water(5/1), 80° C.; (c) Cat. MeONa, MeOH, rt; (d) MeNH$_2$/EtOH, rt; (e) bis(pinacolato)diboron, Cat. Pd(dppf)Cl$_2$, KOAc, DMSO, 80° C..

Example 31

Mannosides with Increased pKa Functionality

To help improve tissue penetration and exposure of mannosides in the bladder, amide derivatives were explored containing functional groups with higher pKa (Table 18). Higher pKa compounds containing basic moieties such as amines tend to have increased tissue penetration. Therefore, mannosides 10a-f were prepared via standard HATU-mediated coupling reaction of 4'-(α-D-mannopyranosyloxy)biphenyl-3-carboxylic acid with various amines. Unexpectedly, aminoethyl amide 10b showed a disappointing 6-fold drop in activity relative to methyl amide 2. However, hydroxyethyl amide 10a was equipotent to 2. It was also found that more hydrophobic tertiary amide piperazine analogs 10c and 10d had largely decreased potency (HAI EC$_{90}$=4 μM). Interestingly, pyridyl amides 10e and 10f showed slightly improved activity most pronounced with 4-pyridyl derivative 10e. While it is unclear to the reason for decreased potency of higher pKa substituents it is plausible that this effect could originate from charge-charge repulsion with Arg98 side chain at the edge of FimH binding pocket.

TABLE 18
Exploration of amide substitution with increased pKa
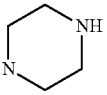
| Compound | R | HAI Titer EC$_{>90}$ (μM) |
|---|---|---|
| 10a | HN-CH$_2$CH$_2$-OH | 0.50 |
| 10b | HN-CH$_2$CH$_2$-NH$_2$ | 3.0 |
| 10c | piperazine (NH) | 4.0 |
| 10d | N-methylpiperazine | 4.0 |
| 10e | HN-(4-pyridyl) | 0.25 |
| 10f | HN-(3-pyridyl -continued

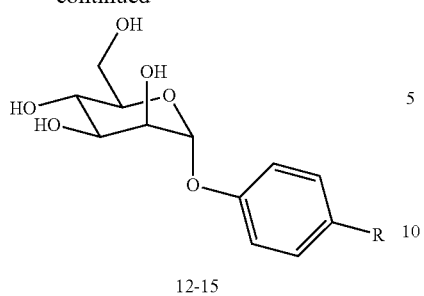

12-15

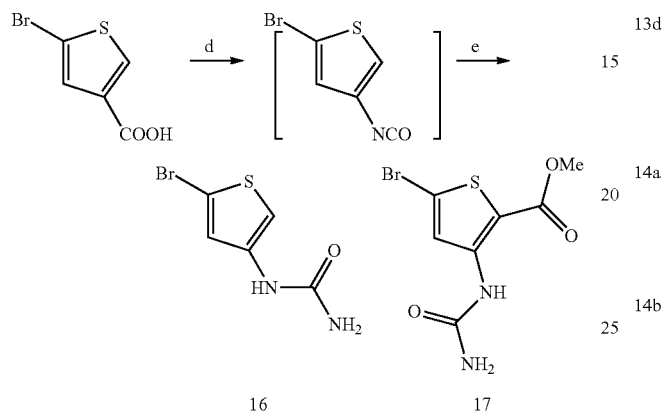

a. Reagents and conditions: (a) bis(pinacolato)diboron, Cat. Pd(dppf)Cl$_2$, KOAc, DMSO, 80° C.; (b) heteroaryl bromide derivatives, Cat. Pd(PPh$_3$)$_4$, Cs$_2$CO$_3$, dioxane/water(5/1), 80° C.; (c) Cat. MeONa, MeOH, rt; (d) DPPA, $^i$PR$_2$NEt, dioxane, 85° C.; (e) NH$_3$/dioxane (0.5M), rt..

TABLE 19

Heterocyclic modifications to biphenyl ring for improving drug-like properties

| Compound | R | HAI Titer EC$_{>90}$ (μM) |
|---|---|---|
| 12a | 4-methyl-pyridine-2-CO$_2$Me | 0.50 |
| 12b | 5-methyl-pyridine-3-CO$_2$Me | 0.19 |
| 13a | methyl-thiophene with OMe ester and NHC(O)NH$_2$ | 0.02 |
| 13b | 5-methyl-thiophene-2-CO$_2$Me | 1.0 |

TABLE 19-continued

Heterocyclic modifications to biphenyl ring for improving drug-like properties

| Compound | R | HAI Titer EC$_{>90}$ (μM) |
|---|---|---|
| 13c | 5-methyl-thiophene-3-NHC(O)NH$_2$ | 1.0 |
| 13d | 5-methyl-thiophene-3-CO$_2$Me | 2.0 |
| 14a | 7-methyl-isoquinoline | 0.75 |
| 14b | 6-methyl-quinazoline | 0.38 |
| 15a | 5-methyl-isoquinoline | 0.25 |
| 15b | 7-methyl-isoquinolin-1(2H)-one | 0.10 |

Example 33

Direct Binding of FimH-Mannoside

In order to better understand how the excellent potency in cell-based HAI and biofilm assays is correlated with FimH binding by biaryl mannosides and to more precisely select the best lead compounds for in vivo pharmacokinetic (PK) studies, a biolayer interferometry method was developed to directly measure the binding affinities (K$_d$) of FimH inhibitors. As shown in Table 20, earlier mannosides 19~33 showing moderate potency in the HAI assay had K$_d$ values as low as 1~10 nM. Strikingly, for compounds 1 and 2, K$_d$ values were in the picomolar range. For mannosides 5, 7, and 8, however, K$_d$ could not be calculated because the off-rates were too low to measure. In order to overcome this obstacle, differential scanning fluorimetry (DSF) was utilized to rank the high-affinity mannosides. DSF measures the melting temperature change of protein when binding to small molecules. Melting temperature shifts are proportional to the free energy of binding, and melting temperatures increase even as ligand concentration exceeds the K$_d$. As illustrated in Table 20 and FIG. 48, the melting temperature of FimH without mannoside was about 60° C. and rose to between 68° C. and 74° C. when binding to mannosides 19-33 of moderate potency. With tight binding mannosides 5b, 7, 8 the melting temperature of FimH ranged from 74° C. to 76° C., suggesting that improved mannosides likely bind FimH with low picomolar affinity. FIG. 48 illustrates that DSF ranks mannosides in a similar fashion to the HAI assay except for 5c and 25, demonstrating that this is a general and reliable method to qualitatively rank FimH-mannoside binding when $K_d$s span many orders of magnitude. Thus, these direct FimH binding studies solidified that the high potencies stemming from mannosides 5b, 7, 8 derives directly from extremely tight binding to the FimH lectin and not other non-specific effects from the cell assays.

TABLE 20

Results of Octet assay and DSF assay

Structure of

[mannoside core structure with R group]

| Compound | R | HAI Titer EC$_{>90}$ (µM) | Octet K$_d$ (nM) | DSF Melting Temp. (° C.) |
|---|---|---|---|---|
| 7 | [biphenyl bis-NHMe amide with F$_3$C and Me substituents] | 0.008 | N.D.* | 76.15 |
| 8 | [biphenyl bis-NHMe amide with two Me substituents] | 0.016 | N.D.* | 75.76 |
| 5c | [biphenyl mono-NHMe amide with F$_3$C and Me substituents] | 0.032 | N.D.* | 72.29 |
| 5b | [biphenyl mono-NHMe amide with two Me substituents] | 0.060 | N.D.* | 74.46 |

TABLE 20-continued

Results of Octet assay and DSF assay

Structure of

[Structure showing sugar moiety with OH groups and O-R substituent]

| Compound | R | HAI Titer EC$_{>90}$ (µM) | Octet K$_d$ (nM) | DSF Melting Temp. (°C.) |
|---|---|---|---|---|
| 18 | [biphenyl with two -C(O)OMe groups] | 0.150 | N.D.* | 72.53 |
| 10f | [biphenyl with -C(O)NH-pyridin-3-yl] | 0.375 | N.D.* | 72.53 |
| 3 | [biphenyl with two -C(O)NHMe groups] | 0.375 | 0.14 | 74.39 |
| 12a | [phenyl-pyridine with -C(O)OMe] | 0.500 | N.D.* | 73.68 |
| 2 | [biphenyl with -C(O)NHMe] | 0.500 | 0.10 | 73.38 |
| 19 | [biphenyl with -S(O)$_2$NHMe] | 1.000 | 0.49 | 72.05 |

TABLE 20-continued

Results of Octet assay and DSF assay

Structure of

| Compound | R | HAI Titer EC$_{>90}$ (µM) | Octet K$_d$ (nM) | DSF Melting Temp. (° C.) |
| --- | --- | --- | --- | --- |
| 1 | 3-(methoxycarbonyl)-4'-methylbiphenyl | 1.000 | 0.08 | 73.39 |
| 20 | 3'-methoxy-4-methylbiphenyl | 1.500 | 1.25 | 71.77 |
| 21 | 2'-methoxy-4-methylbiphenyl | 2.000 | N.D.* | 70.72 |
| 22 | 4'-methyl-[1,1'-biphenyl]-3,5-dicarboxylic acid | 2.000 | 14.5 | 72.39 |
| 23 | dimethyl 5-methylisophthalate | 2.000 | 3.45 | 73.25 |
| 24 | N-(4'-methyl-[1,1'-biphenyl]-3-yl)methanesulfonamide | 2.000 | 2.00 | 70.90 |
| 25 | 4-methyl-3'-(trifluoromethyl)biphenyl | 2.000 | 1.56 | 68.32 |

TABLE 20-continued

Results of Octet assay and DSF assay

Structure of

[mannose core structure with O-R substituent]

| Compound | R | HAI Titer EC$_{>90}$ (μM) | Octet K$_d$ (nM) | DSF Melting Temp. (°C.) |
|---|---|---|---|---|
| 26 | [4'-methyl-biphenyl-3-yl-NHC(O)Me] | 2.000 | 1.14 | 72.30 |
| 27 | [4'-methyl-biphenyl-3-yl-C(O)NH$_2$] | 2.000 | 1.00 | 71.69 |
| 28 | [4'-methyl-biphenyl-3-yl-CH$_2$OH] | 3.000 | 2.61 | 71.16 |
| 29 | [4'-methyl-biphenyl-4-yl-C(O)OMe] | 4.000 | 3.99 | 68.69 |
| 30 | [4'-methyl-biphenyl-3-yl-C(O)OH] | 4.000 | 2.21 | 70.93 |
| 31 | [6-methyl-naphth-2-yl] | 6.000 | 2.72 | 70.75 |
| 32 | [3-methyl-phenyl-C(O)OMe] | 6.000 | 2.72 | 70.75 |
| 33 | [4'-methyl-biphenyl] | 8.000 | 3.00 | 71.17 |
| Phenyl-α-D-mannoside | [methylphenyl] | 30.000 | N.D.* | 68.93 |

TABLE 20-continued

Results of Octet assay and DSF assay

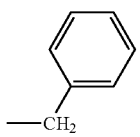

Structure of

| Compound | R | HAI Titer EC$_{>90}$ (µM) | Octet K$_d$ (nM) | DSF Melting Temp. (° C.) |
|---|---|---|---|---|
| 34 | —CH$_2$—C$_6$H$_5$ | 60.000 | 43.66 | 68.11 |

*N.D. = not determined

An electrostatic surface was generated with the most potent mannoside 7 docked to FimH shown in FIG. 49. The large boost in binding affinity to FimH can be attributed to the fact that in the model the ortho trifluoromethyl group orients directly at Ile13 resulting in a very strong hydrophobic interaction with FimH. The added hydrophobicity encompassed by the fluorine atoms in mannoside 7 results in further augmented binding to FimH relative to ortho methyl mannoside 8.

Example 34

Stability and Elimination Kinetics of Mannoside

Mannoside 3 shows efficacy in vivo in the treatment and prevention of established UT's in mice when dosed orally but the compound displayed some metabolic instability from hydrolysis of the glycosidic bond (FIG. 50A) and very rapid elimination kinetics to the urine partly due to its low CLogD value. While renal clearance is an attractive feature for UTI therapy, improved mannosides were desirable encompassing lower clearance rates as well as increased oral bioavailability and bladder tissue permeability. In order to have a general idea of the elimination rate of mannoside 3, pharmacokinetic (PK) studies of its urinary clearance were conducted in mice (FIG. 50B). These experiments demonstrated that the lower oral dosing of 20 mg/kg was unlikely to maintain effective concentrations (as determined by Biofilm IC$_{50}$) due to rapid clearance. Maintenance of mannoside 3 levels above the minimal effective level of 0.74 µM during in an eight-hour period required a larger, 100 mg/kg dose. During the PK study, a small amount of a phenolic biphenyl metabolite (R) (FIG. 50A) was detected in the urine indicating some glycoside bond hydrolysis takes place upon oral dosing. Urine levels of the R group were unchanged from the 100 and 200 mg/kg doses, suggesting that metabolism by glycoside bond hydrolysis is saturated between the 20 and 100 mg/kg doses (FIG. 50B).

Example 35

Parallel Artificial Membrane Permeability Assay (PAMPA)

The low LogD of polyhydroxylated sugar-based mannosides and other carbohydrate-derived compounds can limit their ability to cross cell membranes in the absence of active transport mechanisms and so increasing their hydrophobicity is one strategy to help improve cell permeability and oral bioavailability of this class of molecules. The ortho-substituted mannosides described above were designed for increased hydrophobic contact with FimH but also in part to increase the LogD and were predicted to improve the solubility, oral bioavailability and bladder tissue penetration relative to starting mannosides 1-3. It was anticipated that the newly designed inhibitors would also have increased metabolic stability via protection of the glycosidic bond from acidic hydrolysis in the gut and enzymatic hydrolysis by α-mannosidases in blood and tissues. In order to test these hypotheses experimentally, the Parallel Artificial Membrane Permeability Assay (PAMPA) was used. PAMPA is commonly used as an in vitro model of passive, transcellular permeability to predict oral bioavailability for drug candidates. The most potent biphenyl mannosides was tested in this model for prioritizing compounds to evaluate further in animal PK and efficacy studies. Shown in Table 20, Compound 5b with LogP$_e$ of −3.89 cm$^2$/sec proved to have the highest oral absorption, while the most potent mannosides (determined by HAI assay) 7 and 8 with LogP$_e$ of −6.27 and −8.46 cm$^2$/sec exhibited significantly lower oral bioavailability.

Example 36

Pharmacokinetic Studies for Selected Mannoside Inhibitors

Based on these results, oral PK studies were performed in mice to assess any improvements in the PK of these ortho-substituted mannosides. Compounds were dosed at 50 mg/kg and plasma and urine samples were taken at 30 min and 1, 2, 3, 4, 6 hours after dosing. As demonstrated in FIG. 51, a generally 10-fold higher mannoside concentration was observed in urine (FIG. 51B) compared to plasma (FIG. 51A), indicating a high clearance rate for these mannosides, which in this case aids in clearing uropathogens on the bladder surface. It was found that compounds 8 and 5b consistently maintain a high level of concentration in both urine and plasma, which is well above the predicted minimum effective concentration within a 6-hour period. While 100 mg/kg dosing of mannoside 3 was required to achieve effective mannoside concentrations, only 50 mg/kg dosing of mannoside 5b was required, permitting a much larger therapeutic window for treatment. Taken together with PAMPA results, high oral bioavailability and in vivo efficacy in recently reported animal studies support mannoside 5b as the most promising therapeutic candidate for UTI treatment/prevention.

Conclusions for Examples 30-36

Using a combination of traditional ligand-based and X-ray structure-guided approaches with structure-activity relationship (SAR) driven by cell-based hemagglutination and biofilm assays in combination with direct FimH binding assays, a diverse array of biaryl mannoside FimH inhibitors that exhibit affinities into the picomolar range were identified. While it was found the most potent mannoside 7 with respect to FimH binding affinity and activity in cell assays contains an ortho-trifluoromethyl group off the phenyl ring adjacent to the mannose ring group, the most promising inhibitor from in vivo studies is the ortho-methyl analog 8 showing prolonged compound exposure in plasma and urine PK studies. A variety of heterocyclic biaryl mannosides that either retain or improve FimH binding activity were also discovered. The novel inhibitors of UPEC type 1 mediated bacterial adhesion reported herein show unprecedented activity in hemagglutination and biofilm in vitro assays in addition to desirable pharmacokinetic properties in vivo. Further optimization of lead mannosides is currently being focused on the identification of mannose modifications with reduced sugar-like character. Biaryl mannosides have high potential as innovative therapeutics for the clinical treatment and prevention of urinary tract infections. The unique mechanism of action of targeting the pilus tip adhesin, FimH, circumvents the conventional requirement for drug penetration of the outer membrane and the potential for development of resistance by porin mutations, efflux or degradative enzymes, all mechanisms that promote resistance to antibiotics. Current efforts are directed at the selection of one or more clinical candidate drugs through rigorous preclinical evaluation in several models of recurrent UTI with antibiotic resistant forms of UPEC. These preclinical models will facilitate further optimization of current lead compounds.

Experimental Section for Examples 30-36

General Synthesis, Purification, and Analytical Chemistry Procedures

Starting materials, reagents, and solvents were purchased from commercial vendors unless otherwise noted. $^1$H NMR spectra were measured on a Varian 300 MHz NMR instrument. The chemical shifts were reported as δ ppm relative to TMS using residual solvent peak as the reference unless otherwise noted. The following abbreviations were used to express the multiplicities: s=singlet; d=doublet; t=triplet; q=quartet; m=multiplet; br=broad. High-performed liquid chromatography (HPLC) was carried out on GILSON GX-281 using Waters C18 5 μM, 4.6*50 mm and Waters Prep C18 5 μM, 19*150 mm reverse phase columns, eluted with a gradient system of 5:95 to 95:5 acetonitrile:water with a buffer consisting of 0.05% TFA. Mass spectra (MS) were performed on HPLC/MSD using electrospray ionization (ESI) for detection. All reactions were monitored by thin layer chromatography (TLC) carried out on Merck silica gel plates (0.25 mm thick, 60F254), visualized by using UV (254 nm) or dyes such as $KMnO_4$, p-Anisaldehyde and CAM. Silica gel chromatography was carried out on a Teledyne ISCO CombiFlash purification system using pre-packed silica gel columns (12 g~330 g sizes). All compounds used for biological assays are greater than 95% purity based on NMR and HPLC by absorbance at 220 nm and 254 nm wavelengths.

Procedures for the Preparation of Biphenyl Mannoside Derivatives through Suzuki Coupling Reaction with Bromophenyl Mannoside Derivatives as Intermediate N-methyl-3-[3-methyl-4-[(2R,3S,4S,5S,6R)-3,4,5-trihydroxy-6-(hydroxymethyl)tetrahydropyran-2-yl]oxy-phenyl]benzamide (5b). [(2R,3S,4S,5R,6R)-4,5-diacetoxy-6-(acetoxymethyl)-2-(4-bromo-2-methyl-phenoxy)tetrahydropyran-3-yl]acetate. Under nitrogen atmosphere and at room temperature, boron trifluoride diethyl etherate (3.41 g, 24 mmol) was added dropwise into the solution of α-D-mannose pentaacetate (3.12 g, 8 mmol) and 4-bromo-2-methylphenol (2.99 g, 16 mmol) in 100 ml of anhydrous $CH_2Cl_2$. After a few mins the mixture was heated to reflux and kept stirring for 45 hrs. The reaction was then quenched with water and extracted with $CH_2Cl_2$. The $CH_2Cl_2$ layer was collected dried with $Na_2SO_4$, concentrated. The resulting residue was purified by silica gel chromatography with hexane/ethyl acetate combinations as eluent, giving [(2R,3S,4S,5R,6R)-4,5-diacetoxy-6-(acetoxymethyl)-2-(4-bromo-2-methyl-phenoxy)tetrahydropyran-3-yl]acetate (3.22 g) in 77% yield. $^1$H NMR (300 MHz, CHLOROFORM-d) δ ppm 7.18-7.38 (m, 2H), 6.97 (d, J=8.79 Hz, 1H), 5.50-5.59 (m, 1H), 5.43-5.50 (m, 2H), 5.32-5.42 (m, 1H), 4.28 (dd, J=5.63, 12.50 Hz, 1H), 3.99-4.15 (m, 2H), 2.27 (s, 3H), 2.20 (s, 3H), 2.02-2.11 (three singlets, 9H). MS (ESI): found: [M+Na]$^+$, 539.0.

N-methyl-3-[3-methyl-4-[(2R,3S,4S,5S,6R)-3,4,5-trihydroxy-6-(hydroxymethyl)tetrahydropyran-2-yl]oxy-phenyl]benzamide (5b). Under nitrogen atmosphere, the mixture of [(2R,3S,4S,5R,6R)-4,5-diacetoxy-6-(acetoxymethyl)-2-(4-bromo-2-methyl-phenoxy)tetrahydropyran-3-yl]acetate (0.517 g, 1 mmol), 3-(N-methylaminocarbonyl)phenylboronic acid pinacol ester (0.392 g, 1.5 mmol), cesium carbonate (0.977 g, 3 mmol) and tetrakis(triphenylphosphine)palladium (0.116 g, 0.1 mmol) in dioxane/water (15 mL/3 mL) was heated at 80° C. with stirring for 1 h under a nitrogen atmosphere. After cooling to RT, the mixture was filtered through silica gel column to remove the metal catalyst and salts with hexane/ethyl acetate combinations as eluent. The filtrate was concentrated, and then dried in vacuo. The residue was diluted with 15 mL of methanol containing a catalytic amount of sodium methoxide (0.02 M) and the mixture was stirred at RT overnight. H$^+$ exchange resin (DOWEX 50WX4-100) was added to neutralize the mixture. The resin was filtered off and the filtrate was concentrated. The resulting residue was purified by silica gel chromatography with $CH_2Cl_2$/MeOH combinations as eluent, giving the title compound (0.260 g) in 64% yield for two steps. $^1$H NMR (300 MHz, METHANOL-d$_4$) δ ppm 7.94 (t, J=1.65 Hz, 1H), 7.57-7.72 (m, 2H), 7.33-7.50 (m, 3H), 7.23 (d, J=8.52 Hz, 1H), 5.48 (d, J=1.92 Hz, 1H), 4.00 (dd, J=1.79, 3.43 Hz, 1H), 3.83-3.94 (m, 1H), 3.60-3.76 (m, 3H), 3.46-3.58 (m, 1H), 2.87 (s, 3H), 2.24 (s, 3H). MS (ESI): found: [M+H]$^+$, 404.2.

Methyl 3-[3-fluoro-4-[(2R,3S,4S,5S,6R)-3,4,5-trihydroxy-6-(hydroxymethyl)tetrahydropyran-2-yl]oxy-phenyl]benzoate (4a). [(2R,3S,4S,5R,6R)-4,5-diacetoxy-6-(acetoxymethyl)-2-(4-bromo-2-fluoro-phenoxy)tetrahydropyran-3-yl]acetate: it was prepared using the same procedure as for [(2R,3S,4S,5R,6R)-4,5-diacetoxy-6-(acetoxymethyl)-2-(4-bromo-2-methyl-phenoxy)tetrahydropyran-3-yl]acetate in the synthesis of 5b. Yield: 25%. $^1$H NMR (300 MHz, CHLOROFORM-d) δ ppm 7.30 (dd, J=2.34, 10.03 Hz, 1H), 7.21 (td, J=1.79, 8.79 Hz, 1H), 7.08 (t, J=8.52 Hz, 1H), 5.48-5.58 (m, 2H), 5.46 (d, J=1.65 Hz, 1H), 5.31-5.41 (m, 1H), 4.23-4.31 (m, 1H), 4.13-4.22 (m, 1H), 4.05-

4.13 (m, 1H), 2.20 (s, 3H), 2.02-2.08 (three singlets, 9H). MS (ESI): found: [M+Na]+, 543.0.

Methyl 3-[3-fluoro-4-[(2R,3S,4S,5S,6R)-3,4,5-trihydroxy-6-(hydroxymethyl)tetrahydropyran-2-yl]oxy-phenyl]benzoate (4a). 4a was prepared using the same procedure as for 5b with [(2R,3S,4S,5R,6R)-4,5-diacetoxy-6-(acetoxymethyl)-2-(4-bromo-2-fluoro-phenoxy)tetrahydropyran-3-yl]acetate and 3-methoxycarbonylphenyl boronic acid as the reactants. Yield: 66%. $^1$H NMR (300 MHz, METHANOL-$d_4$) δ ppm 8.21 (t, J=1.65 Hz, 1H), 7.99 (td, J=1.44, 7.83 Hz, 1H), 7.84 (ddd, J=1.10, 1.92, 7.69 Hz, 1H), 7.35-7.62 (m, 4H), 5.55 (d, J=1.92 Hz, 1H), 4.10 (dd, J=1.79, 3.43 Hz, 1H), 3.94 (s, 3H), 3.86-4.00 (m, 1H), 3.59-3.86 (m, 4H). MS (ESI): found [M+Na]+, 431.1.

Methyl 3-[3-chloro-4-[(2R,3S,4S,5S,6R)-3,4,5-trihydroxy-6-(hydroxymethyl)tetrahydropyran-2-yl]oxy-phenyl]benzoate (4b). [(2R,3S,4S,5R,6R)-4,5-diacetoxy-6-(acetoxymethyl)-2-(4-bromo-2-chloro-phenoxy)tetrahydropyran-3-yl]acetate: it was prepared using the same procedure as for [(2R,3S,4S,5R,6R)-4,5-diacetoxy-6-(acetoxymethyl)-2-(4-bromo-2-methyl-phenoxy)tetrahydropyran-3-yl]acetate in the synthesis of 5b. Yield: 46%. $^1$H NMR (300 MHz, CHLOROFORM-d) δ ppm 7.55 (d, J=2.47 Hz, 1H), 7.33 (dd, J=2.47, 8.79 Hz, 1H), 7.06 (d, J=8.79 Hz, 1H), 5.58 (dd, J=3.02, 10.16 Hz, 1H), 5.52 (s, 1H), 5.49-5.54 (m, 1H), 5.33-5.42 (m, 1H), 4.22-4.32 (m, 1H), 4.04-4.17 (m, 2H), 2.21 (s, 3H), 2.07 (s, 3H), 2.05 (s, 3H), 2.04 (s, 3H). MS (ESI): found [M+Na], 561.0.

Methyl 3-[3-chloro-4-[(2R,3S,4S,5S,6R)-3,4,5-trihydroxy-6-(hydroxymethyl)tetrahydropyran-2-yl]oxy-phenyl]benzoate (4b). 4b was prepared using the same procedure as for 5b with [(2R,3S,4S,5R,6R)-4,5-diacetoxy-6-(acetoxymethyl)-2-(4-bromo-2-chloro-phenoxy)tetrahydropyran-3-yl]acetate and 3-methoxycarbonylphenyl boronic acid as the reactants. It was further purified by HPLC (C18, 15*150 mm column; eluent: acetonitrile/water (0.1% TFA)). Yield: 43%. $^1$H NMR (300 MHz, METHANOL-$d_4$) δ ppm 3.59-3.71 (m, 1H) 3.71-3.85 (m, 3H) 3.94 (s, 3H) 4.01 (dd, J=9.34, 3.30 Hz, 1H) 4.12 (dd, J=3.30, 1.92 Hz, 1H) 5.61 (d, J=1.65 Hz, 1H) 7.40-7.49 (m, 1H) 7.49-7.62 (m, 2H) 7.68 (d, J=2.20 Hz, 1H) 7.82 (ddd, J=7.76, 1.85, 1.10 Hz, 1H) 7.98 (dt, J=7.83, 1.30 Hz, 1H) 8.14-8.25 (m, 1H). MS (ESI): found [M+H]+, 425.1.

Methyl 3-[3-methyl-4-[(2R,3S,4S,5S,6R)-3,4,5-trihydroxy-6-(hydroxymethyl)tetrahydropyran-2-yl]oxy-phenyl]benzoate (4c). 4c was prepared using the same procedure as for 5b with [(2R,3S,4S,5R,6R)-4,5-diacetoxy-6-(acetoxymethyl)-2-(4-bromo-2-methyl-phenoxy)tetrahydropyran-3-yl]acetate and 3-methoxycarbonylphenyl boronic acid as the reactants. Yield: 54%. $^1$H NMR (300 MHz, METHANOL-$d_4$) δ ppm 8.20 (t, J=1.51 Hz, 1H), 7.94 (td, J=1.41, 7.90 Hz, 1H), 7.77-7.87 (m, 1H), 7.52 (t, J=7.55 Hz, 1H), 7.39-7.48 (m, 2H), 7.27-7.38 (m, 1H), 5.56 (d, J=1.65 Hz, 1H), 4.08 (dd, J=1.92, 3.30 Hz, 1H), 3.94-4.01 (m, 1H), 3.90-3.94 (m, 3H), 3.68-3.83 (m, 3H), 3.55-3.65 (m, 1H), 2.31 (s, 3H). MS (ESI): found [M+Na]+, 427.1

Methyl 3-[3-(trifluoromethyl)-4-[(2R,3S,4S,5S,6R)-3,4,5-trihydroxy-6-(hydroxymethyl)tetrahydropyran-2-yl]oxy-phenyl]benzoate (4d). [(2R,3S,4S,5R,6R)-4,5-diacetoxy-6-(acetoxymethyl)-2-[4-bromo-2-(trifluoromethyl)phenoxy]tetrahydropyran-3-yl]acetate: it was prepared using the same procedure as for R2R,3S,4S,5R,6R)-4,5-diacetoxy-6-(acetoxymethyl)-2-(4-bromo-2-methyl-phenoxy)tetrahydropyran-3-yl]acetate in the synthesis of 5b. Yield: 54%. $^1$H NMR (300 MHz, CHLOROFORM-d) δ ppm 7.74 (d, J=2.20 Hz, 1H), 7.61 (dd, J=2.33, 8.93 Hz, 1H), 7.15 (d, J=8.79 Hz, 1H), 5.61 (d, J=1.92 Hz, 1H), 5.48-5.56 (m, 1H), 5.33-5.48 (m, 2H), 4.21-4.34 (m, 1H), 3.97-4.14 (m, 2H), 2.21 (s, 3H), 1.99-2.12 (three singlets, 9H). MS (ESI): found [M+Na]+, 593.0.

Methyl 3-[3-(trifluoromethyl)-4-[(2R,3S,4S,5S,6R)-3,4,5-trihydroxy-6-(hydroxymethyl)tetrahydropyran-2-yl]oxy-phenyl]benzoate (4d). 4d was prepared using the same procedure as for 5b with R2R,3S,4S,5R,6R)-4,5-diacetoxy-6-(acetoxymethyl)-2-[4-bromo-2-(trifluoromethyl)phenoxy]tetrahydropyran-3-yl]acetate and 3-methoxycarbonylphenyl boronic acid as the reactants. Yield: 53%. $^1$H NMR (300 MHz, METHANOL-$d_4$) δ ppm 8.23 (t, J=1.51 Hz, 1H), 8.01 (td, J=1.37, 7.69 Hz, 1H), 7.80-7.93 (m, 3H), 7.52-7.67 (m, 2H), 5.66 (d, J=1.65 Hz, 1H), 4.07 (dd, J=1.79, 3.43 Hz, 1H), 3.95 (s, 3H), 3.90-4.00 (m, 1H), 3.66-3.87 (m, 3H), 3.52-3.66 (m, 1H). MS (ESI): found [M+Na]+, 481.0.

Methyl 3-[3-methoxy-4-[(2R,3S,4S,5S,6R)-3,4,5-trihydroxy-6-(hydroxymethyl)tetrahydropyran-2-yl]oxy-phenyl]benzoate (4e). 4e was prepared using the same procedure as for 5b. In the first step of glycosidation reaction 4-bromo-2-methoxyphenol was used as glycosidation acceptor and in the second step of Suzuki coupling reaction 3-methoxycarbonylphenyl boronic acid was used instead. All intermediates were directly taken to the next step reaction without further purification. 4e was further purified by HPLC(C18, 15*150 mm column; eluent: acetonitrile/water (0.1% TFA)). Yield: 3%. $^1$H NMR (300 MHz, METHANOL-$d_4$) δ ppm 8.21 (t, J=1.51 Hz, 1H), 7.96 (td, J=1.44, 7.83 Hz, 1H), 7.84 (ddd, J=1.24, 1.92, 7.83 Hz, 1H), 7.49-7.61 (m, 1H), 7.30 (d, J=8.24 Hz, 1H), 7.24 (d, J=1.92 Hz, 1H), 7.13-7.21 (m, 1H), 5.47 (d, J=1.92 Hz, 1H), 4.11 (dd, J=1.79, 3.43 Hz, 1H), 3.94 (s, 3H), 3.92 (s, 3H), 3.86-4.03 (m, 1H), 3.67-3.86 (m, 4H). MS (ESI): found [M+Na]+, 443.1.

3-[3-Chloro-4-[(2R,3S,4S,5S,6R)-3,4,5-trihydroxy-6-(hydroxymethyl)tetrahydropyran-2-yl]oxy-phenyl]-N-methyl-benzamide (5a). 5a was prepared using the same procedure as for 5b. Yield: 59%. $^1$H NMR (300 MHz, METHANOL-$d_4$) δ ppm 8.03 (t, J=1.51 Hz, 1H), 7.69-7.83 (m, 3H), 7.32-7.67 (m, 3H), 5.60 (d, J=1.65 Hz, 1H), 4.12 (dd, J=1.79, 3.43 Hz, 1H), 4.01 (dd, J=3.57, 9.34 Hz, 1H), 3.69-3.84 (m, 3H), 3.61-3.69 (m, 1H), 2.95 (s, 3H). MS (ESI): found [M+Na]+, 424.1.

N-Methyl-3-[3-(trifluoromethyl)-4-[(2R,3S,4S,5S,6R)-3,4,5-trihydroxy-6-(hydroxymethyl)tetrahydropyran-2-yl]oxy-phenyl]benzamide (5c). 5c was prepared using the same procedure as for 5b. Yield: 65%. $^1$H NMR (300 MHz, METHANOL-$d_4$) δ ppm 7.98 (t, J=1.65 Hz, 1H), 7.77-7.87 (m, 2H), 7.65-7.77 (m, 2H), 7.42-7.60 (m, 2H), 5.58 (d, J=1.65 Hz, 1H), 3.99 (dd, J=1.79, 3.43 Hz, 1H), 3.81-3.91 (m, 1H), 3.59-3.80 (m, 3H), 3.45-3.58 (m, 1H), 2.87 (s, 3H). MS (ESI): found [M+H]+, 458.1.

Methyl 2-(3-methoxycarbonylphenyl)-5-[(2R,3S,4S,5S,6R)-3,4,5-trihydroxy-6-(hydroxymethyl)tetrahydropyran-2-yl]oxy-benzoate (6). Methyl 5-hydroxy-2-(3-methoxycarbonylphenyl)benzoate: The reactants of methyl 2-bromo-5-hydroxybenzoate (0.231 g, 1 mmol), 3-methoxycarbonylphenyl boronic acid (0.214 g, 1.2 mmol), palladium acetate (0.022 g, 0.1 mmol), potassium carbonate (0.346 g, 2.5 mmol) and tetrabutylammonium bromide (0.322 g, 1 mmol) in 1.2 ml of water was heated with stirring at 70° C. for 1 h and 20 mins in a sealed vial by microwave. Then the mixture was partitioned between AcOEt and 1 N HCl aqueous solution. The organic layer was collected, dried with Na$_2$SO$_4$, then concentrated. The resulting residue was purified by silica gel chromatography with AcOEt/Hex combinations as eluent, giving the title compound (0.240 g) in 84% yield. $^1$H NMR (300 MHz, DMSO-$d_6$) δ ppm 10.02 (s, 1H), 7.90 (td, J=2.03, 6.66 Hz, 1H), 7.72-7.81 (m, 1H), 7.45-

7.60 (m, 2H), 7.28 (d, J=8.52 Hz, 1H), 7.16 (d, J=2.47 Hz, 1H), 7.03 (dd, J=2.61, 8.38 Hz, 1H), 3.86 (s, 3H), 3.56 (s, 3H). MS (ESI): found [M+Na]+, 309.2.

Methyl 2-(3-methoxycarbonylphenyl)-5-[(2R,3S,4S,5S,6R)-3,4,5-trihydroxy-6-(hydroxymethyl)tetrahydropyran-2-yl]oxy-benzoate (6). 6 was prepared via glycosidation between α-D-mannose pentaacetate and methyl 5-hydroxy-2-(3-methoxycarbonylphenyl)benzoate following the procedure previously described.[25] Yield: 73%. $^1$H NMR (300 MHz, METHANOL-d$_4$) δ ppm 3.56-3.68 (m, 4H) 3.68-3.84 (m, 3H) 3.86-3.98 (m, 4H) 4.06 (dd, J=3.30, 1.92 Hz, 1H) 5.60 (d, J=1.92 Hz, 1H) 7.29-7.43 (m, 2H) 7.45-7.53 (m, 2H) 7.56 (d, J=2.47 Hz, 1H) 7.84-7.92 (m, 1H) 7.93-8.04 (m, 1H). MS (ESI): found [M+H]+, 449.0.

N1,N3-Dimethyl-5-[3-(trifluoromethyl)-4-[(2R,3S,4S,5S,6R)-3,4,5-trihydroxy-6-(hydroxymethyl)tetrahydropyran-2-yl]oxy-phenyl]benzene-1,3-dicarboxamide (7). N1,N3-dimethyl-5-(4,4,5,5-tetramethyl-1,3,2-dioxaborolan-2-yl)benzene-1,3-dicarboxamide (9): dimethyl 5-bromobenzene-1,3-dicarboxylate (10.6 g, 36.8 mmol) was dissolved in a 33 wt % solution of methylamine in EtOH (30 mL) and stirred for 6 h at RT. The precipitate that formed during the reaction was filtered to give 5.3 g (53%) of the intermediate 5-bromo-N1,N3-dimethyl-benzene-1,3-dicarboxamide as a white solid. Concentration of the remaining filtrate yielded an additional 4.6 g (46%) of product. 5-bromo-N1,N3-dimethyl-benzene-1,3-dicarboxamide (5.3 g, 19.5 mmol), Pd(dppf)Cl$_2$ (0.87 g, 1.2 mmol), bis(pinacolato)diboron (6.1 g, 24 mmol), and potassium acetate (7.8 g, 80 mmol) were dissolved in DMSO (100 mL). The solution was stirred under vacuum and then repressurized with nitrogen. This process was repeated 3 times and then the resultant mixture was stirred at 80° C. for 5 h under a nitrogen atmosphere. After removal of the solvent under high vacuum, the crude material was purified by silica gel chromatography to give 9 as a light tan solid (2.2 g, 35%). $^1$H NMR (300 MHz, DMSO-d$_6$) δ ppm 8.63 (m, 2H), 8.41 (t, J=1.51 Hz, 1H), 8.23 (d, J=1.65 Hz, 2H), 2.79 (d, J=4.40 Hz, 6H), 1.33 (s, 12H). MS (ESI): found: [M+H]+, 319.2.

N1,N3-Dimethyl-5-[3-(trifluoromethyl)-4-[(2R,3S,4S,5S,6R)-3,4,5-trihydroxy-6-(hydroxymethyl)tetrahydropyran-2-yl]oxy-phenyl]benzene-1,3-dicarboxamide (7). Using the procedure outlined in the synthesis of 5b with [(2R,3S,4S,5R,6R)-4,5-diacetoxy-6-(acetoxymethyl)-2-(4-bromo-2-trifluoromethyl-phenoxy)tetrahydropyran-3-yl]acetate (0.57 g) and N1,N3-dimethyl-5-(4,4,5,5-tetramethyl-1,3,2-dioxaborolan-2-yl)benzene-1,3-dicarboxamide (9) (0.48 g), the title compound was obtained (0.340 g) in 69% yield for the two steps. $^1$H NMR (300 MHz, METHANOL-d$_4$) δ ppm 8.17-8.24 (m, 1H), 8.14 (d, J=1.65 Hz, 2H), 7.92 (d, J=1.92 Hz, 1H), 7.87 (dd, J=2.20, 8.79 Hz, 1H), 7.57 (d, J=8.79 Hz, 1H), 5.64 (d, J=1.65 Hz, 1H), 4.04 (dd, J=1.65, 3.30 Hz, 1H), 3.87-3.96 (dd, 1H), 3.64-3.83 (m, 3H), 3.48-3.63 (m, 1H), 2.93 (s, 6H). MS (ESI): found: [M+H]+, 515.1.

N1,N3-Dimethyl-5-[3-methyl-4-[(2R,3S,4S,5S,6R)-3,4,5-trihydroxy-6-(hydroxymethyl)tetrahydropyran-2-yl]oxy-phenyl]benzene-1,3-dicarboxamide (8). 8 was prepared using the same procedure as for 5b with N1,N3-dimethyl-5-(4,4,5,5-tetramethyl-1,3,2-dioxaborolan-2-yl)benzene-1,3-dicarboxamide as the Suzuki coupling partner. Yield: 56%. $^1$H NMR (300 MHz, METHANOL-d$_4$) δ ppm 8.09-8.23 (m, 3H), 7.46-7.59 (m, 2H), 7.33 (d, J=8.52 Hz, 1H), 5.57 (d, J=1.92 Hz, 1H), 4.08 (dd, J=1.92, 3.30 Hz, 1H), 3.97 (dd, J=3.43, 9.48 Hz, 1H), 3.67-3.85 (m, 3H), 3.60 (ddd, J=2.47, 5.01, 7.35 Hz, 1H), 2.96 (s, 6H), 2.32 (s, 3H). MS (ESI): found: [M+H]+, 461.2.

Procedure for the Preparation of Mannosides Via Amide Coupling Reaction:

N-(2-Hydroxyethyl)-3-[4-[(2R,3S,4S,5S,6R)-3,4,5-trihydroxy-6-(hydroxymethyl)tetrahydropyran-2-yl]oxyphenyl]benzamide (10a). Under nitrogen atmosphere, at 0° C. anhydrous DMF (5 mL) was added into the RB flask containing 4'-(α-D-mannopyranosyloxy)biphenyl-3-carboxylic acid[25] (0.038 g, 0.1 mmol) and HATU (0.046 g, 0.12 mmol). After stirring for 10 min, aminoethanol (0.007 g, 0.12 mmol), then N,N-diisopropylethylamine (0.039 g, 0.3 mmol) were added. The mixture was stirred overnight while being warmed to rt naturally. The solvent was removed and the residue was purified by HPLC (C18, 15*150 mm column; eluent: acetonitrile/water (0.1% TFA)) to give the title compound (0.032 g) in 76% yield. $^1$H NMR (300 MHz, DEUTERIUM OXIDE) δ ppm 3.53-3.63 (m, 2H) 3.68-3.94 (m, 6H) 4.11 (dd, J=9.20, 3.43 Hz, 1H) 4.22 (dd, J=3.30, 1.92 Hz, 1H) 5.66 (d, J=1.65 Hz, 1H) 7.21 (d, J=8.79 Hz, 2H) 7.47-7.62 (m, 3H) 7.66-7.78 (m, 2H) 7.87 (t, J=1.65 Hz, 1H). MS (ESI): found [M+H]+, 420.1.

N-(2-Aminoethyl)-3-[4-[(2R,3S,4S,5S,6R)-3,4,5-trihydroxy-6-(hydroxymethyl)tetrahydropyran-2-yl]oxyphenyl]benzamide (10b). 10b was prepared using the same procedure as for 10a. Yield: 60%. $^1$H NMR (300 MHz, METHANOL-d$_4$) δ ppm 3.14-3.26 (m, 2H) 3.57-3.66 (m, 1H) 3.66-3.83 (m, 5H) 3.87-4.00 (m, 1H) 4.03 (dd, J=3.30, 1.92 Hz, 1H) 5.49-5.62 (m, 1H) 7.19-7.31 (m, 2H) 7.49-7.59 (m, 1H) 7.59-7.72 (m, 2H) 7.75-7.89 (m, 2H) 8.03-8.21 (m, 1H). MS (ESI): found [M+H]+, 419.2.

Piperazin-1-yl-[3-[4-[(2R,3S,4S,5S,6R)-3,4,5-trihydroxy-6-(hydroxymethyl)tetrahydropyran-2-yl]oxyphenyl]phenyl]methanone (10c). 10c was prepared using the same procedure as for 10a. Yield: 65%. $^1$H NMR (300 MHz, METHANOL-d$_4$) δ ppm 3.54-3.67 (m, 1H) 3.67-3.85 (m, 4H) 3.85-3.99 (m, 4H) 4.03 (dd, J=3.30, 1.92 Hz, 1H) 5.54 (d, J=1.65 Hz, 1H) 7.19-7.29 (m, 2H) 7.42 (dt, J=7.69, 1.24 Hz, 1H) 7.50-7.64 (m, 3H) 7.67-7.79 (m, 2H). MS (ESI): found [M+H]+, 445.3.

(4-Methylpiperazin-1-yl)-[3-[4-[(2R,3S,4S,5S,6R)-3,4,5-trihydroxy-6-(hydroxymethyl)tetrahydropyran-2-yl]oxyphenyl]phenyl]methanone (10d). 10d was prepared using the same procedure as for 10a. Yield: 87%. $^1$H NMR (300 MHz, METHANOL-d$_4$) δ ppm 2.96 (s, 3H) 3.05-3.65 (m, 9H) 3.68-3.85 (m, 3H) 3.87-3.97 (m, 1H) 4.03 (dd, J=3.30, 1.92 Hz, 1H) 5.54 (d, J=1.65 Hz, 1H) 7.17-7.30 (m, 2H) 7.42 (dt, J=7.62, 1.27 Hz, 1H) 7.50-7.66 (m, 3H) 7.67-7.80 (m, 2H). MS (ESI): found [M+H]+, 459.0.

N-(4-Pyridyl)-3-[4-[(2R,3S,4S,5S,6R)-3,4,5-trihydroxy-6-(hydroxymethyl)tetrahydropyran-2-yl]oxyphenyl]benzamide (10e). 10e was prepared using the same procedure as for 10a. Yield: 93%. $^1$H NMR (300 MHz, METHANOL-d$_4$) δ ppm 3.57-3.69 (m, 1H) 3.69-3.84 (m, 3H) 3.93 (dd, J=9.34, 3.30 Hz, 1H) 4.04 (dd, J=3.30, 1.92 Hz, 1H) 5.56 (d, J=1.65 Hz, 1H) 7.18-7.37 (m, 2H) 7.57-7.78 (m, 3H) 7.82-8.06 (m, 2H) 8.24 (t, J=1.65 Hz, 1H) 8.36-8.51 (m, 2H) 8.68 (d, J=7.42 Hz, 2H). MS (ESI): found [M+H]+, 453.1.

N-(3-Pyridyl)-3-[4-[(2R,3S,4S,5S,6R)-3,4,5-trihydroxy-6-(hydroxymethyl)tetrahydropyran-2-yl]oxyphenyl]benzamide (10f). 10f was prepared using the same procedure as for 10a. Yield: 75%. $^1$H NMR (300 MHz, METHANOL-d$_4$) δ ppm 3.55-3.68 (m, 1H) 3.68-3.85 (m, 3H) 3.88-3.98 (m, 1H) 4.04 (dd, J=3.43, 1.79 Hz, 1H) 5.56 (d, J=1.92 Hz, 1H) 7.20-7.32 (m, 2H) 7.52-7.73 (m, 3H) 7.80-7.91 (m, 1H) 7.91-7.99 (m, 1H) 8.04 (dd, J=8.65, 5.63 Hz, 1H) 8.23 (t, J=1.65 Hz, 1H) 8.59 (d, J=5.49 Hz, 1H) 8.67-8.79 (m, 1H) 9.55 (s, 1H). MS (ESI): found [M+H]+, 453.2.

Procedure for the preparation of biphenyl mannoside derivatives through Suzuki coupling reaction with [(2R,3S,4S,5R,6R)-4,5-diacetoxy-6-(acetoxymethyl)-2-[4-(4,4,5,5-tetramethyl-1,3,2-dioxaborolan-2-yl)phenoxy]tetrahydropyran-3-yl]acetate (9) as intermediates:

methyl 5-[4-[(2R,3S,4S,5S,6R)-3,4,5-trihydroxy-6-(hydroxymethyl)tetrahydropyran-2-yl]oxyphenyl]pyridine-3-carboxylate (12b). [(2R,3S,4S,5R,6R)-4,5-diacetoxy-6-(acetoxymethyl)-2-[4-(4,4,5,5-tetramethyl-1,3,2-dioxaborolan-2-yl)phenoxy]petrahydropyran-3-yl]acetate (11): Under nitrogen atmosphere, the mixture of 4-bromophenyl 2,3,4,6-tetra-O-acetyl-α-D-mannopyranoside (2.791 g, 5.55 mmol), bis(pinacolato)diboron (1.690 g, 6.66 mmol), potassium acetate (2.177 g, 22.18 mmol) and (1.1'-bis(diphenylphosohino)ferrocene)dichloropalladium(II) (0.244 g, 0.33 mmol) in DMSO (50 ml) was heated at 80° C. with stirring for 2.5 h. The solvent was removed and the resulting residue was purified by silica gel chromatography with hexane/ethyl acetate combinations as eluent to give 11 (2.48 g) in 81% yield. $^1$H NMR (300 MHz, CHLOROFORM-d) δ ppm 1.33 (s, 12H) 1.98-2.12 (m, 9H) 2.20 (s, 3H) 3.93-4.19 (m, 2H) 4.21-4.36 (m, 1H) 5.32-5.42 (m, 1H) 5.45 (dd, J=3.57, 1.92 Hz, 1H) 5.51-5.62 (m, 2H) 7.00-7.15 (m, 2H) 7.67-7.84 (m, 2H). MS (ESI): found: [M+Na]$^+$, 573.2.

Methyl 5-[4-[(2R,3S,4S,5S,6R)-3,4,5-trihydroxy-6-(hydroxymethyl)tetrahydropyran-2-yl]oxyphenyl]pyridine-3-carboxylate (12b). Under nitrogen atmosphere, the mixture of [(2R,3S,4S,5R,6R)-4,5-diacetoxy-6-(acetoxymethyl)-2-[4-(4,4,5,5-tetramethyl-1,3,2-dioxaborolan-2-yl)phenoxy]tetrahydropyran-3-yl]acetate (0.132 g, 0.24 mmol), methyl 5-bromonicotinate (0.043 g, 0.2 mmol), cesium carbonate (0.196 g, 0.6 mmol) and tetrakis(triphenylphosphine)palladium (0.023 g, 0.02 mmol) in dioxane/water (5 mL/1 mL) was heated at 80° C. with stirring for 1 h. After cooling down, the mixture was filtered through silica gel column to remove the metal catalyst and salts with hexane/ethyl acetate (2/1) containing 2% triethylamine as eluent. The filtrate was concentrated, then dried in vacuo. Into the residue, 6 mL of methanol with catalytic amount of sodium methoxide (0.02 M) was added and the mixture was stirred at room temperature overnight. The solvent was removed. The resulting residue was purified by silica gel chromatography with CH$_2$Cl$_2$/MeOH combinations containing 2% NH$_3$/H$_2$O as eluent, giving rise to 12b (0.031 g) in 40% yield. $^1$H NMR (300 MHz, CD$_3$OD) δ ppm 3.53-3.65 (m, 1H) 3.67-3.83 (m, 3H) 3.89-3.96 (m, 1H) 3.99 (s, 3H) 4.04 (dd, J=3.43, 1.79 Hz, 1H) 5.57 (d, J=1.92 Hz, 1H) 7.22-7.37 (m, 2H) 7.58-7.73 (m, 2H) 8.54 (t, J=2.06 Hz, 1H) 8.97 (d, J=2.20 Hz, 1H) 9.04 (d, J=1.92 Hz, 1H). MS (ESI): found: [M+H]$^+$, 392.1.

Methyl 4-[4-[(2R,3S,4S,5S,6R)-3,4,5-trihydroxy-6-(hydroxymethyl)tetrahydropyran-2-yl]oxyphenyl]pyridine-2-carboxylate (12a). 12a was prepared using the same procedure as for 12b and was purified by HPLC(C18, 15*150 mm column; eluent: acetonitrile/water (0.1% TFA)). Yield: 15%. $^1$H NMR (300 MHz, METHANOL-d$_4$) δ ppm 3.51-3.63 (m, 1H) 3.65-3.84 (m, 3H) 3.88-3.95 (m, 1H) 4.00-4.13 (m, 4H) 5.62 (d, J=1.65 Hz, 1H) 7.28-7.40 (m, 2H) 7.82-7.95 (m, 2H) 8.13 (dd, J=5.49, 1.92 Hz, 1H) 8.55 (d, J=1.65 Hz, 1H) 8.73 (d, J=5.49 Hz, 1H). MS (ESI): found [M+H]$^+$, 392.2.

Methyl 5-[4-[(2R,3S,4S,5S,6R)-3,4,5-trihydroxy-6-(hydroxymethyl)tetrahydropyran-2-yl]oxyphenyl]-3-ureidothiophene-2-carboxylate (13a). 13a was prepared using the same procedure as for 12b and was purified by HPLC(C18, 15*150 mm column; eluent: acetonitrile/water (0.1% TFA)). Yield: 10%. $^1$H NMR (300 MHz, METHANOL-d$_4$) δ ppm 3.58 (ddd, J=7.21, 4.88, 2.47 Hz, 1H) 3.66-3.83 (m, 3H) 3.83-3.96 (m, 4H) 4.02 (dd, J=3.30, 1.92 Hz, 1H) 5.54 (d, J=1.65 Hz, 1H) 7.12-7.27 (m, 2H) 7.56-7.69 (m, 2H) 8.12 (s, 1H). MS (ESI): found [M+H]$^+$, 455.1.

Methyl 5-[4-[(2R,3S,4S,5S,6R)-3,4,5-trihydroxy-6-(hydroxymethyl)tetrahydropyran-2-yl]oxyphenyl]thiophene-2-carboxylate (13b). 13b was prepared using the same procedure as for 12b and was purified by silica gel chromatography with CH$_2$Cl$_2$/MeOH combinations. Yield: 23%. $^1$H NMR (300 MHz, METHANOL-d$_4$) δ ppm 3.53-3.62 (m, 1H) 3.68-3.81 (m, 3H) 3.85-3.94 (m, 4H) 4.02 (dd, J=3.60, 2.1 Hz, 1H) 5.54 (d, J=1.8 Hz, 1H) 7.19 (m, 2H) 7.34 (d, J=3.9 Hz, 1H) 7.64 (m, 2H) 7.75 (d, J=3.9 Hz, 1H). MS (ESI): found [M+Na]$^+$, 419.1.

(5-bromo-3-thienyl)urea (16). Under nitrogen atmosphere N,N-diisopropylethylamine (0.390 g, 3 mmol) was added to the solution of 5-bromothiophene-3-carboxylic acid (0.207 g, 1 mmol) and diphenylphosphoryl azide (DPPA) (0.330 g, 1.2 mmol) in dioxane (5 ml) at rt. After stirring for 30 min, the mixture was heated at 85 for 1.5 h. After the mixture cooled down to rt, 0.5 M of ammonia solution in dioxane (12 ml) was added. 30 min's later, the solvents was removed and the resulting residue was purified by silica gel chromatography with CH$_2$Cl$_2$/MeOH combinations to give (5-bromo-3-thienyl)urea (0.072 g) in 32% yield. $^1$H NMR (300 MHz, DMSO-d$_6$) δ ppm 8.80 (s, 1H), 7.09 (s, 2H), 5.87 (s, 2H). MS (ESI): found [M+H]$^+$, 223.0.

[5-[4-[(2R,3S,4S,5S,6R)-3,4,5-Trihydroxy-6-(hydroxymethyl)tetrahydropyran-2-yl]oxyphenyl]-3-thienyl]urea (13c). 13c was prepared using the same procedure as for 12b and was purified by HPLC(C18, 15*150 mm column; eluent: acetonitrile/water (0.1% TFA)). Yield: 80%. $^1$H NMR (300 MHz, METHANOL-d$_4$/ACETONITRILE-d$_3$(3/1)) δ 7.50-7.62 (m, 2H), 7.11-7.21 (m, 3H), 7.08 (d, J=1.37 Hz, 1H), 5.53 (d, J=1.65 Hz, 1H), 4.02 (dd, J=1.92, 3.30 Hz, 1H), 3.82-3.95 (m, 1H), 3.66-3.81 (m, 3H), 3.51-3.64 (m, 1H). MS (ESI): found [M+H]$^+$, 397.1.

Methyl 5-[4-[(2R,3S,4S,5S,6R)-3,4,5-trihydroxy-6-(hydroxymethyl)tetrahydropyran-2-yl]oxyphenylphiophene-3-carboxylate (13d). 13d was prepared using the same procedure as for 12b and was purified by silica gel chromatography with CH$_2$Cl$_2$/MeOH combinations. Yield: 33%. $^1$H NMR (300 MHz, METHANOL-d$_4$) δ ppm 3.55-3.63 (m, 1H) 3.68-3.81 (m, 3H) 3.84-3.94 (m, 4H) 4.02 (dd, J=3.30, 1.8 Hz, 1H) 5.53 (d, J=1.8 Hz, 1H) 7.18 (m, 2H) 7.59 (m, 2H) 7.64 (d, J=1.5 Hz, 1H) 8.11 (d, J=1.5 Hz, 1H). MS (ESI): found [M+Na]$^+$, 419.1.

(2R,3S,4S,5S,6R)-2-(Hydroxymethyl)-6-[4-(7-isoquinolyl)phenoxy]tetrahydropyran-3,4,5-triol (14a). 14a was prepared using the same procedure as for 12b and was purified by HPLC(C18, 15*150 mm column; eluent: acetonitrile/water (0.1% TFA)). Yield: 73%. $^1$H NMR (300 MHz, METHANOL-d$_4$) δ 9.73 (s, 1H), 8.59-8.71 (m, 1H), 8.47-8.58 (m, 2H), 8.42 (d, J=6.59 Hz, 1H), 8.33 (d, J=8.79 Hz, 1H), 7.76-7.89 (m, 2H), 7.25-7.41 (m, 2H), 5.60 (d, J=1.92 Hz, 1H), 4.06 (dd, J=1.92, 3.30 Hz, 1H), 3.87-4.00 (m, 1H), 3.68-3.87 (m, 3H), 3.55-3.68 (m, 1H). MS (ESI): found [M+H]$^+$, 384.2.

(2R,3S,4S,5S,6R)-2-(Hydroxymethyl)-6-(4-quinazolin-6-ylphenoxy)tetrahydropyran-3,4,5-triol (14b). 14b was prepared using the same procedure as for 12b. Yield: 28%. $^1$H NMR (300 MHz, METHANOL-d$_4$) δ 9.51 (s, 1H), 9.15 (s, 1H), 8.21-8.35 (m, 2H), 8.02 (d, J=8.52 Hz, 1H), 7.63-7.80 (m, J=8.79 Hz, 2H), 7.14-7.32 (m, J=8.79 Hz, 2H), 5.50 (d, J=1.37 Hz, 1H), 3.94-4.03 (m, 1H), 3.80-3.94 (m, 1H), 3.62-3.80 (m, 3H), 3.48-3.62 (m, 1H). MS (ESI): found [M+H]$^+$, 385.1.

(2R,3S,4S,5S,6R)-2-(Hydroxymethyl)-6-[4-(5-isoquinolyl)phenoxy]tetrahydropyran-3,4,5-triol (15a). 15a was prepared using the same procedure as for 12b and was purified by HPLC(C18, 15*150 mm column; eluent: acetonitrile/water (0.1% TFA)). Yield: 90%. $^1$H NMR (300 MHz, METHANOL-$d_4$) δ 9.80 (s, 1H), 8.45-8.60 (m, 2H), 8.35 (d, J=6.59 Hz, 1H), 8.01-8.21 (m, 2H), 7.45-7.55 (m, 2H), 7.31-7.42 (m, 2H), 5.62 (d, J=1.92 Hz, 1H), 4.07 (dd, J=1.92, 3.30 Hz, 1H), 3.89-3.99 (m, 1H), 3.70-3.86 (m, 3H), 3.60-3.69 (m, 1H). MS (ESI): found [M+H]$^+$, 384.2.

7-[4-[(2R,3S,4S,5S,6R)-3,4,5-Trihydroxy-6-(hydroxymethyl)tetrahydropyran-2-yl]oxyphenyl]-2H-isoquinolin-1-one (15b). 15b was prepared using the same procedure as for 12b and was purified by HPLC(C18, 15*150 mm column; eluent: acetonitrile/water (0.1% TFA)). Yield: 75%. $^1$H NMR (300 MHz, METHANOL-$d_4$) δ 8.51 (d, J=2.20 Hz, 1H), 7.93-8.05 (m, 1H), 7.62-7.77 (m, 3H), 7.21-7.31 (m, 2H), 7.18 (d, J=7.14 Hz, 1H), 6.71 (d, J=7.14 Hz, 1H), 5.56 (d, J=1.92 Hz, 1H), 4.04 (dd, J=1.92, 3.57 Hz, 1H), 3.88-4.00 (m, 1H), 3.69-3.87 (m, 3H), 3.57-3.69 (m, 1H). MS (ESI): found [M+H]$^+$, 400.2.

Affinity Measurement by Bio-Layer Interferometry.

Samples or buffer (200 μL per well) were dispensed into 96-well microtiter plates (Greiner Bio-One, Monroe N.C.) and maintained at 30° C. with 1000 RPM shaking. Pre-manufactured pins for individual assays were made by biotinylating FimH lectin domain[25] at a 1:1 molar ratio with NHS-PEO4-Biotin (Thermo Fisher, Rockford Ill.), diluting it to 50 μg/ml in 20 mM HEPES pH 7.5, 150 mM NaCl (HBS), immobilizing it on high-binding streptavidin-coated biosensor tips (Super Streptavidin, ForteBio, Inc., Menlo Park, Calif.) for 10 minutes at 30° C., blocking the pins with 10 μg/ml biocytin for 2 minutes, washing in HBS for 1 hour, and rinsing in 15% sucrose in HBS. Pins were then air dried for 30 minutes and stored in their original packaging with a dessicant packet. Assays were performed by re-wetting premade pins with HBS for 15 minutes, then storing them in fresh HBS until use. Individual affinity assays were performed on an Octet Red instrument (ForteBio, Inc., Menlo Park, Calif.) and consisted of a short baseline measurement followed by incubation of pins for 10 minutes with 7 twofold dilutions (in HBS) of compound in a concentration range experimentally determined to give well-measured association and dissociation kinetics, then a 30-minute dissociation phase in HBS. Each experimental pin was referenced to a biocytin-blocked pin to control for instrument drift and a second biocytin-blocked pin that was passed through a duplicate experiment in the same 96-well plate to control for nonspecific binding of the compound to the pin. Kinetics data and affinity constants were generated automatically by the global fitting protocol in ForteBio Data Analysis version 6.3. Typical signal for compound binding was approximately 0.2 "nm shift" units, while the noise level of the instrument is around 0.0025 nm.

Differential Scanning Fluorimetry (DSF) Method.

FimH lectin domain (residues 1-158 of UPEC J96 FimH, without an affinity tag) was purified as described previously. Five micrograms FimH in 5 μl HBS were mixed with HBS to yield a final volume of 50 μl containing compound at a final concentration of 100 μM and a "5×" final concentration of SYPRO Orange (sold as a "5000×" stock in DMSO and mixed with HBS to a working stock of 50× immediately before use: Life Technologies Inc.; Grand Island, N.Y.). Compounds were diluted to 100 μM from stocks in DMSO and compared to matched control wells with FimH alone plus 0.2% DMSO. 50 μl reactions were placed in 96-well clear-bottom PCR plates and subjected to a melt curve from 20-90° C. in 0.5° C. increments of 15 seconds each followed by a fluorescence read of the "HEX" channel in a Bio-Rad CFX96 thermocycler (Bio-Rad, Hercules, Calif.). Melt curves were fitted to the Boltzmann equation to determine the melting temperature $(T_m)$ $(y=A2+(A1-A2)/(1+\exp((x-x0)/dx))$ where x0 is the $T_m$) using OriginPro 8 (OriginLab, Northampton Mass.).

Pharmacokinetic Studies.

Compound levels in mouse urine and plasma were made using an AB Sciex API-4000 QTrap (AB Sciex, Foster City, Calif.) as previously described.[36] Selected reaction monitoring (SRM) mode quantification was performed with using the following MS/MS transitions [precursor mass/charge ratio (m/z)/product m/z]: compound 3, 447/285; compound 5a, 424/262; compound 5b, 404/242; compound 5c, 548/296; compound 7, 515/353; compound 8, 461/299; compound 3 R group, 285/254.

Parallel Artificial Membrane Permeability Assay (PAMPA).

Materials. The assay was carried out using Multiscreen PVDF 96-well plates (Millipore, Billerica, Mass.) using the company's Transporter Receiver Plate. The lipid (dioleyoylphosphotidylcholine (DOPC):Stearic Acid (80:20, wt %) in dodecane was obtained from Avanti Polar lipids (Alabaster, Ala.). Hank's Buffered Salt Solution (HBSS), pH 7.4 was obtained from MediaTech (Manassas, Va.).

Methods. Each of the test compounds was diluted to 2.5 mM in DMSO (Sigma, St Louis, Mo.) and further diluted prior to testing to 2.5 μM in HBSS, pH 7.4. The assay was performed using a Millipore 96-well Multiscreen-IP PAMPA plate, 5 μl of the lipid suspension was directly added to the PVDF membrane of the filter plate. Immediately following the addition of the lipid to the membrane, 200 μl of HBSS solution containing the test compound was added to the donor (upper) chamber. HBSS (300 μl) is also added to the receiver plate and the filter and receiver plates assembled and incubated overnight at room temperature in a moistened sealed bag to prevent evaporation. The concentration in the receiver plate as well as an equilibrium plate, that represents a theoretical, partition-free sample, was determined by HPLC-tandem mass spectrometry. Analysis of each compound was performed in triplicate.

Analysis. Analysis of both the acceptor and equilibrium samples were performed using an AB 3200 triple quadripole mass spectrometer linked to a Shimadzu DGU-20A HPLC with a Prevail C18 column (3 μm, 2.1×10 mm) with a flow rate of 0.35 ml/min. The mobile phase used was A: 0.1% Formic Acid in water, B: 0.1% Formic Acid in methanol. The elation gradient method is described in the table. Data acquisition and peak height determination was performed using Analyst v.1.4.2.

| Time, min | A | B |
|---|---|---|
| 0.01 | 95 | 5 |
| 0.50 | 95 | 5 |
| 1.00 | 5 | 95 |
| 2.00 | 5 | 95 |
| 2.01 | 95 | 5 |
| 6.01 | Stop | |

Calculations. The $\log_{in}$ of the effective permeability ($LogP_e$) was calculated using the following equation $$\log P_e = \log\left\{C \cdot -\ln\left(1 - \frac{[\text{drug}]_{acceptor}}{[\text{drug}]_{equilibrium}}\right)\right\} \text{ where}$$

$$C = \left(\frac{V_D \cdot V_A}{(V_D + V_A)\text{Area} \cdot \text{Time}}\right)$$

Where the drug concentration is the peak areas for the analyte and $V_D$ and $V_A$ is the volume of the donor and acceptor compartment respectively. The area is the surface area of the PVDF membrane (0.11 cm$^2$) and time is the incubation in seconds (64,800 sec). Each value is the mean of triplicates performed on the same day.

Introduction for Examples 37-39

Type 1 pili constitute the major UPEC virulence factor, being critical for attachment to and invasion of the bladder epithelium as well as for IBC formation. Type 1 pili belong to a class of extracellular fibers assembled by the chaperone-usher pathway. They are encoded by the fim gene cluster, and their expression is directed by a phase-variable promoter (fimS), which facilitates a switch between piliated and non-piliated bacterial states. UPEC populations are heterogeneous consisting of bacteria that are bald, low-, moderately- and highly piliated. The ratio of each piliated fraction shifts depending on the environment; studies investigating the expression of type 1 pili revealed that UPEC associated with epithelial cells are highly piliated, consistent with the critical role of type 1 pili in urothelium colonization, while bacteria recovered from urine samples of patients have fimS primarily in the OFF phase and are likely non-piliated. Regulation of fimS phase-variation is controlled by the FimB, FimE and FimX recombinases, the expression of which is in turn influenced by numerous regulatory factors. We recently identified the QseC sensor kinase as one of the factors implicated in regulation of type 1 pili expression. In the qseC mutant, the fim promoter is found primarily in the OFF orientation, resulting in reduced type 1 pili expression, an effect that stems from uncontrolled activation of the QseB response regulator in this mutant. In addition to influencing type 1 pili expression in the absence of qseC, over-active QseB aberrantly regulates conserved cellular pathways and impacts several virulence-associated genes, resulting in UPEC attenuation.

Numerous investigations highlighted the importance of type 1 pili in pathogenesis and spurred the onset of research towards the development of anti-adhesion agents, known as mannosides, aimed at inhibiting FimH-host receptor interactions. Given that disruption of QseC simultaneously affects fim expression and a number of other cellular processes, type 1 pili were disengaged from QseC control to determine the infection stages at which other QseC-mediated defects become important. By locking the invertible fim promoter element in the ON orientation, type 1 pili expression was restored in the qseC mutant and it was shown that the resulting mutant is competent in infection initiation and IBC formation. However, even upon expression of type 1 pili the qseC mutant is rapidly outcompeted by the parent strain during co-infection studies and cannot survive long-term in the urinary tract in mono-infections. These findings indicate that although type 1 pili mask the qseC deletion phenotypes at the onset of infection, additional QseC-mediated processes are required for persistence. Therefore, the examples below explore whether co-inhibition of QseC and type 1 pili would have a synergistic effect on clearing UPEC from the urinary tract. Given the lack of available QseC inhibitors a prophylactic approach was taken, using the qseC mutant as a proxy to QseC-inhibition. The data showed that mice pre-treated with mannoside (to block FimH-mediated adhesion) and subsequently challenged with the qseC mutant were more effectively protected against chronic UTI compared to mice challenged with the parent strain. These examples indicate that targeting of QseC can be exploited as a potential preventative strategy, alone or in combination with other anti-virulence agents.

Example 37

Deletion of QseC Impairs the Ability of UPEC to Invade the Bladder

It was previously shown that deletion of qseC in UTI89 leads to reduced bladder bacterial titers during the acute stages of infection (6 and 16 h post infection) in a cystitis murine model. Given that type 1 pili are critical for bladder adherence and invasion and are significantly reduced in the absence of QseC, it was rationalized that the in vivo attenuation of UTI89ΔqseC could be, at least partly, attributed to reduced bacterial internalization. Thus, the ability of UTI89ΔqseC to adhere to and invade the bladder epithelium was assessed and compared to the parent strain. Female C3H/HeN mice were transurethrally inoculated with $10^7$ wild-type (wt) UTI89 or UTI89ΔqseC and bacterial invasion was assessed at 1 and 3 h post infection (h.p.i), time-points previously shown to be sufficient for completion of the invasion events. Enumeration of colony forming units (cfu) recovered from infected bladders indicated that compared to wt UTI89, UTI89ΔqseC had significantly lower overall bacterial titers (intracellular and luminal) at both time-points (FIG. 52A). Treatment of infected bladders with gentamicin to eradicate the luminal bacterial population but leave the intracellular population unharmed revealed decreased intracellular numbers for UTI89ΔqseC (FIG. 52B). Thus, these data indicate that deletion of qseC affects the ability of UTI89 to initiate infection by compromising its ability to colonize and invade the host bladder.

Example 38

Expression of Type 1 Pili Rescues the Adherence Properties of UTI89ΔqseC In Vitro, but does not Influence Other ΔqseC-Related Defects Attenuation of UTI89ΔqseC is linked to reduced bacterial internalization due to decreased type 1 pili production. Therefore, it was investigated whether restoration of type 1 pili expression alone would be sufficient to overcome the in vivo defects of UTI89ΔqseC. It was previously reported that in the absence of QseC the phase-variable fim promoter driving type 1 pili expression, fimS, is primarily switched to the OFF orientation. Therefore, fimS was locked in the ON orientation in the chromosome of wt UTI89 and UTI89ΔqseC to attain expression of type 1 pili independently of QseC (FIG. 53A). Electron microscopy revealed that the resulting strains, UTI89_LON and UTI89ΔqseC_LON, were not hyper-piliated, but rather a larger population of piliated versus non-piliated bacteria was observed compared to wt UTI89 (data not shown). UTI89_LON and UTI89ΔqseC_LON exhibited comparable mannose-sensitive hemagglutination (HA) properties, which were higher than wt UTI89 since inversion of the promoter to the OFF state can no longer occur (FIG. 53B).

Consistently, western blot analyses probing for FimA, the major type 1 pilus subunit, verified that type 1 pili production in UTI89ΔqseC_LON is comparable to UTI89_LON, but again, higher than wt UTI89 (FIG. 53C).

Example 39

Dual Inhibition of Type 1 Pili and QseC Potentiates UPEC Elimination from the Bladder Type 1 pili are sufficient for establishment of acute infection whereas QseC is a critical determinant for persistence in the bladder; thus targeting both factors could constitute an excellent means of potentiating UPEC clearance from the urinary tract by interfering with both the acute and chronic aspects of infection. Mannosides, compounds that bind with high affinity the mannose-binding pocket of the FimH adhesin at the tip of type 1 pili, are potent inhibitors of type 1 pili function. In particular, mannosides 6 and 8, the most potent mannosides tested, drastically reduce bacterial titers within 6 hours of oral delivery when used prophylactically or as a therapeutic strategy. These studies are a significant step towards a new anti-bacterial therapeutic; however, a fraction of the bacterial population persists after mannoside treatment and could lead to relapse, suggesting that mannoside effectiveness can be further optimized. It was therefore rationalized that co-inhibition of QseC may enhance mannoside efficacy. However, no QseC inhibitors are currently available. Although previous work has identified LED209 as an inhibitor of the kinase activity of QseC, It has been established that it is the disruption of the QseC phosphatase property that is responsible for the attenuation of a qseC mutant. To circumvent the lack of available QseC-specific phosphatase inhibitors, UTI89ΔqseC was used as a proxy to QseC inhibition and a prophylactic strategy was employed to investigate whether targeting both factors (type 1 pili and QseC) could effectively protect the host against UTI. Mice were pretreated with mannoside 6, and infected 30 min post treatment with wt UTI89 or UTI89ΔqseC. Mice treated with PBS prior to infection were included as controls. Bladder bacterial titers were enumerated at 2 weeks post infection as a measure of chronic infection. Compared to non-treated mice, there was a 2-log reduction in mannoside-treated mice infected with wt UTI89 (FIG. 54, UTI89 vs. UTI89_MAN) that was similar to the reduction observed in non-treated mice infected with UTI89ΔqseC (FIG. 54, UTI89_MAN vs. UTI89ΔqseC). Notably, in mannoside-treated animals infected with UTI89ΔqseC, bacterial reduction was further enhanced, as indicated by an additional 1.5-log drop compared to mannoside-treated animals infected with wt UTI89 (FIG. 54, UTI89_MAN vs. UTI89ΔqseC_MAN). These data strongly indicate that dual targeting of type 1 pili and QseC could potentiate UPEC elimination from the host bladder.

Materials and Methods for Examples 37-39

Strains, constructs and growth conditions

UTI89_LON and UTI89ΔqseC_LON were created using λ Red Recombinase, so as to mutate 7 out of 9 nucleotides in the left invertible repeat of the fim promoter in the chromosome. Bacteria were incubated in Luria Bertani (LB) media at 37° C. for 4 h under shaking conditions, sub-cultured (1:1000) in fresh LB media and incubated statically at 37° C. for 18 h.

Mouse Infections

Female C3H/HeN mice (Harlan), 7-9 weeks old, were used for all studies described below and in each case mice were infected with $10^7$ bacteria.

Short-term infections: Mice were transurethrally infected with bacteria carrying the GFP-expressing plasmid pCom-GFP, as previously described, and sacrificed at 1 and 3 h.p.i. Bladders were aseptically removed, homogenized and plated for total bacterial enumeration or gentamicin-treated to determine intracellular bacterial titers. Experiment was repeated 3 times.

Ex vivo gentamicin assay: Bladders were bisected and washed 3 times in 500 μl PBS. The washes were collected and plated for cfu enumeration, to determine luminal bacteria. Washed bladders were incubated for 90 min at 37° C. with 100 μg/ml gentamicin to kill adherent extracellular bacteria. Following wash (3×) with PBS, bladders were homogenized in 1 ml PBS and plated to determine intracellular bacterial titers. Two-tailed Mann-Whitney (P<0.05) was used for statistical analyses.

Acute infection studies: Mice were transurethrally infected with $10^7$ bacteria carrying the plasmid pCom-GFP as previously described. Experiments were repeated three times and statistically analyzed using two-tailed Mann-Whitney (P<0.05, considered significant).

Long-term infection studies: Mice were infected with chromosomally marked strains of wt UTI89, UTI89_LON, UTI89ΔqseC or UTI89ΔqseC_LON. Mice were sacrificed at 2 weeks post inoculation and organs were processed for cfu enumeration on LB and LB/Kanamycin agar plates. Experiment was repeated 2 times. Cumulative data from all experiments are presented.

Immunoblots, HA and Phase Assays

Bacteria were grown statically in LB for 18 h at 37° C. Immunoblots (using anti-type 1 pili antibody), HA and phase assays were performed on normalized cells ($OD_{600}$=1) as previously described.

qPCR Analyses

RNA extraction, DNase treatment and reverse transcription were prerformed using reagents and methods as reported by Kostakioti et al. Relative transcript abundance was determined by qPCR as previously described using aceB- or qseB-primers.

TABLE 15

| JMedChem 2010 Example | Patent Example | Compound Name | IUPAC Name | Structure | Molecular Formula | Molecular Weight (g/mol) | HAI Titer EC>90 (μM) | Biofilm IC50 [calculated] (approximated), μM | FimH EC50 (μM)-June 30 | FimH EC50 (μM) | Old Kd | ESI MS [M + H+] | 1H NMR (300 MHz, d4-METHANOL) δ ppm unless otherwise noted |
|---|---|---|---|---|---|---|---|---|---|---|---|---|---|
| 3r | 1 | 1ZFH100 | N-[3-[3,4,5-trihydroxy-6-(hydroxymethyl)tetrahydropyran-2-yl]oxyphenyl]acetamide | 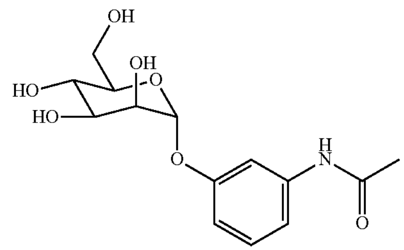 [SMILES: CC(=O)Nc1cccc(OC2OC(CO)C(O)C(O)C2O)c1] | C14H19NO7 | 313.3 | 12.000 | | 0.216 | 0.105 | | 314.3 | 2.11 (s, 3H) 3.54-3.65 (m, 1H) 3.67-3.82 (m, 3H) 3.86-3.95 (m, 1H) 4.00 (dd, J = 3.30, 1.92 Hz, 1H) 5.47 (d, J = 1.37 Hz, 1H) 6.79-6.96 (m, 1H) 7.05-7.31 (m, 2H) 7.43 (t, J = 2.06 Hz, 1H) |
| 3s | 2 | 1ZFH75 | N-[4-[3,4,5-trihydroxy-6-(hydroxymethyl)tetrahydropyran-2-yl]oxyphenyl]acetamide | 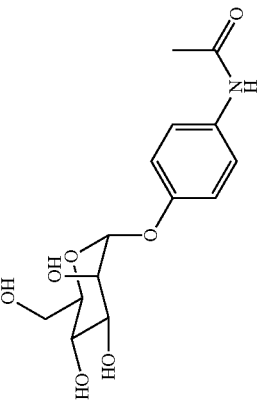 | C14H19NO7 | 313.3 | 8.000 | (~100) ~59.4 | 0.135 | 0.108 | 0.29 | 314 | 2.10 (s, 3H) 3.53-3.65 (m, 1H) 3.67-3.82 (m, 3H) 3.83-3.94 (m, 1H) 3.99 (dd, J = 3.43, 1.79 Hz, 1H) 5.42 (d, J = 1.65 Hz, 1H) 6.98-7.18 (m, 2H) 7.36-7.57 (m, 2H) |
| 3q | 3 | 1ZFH95 | N-[2-[3,4,5-trihydroxy-6-(hydroxymethyl)tetrahydropyran-2-yl]oxyphenyl]acetamide | 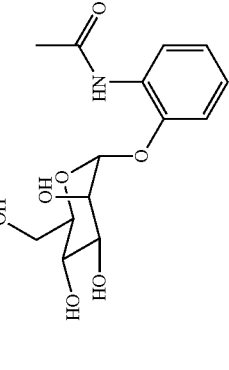 | C14H19NO7 | 313.3 | 125.000 | | | | 1.2 | 335.9 [M + Na+] | 2.17 (s, 3H) 3.56-3.67 (m, 1H) 3.67-3.83 (m, 3H) 3.93 (dd, J = 9.07, 3.30 Hz, 1H) 4.09 (br. s., 1H) 5.46 (s, 1H) 6.92-7.07 (m, 1H) 7.15 (t, J = 7.14 Hz, 1H) 7.34 (d, J = 7.97 Hz, 1H) 7.53-7.75 (m, 1H) |

TABLE 15-continued

| JMedChem 2010 Example | Compound Name | Patent Example | IUPAC Name | Structure | Molecular Formula | Molecular Weight (g/mol) | HAI Titer EC≥90 (μM) | Biofilm IC50 [calculated] (approximated), μM | FimH EC50 (μM)-June 30 | FimH EC50 (μM) | Old Kd | ESI MS [M + H⁺] | 1H NMR (300 MHz, d₄-METHANOL) δ ppm unless otherwise noted |
|---|---|---|---|---|---|---|---|---|---|---|---|---|---|
| 3o | 1ZFH65 | 4 | 4-[3,4,5-trihydroxy-6-(hydroxymethyl)tetrahydropyran-2-yl]oxybenzonitrile | 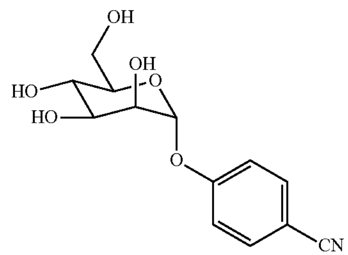 [SMILES: N#Cc1ccc(OC2OC(CO)C(O)C(O)C2O)cc1] | $C_{13}N_{15}NO_6$ | 281.3 | 30.000 | | | | 0.69 | 585.8 [2M + Na⁺] | 3.44-3.60 (m, 1H) 3.60-3.82 (m, 3H) 3.88 (dd, J = 9.34, 3.30 Hz, 1H) 3.96-4.19 (m, 1H) 5.48-5.74 (m, 1H) 7.27 (d, J = 8.79 Hz, 2H) 7.68 (d, J = 8.79 Hz, 2H) |
| 3m | 2ZFH108 | 5 | 2-[3,4,5-trihydroxy-6-(hydroxymethyl)tetrahydropyran-2-yl]oxybenzonitrile | 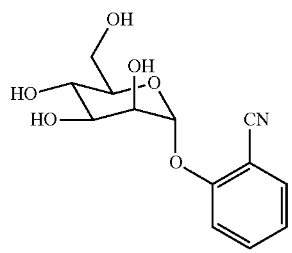 [SMILES: N#Cc1ccccc1OC1OC(CO)C(O)C(O)C1O] | $C_{13}N_{15}NO_6$ | 281.3 | 6.000 | | | | | 282 | 3.51-3.63 (m, 1H) 3.65-3.85 (m, 3H) 3.98 (dd, J = 9.48, 3.43 Hz, 1H) 4.10 (dd, J = 3.30, 1.92 Hz, 1H) 5.66 (d, J = 1.65 Hz, 1H) 7.15 (td, J = 7.55, 1.10 Hz, 1H) 7.48 (d, J = 8.24 Hz, 1H) 7.56-7.70 (m, 2H) |
| 3n | 1ZFH102 | 6 | 3-[3,4,5-trihydroxy-6-(hydroxymethyl)tetrahydropyran-2-yl]oxybenzonitrile | 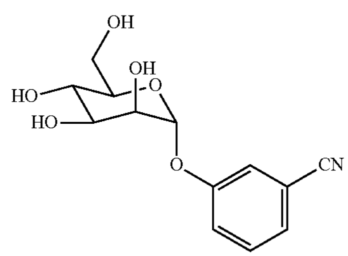 [SMILES: N#Cc1cccc(OC2OC(CO)C(O)C(O)C2O)c1] | $C_{13}N_{15}NO_6$ | 281.3 | 23.000 | (10-100) ~45.5 | 0.209 | 0.116 | 0.5 | 320.1 [M + K⁺] | 3.48-3.60 (m, 1H) 3.63-3.82 (m, 3H) 3.89 (dd, J = 9.48, 3.43 Hz, 1H) 4.02 (dd, J = 3.30, 1.92 Hz, 1H) 5.55 (d, J = 1.37 Hz, 1H) 7.30-7.57 (m, 4H) |

TABLE 15-continued

| JMedChem 2010 Example | Compound Name | Patent Example | IUPAC Name | Structure | Molecular Formula | Molecular Weight (g/mol) | HAI Titer EC>90 (µM) | Biofilm IC50 [calculated] (approximated) µM | FimH EC50 (µM)- June 30 | FimH EC50 (µM) | Old Kd | ESI MS [M + H⁺] | 1H NMR (300 MHz, d₄-METHANOL) δ ppm unless otherwise noted |
|---|---|---|---|---|---|---|---|---|---|---|---|---|---|
| 3k | 1ZFH53 | 7 | methyl 4-[3,4,5-trihydroxy-6-(hydroxymethyl)tetrahydropyran-2-yl]oxybenzoate | 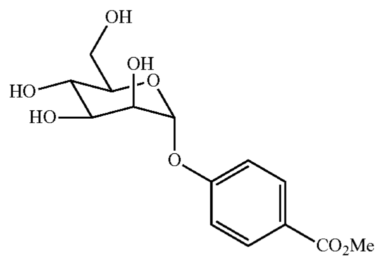 [SMILES: COC(=O)c1ccc(OC2OC(CO)C(O)C(O)C2O)cc1] | $C_{14}H_{18}O_8$ | 314.3 | 8.000 | (10-100) ~62 | 0.0696 | 0.058 | 0.2 | 337.4 [M + Na⁺] | (DEUTERIUM OXIDE) 3.61-3.69 (m, 1H) 3.70-3.80 (m, 3H) 3.90 (s, 3H) 4.06 (dd, J = 3.60, 9.30 Hz, 1H) 4.17 (dd, J = 3.30, 1.80 Hz, 1H), 5.72 (d, J = 1.80 Hz, 1H) 7.20-7.26 (m, 2H) 7.98-8.04 (m, 2H) |
| 3j | 1ZFH101 | 8 | methyl 3-[3,4,5-trihydroxy-6-(hydroxymethyl)tetrahydropyran-2-yl]oxybenzoate | 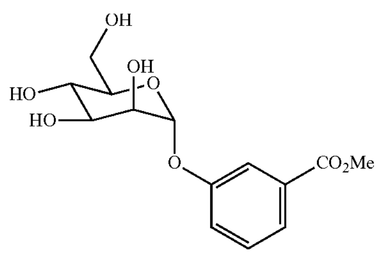 [SMILES: COC(=O)c1cccc(OC2OC(CO)C(O)C(O)C2O)c1] | $C_{14}H_{18}O_8$ | 314.3 | 6.000 | [15.0] | 0.1 | 0.068 | 0.3 | 336.8 [M + Na⁺] | 3.52-3.64 (m, 1H) 3.65-3.82 (m, 3H) 3.84-3.98 (m, 4H) 4.02 (dd, J = 3.30, 1.92 Hz, 1H) 5.54 (d, J = 1.65 Hz, 1H) 7.31-7.51 (m, 2H) 7.62-7.81 (m, 2H) |
| 3w | 1ZFH171 | 9 | methyl 2-[4-[3,4,5-trihydroxy-6-(hydroxymethyl)tetrahydropyran-2-yl]oxyphenyl]acetate | 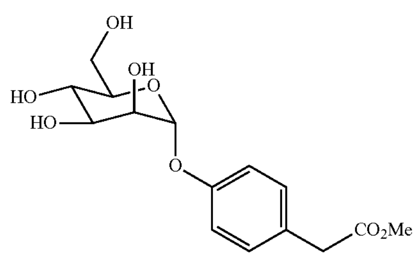 [SMILES: COC(=O)Cc1ccc(OC2OC(CO)C(O)C(O)C2O)cc1] | $C_{15}H_{20}O_8$ | 328.3 | 30.000 | (~100) | | | | 329 | 3.54-3.64 (m, 1H) 3.65-3.82 (m, 6H) 3.86-3.94 (m, 1H) 3.99 (dd, J = 3.30, 1.92 Hz, 1H) 5.45 (d, J = 1.65 Hz, 1H) 6.98-7.14 (m, 2H) 7.20 (d, J = 8.79 Hz, 2H) |

TABLE 15-continued

| JMedChem 2010 Example | Patent Example | Compound Name | IUPAC Name | Structure | Molecular Formula | Molecular Weight (g/mol) | HAI Titer EC>90 (µM) | Biofilm IC50 [calculated] (approximated) µM | FimH EC50 (µM)- June 30 | FimH EC50 (µM) | Old Kd | ESI MS [M + H⁺] | 1H NMR (300 MHz, d₄-METHANOL) δ ppm unless otherwise noted |
|---|---|---|---|---|---|---|---|---|---|---|---|---|---|
| 4 | 10 | 1ZFH177 | dimethyl 5-[3,4,5-trihydroxy-6-(hydroxymethyl)tetrahydropyran-2-yl]oxybenzene-1,3-dicarboxylate | 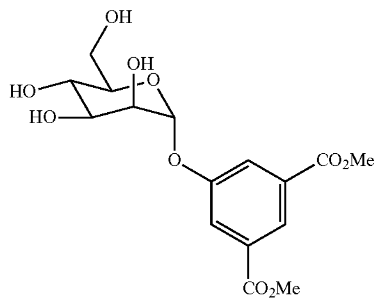 [SMILES: COC(=O)c1cc(OC2OC(CO)C(O)C(O)C2O)cc(C(=O)OC)c1] | $C_{16}H_{20}O_{10}$ | 372.3 | 2.000 | [1.9] | 0.0993 | 0.084 | | 373 | 3.49-3.62 (m, 1H) 3.66-3.85 (m, 3H) 3.86-4.01 (m, 7H) 4.02-4.11 (m, 1H) 5.62 (s, 1H) 7.94 (d, J = 1.10 Hz, 2H) 8.27 (s, 1H) |
| | 11 | 1ZFH187 | methyl 2-[2-hydroxy-5-[3,4,5-trihydroxy-6-(hydroxymethyl)tetrahydropyran-2-yl]oxyphenyl]acetate | | $C_{15}H_{20}O_9$ | 344.3 | 15.000 | | | | | 367.1 [M + Na+] | 3.52-3.84 (m, 9H) 3.87 (dd, J = 8.65, 3.16 Hz, 1H) 3.98 (dd, J = 3.30, 1.92 Hz, 1H) 5.30 (d, J = 1.65 Hz, 1H) 6.70 (d, J = 8.52 Hz, 1H) 6.83-7.04 (m, 2H) |
| 3c | 12 | 2ZFH100 | 2-(hydroxymethyl)-6-(3-nitrophenoxy)tetrahydropyran-3,4,5-triol | 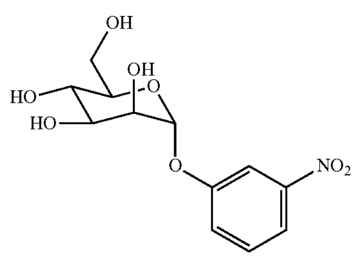 [SMILES: O=[N+]([O-])c1cccc(OC2OC(CO)C(O)C(O)C2O)c1] | $C_{12}H_{15}NO_8$ | 301.3 | 16.000 | | | | | 603.1 [2M + H⁺] | 3.51-3.60 (m, 1H) 3.67-3.81 (m, 3H) 3.87-3.95 (m, 1H) 4.05 (dd, J = 3.30, 1.65 Hz, 1H) 5.61 (d, J = 1.65 Hz, 1H) 7.50-7.60 (m, 2H) 7.85-7.94 (m, 1H) 7.97 (dt, J = 2.75, 1.10 Hz, 1H) |

TABLE 15-continued

| JMedChem 2010 Example | Compound Name | Patent Example | IUPAC Name | Structure | Molecular Formula | Molecular Weight (g/mol) | HAI Titer EC>90 (μM) | Biofilm IC50 [calculated] (approximated), μM | FimH EC50 (μM)-June 30 | FimH EC50 (μM) | Old Kd | ESI MS [M + H+] | 1H NMR (300 MHz, d4-METHANOL) δ ppm unless otherwise noted |
|---|---|---|---|---|---|---|---|---|---|---|---|---|---|
| 5b | 1ZFH152 | 13 | 2-(hydroxymethyl)-6-[(4-nitrophenyl)methoxy]tetrahydropyran-3,4,5-triol | 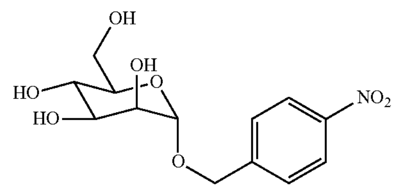 [SMILES: O=[N+]([O-])c1ccc(COC2OC(CO)C(O)C(O)C2O)cc1] | C13H17NO8 | 315.3 | 60.000 | | | | | 377.6 [M + Na+] | 3.53-3.65 (m, 2H) 3.65-3.80 (m, 2H) 3.82-3.88 (m, 1H) 3.89 (dd, J = 3.43, 1.79 Hz, 1H) 4.67 (d, J = 13.19 Hz, 1H) 4.92 (d, J = 13.19 Hz, 1H) 7.60-7.65 (m, 2H) 8.15-8.33 (m, 2H) |
| 3u | 1ZFH157 | 14 | 4-[3,4,5-trihydroxy-6-(hydroxymethyl)tetrahydropyran-2-yl]oxybenzamide | 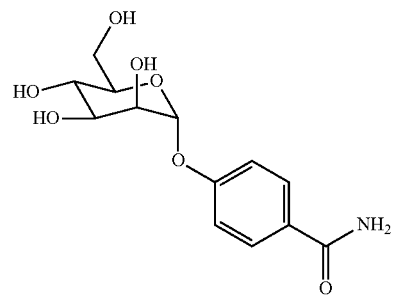 [SMILES: NC(=O)c1ccc(OC2OC(CO)C(O)C(O)C2O)cc1] | C13H17NO7 | 299.3 | 15.000 | | | | | 300.9 | 3.49-3.60 (m, 1H) 3.65-3.81 (m, 3H) 3.86-3.94 (m, 1H) 4.02 (dd, J = 3.43, 1.79 Hz, 1H) 5.57 (d, J = 1.65 Hz, 1H) 7.12-7.28 (m, 2H) 7.79-7.93 (m, 2H) |
| 3t | 2ZFH98 | 15 | 3-[3,4,5-trihydroxy-6-(hydroxymethyl)tetrahydropyran-2-yl]oxybenzamide | 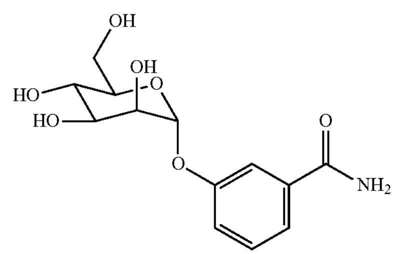 [SMILES: NC(=O)c1cccc(OC2OC(CO)C(O)C(O)C2O)c1] | C13H17NO7 | 299.3 | 16.000 | | | | | 597.9 [2M + H+] | 3.55-3.64 (m, 1H) 3.65-3.82 (m, 3H) 3.87-3.95 (m, 1H) 4.03 (dd, J = 3.30, 1.92 Hz, 1H) 7.26-7.33 (m, 1H) 7.39 (t, J = 7.83 Hz, 1H) 7.53 (dt, J = 7.55, 1.17 Hz, 1H) 7.58-7.65 (m, 1H) |

TABLE 15-continued

| JMedChem 2010 Example | Compound Name | Patent Example | IUPAC Name | Structure | Molecular Formula | Molecular Weight (g/mol) | HAI Titer EC>90 (μM) | Biofilm IC50 [calculated] (approximated) μM | FimH EC50 (μM)-June 30 | FimH EC50 (μM) | Old Kd | ESI MS [M + H+] | 1H NMR (300 MHz, d4-METHANOL) δ ppm unless otherwise noted |
|---|---|---|---|---|---|---|---|---|---|---|---|---|---|
| 5a | 1ZFH60 | 16 | 2-benzyloxy-6-(hydroxymethyl)tetrahydropyran-3,4,5-triol | 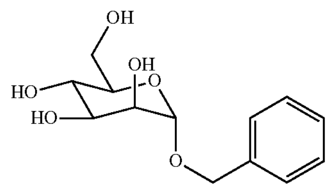 [SMILES: OCC1OC(OCc2ccccc2)C(O)C(O)C1O] | C13H18O6 | 270.3 | 60.000 | | 0.242 | 0.133 | 0.66 | 293.0 [M + Na+] | (DEUTERIUM OXIDE) 3.59-3.88 (m, 5H) 3.92 (dd, J = 3.30, 1.65 Hz, 1H) 4.55 (d, J = 11.54 Hz, 1H) 4.75 (d, J = 11.54 Hz, 1H) 4.95 (d, J = 1.65 Hz, 1H) 7.28-7.56 (m, 5H) |
| | 1ZFH178 | 17 | 2-(4-ethylphenoxy)-6-(hydroxymethyl)tetrahydropyran-3,4,5-triol | | C14H20O6 | 284.3 | 23.000 | (10-100) ~90 | | | | 307.1 [M + Na+] | 1.09-1.26 (m, 3H) 2.57 (q, J = 7.51 Hz, 2H) 3.55-3.67 (m, 1H) 3.67-3.84 (m, 3H) 3.84-3.96 (m, 1H) 4.00 (dd, J = 3.43, 1.79 Hz, 1H) 5.43 (d, J = 1.92 Hz, 1H) 6.93-7.06 (m, 2H) 7.06-7.24 (m, 2H) |
| | 1ZFH179 | 18 | 2-(hydroxymethyl)-6-(4-propylphenoxy)tetrahydropyran-3,4,5-triol | | C15H22O6 | 298.3 | 15.000 | (10-100) ~55 | | | | 321.2 [M + Na+] | 0.92 (t, J = 7.42 Hz, 3H) 1.52-1.70 (m, 2H) 2.45-2.61 (m, 2H) 3.57-3.67 (m, 1H) 3.67-3.83 (m, 3H) 3.83-3.94 (m, 1H) 3.99 (dd, J = 3.30, 1.92 Hz, 1H) 5.42 (d, J = 1.92 Hz, 1H) 6.94-7.05 (m, 2H) 7.05-7.15 (m, 2H) |

TABLE 15-continued

| JMedChem 2010 Example | Compound Name | Patent Example | IUPAC Name | Structure | Molecular Formula | Molecular Weight (g/mol) | HAI Titer EC≥90 (µM) | Biofilm IC50 [calculated] (approximated), µM | FimH EC50 (µM)- June 30 | FimH EC50 (µM) | Old Kd | ESI MS [M + H⁺] | 1H NMR (300 MHz, d₄-METHANOL) δ ppm unless otherwise noted |
|---|---|---|---|---|---|---|---|---|---|---|---|---|---|
| 3e | 2ZFH173 | 19 | 2-(hydroxymethyl)-6-(3-methylphenoxy)tetrahydropyran-3,4,5-triol | 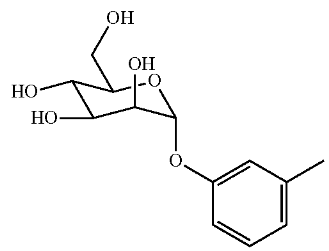 [SMILES: Cc1cccc(OC2OC(CO)C(O)C(O)C2O)c1] | C₁₃H₁₈O₆ | 270.3 | 4.000 | | | | | 540.9 [2M + H⁺] | 2.30 (s, 3H) 3.56-3.66 (m, 1H) 3.68-3.82 (m, 3H) 3.87-3.95 (m, 1H) 3.99 (dd, J = 3.43, 1.79 Hz, 1H) 5.45 (d, J = 1.92 Hz, 1H) 6.79-7.00 (m, 3H) 7.14 (t, J = 7.83 Hz, 1H) |
| 3f | 2ZFH175 | 20 | 2-(hydroxymethyl)-6-(4-methylphenoxy)tetrahydropyran-3,4,5-triol | 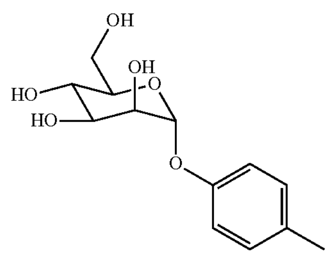 [SMILES: Cc1ccc(OC2OC(CO)C(O)C(O)C2O)cc1] | C₁₃H₁₈O₆ | 270.3 | 8.000 | | | | | 541.4 [2M + H⁺] | 2.26 (s, 3H) 3.57-3.66 (m, 1H) 3.68-3.82 (m, 3H) 3.86-3.95 (m, 1H) 3.99 (dd, J = 3.30, 1.92 Hz, 1H) 5.41 (d, J = 1.92 Hz, 1H) 6.95-7.04 (m, 2H) 7.05-7.13 (m, 2H) |
| 3p | 2ZFH176 | 21 | 2-(hydroxymethyl)-6-(4-methoxyphenoxy)tetrahydropyran-3,4,5-triol | 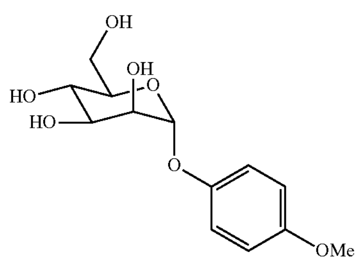 [SMILES: COc1ccc(OC2OC(CO)C(O)C(O)C2O)cc1] | C₁₃H₁₈O₇ | 286.3 | 8.000 | | | | | 308.7 [M + Na⁺] | 3.61-3.68 (m, 1H) 3.69-3.83 (m, 6H) 3.85-3.92 (m, 1H) 3.99 (dd, J = 3.30, 1.92 Hz, 1H) 5.34 (d, J = 1.92 Hz, 1H) 6.78-6.91 (m, 2H) 6.96-7.12 (m, 2H) |

TABLE 15-continued

| JMedChem 2010 Example | Patent Example | Compound Name | IUPAC Name | Structure | Molecular Formula | Molecular Weight (g/mol) | HAI Titer EC>90 (µM) | Biofilm IC50 [calculated] (approximated), µM | FimH EC50 (µM)-June 30 | FimH EC50 (µM) | Old Kd | ESI MS [M + H]+ | 1H NMR (300 MHz, d4-METHANOL) δ ppm unless otherwise noted |
|---|---|---|---|---|---|---|---|---|---|---|---|---|---|
| 3i | 22 | 2ZFH178 | 2-(4-chlorophenoxy)-6-(hydroxymethyl)tetrahydropyran-3,4,5-triol | 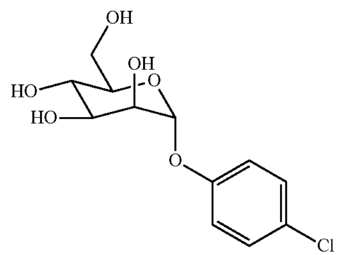 | C12H15ClO6 | 290.7 | 32.000 | | | | | 603.0 [2M + Na+] | 3.52-3.62 (m, 1H) 3.66-3.81 (m, 3H) 3.83-3.91 (m, 1H) 3.99 (dd, J = 3.43, 1.79 Hz, 1H) 5.45 (d, J = 1.65 Hz, 1H) 7.06-7.17 (m, 2H) 7.22-7.32 (m, 2H) |
| 3g | 23 | 2ZFH180 | 2-(2-chlorophenoxy)-6-(hydroxymethyl)tetrahydropyran-3,4,5-triol | 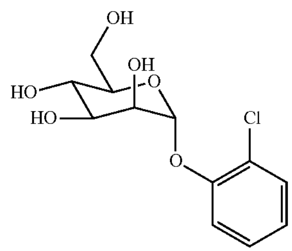 [SMILES: OCC1OC(Oc2ccccc2Cl)C(O)C(O)C1O] | C12H15ClO6 | 290.7 | 4.000 | | | | | 312.7 [M + Na+] | 3.60-3.69 (m, 1H) 3.70-3.81 (m, 3H) 3.98 (d, J = 9.20, 3.43 Hz, 1H) 4.10 (dd, J = 3.30, 1.92 Hz, 1H) 5.53 (d, J = 1.65 Hz, 1H) 7.00 (td, J = 7.69, 1.37 Hz, 1H) 7.25 (ddd, J = 8.24, 7.42, 1.65 hz, 1H) 7.32-7.41 (m, 2H) |
| 3h | 24 | 2ZFH181 | 2-(3-chlorophenoxy)-6-(hydroxymethyl)tetrahydropyran-3,4,5-triol | 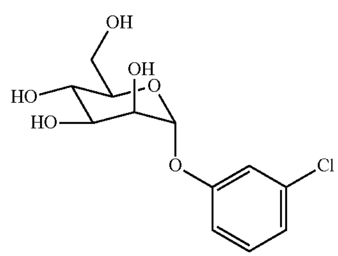 [SMILES: OCC1OC(Oc2cccc(Cl)c2)C(O)C(O)C1O] | C12H15ClO6 | 290.7 | 8.000 | | | | | 328.6 [M + K+] | 3.51-3.61 (m, 1H) 3.67-3.81 (m, 3H) 3.84-3.92 (m, 1H) 4.00 (dd, J = 2.88, 2.06 Hz, 1H) 5.48 (d, J = 1.65 Hz, 1H) 6.97-7.09 (m, 2H) 7.12-7.18 (m, 1H) 7.21-7.30 (m, 2H) |

TABLE 15-continued

| JMedChem 2010 Example | Compound Name | Patent Example | IUPAC Name | Structure | Molecular Formula | Molecular Weight (g/mol) | HAI Titer EC>90 (µM) | Biofilm IC50 [calculated] (approximated), µM | FimH EC50 (µM)- June 30 | FimH EC50 (µM) | Old Kd | ESI MS [M + H+] | 1H NMR (300 MHz, d4-METHANOL) δ ppm unless otherwise noted |
|---|---|---|---|---|---|---|---|---|---|---|---|---|---|
| | 2ZFH46 | 25 | 2-(4-bromophenoxy)-6-(hydroxymethyl)tetrahydropyran-3,4,5-triol | | $C_{12}H_{15}BrO_6$ | 335.2 | 32.000 | | | | | 669 [2M + H]+ | 3.48-3.62 (m, 1H) 3.63-3.82 (m, 3H) 3.82-3.92 (m, 1H) 3.99 (dd, J = 3.30, 1.92 Hz, 1H) 5.45 (d, J = 1.65 Hz, 1H) 6.96-7.14 (m, 2H) 7.34-7.48 (m, 2H) |
| | 1ZFH274 | 26 | 2-[3,5-bis(trifluoromethyl)phenoxy]-6-(hydroxymethyl)tetrahydropyran-3,4,5-triol | | $C_{14}H_{14}F_6O_6$ | 392.2 | 32.000 | | | | | 415.1 [M + Na+] | 3.53 (ddd, J = 9.61, 5.49, 2.75 Hz, 1H) 3.63-3.82 (m, 3H) 3.85-3.95 (m, 1H) 4.06 (dd, J = 3.30, 1.92 Hz, 1H) 5.65 (d, J = 1.65 Hz, 1H) 7.60 (s, 1H) 7.70 (s, 2H) |
| | 1ZFH282 | 27 | 2-(hydroxymethyl)-6-(3,4,5-trifluorophenoxy)tetrahydropyran-3,4,5-triol | | $C_{12}H_{13}F_3O_6$ | 310.2 | 125.000 | | | | | 333.1 [M + Na+] | 3.52 (ddd, J = 9.61, 5.77, 2.47 Hz, 1H) 3.65-3.79 (m, 3H) 3.79-3.89 (m, 1H) 3.99 (dd, J = 3.30, 1.92 Hz, 1H) 5.44 (d, J = 1.65 Hz, 1H) 6.85-7.04 (m, 2H) |

TABLE 15-continued

| JMedChem 2010 Example | Compound Name | Patent Example | IUPAC Name | Structure | Molecular Formula | Molecular Weight (g/mol) | HAI Titer EC>90 (μM) | Biofilm IC50 [calculated] (approximated), μM | FimH EC50 (μM)- June 30 | FimH EC50 (μM) | Old Kd | ESI MS [M + H+] | 1H NMR (300 MHz, d4-METHANOL) δ ppm unless otherwise noted |
|---|---|---|---|---|---|---|---|---|---|---|---|---|---|
| 7b | 1ZFH185 | 28 | 2-(hydroxymethyl)-6-(2-naphthyloxy)tetrahydropyran-3,4,5-triol | 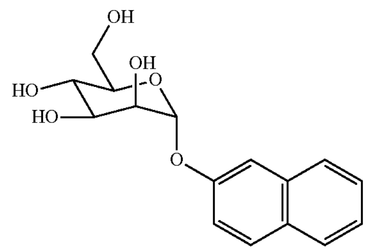 [SMILES: OCC1OC(Oc2ccc3ccccc3c2)C(O)C(O)C1O] | C16H18O6 | 306.3 | 6.000 | | | | | 307 | 3.60-3.69 (m, 1H), 3.70-3.87 (m, 3H), 3.97 (dd, J = 9.34, 3.57 Hz, 1H) 4.07 (dd, J = 3.43, 1.79 Hz, 1H) 5.63 (d, J = 1.65 Hz, 1H), 7.24 (dd, J = 8.79, 2.47 Hz, 1H), 7.30-7.38 (m, 1H), 7.39-7.48 (m, 1H), 7.57 (d, J = 2.47 Hz, 1H) 7.71-7.90 (m, 3H) |
| 8e | 1ZFH253 | 29 | methyl 3-[4-[3,4,5-trihydroxy-6-(hydroxymethyl)tetrahydropyran-2-yl]oxyphenyl]benzoate | 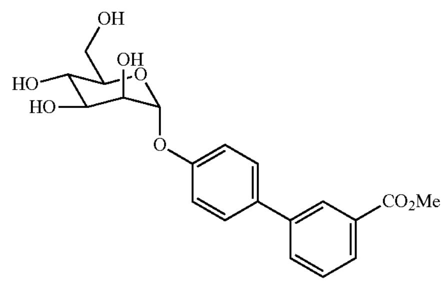 [SMILES: COC(=O)c1cccc(-c2ccc(OC3OC(CO)C(O)C(O)C3O)cc2)c1] | C20H22O8 | 390.4 | 1.000 | [.5] | 0.0527 | 0.051 | | 391.1 | 8.21 (m, 1H), 7.95 (m, 1H), 7.83 (m, 1H), 7.59 (m, 2H), 7.53 (m, 1H), 7.23 (m, 2H), 5.55 (d, J = 1.8 Hz, 1H), 4.03 (dd, J = 1.8, 3.3 Hz, 1H), 3.91-3.96 (m, 4H), 3.70-3.82 (m, 3H), 3.59-3.65 (m, 1H) |
| 7c | 1ZFH256 | 30 | 6-[3,4,5-trihydroxy-6-(hydroxymethyl)tetrahydropyran-2-yl]oxy-3a,7a-dihydro-3H-1,3-benzoxazol-2-one | 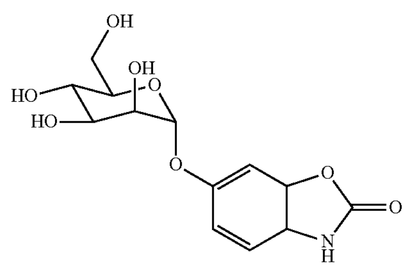 [SMILES: O=C1NC2C=CC(OC3OC(CO)C(O)C(O)C3O)=CC2O1] | C13H17NO8 | 315.3 | 4.000 | (10-25) ~15 | | | | 336 [M + Na+] | 3.59-3.67 (m, 1H), 3.67-3.83 (m, 3H), 3.84-3.91 (m, 1H), 4.01 (dd, J = 3.30, 1.92 Hz, 1H) 5.40 (d, J = 1.65 Hz, 1H), 6.89-7.04 (m, 2H), 7.13 (d, J = 2.20 Hz, 1H) |

TABLE 15-continued

| JMedChem 2010 Example | Compound Name | Patent Example | IUPAC Name | Structure | Molecular Formula | Molecular Weight (g/mol) | HAI Titer EC>90 (µM) | Biofilm IC50 [calculated] (approximated), µM | FimH EC50 (µM)- June 30 | FimH EC50 (µM) | Old Kd | ESI MS [M + H+] | 1H NMR (300 MHz, d4-METHANOL) δ ppm unless otherwise noted |
|---|---|---|---|---|---|---|---|---|---|---|---|---|---|
| 8d | 1ZFH263 | 31 | phenyl-[3-[3,4,5-trihydroxy-6-(hydroxymethyl)tetrahydropyran-2-yl]oxyphenyl]methanone | 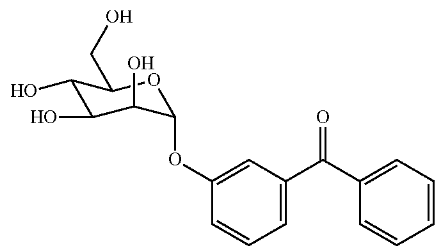 [SMILES: O=C(c1ccccc1)c1cccc(OC2OC(CO)C(O)C(O)C2O)c1] | C19H20O7 | 360.4 | 8.000 | | | | | 361.1 | 3.56-3.66 (m, 1H) 3.70-3.85 (m, 3H) 3.88-3.98 (m, 1H) 4.05 (dd, J = 3.43, 1.79 Hz, 1H) 5.56 (d, J = 1.65 Hz, 1H) 7.33-7.46 (m, 3H) 7.46-7.57 (m, 3H) 7.57-7.67 (m, 1H) 7.70-7.83 (m, 2H) |
| 8b | 1ZFH265 | 32 | methyl 4-[3-[3,4,5-trihydroxy-6-(hydroxymethyl)tetrahydropyran-2-yl]oxyphenyl]benzoate | 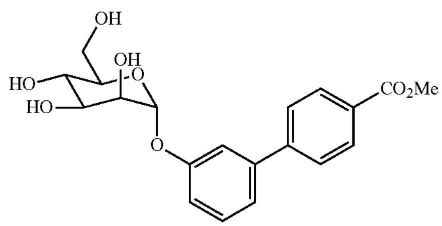 [SMILES: COC(=O)c1ccc(-c2cccc(OC3OC(CO)C(O)C(O)C3O)c2)cc1] | C20H22O8 | 390.4 | 6.000 | | | | | 391.6 | 3.60-3.84 (m, 4H) 3.86-3.98 (m, 4H) 4.04 (dd, J = 3.43, 1.79 Hz, 1H) 5.56 (d, J = 1.92 Hz, 1H) 7.17 (ddd, J = 8.04, 2.40, 1.10 Hz, 1H) 7.28-7.54 (m, 3H) 7.66-7.85 (m, 2H) 8.00-8.22 (m, 2H) |
| 8c | 1ZFH279 | 33 | 2-(hydroxymethyl)-6-(4-phenylphenoxy)tetrahydropyran-3,4,5-triol | 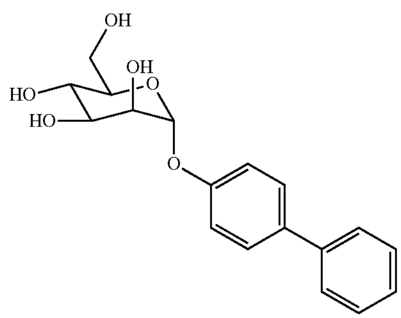 [SMILES: OCC1OC(Oc2ccc(-c3ccccc3)cc2)C(O)C(O)C1O] | C18H20O6 | 332.4 | 8.000 | | | | | 664.9 [2M + H+] | 3.57-3.67 (m, 1H) 3.69-3.84 (m, 3H) 3.87-3.97 (m, 1H) 4.03 (dd, J = 3.57, 1.92 Hz, 1H) 5.53 (d, J = 1.92 Hz, 1H) 7.15-7.23 (m, 2H) 7.24-7.32 (m, 1H) 7.35-7.45 (m, 2H) 7.49-7.60 (m, 4H) |

TABLE 15-continued

| JMedChem 2010 Example | Patent Example | Compound Name | IUPAC Name | Structure | Molecular Formula | Molecular Weight (g/mol) | HAI Titer EC>90 (µM) | Biofilm IC50 [calculated] (approximated), µM | FimH EC50 (µM)-June 30 | FimH EC50 (µM) | Old Kd | ESI MS [M + H+] | 1H NMR (300 MHz, d4-METHANOL) δ ppm unless otherwise noted |
|---|---|---|---|---|---|---|---|---|---|---|---|---|---|
| 8f | 34 | 2ZFH9 | methyl 4-[4-[3,4,5-trihydroxy-6-(hydroxymethyl)tetrahydropyran-2-yl]oxyphenyl]benzoate | 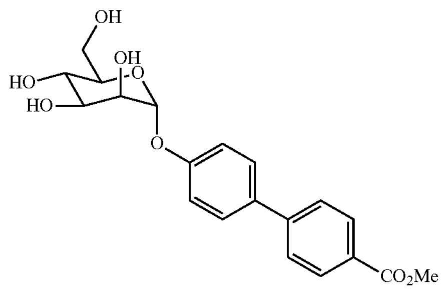 [SMILES: COC(=O)c1ccc(-c2ccc(OC3OC(CO)C(O)C(O)C3O)cc2)cc1] | C20H22O8 | 390.4 | 4.000 | (~1.5) | 0.0693 | 0.049 | | 429.5 [M + K+] | (METHANOL-d4/CHLOROFORM-d) 3.56-3.69 (m, 1H) 3.71-3.86 (m, 3H) 3.88-3.99 (m, 4H) 4.04 (dd, J = 3.30, 1.92 Hz, 1H) 5.54 (d, J = 1.65 Hz, 1H) 7.03-7.23 (m, 2H) 7.53-7.58 (m, 2H) 7.62 (d, J = 8.52 Hz, 2H) 8.04 (d, J = 8.52 Hz, 2H) |
| 15a | 35 | 1ZFH296 | dimethyl 5-[4-[3,4,5-trihydroxy-6-(hydroxymethyl)tetrahydropyran-2-yl]oxyphenyl]benzene-1,3-dicarboxylate | 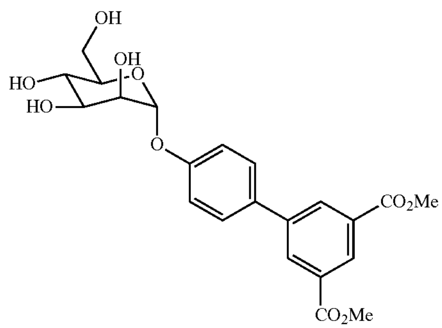 [SMILES: COC(=O)c1cc(C(=O)OC)cc(-c2ccc(OC3OC(CO)C(O)C(O)C3O)cc2)c1] | C22H24O10 | 448.4 | 0.15 N.V. | [.3] | 0.1139 | 0.040 | | 449.6 | 3.57-3.66 (m, 1H) 3.68-3.84 (m, 3H) 3.93 (dd, J = 9.34, 3.30 Hz, 1H) 3.97 (s, 6H) 4.04 (dd, J = 3.30, 1.92 Hz, 1H) 5.56 (d, J = 1.65 Hz, 1H) 7.21-7.36 (m, 2H) 7.59-7.72 (m, 2H) 8.42 (d, J = 1.65 Hz, 2H) 8.55 (t, J = 1.51 Hz, 1H) |
| 8a | 36 | 2ZFH110 | 2-(hydroxymethyl)-6-(2-phenylphenoxy)tetrahydropyran-3,4,5-triol | 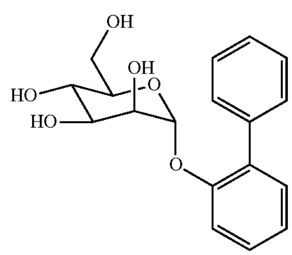 [SMILES: OCC1OC(Oc2ccccc2-c2ccccc2)C(O)C(O)C1O] | C18H20O6 | 332.4 | 62.000 | | | | | 665.1 [2M + H+] | 3.54 (td, J = 4.47, 2.88 Hz, 1H) 3.63-3.78 (m, 4H) 3.82 (t, J = 2.20 Hz, 1H) 5.40 (d, J = 1.92 Hz, 1H) 7.06-7.15 (m, 1H) 7.26-7.35 (m, 3H) 7.35-7.44 (m, 3H) 7.44-7.51 (m, 2H) |

TABLE 15-continued

| JMedChem 2010 Example | Compound Name | Patent Example | IUPAC Name | Structure | Molecular Formula | Molecular Weight (g/mol) | HAI Titer EC>90 (μM) | Biofilm IC50 [calculated] (approximated), μM | FimH EC50 (μM)- June 30 | FimH EC50 (μM) | Old Kd | ESI MS [M + H+] | 1H NMR (300 MHz, d4-METHANOL) δ ppm unless otherwise noted |
|---|---|---|---|---|---|---|---|---|---|---|---|---|---|
| 7d | 2ZFH297 | 37 | methyl 5-[3,4,5-trihydroxy-6-(hydroxymethyl)tetrahydropyran-2-yl]oxybenzothiophene-2-carboxylate | 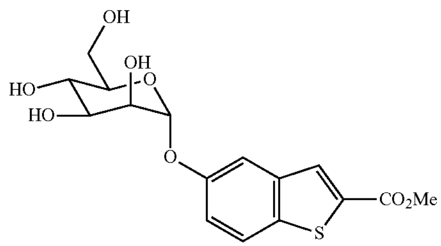 [SMILES: COC(=O)c1cc2cc(OC3OC(CO)C(O)C(O)C3O)ccc2s1] | C16H18O8S | 370.4 | 2.000 | | | | | 371.6 | 3.59-3.67 (m, 1H) 3.68-3.84 (m, 3H) 3.89-3.97 (m, 4H) 4.05 (dd, J = 3.30, 1.92 Hz, 1H) 5.55 (d, J = 1.65 Hz, 1H) 7.27 (dd, J = 8.79, 2.47 Hz, 1H) 7.72 (d, J = 2.47 Hz, 1H) 7.81 (d, J = 8.79 Hz, 1H) 8.01 (s, 1H) |
| 7e | 2ZFH304 | 38 | methyl 6-[3,4,5-trihydroxy-6-(hydroxymethyl)tetrahydropyran-2-yl]oxybenzothiophene-2-carboxylate | 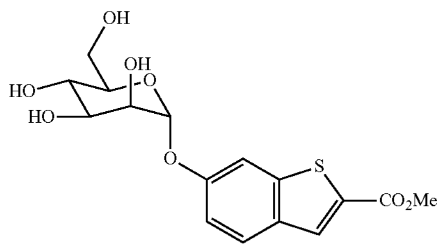 [SMILES: COC(=O)c1cc2ccc(OC3OC(CO)C(O)C(O)C3O)cc2s1] | C16H18O8S | 370.4 | 2.000 | | | | | 371.5 | 3.55-3.64 (m, 1H) 3.67-3.81 (m, 3H) 3.84-3.98 (m, 4H) 4.05 (dd, J = 3.43, 1.79 Hz, 1H) 5.58 (d, J = 1.65 Hz, 1H) 7.19 (dd, J = 8.79, 2.20 Hz, 1H) 7.85 (d, J = 2.20 Hz, 1H) 8.02 (s, 1H) |
| | 2ZFH244 | 39 | methyl 2-(3-methoxycarbonyl-phenyl)-5-[3,4,5-trihydroxy-6-(hydroxymethyl)tetrahydropyran-2-yl]oxy-benzoate | | C22H24O10 | 448.4 | 1.000 | | | | | 449 | 3.56-3.68 (m, 4H) 3.68-3.84 (m, 3H) 3.86-3.98 (m, 4H) 4.06 (dd, J = 3.30, 1.92 Hz, 1H) 5.60 (d, J = 1.92 Hz, 1H) 7.29-7.43 (m, 2H) 7.45-7.53 (m, 2H) 7.56 (d, J = 2.47 Hz, 1H) 7.84-7.92 (m, 1H) 7.93-8.04 (m, 1H) |

TABLE 15-continued

| JMedChem 2010 Example | Compound Name | Patent Example | IUPAC Name | Structure | Molecular Formula | Molecular Weight (g/mol) | HAI Titer EC>90 (µM) | Biofilm IC50 [calculated] (approximated) µM | FimH EC50 (µM)- June 30 | FimH EC50 (µM) | Old Kd | ESI MS [M + H]+ | 1H NMR (300 MHz, d4-METHANOL) δ ppm unless otherwise noted |
|---|---|---|---|---|---|---|---|---|---|---|---|---|---|
| 14b | 2ZFH6 | 40 | N-[3-[4-[3,4,5-trihydroxy-6-(hydroxymethyl)tetrahydropyran-2-yl]oxyphenyl]phenyl]acetamide | 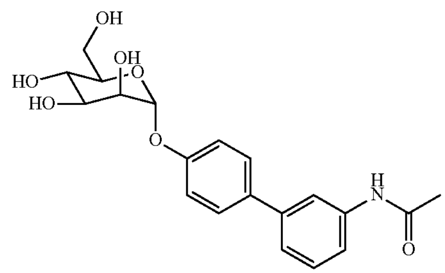 [SMILES: CC(=O)Nc1cccc(-c2ccc(OC3OC(CO)C(O)C(O)C3O)cc2)c1] | C20H23NO7 | 389.4 | 2.000 | (~3) | 0.0747 | 0.065 | | 390.2 | 2.14 (s, 3H) 3.63 (ddd, J = 7.28, 4.94, 2.33 Hz, 1H) 3.68-3.84 (m, 3H) 3.88-3.98 (m, 1H) 4.04 (dd, J = 3.43, 1.79 Hz, 1H) 5.53 (d, J = 1.65 Hz, 1H) 7.09-7.23 (m, 2H) 7.24-7.39 (m, 2H) 7.41-7.62 (m, 3H) 7.78 (t, J = 1.65 Hz, 1H) |
| | 1ZFH231 | 41 | 5-[3,4,5-trihydroxy-6-(hydroxymethyl)tetrahydropyran-2-yl]oxy-3H-benzofuran-2-one | | C14H16O8 | 312.3 | 8.000 | (~25) | | | | 313 | δ ppm 7.19 (m, 1H), 7.11 (m, 2H), 5.52 (d, J = 1.5 Hz, 1H), 4.15-4.18 (m, 1H), 3.97-4.05 (m, 1H), 3.68-3.88 (m, 6H) |
| 3v | 1ZFH236 | 42 | [3-[3,4,5-trihydroxy-6-(hydroxymethyl)tetrahydropyran-2-yl]oxyphenyl] acetate | 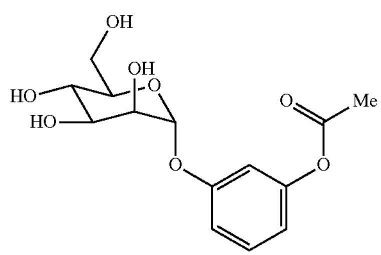 [SMILES: CC(=O)Oc1cccc(OC2OC(CO)C(O)C(O)C2O)c1] | C14H18O8 | 314.3 | 16.000 | | | | | 314.9 | 7.30 (t, J = 8.1 Hz, 1H), 7.00 (m, 1H), 6.90 (t, J = 2.1 Hz, 1H), 6.76 (m, 1H), 5.47 (d, J = 1.8 Hz, 1H), 4.00 (dd, J = 1.8, 3.3 Hz, 1H), 3.88 (dd, J = 3.3, 9.3 Hz, 1H), 3.68-3.79 (m, 3H), 3.54-3.61 (m, 1H) |

TABLE 15-continued

| JMedChem 2010 Example | Compound Name | Patent Example | IUPAC Name | Structure | Molecular Formula | Molecular Weight (g/mol) | HAI Titer EC>90 (µM) | Biofilm IC50 [calculated] (approximated), µM | FimH EC50 (µM)-June 30 | FimH EC50 (µM) | Old Kd | ESI MS [M + H+] | 1H NMR (300 MHz, d4-METHANOL) δ ppm unless otherwise noted |
|---|---|---|---|---|---|---|---|---|---|---|---|---|---|
| 31 | 1ZFH216 | 43 | 3-[3,4,5-trihydroxy-6-(hydroxymethyl)tetrahydropyran-2-yl]oxybenzoic acid | 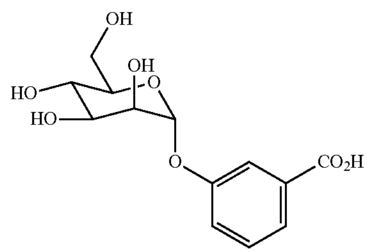 [SMILES: O=C(O)c1cccc(OC2OC(CO)C(O)C(O)C2O)c1] | C13H16O8 | 300.3 | 60.000 | | | | | 323.1 [M + Na+] | 3.52-3.64 (m, 1H) 3.67-3.83 (m, 3H) 3.85-3.96 (m, 1H) 4.03 (dd, J = 3.43, 1.79 Hz, 1H) 5.55 (d, J = 1.65 Hz, 1H) 7.32-7.46 (m, 2H) 7.64-7.78 (m, 2H) |
| 14c | 2ZFH22 | 44 | 3-[4-[3,4,5-trihydroxy-6-(hydroxymethyl)tetrahydropyran-2-yl]oxyphenyl]benzoic acid | 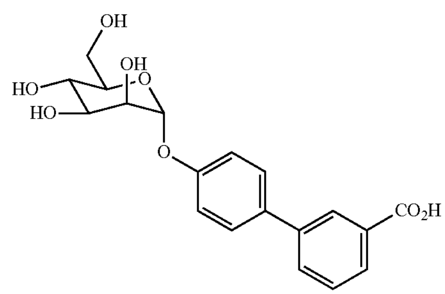 [SMILES: O=C(O)c1cccc(-c2ccc(OC3OC(CO)C(O)C(O)C3O)cc2)c1] | C19H20O8 | 376.4 | 4.000 | (~6) | 0.1449 | 0.053 | | 377.5 | 3.50-3.60 (m, 1H) 3.61-3.77 (m, 3H) 3.81-3.91 (m, 1H) 3.96 (dd, J = 3.16, 1.79 Hz, 1H) 5.47 (d, J = 1.65 Hz, 1H) 7.11-7.20 (m, 2H) 7.44 (t, J = 7.69 Hz, 1H) 7.52 (m, J = 8.79 Hz, 2H) 7.73 (d, J = 7.69 Hz, 1H) 7.89 (d, J = 7.69 Hz, 1H) 8.09-8.20 (m, 1H) |
| 15c | 2ZFH24 | 45 | 5-[4-[3,4,5-trihydroxy-6-(hydroxymethyl)tetrahydropyran-2-yl]oxyphenyl]benzene-1,3-dicarboxylic acid | 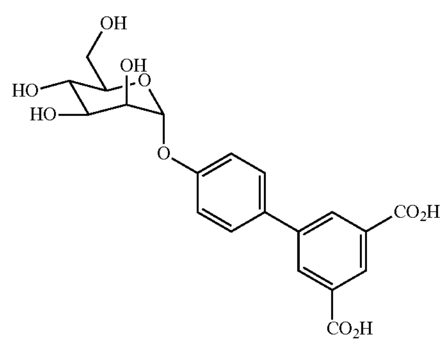 [SMILES: O=C(O)c1cc(C(=O)O)cc(-c2ccc(OC3OC(CO)C(O)C(O)C3O)cc2)c1] | C20H20O10 | 420.4 | 2.000 | (~6) | 0.086 | 0.070 | | 443 [M + Na+] | 3.59-3.67 (m, 1H) 3.70-3.84 (m, 3H) 3.94 (dd, J = 3.30, 9.30 Hz, 1H) 4.05 (dd, J = 3.30, 1.80 Hz, 1H) 5.56 (d, J = 1.80 Hz, 1H) 7.26 (m, 2H) 7.63 (m, 2H) 8.41 (d, J = 1.50 Hz, 2H) 8.57 (t, J = 1.50 Hz, 1H) |

TABLE 15-continued

| JMedChem 2010 Example | Compound Name | Patent Example | IUPAC Name | Structure | Molecular Formula | Molecular Weight (g/mol) | HAI Titer EC>90 (µM) | Biofilm IC50 [calculated] (approximated), µM | FimH EC50 (µM)-June 30 | FimH EC50 (µM) | Old Kd | ESI MS [M + H]+ | 1H NMR (300 MHz, d4-METHANOL) δ ppm unless otherwise noted |
|---|---|---|---|---|---|---|---|---|---|---|---|---|---|
|  | 2ZFH265 | 46 | methyl 2-[3-(methylcarbamoyl)phenyl]-5-[3,4,5-trihydroxy-6-(hydroxymethyl)tetrahydropyran-2-yl]oxy-benzoate |  | C22H25NO9 | 447.4 | 2.000 |  |  |  |  | 448.7 | 2.92 (s, 3H) 3.54-3.67 (m, 4H) 3.68-3.84 (m, 3H) 3.88-3.98 (m, 1H) 4.05 (dd, J = 3.43, 1.79 Hz, 1H) 5.59 (d, J = 1.92 Hz, 1H) 7.32-7.43 (m, 3H) 7.43-7.51 (m, 1H) 7.51-7.61 (m, 1H) 7.70-7.83 (m, 2H) |
|  | 2ZFH266 | 47 | N-methyl-2-[3-(methylcarbamoyl)phenyl]-5-[3,4,5-trihydroxy-6-(hydroxymethyl)tetrahydropyran-2-yl]oxy-benzamide |  | C22H26N2O8 | 446.4 | 12.000 |  |  |  |  | 447.7 | 2.68 (s, 3H) 2.93 (s, 3H) 3.58-3.68 (m, 1H) 3.68-3.83 (m, 3H) 3.89-3.99 (m, 1H) 4.06 (dd, J = 3.30, 1.92 Hz, 1H) 5.59 (d, J = 1.92 Hz, 1H) 7.21-7.35 (m, 2H) 7.35-7.56 (m, 3H) 7.75 (dt, J = 7.14, 1.79 Hz, 1H) 7.79-7.90 (m, 1H) |
| 14v | 2ZFH32 | 48 | 3-[4-[3,4,5-trihydroxy-6-(hydroxymethyl)tetrahydropyran-2-yl]oxyphenyl]benzamide | 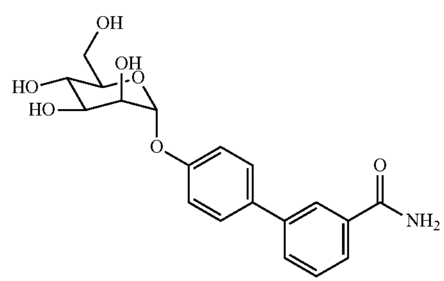 [SMILES: NC(=O)c1cccc(-c2ccc(OC3OC(CO)C(O)C(O)C3O)cc2)c1] | C19H21NO7 | 375.4 | 2.000 | (~3) | 0.1364 | 0.057 |  | 376.3 | 3.58-3.66 (m, 1H), 3.69-3.82 (m, 3H), 3.93 (dd, J = 9.30, 3.30 Hz, 1H), 4.03 (dd, J = 3.30, 1.50 Hz, 1H), 5.54 (d, J = 1.80 Hz, 1H), 7.18-7.26 (m, 2H), 7.51 (t, J = 7.80 Hz, 1H), 7.58-7.66 (m, 2H), 7.73-7.83 (m, 2H), 8.10 (t, J = 1.5 Hz, 1H) |

TABLE 15-continued

| JMedChem 2010 Example | Compound Name | Patent Example | IUPAC Name | Structure | Molecular Formula | Molecular Weight (g/mol) | HAI Titer EC>90 (μM) | Biofilm IC50 [calculated] (approximated), μM | FimH EC50 (μM)-June 30 | FimH EC50 (μM) | Old Kd | ESI MS [M + H]+ | 1H NMR (300 MHz, d4-METHANOL) δ ppm unless otherwise noted |
|---|---|---|---|---|---|---|---|---|---|---|---|---|---|
| 14a | 2ZFH50 | 49 | N-methyl-3-[4-[3,4,5-trihydroxy-6-(hydroxymethyl)tetrahydropyran-2-yl]oxyphenyl]benzamide | 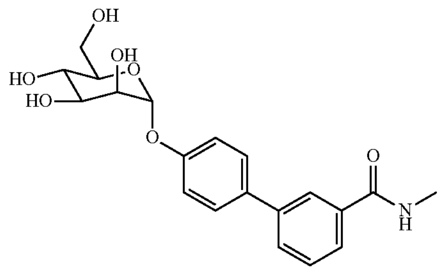 [SMILES: CNC(=O)c1cccc(-c2ccc(OC3OC(CO)C(O)C(O)C3O)cc2)c1] | C20H23NO7 | 389.4 | 0.500 | 0.8 | 0.07 | 0.080 | | 390.1 | 2.94 (s, 3H) 3.63 (ddd, J = 7.28, 4.81, 2.47 Hz, 1H) 3.69-3.85 (m, 3H) 3.87-3.98 (m, 1H) 4.04 (dd, J = 3.30, 1.65 Hz, 1H) 5.54 (d, J = 1.92 Hz, 1H) 7.10-7.27 (m, 2H) 7.42-7.53 (m, 1H) 7.54-7.65 (m, 2H) 7.66-7.79 (m, 2H) 8.01 (t, J = 1.79 Hz, 1H) |
| 15b | 2ZFH56 | 50 | N1,N3-dimethyl-5-[4-[3,4,5-trihydroxy-6-(hydroxymethyl)tetrahydropyran-2-yl]oxyphenyl]benzene-1,3-dicarboxamide | 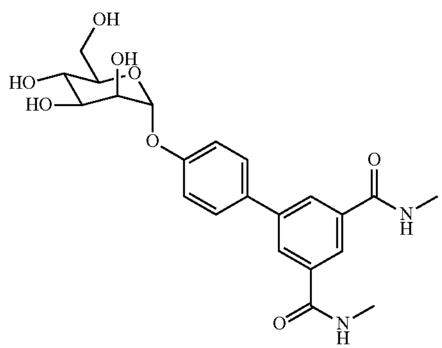 [SMILES: CNC(=O)c1cc(C(=O)NC)cc(-c2ccc(OC3OC(CO)C(O)C(O)C3O)cc2)c1] | C22H26N2O8 | 446.4 | 0.370 | 0.4 | 0.105 | 0.070 | | 447.4 | 2.96 (s, 6H) 3.61-3.66 (m, 1H) 3.67-3.84 (m, 3H) 3.86-3.97 (m, 1H) 4.04 (dd, J = 3.30, 1.92 Hz, 1H) 5.56 (d, J = 1.92 Hz, 1H) 7.21-7.34 (m, 2H) 7.63-7.74 (m, 2H) 8.13-8.26 (m, 3H) |
| | 4ZFH84 | 51 | 1-[5-[4-[3,4,5-trihydroxy-6-(hydroxymethyl)tetrahydropyran-2-yl]oxyphenyl]-3-pyridyl]ethanone | | C19H22N2O7 | 390.4 | 0.500 | | | | | 391.1 | 2.99 (s, 3H) 3.53-3.66 (m, 1H) 3.68-3.84 (m, 3H) 3.87-3.96 (m, 1H) 4.04 (dd, J = 3.30, 1.92 Hz, 1H) 5.59 (d, J = 1.65 Hz, 1H) 7.22-7.40 (m, 2H) 7.65-7.86 (m, 2H) 8.68-8.83 (m, 1H) 8.99 (br. s., 1H) 9.06 (br. s., 1H) |

TABLE 15-continued

| JMedChem 2010 Example | Patent Example | Compound Name | IUPAC Name | Structure | Molecular Formula | Molecular Weight (g/mol) | HAI Titer EC>90 (µM) | Biofilm IC50 [calculated] (approximated), µM | FimH EC50 (µM)-June 30 | FimH EC50 (µM) | Old Kd | ESI MS [M + H]+ | 1H NMR (300 MHz, d4-METHANOL) δ ppm unless otherwise noted |
|---|---|---|---|---|---|---|---|---|---|---|---|---|---|
| 14w | 52 | 3ZFI17 | 2-(hydroxymethyl)-6-[4-[2-(trifluoromethyl)phenyl]phenoxy]tetrahydropyran-3,4,5-triol | 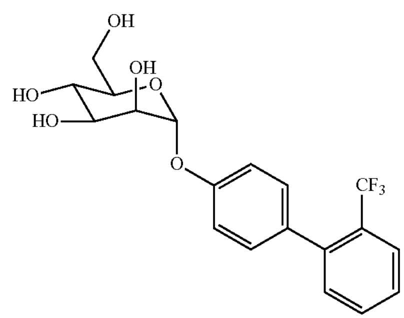 [SMILES: OCC1OC(Oc2ccc(-c3ccccc3C(F)(F)F)cc2)C(O)C(O)C1O] | C19H19F3O6 | 400.3 | 8.000 | | | | | 801.8 [2M + H+] | 3.60-3.70 (m, 1H) 3.70-3.86 (m, 3H) 3.93 (dd, J = 9.34, 3.30 Hz, 1H) 4.04 (dd, J = 3.30, 1.92 Hz, 1H) 5.54 (d, J = 1.65 Hz, 1H) 7.12-7.30 (m, 4H) 7.34 (d, J = 6.87 Hz, 1H) 7.47-7.58 (m, 1H) 7.62 (t, J = 7.14 Hz, 1H) 7.76 (d, J = 7.97 Hz, 1H) |
| 14x | 53 | 3ZFH120 | 2-(hydroxymethyl)-6-[4-[3-(trifluoromethyl)phenyl]phenoxy]tetrahydropyran-3,4,5-triol | 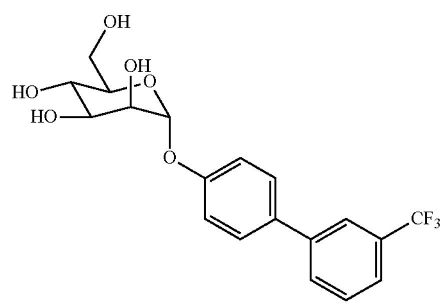 | C19H19F3O6 | 400.3 | 2.000 | | | | | 801.8 [2M + H+] | 3.56-3.66 (m, 1H) 3.67-3.84 (m, 3H) 3.93 (dd, J = 9.34, 3.57 Hz, 1H) 4.03 (dd, J = 3.43, 1.79 Hz, 1H) 5.55 (d, J = 1.65 Hz, 1H) 7.17-7.32 (m, 2H) 7.55-7.66 (m, 4H) 7.79-7.89 (m, 2H) |

TABLE 15-continued

| JMedChem 2010 Example | Compound Name | Patent Example | IUPAC Name | Structure | Molecular Formula | Molecular Weight (g/mol) | HAI Titer EC>90 (μM) | Biofilm IC50 [calculated] (approximated), μM | FimH EC50 (μM)- June 30 | FimH EC50 (μM) | Old Kd | ESI MS [M + H]+ | 1H NMR (300 MHz, d4-METHANOL, δ ppm unless otherwise noted) |
|---|---|---|---|---|---|---|---|---|---|---|---|---|---|
| 14y | 3ZFH29 | 54 | 2-[4-(3-fluorophenyl)phenoxy]-6-(hydroxymethyl)tetrahydropyran-3,4,5-triol | 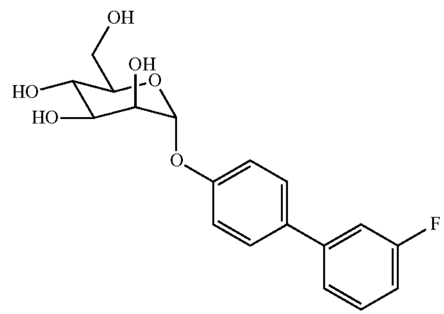 [SMILES: OCC1OC(Oc2ccc(-c3cccc(F)c3)cc2)C(O)C(O)C1O] | C18H19FO6 | 350.3 | 6.000 | | | | | 701.8 [2M + H]+ | 3.56-3.67 (m, 1H) 3.68-3.85 (m, 3H) 3.87-3.97 (m, 1H) 4.03 (dd, J = 3.43, 1.79 Hz, 1H) 5.54 (d, J = 1.65 Hz, 1H) 6.96-7.08 (m, 1H) 7.14-7.24 (m, 2H) 7.26-7.35 (m, 1H) 7.36-7.46 (m, 2H) 7.51-7.62 (m, 2H) |
| 14g | 3ZFH114 | 55 | 2-(hydroxymethyl)-6-[4-[2-(hydroxymethyl)phenyl]phenoxy]tetrahydropyran-3,4,5-triol | 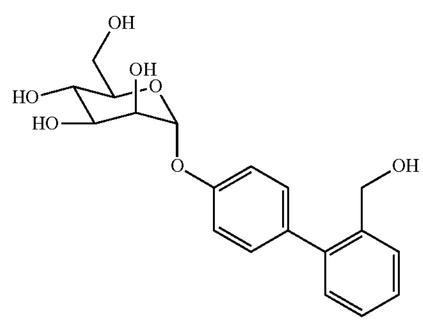 [SMILES: OCc1ccccc1-c1ccc(OC2OC(CO)C(O)C(O)C2O)cc1] | C19H22O7 | 362.4 | 16.000 | | | | | 363.5 | 3.59-3.69 (m, 1H) 3.70-3.83 (m, 3H) 3.89-3.98 (m, 1H) 4.04 (dd, J = 3.57, 1.92 Hz, 1H) 4.51 (s, 2H) 5.53 (d, J = 1.65 Hz, 1H) 7.14-7.25 (m, 3H) 7.27-7.43 (m, 4H) 7.55 (dd, J = 7.55, 1.51 Hz, 1H) |

TABLE 15-continued

| JMedChem 2010 Example | Patent Example | Compound Name | IUPAC Name | Structure | Molecular Formula | Molecular Weight (g/mol) | HAI Titer EC>90 (μM) | Biofilm IC50 [calculated] (approximated), μM | FimH EC50 (μM)- June 30 | FimH EC50 (μM) | Old Kd | ESI MS [M + H+] | 1H NMR (300 MHz, d4-METHANOL) δ ppm unless otherwise noted |
|---|---|---|---|---|---|---|---|---|---|---|---|---|---|
| 14h | 56 | 3ZFH18 | 2-(hydroxymethyl)-6-[4-[3-(hydroxymethyl)phenyl]phenoxy]tetrahydropyran-3,4,5-triol | 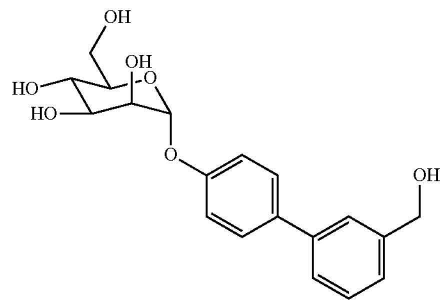 [SMILES: OCc1cccc(-c2ccc(OC3OC(CO)C(O)C(O)C3O)cc2)c1] | C19H22O7 | 362.4 | 3.000 | | | | | 363.5 | 3.59-3.68 (m, 1H) 3.69-3.84 (m, 3H) 3.89-3.97 (m, 1H) 4.03 (dd, J = 3.43, 1.79 Hz, 1H) 4.66 (s, 2H) 5.53 (d, J = 1.65 Hz, 1H) 7.15-7.23 (m, 2H) 7.26-7.33 (m, 1H) 7.38 (t, J = 7.42 Hz, 1H) 7.44-7.50 (m, 1H) 7.52-7.61 (m, 3H) |
| 14i | 57 | 3ZFH24 | 2-(hydroxymethyl)-6-[4-[4-(hydroxymethyl)phenyl]phenoxy]tetrahydropyran-3,4,5-triol | 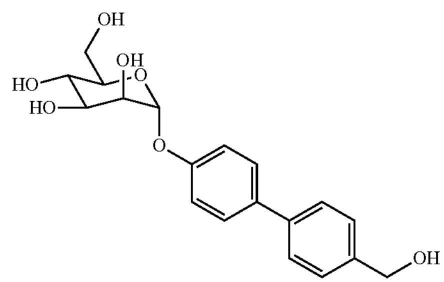 [SMILES: OCc1ccc(-c2ccc(OC3OC(CO)C(O)C(O)C3O)cc2)cc1] | C19H22O7 | 362.4 | 6.000 | | | | | 363.5 | 3.58-3.69 (m, 1H) 3.69-3.83 (m, 3H) 3.89-3.98 (m, 1H) 4.03 (dd, J = 3.30, 1.92 Hz, 1H) 4.63 (s, 2H) 5.52 (d, J = 1.65 Hz, 1H) 7.14-7.28 (m, 2H) 7.40 (d, J = 8.52 Hz, 2H) 7.50-7.66 (m, 4H) |
| 14l | 58 | 3ZFH26 | 2-(hydroxymethyl)-6-[4-(4-hydroxyphenyl)phenoxy]tetrahydropyran-3,4,5-triol | 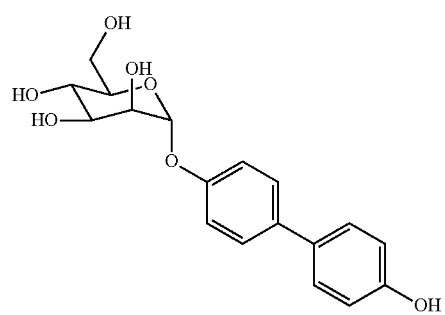 [SMILES: OCC1OC(Oc2ccc(-c3ccc(O)cc3)cc2)C(O)C(O)C1O] | C18H20O7 | 348.4 | 6.000 | | | | | 697.6 [2M + H+] | 3.58-3.68 (m, 1H) 3.69-3.84 (m, 3H) 3.86-3.97 (m, 1H) 4.02 (dd, J = 3.43, 1.79 Hz, 1H) 5.49 (d, J = 1.92 Hz, 1H) 6.79-6.86 (m, 2H) 7.11-7.19 (m, 2H) 7.35-7.42 (m, 2H) 7.43-7.50 (m, 2H) |

TABLE 15-continued

| JMedChem 2010 Example | Patent Example | Compound Name | IUPAC Name | Structure | Molecular Formula | Molecular Weight (g/mol) | HAI Titer EC>90 (μM) | Biofilm IC50 [calculated] (approximated), μM | FimH EC50 (μM)-June 30 | FimH EC50 (μM) | Old Kd | ESI MS [M + H]+ | 1H NMR (300 MHz, d4-METHANOL) δ ppm unless otherwise noted |
|---|---|---|---|---|---|---|---|---|---|---|---|---|---|
| 14j | 59 | 3ZFH111 | 2-(hydroxymethyl)-6-[4-(2-hydroxyphenyl)phenoxy]tetrahydropyran-3,4,5-triol | 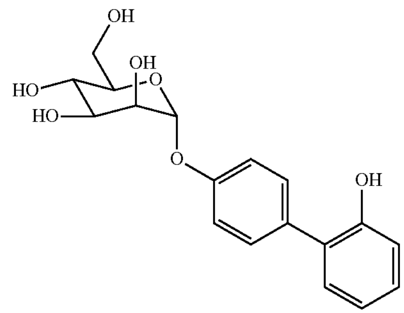 [SMILES: OCC1OC(Oc2ccc(-c3ccccc3O)cc2)C(O)C(O)C1O] | $C_{18}H_{20}O_7$ | 348.4 | 8.000 | | | | | 349.4 | 3.60-3.68 (m, 1H) 3.69-3.84 (m, 3H) 3.89-3.97 (m, 1H) 4.03 (dd, J = 3.30, 1.92 Hz, 1H) 5.52 (d, J = 1.65 Hz, 1H) 6.83-6.92 (m, 2H) 7.07-7.18 (m, 3H) 7.19-7.25 (m, 1H) 7.43-7.55 (m, 2H) |
| 14k | 60 | 3ZFH44 | 2-(hydroxymethyl)-6-[4-(3-hydroxyphenyl)phenoxy]tetrahydropyran-3,4,5-triol | 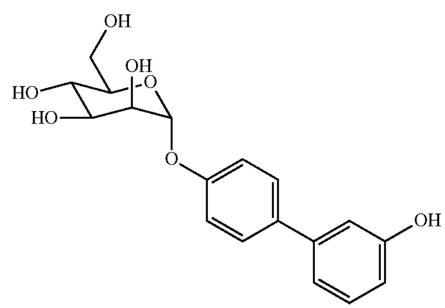 | $C_{18}H_{20}O_7$ | 348.4 | 4.000 | | | | | 349.3 | 3.56-3.67 (m, 1H) 3.68-3.83 (m, 3H) 3.88-3.96 (m, 1H) 4.03 (dd, J = 3.43, 1.79 Hz, 1H) 5.52 (d, J = 1.65 Hz, 1H) 6.73 (ddd, J = 8.10, 2.33, 1.10 Hz, 1H) 6.88-7.06 (m, 2H) 7.07-7.28 (m, 3H) 7.38-7.60 (m, 2H) |

TABLE 15-continued

| JMedChem 2010 Example | Patent Example | Compound Name | IUPAC Name | Structure | Molecular Formula | Molecular Weight (g/mol) | HAI Titer EC>90 (μM) | Biofilm IC50 [calculated] (approximated), μM | FimH EC50 (μM)- June 30 | FimH EC50 (μM) | Old Kd | ESI MS [M + H]+ | 1H NMR (300 MHz, d4-METHANOL) δ ppm unless otherwise noted |
|---|---|---|---|---|---|---|---|---|---|---|---|---|---|
| 14d | 61 | 3ZFH64 | 2-[4-[3,4,5-trihydroxy-6-(hydroxymethyl)tetrahydropyran-2-yl]oxyphenyl]benzonitrile | 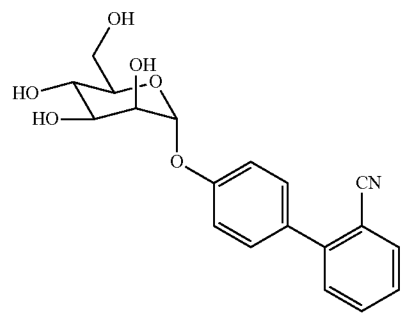 [SMILES: N#Cc1ccccc1-c1ccc(OC2OC(CO)C(O)C(O)C2O)cc1] | C19H19NO6 | 357.4 | 2.000 | | | | | 358.4 | 3.57-3.67 (m, 1H) 3.69-3.85 (m, 3H) 3.88-3.98 (m, 1H) 4.04 (dd, J = 3.43, 1.79 Hz, 1H) 5.57 (d, J = 1.65 Hz, 1H) 7.21-7.32 (m, 2H) 7.45-7.60 (m, 4H) 7.66-7.76 (m, 1H) 7.80 (dd, J = 7.69, 1.37 Hz, 1H) |
| 14e | 62 | 3ZFH68 | 3-[4-[3,4,5-trihydroxy-6-(hydroxymethyl)tetrahydropyran-2-yl]oxyphenyl]benzonitrile | 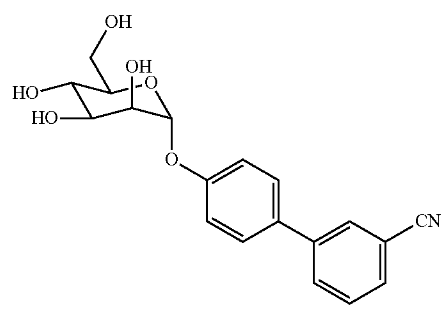 [SMILES: N#Cc1cccc(-c2ccc(OC3OC(CO)C(O)C(O)C3O)cc2)c1] | C19H19NO6 | 357.4 | 1.000 | | | | | 358.3 | 3.54-3.66 (m, 1H) 3.68-3.84 (m, 3H) 3.87-3.99 (m, 1H) 4.03 (dd, J = 3.43, 1.79 Hz, 1H) 5.55 (d, J = 1.65 Hz, 1H) 7.18-7.33 (m, 2H) 7.53-7.73 (m, 4H) 7.84-8.01 (m, 2H) |

TABLE 15-continued

| JMedChem 2010 Example | Patent Example | Compound Name | Structure | IUPAC Name | Molecular Formula | Molecular Weight (g/mol) | HAI Titer EC>90 (μM) | Biofilm IC50 [calculated] (approximated), μM | FimH EC50 (μM)-June 30 | FimH EC50 (μM) | Old Kd | ESI MS [M + H+] | 1H NMR (300 MHz, d4-METHANOL) δ ppm unless otherwise noted |
|---|---|---|---|---|---|---|---|---|---|---|---|---|---|
| 14f | 63 | 3ZFH70 | 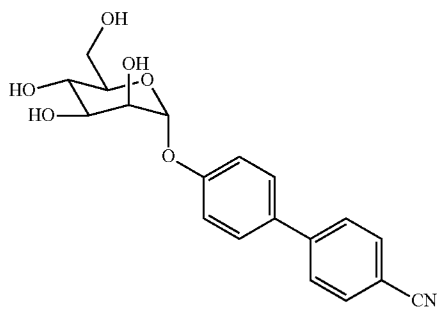 [SMILES: N#Cc1ccc(-c2ccc(OC3OC(CO)C(O)C(O)C3O)cc2)cc1] | 4-[4-[3,4,5-trihydroxy-6-(hydroxymethyl)tetrahydropyran-2-yl]oxyphenyl]benzonitrile | $C_{19}H_{19}NO_6$ | 257.4 | 8.000 | | | | | 358.3 | 3.52-3.67 (m, 1H) 3.67-3.84 (m, 3H) 3.87-3.98 (m, 1H) 4.03 (dd, J = 3.43, 1.79 Hz, 1H) 5.56 (d, J = 1.65 Hz, 1H) 7.17-7.33 (m, 2H) 7.56-7.70 (m, 2H) 7.72-7.85 (m, 4H) |
| 14s | 64 | 3ZFH46 | 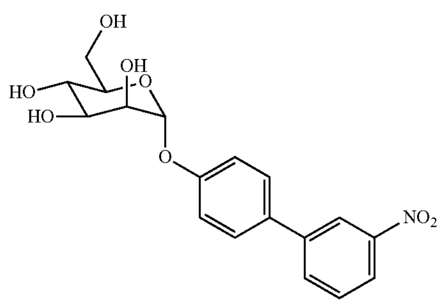 [SMILES: O=[N+]([O-])c1cccc(-c2ccc(OC3OC(CO)C(O)C(O)C3O)cc2)c1] | 2-(hydroxymethyl)-6-[4-(3-nitrophenyl)phenoxy]tetrahydropyran-3,4,5-triol | $C_{18}H_{19}NO_8$ | 377.3 | 0.500 | | | | | 755.8 [2M + H+] | 3.61 (ddd, J = 9.75, 4.94, 2.61 Hz, 1H) 3.68-3.84 (m, 3H) 3.87-3.98 (m, 1H) 4.04 (dd, J = 3.43, 1.79 Hz, 1H) 5.56 (d, J = 1.92 Hz, 1H) 7.18-7.35 (m, 2H) 7.57-7.74 (m, 3H) 7.92-8.08 (m, 1H) 8.17 (dd, J = 8.24, 2.20 Hz, 1H) 8.42 (t, J = 2.06 Hz, 1H) |

TABLE 15-continued

| JMedChem 2010 Example | Compound Name | Patent Example | IUPAC Name | Structure | Molecular Formula | Molecular Weight (g/mol) | HAI Titer EC>90 (μM) | Biofilm IC50 [calculated] (approximated), μM | FimH EC50 (μM)- June 30 | FimH EC50 (μM) | Old Kd | ESI MS [M + H]+ | 1H NMR (300 MHz, d4-METHANOL) δ ppm unless otherwise noted |
|---|---|---|---|---|---|---|---|---|---|---|---|---|---|
| 14t | 3ZFH72 | 65 | 2-(hydroxymethyl)-6-[4-(4-nitrophenyl)phenoxy]tetrahydropyran-3,4,5-triol | 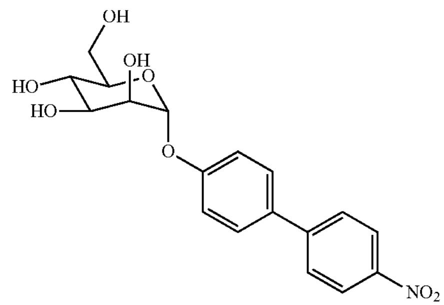 [SMILES: O=[N+]([O-])c1ccc(-c2ccc(OC3OC(CO)C(O)C(O)C3O)cc2)cc1] | C18H19NO8 | 377.3 | 2.000 | | | | | 378.5 | 3.56-3.64 (m, 1H) 3.68-3.84 (m, 3H) 3.87-3.97 (m, 1H) 4.04 (dd, J = 3.43, 1.79 Hz, 1H) 5.57 (d, J =1.65 Hz, 1H) 7.20-7.33 (m, 2H) 7.64-7.76 (m, 2H) 7.79-7.90 (m, 2H) 8.24-8.38 (m, 2H) |
| 8g | 3ZFH93 | 66 | 2-(hydroxymethyl)-6-[4-(3-pyridyl)phenoxy]tetrahydropyran-3,4,5-triol | 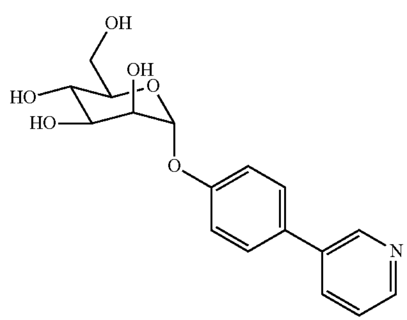 [SMILES: OCC1OC(Oc2ccc(-c3cccnc3)cc2)C(O)C(O)C1O] | C17H19NO6 | 333.3 | 2.000 | | | | | 334.4 | 3.56-3.67 (m, 1H) 3.68-3.85 (m, 3H) 3.87-3.97 (m, 1H) 4.04 (dd, J = 3.30, 1.92 Hz, 1H) 5.56 (d, J =1.92 Hz, 1H) 7.21-7.32 (m, 2H) 7.44-7.55 (m, 1H) 7.56-7.69 (m, 2H) 8.00-8.14 (m, 1H) 8.47 (dd, J = 4.94, 1.37 Hz, 1H) 8.72-8.82 (m, 1H) |

TABLE 15-continued

| JMedChem 2010 Example | Compound Name | Patent Example | IUPAC Name | Structure | Molecular Formula | Molecular Weight (g/mol) | HAI Titer EC>90 (μM) | Biofilm IC50 [calculated] (approximated) μM | FimH EC50 (μM)- June 30 | FimH EC50 (μM) | Old Kd | ESI MS [M + H⁺] | 1H NMR (300 MHz, d₄-METHANOL) δ ppm unless otherwise noted |
|---|---|---|---|---|---|---|---|---|---|---|---|---|---|
| 8h | 3ZFH96 | 67 | 2-(hydroxymethyl)-6-[4-(4-pyridyl)phenoxy]tetrahydropyran-3,4,5-triol | 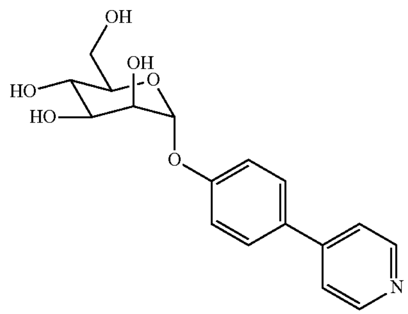 [SMILES: OCC1OC(Oc2ccc(-c3ccncc3)cc2)C(O)C(O)C1O] | $C_{17}H_{19}NO_6$ | 333.3 | 2.000 | | | | | 334.5 | 3.60 (ddd, J = 7.28, 4.94, 2.33 Hz, 1H), 3.67-3.82 (m, 3H), 3.87-3.97 (m, 3H), 4.04 (dd, J = 3.43, 1.79 Hz, 1H) 5.57 (d, J = 1.65 Hz, 1H), 7.19-7.34 (m, 2H), 7.61-7.82 (m, 4H), 8.54 (d, J = 5.22 Hz, 2H) |
| 14p | 3ZFH166 | 68 | N-[3-[4-[3,4,5-trihydroxy-6-(hydroxymethyl)tetrahydropyran-2-yl]oxyphenyl]phenyl]methanesulfonamide | 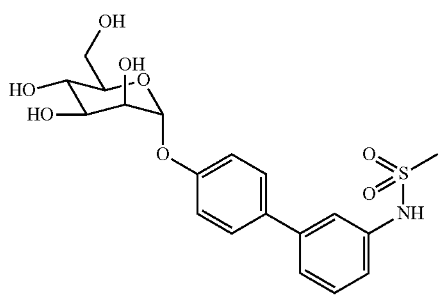 [SMILES: CS(=O)(=O)Nc1cccc(-c2ccc(OC3OC(CO)C(O)C(O)C3O)cc2)c1] | $C_{19}H_{23}NO_8S$ | 425.4 | 2.000 | | | | | 426.2 | 2.98 (s, 3H), 3.56-3.66 (m, 1H), 3.68-3.83 (m, 3H), 3.88-3.97 (m, 1H), 4.03 (dd, J = 3.43, 1.79 Hz, 1H) 5.53 (d, J = 1.92 Hz, 1H), 7.17-7.25 (m, 3H), 7.33-7.42 (m, 2H), 7.43-7.48 (m, 1H), 7.50-7.63 (m, 2H) |

TABLE 15-continued

| JMedChem 2010 Example | Compound Name | Patent Example | IUPAC Name | Structure | Molecular Formula | Molecular Weight (g/mol) | HAI Titer EC>90 (µM) | Biofilm IC50 [calculated] (approximated) µM | FimH EC50 (µM)-June 30 | FimH EC50 (µM) | Old Kd | ESI MS [M + H⁺] | 1H NMR (300 MHz, d₄-METHANOL) δ ppm unless otherwise noted |
|---|---|---|---|---|---|---|---|---|---|---|---|---|---|
| 14o | 3ZFH163 | 69 | N-[2-[4-[3,4,5-trihydroxy-6-(hydroxymethyl)tetrahydropyran-2-yl]oxyphenyl]phenyl]methanesulfonamide | 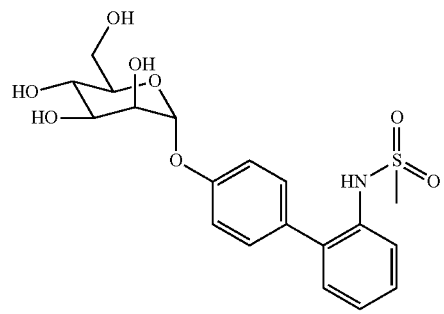 [SMILES: CS(=O)(=O)Nc1ccccc1-c1ccc(OC2OC(CO)C(O)C(O)C2O)cc1] | $C_{19}H_{23}NO_8S$ | 425.4 | 12.000 | | | | | 426.6 | 2.71 (s, 3H) 3.57-3.66 (m, 1H) 3.67-3.83 (m, 3H) 3.93 (dd, J = 9.34, 3.57 Hz, 1H) 4.04 (dd, J = 3.43, 1.79 Hz, 1H) 5.56 (d, J = 1.65 Hz, 1H) 7.18-7.26 (m, 2H) 7.26-7.41 (m, 5H) 7.48 (d, J = 7.69 Hz, 1H) |
| 14r | 3ZFH179 | 70 | N-methyl-3-[4-[3,4,5-trihydroxy-6-(hydroxymethyl)tetrahydropyran-2-yl]oxyphenyl]benzenesulfonamide | 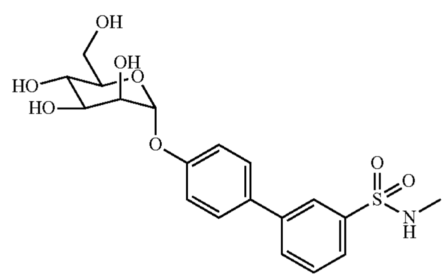 [SMILES: CNS(=O)(=O)c1cccc(-c2ccc(OC3OC(CO)C(O)C(O)C3O)cc2)c1] | $C_{19}H_{23}NO_8S$ | 425.4 | 1.000 | | | | | 426 | 2.55 (s, 3H) 3.56-3.66 (m, 1H) 3.68-3.83 (m, 3H) 3.89-3.97 (m, 1H) 4.04 (dd, J = 3.43, 1.79 Hz, 1H) 5.55 (d, J = 1.92 Hz, 1H) 7.20-7.30 (m, 2H) 7.53-7.68 (m, 3H) 7.77 (dt, J = 8.03, 1.34 Hz, 1H) 7.82-7.89 (m, 1H) 8.02 (t, J = 1.79 Hz, 1H) |

TABLE 15-continued

| JMedChem 2010 Example | Compound Name | Patent Example | IUPAC Name | Structure | Molecular Formula | Molecular Weight (g/mol) | HAI Titer EC>90 (μM) | Biofilm IC50 [calculated] (approximated), μM | FimH EC50 (μM)- June 30 | FimH EC50 (μM) | Old Kd | ESI MS [M + H+] | 1H NMR (300 MHz, d4-METHANOL) δ ppm unless otherwise noted |
|---|---|---|---|---|---|---|---|---|---|---|---|---|---|
| 14q | 3ZFH176 | 71 | N-methyl-2-[4-[3,4,5-trihydroxy-6-(hydroxymethyl)tetrahydropyran-2-yl]oxyphenyl]benzene sulfonamide | 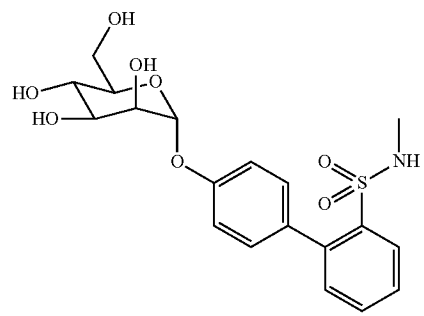 [SMILES: CNS(=O)(=O)c1ccccc1-c1ccc(OC2OC(CO)C(O)C(O)C2O)cc1] | C19H23NO8S | 425.4 | 4.000 | | | | | 426.1 | 2.36 (s, 3H), 3.59-3.68 (m, 1H) 3.68-3.84 (m, 3H) 3.88-3.96 (m, 1H) 4.04 (dd, J = 3.43, 1.79 Hz, 1H) 5.56 (d, J = 1.92 Hz, 1H) 7.13-7.21 (m, 2H) 7.28-7.39 (m, 3H) 7.49-7.58 (m, 1H) 7.58-7.68 (m, 1H) 8.03 (dd, J = 7.83, 1.24 Hz, 1H) |
| 14o | 3ZFH66 | 72 | 2-[4-[3,4,5-trihydroxy-6-(hydroxymethyl)tetrahydropyran-2-yl]oxyphenyl]benzamide | 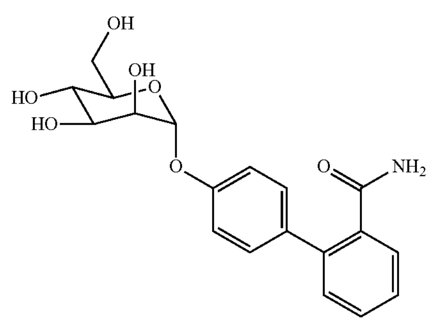 [SMILES: NC(=O)c1ccccc1-c1ccc(OC2OC(CO)C(O)C(O)C2O)cc1] | C19H21NO7 | 375.4 | 6.000 | | | | | 376.4 | 3.56-3.68 (m, 1H) 3.68-3.84 (m, 3H) 3.87-3.97 (m, 1H) 4.02 (dd, J = 3.30, 1.92 Hz, 1H) 5.51 (d, J = 1.92 Hz, 1H) 7.11-7.21 (m, 2H) 7.33-7.44 (m, 4H) 7.44-7.57 (m, 2H) |

TABLE 15-continued

| JMedChem 2010 Example | MedChem Compound Name | Patent Example | IUPAC Name | Structure | Molecular Formula | Molecular Weight (g/mol) | HAI Titer EC>90 (μM) | Biofilm IC50 [calculated] (approximated), μM | FimH EC50 (μM)-June 30 | FimH EC50 (μM) | Old Kd | ESI MS [M + H+] | 1H NMR (300 MHz, d4-METHANOL) δ ppm unless otherwise noted |
|---|---|---|---|---|---|---|---|---|---|---|---|---|---|
| 14n | 3ZFH190 | 73 | 2-(hydroxymethyl)-6-[4-(3-methoxyphenyl)phenoxy]tetrahydropyran-3,4,5-triol | 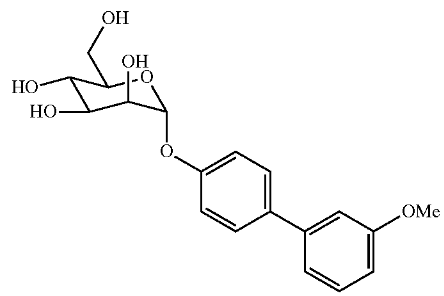 [SMILES: COc1cccc(-c2ccc(OC3OC(CO)C(O)C(O)C3O)cc2)c1] | $C_{19}H_{22}O_7$ | 362.4 | 1.500 | | | | | 363.2 | 3.50-3.59 (m, 1H) 3.60-3.78 (m, 6H) 3.85 (dd, J = 9.34, 3.30 Hz, 1H) 3.95 (dd, J = 3.30, 1.92 Hz, 1H) 5.45 (d, J = 1.65 Hz, 1H) 6.79 (ddd, J = 8.17, 2.54, 0.82 Hz, 1H) 6.96-7.16 (m, 4H) 7.18-7.31 (m, 1H) 7.38-7.54 (m, 2H) |
| 14m | 3ZFH188 | 74 | 2-(hydroxymethyl)-6-[4-(2-methoxyphenyl)phenoxy]tetrahydropyran-3,4,5-triol | 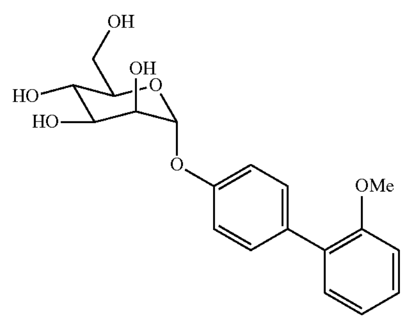 [SMILES: COc1ccccc1-c1ccc(OC2OC(CO)C(O)C(O)C2O)cc1] | $C_{19}H_{22}O_7$ | 362.4 | 2.000 | | | | | 363.2 | 3.60-3.68 (m, 1H) 3.69-3.83 (m, 6H) 3.89-3.97 (m, 1H) 4.03 (dd, J = 3.30, 1.92 Hz, 1H) 5.52 (d, J = 1.92 Hz, 1H) 6.94-7.07 (m, 2H) 7.10-7.17 (m, 2H) 7.21-7.33 (m, 2H) 7.37-7.45 (m, 2H) |

TABLE 15-continued

| JMedChem 2010 Example | Compound Name | Patent Example | IUPAC Name | Structure | Molecular Formula | Molecular Weight (g/mol) | HAI Titer EC>90 (μM) | Biofilm IC50 [calculated] (approximated), μM | FimH EC50 (μM)- June 30 | FimH EC50 (μM) | Old Kd | ESI MS [M + H]+ | 1H NMR (300 MHz, d4-METHANOL) δ ppm unless otherwise noted |
|---|---|---|---|---|---|---|---|---|---|---|---|---|---|
| | 4ZFH49 | 75 | methyl 3-[3-chloro-4-[3,4,5-trihydroxy-6-(hydroxymethyl)tetrahydropyran-2-yl]oxy-phenyl]benzoate | | C20H21ClO8 | 424.8 | 0.032 | | | | | 425.1 | 3.59-3.71 (m, 1H) 3.71-3.85 (m, 3H) 3.94 (s, 3H) 4.01 (dd, J = 9.34, 3.30 Hz, 1H) 4.12 (dd, J = 3.30, 1.92 Hz, 1H) 5.61 (d, J = 1.65 Hz, 1H) 7.40-7.49 (m, 1H) 7.49-7.62 (m, 2H) 7.68 (m, 2H) 7.68 (d, J = 2.20 Hz, 1H) 7.82 (ddd, J = 7.76, 1.85, 1.10 Hz, 1H) 7.98 (dt, J = 7.83, 1.30 Hz, 1H) 8.14-8.25 (m, 1H) |
| | 4ZFH52-JJ | 76 | methyl 5-[4-[3,4,5-trihydroxy-6-(hydroxymethyl)tetrahydropyran-2-yl]oxyphenyl]-3-ureido-thiophene-2-carboxylate | | C19H22N2O9S | 454.4 | 0.016 | | | | | 455.1 | 3.58 (ddd, J = 7.21, 4.88, 2.47 Hz, 1H) 3.66-3.83 (m, 3H) 3.83-3.96 (m, 4H) 4.02 (dd, J = 3.30, 1.92 Hz, 1H) 5.54 (d, J = 1.65 Hz, 1H) 7.12-7.27 (m, 2H) 7.56-7.69 (m, 2H) 8.12 (s, 1H) |

TABLE 15-continued

| JMedChem 2010 Example | Compound Name | Patent Example | IUPAC Name | Structure | Molecular Formula | Molecular Weight (g/mol) | HAI Titer EC>90 (µM) | Biofilm IC50 [calculated] (approximated), µM | FimH EC50 (µM)- June 30 | FimH EC50 (µM) | Old Kd | ESI MS [M + H+] | 1H NMR (300 MHz, d4-METHANOL) δ ppm unless otherwise noted |
|---|---|---|---|---|---|---|---|---|---|---|---|---|---|
| | 3ZFH226 | 77 | dimethyl 5-[4-[3,4,5-trihydroxy-6-(hydroxymethyl)tetrahydropyran-2-yl]oxyphenyl]benzene-1,3-dicarboxylate | | C19H21NO8 | 391.4 | 0.188 | | | | | 392.1 | 3.53-3.65 (m, 1H) 3.67-3.83 (m, 3H) 3.89-3.96 (m, 1H) 3.99 (s, 3H) 4.04 (dd, J = 3.43, 1.79 Hz, 1H) 7.22-7.37 (m, 2H) 7.58-7.73 (m, 2H) 8.54 (t, J = 2.06 Hz, 1H) 8.97 (d, J = 2.20 Hz, 1H) 9.04 (d, J = 1.92 Hz, 1H) |
| | 3ZFH220 | 78 | methyl 4-[4-(α-D-mannopyranosyloxy)phenyl]pyridine-2-carboxylate | | C19H21NO8 | 391.4 | 0.500 | | | | | 392.2 | 3.51-3.63 (m, 1H) 3.65-3.84 (m, 3H) 3.88-3.95 (m, 1H) 4.00-4.13 (m, 4H) 5.62 (d, J = 1.65 Hz, 1H) 7.28-7.40 (m, 2H) 7.82-7.95 (m, 2H) 8.13 (dd, J = 5.49, 1.92 Hz, 1H) 8.55 (d, J = 1.65 Hz, 1H) 8.73 (d, J = 5.49 Hz, 1H) |
| | 4ZFH154 | 79 | methyl 5-[4-[3,4,5-trihydroxy-6-(hydroxymethyl)tetrahydropyran-2-yl]oxyphenyl]thiophene-2-carboxylate | | C18H20O8S | 396.4 | | | | | | 419.1 [M + Na+] | 3.53-3.62 (m, 1H) 3.68-3.81 (m, 3H) 3.85-3.94 (m, 4H) 4.02 (dd, J = 3.60, 2.1 Hz, 1H) 5.54 (d, J = 1.8 Hz, 1H) 7.19 (m, 2H) 7.34 (d, J = 3.9 Hz, 1H) 7.64 (m, 2H) 7.75 (d, J = 3.9 Hz, 1H) |

TABLE 15-continued

| JMedChem 2010 Example | Patent Example | Compound Name | Structure | IUPAC Name | Molecular Formula | Molecular Weight (g/mol) | HAI Titer EC>90 (μM) | Biofilm IC50 [calculated] (approximated), μM | FimH EC50 (μM)-June 30 | FimH EC50 (μM) | Old Kd | ESI MS [M + H⁺] | 1H NMR (300 MHz, d₄-METHANOL) δ ppm unless otherwise noted |
|---|---|---|---|---|---|---|---|---|---|---|---|---|---|
|  | 80 | 4ZFH152 |  | methyl 5-[4-[3,4,5-trihydroxy-6-(hydroxymethyl)tetrahydropyran-2-yl]oxyphenyl]thiophene-3-carboxylate | C18H20O8S | 396.4 |  |  |  |  |  | 419.1 [M + Na+] | 3.55-3.63 (m, 1H) 3.68-3.81 (m, 3H) 3.84-3.94 (m, 4H) 4.02 (dd, J = 3.30, 1.8 Hz, 1H) 5.53 (d, J = 1.8 Hz, 1H) 7.18 (m, 2H) 7.59 (m, 2H) 7.64 (d, J = 1.5 Hz, 1H) 8.11 (d, J = 1.5 Hz, 1H) |
|  | 81 | 4ZFH160 |  | [3-[4-[3,4,5-trihydroxy-6-(hydroxymethyl)tetrahydropyran-2-yl]oxyphenyl]phenyl]urea | C19H22N2O7 | 390.4 |  |  |  |  |  | 391.2 |  |
| 22 | 82 | 2ZFH308 | 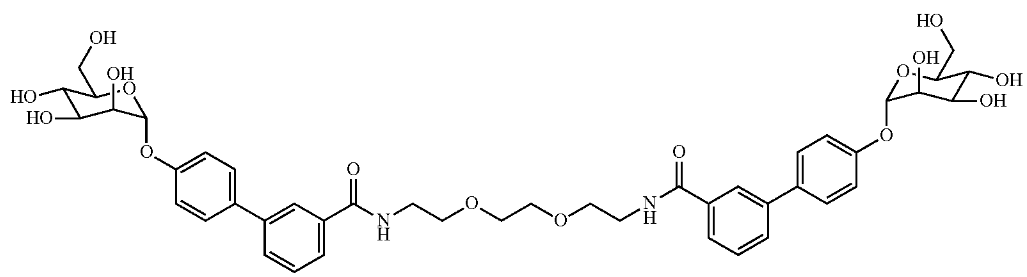 [SMILES: O=C(NCCOCCOCCNC(=O)c1cccc(-c2ccc(OC3OC(CO)C(O)C(O)C3O)cc2)c1)c1cccc(-c2ccc(OC3OC(CO)C(O)C(O)C3O)cc2)c1] | 3-[4-[3,4,5-trihydroxy-6-(hydroxymethyl)tetrahydropyran-2-yl]oxyphenyl]-N-[2-[2-[2-[[3-[4-[3,4,5-trihydroxy-6-(hydroxymethyl)tetrahydropyran-2-yl]oxyphenyl]benzoyl]amino]ethoxy]ethoxy]ethyl]benzamide | C44H52N2O16 | 864.9 | 2 to 0.03 |  |  |  |  | 865.9 | .3.51-3.65 (m, 6H), 3.65-3.82 (m, 14H), 3.88-3.96 (m, 2H), 4.03 (dd, J = 3.57, 1.92 Hz, 2H), 5.52 (d, J = 1.65 Hz, 2H), 7.14-7.24 (m, 4H), 7.40-7.50 (m, 2H), 7.53-7.63 (m, 4H), 7.66-7.77 (m, 4H), 8.00 (t, J = 1.65 Hz, 2H) |

TABLE 15-continued

| JMedChem 2010 Example | Patent Example | Compound Name | IUPAC Name | Structure | Molecular Formula | Molecular Weight (g/mol) | HAI Titer EC>90 (μM) | Biofilm IC50 [calculated] (approximated), μM | FimH EC50 (μM)-June 30 | FimH EC50 (μM) | Old Kd | ESI MS [M + H]+ | 1H NMR (300 MHz, d4-METHANOL) δ ppm unless otherwise noted |
|---|---|---|---|---|---|---|---|---|---|---|---|---|---|
| 21 | 83 | 2ZFH313 | 3-[4-[3,4,5-trihydroxy-6-(hydroxymethyl)tetrahydropyran-2-yl]oxyphenyl]-N-[2-[2-[[3-[4-[3,4,5-trihydroxy-6-(hydroxymethyl)tetrahydropyran-2-yl]oxyphenyl]benzoyl]amino]ethoxy]ethyl]benzamide | 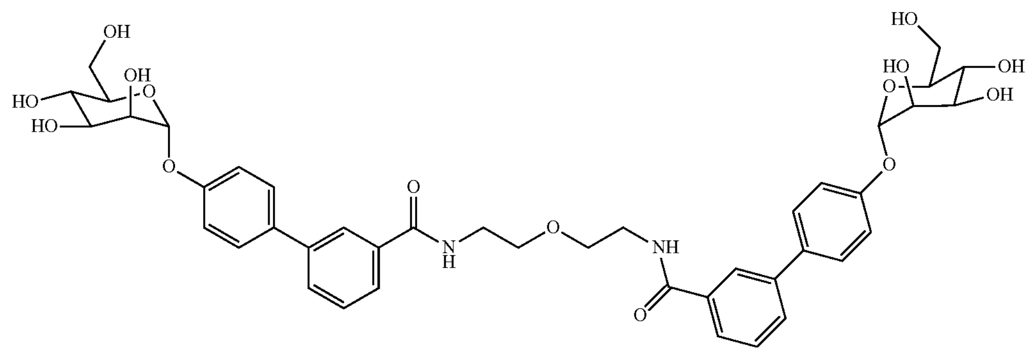 [SMILES: O=C(NCCOCCNC(=O)c1cccc(-c2ccc(OC3OC(CO)C(O)C(O)C3O)cc2)c1)c1cccc(-c2ccc(OC3OC(CO)C(O)C(O)C3O)cc2)c1] | C42H48N2O15 | 830.8 | 1 to 0.03 | | | | | 821.9 | 3.58-3.66 (m, 6H), 3.68-3.82 (m, 10H), 3.93 (dd, J = 9.30, 3.30 Hz, 2H), 4.03 (dd, J = 3.60, 2.10 Hz, 2H), 5.53 (d, J = 1.50 Hz, 2H), 7.14-7.22 (m, 4H), 7.36-7.42 (m, 2H), 7.52-7.58 (m, 4H), 7.64-7.72 (m, 4H), 7.99 (t, J = 1.50 Hz, 2H) |
| | 84 | 2ZFH234 | 3-[4-[3,4,5-trihydroxy-6-(hydroxymethyl)tetrahydropyran-2-yl]oxyphenyl]-N-[8-[[3-[4-[3,4,5-trihydroxy-6-(hydroxymethyl)tetrahydropyran-2-yl]oxyphenyl]benzoyl]amino]octyl]benzamide | | C46H56N2O14 | 860.9 | 2.00 | | | | | | 862 | 1.41 (m, 8H) 1.63 (m, J = 6.87 Hz, 4H) 3.34-3.44 (m, 4H) 3.62 (ddd, J = 9.61, 4.67, 2.75 Hz, 2H) 3.68-3.84 (m, 6H) 3.85-3.97 (m, 2H) 4.03 (dd, J = 3.43, 1.79 Hz, 2H) 5.54 (d, J = 1.92 Hz, 2H) 7.15-7.28 (m, 4H) 7.49 (t, J = 7.69 Hz, 2H) 7.55-7.66 (m, 4H) 7.67-7.81 (m, 4H) 8.01 (t, J = 1.65 Hz, 2H) |

TABLE 15-continued

| JMedChem 2010 Example | Compound Name | Patent Example | IUPAC Name | Structure | Molecular Formula | Molecular Weight (g/mol) | HAI Titer EC>90 (µM) | Biofilm IC50 [calculated] (approximated), µM | FimH EC50 (µM)- June 30 | FimH EC50 (µM) | Old Kd | ESI MS [M + H]+ | 1H NMR (300 MHz, d4-METHANOL) δ ppm unless otherwise noted |
|---|---|---|---|---|---|---|---|---|---|---|---|---|---|
| 3ZFH254 | | 85 | 3-[4-[3,4,5-trihydroxy-6-(hydroxymethyl)tetrahydropyran-2-yl]oxyphenyl]-N-[2-[2-[2-[[3-[4-[3,4,5-trihydroxy-6-(hydroxymethyl)tetrahydropyran-2-yl]oxyphenyl]benzoyl]amino]ethoxy]ethoxy]ethyl]benzamide | | C46H56N2O17 | 908.9 | 1 to 0.03 | | 30 | | | 909.2 | 3.48-3.68 (m, 18H) 3.69-3.28 (m, 6H) 3.88-3.98 (m, 2H) 4.03 (dd, J = 3.30, 1.92 Hz, 2H) 5.53 (d, J = 1.92 Hz, 2H) 7.14-7.28 (m, 4H) 7.41-7.53 (m, 2H) 7.54-7.65 (m, 4H) 7.67-7.78 (m, 4H) 8.00 (t, J = 1.65 Hz, 2H) |
| 3ZFH243 | | 86 | 3-nitro-N-[2-[2-[2-[[2-nitro-5-[4-[3,4,5-trihydroxy-6-(hydroxymethyl)tetrahydropyran-2-yl]oxyphenyl]benzoyl]amino]ethoxy]ethoxy]ethyl]-5-[4-[3,4,5-trihydroxy-6-(hydroxymethyl)tetrahydropyran-2-yl]oxyphenyl]benzamide | | C44H50N4O20 | 954.9 | 4 to 0.03 | | | | | 955.2 | 3.55-3.66 (m, 6H) 3.68-3.86 (m, 14H) 3.93 (dd, J = 9.34, 3.57 Hz, 2H) 4.04 (dd, J = 3.30, 1.92 Hz, 2H) 5.55 (d, J = 1.65 Hz, 2H) 7.14-7.28 (m, 4H) 7.51-7.67 (m, 4H) 8.30 (t, J = 1.65 Hz, 2H) 8.37-8.43 (m, 2H) 8.44-8.53 (m, 2H) |

TABLE 15-continued

| JMedChem 2010 Example | Compound Name | Patent Example | IUPAC Name | Structure | Molecular Formula | Molecular Weight (g/mol) | HAI Titer EC>90 (µM) | Biofilm IC50 [calculated] (approximated), µM | FimH EC50 (µM)-June 30 | FimH EC50 (µM) | Old Kd | ESI MS [M + H+] | 1H NMR (300 MHz, d4-METHANOL) δ ppm unless otherwise noted |
|---|---|---|---|---|---|---|---|---|---|---|---|---|---|
| | 3ZFH271 | 87 | 3-[4-[3,4,5-trihydroxy-6-(hydroxymethyl)tetrahydropyran-2-yl]oxyphenyl]-N-[2-[[3-[4-[3,4,5-trihydroxy-6-(hydroxymethyl)tetrahydropyran-2-yl]oxyphenyl]benzoyl]amino]ethyl]benzamide | | C40H44N2O14 | 776.8 | 1 to 0.125 | | | | | 777.4 | 3.54-3.85 (m, 12H) 3.93 (dd, J = 9.34, 3.30 Hz, 2H) 4.04 (dd, J = 3.43, 1.79 Hz, 2H) 5.52 (d, J = 1.92 Hz, 2H) 7.09-7.25 (m, 4H) 7.45-7.54 (m, 2H) 7.54-7.65 (m, 4H) 7.75 (dd, J = 8.52, 1.37 Hz, 4H) 8.03 (t, J = 1.65 Hz, 2H) |
| | 3ZFH245 | 88 | N-[2-[2-(2-aminoethoxy)ethoxy]ethyl]-3-nitro-5-[4-[3,4,5-trihydroxy-6-(hydroxymethyl)tetrahydropyran-2-yl]oxyphenyl]benzamide | | C25H33N3O11 | 551.5 | 0.25 | | | | | 552.1 | 3.10 (t, J = 5.08 Hz, 2H) 3.51-3.85 (m, 16H) 3.87-3.96 (m, 1H) 4.04 (dd, J = 3.43, 1.79 Hz, 1H) 5.58 (d, J = 1.65 Hz, 1H) 7.24-7.35 (m, 2H) 7.66-7.80 (m, 2H) 8.45 (t, J = 1.65 Hz, 1H) 8.60 (dt, J = 9.27, 1.96 Hz, 2H) |

TABLE 15-continued

| JMedChem 2010 Example | Compound Name | Patent Example | IUPAC Name | Structure | Molecular Formula | Molecular Weight (g/mol) | HAI Titer EC>90 (µM) | Biofilm IC50 [calculated] (approximated) µM | FimH EC50 (µM)- June 30 | FimH EC50 (µM) | Old Kd | ESI MS [M + H]+ | 1H NMR (300 MHz, d4-METHANOL) δ ppm unless otherwise noted |
|---|---|---|---|---|---|---|---|---|---|---|---|---|---|
| 3ZFH256 | | 89 | N-(4-pyridyl)-3-[4-[3,4,5-trihydroxy-6-(hydroxymethyl)tetrahydropyran-2-yl]oxyphenyl]benzamide | | C24H24N2O7 | 452.5 | 0.25 | | | | | 453.1 | 3.57-3.69 (m, 1H) 3.69-3.84 (m, 3H) 3.93 (dd, J = 9.34, 3.30 Hz, 1H) 4.04 (dd, J = 3.30, 1.92 Hz, 1H) 5.56 (d, J = 1.65 Hz, 1H) 7.18-7.37 (m, 2H) 7.57-7.78 (m, 3H) 7.82-8.06 (m, 2H) 8.24 (t, J = 1.65 Hz, 1H) 8.36-8.51 (m, 2H) 8.68 (d, J = 7.42 Hz, 2H) |
| 3ZFH265 | | 90 | N-(3-pyridyl)-3-[4-[3,4,5-trihydroxy-6-(hydroxymethyl)tetrahydropyran-2-yl]oxyphenyl]benzamide | | C24H24N2O7 | 452.5 | 0.375 | | | | | 453.2 | 3.55-3.68 (m, 1H) 3.68-3.85 (m, 3H) 3.88-3.98 (m, 1H) 4.04 (dd, J = 3.43, 1.79 Hz, 1H) 5.56 (d, J = 1.92 Hz, 1H) 7.20-7.32 (m, 2H) 7.52-7.73 (m, 3H) 7.80-7.91 (m, 1H) 7.91-7.99 (m, 1H) 8.04 (dd, J = 8.65, 5.63 Hz, 1H) 8.23 (t, J = 1.65 Hz, 1H) 8.59 (d, J = 5.49 Hz, 1H) 8.67-8.79 (m, 1H) 9.55 (s, 1H) |

TABLE 15-continued

| JMedChem 2010 Example | Compound Name | Patent Example | IUPAC Name | Structure | Molecular Formula | Molecular Weight (g/mol) | HAI Titer EC>90 (µM) | Biofilm IC50 [calculated] (approximated) µM | FimH EC50 (µM)- June 30 | FimH EC50 (µM) | Old Kd | ESI MS [M + H⁺] | 1H NMR (300 MHz, d₄-METHANOL) δ ppm unless otherwise noted |
|---|---|---|---|---|---|---|---|---|---|---|---|---|---|
| | 3ZFH270 | 91 | N-[2-[bis(dimethylamino)methyleneamino]ethyl]-3-[4-[3,4,5-trihydroxy-6-(hydroxymethyl)tetrahydropyran-2-yl]oxyphenyl]benzamide | | $C_{26}H_{36}N_4O_7$ | 516.6 | 2.000 | | | | | 517.2 | 2.98 (s, 12H), 3.42-3.56 (m, 2H), 3.56-3.67 (m, 3H), 3.67-3.84 (m, 3H), 3.93 (dd, J = 9.34, 3.30 Hz, 1H) 4.03 (dd, J = 3.43, 1.79 Hz, 1H) 5.54 (d, J = 1.65 Hz, 1H), 7.18-7.34 (m, 2H), 7.48-7.59 (m, 1H), 7.59-7.72 (m, 2H), 7.74-7.87 (m, 2H), 8.06 (t, J = 1.65 Hz, 1H) |
| | 3ZFH280 | 92 | N-(2-aminoethyl)-3-[4-[3,4,5-trihydroxy-6-(hydroxymethyl)tetrahydropyran-2-yl]oxyphenyl]benzamide | | $C_{21}H_{26}N_2O_7$ | 418.4 | 3.000 | | | | | 419.2 | 3.14-3.26 (m, 2H), 3.57-3.66 (m, 1H), 3.66-3.83 (m, 5H), 3.87-4.00 (m, 1H), 4.03 (dd, J = 3.30, 1.92 Hz, 1H), 5.49-5.62 (m, 1H), 7.19-7.31 (m, 2H), 7.49-7.59 (m, 1H), 7.59-7.72 (m, 2H), 7.75-7.89 (m, 2H), 8.08-8.21 (m, 1H) |

TABLE 15-continued

| JMedChem 2010 Example | Compound Name | Patent Example | IUPAC Name | Structure | Molecular Formula | Molecular Weight (g/mol) | HAI Titer EC>90 (μM) | Biofilm IC50 [calculated] (approximated), μM | FimH EC50 (μM)-June 30 | FimH EC50 (μM) | Old Kd | ESI MS [M + H]+ | 1H NMR (300 MHz, d4-METHANOL) δ ppm unless otherwise noted |
|---|---|---|---|---|---|---|---|---|---|---|---|---|---|
| | 3ZFH286 | 93 | [4-[3-[4-[3,4,5-trihydroxy-6-(hydroxymethyl)tetrahydropyran-2-yl]oxyphenyl]benzoyl]piperazin-1-yl]-[3-[4-[3,4,5-trihydroxy-6-(hydroxymethyl)tetrahydropyran-2-yl]oxyphenyl]phenyl]methanone | | C42H46N2O14 | 802.8 | 2 to 4 | 4.000 | | | | 803.5 | 3.46–3.85 (m, 14H) 3.85–3.97 (m, 4H) 4.03 (dd, J = 3.43, 1.79 Hz, 2H) 5.54 (d, J = 1.65 Hz, 2H) 7.22 (d, J = 8.52 Hz, 4H) 7.39 (d, J = 7.69 Hz, 2H) 7.46–7.76 (m, 10H) |
| | 3ZFH261 | 94 | (4-methylpiperazin-1-yl)-[3-[4-[3,4,5-trihydroxy-6-(hydroxymethyl)tetrahydropyran-2-yl]oxyphenyl]phenyl]methanone | | C24H30N2O7 | 458.5 | | | | | | 459 | 2.96 (s, 3H) 3.05–3.65 (m, 9H) 3.68–3.85 (m, 3H) 3.87–3.97 (M, 1H) 4.03 (dd, J = 3.30, 1.92 Hz, 1H) 5.54 (d, J = 1.65 Hz, 1H) 7.17–7.30 (m, 2H) 7.42 (dt, J = 7.62, 1.27 Hz, 1H) 7.50–7.66 (m, 3H) 7.67–7.80 (m, 2H) |

TABLE 15-continued

| JMedChem 2010 Example | Compound Name | Patent Example | IUPAC Name | Structure | Molecular Formula | Molecular Weight (g/mol) | HAI Titer EC>90 (μM) | Biofilm IC50 [calculated] (approximated), μM | FimH EC50 (μM)- June 30 | FimH EC50 (μM) | Old Kd | ESI MS [M + H+] | 1H NMR (300 MHz, d4-METHANOL) δ ppm unless otherwise noted |
|---|---|---|---|---|---|---|---|---|---|---|---|---|---|
| | 3ZFH284 | 95 | piperazin-1-yl-[3-[4-[3,4,5-trihydroxy-6-(hydroxymethyl)tetrahydropyran-2-yl]oxyphenyl]phenyl]methanone | | $C_{23}H_{28}N_2O_7$ | 444.5 | 4.0000 | | | | | 445.3 | 3.54-3.67 (m, 1H) 3.67-3.85 (m, 4H) 3.85-3.99 (m, 4H) 4.03 (dd, J = 3.30, 1.92 Hz, 1H) 5.54 (d, J = 1.65 Hz, 1H) 7.19-7.29 (m, 2H) 7.42 (dt, J = 7.69, 1.24 Hz, 1H) 7.50-7.64 (m, 3H) 7.67-7.79 (m, 2H) |
| | 3ZFH276 | 96 | N-(2-hydroxyethyl)-3-[4-[3,4,5-trihydroxy-6-(hydroxymethyl)tetrahydropyran-2-yl]oxyphenyl]benzamide | | $C_{21}H_{25}NO_8$ | 419.4 | 0.5000 | | | | | 420.1 | 1H NMR (300 MHz, DEUTERIUM OXIDE) ppm 3.53-3.63 (m, 2H) 3.68-3.94 (m, 6H) 4.11 (dd, J = 9.20, 3.43 Hz, 1H) 4.22 (dd, J = 3.30, 1.92 Hz, 1H) 5.66 (d, J = 1.65 Hz, 1H) 7.21 (d, J = 8.79 Hz, 2H) 7.47-7.62 (m, 3H) 7.66-7.78 (m, 2H) 7.87 (t, J = 1.65 Hz, 1H) |
| | JJ-I-93 | 97 | N,N-dimethyl-3-[4-[3,4,5-trihydroxy-6-(hydroxymethyl)tetrahydropyran-2-yl]oxyphenyl]benzamide | | $C_{21}H_{25}NO_7$ | 403.16 | 3.000 | | | | | 404 | |

TABLE 15-continued

| JMedChem 2010 Example | Compound Name | Patent Example | IUPAC Name | Structure | Molecular Formula | Molecular Weight (g/mol) | HAI Titer EC>90 (μM) | Biofilm IC50 [calculated] (approximated), μM | FimH EC50 (μM)- June 30 | FimH EC50 (μM) | Old Kd | ESI MS [M + H+] | 1H NMR (300 MHz, d4-METHANOL) δ ppm unless otherwise noted |
|---|---|---|---|---|---|---|---|---|---|---|---|---|---|
| 1ZFH128 | | 98 | 2-(4-aminobutoxy)-6-(hydroxymethyl)tetrahydropyran-3,4,5-triol | | C10H21NO6 | 251.28 | | | | | | 252.1 | 1.46~1.78 (m, 4H) 2.61~2.88 (m, 2H), 3.41~3.55 (m, 2H), 3.59 (t, J = 9.3 Hz, 1H), 3.65~3.87 (m, 5H), 4.75 (d, J = 1.65 Hz, 1H) |
| 1ZFH134A | | 99 | 2-(3-hydroxy-6-oxo-xanthen-9-yl)-4-[4-[3,4,5-trihydroxy-6-(hydroxymethyl)tetrahydropyran-2-yl]oxybutylcarbamoyl]benzoic acid | | C31H31NO12 | 609.58 | 125.000 | | | | | 610.6 | |

TABLE 15-continued

| JMedChem 2010 Example | Compound Name | Patent Example | IUPAC Name | Structure | Molecular Formula | Molecular Weight (g/mol) | HAI Titer EC>90 (μM) | Biofilm IC50 [calculated] (approximated) μM | FimH EC50 (μM)- June 30 | FimH EC50 (μM)- Old | Kd | ESI MS [M + H+] | 1H NMR (300 MHz, d4-METHANOL) δ ppm unless otherwise noted |
|---|---|---|---|---|---|---|---|---|---|---|---|---|---|
| 1ZFH134B | | 100 | 2-(3-hydroxy-6-oxo-xanthen-9-yl)-5-[4-[3,4,5-trihydroxy-6-(hydroxymethyl)tetrahydropyran-2-yl]oxybutylcarbamoyl]benzoic acid | | C31H31NO12 | 609.58 | 125.000 | | | | | 610.6 | |
| 4ZFH105 | | 101 | 2-(hydroxymethyl)-6-(4-phenyltriazol-1-yl)tetrahydropyran-3,4,5-triol | | C14H17N3O5 | 307.3 | 32.000 | | | | | [M + Na]+, 330.2 | 3.34-3.44 (m, 1H) 3.70-3.92 (m, 3H) 4.12 (dd, J = 8.52, 3.57 Hz, 1H) 4.71-4.80 (m, 1H) 6.08 (d, J = 2.75 Hz, 1H) 7.30-7.41 (m, 1H) 7.41-7.51 (m, 2H) 7.77-7.90 (m, 2H) 8.51 (s, 1H) |

TABLE 15-continued

| JMedChem 2010 Example | Compound Name | Patent Example | IUPAC Name | Structure | Molecular Formula | Molecular Weight (g/mol) | HAI Titer EC≥90 (μM) | Biofilm IC50 [calculated] (approximated), μM | FimH EC50 (μM)- June 30 | FimH EC50 (μM) | Old Kd | ESI MS [M + H]⁺ | 1H NMR (300 MHz, d₄-METHANOL) δ ppm unless otherwise noted |
|---|---|---|---|---|---|---|---|---|---|---|---|---|---|
| | 4ZFH44 | 102 | methyl 3-[4-[3,4,5-trihydroxy-6-(hydroxymethyl)tetrahydropyran-2-yl]amino]phenyl]benzoate | | $C_{20}H_{23}NO_7$ | 389.4 | 4.000 | | | | | 390.1 | 1H NMR (300 MHz, ACETONITRILE-d3 and D2O) ppm 3.28-3.38 (m, 1H) 3.54-3.59 (m, 2H) 3.64-3.71 (m, 2H) 3.86 (s, 3H) 3.88-3.92 (m, 1H) 4.89 (d, J = 1.10 Hz, 1H) 6.80-6.91 (m, 2H) 7.44-7.58 (m, 3H) 7.75-7.90 (m, 2H) 8.11-8.20 (m, 1H) |
| | 4ZFH55 | 103 | methyl 3-[4-[3,4,5-trihydroxy-6-(hydroxymethyl)tetrahydropyran-2-yl]sulfanyl]phenyl]benzoate | | $C_{20}H_{22}O_7S$ | 406.4 | 4.000 | | | | | 407.1 | .66-3.91 (m, 4H) 3.94 (s, 3H) 4.01-4.16 (m, 2H) 5.51 (d, J = 1.37 Hz, 1H) 7.51-7.69 (m, 5H) 7.81-7.93 (m, 1H) 8.00 (dt, J = 7.83, 1.44 Hz, 1H) 8.24 (t, J = 1.65 Hz, 1H) |

TABLE 15-continued

| JMedChem 2010 Example | Compound Name | Patent Example | IUPAC Name | Structure | Molecular Formula | Molecular Weight (g/mol) | HAI Titer EC$_{>90}$ (μM) | Biofilm IC50 [calculated] (approximated) μM | FimH EC$_{50}$ (μM)- June 30 | FimH EC$_{50}$ (μM) | Old Kd | ESI MS [M + H$^+$] | 1H NMR (300 MHz, d$_4$-METHANOL) δ ppm unless otherwise noted |
|---|---|---|---|---|---|---|---|---|---|---|---|---|---|
| | 4ZFH89 | 104 | methyl 3-[4-[[3,4,5-trihydroxy-6-(hydroxymethyl)tetrahydropyran-2-carbonyl]amino]phenyl]benzoate | | C21H23NO8 | 417.4 | 16.000 | | | | | 418.1 | 3.50 (dt, J = 4.67, 2.33 Hz, 1H) 3.58-3.65 (m, 2H) 3.76 (dd, J = 11.81, 7.42 Hz, 1H) 3.86-4.03 (m, 4H) 4.52 (t, J = 2.61 Hz, 1H) 4.57 (d, J = 2.75 Hz, 1H) 7.55 (t, J = 7.69 Hz, 1H) 7.60-7.68 (m, 2H) 7.68-7.76 (m, 2H) 7.82-7.91 (m, 1H) 7.97 (dt, J = 7.69, 1.37 Hz, 1H) 8.21-8.28 (m, 1H) |
| | methyl 3-(4-hydroxyphenyl)benzoate | | Y-R1 | | | | >1 mM | | | | | | |
| | Benzyl 3-Benzyl 3-amino-3-deoxy-α-D-mannoside | | commercially available | | | | >1 mM | | | | | | |

TABLE 15-continued

| JMedChem 2010 Example | Compound Name | Patent Example | IUPAC Name | Structure | Molecular Formula | Molecular Weight (g/mol) | HAI Titer EC~90 (μM) | Biofilm IC50 [calculated] (approximated) μM | FimH EC50 (μM)- June 30 | FimH EC50 (μM) | Old Kd | ESI MS [M + H+] | 1H NMR (300 MHz, d4-METHANOL) δ ppm unless otherwise noted |
|---|---|---|---|---|---|---|---|---|---|---|---|---|---|
| | Heptyl-mannoside | | commercially available | 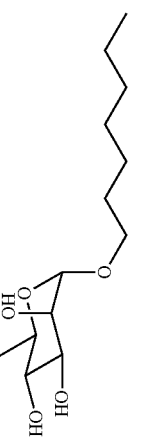 | | | 15.000 | (10-100) ~20 | 0.1077 | 0.070 | | | |
| | Phenyl-α-D-mannoside | | commercially available | 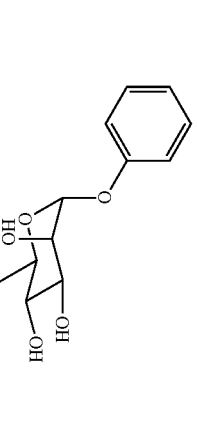 | | | 30.000 | (~100) ~90 | 0.121 | 0.108 | | | |
| | PNP-mannoside | | commercially available | 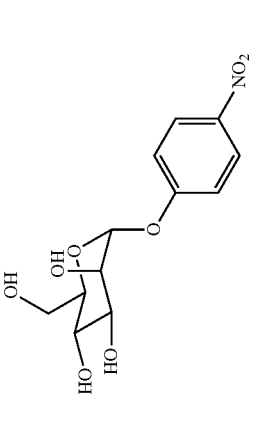 | | | 31.000 | | | | | | |

TABLE 15-continued

| JMedChem 2010 Example | Compound Name | Patent Example | Structure | IUPAC Name | Molecular Formula | Molecular Weight (g/mol) | HAI Titer EC>90 (μM) | Biofilm IC50 [calculated] (approximated) μM | FimH EC50 (μM)- June 30 | FimH EC50 (μM) | Old Kd | ESI MS [M + H⁺] | 1H NMR (300 MHz, d₄-METHANOL) δ ppm unless otherwise noted |
|---|---|---|---|---|---|---|---|---|---|---|---|---|---|
| | 4-aminophenyl-α-D-mannoside | | | commercially available | | | 32.000 | | | | | | |
| | 4-methyl-umbelliferyl-α-D-mannoside | | | commercially available | | | 2.000 | [1.7] | 0.0548 | 0.033 | | | |
| | 1JWJ149 | | | N1,N3-dimethyl-5-[3-(trifluoromethyl)-4-[(3R,4S,5S,6S)-3,4,5-trihydroxy-6-(hydroxymethyl)tetrahydropyran-2-yl]oxy-phenyl]benzene-1,3-dicarboxamide | C₂₃H₂₅F₃N₂O₈ | 514.4 | 0.008 | | | | | |

TABLE 15-continued

| JMedChem 2010 Example | Compound Name | Patent Example | IUPAC Name | Structure | Molecular Formula | Molecular Weight (g/mol) | HAI Titer EC≥90 (µM) | Biofilm IC50 [calculated] (approximated), µM | FimH EC50 (µM)- June 30 | FimH EC50 (µM) | Old Kd | ESI MS [M + H⁺] | 1H NMR (300 MHz, d₄-METHANOL) δ ppm unless otherwise noted |
|---|---|---|---|---|---|---|---|---|---|---|---|---|---|
| | 4ZFH284 | | N1,N3-dimethyl-5-[3-methyl-4-[(3R,4S,5S,6S)-3,4,5-trihydroxy-6-(hydroxymethyl)tetrahydropyran-2-yl]oxy-phenyl]benzene-1,3-dicarboxamide | | $C_{23}H_{28}N_2O_8$ | 460.5 | 0.016 | | | | | | |
| | 4ZFH222 | | methyl 3-[3-(trifluoromethyl)-4-[(3R,4S,5S,6S)-3,4,5-trihydroxy-6-(hydroxymethyl)tetrahydropyran-2-yl]oxy-phenyl]benzoate | | $C_{21}H_{21}F_3O_8$ | 458.4 | 0.032 | | | | | | |
| | 4ZFH272 | | N-methyl-3-[3-(trifluoromethyl)-4-[(3R,4S,5S,6S)-3,4,5-trihydroxy-6-(hydroxymethyl)tetrahydropyran-2-yl]oxy-phenyl]benzamide | | $C_{21}H_{22}F_3NO_7$ | 457.4 | 0.032 | | | | | | |

TABLE 15-continued

| JMedChem 2010 Example | Compound Name | Patent Example | IUPAC Name | Structure | Molecular Formula | Molecular Weight (g/mol) | HAI Titer EC≥90 (μM) | Biofilm IC50 [calculated] (approximated) μM | FimH EC50 (μM)- June 30 | FimH EC50 (μM) | Old Kd | ESI MS [M + H]+ | 1H NMR (300 MHz, d4-METHANOL) δ ppm unless otherwise noted |
|---|---|---|---|---|---|---|---|---|---|---|---|---|---|
| | 4ZFH269 | | N-methyl-3-[3-methyl-4-[(3R,4S,5S,6S)-3,4,5-trihydroxy-6-(hydroxymethyl)tetrahydropyran-2-yl]oxy-phenyl]benzamide | | C21H25NO7 | 403.4 | 0.062 | | | | | | |
| | 4ZFH170 | | 3-[3-chloro-4-[(3R,4S,5S,6S)-3,4,5-trihydroxy-6-(hydroxymethyl)tetrahydropyran-2-yl]oxy-phenyl]-N-methyl-benzamide | | C20H22ClNO7 | 423.8 | 0.125 | | | | | | |
| | 4ZFH224 | | methyl 3-[3-methyl-4-[(3R,4S,5S,6S)-3,4,5-trihydroxy-6-(hydroxymethyl)tetrahydropyran-2-yl]oxy-phenyl]benzoate | | C21H24O8 | 404.4 | 0.125 | | | | | | |
| | 4ZFH228 | | methyl 3-[3-methoxy-4-[(3R,4S,5S,6S)-3,4,5-trihydroxy-6-(hydroxymethyl)tetrahydropyran-2-yl]oxy-phenyl]benzoate | | C21H24O9 | 420.4 | 0.188 | | | | | | |

TABLE 15-continued

| JMedChem 2010 Example | Compound Name | IUPAC Name | Structure | Molecular Formula | Molecular Weight (g/mol) | HAI Titer EC>90 (µM) | Biofilm IC50 [calculated] (approximated), µM | FimH EC50 (µM)- June 30 | FimH EC50 (µM) | Old Kd | ESI MS [M + H]+ | 1H NMR (300 MHz, d4-METHANOL) δ ppm unless otherwise noted |
|---|---|---|---|---|---|---|---|---|---|---|---|---|
| 4ZFH247 | (2S,3S,4S,5R)-2-(hydroxymethyl)-6-(4-quinazolin-6-yl)phenoxy)tetrahydropyran-3,4,5-triol | | | $C_{20}H_{20}N_2O_6$ | 384.4 | 0.375 | | | | | | |
| 4ZFH220 | methyl 3-[3-fluoro-4-[(3R,4S,5S,6S)-3,4,5-trihydroxy-6-(hydroxymethyl)tetrahydropyran-2-yl]oxy-phenyl]benzoate | | | $C_{20}H_{21}FO_8$ | 408.4 | 0.750 | | | | | | |
| 4ZFH275 | (2S,3S,4S,5R)-2-(hydroxymethyl)-6-[4-(7-isoquinolyl)phenoxy]tetrahydropyran-3,4,5-triol | | | $C_{21}H_{21}NO_6$ | 383.4 | 0.750 | | | | | | |

TABLE 15-continued

| JMedChem 2010 Example | Compound Name | Patent Example | Structure | IUPAC Name | Molecular Formula | Molecular Weight (g/mol) | HAI Titer EC>90 (μM) | Biofilm IC50 [calculated] (approximated) μM | FimH EC50 (μM)- June 30 | FimH EC50 (μM) Old Kd | ESI MS [M + H]+ | 1H NMR (300 MHz, d4-METHANOL) δ ppm unless otherwise noted |
|---|---|---|---|---|---|---|---|---|---|---|---|---|
| | 4ZFH218 | | | [4-[4-[(3R,4S,5S,6S)-3,4,5-trihydroxy-6-(hydroxymethyl)tetrahydropyran-2-yl]oxyphenyl]phenyl]urea | C19H22N2O7 | 390.4 | 3.000 | | | | | |
| | 2ZFH20 | | | 5-[(3R,4S,5S,6S)-3,4,5-trihydroxy-6-(hydroxymethyl)tetrahydropyran-2-yl]oxybenzene-1,3-dicarboxylic acid | C14H16O10 | 344.3 | ? | | | | | |
| | 4ZFH131 | | | methyl 3-[4-[[[(3R,4R,5S,6S)-3,4,5-trihydroxy-6-(hydroxymethyl)tetrahydropyran-2-yl]methylcarbamoyl]phenyl]benzoate | C22H25NO8 | 431.44 | 16.000 | | | | | |

TABLE 15-continued

| JMedChem 2010 Example | Compound Name | Patent Example | IUPAC Name | Structure | Molecular Formula | Molecular Weight (g/mol) | HAI Titer EC>90 (μM) | Biofilm IC50 [calculated] (approximated) μM | FimH EC50 (μM)- June 30 | FimH EC50 (μM) | Old Kd | ESI MS [M + H⁺] | 1H NMR (300 MHz, d4-METHANOL) δ ppm unless otherwise noted |
|---|---|---|---|---|---|---|---|---|---|---|---|---|---|
| 4ZFH123 | | | 4-bromo-N-[[(3R,4R,5S,6S)-3,4,5-trihydroxy-6-(hydroxymethyl)tetrahydropyran-2-yl]methyl]benzamide | | $C_{14}H_{18}BrNO_6$ | 376.2 | 16.000 | | | | | | |
| | | | | | $C_{13}H_{17}BrO_6$ | 349.2 | | | | | | | |
| | | | | | $C_{13}H_{14}BrF_3O_6$ | 403.1 | | | | | | | |

TABLE 15-continued

| JMedChem 2010 Example | Compound Name | IUPAC Name | Structure | Molecular Formula | Molecular Weight (g/mol) | HAI Titer EC>90 (μM) | Biofilm IC50 [calculated] (approximated), μM | FimH EC50 (μM)- June 30 | FimH EC50 (μM) | Old Kd | ESI MS [M + H+] | 1H NMR (300 MHz, d4-METHANOL) δ ppm unless otherwise noted |
|---|---|---|---|---|---|---|---|---|---|---|---|---|
| | | | | $C_{12}H_{14}BrClO_6$ | 369.6 | | | | | | | |
| | | | | $C_{13}H_{17}BrO_7$ | 365.2 | | | | | | | |
| | | | | $C_{12}H_{14}BrFO_6$ | 353.14 | | | | | | | |

TABLE 15-continued

| JMedChem 2010 Example | Patent Example | Compound Name | IUPAC Name | Structure | Molecular Formula | Molecular Weight (g/mol) | HAI Titer EC>90 (µM) | Biofilm IC50 [calculated] (approximated), µM | FimH EC50 (µM)- June 30 | FimH EC50 (µM) | Old Kd | ESI MS [M + H+] | 1H NMR (300 MHz, d4-METHANOL) δ ppm unless otherwise noted |
|---|---|---|---|---|---|---|---|---|---|---|---|---|---|
| | | | | | C19H29BO8 | 396.2 | | | | | | | |
| | | | | | C19H26BF3O8 | 450.2 | | | | | | | |
| | | | | | C18H26BClO8 | 416.7 | | | | | | | |

TABLE 15-continued

| JMedChem 2010 Example | Compound Name | Patent Example | IUPAC Name | Structure | Molecular Formula | Molecular Weight (g/mol) | HAI Titer EC>90 (μM) | Biofilm IC50 [calculated] (approximated) μM | FimH EC50 (μM)-June 30 | FimH EC50 (μM) | Old Kd | ESI MS [M + H⁺] | 1H NMR (300 MHz, d₄-METHANOL) δ ppm unless otherwise noted |
|---|---|---|---|---|---|---|---|---|---|---|---|---|---|
| | | | | | $C_{19}H_{29}BO_9$ | 412.2 | | | | | | | |
| | | | | | $C_{18}H_{26}BFO_8$ | 400.2 | | | | | | | |
| | | | | | $C_{22}H_{25}ClN_2O_8$ | 480.9 | | | | | | | |

TABLE 15-continued

| JMedChem 2010 Example | Compound Name | Patent Example | Structure | IUPAC Name | Molecular Formula | Molecular Weight (g/mol) | HAI Titer EC>90 (μM) | Biofilm IC50 [calculated] (approximated) μM | FimH EC50 (μM)- June 30 | FimH EC50 (μM) | Old Kd | ESI MS [M + H+] | 1H NMR (300 MHz, d4-METHANOL) δ ppm unless otherwise noted |
|---|---|---|---|---|---|---|---|---|---|---|---|---|---|
| | | | | | $C_{22}H_{25}FN_2O_8$ | 464.4 | | | | | | | |
| | | | | | $C_{23}H_{28}N_2O_9$ | 476.5 | | | | | | | |
| | | | | | $C_{20}H_{24}N_2O_9S$ | 468.5 | | | | | | | |

TABLE 15-continued
| JMedChem 2010 Example | Patent Example | Compound Name | IUPAC Name | Structure | Molecular Formula | Molecular Weight (g/mol) | HAI Titer EC>90 (μM) | Biofilm IC50 [calculated] (approximated), μM | FimH EC50 (μM)-June 30 | FimH EC50 (μM) | Old Kd | ESI MS [M + H+] | 1H NMR (300 MHz, d4-METHANOL) δ ppm unless otherwise noted |
|---|---|---|---|---|---|---|---|---|---|---|---|---|---|
| | | | | 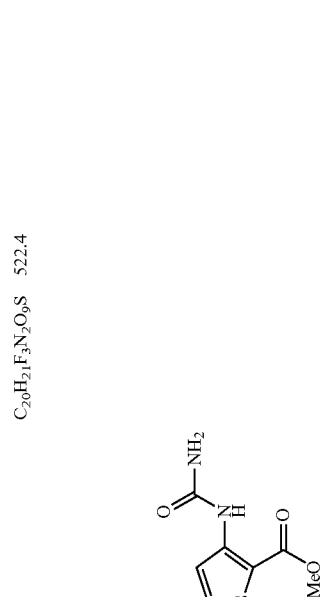 | C20H21F3N2O9S | 522.4 | | | | | | | |
| | | | | 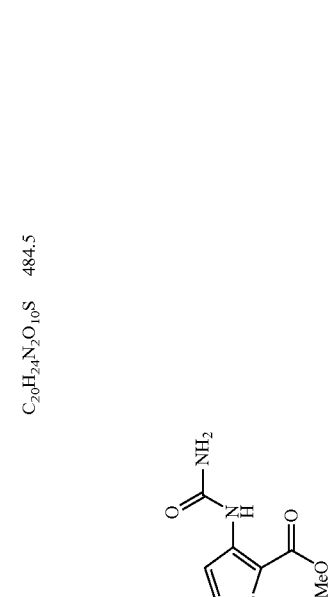 | C20H24N2O10S | 484.5 | | | | | | | |

TABLE 15-continued

| JMedChem 2010 Example | Compound Name | Patent Example | IUPAC Name | Structure | Molecular Formula | Molecular Weight (g/mol) | HAI Titer EC>90 (µM) | Biofilm IC50 [calculated] (approximated), µM | FimH EC50 (µM)-June 30 | FimH EC50 (µM) | Old Kd | ESI MS [M + H⁺] | 1H NMR (300 MHz, d₄-METHANOL) δ ppm unless otherwise noted |
|---|---|---|---|---|---|---|---|---|---|---|---|---|---|
| | | | | | $C_{19}H_{21}ClN_2O_9S$ | 488.9 | | | | | | | |
| | | | | | $C_{19}H_{21}FN_2O_9S$ | 472.4 | | | | | | | |

TABLE 15-continued
| JMedChem 2010 Example | Compound Name | Patent Example | IUPAC Name | Structure | Molecular Formula | Molecular Weight (g/mol) | HAI Titer EC>90 (μM) | Biofilm IC50 [calculated] (approximated) μM | FimH EC50 (μM)- June 30 | FimH EC50 (μM) | FimH Old Kd | ESI MS [M + H+] | 1H NMR (300 MHz, d4-METHANOL) δ ppm unless otherwise noted |
|---|---|---|---|---|---|---|---|---|---|---|---|---|---|
| | | | | 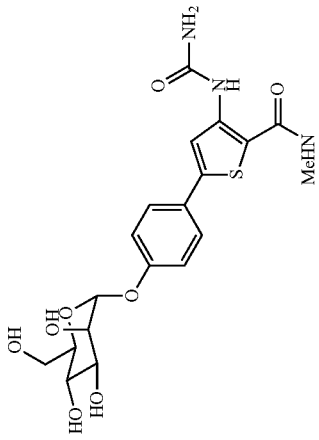 | C19H22N2O8S | 438.4 | | | | | | | |
| | | | | 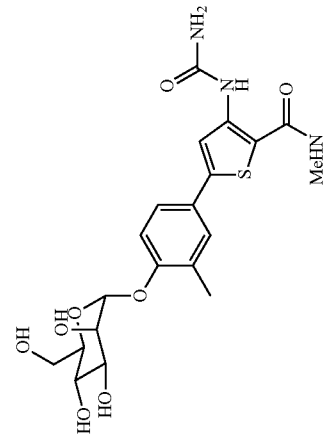 | C20H24N2O8S | 452.5 | | | | | | | |

TABLE 15-continued

| JMedChem 2010 Example | Compound Name | Patent Example | IUPAC Name | Structure | Molecular Formula | Molecular Weight (g/mol) | HAI Titer EC>90 (μM) | Biofilm IC50 [calculated] (approximated), μM | FimH EC50 (μM)- June 30 | FimH EC50 (μM) | Old Kd | ESI MS [M + H+] | 1H NMR (300 MHz, d4-METHANOL) δ ppm unless otherwise noted |
|---|---|---|---|---|---|---|---|---|---|---|---|---|---|
| | | | | | C20H21F3N2O8S | 506.4 | | | | | | | |
| | | | | | C20H24N2O9S | 468.5 | | | | | | | |

TABLE 15-continued

| JMedChem 2010 Example | Compound Name | Patent Example | IUPAC Name | Structure | Molecular Formula | Molecular Weight (g/mol) | HAI Titer EC>90 (µM) | Biofilm IC50 [calculated] (approximated) µM | FimH EC50 (µM)- June 30 | FimH EC50 (µM) Old | Kd | ESI MS [M + H⁺] | 1H NMR (300 MHz, d₄-METHANOL) δ ppm unless otherwise noted |
|---|---|---|---|---|---|---|---|---|---|---|---|---|---|
| | | | | | $C_{19}H_{21}ClN_2O_8S$ | 472.9 | | | | | | | |
| | | | | | $C_{19}H_{21}FN_2O_8S$ | 456.4 | | | | | | | |
| | | | | | $C_{17}H_{20}N_2O_7S$ | 396.4 | | | | | | | |

TABLE 15-continued

| JMedChem 2010 Example | Patent Example | Compound Name | IUPAC Name | Structure | Molecular Formula | Molecular Weight (g/mol) | HAI Titer EC>90 (μM) | Biofilm IC50 [calculated] (approximated) μM | FimH EC50 (μM)- June 30 | FimH EC50 (μM) | Old Kd | ESI MS [M + H+] | 1H NMR (300 MHz, d4-METHANOL) δ ppm unless otherwise noted |
|---|---|---|---|---|---|---|---|---|---|---|---|---|---|
| | | | | | $C_{18}H_{22}N_2O_7S$ | 410.4 | | | | | | | |
| | | | | | $C_{18}H_{19}F_3N_2O_7S$ | 464.4 | | | | | | | |
| | | | | | $C_{17}H_{19}ClN_2O_7S$ | 430.9 | | | | | | | |

TABLE 15-continued

| JMedChem 2010 Example | Compound Name | Patent Example | IUPAC Name | Structure | Molecular Formula | Molecular Weight (g/mol) | HAI Titer EC>90 (μM) | Biofilm IC50 [calculated] (approximated), μM | FimH EC50 (μM)-June 30 | FimH EC50 (μM) | Old Kd | ESI MS [M + H]+ | 1H NMR (300 MHz, d4-METHANOL) δ ppm unless otherwise noted |
|---|---|---|---|---|---|---|---|---|---|---|---|---|---|
| | | | | | C18H22N2O8S | 426.4 | | | | | | | |
| | | | | | C17H19FN2O7S | 414.4 | | | | | | | |
| | | | | | C19H22N2O9S | 454.4 | | | | | | | |

TABLE 15-continued

| JMedChem 2010 Example | Patent Example | Compound Name | IUPAC Name | Structure | Molecular Formula | Molecular Weight (g/mol) | HAI Titer EC>90 (μM) | Biofilm IC50 [calculated] (approximated) μM | FimH EC50 (μM)- June 30 | FimH EC50 (μM) | Old Kd | ESI MS [M + H+] | 1H NMR (300 MHz, d4-METHANOL) δ ppm unless otherwise noted |
|---|---|---|---|---|---|---|---|---|---|---|---|---|---|
| | | | | | C19H22N2O8S | 438.4 | | | | | | | |
| | | | | | C17H20N2O7S | 396.4 | | | | | | | |

TABLE 15-continued

| JMedChem 2010 Example | Compound Name | Patent Example | IUPAC Name | Structure | Molecular Formula | Molecular Weight (g/mol) | HAI Titer EC>90 (µM) | Biofilm IC50 [calculated] (approximated) µM | FimH EC50 (µM)-June 30 | FimH EC50 (µM) Old Kd | ESI MS [M + H+] | 1H NMR (300 MHz, d4-METHANOL) δ ppm unless otherwise noted |
|---|---|---|---|---|---|---|---|---|---|---|---|---|
| | | | | | C21H21NO6 | 383.4 | | | | | | |
| | | | | | C20H20N2O6 | 384.4 | | | | | | |
| | | | | | C20H20N2O6 | 384.4 | | | | | | |

TABLE 15-continued

| JMedChem 2010 Example | Compound Name | Patent Example | IUPAC Name | Structure | Molecular Formula | Molecular Weight (g/mol) | HAI Titer EC>90 (µM) | Biofilm IC50 [calculated] (approximated) µM | FimH EC50 (µM)- June 30 | FimH EC50 (µM) | Old Kd | ESI MS [M + H+] | 1H NMR (300 MHz, d4-METHANOL) δ ppm unless otherwise noted |
|---|---|---|---|---|---|---|---|---|---|---|---|---|---|
| | | | | | C22H23NO7S | 445.5 | | | | | | | |
| | | | | | C22H23NO8 | 429.4 | | | | | | | |
| | | | | | C22H24N2O7 | 428.4 | | | | | | | |

TABLE 15-continued

| JMedChem 2010 Example | Compound Name | Patent Example | IUPAC Name | Structure | Molecular Formula | Molecular Weight (g/mol) | HAI Titer EC>90 (µM) | Biofilm IC50 [calculated] (approximated) µM | FimH EC50 (µM)- June 30 | FimH EC50 (µM) | Old Kd | ESI MS [M + H+] | 1H NMR (300 MHz, d4-METHANOL) δ ppm unless otherwise noted |
|---|---|---|---|---|---|---|---|---|---|---|---|---|---|
| | | | | | C21H23N3O7 | 429.4 | | | | | | | |
| | | | | | C21H22N2O7S | 446.5 | | | | | | | |
| | | | | | C21H22N2O8 | 430.4 | | | | | | | |

TABLE 15-continued

| JMedChem 2010 Example | Patent Example | Compound Name | IUPAC Name | Structure | Molecular Formula | Molecular Weight (g/mol) | HAI Titer EC>90 (μM) | Biofilm IC50 [calculated] (approximated), μM | FimH EC50 (μM)- June 30 | FimH EC50 (μM) | Old Kd | ESI MS [M + H+] | 1H NMR (300 MHz, d4-METHANOL) δ ppm unless otherwise noted |
|---|---|---|---|---|---|---|---|---|---|---|---|---|---|
| | | | | | $C_{21}H_{25}NO_6$ | 387.4 | | | | | | | |
| | | | | | $C_{22}H_{27}NO_6$ | 401.4 | | | | | | | |
| | | | | | $C_{22}H_{24}F_3NO_6$ | 455.4 | | | | | | | |
| | | | | | $C_{21}H_{24}ClNO_6$ | 421.9 | | | | | | | |

TABLE 15-continued
| JMedChem 2010 Example | Compound Name | IUPAC Name | Structure | Molecular Formula | Molecular Weight (g/mol) | HAI Titer EC>90 (μM) | Biofilm IC50 [calculated] (approximated), μM | FimH EC50 (μM)- June 30 | FimH EC50 (μM) | Old Kd | ESI MS [M + H+] | 1H NMR (300 MHz, d4-METHANOL) δ ppm unless otherwise noted |
|---|---|---|---|---|---|---|---|---|---|---|---|---|
| | | | 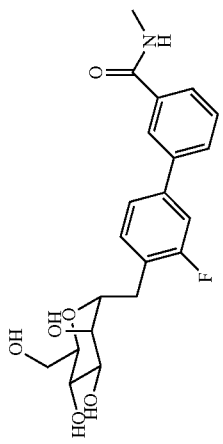 | $C_{21}H_{24}FNO_6$ | 405.4 | | | | | | | |
| | | | 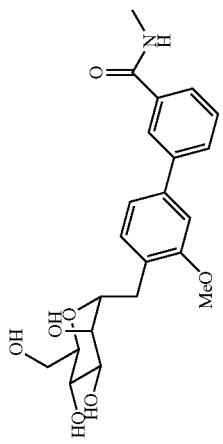 | $C_{22}H_{27}NO_7$ | 417.4 | | | | | | | |
| | | | 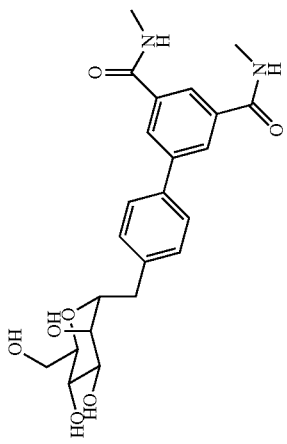 | $C_{23}H_{28}N_2O_7$ | 444.5 | | | | | | | |

TABLE 15-continued

| JMedChem 2010 Example | Compound Name | Patent Example | IUPAC Name | Structure | Molecular Formula | Molecular Weight (g/mol) | HAI Titer EC>90 (µM) | Biofilm IC50 [calculated] (approximated) µM | FimH EC50 (µM)- June 30 | FimH EC50 (µM) | Old Kd | ESI MS [M + H+] | 1H NMR (300 MHz, d4-METHANOL) δ ppm unless otherwise noted |
|---|---|---|---|---|---|---|---|---|---|---|---|---|---|
| | | | | | C24H30N2O7 | 458.5 | | | | | | | |
| | | | | | C24H27F3N2O7 | 512.5 | | | | | | | |
| | | | | | C23H27ClN2O7 | 478.9 | | | | | | | |

TABLE 15-continued

| JMedChem 2010 Example | Compound Name | Patent Example | IUPAC Name | Structure | Molecular Formula | Molecular Weight (g/mol) | HAI Titer EC>90 (μM) | Biofilm IC50 [calculated] (approximated), μM | FimH EC50 (μM)-June 30 | FimH EC50 (μM) | Old Kd | ESI MS [M + H+] | 1H NMR (300 MHz, d4-METHANOL) δ ppm unless otherwise noted |
|---|---|---|---|---|---|---|---|---|---|---|---|---|---|
| | | | | | C23H27FN2O7 | 462.5 | | | | | | | |
| | | | | | C24H30N2O8 | 474.5 | | | | | | | |

TABLE 21

| Compound Name | Structure | HAI Titer EC$_{>50}$ (μM) | Biofilm Prevention IC$_{50}$ (μM) | Biofilm Disruption IC$_{50}$ (μM) | PAMPA (LogPe) | DSF melting Temp (C.) |
|---|---|---|---|---|---|---|
| 1JWJ149 | 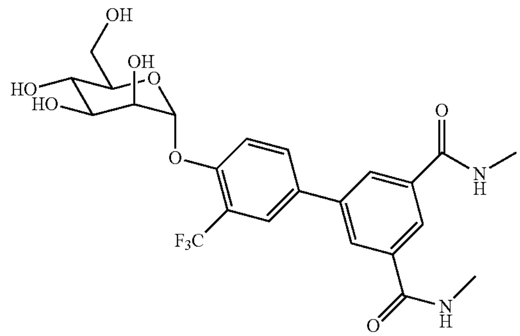 | 0.008 | 0.043 | | −6.27 | 76.15 |
| 4ZFH52 | 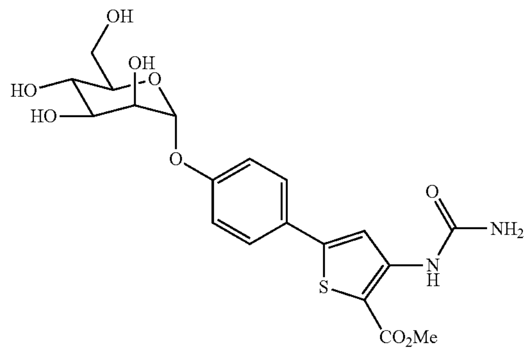 [SMILES: COC(=O)c1sc(-c2ccc(OC3OC(CO)C(O)C(O)C3O)cc2)cc1NC(N)=O] | 0.016 | 0.181 | | | |
| 4ZFH284 | 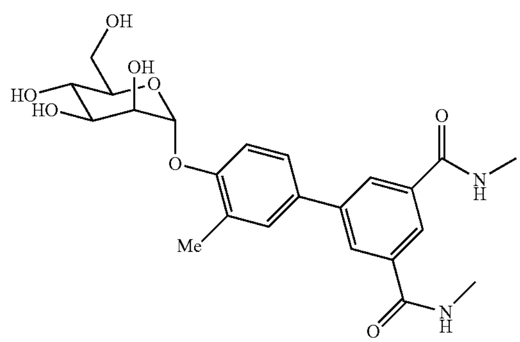 [SMILES: CNC(=O)c1cc(C(=O)NC)cc(-c2ccc(OC3OC(CO)C(O)C(O)C3O)c(C)c2)c1] | 0.016 | ?? | | | |
| 4ZFH272 | 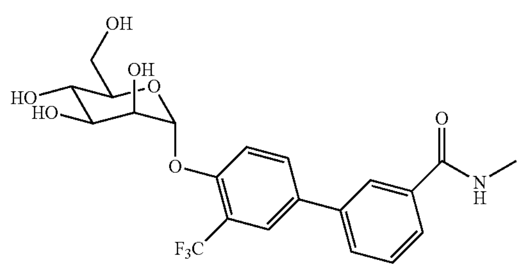 [SMILES: CNC(=O)c1cccc(-c2ccc(OC3OC(CO)C(O)C(O)C3O)c(C(F)(F)F)c2)c1] | 0.032 | 0.127 | | | 72.29 |
| 4ZFH222 | 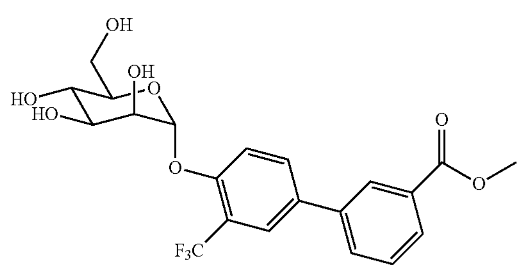 [SMILES: COC(=O)c1cccc(-c2ccc(OC3OC(CO)C(O)C(O)C3O)c(C(F)(F)F)c2)c1] | 0.032 | 8.167 | | −3.91 | |

TABLE 21-continued

| Compound Name | Structure | HAI Titer EC$_{>50}$ (µM) | Biofilm Prevention IC$_{50}$ (µM) | Biofilm Disruption IC$_{50}$ (µM) | PAMPA (LogPe) | DSF melting Temp (C.) |
|---|---|---|---|---|---|---|
| 4ZFH269 | 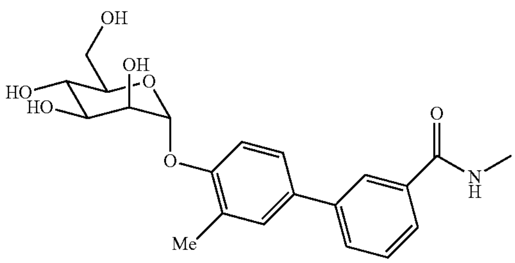 [SMILES: CNC(=O)c1cccc(-c2ccc(OC3OC(CO)C(O)C(O)C3O)c(C)c2)c1] | 0.06 | 0.159 | | −3.89 | 74.46 |
| 5ZFH63 | 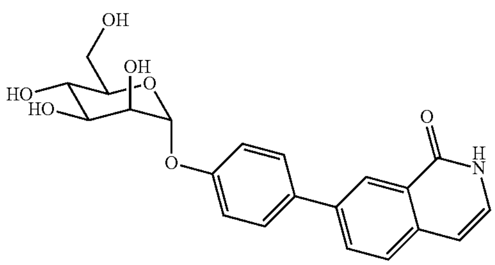 [SMILES: O=c1[nH]ccc2ccc(-c3ccc(OC4OC(CO)C(O)C(O)C4O)cc3)cc12] | 0.100 | | | | |
| 4ZFH224 | 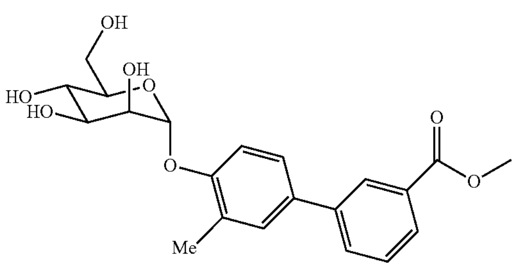 [SMILES: COC(=O)c1cccc(-c2ccc(OC3OC(CO)C(O)C(O)C3O)c(C)c2)c1] | 0.125 | 0.3329 | | | |
| 4ZFH170 | 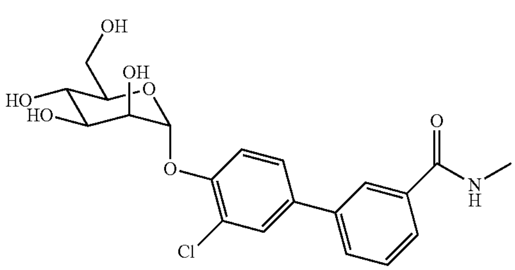 [SMILES: CNC(=O)c1cccc(-c2ccc(OC3OC(CO)C(O)C(O)C3O)c(Cl)c2)c1] | 0.125 | 0.523 | | | |
| 4ZFH228 | 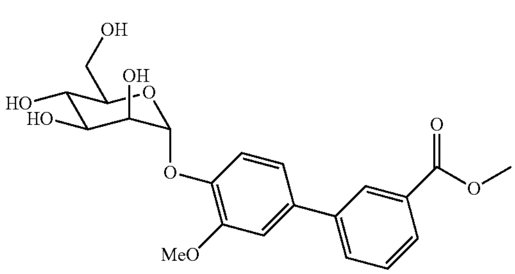 [SMILES: COC(=O)c1cccc(-c2ccc(OC3OC(CO)C(O)C(O)C3O)c(OC)c2)c1] | 0.188 | 0.886 | | | |

TABLE 21-continued
| Compound Name | Structure | HAI Titer EC$_{>50}$ (μM) | Biofilm Prevention IC$_{50}$ (μM) | Biofilm Disruption IC$_{50}$ (μM) | PAMPA (LogPe) | DSF melting Temp (C.) |
| --- | --- | --- | --- | --- | --- | --- |
| 5ZFH61 | 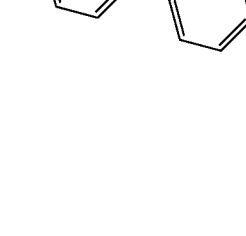 | 0.250 | | | | |
| 4ZFH308 | 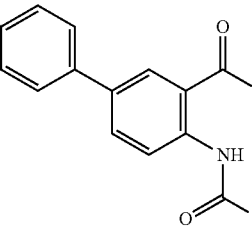 | 0.250 | | | | |
| 5ZFH38 | 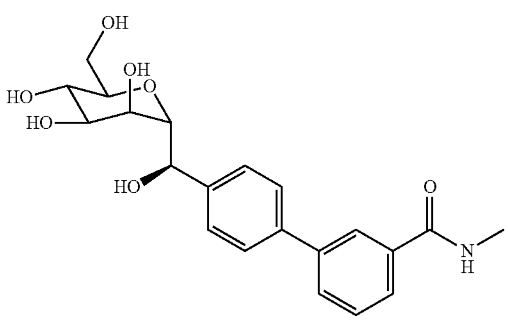 [SMILES: CNC(=O)c1cccc(-c2ccc([C@@H](O)C3OC(CO)C(O)C(O)C3O)cc2)c1] | 0.250 | | | | |
| 4ZFH247 | 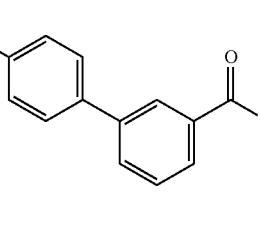 | 0.375 | | | | |

TABLE 21-continued

| Compound Name | Structure | HAI Titer EC$_{>50}$ (µM) | Biofilm Prevention IC$_{50}$ (µM) | Biofilm Disruption IC$_{50}$ (µM) | PAMPA (LogPe) | DSF melting Temp (C.) |
|---|---|---|---|---|---|---|
| 4ZFH306 | 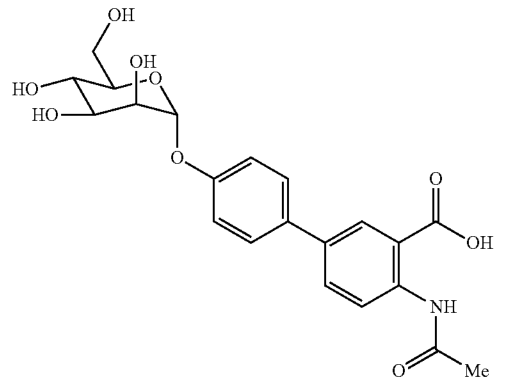 [SMILES: CC(=O)Nc1ccc(-c2ccc(OC3OC(CO)C(O)C(O)C3O)cc2)cc1C(=O)O] | 0.750 | | | | |
| 4ZFH275 | 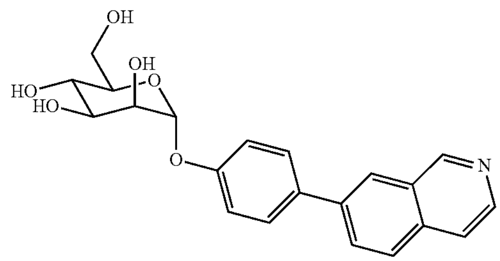 [SMILES: OCC1OC(Oc2ccc(-c3ccc4ccncc4c3)cc2)C(O)C(O)C1O] | 0.750 | | | | |
| 4ZFH220 | 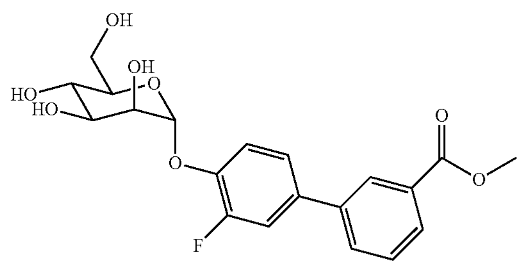 [SMILES: COC(=O)c1cccc(-c2ccc(OC3OC(CO)C(O)C(O)C3O)c(F)c2)c1] | 0.750 | | | | |
| 4ZFH303 | 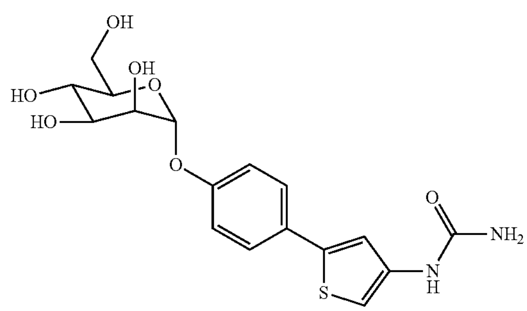 [SMILES: NC(=O)Nc1csc(-c2ccc(OC3OC(CO)C(O)C(O)C3O)cc2)c1] | 1.000 | | | | |
| 4ZFH277 | 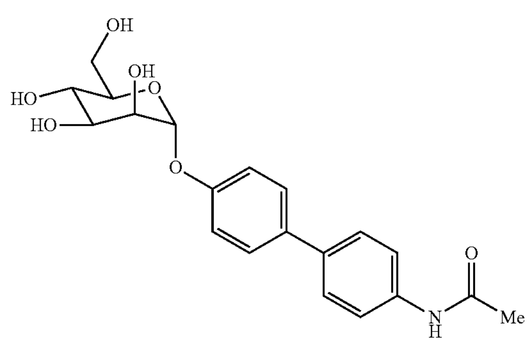 [SMILES: CC(=O)Nc1ccc(-c2ccc(OC3OC(CO)C(O)C(O)C3O)cc2)cc1] | 1.000 | | | | |

TABLE 21-continued

| Compound Name | Structure | HAI Titer EC$_{>50}$ (μM) | Biofilm Prevention IC$_{50}$ (μM) | Biofilm Disruption IC$_{50}$ (μM) | PAMPA (LogPe) | DSF melting Temp (C.) |
|---|---|---|---|---|---|---|
| 5ZFH49 | 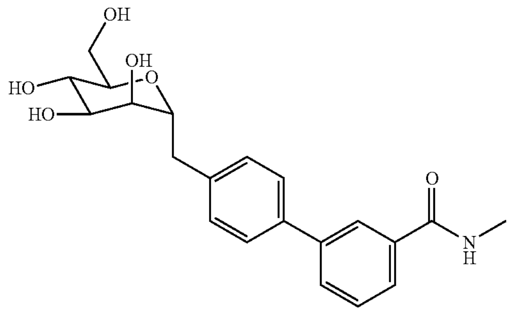 [SMILES: CNC(=O)c1cccc(-c2ccc(CC3OC(CO)C(O)C(O)C3O)cc2)c1] | 1.000 | | | | |
| 4ZFH218 | 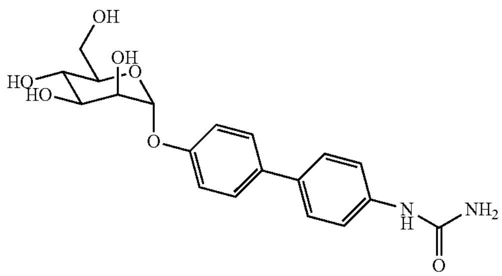 [SMILES: NC(=O)Nc1ccc(-c2ccc(OC3OC(CO)C(O)C(O)C3O)cc2)cc1] | 3.000 | | | −4.35 | |
| 3ZFH26 | 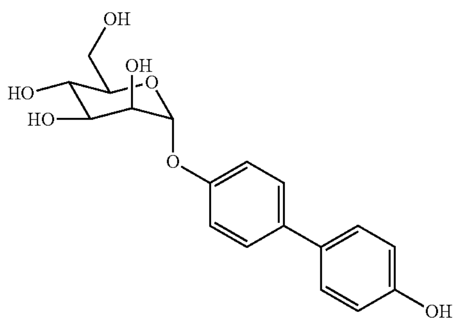 | 6.000 | | | −8.890 | |
| 3ZF117 | 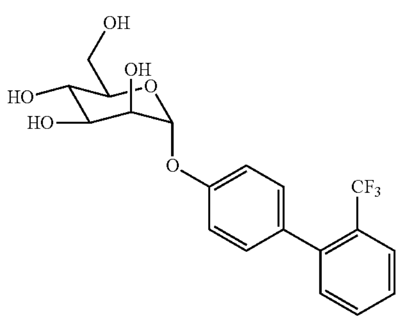 | 8.000 | | | | |
| 4ZFH131 | 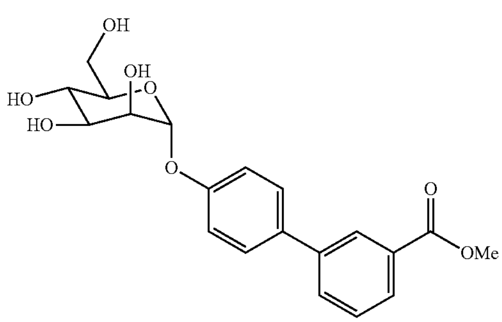 [SMILES: COC(=O)c1cccc(-c2ccc(OC3OC(CO)C(O)C(O)C3O)cc2)c1] | 16.000 | | | | |

TABLE 21-continued

| Compound Name | Structure | HAI Titer EC$_{>50}$ (μM) | Biofilm Prevention IC$_{50}$ (μM) | Biofilm Disruption IC$_{50}$ (μM) | PAMPA (LogPe) | DSF melting Temp (C.) |
|---|---|---|---|---|---|---|
| 4ZFH123 | 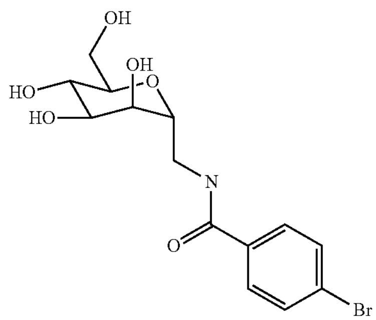 [SMILES: O=C(NCC1OC(CO)C(O)C(O)C1O)c1ccc(Br)cc1] | 16.000 | | | | |
| 5ZFH48 | 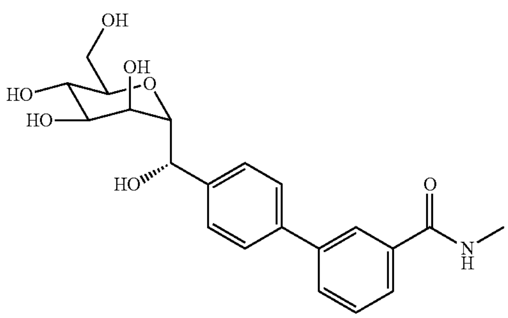 [SMILES: CNC(=O)c1cccc(-c2ccc([C@H](O)C3OC(CO)C(O)C(O)C3O)cc2)c1] | 24.000 | | | | |
| 1ZFH84 | 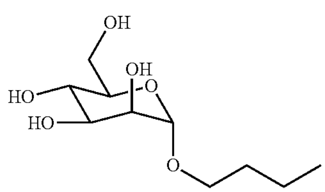 [SMILES: CCCCOC1OC(CO)C(O)C(O)C1O] | 125.000 | (~500) | | | |
| 1ZFH74 | 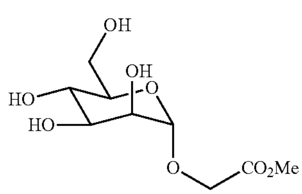 [SMILES: COC(=O)COC1OC(CO)C(O)C(O)C1O] | 500.000 | | | | |
| 2ZFH20 | 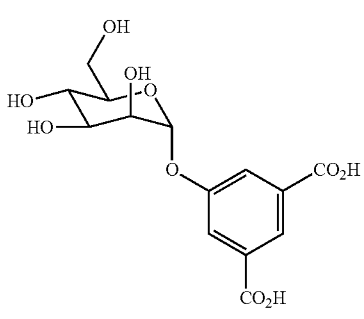 [SMILES: O=C(O)c1cc(OC2OC(CO)C(O)C(O)C2O)cc(C(=O)O)c1] | ? | | | | |

TABLE 21-continued

| Compound Name | Structure | HAI Titer EC$_{>50}$ (μM) | Biofilm Prevention IC$_{50}$ (μM) | Biofilm Disruption IC$_{50}$ (μM) | PAMPA (LogPe) | DSF melting Temp (C.) |
|---|---|---|---|---|---|---|
| 1JWJ93 | 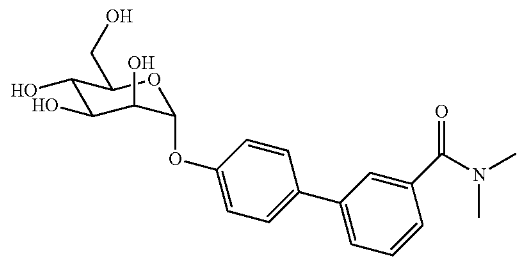 [SMILES: CN(C)C(=O)c1cccc(-c2ccc(OC3OC(CO)C(O)C(O)C3O)cc2)c1] | | | | | |
| 2ZFH238 | 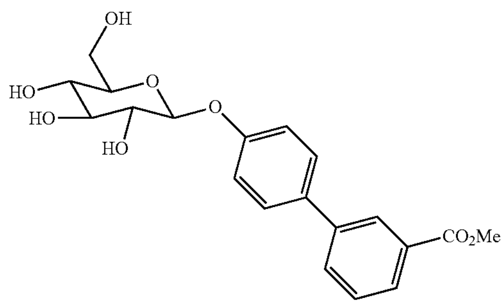 [SMILES: COC(=O)c1cccc(-c2ccc(OC3OC(CO)C(O)C(O)C3O)cc2)c1] | | | >2.5 mM | | |
| 2ZFH236 | 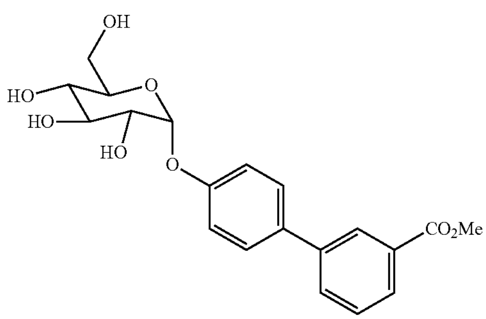 [SMILES: COC(=O)c1cccc(-c2ccc(OC3OC(CO)C(O)C(O)C3O)cc2)c1] | | | >2.5 mM | −4.250 | |
| 1ZFH134 | 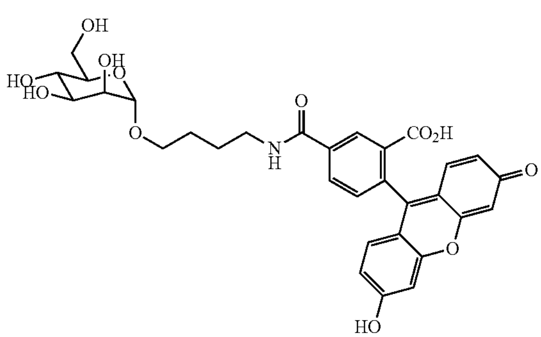 [SMILES: O=C(NCCCCOC1OC(CO)C(O)C(O)C1O)c1ccc(-c2c3ccc(=O)cc-3oc3cc(O)ccc23)c(C(=O)O)c1] | | | 125.000 | | |
| α-D-mannose | 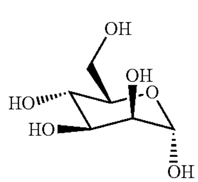 | | | | | |

TABLE 22

| Compound Name | IUPAC Name | Structure | Molecular Formula | Mol. Weight (g/mol) | HAI Titer EC$_{>90}$ μM |
|---|---|---|---|---|---|
| 1JWJ149 | N1,N3-dimethyl-5-[3-(trifluoromethyl)-4-[(3R,4S,5S,6S)-3,4,5-trihydroxy-6-(hydroxymethyl)tetrahydropyran-2-yl]oxy-phenyl]benzene-1,3-dicarboxamide | 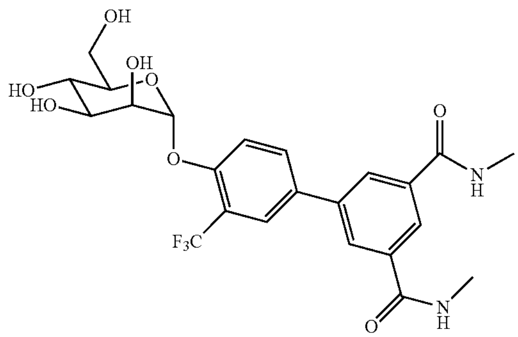 | C$_{23}$H$_{25}$F$_3$N$_2$O$_8$ | 514.4 | 0.008 |
| 4ZFH284 | N1,N3-dimethyl-5-[3-methyl-4-[(3R,4S,5S,6S)-3,4,5-trihydroxy-6-(hydroxymethyl)tetrahydropyran-2-yl]oxy-phenyl]benzene-1,3-dicarboxamide | 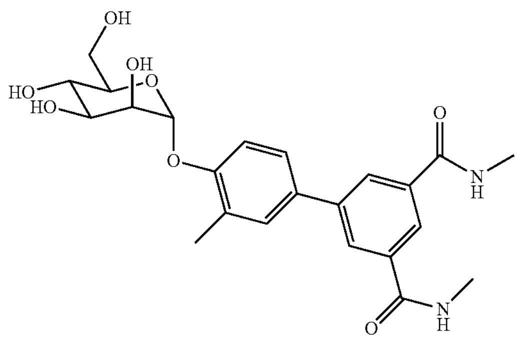 [SMILES: CNC(=O)c1cc(C(=O)NC)cc(-c2ccc(OC3OC(CO)C(O)C(O)C3O)c(C)c2)c1] | C$_{23}$H$_{28}$N$_2$O$_8$ | 460.5 | 0.016 |
| 4ZFH222 | methyl 3-[3-(trifluoromethyl)-4-[(3R,4S,5S,6S)-3,4,5-trihydroxy-6-(hydroxymethyl)tetrahydropyran-2-yl]oxy-phenyl]benzoate | 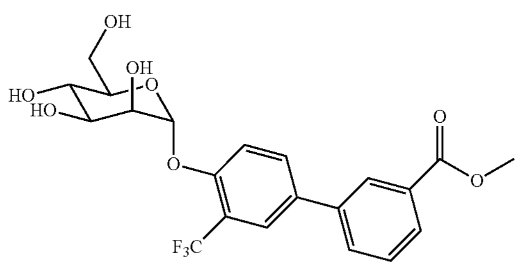 | C$_{21}$H$_{21}$F$_3$O$_8$ | 458.4 | 0.032 |
| 4ZFH272 | N-methyl-3-[3-(trifluoromethyl)-4-[(3R,4S,5S,6S)-3,4,5-trihydroxy-6-(hydroxymethyl)tetrahydropyran-2-yl]oxy-phenyl]benzamide | 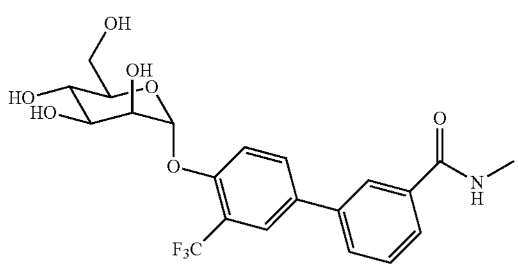 | C$_{21}$H$_{22}$F$_3$NO$_7$ | 457.4 | 0.032 |
| 4ZFH269 | N-methyl-3-[3-methyl-4-[(3R,4S,5S,6S)-3,4,5-trihydroxy-6-(hydroxymethyl)tetrahydropyran-2-yl]oxy-phenyl]benzamide | 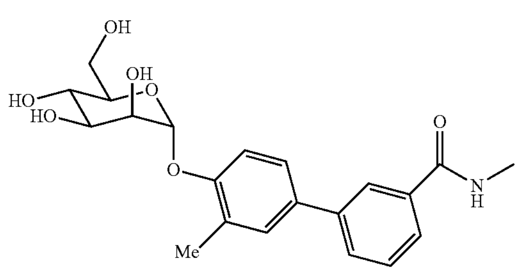 | C$_{21}$H$_{25}$NO$_7$ | 403.4 | 0.062 |

TABLE 22-continued

| Compound Name | IUPAC Name | Structure | Molecular Formula | Mol. Weight (g/mol) | HAI Titer $EC_{>90}$ μM |
|---|---|---|---|---|---|
| 4ZFH170 | 3-[3-chloro-4-[(3R,4S,5S,6S)-3,4,5-trihydroxy-6-(hydroxymethyl)tetrahydropyran-2-yl]oxy-phenyl]-N-methyl-benzamide | 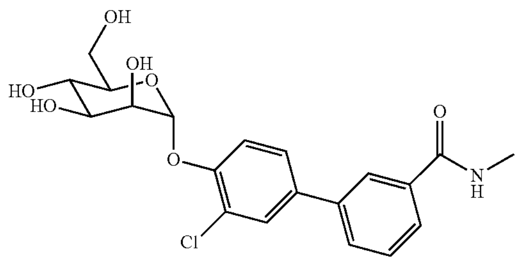 [SMILES: CNC(=O)c1cccc(-c2ccc(OC3OC(CO)C(O)C(O)C3O)c(Cl)c2)c1] | $C_{20}H_{22}ClNO_7$ | 423.8 | 0.125 |
| 4ZFH224 | methyl 3-[3-methyl-4-[(3R,4S,5S,6S)-3,4,5-trihydroxy-6-(hydroxymethyl)tetrahydropyran-2-yl]oxy-phenyl]benzoate | 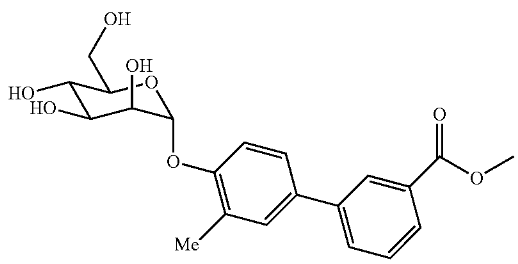 | $C_{21}H_{24}O_8$ | 404.4 | 0.125 |
| 4ZFH228 | methyl 3-[3-methoxy-4-[(3R,4S,5S,6S)-3,4,5-trihydroxy-6-(hydroxymethyl)tetrahydropyran-2-yl]oxy-phenyl]benzoate | 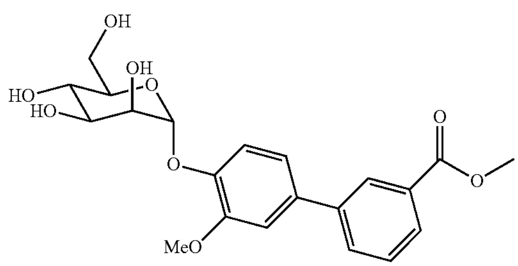 | $C_{21}H_{24}O_9$ | 420.4 | 0.188 |
| 4ZFH247 | (2S,3S,4S,5R)-2-(hydroxymethyl)-6-(4-quinazolin-6-ylphenoxy)tetrahydropyran-3,4,5-triol | 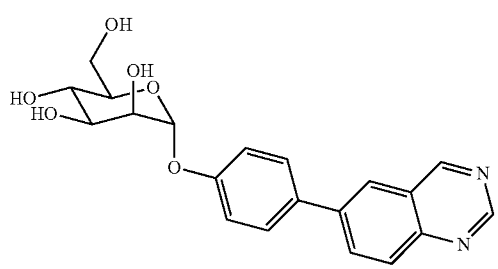 [SMILES: OCC1OC(Oc2ccc(-c3ccc4ncncc4c3)cc2)C(O)C(O)C1O] | $C_{20}H_{20}N_2O_6$ | 384.4 | 0.375 |
| 4ZFH220 | methyl 3-[3-fluoro-4-[(3R,4S,5S,6S)-3,4,5-trihydroxy-6-(hydroxymethyl)tetrahydropyran-2-yl]oxy-phenyl]benzoate | 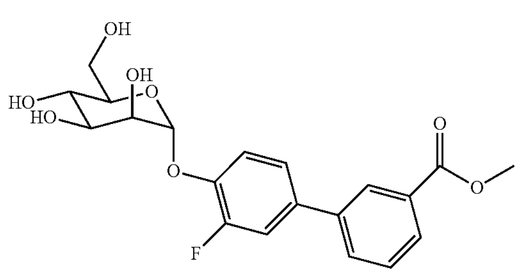 [SMILES: COC(=O)c1cccc(-c2ccc(OC3OC(CO)C(O)C(O)C3O)c(F)c2)c1] | $C_{20}H_{21}FO_8$ | 408.4 | 0.750 |

TABLE 22-continued

| Compound Name | IUPAC Name | Structure | Molecular Formula | Mol. Weight (g/mol) | HAI Titer $EC_{>90} \mu M$ |
|---|---|---|---|---|---|
| 4ZFH275 | (2S,3S,4S,5R)-2-(hydroxymethyl)-6-[4-(7-isoquinolyl)phenoxy]tetrahydropyran-3,4,5-triol | 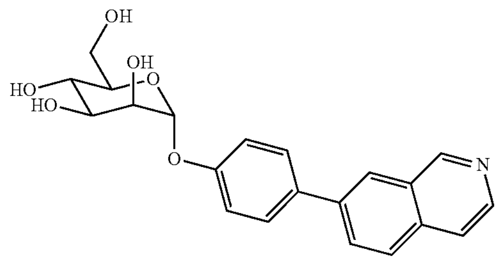 [SMILES: OCC1OC(Oc2ccc(-c3ccc4ccncc4c3)cc2)C(O)C(O)C1O] | $C_{21}H_{21}NO_6$ | 383.4 | 0.750 |
| 4ZFH218 | [4-[4-[(3R,4S,5S,6S)-3,4,5-trihydroxy-6-(hydroxymethyl)tetrahydropyran-2-yl]oxyphenyl]phenyl]urea | 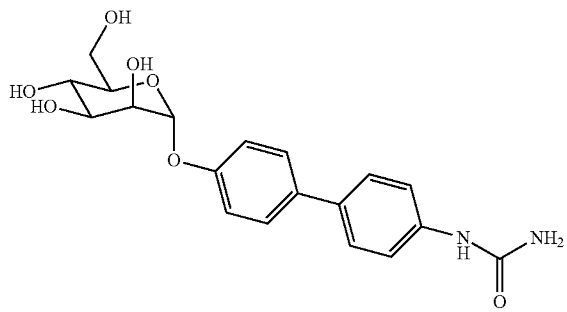 [SMILES: NC(=O)Nc1ccc(-c2ccc(OC3OC(CO)C(O)C(O)C3O)cc2)cc1] | $C_{19}H_{22}N_2O_7$ | 390.4 | 3.000 |
| 2ZFH20 | 5-[(3R,4S,5S,6S)-3,4,5-trihydroxy-6-(hydroxymethyl)tetrahydropyran-2-yl]oxybenzene-1,3-dicarboxylic acid | 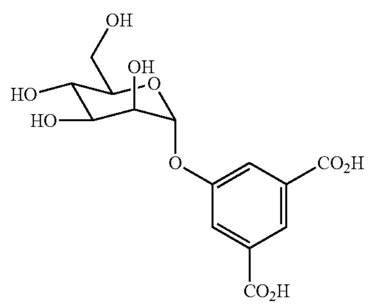 [SMILES: O=C(O)c1cc(OC2OC(CO)C(O)C(O)C2O)cc(C(=O)O)c1] | $C_{14}H_{16}O_{10}$ | 344.3 | ? |
| 4ZFH131 | methyl 3-[4-[[(3R,4R,5S,6S)-3,4,5-trihydroxy-6-(hydroxymethyl)tetrahydropyran-2-yl]methylcarbamoyl]phenyl]benzoate | 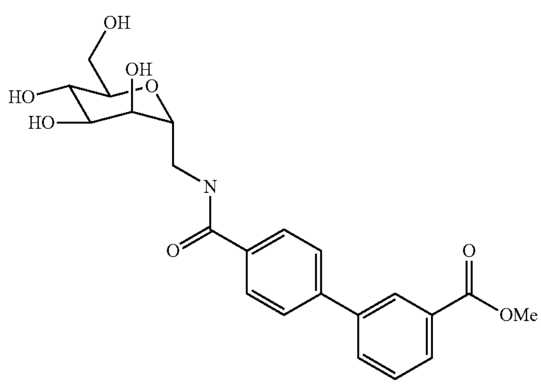 [SMILES: COC(=O)c1cccc(-c2ccc(C(=O)NCC3OC(CO)C(O)C(O)C3O)cc2)c1] | $C_{22}H_{25}NO_8$ | 431.44 | 16.000 |
| 4ZFH123 | 4-bromo-N-[[(3R,4R,5S,6S)-3,4,5-trihydroxy-6-(hydroxymethyl)tetrahydropyran-2-yl]methyl]benzamide | 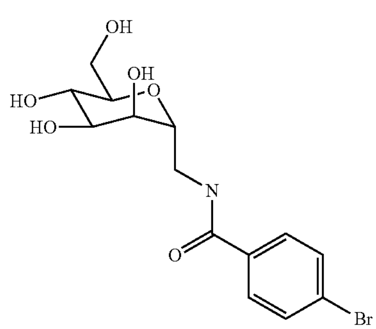 [SMILES: O=C(NCC1OC(CO)C(O)C(O)C1O)c1ccc(Br)cc1] | $C_{14}H_{18}BrNO_6$ | 376.2 | 16.000 |

TABLE 22-continued

| Compound Name | IUPAC Name | Structure | Molecular Formula | Mol. Weight (g/mol) | HAI Titer $EC_{>90}\,\mu M$ |
|---|---|---|---|---|---|
| | | | $C_{13}H_{17}BrO_6$ | 349.2 | |
| | | | $C_{13}H_{14}BrF_3O_6$ | 403.1 | |
| | | | $C_{12}H_{14}BrClO_6$ | 369.6 | |
| | | | $C_{13}H_{17}BrO_7$ | 365.2 | |
| | | | $C_{12}H_{14}BrFO_6$ | 353.14 | |

TABLE 22-continued

| Compound Name | IUPAC Name | Structure | Molecular Formula | Mol. Weight (g/mol) | HAI Titer EC>90 μM |
|---|---|---|---|---|---|
| | | | $C_{19}H_{29}BO_8$ | 396.2 | |
| | | | $C_{19}H_{26}BF_3O_8$ | 450.2 | |
| | | | $C_{18}H_{26}BClO_8$ | 416.7 | |
| | | | $C_{19}H_{29}BO_9$ | 412.2 | |
| | | | $C_{18}H_{26}BFO_8$ | 400.2 | |

TABLE 22-continued

| Compound Name | IUPAC Name | Structure | Molecular Formula | Mol. Weight (g/mol) | HAI Titer EC$_{>90}$ μM |
|---|---|---|---|---|---|
| | | | C$_{22}$H$_{25}$ClN$_2$O$_8$ | 480.9 | |
| | | | C$_{22}$H$_{25}$FN$_2$O$_8$ | 464.4 | |
| | | | C$_{23}$H$_{28}$N$_2$O$_9$ | 476.5 | |
| | | | C$_{20}$H$_{24}$N$_2$O$_9$S | 468.5 | |

TABLE 22-continued
| Compound Name | IUPAC Name | Structure | Molecular Formula | Mol. Weight (g/mol) | HAI Titer EC$_{>90}$ μM |
|---|---|---|---|---|---|
| | | 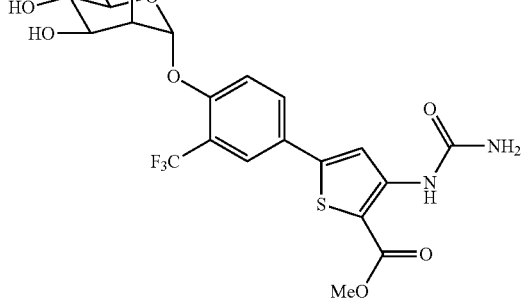 | C$_{20}$H$_{21}$F$_3$N$_2$O$_9$S | 522.4 | |
| | | 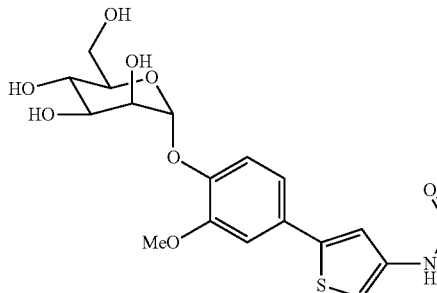 | C$_{20}$H$_{24}$N$_2$O$_{10}$S | 484.5 | |
| | | 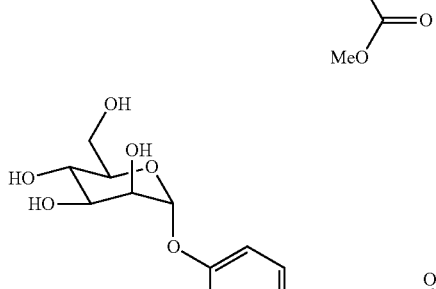 | C$_{19}$H$_{21}$ClN$_2$O$_9$S | 488.9 | |
| | | 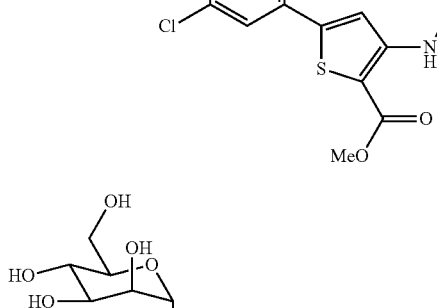 | C$_{19}$H$_{21}$FN$_2$O$_9$S | 472.4 | |

TABLE 22-continued

| Compound Name | IUPAC Name | Structure | Molecular Formula | Mol. Weight (g/mol) | HAI Titer EC$_{>90}$ μM) |
|---|---|---|---|---|---|
| | | | C$_{19}$H$_{22}$N$_2$O$_8$S | 438.4 | |
| | | | C$_{20}$H$_{24}$N$_2$O$_8$S | 452.5 | |
| | | | C$_{20}$H$_{21}$F$_3$N$_2$O$_8$ | 506.4 | |
| | | | C$_{20}$H$_{24}$N$_2$O$_9$S | 468.5 | |

TABLE 22-continued

| Compound Name | IUPAC Name | Structure | Molecular Formula | Mol. Weight (g/mol) | HAI Titer EC$_{>90}$ μM |
|---|---|---|---|---|---|
| | | | $C_{19}H_{21}ClN_2O_8S$ | 472.9 | |
| | | | $C_{19}H_{21}FN_2O_8S$ | 456.4 | |
| | | | $C_{17}H_{20}N_2O_7S$ | 396.4 | |
| | | | $C_{18}H_{22}N_2O_7S$ | 410.4 | |

TABLE 22-continued
| Compound Name | IUPAC Name | Structure | Molecular Formula | Mol. Weight (g/mol) | HAI Titer EC$_{>90}$ μM |
|---|---|---|---|---|---|
| | | 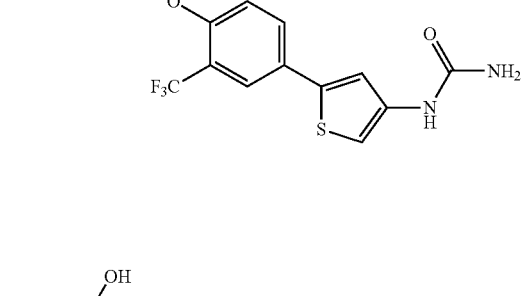 | C$_{18}$H$_{19}$F$_3$N$_2$O$_7$S | 464.4 | |
| | | 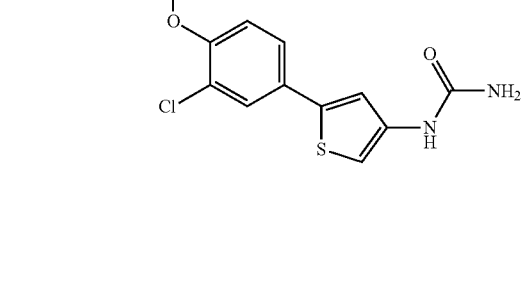 | C$_{17}$H$_{19}$ClN$_2$O$_7$S | 430.9 | |
| | | 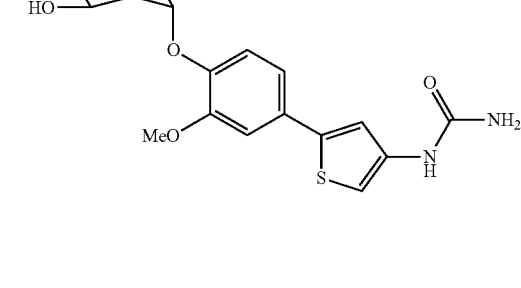 | C$_{18}$H$_{22}$N$_2$O$_8$S | 426.4 | |
| | | 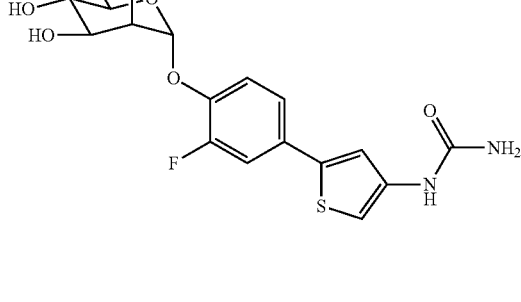 | C$_{17}$H$_{19}$FN$_2$O$_7$S | 414.4 | |

TABLE 22-continued

| Compound Name | IUPAC Name | Structure | Molecular Formula | Mol. Weight (g/mol) | HAI Titer EC$_{>90}$ µM |
|---|---|---|---|---|---|
| | | | C$_{19}$H$_{22}$N$_2$O$_9$S | 454.4 | |
| | | | C$_{19}$H$_{22}$N$_2$O$_8$S | 438.4 | |
| | | | C$_{17}$H$_{20}$N$_2$O$_7$S | 396.4 | |
| | | | C$_{21}$H$_{21}$NO$_6$ | 383.4 | |

| Compound Name | IUPAC Name | Structure | Molecular Formula | Mol. Weight (g/mol) | HAI Titer EC$_{>90}$ μM) |
|---|---|---|---|---|---|
| | | 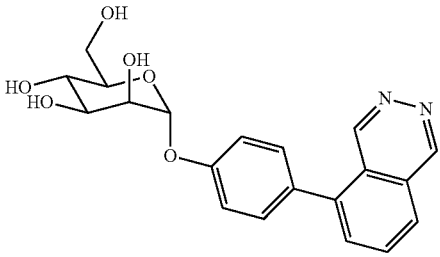 [SMILES: OCC1OC(Oc2ccc(-c3cccc4cnncc34)cc2)C(O)C(O)C1O] | C$_{20}$H$_{20}$N$_2$O$_6$ | 384.4 | |
| | | 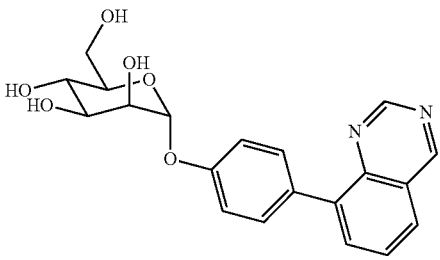 [SMILES: OCC1OC(Oc2ccc(-c3cccc4cncnc34)cc2)C(O)C(O)C1O] | C$_{20}$H$_{20}$N$_2$O$_6$ | 384.4 | |
| | | 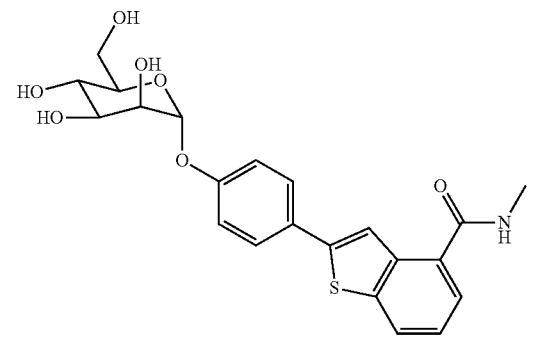 | C$_{22}$H$_{23}$NO$_7$S | 445.5 | |
| | | 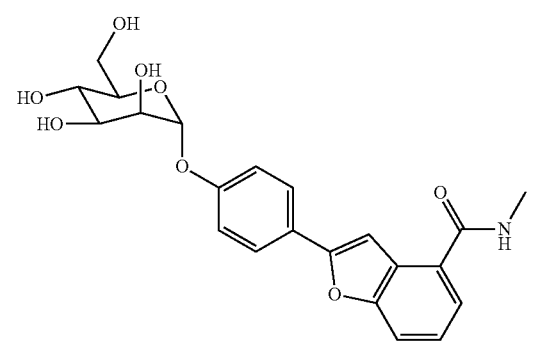 [SMILES: CNC(=O)c1cccc2oc(-c3ccc(OC4OC(CO)C(O)C(O)C4O)cc3)cc12] | C$_{22}$H$_{23}$NO$_8$ | 429.4 | |
| | | 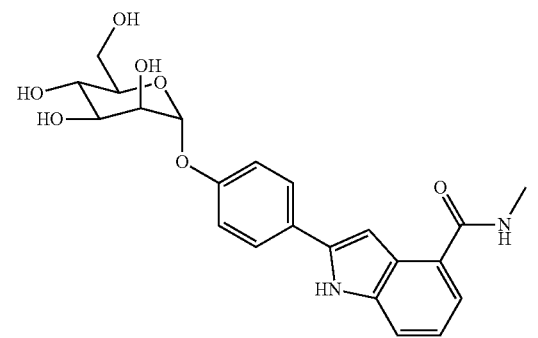 [SMILES: CNC(=O)c1cccc2[nH]c(-c3ccc(OC4OC(CO)C(O)C(O)C4O)cc3)cc12] | C$_{22}$H$_{24}$N$_2$O$_7$ | 428.4 | |

TABLE 22-continued

| Compound Name | IUPAC Name | Structure | Molecular Formula | Mol. Weight (g/mol) | HAI Titer EC>90 µM |
|---|---|---|---|---|---|
| | | | $C_{21}H_{23}N_3O_7$ | 429.4 | |
| | | | $C_{21}H_{22}N_2O_7S$ | 446.5 | |
| | | | $C_{21}H_{22}N_2O_8$ | 430.4 | |
| | | | $C_{21}H_{25}NO_6$ | 387.4 | |
| | | | $C_{22}H_{27}NO_6$ | 401.4 | |

TABLE 22-continued
| Compound Name | IUPAC Name | Structure | Molecular Formula | Mol. Weight (g/mol) | HAI Titer EC$_{>90}$ μM |
|---|---|---|---|---|---|
| | | 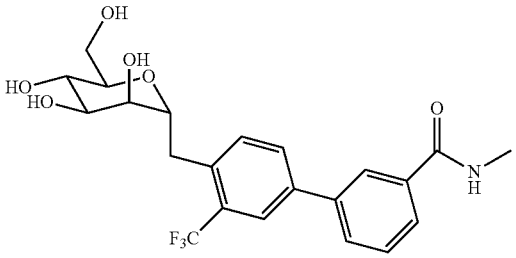 [SMILES: CNC(=O)c1cccc(-c2ccc(CC3OC(CO)C(O)C(O)C3O)c(C(F)(F)F)c2)c1] | C$_{22}$H$_{24}$F$_3$NO$_6$ | 455.4 | |
| | | 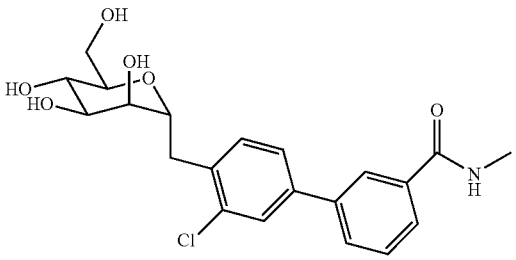 [SMILES: CNC(=O)c1cccc(-c2ccc(CC3OC(CO)C(O)C(O)C3O)c(Cl)c2)c1] | C$_{21}$H$_{24}$ClNO$_6$ | 421.9 | |
| | | 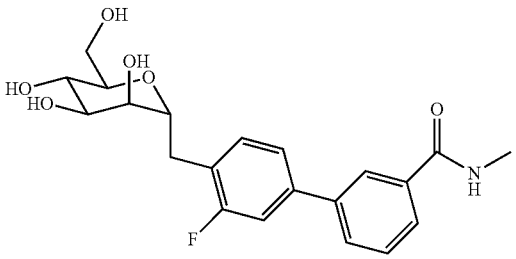 | C$_{21}$H$_{24}$FNO$_6$ | 405.4 | |
| | | 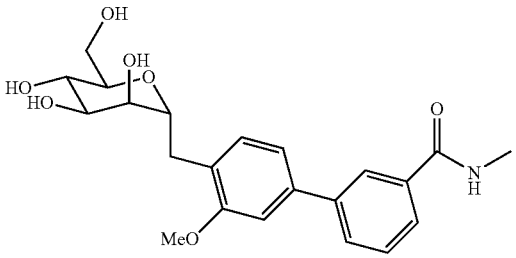 [SMILES: CNC(=O)c1cccc(-c2ccc(CC3OC(CO)C(O)C(O)C3O)c(OC)c2)c1] | C$_{22}$H$_{27}$NO$_7$ | 417.4 | |
| | | 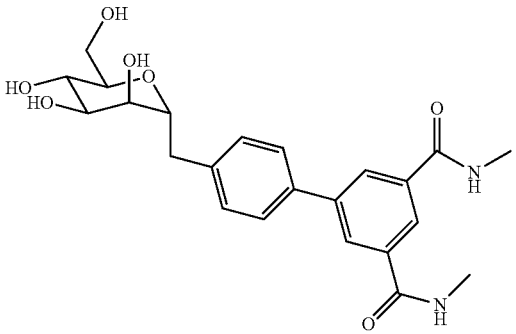 [SMILES: CNC(=O)c1cc(C(=O)NC)cc(-c2ccc(CC3OC(CO)C(O)C(O)C3O)cc2)c1] | C$_{23}$H$_{28}$N$_2$O$_7$ | 444.5 | |

TABLE 22-continued
| Compound Name | IUPAC Name | Structure | Molecular Formula | Mol. Weight (g/mol) | HAI Titer EC$_{>90}$ μM |
|---|---|---|---|---|---|
| | | 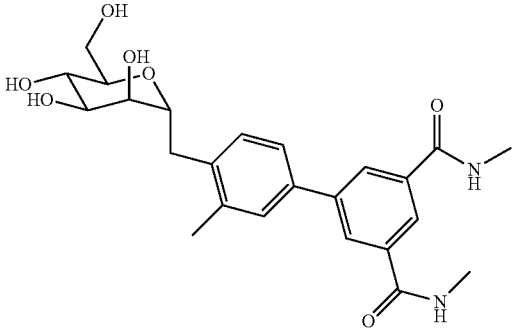 [SMILES: CNC(=O)c1cc(C(=O)NC)cc(-c2ccc(CC3OC(CO)C(O)C(O)C3O)c(C)c2)c1] | C$_{24}$H$_{30}$N$_2$O$_7$ | 458.5 | |
| | | 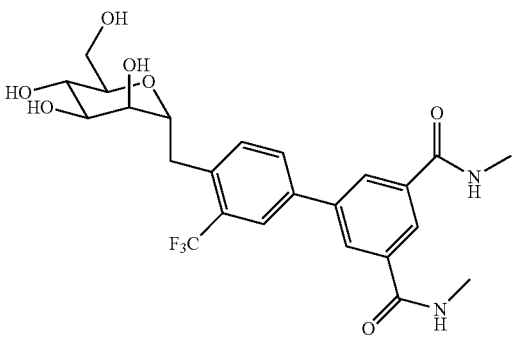 [SMILES: CNC(=O)c1cc(C(=O)NC)cc(-c2ccc(CC3OC(CO)C(O)C(O)C3O)c(C(F)(F)F)c2)c1] | C$_{24}$H$_{27}$F$_3$N$_2$O$_7$ | 512.5 | |
| | | 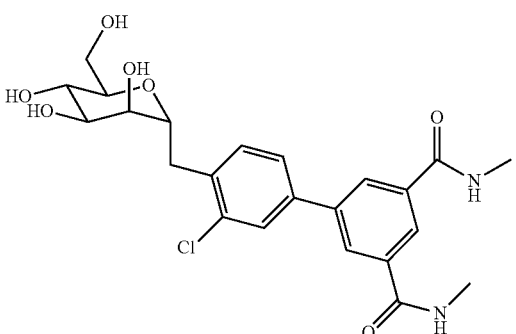 | C$_{23}$H$_{27}$ClN$_2$O$_7$ | 478.9 | |
| | | 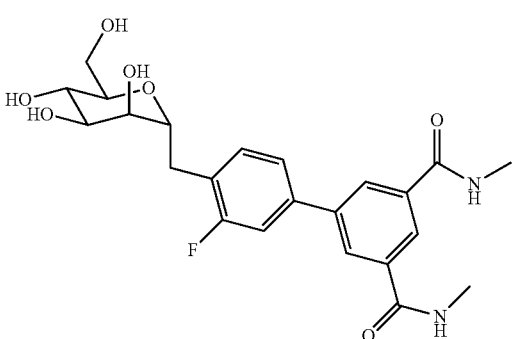 | C$_{23}$H$_{27}$FN$_2$O$_7$ | 462.5 | |

TABLE 22-continued

| Compound Name | IUPAC Name | Structure | Molecular Formula | Mol. Weight (g/mol) | HAI Titer EC$_{>90}$ μM |
|---|---|---|---|---|---|
| | | 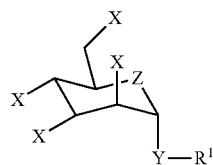 | C$_{24}$H$_{30}$N$_2$O$_8$ | 474.5 | |

What is claimed is:

1. A compound of Formula (I):

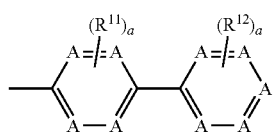

(I)

wherein:

X is selected from the group consisting of hydrogen, OR$^2$, SR$^2$, and NR$^z$;

Z is selected from the group consisting of O, S, CR$^3$ and NR$^4$;

Y is selected from the group consisting of oxygen, sulfur, CR$^3$, NR$^4$, —N(R$^5$)CO—, —CH$_2$N(R$^5$)—, —CH$_2$N(R$^5$)CO—, CO$_2$, SO$_2$, —CH$_2$O—, —CH$_2$S—, CO, —CON(R$^5$)—, —SO$_2$N(R$^5$)—, —O(CH$_2$)$_n$—, —S(CH$_2$)$_n$—, —N(CH$_2$)$_n$—, —(CH$_2$)$_n$—, NR$^5$, and an optionally substituted alkyl, alkene, alkyne, or heterocycle;

R$^2$ is independently selected from the group consisting of hydrogen, COR$^x$, CONR$^x$, hydrocarbyl, and substituted hydrocarbyl;

R$^3$, R$^4$, R$^5$ are independently selected from the group consisting of hydrogen, hydrocarbyl, and substituted hydrocarbyl;

R$^z$ is independently selected from the group consisting of hydrogen hydrocarbyl, substituted hydrocarbyl, —COR$^x$, —CONR$^x$R$^x$SO$_2$R$^x$, and —CO$_2$R$^x$;

R$^x$ is independently selected from the group consisting of hydrogen, NR$^4$R$^5$, and an optionally substituted alkyl, cycloalkyl, heterocycle, or aryl;

n is an integer from 1 to 10; and

R$^1$ is Formula (IV):

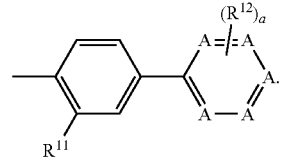

(IV)

wherein:

A is independently selected from the group consisting of CR$^6$ and N;

R$^6$ is independently selected from the group consisting of hydrogen, hydrocarbyl, and substituted hydrocarbyl;

R$^{11}$ and R$^{12}$ are independently selected from the group consisting of OR$^{15}$, —NR$^{15}$R$^{16}$, —NR$^{15}$COR$^{16}$, —NR$^{15}$CO$_2$R$^{16}$, —NR$^{15}$CONR$^{16}$, —NR$^{15}$SO$_2$R$^{16}$, —COR$^{15}$, —SO$_2$R$^{16}$, nitro, cyano, halogen, aryl, heterocycle, —COOR$^{15}$, —CONR$^{16}$R$^{17}$, —SO$_2$NR$^{18}$R$^{19}$, alkenyl, alkynyl, hydrocarbyl, and substituted hydrocarbyl;

R$^{15}$, R$^{16}$, R$^{17}$, R$^{18}$, R$^{19}$ are independently selected from the group consisting of hydrogen, hydrocarbyl, substituted hydrocarbyl, aryl, and heterocycle, and R$^{16}$ and R$^{17}$ together can optionally form a ring, and R$^{18}$ and R$^{19}$ together can optionally form a ring; and (a) of R$^{11}$ is the integer 1 and (a) of R$^{12}$ is either the integer 1 or the integer 2.

2. The compound of claim 1, wherein X is OR$^2$ and Z is O.

3. The compound of claim 1, wherein X is OR$^2$; Z is O; R$^{11}$ is selected from the group consisting of —OR$^{15}$, methyl, halogen, CO$_2$Me, hydrocarbyl, and substituted hydrocarbyl.

4. The compound of claim 3, wherein Formula (IV) is:

5. The compound of claim 1, wherein X is OR$^2$; Z is O; Y is selected from the group consisting of oxygen, sulfur, CR$^3$, NR$^4$, —N(R$^5$)CO—, —CH$_2$N(R$^5$)—, —CH$_2$O—, —CON (R$^5$)—, —CH$_2$N(R$^5$)CO, and —(CH$_2$)$_n$— and an optionally substituted alkyl.

6. The compound of claim 1, wherein X is OR$^2$; Z is O; Y is selected from the group consisting of oxygen, sulfur, NH, —CH$_2$O—, —CONH, —CH$_2$NHCO—, —(CH$_2$)$_n$— and an optionally substituted alkyl.

7. The compound of claim 5, wherein Y is selected from the group consisting of oxygen, sulfur, NH, —(CH$_2$)$_n$— and an optionally substituted alkyl; and R$^{12}$ is selected from the group consisting of —COOR$^{15}$ and —CONR$^{16}$R$^{17}$.

8. The compound of claim 1, wherein X is OR$^2$; Z is O; Y is selected from the group consisting of oxygen and an optionally substituted alkyl; Formula (IV) is:

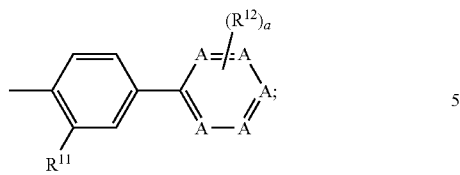

$R^{11}$ is selected from the group consisting of —$OR^{15}$, methyl, halogen, $CO_2Me$, and hydrocarbyl; and $R^{12}$ is selected from the group consisting of —$COOR^{15}$ and —$CONR^{16}R^{17}$.

9. A method of treating a urinary tract infection, the method comprising administering a compound of claim 1 to a subject in need thereof.

10. The method of claim 9, wherein the subject is further administered a bactericidal composition.

11. A method of reducing the resistance of a bacterium to a bactericidal compound, the method comprising administering a compound of claim 1 to a subject in need thereof.

* * * * *